US012150983B2

(12) United States Patent
Ackerman et al.

(10) Patent No.: US 12,150,983 B2

(45) Date of Patent: Nov. 26, 2024

(54) PORCINE CORONAVIRUS VACCINES

(71) Applicant: Boehringer Ingelheim Animal Health USA Inc., Duluth, GA (US)

(72) Inventors: Scott Ackerman, Huxley, IA (US); Joseph Ralph Hermann, Waukee, IA (US); Luis Alejandro Hernandez, Story City, IA (US); Lea Ann Hobbs, Nevada, IA (US); Arun V. Iyer, Ames, IA (US); Sean O'Conner, Ankeny, IA (US); Abby Rea Patterson, Story City, IA (US); Eric Martin Vaughn, Ames, IA (US); Joseph Gilbert Victoria, Ames, IA (US)

( * ) Notice: Subject to any disclaimer, the term of this patent is extended or adjusted under 35 U.S.C. 154(b) by 688 days.

(21) Appl. No.: 16/481,010

(22) PCT Filed: Jan. 26, 2018

(86) PCT No.: PCT/US2018/015507

§ 371 (c)(1),
(2) Date: Jul. 25, 2019

(87) PCT Pub. No.: WO2018/140766

PCT Pub. Date: Aug. 2, 2018

(65) Prior Publication Data

US 2020/0038504 A1 Feb. 6, 2020

Related U.S. Application Data

(60) Provisional application No. 62/452,026, filed on Jan. 30, 2017.

(51) Int. Cl.

*A61K 39/215* (2006.01)
*A61P 31/14* (2006.01)

(Continued)

(52) U.S. Cl.

CPC ............ *A61K 39/215* (2013.01); *A61P 31/14* (2018.01); *C12N 7/00* (2013.01);

(Continued)

(58) Field of Classification Search

None

See application file for complete search history.

(56) References Cited

U.S. PATENT DOCUMENTS 10,280,199 B2 * 5/2019 Kim ....................... A61K 39/12
2015/0283229 A1 * 10/2015 Hernandez ........... A61K 39/215
435/235.1

(Continued)

FOREIGN PATENT DOCUMENTS

CN 104248462 A 12/2014
WO 2015153425 A1 10/2015

(Continued)

OTHER PUBLICATIONS

Chia-Yu Chang, Wei-Ting Hsu, Yu-Chan Chao, and Hui-Wen Chang. "Display of Porcine Epidemic Diarrhea Virus Spike Protein on Baculovirus to Improve Immunogenicity and Protective Efficacy" Viruses (2018) 10, 346.

(Continued)

*Primary Examiner* — M Franco G Salvoza

(57) ABSTRACT

The present invention relates to a vaccine for protecting a pig against diseases associated with corona virus infection including porcine epidemic diarrhea virus (PEDV) and/or porcine deltacorona virus (PDCoV). The vaccine commonly includes inactivated/killed PEDV (e.g., chemically inactivated PED virus), and/or recombinant PEDV antigen, and/or an adjuvant inactivated/killed PDCoV (e.g., chemically inactivated PDCoV virus), and/or recombinant PDCoV antigen and an adjuvant. Methods for protecting pigs against diseases associated with PEDV and/or PDCoV and methods (Continued)

of producing the porcine epidemic diarrhea virus and/or porcine deltacorona virus vaccine are also provided.

11 Claims, 8 Drawing Sheets

Specification includes a Sequence Listing.

(51) Int. Cl.
*C12N 7/00* (2006.01)
*A61K 39/00* (2006.01)

(52) U.S. Cl.
CPC *A61K 2039/5252* (2013.01); *A61K 2039/552* (2013.01); *A61K 2039/55566* (2013.01); *C12N 2710/14043* (2013.01); *C12N 2710/14071* (2013.01); *C12N 2770/20034* (2013.01); *C12N 2770/20071* (2013.01)

(56) References Cited

U.S. PATENT DOCUMENTS

2015/0328307 A1* 11/2015 Lawrence ................ C12N 7/00 424/199.1
2016/0339097 A1 11/2016 Kim

FOREIGN PATENT DOCUMENTS

WO 2016007576 1/2016
WO WO-2016007576 A2 * 1/2016 ............. A61K 39/12

OTHER PUBLICATIONS

Hernandez, Luis A., Cathy L. Miller, and Eric M. Vaughn. "Particle and subunit-based hemagglutinin vaccines provide protective efficacy against H1N1 influenza in pigs." Veterinary microbiology 191 (2016): 35-43.
Yang, Ding-Gang, Yao-Chi Chung, Yiu-Kay Lai, Chia-Wei Lai, Hung-Jen Liu, and Yu-Chen Hu. "Avian influenza virus hemagglutinin display on baculovirus envelope: cytoplasmic domain affects virus properties and vaccine potential." Molecular Therapy 15, No. 5 (2007): 989-996.
Puranaveja S. et al., "Chinese-like strain of porcine epidemic diarrhea virus, Thailand", Emerging Infectious Diseases. 2009, vol. 15, No. 7, pp. 1112-1115.
Stevenson G.W., et al. "Emergence of porcine epidemic diarrhea virus in the United States: clinical signs, lesions, and viral genomic sequences", Journal of Veterinary Diagnostic Investigation, 2013, vol. 25, No. 5, pp. 649-654.
Marthaler D, et al., "Complete genome sequence of porcine epidemic diarrhea virus strain USA/Colorado/2013 from the United States", Genome Announcements, 2013, vol. 1, Issue 4, e00555-13.
Song D, et al., "Porcine epidemic diarrhoea virus: a comprehensive review of molecular epidemiology, diagnosis, and vaccines", Virus Genes, 2012, vol. 44, pp. 167-175.
Tuang YW, et al., "Origin, evolution, and genotyping of emergent porcine epidemic diarrhea virus strains in the United States", mBio, 2013, vol. 5, Issue 5, e00737-13.
Jing Bi, et al., "Complete genome sequence of porcine epidemic diarrhea virus strain AJ1102 isolated from a suckling piglet with acute diarrhea in China", Journal of Virology, 2012, vol. 86, No. 19, pp. 10910-10911.
Jianfei Chen, et al., "Complete genome sequence of a Chinese virulent porcine epidemic diarrhea virus strain", Journal of Virology, 2011, vol. 85, No. 21, pp. 11538-11539.
Jianfei Chen, et al., "Complete genome sequence of a porcine epidemic diarrhea virus variant", Journal of Virology, 2012, p. 3408.
Fan H, et al., "Complete genome sequence of a novel porcine epidemic diarrhea virus in south China", Journal of Virology, 2012, vol. 86, No. 18, pp. 10248-10249.
Gao Y, et al., "Phylogenetic analysis of porcine epidemic diarrhea virus field strains prevailing recently in China", 2013, Arch. Virol. 158:711-715.
Li B, et al., "Complete genome sequence of a recombinant porcine epidemic diarrhea virus strain from eastern China", Genome Announcements, 2013, vol. 1, Issue 2, e00105-13.
Luo Y, et al., "Complete genome sequence of a highly prevalent isolate of porcine epidemic diarrhea virus in south China", Journal of Virology, 2012, vol. 86, No. 17, pp. 9551-9551.
Wang XM, et al., "Complete genome sequence of a variant porcine epidemic diarrhea virus strain isolated in central China", Genome Announcements, 2013, vol. 1, Issue 1, e00243-12.
Wei ZY, et al., "Complete genome sequence of novel porcine epidemic diarrhea virus strain GD-1 in China", Journal of Virology, 2012, vol. 86, No. 24, pp. 13824-13825.
Zhao M, et al., "Complete genome sequence of a Vero cell-adapted isolate of porcine epidemic diarrhea virus in eastern China", Journal of Virology, 2012, vol. 86, No. 24, pp. 13858-13859.
S.J. Park, et al., "Molecular characterization and phylogenetic analysis of porcine epidemic diarrhea virus (PEDV) field solates in Korea", Arch. Virol., 2011, vol. 156, pp. 577-585.
C.H. Kweon, et al., "Derivation of attenuated porcine epidemic diarrhea virus (PEDV) as vaccine candidate", Vaccine, 1999, vol. 17, pp. 2546-2553.
T. Sato, et al., "Mutations in the spike gene of porcine epidemic diarrhea virus associated with growth adaptation in vitro and attenuation of virulence in vivo", Virus Genes, 2011, vol. 43, pp. 72-78.
Park, S.J. et al., "Complete genome sequences of a Korean virulent porcine epidemic diarrhea virus and its attenuated counterpart", Journal of Virology, 2012, vol. 86, 5964.
Woo, P.C., et al., "Discovery of seven novel Mammalian and avian coronaviruses in the genus deltacoronavirus supports bat coronaviruses as the gene source of alphacoronavirus and betacoronavirus and avian coronaviruses as the gene source of gammacoronavirus and deltacoronavirus", Journal of Virology, 2012, vol. 86, No. 7, pp. 3995-4008.
Hu, H., et al., "Isolation and Characterization of Porcine Deltacoronavirus from Pigs with Diarrhea in the United States" J Clin Microbiol, 2015, vol. 53, No. 5, pp. 1537-1548.
Chen, Q., et al., "Pathogenicity and pathogenesis of a United States porcine deltacoronavirus cell culture isolate in 5-day-old neonatal piglets", Virology, 2015. vol. 482, pp. 51-59.
Li, G., et al., "Full-Length Genome Sequence of Porcine Deltacoronavirus Strain USA/IA/2014/8734", Genome Announcements, 2014, vol. 2, Issue 2, e00278-14.
Marthaler, D., et al., "Rapid detection, complete genome sequencing, and phylogenetic analysis of porcine deltacoronavirus", Emerging Infectious Diseases, 2014, vol. 20, No. 8, pp. 1347-1350.
Marthaler, D., et al., "Complete Genome Sequence of Strain SDCV/USA/Illinois121/2014, a Porcine Deltacoronavirus from the United States", Genome Announcements, 2014, vol. 2, Issue 2, e00218-14.
Wang, L., et al., "Detection and genetic characterization of deltacoronavirus in Pigs, Ohio, USA, 2014", Emerging Infectious Diseases, 2014. vol. 20, No. 7 pp. 1227-1230.
Lee, S. and C. Lee, "Complete Genome Characterization of Korean Porcine Deltacoronavirus Strain KOR/KNU14-04/2014", Genome Announcements, 2014. vol. 2, Issue 6, e01191-14.
Dong, N., et al., "Porcine Deltacoronavirus in Mainland China", Emerging Infectious Diseases, 2015, vol. 21, No. 12, pp. 2254-2255.
Song, D., et al., "Newly Emerged Porcine Deltacoronavirus Associated With Diarrhoea in Swine in China: Identification, Prevalence and Full-Length Genome Sequence Analysis", Transboundary and Emerging Diseases, 2015, vol. 62, pp. 575-580.
Ma, Y., et al., Origin, evolution, and virulence of porcine deltacoronaviruses in the United States. MBio, 2015. 6(2): p. e00064.
The 7th Annual International Symposium on Emerging and Re-emerging Pig Diseases. Kyoto, Japan Jun. 21-24, 2015.
Meng, F., et al., Evaluation On The Efficacy And Immunogenicity Of Recombinant DNA Plasmids Expressing Spike Genes From

(56) References Cited

OTHER PUBLICATIONS

Porcine Transmissible Gastroenteritis Virus And Porcine Epidemic Diarrhea Virus, PLOS One, US, vol. 8, No. 3, Mar. 2013, pp. e57468-1, XP-002743578.

* cited by examiner

Protein Map of SDCV S1-IgG2a Fc

B. Protein Map of SDCVS BD

Serological response following vaccination as detected by IFA:

*Indicates that the value is significantly different from the Placebo group (Dunnett's method)

Serological response following vaccination as detected by S1-IgG2a-Fc based ELISA:

Protein Map of PEDV 2a BD Baculodisplay Baculovirus

Protein Map of PEDV 2b BD Baculodisplay Baculovirus

Percentage of surviving pigs by group and study day

IgA levels in vaccinated animals (Least square mean anti-PEDV IgA by group and sample)

SEQUENCE LISTING

```
<160> NUMBER OF SEQ ID NOS: 53

<210> SEQ ID NO 1
<211> LENGTH: 25505
<212> TYPE: DNA
<213> ORGANISM: Artificial Sequence
<220> FEATURE:
<223> OTHER INFORMATION: Porcine Deltacorona Virus Genome cDNA - NSVL

<400> SEQUENCE: 1

gcacctgaaa ccaagacgcg tcagtagtag ggactactgg tgcagccatg atagattggt      60

gtcggtagag aactagcgaa gctagggaga taaaattata gactaatgct ataattttta     120

tctttagtct ataattttat ctccctagct tcgctagttc tctaccgaca ccaatccagg     180

tgcgtctgcc accaagttgg ctacccttcc taggggcgct ttcgcgcttg ctcaccatta     240

gattacctgg aaaccagcca ttcaggttgg agtttcccca ggctcttttg tgtgggcatt     300

agcggcttgt ggtttttgca caaaatctaa gctacttacc gttcctctga ccatccacca     360

cttctataga cagcactgat taccgtaggg tttaagtcac accggtctgc accgcccgtc     420

agcggacaca ttacccagca tagcactcct tgcaccgagc ctaggtagga taaaaccccc     480

taccgggtga ctcttaaggc gtttcctcca cgggatagcc actagtcact aggtgtaagt     540

gatctgatct gggcgtattg tgttgcgcaa gtgtgatacc cataggagcg tggaatccta     600

ttctgcggct cagtgcctga tatagctgtg aaatggccaa gaacaagtcc aagcgcgacg     660

ctattgcgtt gcctgaaaat gtaccaccac ctctgcaact tttcattcat gttgcagctg     720

ctgaagaggg tcaccctaag gttactactt accttggcaa ctataacctc tatgccacca     780

aggctccgcc tggcgtgcag gttcttagtg ctaaaacctc tcttactgac tttgagaatg     840

tctttggagc tcaacccacc ttgcgatcaa ttcgtaatct ggtttgtgag gctcgctcgg     900
```

-continued

```
ctgaatggac aacttccaag aatgcttttg cactcaaagc cactcaactt gactactctg    960
atgccgtttt gagggcaatg attcgtttct gccctccaaa ggtgtccaca ctcgttgcct   1020
ttgctctttt tggccgattg gttaaaattg aggacaagga acttgctgag ttagctcgtg   1080
atactgccct tgagttggcg tacacggcta aaattggtac atctcttgct gacacgagat   1140
ctgtctcact tattcataag gacgcttatc taactctcag taatgaggtt gttggcgtaa   1200
cttttactgc cgcacttatg gcaaaggcta ccactgttaa tggagcaatg caatactcaa   1260
acttttacct ctaccctcgt gccactatta aggtaaccga tggtaaggct gaagcaattg   1320
caactaagcc tctgtctgct gccactaaag gcaagcaaat cacagaggat gtcaaccttc   1380
tccctgacta tcagcagctg cttgttgatc aagtgactgg cactgaggtt aaggttggag   1440
ctctaaccta tgttaagacc actgattcgc cacccccttta ctttcccaaa gtcaagggtg   1500
gtgttattgg tattgcactt aagcagcagg gcactgcggc taagaagctc aatgtagtct   1560
tccatgctca acctgatgat gttctgctag ccttcataca acttcagcaa ttcttgaacc   1620
gtacttcgga ttcaagtgtt gaaattactg attgccagag ttatgaagta tctccaactg   1680
tgacggtcaa aattggcccg tctaaacctg gggatgtcat cgtggctact gatgaggaat   1740
accttaaatg ctttgaaacc cctgaggtag gtaggctcta taaggttttc caaactcaat   1800
cttgggctat cattgagcgt gccttctcca gtttgaagat ccgcgtgtcc aaagctttat   1860
cagcatttat aagttttctg caaaaccttg cagataactt tactgcaata agtggtgttg   1920
tcactgcact cattcgtgaa ctccaggatc ttaccctgga tgtggcgaca cgtatcacta   1980
acatacaatt tgtttaccgt gccggtaagc ttattgtcga cacgacaagt gtcatagcta   2040
aacttttcca gccattttgt gattttatat cacctttcct tcggaaagtt gctggttttg   2100
caatttacac tgttggtaat cgcatgctta tgtttaccag cactggcacc tttcttctca   2160
caaaggcaac tactaagata ctcaataagg caaagtacat ctttgatgtg gagcctgagt   2220
acccagtaga tgtaacaaca tccaaagttg tagtacatga agcactccag caaaccgaca   2280
ctaagcctac tagagctctg gaggctgttg atgtcgttgt tggtaatact gtactgcaaa   2340
tggctactga tggcactgcg ttctacccat cggatggtac gcacgcctct cttccaggat   2400
tcaaagcagg ttcggatgag cttttcataa gcttcaactg cgacctcttt gatgatgaga   2460
ctaatgctca aatcaacgaa atactcgctg catatgagct taaccaacta gtggctccag   2520
gtgattctac accgcgtcaa attgcgacgt tggttgtcga tacacttgca gatgctataa   2580
cagaccactt tccggagaaa accattgatc tacctgaaga ctatcaagtc ttttctgacc   2640
atgatgacct cccactcgca caataccaca tccctgatca cctgagcctg tatattcagg   2700
ctatggaagg tgaagatgat agtggtgatg aaatatgtat tgaggacgat gattacgact   2760
gtcctcaagc cgacgaagac acagaaggag taattcccca acagtgggaa cttcctgatg   2820
ttgataaatt tttactcaag atccaggaac ggaagaccag cagcgacgaa gtacttagcg   2880
tcgacgtcta tcctaaacca gagccggtcg gcaatgttgg gattgacgac agcgcgtcgg   2940
aaaagaagcc aaatggggac tcagtaccgg atcctgaggt ccatccaaca ctagagagtg   3000
tggatgttga acgaccaacc gaaacagcaa accaggctgt tgaagacaaa ccttctgata   3060
ccacctttgt ggttgatgag gaacaattac aagaatcaac accagaacat gaactccgct   3120
cctatgaagg ggagtttgat tctgatgatg aaattattat tcctatagta ccagtaacac   3180
ctgcggattt aaaaccacag actattacta taaaggagta ctttaagtct gaaaaacttg   3240
```

-continued

```
agactattaa cgaaggatcc acagagtcag ttacacaatc tgacgattcg tttgacgagt   3300
catttgttga tgctgagtct gatgatccac aagatcctgc tgtatatgat gatacaacaa   3360
ttataacgga cagcactgat gtaggcgatg agcctgagac aactctagct accatcgtta   3420
acacacctct gacactcgat aataacttgc cacctgaagc cattaaacaa cccagcccaa   3480
ctaaggttga gttagttgtt ggtgaattgg cgagtattaa atttgacaat tctgttctag   3540
tcaaccctgc taatgcgcaa ttaacaaatg gcggtggagc tgctcgtgca attgcaaaat   3600
tagctggtcc aaaatatcaa gagtactgta atagtgtggc tcctatctca ggaccgctta   3660
ccacggactc ttttgatgcc aagaaatttg gtgtagcctg catcttgcat gtagtgccac   3720
ccaaaggttc tgaccctaat gtacaagaac tcctgtatca agcttacaag agtatcctta   3780
ctgaaccagc acactatgtt atacctatac taggtgctgg tatctttgga tgcaacccag   3840
tccactctct ggatgcgttc aggaaagcat gtccaagtga cataggtcgt gtcacccttg   3900
tcactatgaa caaaaaccat ttgcaggtgt gggatgctct caataggacc attgtacgca   3960
ccactactga ctatgatcaa gttaccacca aggcccttac accccaggga gtgttagaag   4020
ccaatctctt tgatggtgag gactttgttc aagaaccaaa acccggtcaa atctaccttg   4080
aggttactga agaagttcag aaccaagcca aggaacttga ccttaacctt cagcaatact   4140
gcgtctacct gaagacttgc caccataaat gggttgtgag tcgtacgaac gggttgatgc   4200
atctaaaaca aaaagataac aattgttttg ttagtgcagg tgtaaacctg tttcaaaaca   4260
ctgcttatca acttagacct gctattgatg ctctctatag ggagtatctt aatggtaatc   4320
caaatagatt tgttgcttgg atctacgcat ccactaaccg tcgtgttggt gagatgggtt   4380
gtccacagca agttatttct ttgctcgtta gtaactctga cgcagcattt tcagcaacta   4440
cagcctgttg taacacctac tttaaccaca caggtgttat ttcagtagct cgtgaatatg   4500
acccaataca accaaaggtc tactgcatga agtgtgatgt gtggactccc tttacacccc   4560
agagtggaaa aggtgcagtt gcaattggta tttctgcaga tgaacctacc ggtcctgcca   4620
ttaaatttgc cgcagctcac tgctggtaca ctaatggcaa gaaaacagtt aatggctatg   4680
acactaaagc taatgttgta gctacctatc ataggtttga cgtgcctaag cctcaacttg   4740
tcgaggacgt ggttgcgctg cctactaaaa atgactttga agttctcaat gttgaagaac   4800
tgccgcagga tagtgtgctc catttggacc cacctcctgt acaggcctta caacctaagg   4860
ctaaccaaca cattgagatt ctagaaaacc cagattatct ggacattttg gatctttgga   4920
ttcgtaaacc caaattcatc ctcgtaaagt cgtggagtgt tttgggtaga gcactatgta   4980
aggcaggtaa agttgtcttt gtcaatgctt cgcttttgac ccgtttctac aattaccttg   5040
tagagattgg tgctcttgac tcaacaataa ggttgtcagt cgatcttacc tgtaaatttg   5100
ttagaacggt tctcccatcg tctaacactg tacacaaaac ttgtcttggt ctgtattatt   5160
cagcccagac actttttgtt tctttagcac cattccttat gttaccagct gtagttagtc   5220
tgcttaattc aggctataca attggcacat atttgtatgc aaaaaactggc tggccttgta   5280
attacaatgc cacgcaacac tttgattata attcttactg tgcaggtgac ttggtttgtc   5340
aagcctgttt tgacggtcaa gactccctac atttgtatcc gcatttacgt gttaatcagc   5400
agccccttca gaccactgac tacactgttt atgcgctttc actaatacta ctattagcta   5460
acatgactct tgtcatgggc acgctaatag ttactttctt tgtgaacttc tatggtgtgc   5520
aaataccatt ttatggtaca cttttgatag attatcaatc cgcactggtg attactttct   5580
cagtgtacta cttttataag gtaatgaagt tttccgcca tctcacacat ggatgtaaaa   5640
```

-continued

```
ttccaacgtg tgtggtatgt gccaaacttc gtaccccacc tactataaca gttgagactg   5700
tcgttcaggg caggaaatac ccatctgtta ttgaaacaaa tggcgggttt acaatttgta   5760
aagaacacaa cttctattgc aaggactgct ctttacaaac acccggcact ttcatcccga   5820
cagaagctat tgagtcgctc tcacgagcta ccaggcttag tgtcaaacca acagcaccag   5880
cattcttact tgctagagat gttgagtgcc aaactgatgt tgtcgttgct cgcgcaatgc   5940
ataaccaaaa tgcgcatgtg tgcatttcaa aatactctga tatccgtacc gttgaccaac   6000
tacttaagcc tactccactg ttttcataca ctcccgatgt tatcatcgcg gcagactttg   6060
acaacagagg tagtcttaag acagctaaag aattagctgt ggttttgtca atggacctta   6120
aacgtactat aattatcatt gatcaggcct attctagacc tattgataat tatcaggaag   6180
ttgcttctcg tattgagaag tattacccag ttgcaaagat cacacccaca ggtgacatct   6240
ttacagacat taagcaagcg accaatggcc aagctagtga ctctgctatt aatgcagctg   6300
ttctggctgt ccagcgcggt cttgatttta caattgacaa ccctaacaac atattaccac   6360
attacgcctt tgacttttca accctcaatg cagaagacca gtctaccatt ttggagagtg   6420
gttgtgctaa aggcaatctc aagggcacta atgttggtgt tgttctttca gctagccttg   6480
ttacacgtct tagtcagcag gctatacgtg tgattgctaa tgctgcttca cgtaatggtg   6540
ttacatgcgc tgttactcct tctacacttg ttatgcgtgg gaatattgca acacagccct   6600
tgactcgcat caaagctggt gcacctccca tgcgtcaaaa aattttatgt gttatcctgg   6660
cacttgctat tgtgtacttt gctgctatgg cttttggctt tttggcaagt caacttacgc   6720
ttaatacagt gcctacgatt aaatctgata tccgcgcctc taccttctac gttgttagag   6780
atggagtctt ggatactgtt cgttcaaatg acaagtgctt tgcaaataag tttttggcat   6840
ttgatagctt cattcaagca ccttacacta attcacctga ctgtccagtt gttgtgggag   6900
ttgttgatgt aacgacgcac tctattcctg gaattccagc aggtgtcatt catagagacg   6960
gtctcatact taacatttat gaacagtctc tttatgaaac tcatcagcgt cagtctatgg   7020
ttagggatgc gttgtcactc aagacagcaa atctctttaa cctaggcaag cgtgttgtag   7080
taggatacac tcaacatgaa gttgttgtgg gtacctccta ttttaattct cctgcacttt   7140
ttaatgcaaa gtgcaccttc ttacagtatc aggacactag acaactctat tgctatgata   7200
ctgttcctac tgaacataag ctctactctg atgtgcttcc gcacgtcgag tataaggcta   7260
ttgacattaa tggtgatctt gttcctttca agataccaga gcagataatg ttctatccac   7320
atattgtgcg ctatactagc aattcctatt gccgtatggg gcattgtttt aatactaacc   7380
ctggtatttg catttcattt acggacgaat ttccgtatag tgaaaatgtc aaacctggtg   7440
tgtactgtgc tgatacctct ttgcagttgt tttcaaacct cgttttgggc actgtatctg   7500
gtattcacat ctttacatca acagctgcat tgcttggatc tactattgtg atcatactat   7560
gcgttgttgc tgttcttgca gttcagcgat tcttcaagga gtacacaact tttgttatgt   7620
acacttgtgg tcttgctctt gtcaacattg taggcattgc acttatgtac aagtgccttg   7680
tcttcgcgat tttctattat gcaatctacc tttactttgt ccttactttc ccctccttta   7740
agaggaatgt ggcattgttt tacttcgctg tagtgatcgt gccgcacgtg agtaacatgc   7800
aattgcttgc gctcattgtg tgtagcatta tctactttct ctacacctat gttcatactg   7860
tagctaagac agctgggaaa ttttcttcct tcttagacgc agctaaagct acttttgtca   7920
ttgacaatga aaagtacgtg ttgcttaaag acctcgctgg tgctgaattt gaccagtatc   7980
```

```
tggcctctta caacaagtac aaatattttt ctggtactgc ttctgataag gattatgata   8040
aggtctgtat ggcatttctt gccaaggctt tgtcatcttt tcgtgaagga ggcggttcac   8100
agttgtacac accacctaaa tttgcagttg ttcagagtct taagaccaag ctgcaagcag   8160
gtatcaaaat cctcctgcac ccttcaggtg tagttgagcg atgtatggtc tcagttgtct   8220
acaatggatc tgcattgaat ggcatctggc ttaagaatgt tgtctactgc ccacgccatg   8280
taattggaaa attccgtggt gaccagtgga ctcacatggt ctcaattgct gattgccgcg   8340
actttatagt caagtgtcca atacagggta ttcagctaaa tgtccaatca gttaagatgg   8400
taggagctct cctccagtta actgttcata ccaacaacac agccactcca gactataagt   8460
ttgaaaggct acaaccagga tcatcgatga caattgcttg tgcttatgat ggcattgtac   8520
ggcatgtcta tcacgtggtc ctccaactta ataatcttat ttatgcaagc ttccttaacg   8580
gagcttgtgg tagtgtgggt tacactctta agggtaaaac actctactta cattacatgc   8640
accacattga gtttaacaac aaaactcata gtggtacaga tcttgaaggt aacttctatg   8700
gcccctatgt ggatgaggaa gttattcagc aacaaacagc attccagtat tacactgata   8760
atgttgttgc tcaattatat gcacacttac tgactgttga tgctagacca aaatggctgg   8820
cacaatctca gataagtatc gaggatttca actcatgggc tgctaacaat tcctttgcta   8880
acttcccatg tgaacaaact aatatgtcct acattatggg actctcgcaa acagctcgag   8940
tccctgtaga acgtatcctc aataccatta tacagctaac caccaataga gatggtgctt   9000
gtattatggg atcttatgat ttcgagtgcg attggacgcc agagatggta tacaatcagg   9060
ctccaatttc attgcagtca ggagtagtta agaaaacttg tacgtggttc ttccacttct   9120
tgtttatggc tattaccatg ctactcgctg ccatgcatgt tttccctgta cacttgtatc   9180
caatagtact gccatgcttc actgtcgtgg cattcctgtt gactttaacc attaaacaca   9240
ctgttgtgtt taccactaca tacttgcttc cgtcactttt gatgatggtt gtaaatgcta   9300
acactttttg gataccgaac acatttctgc gcacctgcta cgaaactata ttcggttccc   9360
caattgctca gcgactgtat ggttacactg ttgctcttta tatgctgatc tatgctggac   9420
ttgcaatcaa ctatacgttg aaaacactcc ggtatagagc aacttcattc ttatcttttt   9480
gcatgcagtg gtttcaatat ggttatgttg cacacattgc gtacaaactg cttaataaac   9540
cctggacaga atcactactc ttcacagcct tcacaatgct aaccagtcat cccttgttgg   9600
ctgctcttag ctggtggcta gctggtcgcg taactctgcc cattatcatg cctgacttag   9660
ctattcgtgt tttggcgtat aacgtcattg gctatgtcat atgtgttcga tttggcctta   9720
tgtggcttgc aaatcggttc acaactgtac ctatgggcac ataccagtat atggtgtctg   9780
tagagcaact taagtacatg atggcagtta agatgtcccc accgcgtaat gcgtttgagg   9840
tgcttatagc caacattaga cttcttggtt tgggtggaaa ccgtaacatt gctgtttcta   9900
ctgtccaaaa caaaattctt gatgcaaaag ctactgctgt tgttgttgct aaccttcttg   9960
aaaaggctgg cgtcacaaac aagcacgcta tttgcaaaaa gattgtgaaa ctccacaatg  10020
ataccettaa agccaccact tatgaggagg ttgaggtagc acttgtgaaa cttctttctc  10080
acataattga gttcttgcca actgatcagg tagatgctta tctagctgat gcggccaatg  10140
ctcaacatgt taatacctat ttagacaact tgcttgagaa caaagctgtt gttcaggctg  10200
ttgccgatat caacattaat ctggattctt atagaattta taaggaggca gatgctattt  10260
ataaacgatc tgttgagatg aacgaatctc cgcaggagca aaagaaaaag cttaaagctg  10320
ttaacattgc aaaggcggaa tgggagcgtg aggctgcttc tcagcgtaag cttgaaaagc  10380
```

ttgctgatgc tgctatgaag tctatgtatc ttgcagaacg tgctgaggat cgtcgcatta 10440
agctaacctc tggacttact gcaatgcttt accatatgct tagacgtctt gactcagata 10500
gggtaaaagc tctgtttgag tgcgctaagg cacaaatctt gccaatacat gctgtagtcg 10560
gaatttctaa tgacaacctt aaagttattt ttaacgataa ggacagctac tctcattatg 10620
tagagggcaa cacacttata cataagggag ttcgctacac tattgtgaag aaactctcct 10680
tagataatgc acctattgaa ggcgtaccag aagaattccc tgtggtcgtt gagactgtta 10740
gggaaggtgt gccccagttg caaaataatg agctatgttt gcgcaatgtt ttcactgctc 10800
agaacacagc tcaggacttc aatggcaatg aatccactgt aaaatctttt tatgttacta 10860
gaaccggtaa gaagattttg gttgccatta catcaactaa agacaatctt aagactgtga 10920
cctgccttac tgagaccggt aagacagtcc ttaacttgga ccccccatg cgcttcacac 10980
ataccgtagg tggaaaacag tctgttgtct atctctattt tattcagaat attagttcac 11040
tcaacagagg tatggttatt ggccacatct ctgaaactac tatccttcag gcaagtggca 11100
ctcaaattga gtaccagcaa aatgcctctc ttttgaccta tttggctttc gctgtagacc 11160
ctaagacagc ctaccttaag catcttgctg atggtgggtc tcctatacag ggttgtattc 11220
agatgattgc tactatgggt cctggatttg cagttactac taaaccacaa cctaatgagc 11280
atcagtattc ttatggtggt gcttcaattt gtctttattg ccgtgctcat ataccacatc 11340
ctggtgttga tggacggtgc ccctacaaag gccgctttgt tcacatcgac aaagataagg 11400
aacctgtttc cttcgctttg actcatgagc catgcagttc ttgtcaacgg tgggttaatt 11460
atgactgcac ctgcggatct agtctgcaga attcggctta tttaaacgcg taacgggttc 11520
tagtgacgcc cggctagaac ccctgcagcc tggaactcaa ccagatgctg taaaaagggc 11580
cttccatgtg cataatgata ccacctctgg tatattctta agcacaaaat ctaactgcgc 11640
tcggtttaaa accacacgca gtgccctgcc tttacctaat aagggagagg ttgaattgta 11700
ctttgttact aagcagtgtg cagctaaagt cttcgaaatc gaggaggaat gctacaacgc 11760
tcttagtaca gagctttata ctactgatga tacatttggt gtccttgcca aaactgagtt 11820
ctttaagttt gacaagatac ctaatgtcaa tcgccagtat ctgactaaat atacactcct 11880
ggacttggct tatgctctac gtcatttgtc aacatctaag gatgttattc aagaaatctt 11940
gatcaccatg tgcggaaccc ctgaagattg gtttggggaa aattggtttg atccaattga 12000
gaacccatcc ttttacaagg agttccataa acttggggat attcttaacc gttgtgttct 12060
taatgccaat aagtttgcta gtgcctgtat agacgctggt cttgttggca tattaacacc 12120
cgacaaccaa gacctcctgg gtcagatcta tgactttgga gattttatta ttacacaacc 12180
aggtaatgga tgtgtggact tagcatccta ttattcttat ttaatgccca ttatgtccat 12240
gactcacatg ttaaagtgtg agtgtatgga tagtgatggc aacccacttg agtatgatgg 12300
atttcagtat gacttcacgg acttcaagct tggcttgttc gagaagtatt ttaagtactg 12360
ggaccgtcct tatcatccta acactgttga atgtccagat gaccgttgcg tattgcactg 12420
tgcgaacttc aatgtgttgt ttgctatgtg tatacctaat acggcatttg gcaatctttg 12480
ttcaagagct actgttgatg gccaccttgt ggtccagaca gtgggtgtac acttgaaaga 12540
actcggtata gtccttaacc aggacgttac cacacacatg gcaaatatta atctaaacac 12600
tctattgcga ttggttggtg atcccaccac tattgcaagt gtctcagaca agtgtgtaga 12660
tttaagaact ccttgtcaga ccttggctac tatgtctagc ggaattgcta aacagtcagt 12720

-continued caagcccggg cattttaatc aacacttcta caagcatttg cttgatagta acctattaga 12780
ccaacttgga atagacattc gccacttcta ctatatgcag gatggtgaag cggctatcac 12840
agactacagc tactacaggt ataatacccc cacgatggta gatatcaaga tgttcttatt 12900
ttgccttgag gtggcagata agtatcttga gccctacgaa ggtggatgta ttaatgcaca 12960
gtcagttgtg gtctctaatt tggacaagtc agcgggctac ccctttaaca agctaggtaa 13020
ggctcgtaac tattacgaca tgactcatgc cgagcaaaat caactgtttg agtatacaaa 13080
acgcaatgtt ttgcctacac tcactcagat gaaccttaag tatgcaattt cagccaagga 13140
tcgtgctcgc actgtggcag gagtgtctat aattagcacc atgactaaca ggcagtacca 13200
tcaaaagatg ctgaaatcta tttcacttgc acgcaatcag accatcgtga ttggaacaac 13260
caaattctat ggtggttggg acaacatgtt acgacgactg atgtgtaata tcaacaatcc 13320
cattttagtg ggttgggatt accctaagtg tgatcgttct atgccaaaca tgctgcgcat 13380
tgccgcttcg tgcttgctag cacgaaaaca cacttgctgt aaccaaagcc agcgattcta 13440
ccgtttggct aatgaatgtt gccaagtact atctgaagtg gtagtctctg gtaacaacct 13500
ctatgtaaaa ccaggtggca ctagcagtgg tgatgcaacc acagcttatg ccaactcggt 13560
atttaacatc ttacaggtgg tttctgctaa tgtagccacc ttcttatcaa cttccaccac 13620
gacacatctt aataaggaca ttgcggactt gcatcgtagt ctttatgaag atatttatcg 13680
tggtgactct aatgatatca ccgtcatcaa tagattctac cagcatctcc aaagttactt 13740
tggacttatg atattgtctg atgatggtgt cgcatgcata gactcagccg ttgcaaaggc 13800
tggagctgtt gctgatcttg atggtttccg agacattttg ttttaccaaa acaatgttta 13860
catggcagac tcaaagtgtt ggacagaaac tgacatgaat gttggccctc atgaattttg 13920
ctcacagcat actgtgttag cagagcatga tggtaaacct tactacttac cttacccaga 13980
tgtctctcgc attctgggtg catgcatctt tgtggatgac gttaacaagg ctgaccctgt 14040
tcagaacctt gaacgttaca tctcacttgc aattgatgca tatcccctca ccaaggttga 14100
ccctattaag ggtaaagtct tttatttgtt actagactac atacgtgttc ttgytcagga 14160
gttacaggac ggtatccttg atgctttcca atcactcact gacatgtcgt atgtaaataa 14220
ctttatgaat gaggcctttt atgctcagat gtatgagcaa agtcctacac tacaggccag 14280
cggtgtttgt gtggtgtgta attcacccac tatactgcgc tgtggtgatt gcattcgtcg 14340
accactactt tgttgcgtct gtgcctacca gcatgttacg cagactacac ataaacgtat 14400
cattgctatc aacaactaca tctgtagtgt tgagaattgc aatgaggaca atgttgaaaa 14460
acttttcatt tctggcactg cgatttattg tgagaatcac aaacccacgc tgtgcatacc 14520
cattgtagct aatggttctg tttttggtat ctatcgccac actgcccgtg gtagtgatga 14580
catagacctc tttaacgagc ttgctacatc taactatgac actattgaac cttatcagaa 14640
ggccaatcgt gcacctttat cacttatgct cttcgctgct gaaaccatta aggcactcga 14700
ggagtctatc aagaagtcat atgctaccgc aaccgtcaag gatgtgtatg accaacgctt 14760
cattaaactt ctatgggaac agggtaaaaa gccgccaccc ataacgaaga accacatttt 14820
cactggctac cattttaaca agaatggaaa aacccaagtt ggtgattaca ttcttgctaa 14880
aacagatggc agtgacactt atacttacag aggaacatct acctacaaac tccaaacagg 14940
tgatgttcta gtcttaatgg cacatgttgt tacaccgctc tcagcacccc ctgtgttaac 15000
gcagacaaca tatgtcagaa aatcactttt acccgactct gttggtgcgt cttattatgt 15060
gcaacatttt aagtcatata atgagatagc tatgcagagg gttacaacag tattaggtcc 15120

-continued accaggcaca ggtaagtcaa cctttgctat tggtttggct aagtactttc ccagtgcacg 15180
tatttgctac actgcgtctt cgcatgcagc aatcgatgca ctctgtgaaa aagctttcaa 15240
gacaatacct gtaggccaat gcagtcgtat cgtacccaca cgtacaactg ttgagtgctt 15300
tcaggagttt gtcgtaaata acacaactgc acagtatatc ttctcgacta tcaatgcctt 15360
acctgacatt aagtgtgaca ttgtagttgt agatgaggtt tctatgttga ccaattatga 15420
gctttcctct gtgaatgctc gtttggttta caatcacatt gtgtatgttg gtgatcctta 15480
tcagttacct tcacctagaa ctatgcttac gtctggccag ctttcgccag ctgactataa 15540
cgtagttact gatataatgg tacatgcagg agcggatgtt atgctcgaca tgtgctacag 15600
atgcccacgt gaaatcgttg agacagtgtc taaacttgtc tacgataaca aactaaaagc 15660
ggcgaaaccg aactcaagac agtgttacaa gaccattgtg aactttggtc ctggagacgt 15720
tgctcatgag ggacaatctg cctacaacga agcacagttg cgtttcgcac tcgcatttag 15780
acaacaaaag cggtgggata acgtgacttt catatctcca tataatgcta tgaatgtgaa 15840
agcatcctta gcaggtttct ctactcagac cgttgactct tctcaaggtt ctgagtatga 15900
ttatgttatc ttttgcgtga ccactgattc agcacacgca cttaacatgg ctcgtttgaa 15960
cgttgccctt acacgcgcaa agataggtat ccttgtggtg tttaggcagg caaacgaact 16020
ttacaatagt ttgcagtttg aatctattga ttcacagctt cagtcgagtg ctgagaaaaa 16080
cctcacacca ctgtttaagc gctgcggcta tgagtataat ggcgtccatc cagctcatgc 16140
tttgacctgg catgattgtg gtgcagagta ccgctgtgag gagccacttg ctaaattagt 16200
aggagttgcc gatggcactc ttatatcata caaaacccta gtatccacac ttgggtttct 16260
tccatcactt aaaattgatg catatcataa tatgttccta acacgtgacg cgtgtcgcac 16320
ctatgttcag agttggatcg gcatagatgt tgaagcagca cacgccataa aacctaacac 16380
cgggactaac ctgccattgc aaataggttt tagtaccgga aagaattttt cagtcactcc 16440
agagggaatt tgggtaaacg agcacggatc ttgcactgag cccgtccctg ccaaaatacc 16500
tcctggagaa caatttcgtc accttaaaaa ggacatgcgc caggcgcgtc cttggaaggt 16560
tgttcgacgt gagattgcta ctcacattgc tgaggtagct cctcacactg attatatatg 16620
ctttgtcact tgggctcacc agcttgagct agcgacaatg cgctactttg tcaaactagg 16680
tatggaagag aaatgctttt gtggcaggcg ggcttgtttc actaatggaa ctgagttcgc 16740
ttgcaaagca caccattctc tcaccattcc acaatgtgat tatgtgtaca atccattcct 16800
catcgacgtg gctacgtggg gattctcggg acggctttcc accaaccatg acgctgtgtg 16860
cacatatcat gctaatgccc atgttgcatc agctgatgca atcatgacgg tatgtttagc 16920
tatccatgaa ctgttcagta ctgttgactg gaactttgaa tttccagtaa ctgctgagca 16980
atcgcaactt aacaaggcct gtcgcttagt acaggcgaat tacttaaata tactactcac 17040
tacaaccaaa gccacggtgg ttcacgatat tggtaaccca aaaggtatcc ctatcgtgcg 17100
caaacctggt gttaaatatc acttctatga tcaagcaccc attgtcaaac acgttcaaaa 17160
actaaagtac aagccagaga tggaggcccg tttcaccgat ggtttgacta tgttttggaa 17220
ttgtaatgtt gacacatacc ctgctaacgc ccttgtgtgc cgctacgaca ctcatcggca 17280
gaagcattta attggaccta atggttcagc actatatgtt aataagcatg cttttctcac 17340
ccctgagatg catacttatg ctacacataa actcaacttg gctccactca tctactactc 17400
caccacagat tgtagtagtg aacagcctat tgttgttacc tacagagatt gtgtcacccg 17460

-continued gtgcaatact ggaaaaactc tctgtccaaa tcatgctctt gaataccaag agtttatcaa 17520
tgcatacaat ctcatggctc gccatggatt taatgtttac ataccacgca atgtcaacgt 17580
ttacaactgt tggcttactt tcactaatct ccaaaacctt gaaaacttag cttacaactg 17640
ttattataag aactgcaatg ctcacgttga tgggcagctt gatgtagtta ttaataataa 17700
cgctgtatat gctaaggtcg acaataatct tgtcaaactt ttcgacaacc gcactaactt 17760
acctgtctca gtggcctttg aacattacac taacaggcat acccgttcac tgccaactac 17820
acagctgtta tctggtttag gcgtaaccgc caccagaaat ttcactgtgt ggttcgacaa 17880
tgatacaatt ttccaataca ctattaatgt atctacgtat actgacatcg accctagtac 17940
ccatgttgtc ctctgtgatg ataggtacgg aacagattgg agtcagttta accaacttcc 18000
taatgcagta ttcctcacca aaactaaggt gaagaaaaca gaaccgtttg tttgtacagc 18060
actgacccta aatggcgtcg ccattgacgg tgaagagcta tacatctatg tacgctataa 18120
caatcaactg accacatttg ctactacttg tacacagggt agaaatgttg agcagtttat 18180
acctaaaaca cctatggaaa gagacttcct tgagatgtct caacagtcct tcatccagca 18240
acatcaattg caggaactgg gtgttgaaca cattatctat ggtgatgatt ccagtccagt 18300
cattggcgga actcacacac ttatctcact agttaaaaac aagtttgaac atcagcttgt 18360
caaccatgtt tacaacccag tccagaactg tgttgttacc tcacctaacg caagctccaa 18420
gaacgtttgc actgttcttg atgttcttct tgatgactac attgacatca taagacaagc 18480
acatgccagt tacacaagta aatccaaagt attcactgtg tcaattgaca accaacaaat 18540
tagattcatg ctttggcatg atgagcaagt caagacttgc tacccaatct tacagtcact 18600
taccaatggt taccagatgc catctgtgta caaaacattg gttactgact tacaaccagc 18660
tgacatccct aattatcatt cctacacccc ccgggtgcct ggagtagtta agaatgttat 18720
caagtaccgc caactttca actacatagt taaaaaggat aggttggcag taccacacaa 18780
tatgaccgta ttacaccttg gagctgcatc tgcactaggt acagcaccag gttcttcagt 18840
cataaaacaa atgtttcctg aaggaactgt tcttattgac ctcgatataa gagagttcac 18900
ttcagatgct aaccaaataa tagttacaga ctacagaact tacataccac cacaccacgt 18960
agacgtcata ttttctgacc tctactgttg tgatgacata cacttctttg acaatctaat 19020
aaggatagtt aaggagaggc tcgccctcgg tggttctatc tttgttaaga taactgaaca 19080
ttcattctca cccgaactct actcacttgc gggttggttc gatgattatc aactattttg 19140
cacagcagtc aatgcctcgt cttcagaagc atttttatgc tgttttaatt atttggggct 19200
tgctaaggaa aacattaatg gttttaactt acatgcttcc tatattcaat ggcgcaatga 19260
aatagcgttg acaccaacct attctccttt agcggacaac ccggctacgg cctgtaagct 19320
aaaagcaacg cctattatct cggctcgtga gttagagaag aagcctattc ttcgctatct 19380
cgttgcatca gggcgccttc ttgtgaggcc accagaatgc agagagctct attgattatg 19440
accttatttt gtctcgttcg agcaaagttt gctgatgatc tactcgattt gctcaccttc 19500
ccgggtgcac atcgcttctt acataaaccc acgaggaatt ccagcagtct ctactcgcgg 19560
gctaataata attttgatgt tggcgttctt cctggctacc ccactaagaa cgttaacctc 19620
ttctcaccac ttactaactc cactttgccc attaatggcc ttcatcggag ttaccaacca 19680
ctcatgctga attgtcttac taaaataact aaccacactc tcagcatgta tctcctacct 19740
agtgagatac aaacttatag ctgcggcggt gccatggtta aataccagac acatgatgca 19800
gttcgtatca ttttagacct cactgccact gaccacatct ctgttgaagt cgttggccaa 19860
catggtgaaa attatgtgtt tgtttgcagt gagcagtcta cctacaccac tgcattacac 19920
aaatctacct tcttctcact taattctgag ctttattgct ttactaataa cacctactta 19980
ggtattcttc cacctgattt aactgacttt acggtctacc gtactggtca gttctatgct 20040
aatggttacc ttttaggtac tttacctatt acggttaact atgttaggtt gtatcggggt 20100
catttgtctg ccaatagtgc ccactttgcc cttgcaaacc taaccgatac actcataaca 20160
cttaccaata ctactatatc gcaaatcact tattgtgata agtctgtagt tgattcaata 20220
gcatgccagc gctcttctca cgaagtggag gatgggtttt actccaaccc taaatctgcc 20280
gttagagcta ggcaacgtac tattgttaca ctacctaagc tccctgagct tgaagtagtg 20340
cagttaaata tttctgcaca catggatttt ggcgaagcca gacttgacag cgttaccatc 20400
aatggtaaca catcctattg tgtcactaag ccttacttca ggcttgaaac taactttatg 20460
tgtacaggtt gcactatgaa tctgcgcact gatacctgta gttttgacct gtcagcagta 20520
aacaatggca tgtcattctc tcaattctgt ctaagcactg aatctggtgc ttgtgagatg 20580
aaaattattg ttacctacgt atggaattac ttgctaaggc agcgtttgta tgttactgct 20640
gtagagggcc agactcacac tggaaccact tcagtacatg caacagacac ttctagtgta 20700
atcactgatg tctgcactga ctacactatc tatggagtct ctggtactgg cattattaag 20760
ccatcagatc tcttattgca caatggcata gtattcacct ctccaacagg tgagctttat 20820
gcatttaaaa atataaccac tggcaaaacc cttcaggtct taccgtgtga aacccccttct 20880
caactgattg tgataaacaa caccgttgtc ggtgctatca catccagtaa ttcaactgaa 20940
aataataggt ttactactac tattgtcaca cctactttct tttattccac aaatgccacc 21000
actttcaact gcactaagcc tgttttgtcc tatggaccta tcagcgtgtg tagtgatggt 21060
gcaattgtgg gaacatccac attacagaat actcgaccat ccatagtttc actatacgat 21120
ggcgaagttg aaataccatc tgcattttct ctttccgttc agacggagta cttgcaagtt 21180
caagcagagc aagttatagt tgattgtcct cagtatgtat gcaatggcaa cagccgttgt 21240
ctacaattac tggcacaata cacctcagct tgctctaaga ttgaagcagc tctgcattcc 21300
tctgcacagt tggatagcag agagattata aatatgtttc aaacatcaac acagtccttg 21360
cagttagcta atattaccaa cttcaagggt gactacaatt ttagcagcat actaaccacc 21420
agaattggtg gcagatctgc tattgaagac cttctttta ataaagttgt tactagtggc 21480
cttggcactg ttgatcagga ctacaaatcc tgctctagag acatggccat cgctgactta 21540
gtttgttccc agtattacaa tggcatcatg gttctacctg gtgttgttga tgctgagaaa 21600
atggcaatgt atactggctc tcttactgga gctatggtat ttggaggact gactgccgca 21660
gcggcaatac catttgccac ggcagtacaa gctcgcctca attatgtcgc actgcaaaca 21720
aatgtactac aagaaaacca gaaaattctt gcagaatcat ttaaccaagc agttggcaat 21780
atatcacttg cactatcttc tgttaatgat gccatccagc aaacttctga ggctcttaac 21840
accgtagcta ttgctattaa aaagattcaa acagttgtta accagcaggg cgaggcatta 21900
tcacacctga ctgcacagct gtcaaacaat tttcaagcaa tttcgacttc tattcaagac 21960
atttacaacc gtcttgagga agtagaggct aaccagcaag ttgaccgtct catcacagga 22020
cggttggctg cacttaatgc atatgttact cagttactca atcagatgtc tcagattaga 22080
caatctcgat tgttagctca gcaaaagatt aatgagtgtg tcaaatcaca gtcgtccaga 22140
tacggtttct gtggaaatgg cacacacatc ttctcactta cacagactgc accaaatggc 22200

```
atatttttca tgcatgcagt gctagtaccc aacaaattca cacgtgtcaa cgcttctgcc  22260
ggcatttgtg tggataatac gagaggctac tcattgcagc ctcaacttat actctaccag  22320
tttaataact cctggagagt tacacctaga aatatgtatg aacccagact gccccggcag  22380
gctgatttca tacaattaac tgattgcagc gttacttttt acaacaccac cgctgctaat  22440
cttcccaata ttatccctga cattatagat gtcaatcaaa cagtcagtga tattattgac  22500
aatttaccta cagcaacacc tcctcagtgg gatgttggta tctataacaa cactattctc  22560
aacctcaccg ttgagattaa tgatctacaa gagcggtcta aaaacctctc acagattgca  22620
gatcgtttac aaaattatat tgacaatctt aacaatactc tagttgacct tgaatggctc  22680
aacagagtgg aaacttacct taaatggccg tggtatatat ggcttgccat tgccctggct  22740
cttattgcat ttgtgacaat cctcataaca atctttcttt gtactggttg ttgtggtggt  22800
tgctttggtt gttgtggcgg ttgttttggc cttttctcta agaagaaaag gtataccgac  22860
gaccaaccaa caccgtcctt taagtttaag gaatggtagt cgacgactgg gccgttacca  22920
tccctggaca atatattatt gctatactag ttgtcatctg cattggtgtg gcactacttt  22980
ttattaatac ttgcttagct tgtgttaaat tattttacaa gtgctaccta ggggcagcat  23040
atcttgttag gcctattata gtgtactact ccaagccgaa ccccgtacct gaggatgagt  23100
ttgtaaaagt acaccaattt cctagaaaca ctcactatgt ctgacgcaga agagtggcaa  23160
attattgttt tcattgcgat catatgggcg cttggcgtca tcctccaggg aggctatgcc  23220
acgcgtaatc gtgtgatcta tgttattaaa cttattctgc tttggctgct ccaacccttc  23280
accctagtgg tgaccatttg gaccgcagtc gacagatcat ctaagaagga cgcagttttc  23340
attgtgtcca taatttttgc cgtactgacc ttcatatcct gggccaagta ctggtatgac  23400
tcaattcgtt tattaatgaa aaccagatct gcatgggcac tctcacctga gagtagactc  23460
cttgcaggga ttatggatcc aatgggtaca tggaggtgca ttcccattga ccacatggct  23520
ccaattctca caccagtcgt taagcatggc aagctcaagc tacatgggca agagctggcc  23580
aatggcatat cagtcagaaa tccgccacag gatatggtga tagtgtcacc aagtgacacc  23640
tttcactaca cttttaagaa acctgtggaa tcaaacaacg atccagaatt tgctgttctg  23700
atataccagg gtgaccgcgc ttcaaacgct ggacttcaca ccataaccac ttcaaaggcc  23760
ggtgacgctc gcctgtataa gtatatgtaa tgtgcaactg ccatctgcag ctgcgagatt  23820
tatatagatt gtgcaataag cggcacatca gaagagagga tgttcctgag cttattgacc  23880
ctctcgttaa aactcgctgt tttgcttaca gtctcgtggt tcttgctaat gctaatccaa  23940
ttgcatttag catactacct cggaaaattc ttatcaatgg tgagccttta ctgcttgaat  24000
atggtagcat atatggtaaa gactttatca ttcgaccatc gctccaagtc attcttgaag  24060
atgaattaaa ttaaagtttt gacaccaatc tatcatggct gcaccagtag tccctactac  24120
tgacgcgtct tggtttcagg tgctcaaagc tcaaaacaaa aaggctactc atcctcagtt  24180
tcgtggcaat ggagttccgc ttaactccgc catcaaaccc gttgaaaacc atggctactg  24240
gctgcgttac accagacaaa agccaggtgg tactcccatt cctccatcct atgcctttta  24300
ttatactggc acaggtccca gaggaaatct taagtatggt gaactccctc ctaatgatac  24360
cccagcaacc actcgtgtta cttgggttaa gggttcggga gctgacactt ctattaaacc  24420
tcatgttgcc aaacgcaacc ccaacaatcc taaacatcag ctgctacctc tccgattccc  24480
aaccggagat ggcccagctc aaggtttcag agttgacccc ttcaacgcta gaggaagacc  24540
tcaggagcgt ggaagtggcc caagatctca atctgttaac tccagaggca caggcaatca  24600
```

```
gcccaggaaa cgcgaccaat ctgcaccagc tgcggtacgt cgtaagaccc agcatcaagc  24660
tcccaagcgg actttaccca agggtaaaac catttctcag gtatttggca accggtctcg  24720
tactggtgcc aatgtcggct ctgcagacac tgagaagacg ggtatggctg atcctcgcat  24780
catggctcta gccagacatg tgcctggtgt tcaggaaatg ctttttgctg gccaccttga  24840
gagcaacttt caggcggggg caattaccct taccttctcc tactcaatca cagtcaagga  24900
gggttctcct gactatgaga gacttaagga tgcgctcaat acggtcgtta accagaccta  24960
tgagccacct accaaaccaa ctaaggacaa gaagcctgac aaacaagacc agtctgctaa  25020
acccaaacag cagaagaaac ctaaaaaggt aactctgcca gcagacaaac aggattggga  25080
gtgggatgat gcttttgaga taaagcagga atcagcagcg tagacatcaa tctatgtctg  25140
ttaaacccac ccaactccac tcaaatatct ctttggttcc agagagtcgt agtgtatagc  25200
cagagagcca gtcagagggc gctatcatgc aaactagggc tggctactct agcacagaat  25260
cacatcccga taatcaacag tgctagaagg ttgattatac catttaatat gccgaggcca  25320
cgcggagtac gatcgagggt acagcataat ctcaactttt gttgagccac aattttaatc  25380
ctaattggag aaggccaaag gactgtacta cttttgtggg tgtagcagtc gcccagtggg  25440
aaagcgccaa ctaggttaca attgtggtgg ggacaaatta ggggaaatta aattggctta  25500
tagct                                                             25505
```

<210> SEQ ID NO 2
<211> LENGTH: 25505
<212> TYPE: RNA
<213> ORGANISM: Deltacoronavirus
<220> FEATURE:
<223> OTHER INFORMATION: Porcine Deltacorona Virus ssRNA +

<400> SEQUENCE: 2

```
gcaccugaaa ccaagacgcg ucaguaguag ggacuacugg ugcagccaug auagauuggu     60
gucgguagag aacuagcgaa gcuagggaga uaaaauuaua gacuaaugcu auaauuuuua    120
ucuuuagucu auaauuuuau cucccuagcu ucgcuaguuc ucuaccgaca ccaauccagg    180
ugcgucugcc accaaguugg cuacccuucc uaggggcgcu uucgcgcuug cucaccauua    240
gauuaccugg aaaccagcca uucagguugg aguuucccca ggcucuuuug ugugggcauu    300
agcggcuugu gguuuuugca caaaaucuaa gcuacuuacc guuccucuga ccauccacca    360
cuucuauaga cagcacugau uaccguaggg uuuaagucac accggucugc accgcccguc    420
agcggacaca uuacccagca uagcacuccu ugcaccgagc cuagguagga uaaaaccccc    480
uaccggguga cucuuaaggc guuuccucca cgggauagcc acuagucacu agguguaagu    540
gaucugaucu gggcguauug uguugcgcaa gugugauacc cauaggagcg uggaauccua    600
uucugcggcu cagugccuga uauagcugug aaauggccaa gaacaagucc aagcgcgacg    660
cuauugcguu gccugaaaau guaccaccac cucugcaacu uuucauucau guugcagcug    720
cugaagaggg ucacccuaag guuacuacuu accuuggcaa cuauaaccuc uaugccacca    780
aggcuccgcc uggcgugcag guucuuagug cuaaaaccuc ucuuacugac uuugagaaug    840
ucuuuggagc ucaacccacc uugcgaucaa uucguaaucu gguuugugag gcucgcucgg    900
cugaauggac aacuuccaag aaugcuuuug cacucaaagc cacucaacuu gacuacucug    960
augccguuuu gagggcaaug auucguuucu gcccuccaaa ggugucccaca cucguugccu   1020
uugcucuuuu uggccgauug guuaaaauug aggacaagga acuugcugag uuagcucgug   1080
```

auacugcccu ugaguuggcg uacacggcua aaauugguac aucucuugcu gacacgagau 1140
cugucucacu uauucauaag gacgcuuauc uaacucucag uaaugagguu guuggcguaa 1200
cuuuuacugc cgcacuuaug gcaaaggcua ccacuguuaa uggagcaaug caauacucaa 1260
acuuuuaccu cuacccucgu gccacuauua agguaaccga ugguaaggcu gaagcaauug 1320
caacuaagcc ucugucugcu gccacuaaag gcaagcaaau cacagaggau gucaaccuuc 1380
ucccugacua ucagcagcug cuuguugauc aagugacugg cacugagguu aagguuggag 1440
cucuaaccua uguuaagacc acugauucgc caccccuuua cuuucccaaa gucaagggug 1500
guguuauugg uauugcacuu aagcagcagg gcacugcggc uaagaagcuc aauguagucu 1560
uccaugcuca accugaugau guucugcuag ccuucauaca acuucagcaa uucuugaacc 1620
guacuucgga uucaaguguu gaaauuacug auugccagag uuaugaagua ucuccaacug 1680
ugacggucaa aauuggcccg ucuaaaccug ggaugucau cguggcuacu gaugaggaau 1740
accuuaaaug cuuugaaacc ccugagguag guaggcucua uaagguuuuc caaacucaau 1800
cuugggcuau cauugagcgu gccuucucca guuugaagau ccgcgugucc aaagcuuuau 1860
cagcauuuau aaguuuucug caaaaccuug cagauaacuu uacugcaaua agugguguug 1920
ucacugcacu cauucgugaa cuccaggauc uuacccugga uguggcgaca cguaucacua 1980
acauacaauu uguuuaccgu gccgguaagc uuauugucga cacgacaagu gucauagcua 2040
aacuuuucca gccauuuugu gauuuuauau caccuuuccu ucggaaaguu gcugguuuug 2100
caauuuacac uguugguaau cgcaugcuua uguuuaccag cacuggcacc uuucuucuca 2160
caaaggcaac uacuaagaua cucaauaagg caaaguacau cuuugaugug gagccugagu 2220
acccaguaga uguaacaaca uccaaaguug uaguacauga agcacuccag caaaccgaca 2280
cuaagccuac uagagcucug gaggcuguug augucguugu ugguaauacu guacugcaaa 2340
uggcuacuga uggcacugcg uucuacccau cggaugguac gcacgccucu cuuccaggau 2400
ucaaagcagg uucggaugag cuuuucauaa gcuucaacug cgaccucuuu gaugaugaga 2460
cuaaugcuca aaucaacgaa auacucgcug cauaugagcu uaaccaacua guggcuccag 2520
gugauucuac accgcgucaa auugcgacgu ugguugucga uacacuugca gaugcuauaa 2580
cagaccacuu uccggagaaa accauugauc uaccugaaga cuaucaaguc uuuucugacc 2640
augaugaccu cccacucgca caauaccaca ucccugauca ccugagccug uauauucagg 2700
cuauggaagg ugaagaugau agguggugaug aaauauguau ugaggacgau gauuacgacu 2760
guccucaagc cgacgaagac acagaaggag uaauucccca acagugggaa cuuccugaug 2820
uugauaaauu uuuacucaag auccaggaac ggaagaccag cagcgacgaa guacuuagcg 2880
ucgacgucua uccuaaacca gagccggucg gcaauguugg gauugacgac agcgcgucgg 2940
aaaagaagcc aaauggggac ucaguaccgg auccugaggu ccauccaaca cuagagagug 3000
uggauguuga acgaccaacc gaaacagcaa accaggcugu ugaagacaaa ccuucugaua 3060
ccaccuuugu gguugaugag gaacaauuac aagaaucaac accagaacau gaacuccgcu 3120
ccuaugaagg ggaguuugau ucugaugaug aaauuauuau uccuauagua ccaguaacac 3180
cugcggauuu aaaaccacag acuauuacua uaaaggagua cuuuaagucu gaaaaacuug 3240
agacuauuaa cgaaggaucc acagagucag uuacacaauc ugacgauucg uuugacgagu 3300
cauuuguuga ugcugagucu gaugauccac aagauccugc uguauaugau gauacaacaa 3360
uuauaacgga cagcacugau guaggcgaug agccugagac aacucuagcu accaucguua 3420
acacaccucu gacacucgau aauaacuugc caccugaagc cauuaaacaa cccagcccaa 3480

-continued cuaagguuga guuaguuguu ggugaauugg cgaguauuaa auuugacaau ucuguucuag 3540
ucaacccugc uaaugcgcaa uuaacaaaug gcgguggagc ugcucgugca auugcaaaau 3600
uagcuggucc aaaauaucaa gaguacugua auagugugge uccuaucuca ggaccgcuua 3660
ccacggacuc uuuugaugcc aagaaauuug guguagccug caucuugcau guagugccac 3720
ccaaagguuc ugacccuaau guacaagaac uccuguauca agcuuacaag aguauccuua 3780
cugaaccagc acacuauguu auaccuauac uaggugcugg uaucuuugga ugcaacccag 3840
uccacucucu ggaugcguuc aggaaagcau guccaaguga cauaggucgu gucacccuug 3900
ucacuaugaa caaaaaccau uugcaggugu gggaugcucu caauaggacc auuguacgca 3960
ccacuacuga cuaugaucaa guuaccacca aggcccuuac accccaggga guguuagaag 4020
ccaaucucuu ugauggugag gacuuuguuc aagaaccaaa acccggucaa aucuaccuug 4080
agguuacuga agaaguucag aaccaagcca aggaacuuga ccuuaaccuu cagcaauacu 4140
gcgucuaccu gaagacuugc caccauaaau ggguugugag ucguacgaac ggguugaugc 4200
aucuaaaaca aaaagauaac aauuguuuug uuagugcagg uguaaaccug uuucaaaaca 4260
cugcuuauca acuuagaccu gcuauugaug cucucuauag ggaguaucuu aaugguaauc 4320
caaauagauu uguugcuugg aucuacgcau ccacuaaccg ucguguuggu gagaugggu 4380 guccacagca aguuauuucu uugcucguua guaacucuga cgcagcauuu ucagcaacua 4440
cagccuguug uaacaccuac uuuaaccaca cagguguuau uucaguagcu cgugaauaug 4500
acccaauaca accaaagguc uacugcauga agugugaugu guggacuccc uuuacacccc 4560
agaguggaaa aggugcaguu gcaauuggua uuucugcaga ugaaccuacc gguccugcca 4620
uuaaauuugc cgcagcucac ugcugguaca cuaauggcaa gaaaacaguu aauggcuaug 4680
acacuaaagc uaauguugua gcuaccuauc auagguuuga cgugccuaag ccucaacuug 4740
ucgaggacgu gguugcgcug ccuacuaaaa augacuuuga aguucucaau guugaagaac 4800
ugccgcagga uagugugcuc cauuuggacc caccuccugu acaggccuua caaccuaagg 4860
cuaaccaaca cauugagauu cuagaaaacc cagauuaucu ggacauuuug gaucuuugga 4920
uucguaaacc caaauucauc cucguaaagu cguggagugu uuuggguaga gcacuaugua 4980
aggcagguaa aguugucuuu gucaaugcuu cgcuuuugac ccguuucuac aauuaccuug 5040
uagagauugg ugcucuugac ucaacaauaa gguugucagu cgaucuuacc uguaaauuug 5100
uuagaacggu ucucccaucg ucuaacacug uacacaaaac uugucuuggu cuguauuauu 5160
cagcccagac acuuuuuguu ucuuuagcac cauuccuuau guuaccagcu guaguuaguc 5220
ugcuuaauuc aggcuauaca auuggcacau auuuguaugc aaaaacuggc uggccuugua 5280
auuacaaugc cacgcaacac uuugauuaua auucuuacug ugcaggugac uugguuuguc 5340
aagccuguuu ugacggucaa gacucccuac auuuguaucc gcauuuacgu guuaaucagc 5400
agccccuuca gaccacugac uacacuguuu augcgcuuuc acuaauacua cuauuagcua 5460
acaugacucu ugucaugggc acgcuaauag uuacuuucuu ugugaacuuc uaugguguge 5520 aaauaccauu uuaugguaca cuuuugauag auuaucaauc cgcacuggug auuacuuucu 5580
caguguacua cuuuuauaag guaaugaagu uuuuccgcca ucucacacau ggauguaaaa 5640
uuccaacgug ugugguaugu gccaaacuuc guaccccacc uacuauaaca guugagacug 5700
ucguucaggg caggaaauac ccaucuguua uugaaacaaa uggcggguuu acaauuugua 5760
aagaacacaa cuucuauugc aaggacugcu cuuuacaaac acccggcacu uucaucccga 5820

-continued cagaagcuau ugagucgcuc ucacgagcua ccaggcuuag ugucaaacca acagcaccag 5880
cauucuuacu ugcuagagau guugagugcc aaacugaugu ugucguugcu cgcgcaaugc 5940
auaaccaaaa ugcgcaugug ugcauuucaa aauacucuga uauccguacc guugaccaac 6000
uacuuaagcc uacuccacug uuuucauaca cucccgaugu uaucaucgcg gcagacuuug 6060
acaacagagg uagucuuaag acagcuaaag aauuagcugu gguuuuguca auggaccuua 6120
aacguacuau aauuaucauu gaucaggccu auucuagacc uauugauaau uaucaggaag 6180
uugcuucucg uauugagaag uauuacccag uugcaaagau cacacccaca ggugacaucu 6240
uuacagacau uaagcaagcg accaauggcc aagcuaguga cucugcuauu aaugcagcug 6300
uucuggcugu ccagcgcggu cuugauuuua caauugacaa cccuaacaac auauuaccac 6360
auuacgccuu ugacuuuuca acccucaaug cagaagacca gucuaccauu uuggagagug 6420
guugugcuaa aggcaaucuc aagggcacua auguuggugu uguucuuuca gcuagccuug 6480
uuacacgucu uagucagcag gcuauacgug ugauugcuaa ugcugcuuca cguaauggug 6540
uuacaugcgc uguuacuccu ucuacacuug uuaugcgugg gaauauugca acacagcccu 6600
ugacucgcau caaagcuggu gcaccuccca ugcgucaaaa aauuuuaugu guuauccugg 6660
cacuugcuau uguguacuuu gcugcuaugg cuuuuggcuu uuuggcaagu caacuuacgc 6720
uuaauacagu gccuacgauu aaaucugaua uccgcgccuc uaccuucuac guuguuagag 6780
auggagucuu ggauacuguu cguucaaaug acaagugcuu ugcaaauaag uuuuuggcau 6840
uugauagcuu cauucaagca ccuuacacua auucaccuga cuguccaguu guuguguggag 6900
uuguugaugu aacgacgcac ucuauuccug gaauuccagc aggugucauu cauagagacg 6960
gucucauacu uaacauuuau gaacagucuc uuuaugaaac ucaucagcgu cagucuaugg 7020
uuagggaugc guugucacuc aagacagcaa aucucuuuaa ccuaggcaag cguguuguag 7080
uaggauacac ucaacaugaa guuguuugugg guaccuccua uuuuaauucu ccugcacuuu 7140
uuaaugcaaa gugcaccuuc uuacaguauc aggacacuag acaacucuau ugcuaugaua 7200
cuguuccuac ugaacauaag cucuacucug augugcuucc gcacgucgag uauaaggcua 7260
uugacauuaa uggugaucuu guuccuuuca agauaccaga gcagauaaug uucuauccac 7320
auauugugcg cuauacuagc aauuccuauu gccguauggg gcauuguuuu aauacuaacc 7380
cugguauuug cauuucauuu acggacgaau uuccguauag ugaaaauguc aaaccuggug 7440
uguacugugc ugauaccucu uugcaguugu uuucaaaccu cguuuugggc acuguaucug 7500
guauucacau cuuuacauca acagcugcau ugcuuggauc uacuauugug aucauacuau 7560
gcguuguugc uguucuugca guucagcgau ucuucaagga guacacaacu uuuguuaugu 7620
acacuugugg ucuugcucuu gucaacauug uaggcauugc acuuuaugua aagugccuug 7680
ucuucgcgau uuucuauuau gcaaucuacc uuuacuuugu ccuuacuuuc cccuccuuua 7740
agaggaaugu ggcauuguuu uacuucgcug uagugaucgu gccgcacgug aguaacaugc 7800
aauugcuugc gcucauugug uguagcauua ucuacuuucu cuacaccuau guucauacug 7860
uagcuaagac agcugggaaa uuuucuuccu ucuuagacgc agcuaaagcu acuuuuguca 7920
uugacaauga aaaguacgug uugcuuaaag accucgcugg ugcugaauuu gaccaguauc 7980
uggccucuua caacaaguac aaauauuuuu cugguacugc uucugauaag gauuaugaua 8040
aggucuguau ggcauuucuu gccaaggcuu ugucaucuuu ucgugaagga ggcgguucac 8100
aguuguacac accaccuaaa uuugcaguug uucagagucu uaagaccaag cugcaagcag 8160
guaucaaaau ccuccugcac ccuucaggug uaguugagcg auguauggugc ucaguugucu 8220

-continued acaauggauc ugcauugaau ggcaucuggc uuaagaaugu ugucuacugc ccacgccaug 8280
uaauuggaaa auuccguggu gaccagugga cucacauggu cucaauugcu gauugccgcg 8340
acuuuauagu caagugucca auacagggua uucagcuaaa uguccaauca guuaagaugg 8400
uaggagcucu ccuccaguua acuguucaua ccaacaacac agccacucca gacuauaagu 8460
uugaaaggcu acaaccagga ucaucgauga caauugcuug ugcuuaugau ggcauuguac 8520
ggcaugucua ucacgugguc cuccaacuua auaaucuuau uuaugcaagc uuccuuaacg 8580
gagcuugugg uaguguggu uacacucuua aggguaaaac acucuacuua cauuacaugc 8640
accacauuga guuuaacaac aaaacucaua gugguacaga ucuugaaggu aacuucuaug 8700
gccccuaugu ggaugaggaa guuauucagc aacaaacagc auuccaguau uacacugaua 8760
auguuguugc ucaauuauau gcacacuuac ugacuguuga ugcuagacca aaauggcugg 8820
cacaaucuca gauaaguauc gaggauuuca acucaugggc ugcuaacaau uccuuugcua 8880
acuucccaug ugaacaaacu aauaugucc acauuauggg acucucgcaa acagcucgag 8940
ucccuguaga acguauccuc aauaccauua uacagcuaac caccaauaga gauggugcuu 9000
guauuauggg aucuuaugau uucgagugcg auuggacgcc agagauggua uacaaucagg 9060
cuccaauuuc auugcaguca ggaguaguua agaaaacuug uacgugguuc uuccacuucu 9120
uguuuauggc uauuaccaug cuacucgcug ccaugcaugu uuucccugua cacuuguauc 9180
caauaguacu gccaugcuuc acugucgugg cauuccuguu gacuuuaacc auuaaacaca 9240
cuguuguguu uaccacuaca uacuugcuuc cgucacuuuu gaugaugguu guaaaugcua 9300
acacuuuuug gauaccgaac acauuucugc gcaccugcua cgaaacuaua uucgguuccc 9360
caauugcuca gcgacuguau gguuacacug uugcucuuua uaugcugauc uaugcuggac 9420
uugcaaucaa cuauacguug aaaacacucc gguauagagc aacuucauuc uuaucuuuuu 9480
gcaugcagug guuucaauau gguuauguug cacacauugc guacaaacug cuuaauaaac 9540
ccuggacaga aucacuacuc uucacagccu ucacaaugcu aaccagucau cccuuguugg 9600
cugcucuuag cugguggcua gcuggucgcg uaacucugcc cauuaucaug ccugacuuag 9660
cuauucgugu uuuggcguau aacgucauug gcuaugucau auguguucga uuuggccuua 9720
uguggcuugc aaaucgguuc acaacuguac cuaugggcac auaccaguau auggugucug 9780
uagagcaacu uaaguacaug auggcaguua agaugucccc accgcguaau gcguuugagg 9840
ugcuuauagc caacauuaga cuucuugguu ugggugaaa ccguaacauu gcuguuucua 9900
cuguccaaaa caaaauucuu gaugcaaaag cuacugcugu uguuguugcu aaccuucuug 9960
aaaaggcugg cgucacaaac aagcacgcua uuugcaaaaa gauugugaaa cuccacaaug 10020
auacccuuaa agccaccacu uaugaggagg uugagguagc acuugugaaa cuucuuucuc 10080
acauaauuga guucuugcca acugaucagg uagaugcuua ucuagcugau gcggccaaug 10140
cucaacaugu uaaauaccuau uuagacaacu ugcuugagaa caaagcuguu guucaggcug 10200
uugccgauau caacauuaau cuggauucuu auagaauuua uaaggaggca gaugcuauuu 10260
auaaacgauc uguugagaug aacgaaucuc cgcaggagca aaagaaaaag cuuaaagcug 10320
uuaacauugc aaaggcggaa ugggagcgug aggcugcuuc ucagcguaag cuugaaaagc 10380
uugcugaugc ugcuaugaag ucuauguauc uugcagaacg ugcugaggau cgucgcauua 10440
agcuaaccuc uggacuuacu gcaaugcuuu accauaugcu uagacgucuu gacucagaua 10500
ggguaaaagc ucuguuugag ugcgcuaagg cacaaaucuu gccaauacau gcuguagucg 10560

-continued gaauuucuaa ugacaaccuu aaaguuauuu uuaacgauaa ggacagcuac ucucauuaug 10620
uagagggcaa cacacuuaua cauaagggag uucgcuacac uauugugaag aaacucuccu 10680
uagauaaugc accuauugaa ggcguaccag aagaauuccc uguggucguu gagacuguua 10740
gggaaggugu gccccaguug caaaauaaug agcuauguuu gcgcaauguu uucacugcuc 10800
agaacacagc ucaggacuuc aauggcaaug aauccacugu aaaaucuuuu uauguuacua 10860
gaaccgguaa gaagauuuug guugccauua caucaacuaa agacaaucuu aagacuguga 10920
ccugccuuac ugagaccggu aagacagucc uuaacuugga ccccccuaug cgcuucacac 10980
auaccguagg uggaaaacag ucuguugucu aucucuauuu uauucagaau auuaguucac 11040
ucaacagagg uaugguuauu ggccacaucu cugaaacuac uauccuucag gcaaguggca 11100
cucaaauuga guaccagcaa aaugccucuc uuuugaccua uuuggcuuuc gcuguagacc 11160
cuaagacagc cuaccuuaag caucuugcug augguggguc uccuauacag gguuguauuc 11220
agaugauugc uacuaugggu ccuggauuug caguuacuac uaaaccacaa ccuaaugagc 11280
aucaguauuc uuaugguggu gcuucaauuu gucuuuauug ccgugcucau auaccacauc 11340
cugguguuga uggacggugc cccuacaaag gccgcuuugu ucacaucgac aaagauaagg 11400
aaccuguuuc cuucgcuuug acucaugagc caugcaguuc uugucaacgg uggguuaauu 11460
augacugcac cugcggaucu agucugcaga auucggcuua uuuaaacgcg uaacggguuc 11520
uagugacgcc cggcuagaac cccugcagcc uggaacucaa ccagaugcug uaaaaagggc 11580
cuuccaugug cauaaugaua ccaccucugg uauauucuua agcacaaaau cuaacugcgc 11640
ucgguuuaaa accacacgca gugcccugcc uuuaccuaau aagggagagg uugaauugua 11700
cuuuguuacu aagcagugug cagcuaaagu cuucgaaauc gaggaggaau gcuacaacgc 11760
ucuuaguaca gagcuuuaua cuacugauga uacauuuggu guccuugcca aaacugaguu 11820
cuuuaaguuu gacaagauac cuaaugucaa ucgccaguau cugacuaaau auacacuccu 11880
ggacuuggcu uaugcucuac gucauuuguc aacaucuaag gauguuauuc aagaaaucuu 11940
gaucaccaug ugcggaaccc cugaagauug guuuggggaa aauugguuug auccaauuga 12000
gaacccaucc uuuuacaagg aguuccauaa acuuggggau auucuuaacc guuguguucu 12060
uaaugccaau aaguuugcua gugccuguau agacgcuggu cuuguuggca uauuaacacc 12120
cgacaaccaa gaccuccugg gucagaucua ugacuuugga gauuuuauua uuacacaacc 12180
agguaaugga uguguggacu uagcauccua uuauucuuau uuaaugccca uuauguccau 12240
gacucacaug uuaaagugug aguguaugga uagugauggc aacccacuug aguaugaugg 12300
auuucaguau gacuucacgg acuucaagcu uggcuuguuc gagaaguauu uuaaguacug 12360
ggaccguccu uaucauccua acacuguuga auguccagau gaccguugcg uauugcacug 12420
ugcgaacuuc aauguguugu uugcuaugug uauaccuaau acggcauuug gcaaucuuug 12480
uucaagagcu acuguugaug gccaccuugu gguccagaca gugggguguac acuugaaaga 12540 acucgguaua guccuuaacc aggacguuac cacacacaug gcaaauauua aucuaaacac 12600
ucuauugcga uugguuggug aucccaccac uauugcaagu gucucagaca aguguguaga 12660
uuuaagaacu ccuugucaga ccuuggcuac uaugucuagc ggaauugcua aacagucagu 12720
caagcccggg cauuuuaauc aacacuucua caagcauuug cuugauagua accuauuaga 12780
ccaacuugga auagacauuc gccacuucua cuauaugcag gauggugaag cggcuaucac 12840
agacuacagc uacuacaggu auaauacccc cacgauggua gauaucaaga uguucuuauu 12900
uugccuugag guggcagaua aguaucuuga gcccuacgaa gguggaugua uuaaugcaca 12960

-continued

```
gucaguugug gucucuaauu uggacaaguc agcgggcuac cccuuuaaca agcuagguaa  13020
ggcucguaac uauuacgaca ugacucaugc cgagcaaaau caacuguuug aguauacaaa  13080
acgcaauguu uugccuacac ucacucagau gaaccuuaag uaugcaauuu cagccaagga  13140
ucgugcucgc acuguggcag gagugucuau aauuagcacc augacuaaca ggcaguacca  13200
ucaaaagaug cugaaaucua uuucacuugc acgcaaucag accaucguga uuggaacaac  13260
caaauucuau gguggguugg acaacauguu acgacgacug auguguaaua ucaacaaucc  13320
cauuuuagug gguugggauu acccuaagug ugaucguucu augccaaaca ugcugcgcau  13380
ugccgcuucg ugcuugcuag cacgaaaaca cacuugcugu aaccaaagcc agcgauucua  13440
ccguuuggcu aaugaauguu gccaaguacu aucugaagug guagucucug guaacaaccu  13500
cuauguaaaa ccagguggca cuagcagugg ugaugcaacc acagcuuaug ccaacucggu  13560
auuuaacauc uuacaggugg uuucugcuaa uguagccacc uucuuaucaa cuuccaccac  13620
gacacaucuu aauaaggaca uugcggacuu gcaucguagu cuuuaugaag auauuuaucg  13680
uggugacucu aaugauauca ccgucaucaa uagauucuac cagcaucucc aaaguuacuu  13740
uggacuuaug auauugucug augauggugu cgcaugcaua gacucagccg uugcaaaggc  13800
uggagcuguu gcugaucuug augguuuccg agacauuuug uuuuaccaaa acaauguuua  13860
cauggcagac ucaaaguguu ggacagaaac ugacaugaau guuggcccuc augaauuuug  13920
cucacagcau acuguguuag cagagcauga ugguaaaccu uacuacuuac cuuacccaga  13980
ugucucucgc auucugggug caugcaucuu uguggaugac guuaacaagg cugacccugu  14040
ucagaaccuu gaacguuaca ucucacuugc aauugaugca uauccccuca ccaagguuga  14100
cccuauuaag gguaaagucu uuuauuuguu acuagacuac auacguguuc uugyucagga  14160
guuacaggac gguauccuug augcuuucca aucacucacu gacaugucgu auguaaauaa  14220
cuuuaugaau gaggccuuuu augcucagau guaugagcaa aguccuacac uacaggccag  14280
cgguguuugu guggugugua auucacccac uauacugcgc uguggugauu gcauucgucg  14340
accacuacuu uguugcgucu gugccuacca gcauguuacg cagacuacac auaaacguau  14400
cauugcuauc aacaacuaca ucuguagugu ugagaauugc aaugaggaca auguugaaaa  14460
acuuuucauu ucuggcacug cgauuuauug ugagaaucac aaacccacgc ugugcauacc  14520
cauuguagcu aaugguucug uuuuugguau cuaucgccac acugcccgug guagugauga  14580
cauagaccuc uuuaacgagc uugcuacauc uaacuaugac acuauugaac cuuaucagaa  14640
ggccaaucgu gcaccuuuau cacuuaugcu cuucgcugcu gaaaccauua aggcacucga  14700
ggagucuauc aagaagucau augcuaccgc aaccgucaag gauguguaug accaacgcuu  14760
cauuaaacuu cuaugggaac aggguaaaaa gccgccaccc auaacgaaga accacauuuu  14820
cacuggcuac cauuuuaaca agaauggaaa aacccaaguu ggugauuaca uucuugcuaa  14880
aacagauggc agugacacuu auacuuacag aggaacaucu accuacaaac uccaaacagg  14940
ugauguucua gucuuaaugg cacauguugu uacaccgcuc ucagcacccc cuguguuaac  15000
gcagacaaca uaugucagaa aaucacuuuu acccgacucu guuggugcgu cuuauuaugu  15060
gcaacauuuu aagucauaua augagauagc uaugcagagg guuacaacag uauuaggucc  15120
accaggcaca gguaagucaa ccuuugcuau ugguuuggcu aaguacuuuc ccagugcacg  15180
uauuugcuac acugcgucuu cgcaugcagc aaucgaugca cucugugaaa aagcuuucaa  15240
gacaauaccu guaggccaau gcagucguau cguacccaca cguacaacug uugagugcuu  15300
```

-continued

```
ucaggaguuu gucguaaaua acacaacugc acaguauauc uucucgacua ucaaugccuu  15360
accugacauu aagugugaca uuguaguugu agaugagguu ucuauguuga ccaauuauga  15420
gcuuuccucu gugaaugcuc guuugguuua caaucacauu guguauguug gugauccuua  15480
ucaguuaccu ucaccuagaa cuaugcuuac gucuggccag cuuucgccag cugacuauaa  15540
cguaguuacu gauauaaugg uacaugcagg agcggauguu augcucgaca ugugcuacag  15600
augcccacgu gaaaucguug agacagugucu uaaacuuguc uacgauaaca aacuaaaagc  15660
ggcgaaaccg aacucaagac aguguuacaa gaccauugug aacuuugguc cuggagacgu  15720
ugcucaugag ggacaaucug ccuacaacga agcacaguug cguuucgcac ucgcauuuag  15780
acaacaaaag cggugggaua acgugacuuu cauaucucca uauaaugcua ugaaugugaa  15840
agcauccuua gcagguuucu cuacucagac cguugacucu ucucaagguu cugaguauga  15900
uuauguuauc uuuugcguga ccacugauuc agcacacgca cuuaacaugg cucguuugaa  15960
cguugcccuu acacgcgcaa agauagguau ccuuguggug uuuaggcagg caaacgaacu  16020
uuacaauagu uugcaguuug aaucuauuga uucacagcuu cagucgagug cugagaaaaa  16080
ccucacacca cuguuuaagc gcugcggcua ugaguauaau ggcguccauc cagcucaugc  16140
uuugaccugg caugauugug gugcagagua ccgcugugag gagccacuug cuaaauuagu  16200
aggaguugcc gauggcacuc uuauaucaua caaaacccua guauccacac uuggguuucu  16260
uccaucacuu aaaauugaug cauaucauaa uauguuccua acacgugacg cgugucgcac  16320
cuauguucag aguuggaucg gcauagaugu ugaagcagca cacgccauaa aaccuaacac  16380
cgggacuaac cugccauugc aaauagguuu uaguaccgga aagaauuuuu cagucacucc  16440
agagggaauu uggguaaacg agcacggauc uugcacugag cccgucccug ccaaaauacc  16500
uccuggagaa caauuucguc accuuaaaaa ggacaugcgc caggcgcguc cuuggaaggu  16560
uguucgacgu gagauugcua cucacauugc ugagguagcu ccucacacug auuauauaug  16620
cuuugucacu ugggcucacc agcuugagcu agcgacaaug cgcuacuuug ucaaacuagg  16680
uauggaagag aaaugcuuuu guggcaggcg ggcuuguuuc acuaauggaa cugaguucgc  16740
uugcaaagca caccauucuc ucaccauucc acaaugugau uauguguaca auccauuccu  16800
caucgacgug gcuacguggg gauucucggg acggcuuucc accaaccaug acgcugugug  16860
cacauaucau gcuaaugccc auguugcauc agcugaugca aucaugacgg uauguuuagc  16920
uauccaugaa cuguucagua cuguugacug gaacuuugaa uuuccaguaa cugcugagca  16980
aucgcaacuu aacaaggccu gucgcuuagu acaggcgaau uacuuaaaua uacuacucac  17040
uacaaccaaa gccacggugg uucacgauau ugguaaccca aaagguaucc cuaucgugcg  17100
caaaccuggu guuaaauauc acuucuauga ucaagcaccc auugucaaac acguucaaaa  17160
acuaaaguac aagccagaga uggaggcccg uuucaccgau gguuugacua uguuuuggaa  17220
uuguaauguu gacacauacc cugcuaacgc ccuugugugc cgcuacgaca cucaucggca  17280
gaagcauuua auuggaccua augguucagc acuauauguu aauaagcaug cuuuucucac  17340
cccugagaug cauacuuaug cuacacauaa acucaacuug gcuccacuca ucuacuacuc  17400
caccacagau uguaguagug aacagccuau uguuguuacc uacagagauu gugucacccg  17460
gugcaauacu ggaaaaacuc ucuguccaaa ucaugcucuu gaauaccaag aguuuaucaa  17520
ugcauacaau cucauggcuc gccauggauu uaauguuuac auaccacgca augucaacgu  17580
uuacaacugu uggcuuacuu ucacuaaucu ccaaaaccuu gaaaacuuag cuuacaacug  17640
uuauuauaag aacugcaaug cucacguuga ugggcagcuu gauguaguua uuaauaauaa  17700
```

-continued

```
cgcuguauau gcuaaggucg acaauaaucu ugucaaacuu uucgacaacc gcacuaacuu  17760
accugucuca guggccuuug aacauuacac uaacaggcau acccguucac ugccaacuac  17820
acagcuguua ucugguuuag gcguaaccgc caccagaaau uucacugugu gguucgacaa  17880
ugauacaauu uuccaauaca cuauuaaugu aucuacguau acugacaucg acccuaguac  17940
ccauguuguc cucugugaug auagguacgg aacagauugg agucaguuua accaacuucc  18000
uaaugcagua uuccucacca aaacuaaggu gaagaaaaca gaaccguuug uuuguacagc  18060
acugacccua aauggcgucg ccauugacgg ugaagagcua uacaucuaug uacgcuauaa  18120
caaucaacug accacauuug cuacuacuug uacacagggu agaaauguug agcaguuuau  18180
accuaaaaca ccuauggaaa gagacuuccu ugagaugucu caacaguccu ucauccagca  18240
acaucaauug caggaacugg guguugaaca cauuaucuau ggugaugauu ccaguccagu  18300
cauuggcgga acucacacac uuaucucacu aguuaaaaac aaguuugaac aucagcuugu  18360
caaccauguu uacaacccag uccagaacug uguuguuacc ucaccuaacg caagcuccaa  18420
gaacguuugc acuguucuug auguucuucu ugaugacuac auugacauca uaagacaagc  18480
acaugccagu uacacaagua aauccaaagu auucacugug ucaauugaca accaacaaau  18540
uagauucaug cuuuggcaug augagcaagu caagacuugc uacccaaucu uacagucacu  18600
uaccaauggu uaccagaugc caucugugua caaaacauug guuacugacu uacaaccagc  18660
ugacauccu aauuaucauu ccuacacccc ccgggugccu ggaguaguua agaauguuau  18720
caaguaccgc caacuuuuca acuacauagu uaaaaaggau agguuggcag uaccacacaa  18780
uaugaccgua uuacaccuug gagcugcauc ugcacuaggu acagcaccag guucuucagu  18840
cauaaaacaa auguuuccug aaggaacugu ucuuauugac cucgauauaa gagaguucac  18900
uucagaugcu aaccaaauaa uaguuacaga cuacagaacu uacauaccac cacaccacgu  18960
agacgucaua uuuucugacc ucuacuguug ugaugacaua cacuucuuug acaaucuaau  19020
aaggauaguu aaggagaggc ucgcccucgg ugguucuauc uuuguuaaga uaacugaaca  19080
uucauucuca cccgaacucu acucacuugc ggguugguuc gaugauuauc aacuauuuug  19140
cacagcaguc aaugccucgu cuucagaagc auuuuuaugc uguuuuaauu auuuggggcu  19200
ugcuaaggaa aacauuaaug guuuuaacuu acaugcuucc uauauucaau ggcgcaauga  19260
aauagcguug acaccaaccu auucuccuuu agcggacaac ccggcuacgg ccuguaagcu  19320
aaaagcaacg ccuauuaucu cggcucguga guuagagaag aagccuauuc uucgcuaucu  19380
cguugcauca gggcgccuuc uugugaggcc accagaaugc agagagcucu auugauuaug  19440
accuuauuuu gucucguucg agcaaaguuu gcugaugauc uacucgauuu gcucaccuuc  19500
ccgggugcac aucgcuucuu acauaaaccc acgaggaauu ccagcagucu cuacucgcgg  19560
gcuaauaaua auuuugaugu uggcguucuu ccuggcuacc ccacuaagaa cguuaaccuc  19620
uucucaccac uuacuaacuc cacuuugccc auuaauggcc uucaucggag uuaccaacca  19680
cucaugcuga auugucuuac uaaaauaacu aaccacacuc ucagcaugua ucuccuaccu  19740
agugagauac aaacuuauag cugcggcggu gccaugguua aauaccagac acaugaugca  19800
guucguauca uuuuagaccu cacugccacu gaccacaucu cuguugaagu cguuggccaa  19860
cauggugaaa auuauguguu uguuugcagu gagcagucua ccuacaccac ugcauuacac  19920
aaaucuaccu ucuucucacu uaauucugag cuuuauugcu uuacuaauaa caccuacuua  19980
gguauucuuc caccugauuu aacugacuuu acggucuacc guacugguca guucuaugcu  20040
```

-continued aaugguuacc uuuuagguac uuuaccuauu acgguuaacu auguuagguu guaucggggu 20100
cauuugucug ccaauagugc ccacuuugcc cuugcaaacc uaaccgauac acucauaaca 20160
cuuaccaaua cuacuauauc gcaaaucacu uauugugaua agucuguagu ugauucaaua 20220
gcaugccagc gcucuucuca cgaaguggag gaugggguuu acuccaaccc uaaaucugcc 20280
guuagagcua ggcaacguac uauuguuaca cuaccuaagc ucccugagcu ugaaguagug 20340
caguuaaaua uuucugcaca cauggauuuu ggcgaagcca gacuugacag cguuaccauc 20400
aaugguaaca cauccuauug ugucacuaag ccuuacuuca ggcuugaaac uaacuuuaug 20460
uguacagguu gcacuaugaa ucugcgcacu gauaccugua guuuugaccu gucagcagua 20520
aacaauggca ugucauucuc ucaauucugu cuaagcacug aaucuggugc uugugagaug 20580
aaaauuauug uuaccuacgu auggaauuac uugcuaaggc agcguuugua uguuacugcu 20640
guagagggcc agacucacac uggaaccacu ucaguacaug caacagacac uucuagugua 20700
aucacugaug ucugcacuga cuacacuauc uauggagucu cugguacugg cauuauuaag 20760
ccaucagauc ucuuauugca caauggcaua guauucaccu cuccaacagg ugagcuuuau 20820
gcauuuaaaa auauaaccac uggcaaaacc cuucaggucu uaccguguga aaccccuucu 20880
caacugauug ugauaaacaa caccguuguc ggugcuauca cauccaguaa uucaacugaa 20940
aauaauaggu uuacuacuac uauugucaca ccuacuuucu uuuauuccac aaaugccacc 21000
acuuucaacu gcacuaagcc uguuuugucc uauggaccua ucagcgugug uagugauggu 21060
gcaauugugg gaacauccac auuacagaau acucgaccau ccauaguuuc acuauacgau 21120
ggcgaaguug aaauaccauc ugcauuuucu cuuuccguuc agacggagua cuugcaaguu 21180
caagcagagc aaguuauagu ugauuguccu caguauguau gcaauggcaa cagccguugu 21240
cuacaauuac uggcacaaua caccucagcu ugcucuaaga uugaagcagc ucugcauucc 21300
ucugcacagu uggauagcag agagauuaua aauauguuuc aaacaucaac acaguccuug 21360
caguuagcua auauuaccaa cuucaagggu gacuacaauu uuagcagcau acuaaccacc 21420
agaauuggug gcagaucugc uauugaagac cuucuuuuua auaaaguugu uacuaguggc 21480
cuuggcacug uugaucagga cuacaaaucc ugcucuagag acauggccau cgcugacuua 21540
guuuguuccc aguauuacaa uggcaucaug guucuaccug guguuguuga ugcugagaaa 21600
auggcaaugu auacuggcuc ucuuacugga gcuaugguau uuggaggacu gacugccgca 21660
gcggcaauac cauuugccac ggcaguacaa gcucgccuca auuaugucgc acugcaaaca 21720
aauguacuac aagaaaacca gaaaauucuu gcagaaucau uuaaccaagc aguuggcaau 21780
auaucacuug cacuaucuuc uguuaaugau gccauccagc aaacuucuga ggcucuuaac 21840
accguagcua uugcuauuaa aaagauucaa acaguuguua accagcaggg cgaggcauua 21900
ucacaccuga cugcacagcu gucaaacaau uuucaagcaa uuucgacuuc uauucaagac 21960
auuuacaacc gucuugagga aguagaggcu aaccagcaag uugaccgucu caucacagga 22020
cgguuggcug cacuuaaugc auauguuacu caguuacuca aucagauguc ucagauuaga 22080
caaucucgau uguuagcuca gcaaaagauu aaugagugug ucaaaucaca gucguccaga 22140
uacgguuucu guggaaaugg cacacacauc uucucacuua cacagacugc accaaauggc 22200
auauuuuuca ugcaugcagu gcuaguaccc aacaaauuca cacgugucaa cgcuucugcc 22260
ggcauuugug uggauaauac gagaggcuac ucauugcagc cucaacuuau acucuaccag 22320
uuuaauaacu ccuggagagu uacaccuaga aauauguaug aacccagacu gccccggcag 22380
gcugauuuca uacaauuaac ugauugcagc guuacuuuuu acaacaccac cgcugcuaau 22440

-continued cuucccaaua uuaucccuga cauuauagau gucaaucaaa cagucaguga uauuauugac 22500
aauuuaccua cagcaacacc uccucagugg gauguuggua ucuauaacaa cacuauucuc 22560
aaccucaccg uugagauuaa ugaucuacaa gagcggucua aaaaccucuc acagauugca 22620
gaucguuuac aaaauuauau ugacaaucuu aacaauacuc uaguugaccu ugaauggcuc 22680
aacagagugg aaacuuaccu uaaauggccg ugguauauau ggcuugccau ugcccuggcu 22740
cuuauugcau uugugacaau ccucauaaca aucuuucuuu guacugguug uuguggugu 22800
ugcuuugguu guuguggcgg uuguuuuggc cuuuucucua agaagaaaag guauaccgac 22860
gaccaaccaa caccguccuu uaaguuuaag gaaugguagu cgacgacugg gccguuacca 22920
ucccuggaca auauauuauu gcuauacuag uugucaucug cauuggugug gcacuacuuu 22980
uuauuaauac uugcuuagcu uguguuaaau uauuuuacaa gugcuaccua ggggcagcau 23040
aucuuguuag gccuauuaua guguacuacu ccaagccgaa ccccguaccu gaggaugagu 23100
uuguaaaagu acaccaauuu ccuagaaaca cucacuaugu cugacgcaga agaguggcaa 23160
auuauuguuu ucauugcgau cauaugggcg cuuggcguca ucccuccaggg aggcuaugcc 23220
acgcguaauc gugugaucua uguuauuaaa cuuauucugc uuuggcugcu ccaacccuuc 23280
acccuagugg ugaccauuug gaccgcaguc gacagaucau cuaagaagga cgcaguuuuc 23340
auuguguccca uaauuuuugc cguacugacc uucauauccu gggccaagua cugguaugac 23400
ucaauucguu uauuaaugaa aaccagaucu gcaugggcac ucucaccuga gaguagacuc 23460
cuugcaggga uuauggaucc aaugggguaca uggaggugca uucccauuga ccacauggcu 23520
ccaauucuca caccagucgu uaagcauggc aagcucaagc uacaugggca agagcuggcc 23580
aauggcauau cagucagaaa uccgccacag gauaugguga uagugucacc aagugacacc 23640
uuucacuaca cuuuuaagaa accuguggaa ucaaacaacg auccagaauu ugcuguucug 23700
auauaccagg gugaccgcgc uucaaacgcu ggacuucaca ccauaaccac uucaaaggcc 23760
ggugacgcuc gccuguauaa guauauguaa ugugcaacug ccaucugcag cugcgagauu 23820
uauauagauu gugcaauaag cggcacauca gaagagagga uguuccugag cuuauugacc 23880
cucucguuaa aacucgcugu uuugcuuaca gucucguggu ucuugcuaau gcuaauccaa 23940
uugcauuuag cauacuaccu cggaaaauuc uuaucaaugg ugagccuuua cugcuugaau 24000
augguagcau auaugguaaa gacuuuauca uucgaccauc gcuccaaguc auucuugaag 24060
augaauuaaa uuaaaguuuu gacaccaauc uaucauggcu gcaccaguag ucccuacuac 24120
ugacgcgucu ugguuucagg ugcucaaagc ucaaaacaaa aaggcuacuc auccucaguu 24180
ucguggcaau ggaguuccgc uuaacuccgc caucaaaccc guugaaaacc auggcuacug 24240
gcugcguuac accagacaaa agccaggugg uacucccauu ccuccauccu augccuuuua 24300
uuauacuggc acaggucccca gaggaaaucu uaaguauggu gaacucccuc cuaaugauac 24360
cccagcaacc acucguguua cuuggguuaa ggguucggga gcugacacuu cuauuaaacc 24420
ucauguugcc aaacgcaacc ccaacaaucc uaaacaucag cugcuaccuc uccgauuccc 24480
aaccggagau ggcccagcuc aagguuucag aguugacccc uucaacgcua gaggaagacc 24540
ucaggagcgu ggaaguggcc caagaucuca aucuguuaac uccagaggca caggcaauca 24600
gcccaggaaa cgcgaccaau cugcaccagc ugcgguacgu cguaagaccc agcaucaagc 24660
ucccaagcgg acuuuaccca aggguaaaac cauuucucag guauuuggca accggucucg 24720
uacuggugcc aaugucggcu cugcagacac ugagaagacg gguauggcug auccucgcau 24780
cauggcucua gccagacaug ugccuggugu ucaggaaaug cuuuuugcug gccaccuuga 24840
gagcaacuuu caggcggggg caauuacccu uaccuucucc uacucaauca cagucaagga 24900
ggguucuccu gacuaugaga gacuuaagga ugcgcucaau acggucguua accagaccua 24960
ugagccaccu accaaaccaa cuaaggacaa gaagccugac aaacaagacc agucugcuaa 25020
acccaaacag cagaagaaac cuaaaaaggu aacucugcca gcagacaaac aggauuggga 25080
gugggaugau gcuuuugaga uaaagcagga aucagcagcg uagacaucaa ucuaugucug 25140
uuaaacccac ccaacuccac ucaaauaucu cuuugguucc agagagucgu aguguauagc 25200
cagagagcca gucagagggc gcuaucaugc aaacuagggc uggcuacucu agcacagaau 25260
cacaucccga uaaucaacag ugcuagaagg uugauuauac cauuuaauau gccgaggcca 25320
cgcggaguac gaucgagggu acagcauaau cucaacuuuu guugagccac aauuuuaauc 25380
cuaauuggag aaggccaaag gacuguacua cuuuuguggg uguagcaguc gcccaguggg 25440
aaagcgccaa cuagguuaca auugugugg ggacaaauua ggggaaauua aauuggcuua 25500
uagcu 25505

<210> SEQ ID NO 3
<211> LENGTH: 3459
<212> TYPE: DNA
<213> ORGANISM: Artificial Sequence
<220> FEATURE:
<223> OTHER INFORMATION: Deltacorona Virus SPIKE antigen CDS (NSVL) cDNA

<400> SEQUENCE: 3
atgaccttat tttgtctcgt tcgagcaaag tttgctgatg atctactcga tttgctcacc 60
ttcccgggtg cacatcgctt cttacataaa cccacgagga attccagcag tctctactcg 120
cgggctaata ataattttga tgttggcgtt cttcctggct accccactaa gaacgttaac 180
ctcttctcac cacttactaa ctccactttg cccattaatg gccttcatcg gagttaccaa 240
ccactcatgc tgaattgtct tactaaaata actaaccaca ctctcagcat gtatctccta 300
cctagtgaga tacaaactta tagctgcggc ggtgccatgg ttaaatacca gacacatgat 360
gcagttcgta tcattttaga cctcactgcc actgaccaca tctctgttga agtcgttggc 420
caacatggtg aaaattatgt gtttgtttgc agtgagcagt ctacctacac cactgcatta 480
cacaaatcta ccttcttctc acttaattct gagctttatt gctttactaa taacacctac 540
ttaggtattc ttccacctga tttaactgac tttacggtct accgtactgg tcagttctat 600
gctaatggtt accttttagg tactttacct attacggtta actatgttag gttgtatcgg 660
ggtcatttgt ctgccaatag tgcccacttt gcccttgcaa acctaaccga tacactcata 720
acacttacca atactactat atcgcaaatc acttattgtg ataagtctgt agttgattca 780
atagcatgcc agcgctcttc tcacgaagtg gaggatgggt tttactccaa ccctaaatct 840
gccgttagag ctaggcaacg tactattgtt acactaccta agctccctga gcttgaagta 900
gtgcagttaa atatttctgc acacatggat tttggcgaag ccagacttga cagcgttacc 960
atcaatggta acacatccta ttgtgtcact aagccttact tcaggcttga aactaacttt 1020
atgtgtacag gttgcactat gaatctgcgc actgatacct gtagttttga cctgtcagca 1080
gtaaacaatg gcatgtcatt ctctcaattc tgtctaagca ctgaatctgg tgcttgtgag 1140
atgaaaatta ttgttaccta cgtatggaat tacttgctaa ggcagcgttt gtatgttact 1200
gctgtagagg gccagactca cactggaacc acttcagtac atgcaacaga cacttctagt 1260
gtaatcactg atgtctgcac tgactacact atctatggag tctctggtac tggcattatt 1320
aagccatcag atctcttatt gcacaatggc atagtattca cctctccaac aggtgagctt 1380
tatgcattta aaaatataac cactggcaaa acccttcagg tcttaccgtg tgaaacccct 1440
tctcaactga ttgtgataaa caacaccgtt gtcggtgcta tcacatccag taattcaact 1500
gaaaataata ggtttactac tactattgtc acacctactt tcttttattc cacaaatgcc 1560
accactttca actgcactaa gcctgttttg tcctatggac ctatcagcgt gtgtagtgat 1620
ggtgcaattg tgggaacatc cacattacag aatactcgac catccatagt ttcactatac 1680
gatggcgaag ttgaaatacc atctgcattt tctctttccg ttcagacgga gtacttgcaa 1740
gttcaagcag agcaagttat agttgattgt cctcagtatg tatgcaatgg caacagccgt 1800
tgtctacaat tactggcaca atacacctca gcttgctcta agattgaagc agctctgcat 1860
tcctctgcac agttggatag cagagagatt ataaatatgt ttcaaacatc aacacagtcc 1920
ttgcagttag ctaatattac caacttcaag ggtgactaca attttagcag catactaacc 1980
accagaattg gtggcagatc tgctattgaa gaccttcttt ttaataaagt tgttactagt 2040
ggccttggca ctgttgatca ggactacaaa tcctgctcta gagacatggc catcgctgac 2100
ttagtttgtt cccagtatta caatggcatc atggttctac ctggtgttgt tgatgctgag 2160
aaaatggcaa tgtatactgg ctctcttact ggagctatgg tatttggagg actgactgcc 2220
gcagcggcaa taccatttgc cacggcagta caagctcgcc tcaattatgt cgcactgcaa 2280
acaaatgtac tacaagaaaa ccagaaaatt cttgcagaat catttaacca agcagttggc 2340
aatatatcac ttgcactatc ttctgttaat gatgccatcc agcaaacttc tgaggctctt 2400
aacaccgtag ctattgctat taaaaagatt caaacagttg ttaaccagca gggcgaggca 2460
ttatcacacc tgactgcaca gctgtcaaac aattttcaag caatttcgac ttctattcaa 2520
gacatttaca accgtcttga ggaagtagag gctaaccagc aagttgaccg tctcatcaca 2580
ggacggttgg ctgcacttaa tgcatatgtt actcagttac tcaatcagat gtctcagatt 2640
agacaatctc gattgttagc tcagcaaaag attaatgagt gtgtcaaatc acagtcgtcc 2700
agatacggtt tctgtggaaa tggcacacac atcttctcac ttacacagac tgcaccaaat 2760
ggcatatttt tcatgcatgc agtgctagta cccaacaaat tcacacgtgt caacgcttct 2820
gccggcattt gtgtggataa tacgagaggc tactcattgc agcctcaact tatactctac 2880
cagtttaata actcctggag agttacacct agaaatatgt atgaacccag actgccccgg 2940
caggctgatt tcatacaatt aactgattgc agcgttactt tttacaacac caccgctgct 3000
aatcttccca atattatccc tgacattata gatgtcaatc aaacagtcag tgatattatt 3060
gacaatttac ctacagcaac acctcctcag tgggatgttg gtatctataa caacactatt 3120
ctcaacctca ccgttgagat taatgatcta caagagcggt ctaaaaacct ctcacagatt 3180
gcagatcgtt tacaaaatta tattgacaat cttaacaata ctctagttga ccttgaatgg 3240
ctcaacagag tggaaactta ccttaaatgg ccgtggtata tatggcttgc cattgccctg 3300
gctcttattg catttgtgac aatcctcata acaatctttc tttgtactgg ttgttgtggt 3360
ggttgctttg gttgttgtgg cggttgtttt ggccttttct ctaagaagaa aaggtatacc 3420
gacgaccaac caacaccgtc ctttaagttt aaggaatgg 3459

<210> SEQ ID NO 4
<211> LENGTH: 1153
<212> TYPE: PRT
<213> ORGANISM: Porcine Deltacorona Virus

<400> SEQUENCE: 4

Met Thr Leu Phe Cys Leu Val Arg Ala Lys Phe Ala Asp Asp Leu Leu
1               5                   10                  15

Asp Leu Leu Thr Phe Pro Gly Ala His Arg Phe Leu His Lys Pro Thr
            20                  25                  30

Arg Asn Ser Ser Ser Leu Tyr Ser Arg Ala Asn Asn Asn Phe Asp Val
        35                  40                  45

Gly Val Leu Pro Gly Tyr Pro Thr Lys Asn Val Asn Leu Phe Ser Pro
    50                  55                  60

Leu Thr Asn Ser Thr Leu Pro Ile Asn Gly Leu His Arg Ser Tyr Gln
65                  70                  75                  80

Pro Leu Met Leu Asn Cys Leu Thr Lys Ile Thr Asn His Thr Leu Ser
                85                  90                  95

Met Tyr Leu Leu Pro Ser Glu Ile Gln Thr Tyr Ser Cys Gly Gly Ala
            100                 105                 110

Met Val Lys Tyr Gln Thr His Asp Ala Val Arg Ile Ile Leu Asp Leu
        115                 120                 125

Thr Ala Thr Asp His Ile Ser Val Glu Val Val Gly Gln His Gly Glu
    130                 135                 140

Asn Tyr Val Phe Val Cys Ser Glu Gln Ser Thr Tyr Thr Thr Ala Leu
145                 150                 155                 160

His Lys Ser Thr Phe Phe Ser Leu Asn Ser Glu Leu Tyr Cys Phe Thr
                165                 170                 175

Asn Asn Thr Tyr Leu Gly Ile Leu Pro Pro Asp Leu Thr Asp Phe Thr
            180                 185                 190

Val Tyr Arg Thr Gly Gln Phe Tyr Ala Asn Gly Tyr Leu Leu Gly Thr
        195                 200                 205

Leu Pro Ile Thr Val Asn Tyr Val Arg Leu Tyr Arg Gly His Leu Ser
    210                 215                 220

Ala Asn Ser Ala His Phe Ala Leu Ala Asn Leu Thr Asp Thr Leu Ile
225                 230                 235                 240

Thr Leu Thr Asn Thr Thr Ile Ser Gln Ile Thr Tyr Cys Asp Lys Ser
                245                 250                 255

Val Val Asp Ser Ile Ala Cys Gln Arg Ser Ser His Glu Val Glu Asp
            260                 265                 270

Gly Phe Tyr Ser Asn Pro Lys Ser Ala Val Arg Ala Arg Gln Arg Thr
        275                 280                 285

Ile Val Thr Leu Pro Lys Leu Pro Glu Leu Glu Val Val Gln Leu Asn
    290                 295                 300

Ile Ser Ala His Met Asp Phe Gly Glu Ala Arg Leu Asp Ser Val Thr
305                 310                 315                 320

Ile Asn Gly Asn Thr Ser Tyr Cys Val Thr Lys Pro Tyr Phe Arg Leu
                325                 330                 335

Glu Thr Asn Phe Met Cys Thr Gly Cys Thr Met Asn Leu Arg Thr Asp
            340                 345                 350

Thr Cys Ser Phe Asp Leu Ser Ala Val Asn Asn Gly Met Ser Phe Ser
        355                 360                 365

Gln Phe Cys Leu Ser Thr Glu Ser Gly Ala Cys Glu Met Lys Ile Ile
    370                 375                 380

Val Thr Tyr Val Trp Asn Tyr Leu Leu Arg Gln Arg Leu Tyr Val Thr
385                 390                 395                 400

Ala Val Glu Gly Gln Thr His Thr Gly Thr Thr Ser Val His Ala Thr
                405                 410                 415

```
Asp Thr Ser Ser Val Ile Thr Asp Val Cys Thr Asp Tyr Thr Ile Tyr
            420                 425                 430

Gly Val Ser Gly Thr Gly Ile Ile Lys Pro Ser Asp Leu Leu Leu His
        435                 440                 445

Asn Gly Ile Val Phe Thr Ser Pro Thr Gly Glu Leu Tyr Ala Phe Lys
    450                 455                 460

Asn Ile Thr Thr Gly Lys Thr Leu Gln Val Leu Pro Cys Glu Thr Pro
465                 470                 475                 480

Ser Gln Leu Ile Val Ile Asn Asn Thr Val Val Gly Ala Ile Thr Ser
                485                 490                 495

Ser Asn Ser Thr Glu Asn Asn Arg Phe Thr Thr Thr Ile Val Thr Pro
            500                 505                 510

Thr Phe Phe Tyr Ser Thr Asn Ala Thr Thr Phe Asn Cys Thr Lys Pro
        515                 520                 525

Val Leu Ser Tyr Gly Pro Ile Ser Val Cys Ser Asp Gly Ala Ile Val
    530                 535                 540

Gly Thr Ser Thr Leu Gln Asn Thr Arg Pro Ser Ile Val Ser Leu Tyr
545                 550                 555                 560

Asp Gly Glu Val Glu Ile Pro Ser Ala Phe Ser Leu Ser Val Gln Thr
                565                 570                 575

Glu Tyr Leu Gln Val Gln Ala Glu Gln Val Ile Val Asp Cys Pro Gln
            580                 585                 590

Tyr Val Cys Asn Gly Asn Ser Arg Cys Leu Gln Leu Leu Ala Gln Tyr
        595                 600                 605

Thr Ser Ala Cys Ser Lys Ile Glu Ala Ala Leu His Ser Ser Ala Gln
    610                 615                 620

Leu Asp Ser Arg Glu Ile Ile Asn Met Phe Gln Thr Ser Thr Gln Ser
625                 630                 635                 640

Leu Gln Leu Ala Asn Ile Thr Asn Phe Lys Gly Asp Tyr Asn Phe Ser
                645                 650                 655

Ser Ile Leu Thr Thr Arg Ile Gly Gly Arg Ser Ala Ile Glu Asp Leu
            660                 665                 670

Leu Phe Asn Lys Val Val Thr Ser Gly Leu Gly Thr Val Asp Gln Asp
        675                 680                 685

Tyr Lys Ser Cys Ser Arg Asp Met Ala Ile Ala Asp Leu Val Cys Ser
    690                 695                 700

Gln Tyr Tyr Asn Gly Ile Met Val Leu Pro Gly Val Val Asp Ala Glu
705                 710                 715                 720

Lys Met Ala Met Tyr Thr Gly Ser Leu Thr Gly Ala Met Val Phe Gly
                725                 730                 735

Gly Leu Thr Ala Ala Ala Ala Ile Pro Phe Ala Thr Ala Val Gln Ala
            740                 745                 750

Arg Leu Asn Tyr Val Ala Leu Gln Thr Asn Val Leu Gln Glu Asn Gln
        755                 760                 765

Lys Ile Leu Ala Glu Ser Phe Asn Gln Ala Val Gly Asn Ile Ser Leu
    770                 775                 780

Ala Leu Ser Ser Val Asn Asp Ala Ile Gln Gln Thr Ser Glu Ala Leu
785                 790                 795                 800

Asn Thr Val Ala Ile Ala Ile Lys Lys Ile Gln Thr Val Val Asn Gln
                805                 810                 815

Gln Gly Glu Ala Leu Ser His Leu Thr Ala Gln Leu Ser Asn Asn Phe
            820                 825                 830
```

-continued

```
Gln Ala Ile Ser Thr Ser Ile Gln Asp Ile Tyr Asn Arg Leu Glu Glu
        835                 840                 845

Val Glu Ala Asn Gln Gln Val Asp Arg Leu Ile Thr Gly Arg Leu Ala
    850                 855                 860

Ala Leu Asn Ala Tyr Val Thr Gln Leu Leu Asn Gln Met Ser Gln Ile
865                 870                 875                 880

Arg Gln Ser Arg Leu Leu Ala Gln Gln Lys Ile Asn Glu Cys Val Lys
                885                 890                 895

Ser Gln Ser Ser Arg Tyr Gly Phe Cys Gly Asn Gly Thr His Ile Phe
            900                 905                 910

Ser Leu Thr Gln Thr Ala Pro Asn Gly Ile Phe Phe Met His Ala Val
        915                 920                 925

Leu Val Pro Asn Lys Phe Thr Arg Val Asn Ala Ser Ala Gly Ile Cys
    930                 935                 940

Val Asp Asn Thr Arg Gly Tyr Ser Leu Gln Pro Gln Leu Ile Leu Tyr
945                 950                 955                 960

Gln Phe Asn Asn Ser Trp Arg Val Thr Pro Arg Asn Met Tyr Glu Pro
                965                 970                 975

Arg Leu Pro Arg Gln Ala Asp Phe Ile Gln Leu Thr Asp Cys Ser Val
            980                 985                 990

Thr Phe Tyr Asn Thr Thr Ala Ala  Asn Leu Pro Asn Ile  Ile Pro Asp
        995                 1000                1005

Ile Ile  Asp Val Asn Gln Thr  Val Ser Asp Ile Ile  Asp Asn Leu
    1010                1015                1020

Pro Thr  Ala Thr Pro Pro Gln  Trp Asp Val Gly Ile  Tyr Asn Asn
    1025                1030                1035

Thr Ile  Leu Asn Leu Thr Val  Glu Ile Asn Asp Leu  Gln Glu Arg
    1040                1045                1050

Ser Lys  Asn Leu Ser Gln Ile  Ala Asp Arg Leu Gln  Asn Tyr Ile
    1055                1060                1065

Asp Asn  Leu Asn Asn Thr Leu  Val Asp Leu Glu Trp  Leu Asn Arg
    1070                1075                1080

Val Glu  Thr Tyr Leu Lys Trp  Pro Trp Tyr Ile Trp  Leu Ala Ile
    1085                1090                1095

Ala Leu  Ala Leu Ile Ala Phe  Val Thr Ile Leu Ile  Thr Ile Phe
    1100                1105                1110

Leu Cys  Thr Gly Cys Cys Gly  Gly Cys Phe Gly Cys  Cys Gly Gly
    1115                1120                1125

Cys Phe  Gly Leu Phe Ser Lys  Lys Lys Arg Tyr Thr  Asp Asp Gln
    1130                1135                1140

Pro Thr  Pro Ser Phe Lys Phe  Lys Glu Trp
    1145                1150


<210> SEQ ID NO 5
<211> LENGTH: 25426
<212> TYPE: DNA
<213> ORGANISM: Artificial Sequence
<220> FEATURE:
<223> OTHER INFORMATION: Porcine Deltacorona Virus BIVI-Isolate 2.0307
      Genome cDNA

<400> SEQUENCE: 5

gattggtgtc ggtagagaac tagcgaagct agggagataa aattatagac taatgctata     60

atttttatct ttagtctata attttatctc cctagcttcg ctagttctct accgacacca    120

atccaggtgc gtctgccacc aagttggcta cccttcctag ggcgctttc gcgcttgctc    180
```

-continued

```
accattagat tacctggaaa ccagccattc aggttggagt ttccccaggc tcttttgtgt    240
gggcattagc ggcttgtggt ttttgcacaa aatctaagct acttaccgtt cctctgacca    300
tccaccactt ctatagacag cactgattac cgtagggttt aagtcacacc ggtctgcacc    360
gcccgtcagc ggacacatta cccagcatag cactccttgc accgagccta ggtaggataa    420
aaccccctac cgggtgactc ttaaggcgtt tcctccacgg gatagccact agtcactagg    480
tgtaagtgat ctgatctggg cgtattgtgt tgcgcaagtg tgatacccat aggagcgtgg    540
aatcctattc tgcggctcag tgcctgatat agctgtgaaa tggccaagaa caagtccaag    600
cgcgacgcta ttgcgttgcc tgaaaatgta ccaccacctc tgcaactttt cattcatgtt    660
gcagctgctg aagagggtca ccctaaggtt actacttacc ttggcaacta taacctctat    720
gccaccaagg ctccgcctgg cgtgcaggtt cttagtgcta aaacctctct tactgacttt    780
gagaatgtct ttggagctca acccaccttg cgatcaattc gtaatctggt ttgtgaggct    840
cgctcggctg aatggacaac ttccaagaat gcttttgcac tcaaagccac tcaacttgac    900
tactctgatg ccgttttgag ggcaatgatt cgtttctgcc ctccaaaggt gtccacactc    960
gctgcctttg ctctttttgg ccgattggtt aaaattgagg acaaggaact tgctgagtta   1020
gctcgtgata ctgcccttga gttggcgtac acggctaaaa ttggtacatc tcttgctgac   1080
acgagatctg tctcacttat tcataaggac gcttatctaa ctctcagtaa tgaggttgtt   1140
ggcgtaactt ttactgccgc acttatggca aaggctacca ctgttaatgg agcaatgcaa   1200
tactcaaact tttacctcta ccctcgtgcc actattaagg taaccgatgg taaggctgaa   1260
gcaattgcaa ctaagcctct gtctgctgcc actaaaggca agcaaatcac agaggatgtc   1320
aacctcctcc ctgactatca gcagctgctt gttgatcaag tgactggcac tgaggttaag   1380
gttggagctc taacctatgt taagaccact gattcgccac ccctttactt tcccaaagtc   1440
aagggtggtg ttattggtat tgcacttaag cagcagggca ctgcggctaa gaagctcaat   1500
gtagtcttcc atgctcaacc tgatgatgtt ctgctagcct tcatacaact tcagcaattc   1560
ttgaaccgta cttcggattc aagtgttgaa attactgatt gccagagtta tgaagtatct   1620
ccaactgtga cggtcaaaat tggcccgtct aaacctgggg atgtcatcgt ggctactgat   1680
gaggaatacc ttaaatgctt tgaaacccct gaggtaggta ggctctataa ggttttccaa   1740
actcaatctt gggctatcat tgagcgtgcc ttctccagtt tgaagatccg cgtgtccaaa   1800
gctttatcag catttataag ttttctgcaa aaccttgcag ataactttac tgcaataagt   1860
ggtgttgtca ctgcactcat tcgtgaactc caggatctta ccctggatgt ggcgacacgt   1920
atcactaaca tacaatttgt ttaccgtgcc ggtaagctta ttgtcgacac gacaagtgtc   1980
atagctaaac ttttccagcc attttgtgat tttatatcac ctttccttcg gaaagttgct   2040
ggttttgcaa tttacactgt tggtaatcgc atgcttatgt ttaccagcac tggcaccttt   2100
cttctcacaa aggcaactac taagatactc aataaggcaa agtacatctt tgatgtggag   2160
cctgagtacc cagtagatgt aacaacatcc aaagttgtag tacatgaagc actccagcaa   2220
accgacacta agcctactag agctctggag gctgttgatg tcgttgttgg taatactgta   2280
ctgcaaatgg ctactgatgg cactgcgttc tacccatcgg atggtacgca cgcctctctt   2340
ccaggattca aagcaggttc ggatgagctt ttcataagct tcaactgcga cctctttgat   2400
gatgagacta atgctcaaat caacgaaaca ctcgctgcat atgagcttaa ccaactagtg   2460
gctccaggtg attctacacc gcgtcaaatt gcgacgttgg ttgtcgatac acttgcagat   2520
```

-continued

```
gctataacag accactttcc ggagaaaacc attgatctac ctgaagacta tcaagtcttt   2580
tctgaccatg atgacctccc actcgcacaa taccacatcc ctgatcacct gagcctgtat   2640
attcaggcta tggaaggtga agatgatagt ggtgatgaaa tatgtattga ggacgatgat   2700
tacgactgtc ctcaagccga cgaagacaca gaaggagtaa ttccccaaca gtgggaactt   2760
cctgatgttg ataaattttt actcaagatc caggaacgga agaccagcag cgacgaagta   2820
cttagcgtcg acgtctatcc taaaccagag ccggtcggca atgttgggat tgacgacagc   2880
gcgtcggaaa agaagccaaa tggggactca gtaccggatc ctgaggtcca tccaacacta   2940
gagagtgtgg atgttgaacg accaaccgaa acagcaaacc aggctgttga agacaaacct   3000
tctgatacca cctttgtggt tgatgaggaa caattacaag aatcaacacc agaacatgaa   3060
ctccgctcct atgaaggga gtttgattct gatgatgaaa ttattattcc tatagtacca   3120
gtaacacctg cggatttaaa accacagact attactataa aggagtactt taagtctgaa   3180
aaacttgaga ctattaacga aggatccaca gagtcagtta cacaatctga cgattcgttt   3240
gacgagtcat ttgttgatgc tgagtctgat gatccacaag atcctgctgt atatgatgat   3300
acaacaatta taacggacag cactgatgta ggcgatgagc ctgagacaac tctagctacc   3360
atcgttaaca cacctctgac actcgataat aacttgccac ctgaagccat taaacaaccc   3420
agcccaacta aggttgagtt agttgttggt gaattggcga gtattaaatt tgacaattct   3480
gttctagtca accctgctaa tgcgcaatta acaaatggcg gtggagctgc tcgtgcaatt   3540
gcaaaattag ctggtccaaa atatcaagag tactgtaata gtgtggctcc tatctcagga   3600
ccgcttacca cggactcttt tgatgccaag aaatttggtg tagcctgcat cttgcatgta   3660
gtgccaccca aaggttctga ccctaatgta caagaactcc tgtatcaagc ttacaagagt   3720
atccttactg aaccagcaca ctatgttata cctatactag gtgctggtat ctttggatgc   3780
aatccagtcc actctctgga tgcgttcagg aaagcatgtc caagtgacat aggtcgtgtc   3840
acccttgtca ctatgaacaa aaaccatttg caggtgtggg atgctctcaa taggaccatt   3900
gtacgcacca ctactgacta tgatcaagtt accaccaagg cccttacacc ccagggagtg   3960
ttagaagcca atctctttga tggtgaggac tttgttcaag aaccaaaacc cggtcaaatc   4020
taccttgagg ttactgaaga agttcagaac caagccaagg aacttgacct taaccttcag   4080
caatactgcg tctacctgaa gacttgccac cataaatggg ttgtgagtcg tacgaacggg   4140
ttgatgcatc taaaacaaaa agataacaat tgttttgtta gtgcaggtgt aaacctgttt   4200
caaaacactg cttatcaact tagacctgct attgatgctc tctataggga gtatcttaat   4260
ggtaatccaa atagatttgt tgcttggatc tacgcatcca ctaaccgtcg tgttggtgag   4320
atgggttgtc cacagcaagt tatttctttg ctcgttagta actctgacgc agcattttca   4380
gcaactacag cctgttgtaa cacctacttt aaccacacag gtgttatttc agtagctcgt   4440
gaatatgacc caatacaacc aaaggtctac tgcatgaagt gtgatgtgtg gactcccttt   4500
acaccccaga gtggaaaagg tgcagttgca attggtattt ctgcagatga acctaccggt   4560
cctgccatta aatttgccgc agctcactgc tggtacacta atggcaagaa aacagttaat   4620
ggctatgaca ctaaagctaa tgttgtagct acctatcata ggtttgacgt gcctaagcct   4680
caacttgtcg aggacgtggt tgcgctgcct actaaaaatg actttgaagt tctcaatgtt   4740
gaagaactgc cgcaggatag tgtgctccat ttggacccac ctcctgtaca ggccttacaa   4800
cctaaggcta accaacacat tgagattcta gaaaacccag attatctgga cattttggat   4860
ctttggattc gtaaacccaa attcatcctc gtaaagtcgt ggagtgtttt gggtagagca   4920
```

ctatgtaagg caggtaaagt tgtctttgtc agtgcttcgc ttttgacccg tttctacaat 4980
taccttgtag agattggtgc tcttgactca acaataaggt tgtcagtcga tcttacctgt 5040
aaatttgtta gaacggttct cccatcgtct aacactgtac acaaaacttg tcttggtctg 5100
tattattcag cccagacact ttttgtttct ttagcaccat tccttatgtt accagctgta 5160
gttagtctgc ttaattcagg ctatacaatt ggcacatatt tgtatgcaaa aactggctgg 5220
ccttgtaatt acaatgccac gcaacacttt gattataatt cttactgtgc aggtgacttg 5280
gtttgtcaag cctgttttga cggtcaagac tccctacatt tgtatccgca tttacgtgtt 5340
aatcagcagc cccttcagac cactgactac actgtttatg cgctttcact aatactacta 5400
ttagctaaca tgactcttgt catgggcacg ctaatagtta ctttctttgt gaacttctat 5460
ggtgtgcaaa taccatttta tggtacactt ttgatagatt atcaatccgc actggtgatt 5520
actttctcag tgtactactt ttataaggta atgaagtttt tccgccatct cacacatgga 5580
tgtaaaattc caacgtgtgt ggtatgtgcc aaacttcgta ccccacctac tataacagtt 5640
gagactgtcg ttcagggcag gaaataccca tctgttattg aaacaaatgg cgggtttaca 5700
atttgtaaag aacacaactt ctattgcaag gactgctctt tacaaacacc cggcactttc 5760
atcccgacag aagctattga gtcgctctca cgagctacca ggcttagtgt caaaccaaca 5820
gcaccagcat tcttacttgc tagagatgtt gagtgccaaa ctgatgttgt cgttgctcgc 5880
gcaatgcata accaaaatgc gcatgtgtgc atttcaaaat actctgatat ccgtaccgtt 5940
gaccaactac ttaagcctac tccactgttt tcatacactc ccgatgttat catcgcggca 6000
gactttgaca acagaggtag tcttaagaca gctaaagaat tagctgtggt tttgtcaatg 6060
gaccttaaac gtactataat tatcattgat caggcctatt ctagacctat tgataattat 6120
caggaagttg cttctcgtat tgagaagtat tacccagttg caaagatcac acccacaggt 6180
gacatcttta cagacattaa gcaagcgacc aatggccaag ctagtgactc tgctattaat 6240
gcagctgttc tggctgtcca gcgcggtctt gattttacaa ttgacaaccc taacaacata 6300
ttaccacatt acgcctttga cttttcgacc ctcaatgcag aagaccagtc taccattttg 6360
gagagtggtt gtgctaaagg caatctcaag ggcactaatg ttggtgttgt tctttcagct 6420
agccttgtta cacgtcttag tcagcaggct atacgtgtga ttgctaatgc tgcttcacgt 6480
aatggtgtta catgcgctgt tactccttct acacttgtta tgcgtgggaa tattgcaaca 6540
cagcccttga ctcgcatcaa agctggtgca cctcccatgc gtcaaaaaat tttatgtgtt 6600
atcctggcac ttgctattgt gtactttgct gctatggctt ttggcttttt ggcaagtcaa 6660
attacgctta atacagtgcc tacgattaaa tctgatatcc gcgcctctac cttctacgtt 6720
gttagagatg gagtcttgga tactgttcgt tcaaatgaca agtgctttgc aaataagttt 6780
ttggcatttg atagcttcat tcaagcacct tacactaatt cacctgactg tccagttgtt 6840
gtgggagttg ttgatgtaac gacgcactct attcctggaa ttccagcagg tgtcattcat 6900
agagacggtc tcatacttaa catttatgaa cagtctcttt atgaaactca tcagcgtcag 6960
tctatggtta gggatgcgtt gtcactcaag acagcaaatc tctttaacct aggcaagcgt 7020
gttgtagtag gatacactca acatgaagtt gttgtgggta cctcctattt taattctcct 7080 gcactttttta atgcaaagtg caccttctta cagtatcagg acactagaca actctattgc 7140
tatgatactg ttcctactga acataagctc tactctgatg tgcttccgca cgtcgagtat 7200
aaggctattg acattaatgg tgatcttgtt cctttcaaga taccagagca gataatgttc 7260

-continued

```
tatccacata ttgtgcgcta tactagcaat tcctattgcc gtatggggca ttgttttaat   7320
actaaccctg gtatttgcat ttcatttacg gacgaatttc cgtatagtga aaatgtcaaa   7380
cctggtgtgt actgtgctga tacctctttg cagttgtttt caaacctcgt tttgggcact   7440
gtatctggta ttcacatctt tacatcaaca gctgcattgc ttggatctac tattgtgatc   7500
atactatgcg ttgttgctgt tcttgcagtt cagcgattct tcaaggagta cacaactttt   7560
gttatgtaca cttgtggtct tgctcttgtc aacattgtag gcattgcact tatgtacaag   7620
tgccttgtct tcgcgatttt ctattatgca atctaccttt actttgtcct tactttcccc   7680
tcctttaaga ggaatgtggc attgttttac ttcgctgtag tgatcgtgcc gcacgtgagt   7740
aacatgcaat tgcttgcgct cattgtgtgt agcattatct actttctcta cacctatgtt   7800
catactgtag ctaagacagc tgggaaattt tcttccttct tagacgcagc taaagctact   7860
tttgtcattg acaatgaaaa gtacgtgttg cttaaagacc tcgctggtgc tgaatttgac   7920
cagtatctgg cctcttacaa caagtacaaa tatttttctg gtactgcttc tgataaggat   7980
tatgataagg tctgtatggc atttcttgcc aaggctttgt catcttttcg tgaaggaggc   8040
ggttcacagt tgtacacacc acctaaattt gcagttgttc agagtcttaa gaccaagctg   8100
caagcaggta tcaaaatcct cctgcaccct tcaggtgtag ttgagcgatg tatggtctca   8160
gttgtctaca atggatctgc attgaatggc atctggctta agaatgttgt ctactgccca   8220
cgccatgtaa ttggaaaatt ccgtggtgac cagtggactc acatggtctc aattgctgat   8280
tgccgcgact ttatagtcaa gtgtccaata cagggtattc agctaaatgt ccaatcagtt   8340
aagatggtag gagctctcct ccagttaact gttcatacca acaacacagc cactccagac   8400
tataagtttg aaaggctcca accaggatca tcgatgacaa ttgcttgtgc ttatgatggc   8460
attgtacggc atgtctatca cgtggtcctc caacttaata atcttattta tgcaagcttc   8520
cttaacggag cttgtggtag tgtgggttac actcttaagg gtaaaacact ctacttacat   8580
tacatgcacc acattgagtt taacaacaaa actcatagtg gtacagatct tgaaggtaac   8640
ttctatggcc cctatgtgga tgaggaagtt attcagcaac aaacagcatt ccagtattac   8700
actgataatg ttgttgctca attatatgca cacttactga ctgttgatgc tagaccaaaa   8760
tggctggcac aatctcagat aagtatcgag gatttcaact catgggctgc taacaattcc   8820
tttgctaact tcccatgtga acaaactaat atgtcctaca ttatgggact ctcgcaaaca   8880
gctcgagtcc ctgtagaacg tatcctcaat accattatac agctaaccac caatagagat   8940
ggtgcttgta ttatgggatc ttatgatttc gagtgcgatt ggacgccaga gatggtatac   9000
aatcaggctc caatttcatt gcagtcagga gtagttaaga aaacttgtac gtggttcttc   9060
cacttcttgt ttatggctat taccatgcta ctcgctgcca tgcatgtttt ccctgtacac   9120
ttgtatccaa tagtactgcc atgcttcact gtcgtggcat tcctgttgac tttaaccatt   9180
aaacacactg ttgtgtttac cactacatac ttgcttccgt cacttttgat gatggttgta   9240
aatgctaaca ctttttggat accgaacaca tttctgcgca cctgctacga aactatattc   9300
ggttccccaa ttgctcagcg actgtatggt tacactgttg ctctttatat gctgatctat   9360
gctggacttg caatcaacta tacgttgaaa acactccggt atagagcaac ttcattctta   9420
tctttttgca tgcagtggtt tcaatatggt tatgttgcac acattgcgta caaactgctt   9480
aataaaccct ggacagaatc actactcttc acagccttca caatgctaac cagtcatcct   9540
ttgttggctg ctcttagctg gtggctagct ggtcgcgtaa ctctgcccat tatcatgcct   9600
gacttagcta ttcgtgtttt ggcgtataac gtcattggct atgtcatatg tgttcgattt   9660
```

```
ggccttatgt ggcttgcaaa tcggttcaca actgtaccta tgggcacata ccagtatatg   9720
gtgtctgtag agcaacttaa gtacatgatg gcagttaaga tgtccccacc gcgtaatgcg   9780
tttgaggtgc ttatagccaa cattagactt cttggtttgg gtggaaaccg taacattgct   9840
gtttctactg tccaaaacaa aattcttgat gcaaaagcta ctgctgttgt tgttgctaac   9900
cttcttgaaa aggctggcgt cacaaacaag cacgctattt gcaaaaagat tgtgaaactc   9960
cacaatgata cccttaaagc caccacttat gaggaggttg aggtagcact tgtgaaactt  10020
ctttctcaca taattgagtt cttgccaact gatcaggtag atgcttatct agctgatgcg  10080
gccaatgctc aacatgttaa tacctatttt gacaacttgc ttgagaacaa agctgttgtt  10140
caggctgttg ccgatatcaa cattaatctg gattcttata gaatttataa ggaggcagat  10200
gctatttata aacgatctgt tgagatgaac gaatctccgc aggagcaaaa gaaaaagctt  10260
aaagctgtta acattgcaaa ggcggaatgg gagcgtgagg ctgcttctca gcgtaagctt  10320
gaaaagcttg ctgatgctgc tatgaagtct atgtatcttg cagaacgtgc tgaggatcgt  10380
cgcattaagc taacctctgg acttactgca atgctttacc atatgcttag acgtcttgac  10440
tcagataggg taaaagctct gtttgagtgc gctaaggcac aaatcttgcc aatacatgct  10500
gtagtcggaa tttctaatga caaccttaaa gttattttta acgataagga cagctactct  10560
cattatgtag agggcaacac acttatacat aagggagttc gctacactat tgtgaagaaa  10620
ctctccttag ataatgcacc tattgaaggc gtaccagaag aattccctgt ggtcgttgag  10680
actgttaggg aaggtgtgcc ccagttgcaa aataatgagc tatgtttgcg caatgttttc  10740
actgctcaga acacagctca ggacttcaat ggcaatgaat ccactgtaaa atctttttat  10800
gttactagaa ccggtaagaa gattttggtt gccattacat caactaaaga caatcttaag  10860
actgtgacct gccttactga gaccggtaag acagtcctta acttggaccc ccctatgcgc  10920
ttcgcacata ccgtaggtgg aaaacagtct gttgtctatc tctattttat tcagaatatt  10980
agttcactca acagaggtat ggttattggc cacatctctg aaactactat ccttcaggca  11040
agtggcactc aaattgagta ccagcaaaat gcctctcttt tgacctattt ggctttcgct  11100
gtagacccta agacagccta ccttaagcat cttgctgatg gtgggtctcc tatacagggt  11160
tgtattcaga tgattgctac tatgggtcct ggatttgcag ttactactaa accacaacct  11220
aatgagcatc agtattctta tggtggtgct tcaatttgtc tttattgccg tgctcatata  11280
ccacatcctg gtgttgatgg acggtgcccc tacaaaggcc gctttgttca catcgacaaa  11340
gataaggaac ctgtttcctt cgccttgact catgagccat gcagttcttg tcaacggtgg  11400
gttaattatg actgcacctg cggatctagt ctgcagaatt cggcttattt aaacgagtaa  11460
cgggttctag tgacgcccgg ctagaacccc tgcagcctgg aactcaacca gatgctgtaa  11520
aaagggcctt ccatgtgcat aatgatacca cctctggtat attcttaagc acaaaatcta  11580
actgcgctcg gtttaaaacc acacgcagtg ccctgccttt acctaataag ggagaggttg  11640
aattgtactt tgttactaag cagtgtgcag ctaaagtctt cgaaatcgag gaggaatgct  11700
acaacgctct tagtacagag ctttatacta ctgatgatac atttggtgtc cttgccaaaa  11760
ctgagttctt taagtttgac aagataccta atgtcaatcg ccagtatctg actaaatata  11820
cactcctgga cttggcttat gctctacgtc atttgtcaac atctaaggat gttattcaag  11880
aaatcttgat caccatgtgc ggaacccctg aagattggtt tggggaaaat tggtttgatc  11940
caattgagaa cccatccttt tacaaggagt tccataaact tggggatatt cttaaccgtt  12000
```

-continued gtgttcttaa tgccaataag tttgctagtg cctgtataga cgctggtctt gttggcatat 12060
taacacccga caaccaagac ctcctgggtc agatctatga ctttggagat tttattatta 12120
cacaaccagg taatggatgt gtggacttag catcctatta ttcttattta atgcccatta 12180
tgtccatgac tcacatgtta aagtgtgagt gtatggatag tgatggcaac ccacttgagt 12240
atgatggatt tcagtatgac ttcacggact tcaagcttgg cttgttcgag aagtatttta 12300
agtactggga ccgtccttac catcctaaca ctgttgaatg tccagatgac cgttgcgtat 12360
tgcactgtgc gaacttcaat gtgttgtttg ctatgtgtat acctaatacg gcatttggca 12420
atctttgttc aagagctact gttgatggcc accttgtggt ccagacagtg ggtgtacact 12480
tgaaagaact cggtatagtc cttaaccagg acgttaccac acacatggca aatattaatc 12540
taaacactct attgcgattg gttggtgatc ccaccactat tgcaagtgtc tcagacaagt 12600
gtgtagattt aagaactcct tgtcagacct tggctactat gtctagcgga attgctaaac 12660
agtcagtcaa gcccgggcat tttaatcaac acttctacaa gcatttgctt gatagtaacc 12720
tattagacca acttggaata gacattcgcc acttctacta tatgcaggat ggtgaagcgg 12780
ctatcacaga ctacagctac tacaggtata ataccccccac gatggtagat atcaagatgt 12840
tcttattttg ccttgaggtg gcagataagt atcttgagcc ctacgaaggt ggatgtatta 12900
atgcacagtc agttgtggtc tctaatttgg acaagtcagc gggctacccc tttaacaagc 12960
taggtaaggc tcgtaactat tacgacatga ctcatgccga gcaaaatcaa ctgtttgagt 13020
atacaaaacg caatgttttg cctacactca ctcagatgaa ccttaagtat gcaatttcag 13080
ccaaggatcg tgctcgcact gtggcaggag tgtctataat tagcaccatg actaacaggc 13140
agtaccatca aaagatgctg aaatctattt cacttgcacg caatcagacc atcgtgattg 13200
gaacaaccaa attctatggt ggttgggaca acatgttacg acgactgatg tgtaatatca 13260
acaatcccat tttagtgggt tgggattacc ctaagtgtga tcgttctatg ccaaacatgc 13320
tgcgcattgc cgcttcgtgc ttgctagcac gaaaacacac ttgctgtaac caaagccagc 13380
gattctaccg tttggctaat gaatgttgcc aagtactatc tgaagtggta gtctctggta 13440
acaacctcta tgtaaaacca ggtggcacta gcagtggtga tgcaaccaca gcttatgcca 13500
attcggtatt taacatctta caggtggttt ctgctaatgt agccaccttc ttatcaactt 13560
ccaccacgac acatcttaat aaggacattg cggacttgca tcatagtctt tatgaagata 13620
tttatcgtgg tgactctaat gatatcactg tcatcaatag attctaccag catctccaaa 13680
gttactttgg acttatgata ttgtctgatg atggtgtcgc atgcatagac tcagccgttg 13740
caaaggctgg agctgttgct gatcttgatg gtttccgaga cattttgttt taccaaaaca 13800
atgtttacat ggcagactca aagtgttgga cagaaactga catgaatgtt ggccctcatg 13860
aattttgctc acagcatact gtgttagcag agcatgatgg taaaccttac tacttacctt 13920
acccagatgt ctctcgcatt ctgggtgcat gcatctttgt ggatgacgtt aacaaggctg 13980
accctgttca gaaccttgaa cgttacatct cacttgcaat tgatgcatat cccctcacca 14040
aggttgaccc tattaagggt aaagtctttt atttgttact agactacata cgtgttcttg 14100
ctcaggagtt acaggatggt atccttgatg ctttccaatc actcactgac atgtcgtatg 14160
taaataactt tatgaatgag gccttttatg ctcagatgta tgagcaaagt cctacactac 14220
aggccagcgg tgtttgtgtg gtgtgtaatt cacccactat actgcgctgt ggtgattgca 14280
ttcgtcgacc actactttgt tgcgtctgtg cctaccagca tgttacgcag actacacata 14340
aacgtatcat tgctatcaac aactacatct gtagtgttga gaattgcaat gaggacaatg 14400

```
ttgaaaaact tttcatttct ggcactgcga tttattgtga gaatcacaaa cctacgctgt  14460
gcatacccat tgtagctaac ggttctgttt ttggtatcta tcgccacact gcccgtggta  14520
gtgatgacat agacctcttt aacgagcttg ctacatctaa ctatgacact attgaacctt  14580
atcagaaggc caatcgtgca cctttatcac ttatgctctt cgctgctgaa accattaagg  14640
cactcgagga gtctatcaag aagtcatatg ctaccgcaac cgtcaaggat gtgtatgacc  14700
aacgcttcat taaacttcta tgggaacagg gtaaaaagcc gccacccata acgaagaacc  14760
acattttcac tggctaccat tttaacaaga atggaaaaac ccaagttggt gattacattc  14820
ttgctaaaac agatggcagt gacacttata cttacagagg aacatctacc tacaaactcc  14880
aaacaggtga tgttctagtc ttaatggcac atgttgttac accgctctca gcaccccctg  14940
tgctaacgca gacaacatat gtcagaaaat cacttttacc cgactctgtt ggtgcgtctt  15000
attatgtgca acattttaag tcatataatg agatagctat gcagagggtt acaacagtat  15060
taggtccacc aggcacaggt aagtcaacct ttgctattgg tttggctaag tactttccca  15120
gtgcacgtat ttgctacact gcgtcttcgc atgcagcaat cgatgcactc tgtgaaaaag  15180
ctttcaagac aatacctgta ggccaatgca gtcgtatcgt acccacacgt acaactgttg  15240
agtgctttca ggagtttgtc gtaaataaca caactgcaca gtatatcttc tcgactatca  15300
atgccttacc tgacattaag tgtgacattg tagttgtaga tgaggtttct atgttgacca  15360
attatgagct ttcctctgtg aatgctcgtt tggtttacaa tcacattgtg tatgttggtg  15420
atccttatca gttaccttca cctagaacta tgcttacgtc tggccagctt tcgccagctg  15480
actataacgt agttactgat ataatggtac atgcaggagc ggatgttatg ctcgacatgt  15540
gctacagatg cccacgtgaa atcgttgaga cagtgtctaa acttgtctac gataacaaac  15600
taaaagcggc gaaaccgaac tcaagacagt gttacaagac cattgtgaac tttggtcctg  15660
gagacgttgc tcatgaggga caatctgcct acaacgaagc acagttgcgt ttcgcactcg  15720
catttagaca acaaaagcgg tgggataacg tgactttcat atctccatat aatgctatga  15780
atgtgaaagc atccttagca ggtttctcta ctcagaccgt tgactcttct caaggttctg  15840
agtatgatta tgttatcttt tgcgtgacca ctgattcagc acacgcactt aacatggctc  15900
gtttgaacgt tgcccttaca cgtgcaaaga taggtatcct tgtggtgttt aggcaggcaa  15960
acgaacttta caatagtttg cagtttgaat ctattgattc acagcttcag tcgagtgctg  16020
agaaaaacct cacaccactg tttaagcgct gcggctatga gtataatggc gtccatccag  16080
ctcatgcttt gacctggcat gattgtggtg cagagtaccg ctgtgaggag ccacttgcta  16140
aattagtagg agttgccgat ggcactctta tatcatacaa aaccctagta tccacacttg  16200
ggtttcttcc atcacttaaa attgatgcat atcataatat gttcctaaca cgtgatgcgt  16260
gtcgcaccta tgttcagagt tggatcggca tagatgttga agcagcacac gccataaaac  16320
ctaacaccgg gactaacctg ccattgcaaa taggttttag taccggaaag aatttttcag  16380
tcactccaga gggaatttgg gtaaacgagc acggatcttg cactgagccc gtccctgcca  16440
aaatacctcc tggagaacaa tttcgtcacc ttaaaaagga catgcgccag gcgcgtcctt  16500
ggatggttgt tcgacgtgag attgctactc acattgctga ggtagctcct cacactgatt  16560
atatatgctt tgtcacttgg gctcaccagc ttgagctagc gacaatgcgc tactttgtca  16620
aactaggtat ggaagagaga tgcttttgtg gcaggcgggc ttgtttcact aatggaactg  16680
agttcgcttg caaagcacac cattctctca ccattccaca atgtgattat gtgtacaatc  16740
```

-continued cattcctcat cgacgtggct acgtggggat tctcgggacg gctttccacc aaccatgacg 16800
cggtgtgcac atatcatgct aatgcccatg ttgcatcagc tgatgcaatc atgacggtat 16860
gtttagctat ccatgaactg ttcagtactg ttgactggaa ctttgaattt ccagtaactg 16920
ctgagcaatc gcaacttaac aaggcctgtc gcttagtaca ggcgaattac ttaaatatac 16980
tactcactac aaccaaagcc acggtggttc acgatattgg taacccaaaa ggtatcccta 17040
tcgtgcgcaa acctggtgtt aaatatcact tctatgatca agcacccatt gtcaaacacg 17100
ttcaaaaact aaagtacaag ccagagatgg aggcccgttt caccgatggt ttgactatgt 17160
tttggaattg taatgttgac acataccctg ctaacgccct tgtgtgccgc tacgacactc 17220
atcggcagaa gcatttaatt ggacctaatg gttcagcact atatgttaat aagcatgctt 17280
ttctcacccc tgagatgcat acttatgcta cacataaact caacttggct ccactcatct 17340
actactccac cacagattgt agtagtgaac agcctattgt tgttacctac agagattgtg 17400
tcacccggtg caatactgga aaaactctct gtccaaatca tgctcttgaa tatcaagagt 17460
ttatcaatgc atacaatctc atggctcgcc atggatttaa tgtttacata ccacgcaatg 17520
tcaacgttta caactgttgg cttactttca ctaatctcca aaaccttgaa aacttagctt 17580
acaactgtta ttataagaac tgcaatgctc acgttgatgg gcagcttgat gtagttatta 17640
ataataacgc tgtatatgct aaggtcgaca ataatcttgt caaacttttc gacaaccgca 17700
ctaacttacc tgtctcagtg gcctttgaac attacactaa caggcatacc cgttcactgc 17760
caactacaca gctgttatct ggtttaggcg taaccgccac cagaaatttc actgtgtggt 17820
tcgacaatga tacaattttc caatacacta ttaatgtatc tacgtatact gacatcgacc 17880
ctagtaccca tgttgtcctc tgtgatgata ggtacggaac agattggagt cagtttaacc 17940
aacttcctaa tgcagtattc ctcaccaaaa ctaaggtgaa gaaaacagaa ccgtttgttt 18000
gtacagcact gaccctaaat ggcgtcgcca ttgacggtga agagctatac atctatgtac 18060
gctataacaa tcaactgacc acatttgcta ctacttgtac acagggtaga aatgttgagc 18120
agtttatacc taaaacacct atggaaagag acttccttga gatgtctcaa cagtccttca 18180
tccagcaaca tcaattgcag gaactgggtg ttgaacacat tatctatggt gatgattcca 18240
gtccagtcat tggcggaact cacacactta tctcactagt taaaaacaag tttgaacatc 18300
agcttgtcaa ccatgtttac aacccagtcc agaactgtgt tgttacctca cctaacgcaa 18360
gctccaagaa cgtttgcact gttcttgatg ttctacttga tgactacatt gacatcataa 18420
gacaagcaca tgccagttac acaagtaaat ccaaagtatt cactgtgtca attgacaacc 18480
aacaaattag attcatgctt tggcatgatg agcaagtcaa gacttgctac ccaatcttac 18540
agtcacttac caatggttac cagatgccat ctgtgtacaa aacattggtt actgacttac 18600
aaccagctga catccctaat tatcattcct acaccccccg ggtgcctgga gtagttaaga 18660
atgttatcaa gtaccgccaa cttttcaact acatagttaa aaaggatagg ttggcagtac 18720
cacacaatat gaccgtatta caccttggag ctgcatctgc actaggtaca gcaccaggtt 18780
cttcagtcat aaaacaaatg tttcctgaag gaactgttct tattgacctc gatataagag 18840
agttcacttc agatgctaac caaataatag ttacagacta cagaacttac ataccaccac 18900
accacgtaga cgtcatattt tctgacctct actgttgtga tgacatacac ttctttgaca 18960
atctaataag gatagttaag gagaggctcg ccctcggtgg ttctatcttt gttaagataa 19020
ctgaacattc attctcaccc gaactctact cacttgcggg ttggttcgat gattatcaac 19080
tattttgcac agcagtcaat gcctcgtctt cagaagcatt tttatgctgt tttaattatt 19140
tggggcttgc taaggaaaac attaatggtt ttaacttaca tgcttcctat attcaatggc 19200
gcaatgaaat agcgttgaca ccaacctatt ctcctttagc ggacaacccg gctacggcct 19260
gtaagctaaa agcaacgcct attatctcgg ctcgtgagtt agagaagaag cctattcttc 19320
gctatctcgt tgcatcaggg cgccttcttg tgaggccacc agaatgcaga gagctctatt 19380
gattatgacc ttactttgtc tcgttcgagc aaagtttgct gatgatctac tcgacttgct 19440
caccttcccg ggtgcacatc gcttcttaca taaacccacg aggaattcca gcagtctcta 19500
ctcgcgggct aataataatt ttgatgttgg cgttcttcct ggctacccca ctaagaacgt 19560
taacctcttc tcaccactta ctaactccac tttgcccatt aatggccttc atcggagtta 19620
ccaaccactc atgctgaatt gtcttactaa aataactaac cacactctca gcatgtatct 19680
cctacctagt gagatacaaa cttatagctg cggcggtgcc atggttaaat accagacaca 19740
tgatgcagtt cgtatcattt tagacctcac tgccactgac cacatctctg ttgaagtcgt 19800
tgaccaacat ggtgaaaatt atgtgtttgt ttgcagtgag cagtttaact acaccactgc 19860
attacacaat tctaccttct tctcacttaa ttctgcgctt tattgcttta ctaataacac 19920
ctacttaggt attcttccac ctgatttaac tgactttacg gtctaccgta ctggtcagtt 19980
ctatgctaat ggttaccttt taggtacttt acctattacg gttaactatg ttaggttgta 20040
tcggggtcat ttgtctgcca atagtgccca ctttgccctt gcaaacctaa ccgatacact 20100
cataacactt accaatacta ctatatcgca aatcacttat tgtgataagt cagtagttga 20160
ttcaatagca tgccagcgct cttctcacga agtggaggat gggttttact ccgaccctaa 20220
atctgccgtt agagctaggc aacgtactat tgttacacta cctaagctcc ctgagcttga 20280
agtagtgcag ttaaatattt ctgcacacat ggattttggc gaagccagac ttgacagcgt 20340
taccatcaat ggtaacacat cctattgtgt cactaagcct tacttcaggc ttgaaactaa 20400
ctttatgtgt acaggttgca ctatgaatct gcgcactgat acctgtagtt ttgacctgtc 20460
agcagtaaac aatggcatgt cattctctca attctgtcta agcactgaat ctggtgcttg 20520
tgagatgaaa attattgtta cctacgtatg gaattacttg ctaaggcagc gtttgtatgt 20580
tactgctgta gagggccaga ctcacactgg aaccacttca gtacatgcaa cagacacttc 20640
tagtgtaatc actgatgtct gcactgacta cactatctat ggagtctctg gtactggcat 20700
tattaagcca tcagatctct tattgcacaa tggcatagca ttcacctctc caacaggtga 20760
gctttatgca tttaaaaata taaccactgg caaaaccctt caggtcttac cgtgtgaaac 20820
cccttctcaa ctgattgtga taaacaacac cgttgtcggt gctatcacat ccagtaattc 20880
aactgaaaat aataggttta ctactactat tgtcacacct actttctttt attccacaaa 20940
tgccaccact ttcaactgca ctaagcctgt tttgtcctat ggacctatca gcgtgtgtag 21000
tgatggtgca attgtgggaa catccacatt acagaatact cgaccatcca tagttttact 21060
atacgatggc gaagttgaaa taccatctgc attttctctt tccgttcaga cggagtactt 21120
gcaagttcaa gcagagcaag ttatagttga ttgtcctcag tatgtatgca atggcaacag 21180
ccgttgtcta caattactgg cacaatacac ctcagcttgc tctaacattg aagcagctct 21240
gcattcctct gcacagttgg atagcagaga gattataaat atgtttcaaa catcaacaca 21300
gtccttgcag ttagctaata ttaccaactt caagggtgac tacaatttta gcagcatact 21360
aaccaccaga attggtggca gatctgctat tgaagacctt ctttttaata aagttgttac 21420
tagtggcctt ggcactgttg atcaggacta caaatcctgc tctagagaca tggccatcgc 21480

-continued tgacttagtt tgttcccagt attacaatgg catcatggtt ctacctggtg ttgttgatgc 21540
tgagaaaatg gcaatgtata ctggctctct tactggagct atggtatttg gaggactgac 21600
tgccgcagcg gcaataccat ttgccacggc agtacaagct cgcctcaatt atgtcgcact 21660
gcaaacaaat gtactacaag aaaaccagaa aattcttgca gaatcattta accaagcagt 21720
tggcaatata tcacttgcac tatcttctgt taatgatgcc atccagcaaa cttctgaggc 21780
tcttaacacc gtagctattg ctattaaaaa gattcaaaca gttgttaacc agcagggcga 21840
ggcattatca cacctgactg cacagctgtc aaacaatttt caagcaattt cgacttctat 21900
tcaagacatt tacaaccgtc ttgaggaagt agaggctaac cagcaagttg accgtctcat 21960
cacaggacgg ttggctgcac ttaatgcata tgttactcag ttactcaatc agatgtctca 22020
gattagacaa tctcgattgt tagctcagca aaagattaat gagtgtgtca aatcacagtc 22080
gtccagatac ggtttctgtg gaaatggcac acacatcttc tcacttacac agactgcacc 22140
aaatggcata tttttcatgc atgcagtgct agtacccaac aaattcacac gtgtcaacgc 22200
ttctgccggc atttgtgtgg ataatacgag aggctactca ttgcagcctc aacttatact 22260
ctaccagttt aataactcct ggagagttac acctagaaat atgtatgaac ccagactgcc 22320
ccggcaggct gatttcatac aattaactga ttgcagcgtt actttttaca acaccaccgc 22380
tgctaatctt cccaatatta tccctgacat tatagatgtc aatcaaacag tcagtgatat 22440
tattgacaat ttacctacag caacacctcc tcagtgggat gttggtatct ataacaacac 22500
tattctcaac ctcaccgttg agattaatga tctacaagag cggtctaaaa acctctcaca 22560
gattgcagat cgtttacaaa attatattga caatcttaac aatactctag ttgaccttga 22620
atggctcaac agagtggaaa cttaccttaa atggccgtgg tatatatggc ttgccattgc 22680
cctggctctt attgcatttg tgacaatcct cataacaatc tttctttgta ctggttgttg 22740
tggtggttgc tttggttgtt gtggcggttg ttttggcctt ttctctaaga agaaaaggta 22800
taccgacgac caaccaacac cgtcctttaa gtttaaggaa tggtagtcga cgactgggcc 22860
gttaccatcc ctggacaata tattattgct atactagttg tcatctgcat tggtgtggca 22920 ctactttttta ttaatacttg cttagcttgt gttaaattat tttacaagtg ctacctaggg 22980
gcagcatatc ttgttaggcc tattatagtg tactactcca agccgaaccc cgtacctgag 23040
gatgagtttg taaaagtaca ccaatttcct agaaacactc actatgtctg acgcagaaga 23100
gtggcaaatt attgttttca ttgcgatcat atgggcgctt ggcgtcatcc tccagggagg 23160
ctatgccacg cgtaatcgtg tgatctatgt tattaaactt attctgcttt ggctgctcca 23220
acccttcacc ctagtggtga ccatttggac cgcagtcgac agatcatcta agaaggacgc 23280
agttttcatt gtgtccataa tttttgccgt actgaccttc atatcctggg ccaagtactg 23340
gtatgactca attcgtttat taatgaaaac cagatctgca tgggcactct cacctgagag 23400
tagactcctt gcagggatta tggatccaat gggtacatgg aggtgcattc ccatcgacca 23460
catggctcca attctcacac cagtcgttaa gcatggcaag ctcaagctac atgggcaaga 23520
gctggccaat ggcatatcag tcagaaatcc gccacaggat atggtgatag tgtcaccaag 23580
tgacaccttt cactacactt ttaagaaacc tgtggaatca aacaacgatc cagaatttgc 23640
tgttctgata taccagggtg accgcgcttc aaacgctgga cttcacacca taaccacttc 23700
aaaggccggt gacgctcgcc tgtataagta tatgtaatgt gcaactgcca tctgcagctg 23760
cgagatttat atagattgtg caataagcgg cacatcagaa gagaggatgt tcctgagctt 23820
attgaccctc tcgttaaaac tcgctgtttt gcttacagtc tcgtggttct tgctaatgct 23880
aatccaattg catttagcat actacctcgg aaaattctta tcaatggtga gcctttactg 23940
cttgaatatg gtagcatata tggtaaagac tttatcattc gaccatcgct ccaagtcatt 24000
cttgaagatg aattaaatta aagttttgac accaatctat catggctgca ccagtagtcc 24060
ctactactga cgcgtcttgg tttcaggtgc tcaaagctca aaacaaaaag gctactcatc 24120
ctcagtttcg tggcaatgga gttccgctta actccgccat caaacccgtt gaaaaccatg 24180
gctactggct gcgttacacc agacaaaagc caggtggtac tcccattcct ccatcctatg 24240
ccttttatta tactggcaca ggtcccagag gaaatcttaa gtatggtgaa ctccctccta 24300
atgatacccc agcaaccact cgtgttactt gggttaaggg ttcgggagct gacacttcta 24360
ttaaacctca tgttgccaaa cgcaacccca acaatcctaa acatcagctg ctacctctcc 24420
gattcccaac cggagatggc ccagctcaag gtttcagagt tgacccttc aacgctagag 24480 gaagacctca ggagcgtgga agtggcccaa gatctcaatc tgttaactcc agaggcacag 24540
gcaatcagcc caggaaacgc gaccaatctg caccagctgc ggtacgtcgt aagacccagc 24600
atcaagctcc caagcggact ttacccaagg gtaaaaccat ttctcaggta tttggcaacc 24660
ggtctcgtac tggtgccaat gtcggctctg cagacactga gaagacgggt atggctgatc 24720
ctcgcatcat ggctctagcc agacatgtgc ctggtgttca ggaaatgctt tttgctggcc 24780
accttgagag caactttcag gcgggggcaa ttacccttac cttctcctac tcaatcacag 24840
tcaaggaggg ttctcctgac tatgagagac ttaaggatgc gctcaatacg gtcgttaacc 24900
agacctatga gccacctacc aaaccaacta aggacaagaa gcctgacaaa caagaccagt 24960
ctgctaaacc caaacagcag aagaaaccta aaaaggtaac tctgccagca gacaaacagg 25020
attgggagtg ggatgatgct tttgagataa agcaggaatc agcagcgtag acatcaatct 25080
atgtctgtta aacccaccca actccactca aatatctctt tggttccaga gagtcgtagt 25140
gtatagccag agagccagtc agagggcgct atcatgcaaa ctagggctgg ctactctagc 25200
acagaatcac atcccgataa tcaacagtgc tagaaggttg attataccat ttaatatgcc 25260
gaggccacgc ggagtacgat cgagggtaca gcataatctc aacttttgtt gagccacaat 25320
tttaatccta attggagaag gccaaaggac tgtactactt ttgtgggtgt agcagtcgcc 25380
cagtgggaaa gcgccaacta ggttacaatt gtggtgggga caaatt 25426

<210> SEQ ID NO 6
<211> LENGTH: 25426
<212> TYPE: RNA
<213> ORGANISM: Artificial Sequence
<220> FEATURE:
<223> OTHER INFORMATION: Porcine Deltacorona Virus BIV-Isolate 2.0307
ssRNA + Genome

<400> SEQUENCE: 6 gauuggugucggu agagaac uagcgaagcu agggagauaa aauuauagac uaaugcuaua 60
auuuuuaucu uuagucuaua auuuuaucuc ccuagcuucg cuaguucucu accgacacca 120
auccaggugc gucugccacc aaguuggcua cccuuccuag gggcgcuuuc gcgcuugcuc 180
accauuagau uaccuggaaa ccagccauuc agguuggagu uuccccaggc ucuuuugugu 240
gggcauuagc ggcuuguggu uuuugcacaa aaucuaagcu acuuaccguu ccucugacca 300
uccaccacuu cuauagacag cacugauuac cguaggguuu aagucacacc ggucugcacc 360
gcccgucagc ggacacauua cccagcauag cacuccuugc accgagccua gguaggauaa 420
aacccccuac cgggugacuc uuaaggcguu uccuccacgg gauagccacu agucacuagg 480

-continued

```
uguaagugau cugaucuggg cguauugugu ugcgcaagug ugauacccau aggagcgugg    540
aauccuauuc ugcggcucag ugccugauau agcugugaaa uggccaagaa caaguccaag    600
cgcgacgcua uugcguugcc ugaaaaugua ccaccaccuc ugcaacuuuu cauucauguu    660
gcagcugcug aagaggguca cccuaagguu acuacuuacc uuggcaacua uaaccucuau    720
gccaccaagg cuccgccugg cgugcagguu cuuagugcua aaaccucucu uacugacuuu    780
gagaaugucu uuggagcuca acccaccuug cgaucaauuc guaaucuggu uugugaggcu    840
cgcucggcug aauggacaac uuccaagaau gcuuuugcac ucaaagccac ucaacuugac    900
uacucugaug ccguuuugag ggcaaugauu cguuucugcc cuccaaaggu guccacacuc    960
gcugccuuug cucuuuuugg ccgauugguu aaaauugagg acaaggaacu ugcugaguua   1020
gcucgugaua cugcccuuga guuggcguac acggcuaaaa uugguacauc ucuugcugac   1080
acgagaucug ucucacuuau ucauaaggac gcuuaucuaa cucucaguaa ugagguuguu   1140
ggcguaacuu uuacugccgc acuuauggca aaggcuacca cuguuaaugg agcaaugcaa   1200
uacucaaacu uuuaccucua cccucgugcc acuauuaagg uaaccgaugg uaaggcugaa   1260
gcaauugcaa cuaagccucu gucugcugcc acuaaaggca agcaaaucac agaggauguc   1320
aaccuccucc cugacuauca gcagcugcuu guugaucaag ugacuggcac ugagguuaag   1380
guuggagcuc uaaccuaugu uaagaccacu gauucgccac cccuuuacuu ucccaaaguc   1440
aagggguggug uuauugguau ugcacuuaag cagcagggca cugcggcuaa gaagcucaau   1500
guagucuucc augcucaacc ugaugauguu cugcuagccu ucauacaacu ucagcaauuc   1560
uugaaccgua cuucggauuc aaguguugaa auuacugauu gccagaguua ugaaguaucu   1620
ccaacugug a cggucaaaau uggcccgucu aaaccugggg augucaucgu ggcuacugau   1680
gaggaauacc uuaaaugcuu ugaaaccccu gagguaggua ggcucuauaa gguuuuccaa   1740
acucaaucuu gggcuaucau ugagcgugcc uucuccaguu ugaagauccg cguguccaaa   1800
gcuuuaucag cauuuauaag uuuucugcaa aaccuugcag auaacuuuac ugcaauaagu   1860
gguguuguca cugcacucau ucgugaacuc caggaucuua cccuggaugu ggcgacacgu   1920
aucacuaaca uacaauuugu uuaccgugcc gguaagcuua uugucgacac gacaaguguc   1980
auagcuaaac uuuuccagcc auuuugugau uuuauaucac cuuuccuucg gaaaguugcu   2040
gguuuugcaa uuuacacugu ugguaaucgc augcuuaugu uuaccagcac uggcaccuuu   2100
cuucucacaa aggcaacuac uaagauacuc aauaaggcaa aguacaucuu ugauguggag   2160
ccugaguacc caguagaugu aacaacaucc aaaguuguag uacaugaagc acuccagcaa   2220
accgacacua agccuacuag agcucuggag gcuguugaug ucguuguugg uaauacugua   2280
cugcaaaugg cuacugaugg cacugcguuc uacccaucgg augguacgca cgccucucuu   2340
ccaggauuca aagcagguuc ggaugagcuu uucauaagcu ucaacugcga ccucuuugau   2400
gaugagacua augcucaaau caacgaaaca cucgcugcau augagcuuaa ccaacuagug   2460
gcuccaggug auucuacacc gcgucaaauu gcgacguugg uugucgauac acuugcagau   2520
gcuauaacag accacuuucc ggagaaaacc auugaucuac cugaagacua ucaagucuuu   2580
ucugaccaug augaccuccc acucgcacaa uaccacaucc cugaucaccu gagccuguau   2640
auucaggcua uggaagguga agaugauagu ggugaugaaa uauguauuga ggacgaugau   2700
uacgacuguc cucaagccga cgaagacaca gaaggaguaa uuccccaaca gugggaacuu   2760
ccugauguug auaaauuuuu acucaagauc caggaacgga agaccagcag cgacgaagua   2820
```

cuuagcgucg acgucuaucc uaaaccagag ccggucggca auguugggau ugacgacagc 2880
gcgucggaaa agaagccaaa uggggacuca guaccggauc cugaggucca uccaacacua 2940
gagagugugg auguugaacg accaaccgaa acagcaaacc aggcuguuga agacaaaccu 3000
ucugauacca ccuuuguggu ugaugaggaa caauuacaag aaucaacacc agaacaugaa 3060
cuccgcuccu augaagggga guuugauucu gaugaugaaa uuauuauucc uauaguacca 3120
guaacaccug cggauuuaaa accacagacu auuacuauaa aggaguacuu uaagucugaa 3180
aaacuugaga cuauuaacga aggauccaca gagucaguua cacaaucuga cgauucguuu 3240
gacgagucau uuguugaugc ugagucugau gauccacaag auccugcugu auaugaugau 3300
acaacaauua uaacggacag cacugaugua ggcgaugagc cugagacaac ucuagcuacc 3360
aucguuaaca caccucugac acucgauaau aacuugccac cugaagccau uaaacaaccc 3420
agcccaacua agguugaguu aguuguuggu gaauuggcga guauuaaauu ugacaauucu 3480
guucuaguca acccugcuaa ugcgcaauua acaaauggcg guggagcugc ucgugcaauu 3540
gcaaaauuag cugguccaaa auaucaagag uacuguaaua gugugggcucc uaucucagga 3600
ccgcuuacca cggacucuuu ugaugccaag aaauuuggug uagccugcau cuugcaugua 3660
gugccaccca aagguucuga cccuaaugua caagaacucc uguaucaagc uuacaagagu 3720
auccuuacug aaccagcaca cuauguuaua ccuauacuag gugcugguau cuuuggaugc 3780
aauccagucc acucucugga ugcguucagg aaagcauguc caagugacau aggucguguc 3840
acccuuguca cuaugaacaa aaaccauuug cagguguggg augcucucaa uaggaccauu 3900
guacgcacca cuacugacua ugaucaaguu accaccaagg cccuuacacc ccagggagug 3960
uuagaagcca aucucuuuga uggugaggac uuuguucaag aaccaaaacc cggucaaauc 4020
uaccuugagg uuacugaaga aguucagaac caagccaagg aacuugaccu uaaccuucag 4080
caauacugcg ucuaccugaa gacuugccac cauaaauggg uugugagucg uacgaacggg 4140
uugaugcauc uaaaacaaaa agauaacaau uguuuuguua gugcaggugu aaaccuguuu 4200
caaaacacug cuuaucaacu uagaccugcu auugaugcuc ucuauaggga guaucuuaau 4260
gguaauccaa auagauuugu ugcuuggauc uacgcaucca cuaaccgucg uguuggugag 4320
augggguuguc cacagcaagu uauuucuuug cucguuagua acucugacgc agcauuuuca 4380
gcaacuacag ccuguuguaa caccuacuuu aaccacacag guguuauuuc aguagcucgu 4440
gaauaugacc caauacaacc aaaggucuac ugcaugaagu gugaugugug gacucccuuu 4500
acaccccaga guggaaaagg ugcaguugca auugguauuu cugcagauga accuaccggu 4560
ccugccauua aauuugccgc agcucacugc ugguacacua auggcaagaa aacaguuaau 4620
ggcuaugaca cuaaagcuaa uguuguagcu accuaucaua gguuugacgu gccuaagccu 4680
caacuugucg aggacguggu ugcgcugccu acuaaaaaug acuuugaagu ucucaauguu 4740
gaagaacugc cgcaggauag ugugcuccau uuggacccac cuccuguaca ggccuuacaa 4800
ccuaaggcua accaacacau ugagauucua gaaaacccag auuaucugga cauuuuggau 4860
cuuuggauuc guaaacccaa auucauccuc guaaagucgu ggaguguuuu ggguagagca 4920
cuauguaagg cagguaaagu ugucuuuguc agugcuucgc uuuugacccg uuucuacaau 4980
uaccuuguag agauuggugc ucuugacuca acaauaaggu ugucagucga ucuuaccugu 5040
aaauuuguua gaacgguucu cccaucgucu aacacuguac acaaaacuug ucuuggucug 5100
uauuauucag cccagacacu uuuuguuucu uuagcaccau uccuuauguu accagcugua 5160
guuagucugc uuaauucagg cuauacaauu ggcacauauu uguaugcaaa aacuggcugg 5220

-continued

```
ccuuguaauu acaaugccac gcaacacuuu gauuauaauu cuuacugugc aggugacuug   5280
guuugucaag ccuguuuuga cggucaagac ucccuacauu uguauccgca uuuacguguu   5340
aaucagcagc cccuucagac cacugacuac acuguuuaug cgcuuucacu aauacuacua   5400
uuagcuaaca ugacucuugu caugggcacg cuaauaguua cuuucuuugu gaacuucuau   5460
ggugugcaaa uaccauuuua ugguacacuu uugauagauu aucaauccgc acugguguauu   5520
acuuucucag uguacuacuu uuauaaggua augaaguuuu uccgccaucu cacacaugga   5580
uguaaaauuc caacgugugu gguaugugcc aaacuucgua ccccaccuac uauaacaguu   5640
gagacugucg uucagggcag gaaauaccca ucuguuauug aaacaaaugg cggguuuaca   5700
auuuguaaag aacacaacuu cuauugcaag gacugcucuu uacaaacacc cggcacuuuc   5760
aucccgacag aagcuauuga gucgcucuca cgagcuacca ggcuuagugu caaaccaaca   5820
gcaccagcau ucuuacuugc uagagauguu gagugccaaa cugauguugu cguugcucgc   5880
gcaaugcaua accaaaaugc gcaugugugc auuucaaaau acucugauau ccguaccguu   5940
gaccaacuac uuaagccuac uccacuguuu ucauacacuc ccgauguuau caucgcggca   6000
gacuuugaca acagagguag ucuuaagaca gcuaaagaau uagcugugggu uuugucaaug   6060
gaccuuaaac guacuauaau uaucauugau caggccuauu cuagaccuau ugauaauuau   6120
caggaaguug cuucucguau ugagaaguau uacccaguug caaagaucac acccacaggu   6180
gacaucuuua cagacauuaa gcaagcgacc aauggccaag cuagugacuc ugcuauuaau   6240
gcagcuguuc uggcugucca gcgcggucuu gauuuuacaa uugacaaccc uaacaacaua   6300
uuaccacauu acgccuuuga cuuuucgacc cucaaugcag aagaccaguc uaccauuuug   6360
gagagugguu gugcuaaagg caaucucaag ggcacuaaug uuggguguugu ucuuucagcu   6420
agccuuguua cacgucuuag ucagcaggcu auacguguga uugcuaaugc ugcuucacgu   6480
aaugguguua caugcgcugu uacuccuucu acacuuguua ugcgugggaa uauugcaaca   6540
cagcccuuga cucgcaucaa agcuggugca ccucccaugc gucaaaaaau uuuauguguu   6600
auccuggcac uugcuauugu guacuuugcu gcuauggcuu uuggcuuuuu ggcaagucaa   6660
auuacgcuua auacagugcc uacgauuaaa ucugauaucc gcgccucuac cuucuacguu   6720
guuagagaug gagucuugga uacuguucgu ucaaaugaca agugcuuugc aaauaaguuu   6780
uuggcauuug auagcuucau ucaagcaccu uacacuaauu caccugacug uccaguuguu   6840
gugggggaguug uugauguaac gacgcacucu auuccuggaa uuccagcagg ugucauucau   6900
agagacgguc ucauacuuaa cauuuaugaa cagucucuuu augaaacuca ucagcgucag   6960
ucuaugguua gggaugcguu gucacucaag acagcaaauc ucuuuaaccu aggcaagcgu   7020
guuguaguag gauacacuca acaugaaguu guuguggggua ccuccuauuu uaauucuccu   7080
gcacuuuuua augcaaagug caccuucuua caguaucagg acacuagaca acucuauugc   7140
uaugauacug uuccuacuga acauaagcuc uacucugaug ugcuuccgca cgucgaguau   7200
aaggcuauug acauuaaugg ugaucuuguu ccuuucaaga uaccagagca gauaauguuc   7260
uauccacaua uugugcgcua uacuagcaau uccuauugcc guaugggggca uuguuuuaau   7320
acuaacccug guauuugcau uucauuuacg gacgaauuuc cguauaguga aaaugucaaa   7380
ccugguguguu acugugcuga uaccucuuug caguuguuuu caaaccucgu uuugggcacu   7440
guaucuggua uucacaucuu uacaucaaca gcugcauugc uuggaucuac uauugugauc   7500
auacuaugcg uuguugcugu ucuugcaguu cagcgauucu ucaaggagua cacaacuuuu   7560
```

-continued

```
guuauguaca cuuguggucu ugcucuuguc aacauuguag gcauugcacu uauguacaag   7620
ugccuugucu ucgcgauuuu cuauuaugca aucuaccuuu acuuuguccu uacuuucccc   7680
uccuuuaaga ggaauguggc auuguuuuac uucgcuguag ugaucgugcc gcacgugagu   7740
aacaugcaau ugcuugcgcu cauugugugu agcauuaucu acuuucucua caccuauguu   7800
cauacuguag cuaagacagc ugggaaauuu ucuuccuucu uagacgcagc uaaagcuacu   7860
uuugucauug acaaugaaaa guacguguug cuuaaagacc ucgcuggugc ugaauuugac   7920
caguaucugg ccucuuacaa caaguacaaa uauuuuucug guacugcuuc ugauaaggau   7980
uaugauaagg ucuguauggc auuucuugcc aaggcuuugu caucuuuucg ugaaggaggc   8040
gguucacagu uguacacacc accuaaauuu gcaguuguuc agagucuuaa gaccaagcug   8100
caagcaggua ucaaaauccu ccugcacccu ucaggugguag uugagcgaug uauggucuca   8160
guugucuaca auggaucugc auugaauggc aucuggcuua agaauguugu cuacugccca   8220
cgccauguaa uuggaaaauu ccguggugac caguggacuc acauggucuc aauugcugau   8280
ugccgcgacu uuauagucaa guguccaaua cagggguauuc agcuaaaugu ccaaucaguu   8340
aagaugguag gagcucuccu ccaguuaacu guucauacca acaacacagc cacuccagac   8400
uauaaguuug aaaggcucca accaggauca ucgaugacaa uugcuugugc uuaugauggc   8460
auuguacggc augucuauca cgugguccuc caacuuaaua aucuuauuua ugcaagcuuc   8520
cuuaacggag cuuguggguag ugugggguuac acucuuaagg guaaaacacu cuacuuacau   8580
uacaugcacc acauugaguu uaacaacaaa acucauagug guacagaucu ugaagguaac   8640
uucuauggcc ccuaugugga ugaggaaguu auucagcaac aaacagcauu ccaguauuac   8700
acugauaaug uuguugcuca auuauaugca cacuuacuga cuguugaugc uagaccaaaa   8760
uggcuggcac aaucucagau aaguaucgag gauuucaacu caugggcugc uaacaauucc   8820
uuugcuaacu ucccauguga acaaacuaau auguccuaca uuaugggacu cucgcaaaca   8880
gcucgagucc cuguagaacg uauccucaau accauuauac agcuaaccac caauagagau   8940
ggugcuugua uuaugggauc uuaugauuuc gagugcgauu ggacgccaga gaugguauac   9000
aaucaggcuc caauuucauu gcagucagga guaguuaaga aaacuuguac gugguucuuc   9060
cacuucuugu uuauggcuau uaccaugcua cucgcugcca ugcauguuuu cccuguacac   9120
uuguauccaa uaguacugcc augcuucacu gucguggcau ucccuguugac uuuaaccauu   9180
aaacacacug uuguguuuac cacuacauac uugcuuccgu cacuuuugau gaugguugua   9240
aaugcuaaca cuuuuuggau accgaacaca uuucugcgca ccugcuacga aacuauauuc   9300
gguuccccaa uugcucagcg acuguauggu uacacuguug cucuuuauau gcugaucuau   9360
gcuggacuug caaucaacua uacguugaaa acacuccggu auagagcaac uucauucuua   9420
ucuuuuugca ugcagugguu ucaauauggu uauguugcac acauugcgua caaacugcuu   9480
aauaaacccu ggacagaauc acuacucuuc acagccuuca caaugcuaac cagucauccu   9540
uuguuggcug cucuuagcug guggcuagcu ggucgcguaa cucugcccau uaucaugccu   9600
gacuuagcua uucguguuuu ggcguauaac gucauuggcu augucauaug uguucgauuu   9660
ggccuuaugu ggcuugcaaa ucgguucaca acuguaccua ugggcacaua ccaguauaug   9720
gugucuguag agcaacuuaa guacaugaug gcaguuaaga uguccccacc gcguaaugcg   9780
uuugaggugc uuauagccaa cauuagacuu cuugguuugg guggaaaccg uaacauugcu   9840
guuucuacug uccaaaacaa aauucuugau gcaaaagcua cugcuguugu uguugcuaac   9900
cuucuugaaa aggcuggcgu cacaaacaag cacgcuauuu gcaaaaagau ugugaaacuc   9960
```

cacaaugaua cccuuaaagc caccacuuau gaggagguug agguagcacu ugugaaacuu 10020
cuuucucaca uaauugaguu cuugccaacu gaucagguag augcuuaucu agcugaugcg 10080
gccaaugcuc aacauguuaa uaccuauuuu gacaacuugc uugagaacaa agcuguuguu 10140
caggcuguug ccgauaucaa cauuaaucug gauucuuaua gaauuuauaa ggaggcagau 10200
gcuauuuaua aacgaucugu ugagaugaac gaaucuccgc aggagcaaaa gaaaaagcuu 10260
aaagcuguua acauugcaaa ggcggaaugg gagcgugagg cugcuucuca gcguaagcuu 10320
gaaaagcuug cugaugcugc uaugaagucu auguaucuug cagaacgugc ugaggaucgu 10380
cgcauuaagc uaaccucugg acuuacugca augcuuuacc auaugcuuag acgucuugac 10440
ucagauaggg uaaaagcucu guuugagugc gcuaaggcac aaaucuugcc aauacaugcu 10500
guagucggaa uuucuaauga caaccuuaaa guuauuuuua acgauaagga cagcuacucu 10560
cauuauguag agggcaacac acuuauacau aagggaguuc gcuacacuau ugugaagaaa 10620
cucuccuuag auaaugcacc uauugaaggc guaccagaag aauucccugu ggucguugag 10680
acuguuaggg aaggugugcc ccaguugcaa aauaaugagc uauguuugcg caauguuuuc 10740
acugcucaga acacagcuca ggacuucaau ggcaaugaau ccacuguaaa aucuuuuuau 10800
guuacuagaa ccgguaagaa gauuuugguu gccauuacau caacuaaaga caaucuuaag 10860
acugugaccu gccuuacuga gaccgguaag acaguccuua acuuggaccc cccuaugcgc 10920
uucgcacaua ccguaggugg aaaacagucu guugucuauc ucuauuuuau ucagaauauu 10980
aguucacuca acagagguau gguuauuggc cacaucucug aaacuacuau ccuucaggca 11040
aguggcacuc aaauugagua ccagcaaaau gccucucuuu ugaccuauuu ggcuuucgcu 11100
guagacccua agacagccua ccuuaagcau cuugcugaug gugggucucc uauacagggu 11160
uguauucaga ugauugcuac uaugggaccu ggauuugcag uuacuacuaa accacaaccu 11220
aaugagcauc aguauucuua ugguggugcu ucaauuuguc uuuauugccg ugcucauaua 11280
ccacauccug guguugaugg acggugcccc uacaaaggcc gcuuuguuca caucgacaaa 11340
gauaaggaac cuguuuccuu cgccuugacu caugagccau gcaguucuug ucaacggugg 11400
guuaauuaug acugcaccug cggaucuagu cugcagaauu cggcuuauuu aaacgaguaa 11460
cggguucuag ugacgcccgg cuagaacccc ugcagccugg aacucaacca gaugcuguaa 11520
aaagggccuu ccaugugcau aaugauacca ccucugguau auucuuaagc acaaaaucua 11580
acugcgcucg guuuaaaacc acacgcagug cccugccuuu accuaauaag ggagagguug 11640
aauuguacuu uguuacuaag cagugugcag cuaaagucuu cgaaaucgag gaggaaugcu 11700
acaacgcucu uaguacagag cuuuauacua cugaugauac auuuggugu c cuugccaaaa 11760 cugaguucuu uaaguuugac aagauaccua augucaaucg ccaguaucug acuaaauaua 11820
cacuccugga cuuggcuuau gcucuacguc auuugucaac aucuaaggau guuauucaag 11880
aaaucuugau caccaugugc ggaaccccug aagauugguu uggggaaaau ugguuugauc 11940
caauugagaa cccauccuuu uacaaggagu uccauaaacu uggggauauu cuuaaccguu 12000
guguucuuaa ugccaauaag uuugcuagug ccuguauaga cgcuggucuu guuggcauau 12060
uaacacccga caaccaagac cuccugggu c agaucuauga cuuuggagau uuuauuauua 12120
cacaaccagg uaauggaugu guggacuuag cauccuauua uucuuauuua augcccauua 12180
uguccaugac ucacauguua aagugugagu guauggauag ugauggcaac ccacuugagu 12240
augauggauu ucaguaugac uucacggacu ucaagcuugg cuuguucgag aaguauuuua 12300

-continued aguacuggga ccguccuuac cauccuaaca cuguugaaug uccagaugac cguugcguau 12360
ugcacugugc gaacuucaau guguuguuug cuauguguau accuaauacg gcauuuggca 12420
aucuuuguuc aagagcuacu guugauggcc accuugugu ccagacagug gguguacacu 12480
ugaaagaacu cgguauaguc cuuaaccagg acguuaccac acacauggca aauauuaauc 12540
uaaacacucu auugcgauug guuggugauc ccaccacuau ugcaaguguc ucagacaagu 12600
guguagauuu aagaacuccu ugucagaccu uggcuacuau gucuagcgga auugcuaaac 12660
agucagucaa gcccgggcau uuuaaucaac acuucuacaa gcauuugcuu gauaguaacc 12720
uauuagacca acuuggaaua gacauucgcc acuucuacua uaugcaggau ggugaagcgg 12780
cuaucacaga cuacagcuac uacagguaua auacccccac gaugguagau aucaagaugu 12840
ucuuauuuug ccuugaggug gcagauaagu aucuugagcc cuacgaaggu ggauguauua 12900
augcacaguc aguuguggu ucuaauuugg acaagucagc gggcuacccc uuuaacaagc 12960
uagguaaggc ucguaacuau uacgacauga cucaugccga gcaaaaucaa cuguuugagu 13020
auacaaaacg caauguuuug ccuacacuca cucagaugaa ccuuaaguau gcaauuucag 13080
ccaaggaucg ugcucgcacu guggcaggag ugucuauaau uagcaccaug acuaacaggc 13140
aguaccauca aaagaugcug aaaucuauuu cacuugcacg caaucagacc aucgugauug 13200
gaacaaccaa auucuauggu gguugggaca acauguuacg acgacugaug uguaauauca 13260
acaaucccau uuuagugggu ugggauuacc cuaaguguga ucguucuaug ccaaacaugc 13320
ugcgcauugc cgcuucgugc uugcuagcac gaaaacacac uugcuguaac caaagccagc 13380
gauucuaccg uuuggcuaau gaauguugcc aaguacuauc ugaaguggua gucucuggua 13440
acaaccucua uguaaaacca gguggcacua gcagugguga ugcaaccaca gcuuaugcca 13500
auucgguauu uaacaucuua cagguugguuu cugcuaaugu agccaccuuc uuaucaacuu 13560
ccaccacgac acaucuuaau aaggacauug cggacuugca ucauagucuu uaugaagaua 13620
uuuaucgugg ugacucuaau gauaucacug ucaucaauag auucuaccag caucuccaaa 13680
guuacuuugg acuuaugaua uugucugaug auggugucgc augcauagac ucagccguug 13740
caaaggcugg agcuguugcu gaucuugaug guuuccgaga cauuuuguuu uaccaaaaca 13800
auguuuacau ggcagacuca aaguguugga cagaaacuga caugaauguu ggcccucaug 13860
aauuuugcuc acagcauacu guguuagcag agcaugaugg uaaaccuuac uacuuaccuu 13920
acccagaugu cucucgcauu cugggugcau gcaucuuugu ggaugacguu aacaaggcug 13980
acccuguuca gaaccuugaa cguuacaucu cacuugcaau ugaugcauau ccccucacca 14040
agguugaccc uauuaagggu aaagucuuuu auuuguuacu agacuacaua cguguucuug 14100
cucaggaguu acaggauggu auccuugaug cuuuccaauc acucacugac augucguaug 14160
uaaauaacuu uaugaaugag gccuuuuaug cucagaugua ugagcaaagu ccuacacuac 14220
aggccagcgg uguuuguugug guguguaauu cacccacuau acugcgcugu ggugauugca 14280
uucgucgacc acuacuuugu ugcgucugug ccuaccagca uguuacgcag acuacacaua 14340
aacguaucau ugcuaucaac aacuacaucu guaguguuga gaauugcaau gaggacaaug 14400
uugaaaaacu uuucauuucu ggcacugcga uuuauuguga gaaucacaaa ccuacgcugu 14460
gcauacccau uguagcuaac gguucuguuu uugguaucua ucgccacacu gcccguggua 14520
gugaugacau agaccucuuu aacgagcuug cuacaucuaa cuaugacacu auugaaccuu 14580
aucagaaggc caaucgugca ccuuuaucac uuaugcucuu cgcugcugaa accauuaagg 14640
cacucgagga gucuaucaag aagucauaug cuaccgcaac cgucaaggau guguaugacc 14700
aacgcuucau uaaacuucua ugggaacagg guaaaaagcc gccacccaua acgaagaacc 14760
acauuuucac uggcuaccau uuuaacaaga auggaaaaac ccaaguuggu gauuacauuc 14820
uugcuaaaac agauggcagu gacacuuaua cuuacagagg aacaucuacc uacaaacucc 14880
aaacaggguga uguucuaguc uuaauggcac auguuguuac accgcucuca gcacccccug 14940
ugcuaacgca gacaacauau gucagaaaau cacuuuuacc cgacucuguu ggugcgucuu 15000
auuaugugca acauuuuaag ucauauaaug agauagcuau gcagaggguu acaacaguau 15060
uagguccacc aggcacaggu aagucaaccu uugcuauugg uuuggcuaag uacuuuccca 15120
gugcacguau uugcuacacu gcgucuucgc augcagcaau cgaugcacuc ugugaaaaag 15180
cuuucaagac aauaccugua ggccaaugca gucguaucgu acccacacgu acaacuguug 15240
agugcuuuca ggaguuuguc guaaauaaca caacugcaca guauaucuuc ucgacuauca 15300
augccuuacc ugacauuaag ugugacauug uaguuguaga ugagguuucu auguugacca 15360
auuaugagcu uuccucugug aaugcucguu ugguuuacaa ucacauugug uauguuggug 15420
auccuuauca guuaccuuca ccuagaacua ugcuuacguc uggccagcuu ucgccagcug 15480
acuauaacgu aguuacugau auaaugguac augcaggagc ggauguuaug cucgacaugu 15540
gcuacagaug cccacgugaa aucguugaga cagugucuaa acuugucuac gauaacaaac 15600
uaaaagcggc gaaaccgaac ucaagacagu guuacaagac cauugugaac uuuggguccug 15660
gagacguugc ucaugaggga caaucugccu acaacgaagc acaguugcgu uucgcacucg 15720
cauuuagaca acaaaagcgg ugggauaacg ugacuuucau aucuccauau aaugcuauga 15780
augugaaagc auccuuagca gguuucucua cucagaccgu ugacucuucu caagguucug 15840
aguaugauua uguuaucuuu ugcgugacca cugauucagc acacgcacuu aacauggcuc 15900
guuugaacgu ugcccuuaca cgugcaaaga uagguauccu ugugguguuu aggcaggcaa 15960
acgaacuuua caauaguuug caguuugaau cuauugauuc acagcuucag ucgagugcug 16020
agaaaaaccu cacaccacug uuuaagcgcu gcggcuauga guauaauggc guccauccag 16080
cucaugcuuu gaccuggcau gauuguggug cagaguaccg cugugaggag ccacuugcua 16140
aauuaguagg aguugccgau ggcacucuua uaucauacaa aacccuagua uccacacuug 16200
gguuucuucc aucacuuaaa auugaugcau aucauaauau guuccuaaca cgugaugcgu 16260
gucgcaccua uguucagagu uggaucggca uagauguuga agcagcacac gccauaaaac 16320
cuaacaccgg gacuaaccug ccauugcaaa uagguuuuag uaccggaaag aauuuuucag 16380
ucacuccaga gggaauuugg guaaacgagc acggaucuug cacugagccc gucccugcca 16440
aaauaccucc uggagaacaa uuucgucacc uuaaaaagga caugcgccag gcgcguccuu 16500
ggaugguugu ucgacgugag auugcuacuc acauugcuga gguagcuccu cacacugauu 16560
auauaugcuu ugucacuugg gcucaccagc uugagcuagc gacaaugcgc uacuuuguca 16620
aacuagguau ggaagagaga ugcuuuugug gcaggcgggc uuguuucacu aauggaacug 16680
aguucgcuug caaagcacac cauucucuca ccauuccaca augugauuau guguacaauc 16740
cauuccucau cgacguggcu acgugggau ucucgggacg gcuuuccacc aaccaugacg 16800
cggugugcac auaucaugcu aaugcccaug uugcaucagc ugaugcaauc augacgguau 16860
guuuagcuau ccaugaacug uucaguacug uugacuggaa cuuugaauuu ccaguaacug 16920
cugagcaauc gcaacuuaac aaggccuguc gcuuaguaca ggcgaauuac uuaaauauac 16980
uacucacuac aaccaaagcc acgguggguuc acgauauugg uaacccaaaa gguaucccua 17040

-continued ucgugcgcaa accugguguu aaauaucacu ucuaugauca agcacccauu gucaaacacg 17100
uucaaaaacu aaaguacaag ccagagaugg aggcccguuu caccgauggu uugacuaugu 17160
uuuggaauug uaauguugac acauacccug cuaacgcccu ugugugccgc uacgacacuc 17220
aucggcagaa gcauuuaauu ggaccuaaug guucagcacu auauguuaau aagcaugcuu 17280
uucucacccc ugagaugcau acuuaugcua cacauaaacu caacuuggcu ccacucaucu 17340
acuacuccac cacagauugu aguagugaac agccuauugu uguuaccuac agagauugug 17400
ucacccggug caauacugga aaaacucucu guccaaauca ugcucuugaa uaucaagagu 17460
uuaucaaugc auacaaucuc auggcucgcc auggauuuaa uguuuacaua ccacgcaaug 17520
ucaacguuua caacuguugg cuuacuuuca cuaaucucca aaaccuugaa aacuuagcuu 17580
acaacuguua uuauaagaac ugcaaugcuc acguugaugg gcagcuugau guaguuauua 17640
auaauaacgc uguauaugcu aaggucgaca auaaucuugu caaacuuuuc gacaaccgca 17700
cuaacuuacc ugucucagug gccuuugaac auuacacuaa caggcauacc cguucacugc 17760
caacuacaca gcuguuaucu gguuuaggcg uaaccgccac cagaaauuuc acuguguggu 17820
ucgacaauga uacaauuuuc caauacacua uuaauguauc uacguauacu gacaucgacc 17880
cuaguaccca uguuguccuc ugugaugaua gguacggaac agauuggagu caguuuaacc 17940
aacuuccuaa ugcaguauuc cucaccaaaa cuaaggugaa gaaaacagaa ccguuuguuu 18000
guacagcacu gacccuaaau ggcgucgcca uugacgguga agagcuauac aucuauguac 18060
gcuauaacaa ucaacugacc acauuugcua cuacuuguac acaggguaga aauguugagc 18120
aguuuauacc uaaaacaccu auggaaagag acuuccuuga gaugucucaa caguccuuca 18180
uccagcaaca ucaauugcag gaacugggug uugaacacau uaucuauggu gaugauucca 18240
guccagucau uggcggaacu cacacacuua ucucacuagu uaaaaacaag uuugaacauc 18300
agcuugucaa ccauguuuac aacccagucc agaacugugu uguuaccuca ccuaacgcaa 18360
gcuccaagaa cguuugcacu guucuugaug uucuacuuga ugacuacauu gacaucauaa 18420
gacaagcaca ugccaguuac acaaguaaau ccaaaguauu cacuguguca auugacaacc 18480
aacaaauuag auucaugcuu uggcaugaug agcaagucaa gacuugcuac ccaaucuuac 18540
agucacuuac caaugguuac cagaugccau cuguguacaa aacauugguu acugacuuac 18600
aaccagcuga caucccuaau uaucauuccu acacccccg ggugccugga guaguuaaga 18660
auguuaucaa guaccgccaa cuuuucaacu acauaguuaa aaaggauagg uuggcaguac 18720
cacacaauau gaccguauua caccuuggag cugcaucugc acuagguaca gcaccagguu 18780
cuucagucau aaaacaaaug uuuccugaag gaacuguucu uauugaccuc gauauaagag 18840
aguucacuuc agaugcuaac caaauaauag uuacagacua cagaacuuac auaccaccac 18900
accacguaga cgucauauuu ucugaccucu acuguuguga ugacauacac uucuuugaca 18960
aucuaauaag gauaguuaag gagaggcucg cccucggugg uucuaucuuu guuaagauaa 19020
cugaacauuc auucucaccc gaacucuacu cacuugcggg uugguucgau gauuaucaac 19080
uauuuugcac agcagucaau gccucgucuu cagaagcauu uuuaugcugu uuuaauuauu 19140
uggggcuugc uaaggaaaac auuaaugguu uuaacuuaca ugcuuccuau auucaauggc 19200
gcaaugaaau agcguugaca ccaaccuauu cuccuuuagc ggacaacccg gcuacggccu 19260
guaagcuaaa agcaacgccu auuaucucgg cucgugaguu agagaagaag ccuauucuuc 19320
gcuaucucgu ugcaucaggg cgccuucuug ugaggccacc agaaugcaga gagcucuauu 19380
gauuaugacc uuacuuuguc ucguucgagc aaaguuugcu gaugaucuac ucgacuugcu 19440
caccuucccg ggugcacauc gcuucuuaca uaaacccacg aggaauucca gcagucucua 19500
cucgcgggcu aauaauaauu uugauguugg cguucuuccu ggcuacccca cuaagaacgu 19560
uaaccucuuc ucaccacuua cuaacuccac uuugcccauu aauggccuuc aucggaguua 19620
ccaaccacuc augcugaauu gucuuacuaa aauaacuaac cacacucuca gcauguaucu 19680
ccuaccuagu gagauacaaa cuuauagcug cggcggugcc augguuaaau accagacaca 19740
ugaugcaguu cguaucauuu uagaccucac ugccacugac cacaucucug uugaagucgu 19800
ugaccaacau ggugaaaauu auguguuugu uugcagugag caguuuaacu acaccacugc 19860
auuacacaau ucuaccuucu ucucacuuaa uucugcgcuu uauugcuuua cuaauaacac 19920
cuacuuaggu auucuuccac cugauuuaac ugacuuuacg gucuaccgua cuggucaguu 19980
cuaugcuaau gguuaccuuu uagguacuuu accuauuacg guuaacuaug uuagguugua 20040
ucggggucau uugucugcca auagugccca cuuugcccuu gcaaaccuaa ccgauacacu 20100
cauaacacuu accaauacua cuauaucgca aaucacuuau ugugauaagu caguaguuga 20160
uucaauagca ugccagcgcu cuucucacga aguggaggau ggguuuuacu ccgacccuaa 20220
aucugccguu agagcuaggc aacguacuau uguuacacua ccuaagcucc cugagcuuga 20280
aguagugcag uuaaaauauu cugcacacau ggauuuuggc gaagccagac uugacagcgu 20340
uaccaucaau gguaacacau ccuauugugu cacuaagccu uacuucaggc uugaaacuaa 20400
cuuuaugugu acagguugca cuaugaaucu gcgcacugau accuguaguu uugaccuguc 20460
agcaguaaac aauggcaugu cauucucuca auucugucua agcacugaau cuggugcuug 20520
ugagaugaaa auuauuguua ccuacguaug gaauuacuug cuaaggcagc guuuguaugu 20580
uacugcugua gagggccaga cucacacugg aaccacuuca guacaugcaa cagacacuuc 20640
uaguguaauc acugaugucu gcacugacua cacuaucuau ggagucucug guacuggcau 20700
uauuaagcca ucagaucucu uauugcacaa uggcauagca uucaccucuc caacagguga 20760
gcuuuaugca uuuaaaaaua uaaccacugg caaaacccuu caggucuuac cgugugaaac 20820
cccuucucaa cugauuguga uaaacaacac cguugucggu gcuaucacau ccaguaauuc 20880
aacugaaaau aauagguuua cuacuacuau ugucacaccu acuuucuuuu auuccacaaa 20940
ugccaccacu uucaacugca cuaagccugu uuuguccuau ggaccuauca gcguguguag 21000
ugauggugca auugugggaa cauccacauu acagaauacu cgaccaucca uaguuuuacu 21060
auacgauggc gaaguugaaa uaccaucugc auuuucucuu uccguucaga cggaguacuu 21120
gcaaguucaa gcagagcaag uuauaguuga uuguccucag uauguaugca auggcaacag 21180
ccguugucua caauuacugg cacaauacac cucagcuugc ucuaacauug aagcagcucu 21240
gcauuccucu gcacaguugg auagcagaga gauuauaaau auguuucaaa caucaacaca 21300
guccuugcag uuagcuaaua uuaccaacuu caagggugac uacaauuuua gcagcauacu 21360
aaccaccaga auugguggca gaucugcuau ugaagaccuu cuuuuuaaua aaguuguuac 21420
uaguggccuu ggcacuguug aucaggacua caaauccugc ucuagagaca uggccaucgc 21480
ugacuuaguu uguucccagu auuacaaugg caucaugguu cuaccuggug uuguugaugc 21540
ugagaaaaug gcaauguaua cuggcucucu uacuggagcu augguauuug gaggacugac 21600
ugccgcagcg gcaauaccau uugccacggc aguacaagcu cgccucaauu augucgcacu 21660
gcaaacaaau guacuacaag aaaaccagaa aauucuugca gaaucauuua accaagcagu 21720
uggcaauaua ucacuugcac uaucuucugu uaaugaugcc auccagcaaa cuucugaggc 21780
ucuuaacacc guagcuauug cuauuaaaaa gauucaaaca guuguuaacc agcagggcga 21840
ggcauuauca caccugacug cacagcuguc aaacaauuuu caagcaauuu cgacuucuau 21900
ucaagacauu uacaaccguc uugaggaagu agaggcuaac cagcaaguug accgucucau 21960
cacaggacgg uuggcugcac uuaaugcaua uguuacucag uuacucaauc agaugucuca 22020
gauuagacaa ucucgauugu uagcucagca aaagauuaau gagugugca aaucacaguc 22080 guccagauac gguuucugug gaaauggcac acacaucuuc ucacuuacac agacugcacc 22140
aaauggcaua uuuuucaugc augcagugcu aguacccaac aaauucacac gugucaacgc 22200
uucugccggc auuugugugg auaauacgag aggcuacuca uugcagccuc aacuuauacu 22260
cuaccaguuu aauaacuccu ggagaguuac accuagaaau auguaugaac ccagacugcc 22320
ccggcaggcu gauuucauac aauuaacuga uugcagcguu acuuuuuaca acaccaccgc 22380
ugcuaaucuu cccaauauua ucccugacau uauagauguc aaucaaacag ucagugauau 22440
uauugacaau uuaccuacag caacaccucc ucagugggau guugguaucu auaacaacac 22500
uauucucaac cucaccguug agauuaauga ucuacaagag cggucuaaaa accucucaca 22560
gauugcagau cguuuacaaa auuauauuga caaucuuaac aauacucuag uugaccuuga 22620
auggcucaac agaguggaaa cuuaccuuaa auggccgugg uauauauggc uugccauugc 22680
ccuggcucuu auugcauuug ugacaauccu cauaacaauc uuucuuugua cugguuguug 22740 ugguggguugc uuugguuguu guggcgguug uuuuggccuu uucucuaaga agaaaaggua 22800
uaccgacgac caaccaacac cguccuuuaa guuuaaggaa ugguagucga cgacugggcc 22860
guuaccaucc cuggacaaua uauuauugcu auacuaguug ucaucugcau uggugugga 22920 cuacuuuuua uuaauacuug cuuagcuugu guuaaauuau uuuacaagug cuaccuaggg 22980
gcagcauauc uuguuaggcc uauuauagug uacuacucca agccgaaccc cguaccugag 23040
gaugaguuug uaaaaguaca ccaauuuccu agaaacacuc acuaugucug acgcagaaga 23100
guggcaaauu auuguuuuca uugcgaucau augggcgcuu ggcgucaucc uccagggagg 23160
cuaugccacg cguaaucgug ugaucuaugu uauuaaacuu auucugcuuu ggcugcucca 23220
acccuucacc cuagugguga ccauuuggac cgcagucgac agaucaucua agaaggacgc 23280 aguuucauu guguccauaa uuuugccgu acugaccuuc auauccuggg ccaaguacug 23340
guaugacuca auucguuuau uaaugaaaac cagaucugca ugggcacucu caccugagag 23400
uagacuccuu gcagggauua uggauccaau ggguacaugg aggugcauuc ccaucgacca 23460
cauggcucca auucucacac cagucguuaa gcauggcaag cucaagcuac augggcaaga 23520
gcuggccaau ggcauaucag ucagaaaucc gccacaggau auggugauag ugucaccaag 23580
ugacaccuuu cacuacacuu uuaagaaacc uguggaauca aacaacgauc cagaauuugc 23640
uguucugaua uaccagggug accgcgcuuc aaacgcugga cuucacacca uaaccacuuc 23700
aaaggccggu gacgcucgcc uguauaagua uauguaaugu gcaacugcca ucugcagcug 23760
cgagauuuau auagauugug caauaagcgg cacaucagaa gagaggaugu uccugagcuu 23820
auugacccuc ucguuaaaac ucgcuguuuu gcuuacaguc ucgugguucu ugcuaaugcu 23880
aauccaauug cauuuagcau acuaccucgg aaaauucuua ucaaugguga gccuuuacug 23940
cuugaauaug guagcauaua ugguaaagac uuuaucauuc gaccaucgcu ccaagucauu 24000
cuugaagaug aauuaaauua aaguuuugac accaaucuau cauggcugca ccaguagucc 24060
cuacuacuga cgcgucuugg uuucaggugc ucaaagcuca aaacaaaaag gcuacucauc 24120
cucaguuucg uggcaaugga guuccgcuua acuccgccau caaacccguu gaaaaccaug 24180
gcuacuggcu gcguuacacc agacaaaagc cagguggaac ucccauuccu ccauccuaug 24240
ccuuuuauua uacuggcaca ggucccagag gaaaucuuaa guauggugaa cucccuccua 24300
augauacccc agcaaccacu cguguuacuu ggguuaaggg uucgggagcu gacacuucua 24360
uuaaaccuca uguugccaaa cgcaacccca acaauccuaa acaucagcug cuaccucucc 24420
gauucccaac cggagauggc ccagcucaag guuucagagu ugaccccuuc aacgcuagag 24480
gaagaccuca ggagcgugga aguggcccaa gaucucaauc uguuaacucc agaggcacag 24540
gcaaucagcc caggaaacgc gaccaaucug caccagcugc gguacgucgu aagacccagc 24600
aucaagcucc caagcggacu uuacccaagg guaaaaccau uucucaggua uuuggcaacc 24660
ggucucguac uggugccaau gucggcucug cagacacuga gaagacgggu auggcugauc 24720
cucgcaucau ggcucuagcc agacaugugc cugguguuca ggaaaugcuu uuugcuggcc 24780
accuugagag caacuuucag gcgggggcaa uuacccuuac cuucuccuac ucaaucacag 24840
ucaaggaggg uucuccugac uaugagagac uuaaggaugc gcucaauacg gucguuaacc 24900
agaccuauga gccaccuacc aaaccaacua aggacaagaa gccugacaaa caagaccagu 24960
cugcuaaacc caaacagcag aagaaaccua aaagguaac ucugccagca gacaaacagg 25020
auugggagug ggaugaugcu uuugagauaa agcaggaauc agcagcguag acaucaaucu 25080
augucuguua aacccaccca acuccacuca aauaucucuu ugguuccaga gagucguagu 25140
guauagccag agagccaguc agagggcgcu aucaugcaaa cuagggcugg cuacucuagc 25200
acagaaucac aucccgauaa ucaacagugc uagaagguug auuauaccau uuaauaugcc 25260
gaggccacgc ggaguacgau cgaggguaca gcauaaucuc aacuuuuguu gagccacaau 25320
uuuaauccua auuggagaag gccaaaggac uguacuacuu uugugggugu agcagucgcc 25380
cagugggaaa gcgccaacua gguuacaauu guggugggga caaauu 25426

<210> SEQ ID NO 7
<211> LENGTH: 3480
<212> TYPE: DNA
<213> ORGANISM: Artificial Sequence
<220> FEATURE:
<223> OTHER INFORMATION: Porcine Deltacorona Virus BIV-Isolate 2.0307 Spike Antigen cDNA

<400> SEQUENCE: 7
atgcagagag ctctattgat tatgacctta ctttgtctcg ttcgagcaaa gtttgctgat 60
gatctactcg acttgctcac cttcccgggt gcacatcgct tcttacataa acccacgagg 120
aattccagca gtctctactc gcgggctaat aataattttg atgttggcgt tcttcctggc 180
taccccacta agaacgttaa cctcttctca ccacttacta actccacttt gcccattaat 240
ggccttcatc ggagttacca accactcatg ctgaattgtc ttactaaaat aactaaccac 300
actctcagca tgtatctcct acctagtgag atacaaactt atagctgcgg cggtgccatg 360
gttaaatacc agacacatga tgcagttcgt atcattttag acctcactgc cactgaccac 420
atctctgttg aagtcgttga ccaacatggt gaaaattatg tgtttgtttg cagtgagcag 480
tttaactaca ccactgcatt acacaattct accttcttct cacttaattc tgcgctttat 540
tgctttacta ataacaccta cttaggtatt cttccacctg atttaactga ctttacggtc 600
taccgtactg gtcagttcta tgctaatggt taccttttag gtactttacc tattacggtt 660
aactatgtta ggttgtatcg ggtcatttg tctgccaata gtgcccactt tgcccttgca 720
aacctaaccg atacactcat aacacttacc aatactacta tatcgcaaat cacttattgt 780
gataagtcag tagttgattc aatagcatgc cagcgctctt ctcacgaagt ggaggatggg 840
ttttactccg accctaaatc tgccgttaga gctaggcaac gtactattgt tacactacct 900
aagctccctg agcttgaagt agtgcagtta aatatttctg cacacatgga ttttggcgaa 960
gccagacttg acagcgttac catcaatggt aacacatcct attgtgtcac taagccttac 1020
ttcaggcttg aaactaactt tatgtgtaca ggttgcacta tgaatctgcg cactgatacc 1080
tgtagttttg acctgtcagc agtaaacaat ggcatgtcat tctctcaatt ctgtctaagc 1140
actgaatctg gtgcttgtga gatgaaaatt attgttacct acgtatggaa ttacttgcta 1200
aggcagcgtt tgtatgttac tgctgtagag ggccagactc acactggaac cacttcagta 1260
catgcaacag acacttctag tgtaatcact gatgtctgca ctgactacac tatctatgga 1320
gtctctggta ctggcattat taagccatca gatctcttat tgcacaatgg catagcattc 1380
acctctccaa caggtgagct ttatgcattt aaaaatataa ccactggcaa aacccttcag 1440
gtcttaccgt gtgaaacccc ttctcaactg attgtgataa acaacaccgt tgtcggtgct 1500
atcacatcca gtaattcaac tgaaaataat aggtttacta ctactattgt cacacctact 1560
ttcttttatt ccacaaatgc caccactttc aactgcacta agcctgtttt gtcctatgga 1620
cctatcagcg tgtgtagtga tggtgcaatt gtgggaacat ccacattaca gaatactcga 1680
ccatccatag ttttactata cgatggcgaa gttgaaatac catctgcatt ttctctttcc 1740
gttcagacgg agtacttgca agttcaagca gagcaagtta tagttgattg tcctcagtat 1800
gtatgcaatg gcaacagccg ttgtctacaa ttactggcac aatacacctc agcttgctct 1860
aacattgaag cagctctgca ttcctctgca cagttggata gcagagagat tataaatatg 1920
tttcaaacat caacacagtc cttgcagtta gctaatatta ccaacttcaa gggtgactac 1980
aattttagca gcatactaac caccagaatt ggtggcagat ctgctattga agaccttctt 2040
tttaataaag ttgttactag tggccttggc actgttgatc aggactacaa atcctgctct 2100
agagacatgg ccatcgctga cttagtttgt tcccagtatt acaatggcat catggttcta 2160
cctggtgttg ttgatgctga gaaaatggca atgtatactg gctctcttac tggagctatg 2220
gtatttggag gactgactgc cgcagcggca ataccatttg ccacggcagt acaagctcgc 2280
ctcaattatg tcgcactgca aacaaatgta ctacaagaaa accagaaaat tcttgcagaa 2340
tcatttaacc aagcagttgg caatatatca cttgcactat cttctgttaa tgatgccatc 2400
cagcaaactt ctgaggctct taacaccgta gctattgcta ttaaaaagat tcaaacagtt 2460
gttaaccagc agggcgaggc attatcacac ctgactgcac agctgtcaaa caattttcaa 2520
gcaatttcga cttctattca agacatttac aaccgtcttg aggaagtaga ggctaaccag 2580
caagttgacc gtctcatcac aggacggttg gctgcactta atgcatatgt tactcagtta 2640
ctcaatcaga tgtctcagat tagacaatct cgattgttag ctcagcaaaa gattaatgag 2700
tgtgtcaaat cacagtcgtc cagatacggt ttctgtggaa atggcacaca catcttctca 2760
cttacacaga ctgcaccaaa tggcatattt ttcatgcatg cagtgctagt acccaacaaa 2820
ttcacacgtg tcaacgcttc tgccggcatt tgtgtggata atacgagagg ctactcattg 2880
cagcctcaac ttatactcta ccagtttaat aactcctgga gagttacacc tagaaatatg 2940
tatgaaccca gactgccccg gcaggctgat ttcatacaat taactgattg cagcgttact 3000
ttttacaaca ccaccgctgc taatcttccc aatattatcc ctgacattat agatgtcaat 3060
caaacagtca gtgatattat tgacaattta cctacagcaa cacctcctca gtgggatgtt 3120

-continued ggtatctata acaacactat tctcaacctc accgttgaga ttaatgatct acaagagcgg 3180
tctaaaaacc tctcacagat tgcagatcgt ttacaaaatt atattgacaa tcttaacaat 3240
actctagttg accttgaatg gctcaacaga gtggaaactt accttaaatg gccgtggtat 3300
atatggcttg ccattgccct ggctcttatt gcatttgtga caatcctcat aacaatcttt 3360
ctttgtactg gttgttgtgg tggttgcttt ggttgttgtg gcggttgttt tggccttttc 3420
tctaagaaga aaaggtatac cgacgaccaa ccaacaccgt cctttaagtt taaggaatgg 3480

<210> SEQ ID NO 8
<211> LENGTH: 1158
<212> TYPE: PRT
<213> ORGANISM: Porcine Deltacorona Virus

<400> SEQUENCE: 8

Met Gln Arg Ala Leu Leu Ile Met Thr Leu Leu Cys Leu Val Arg Ala
1               5                   10                  15

Lys Phe Ala Asp Asp Leu Leu Asp Leu Leu Thr Phe Pro Gly Ala His
            20                  25                  30

Arg Phe Leu His Lys Pro Thr Arg Asn Ser Ser Ser Leu Tyr Ser Arg
        35                  40                  45

Ala Asn Asn Asn Phe Asp Val Gly Val Leu Pro Gly Tyr Pro Thr Lys
    50                  55                  60

Asn Val Asn Leu Phe Ser Pro Leu Thr Asn Ser Thr Leu Pro Ile Asn
65                  70                  75                  80

Gly Leu His Arg Ser Tyr Gln Pro Leu Met Leu Asn Cys Leu Thr Lys
                85                  90                  95

Ile Thr Asn His Thr Leu Ser Met Tyr Leu Leu Pro Ser Glu Ile Gln
            100                 105                 110

Thr Tyr Ser Cys Gly Gly Ala Met Val Lys Tyr Gln Thr His Asp Ala
        115                 120                 125

Val Arg Ile Ile Leu Asp Leu Thr Ala Thr Asp His Ile Ser Val Glu
    130                 135                 140

Val Val Asp Gln His Gly Glu Asn Tyr Val Phe Val Cys Ser Glu Gln
145                 150                 155                 160

Phe Asn Tyr Thr Thr Ala Leu His Asn Ser Thr Phe Phe Ser Leu Asn
                165                 170                 175

Ser Ala Leu Tyr Cys Phe Thr Asn Asn Thr Tyr Leu Gly Ile Leu Pro
            180                 185                 190

Pro Asp Leu Thr Asp Phe Thr Val Tyr Arg Thr Gly Gln Phe Tyr Ala
        195                 200                 205

Asn Gly Tyr Leu Leu Gly Thr Leu Pro Ile Thr Val Asn Tyr Val Arg
    210                 215                 220

Leu Tyr Arg Gly His Leu Ser Ala Asn Ser Ala His Phe Ala Leu Ala
225                 230                 235                 240

Asn Leu Thr Asp Thr Leu Ile Thr Leu Thr Asn Thr Thr Ile Ser Gln
                245                 250                 255

Ile Thr Tyr Cys Asp Lys Ser Val Val Asp Ser Ile Ala Cys Gln Arg
            260                 265                 270

Ser Ser His Glu Val Glu Asp Gly Phe Tyr Ser Asp Pro Lys Ser Ala
        275                 280                 285

Val Arg Ala Arg Gln Arg Thr Ile Val Thr Leu Pro Lys Leu Pro Glu
    290                 295                 300

Leu Glu Val Val Gln Leu Asn Ile Ser Ala His Met Asp Phe Gly Glu
305                 310                 315                 320

```
Ala Arg Leu Asp Ser Val Thr Ile Asn Gly Asn Thr Ser Tyr Cys Val
                325                 330                 335

Thr Lys Pro Tyr Phe Arg Leu Glu Thr Asn Phe Met Cys Thr Gly Cys
            340                 345                 350

Thr Met Asn Leu Arg Thr Asp Thr Cys Ser Phe Asp Leu Ser Ala Val
        355                 360                 365

Asn Asn Gly Met Ser Phe Ser Gln Phe Cys Leu Ser Thr Glu Ser Gly
    370                 375                 380

Ala Cys Glu Met Lys Ile Ile Val Thr Tyr Val Trp Asn Tyr Leu Leu
385                 390                 395                 400

Arg Gln Arg Leu Tyr Val Thr Ala Val Glu Gly Gln Thr His Thr Gly
                405                 410                 415

Thr Thr Ser Val His Ala Thr Asp Thr Ser Ser Val Ile Thr Asp Val
            420                 425                 430

Cys Thr Asp Tyr Thr Ile Tyr Gly Val Ser Gly Thr Gly Ile Ile Lys
        435                 440                 445

Pro Ser Asp Leu Leu Leu His Asn Gly Ile Ala Phe Thr Ser Pro Thr
    450                 455                 460

Gly Glu Leu Tyr Ala Phe Lys Asn Ile Thr Thr Gly Lys Thr Leu Gln
465                 470                 475                 480

Val Leu Pro Cys Glu Thr Pro Ser Gln Leu Ile Val Ile Asn Asn Thr
                485                 490                 495

Val Val Gly Ala Ile Thr Ser Ser Asn Ser Thr Glu Asn Asn Arg Phe
            500                 505                 510

Thr Thr Thr Ile Val Thr Pro Thr Phe Phe Tyr Ser Thr Asn Ala Thr
        515                 520                 525

Thr Phe Asn Cys Thr Lys Pro Val Leu Ser Tyr Gly Pro Ile Ser Val
    530                 535                 540

Cys Ser Asp Gly Ala Ile Val Gly Thr Ser Thr Leu Gln Asn Thr Arg
545                 550                 555                 560

Pro Ser Ile Val Leu Leu Tyr Asp Gly Glu Val Glu Ile Pro Ser Ala
                565                 570                 575

Phe Ser Leu Ser Val Gln Thr Glu Tyr Leu Gln Val Gln Ala Glu Gln
            580                 585                 590

Val Ile Val Asp Cys Pro Gln Tyr Val Cys Asn Gly Asn Ser Arg Cys
        595                 600                 605

Leu Gln Leu Leu Ala Gln Tyr Thr Ser Ala Cys Ser Asn Ile Glu Ala
    610                 615                 620

Ala Leu His Ser Ser Ala Gln Leu Asp Ser Arg Glu Ile Ile Asn Met
625                 630                 635                 640

Phe Gln Thr Ser Thr Gln Ser Leu Gln Leu Ala Asn Ile Thr Asn Phe
                645                 650                 655

Lys Gly Asp Tyr Asn Phe Ser Ser Ile Leu Thr Thr Arg Ile Gly Gly
            660                 665                 670

Arg Ser Ala Ile Glu Asp Leu Leu Phe Asn Lys Val Val Thr Ser Gly
        675                 680                 685

Leu Gly Thr Val Asp Gln Asp Tyr Lys Ser Cys Ser Arg Asp Met Ala
    690                 695                 700

Ile Ala Asp Leu Val Cys Ser Gln Tyr Tyr Asn Gly Ile Met Val Leu
705                 710                 715                 720

Pro Gly Val Val Asp Ala Glu Lys Met Ala Met Tyr Thr Gly Ser Leu
                725                 730                 735
```

```
Thr Gly Ala Met Val Phe Gly Gly Leu Thr Ala Ala Ala Ala Ile Pro
            740                 745                 750

Phe Ala Thr Ala Val Gln Ala Arg Leu Asn Tyr Val Ala Leu Gln Thr
        755                 760                 765

Asn Val Leu Gln Glu Asn Gln Lys Ile Leu Ala Glu Ser Phe Asn Gln
    770                 775                 780

Ala Val Gly Asn Ile Ser Leu Ala Leu Ser Ser Val Asn Asp Ala Ile
785                 790                 795                 800

Gln Gln Thr Ser Glu Ala Leu Asn Thr Val Ala Ile Ala Ile Lys Lys
                805                 810                 815

Ile Gln Thr Val Val Asn Gln Gln Gly Glu Ala Leu Ser His Leu Thr
            820                 825                 830

Ala Gln Leu Ser Asn Asn Phe Gln Ala Ile Ser Thr Ser Ile Gln Asp
        835                 840                 845

Ile Tyr Asn Arg Leu Glu Glu Val Glu Ala Asn Gln Gln Val Asp Arg
    850                 855                 860

Leu Ile Thr Gly Arg Leu Ala Ala Leu Asn Ala Tyr Val Thr Gln Leu
865                 870                 875                 880

Leu Asn Gln Met Ser Gln Ile Arg Gln Ser Arg Leu Leu Ala Gln Gln
                885                 890                 895

Lys Ile Asn Glu Cys Val Lys Ser Gln Ser Ser Arg Tyr Gly Phe Cys
            900                 905                 910

Gly Asn Gly Thr His Ile Phe Ser Leu Thr Gln Thr Ala Pro Asn Gly
        915                 920                 925

Ile Phe Phe Met His Ala Val Leu Val Pro Asn Lys Phe Thr Arg Val
    930                 935                 940

Asn Ala Ser Ala Gly Ile Cys Val Asp Asn Thr Arg Gly Tyr Ser Leu
945                 950                 955                 960

Gln Pro Gln Leu Ile Leu Tyr Gln Phe Asn Asn Ser Trp Arg Val Thr
                965                 970                 975

Pro Arg Asn Met Tyr Glu Pro Arg Leu Pro Arg Gln Ala Asp Phe Ile
            980                 985                 990

Gln Leu Thr Asp Cys Ser Val Thr  Phe Tyr Asn Thr Thr  Ala Ala Asn
        995                 1000                1005

Leu Pro  Asn Ile Ile Pro Asp  Ile Ile Asp Val Asn  Gln Thr Val
    1010                1015                1020

Ser Asp  Ile Ile Asp Asn Leu  Pro Thr Ala Thr Pro  Pro Gln Trp
    1025                1030                1035

Asp Val  Gly Ile Tyr Asn Asn  Thr Ile Leu Asn Leu  Thr Val Glu
    1040                1045                1050

Ile Asn  Asp Leu Gln Glu Arg  Ser Lys Asn Leu Ser  Gln Ile Ala
    1055                1060                1065

Asp Arg  Leu Gln Asn Tyr Ile  Asp Asn Leu Asn Asn  Thr Leu Val
    1070                1075                1080

Asp Leu  Glu Trp Leu Asn Arg  Val Glu Thr Tyr Leu  Lys Trp Pro
    1085                1090                1095

Trp Tyr  Ile Trp Leu Ala Ile  Ala Leu Ala Leu Ile  Ala Phe Val
    1100                1105                1110

Thr Ile  Leu Ile Thr Ile Phe  Leu Cys Thr Gly Cys  Cys Gly Gly
    1115                1120                1125

Cys Phe  Gly Cys Cys Gly Gly  Cys Phe Gly Leu Phe  Ser Lys Lys
    1130                1135                1140

Lys Arg  Tyr Thr Asp Asp Gln  Pro Thr Pro Ser Phe  Lys Phe Lys
```

1145 1150 1155

<210> SEQ ID NO 9
<211> LENGTH: 25498
<212> TYPE: DNA
<213> ORGANISM: Artificial Sequence
<220> FEATURE:
<223> OTHER INFORMATION: Porcine Deltacorona Virus BIV-Isolate 5.0327
Genome cDNA

<400> SEQUENCE: 9
ctttgagcac ctgaaaccaa gacgcgtcag tagtagggac tactggtgca gccatgatag 60
attggtgtcg gtagagaact agcgaagcta gggagataaa attatagact aatgctataa 120
tttttatctt tagtctataa ttttatctcc ctagcttcgc tagttctcta ccgacaccaa 180
tccaggtgcg tctgccacca agttggctac ccttcctagg ggcgctttcg cgcttgctca 240
ccattagatt acctggaaac cagccattca ggttggagtt tccccaggct cttttgtgtg 300
ggcattagcg gcttgtggtt tttgcacaaa atctaagcta cttaccgttc ctctgaccat 360
ccaccacttc tatagacagc actgattacc gtagggttta agtcacaccg gtctgcaccg 420
cccgtcagcg gacacattac ccagcatagc actccttgca ccgcgcctag gtaggataaa 480
accccctacc gggtgactct taaggcgttt cctccacggg atagccacta gtcactaggt 540
gtaagtgatc tgatctgggc gtattgtgtt gcgcaagtgt gatacccata ggagcgtgga 600
atcctattct gcggctcagt gcctgatata gctgtgaaat ggccaagaac aagtccaagc 660
gcgacgctat tgcgttgcct gaaaatgtac caccacctct gcaacttttc attcatgttg 720
cagctgctga agagggtcac cctaaggtta ctacttacct tggcaactat aacctctatg 780
ccaccaaggc tccgcctggc gtgcaggttc ttagtgctaa aacctctctt actgactttg 840
agaatgtctt tggagctcaa cccaccttgc gatcaattcg taatctggtt tgtgaggctc 900
gctcggctga atggacaact tccaagaatg cttttgcact caaagccact caacttgact 960
actctgatgc cgttttgagg gcaatgattc gtttctgccc tccaaaggtg tccacactcg 1020
ctgcctttgc tctttttggc cgattggtta aaattgagga caaggaactt gctgagttag 1080
ctcgtgatac tgcccttgag ttggcgtaca cggctaaaat tggtacatct cttgctgaca 1140
cgagatctgt ctcacttatt cataaggacg cttatctaac tctcagtaat gaggttgttg 1200
gcgtaacttt tactgccgca cttatggcaa aggctaccac tgttaatgga gcaatgcaat 1260
actcaaactt ttacctctac cctcgtgcca ctattaaggt aaccgatggt aaggctgaag 1320
caattgcaac taagcctctg tctgctgcca ctaaaggcaa gcaaatcaca gaggatgtca 1380
accttctccc tgactatcag cagctgcttg ttgatcaagt gactggcact gaggttaagg 1440
ttggagctct aacctatgtt aagaccactg attcgccacc cctttacttt cccaaagtca 1500
agggtggtgt tattggtatt gcacttaagc agcagggcac tgtggctaag aagctcaatg 1560
tagtcttcca tgctcaacct gatgatgttc tgctagcctt catacaactt cagcaattct 1620
tgaaccgtac ttcggattca agtgttgaaa ttactgattg ccagagttat gaagtatctc 1680
caactgtgac ggtcaaaatt ggcccgtcta aacctgggga tgtcatcgtg gctactgatg 1740
aggaatacct taaatgcttt gaaacccctg aggtaggtag gctctataag gttttccaaa 1800
ctcaatcttg ggctatcatt gagcgtgcct tctccagttt gaagatccgc gtgtccaaag 1860
ctttatcagc atttataagt tttctgcaaa accttgcaga taactttact gcaataagtg 1920
gtgttgtcac tgcactcatt cgtgaactcc aggatcttac cctggatgtg gcgacacgta 1980

-continued

```
tcactaacat acaatttgtt taccgtgccg gtaagcttat tgtcgacacg acaagtgtca   2040
tagctaaact tttccagcca ttttgtgatt ttatatcacc tttccttcgg aaagttgctg   2100
gttttgcaat ttacactgtt ggtaatcgca tgcttatgtt taccagcact ggcacctttc   2160
ttctcacaaa ggcaactact aagatactca ataaggcaaa gtacatcttt gatgtggagc   2220
ctgagtaccc agtagatgta acaacatcca aagttgtagt acatgaagca ctccagcaaa   2280
ccgacactaa gcctactaga gctctggagg ctgttgatgt cgttgttggt aatactgtac   2340
tgcaaatggc tactgatggc actgcgttct acccatcgga tggtacgcac gcctctcttc   2400
caggattcaa agcaggttcg gatgagcttt tcataagctt caactgcgac ctctttgatg   2460
atgagactaa tgctcaaatc aacgaaacac tcgctgcata tgagcttaac caactagtgg   2520
ctccaggtga ttctacaccg cgtcaaattg cgacgttggt tgtcgataca cttgcagatg   2580
ctataacaga ccactttccg gagaaaacca ttgatctacc tgaagactat caagtctttt   2640
ctgaccatga tgacctccca ctcgcacaat accacatccc tgatcacctg agcctgtata   2700
ttcaggctat ggaaggtgaa gatgatagtg gtgatgaaat atgtattgag gacgatgatt   2760
acgactgtcc tcaagccgac gaagacacag aaggagtaat tccccaacag tgggaacttc   2820
ctgatgttga taaattttta ctcaagatcc aggaacggaa gaccagcagc gacgaagtac   2880
ttagcgtcga cgtctatcct aaaccagagc cggtcggcaa tgttgggatt gacgacagcg   2940
cgtcggaaaa gaagccaaat ggggactcag taccggatcc tgaggtccat ccaacactag   3000
agagtgtgga tgttgaacga ccaaccgaaa cagcaaacca ggctgttgaa gacaaacctt   3060
ctgataccac ctttgtggtt gatgaggaac aattacaaga atcaacacca gaacatgaac   3120
tccgctccta tgaaggggag tttgattctg atgatgaaat tattattcct atagtaccag   3180
taacacctgc ggatttaaaa ccacagacta ttactataaa ggagtacttt aagtctgaaa   3240
aacttgagac tattaacgaa ggatccacag agtcagttac acaatctgac gattcgtttg   3300
acgagtcatt tgttgatgct gagtctgatg atccacaaga tcctgctgta tatgatgata   3360
caacaattat aacggacagc actgatgtag gcgatgagcc tgagacaact ctagctacca   3420
tcgttaacac acctctgaca ctcgataata acttgccacc tgaagccatt aaacaaccca   3480
gcccaactaa ggttgagtta gttgttggtg aattggcgag tattaaattt gacaattctg   3540
ttctagtcaa ccctgctaat gcgcaattaa caaatggcgg tggagctgct cgtgcaattg   3600
caaaattagc tggtccaaaa tatcaagagt actgtaatag tgtggctcct atctcaggac   3660
cgcttaccac ggactctttt gatgccaaga aatttggtgt agcctgcatc ttgcatgtag   3720
tgccacccaa aggttctgac cctaatgtac aagaactcct gtatcaagct tacaagagta   3780
tccttactga accagcacac tatgttatac ctatactagg tgctggtatc tttggatgca   3840
acccagtcca ctctctggat gcgttcagga aagcatgtcc aagtgacata ggtcgtgtca   3900
cccttgtcac tatgaacaaa aaccatttgc aggtgtggga tgctctcaat aggaccattg   3960
tacgcaccac tactgactat gatcaagtta ccaccaaggc ccttacaccc cagggagtgt   4020
tagaagccaa tctctttgat ggtgaggact ttgttcaaga accaaaaccc ggtcaaatct   4080
accttgaggt tactgaagaa gttcagaacc aagccaagga acttgacctt aaccttcagc   4140
aatactgcgt ctacctgaag acttgccacc ataaatgggt tgtgagtcgt acgaacgggt   4200
tgatgcatct aaaacaaaaa gataacaatt gttttgttag tgcaggtgta aacctgtttc   4260
aaaacactgc ttatcaactt agacctgcta ttgatgctct ctatagggag tatcttaatg   4320
gtaatccaaa tagatttgtt gcttggatct acgcatccac taaccgtcgt gttggtgaga   4380
```

```
tgggttgtcc acagcaagtt atttctttgc tcgttagtaa ctctgacgca gcattttcag   4440
caactacagc ctgttgtaac acctacttta accacacagg tgttatttca gtagctcgtg   4500
aatatgaccc aatacaacca aaggtctact gcatgaagtg tgatgtgtgg actcccttta   4560
caccccagag tggaaaaggt gcagttgcaa ttggtatttc tgcagatgaa cctaccggtc   4620
ctgccattaa atttgccgca gctcactgct ggtacactaa tggcaagaaa acagttaatg   4680
gctatgacac taaagctaat gttgtagcta cctatcatag gtttgacgtg cctaagcctc   4740
aacttgtcga ggacgtggtt gcgctgccta ctaaaaatga ctttgaagtt ctcaatgttg   4800
aagaactgcc gcaggatagt gtgctccatt tggacccacc tcctgtacag gccttacaac   4860
ctaaggctaa ccaacacatt gagattctag aaaacccaga ttatctggac attttggatc   4920
tttggattcg taaacccaaa ttcatcctcg taaagtcgtg gagtgttttg ggtagagcac   4980
tatgtaaggc aggtaaagtt gtctttgtca gtgcttcgct tttgacccgt ttctacaatt   5040
accttgtaga gattggtgct cttgactcaa caataaggtt gtcagtcgat cttacctgta   5100
aatttgttag aacggttctc ccatcgtcta acactgtaca caaaacttgt cttggtctgt   5160
attattcagc ccagacactt tttgtttctt tagcaccatt ccttatgtta ccagctgtag   5220
ttagtctgct taattcaggc tatacaattg gcacatattt gtatgcaaaa actggctggc   5280
cttgtaatta caatgccacg caacactttg attataattc ttactgtgca ggtgacttgg   5340
tttgtcaagc ctgttttgac ggtcaagact ccctacattt gtatccgcat ttacgtgtta   5400
atcagcagcc ccttcagacc actgactaca ctgtttatgc gctttcacta atactactat   5460
tagctaacat gactcttgtc atgggcacgc taatagttac tttctttgtg aacttctatg   5520
gtgtgcaaat accattttat ggtacacttt tgatagatta tcaatccgca ctggtgatta   5580
ctttctcagt gtactacttt tataaggtaa tgaagttttt ccgccatctc acacatggat   5640
gtaaaattcc aacgtgtgtg gtatgtgcca aacttcgtac ccccacctact ataacagttg   5700
agactgtcgt tcagggcagg aaatacccat ctgttattga aacaaatggc gggtttacaa   5760
tttgtaaaga acacaacttc tattgcaagg actgctcttt acaaacaccc ggcactttca   5820
tcccgacaga agctattgag tcgctctcac gagctaccag gcttagtgtc aaaccaacag   5880
caccagcatt cttacttgct agagatgttg agtgccaaac tgatgttgtc gttgctcgcg   5940
caatgcataa ccaaaatgcg catgtgtgca tttcaaaata ctctgatatc cgtaccgttg   6000
accaactact taagcctact ccactgtttt catacactcc cgatgttatc atcgcggcag   6060
actttgacaa cagaggtagt cttaagacag ctaaagaatt agctgtggtt ttgtcaatgg   6120
accttaaacg tactataatt atcattgatc aggcctattc tagacctatt gataattatc   6180
aggaagttgc ttctcgtatt gagaagtatt acccagttgc aaagatcaca cccacaggtg   6240
acatctttac agacattaag caagcgacca atggccaagc tagtgactct gctattaatg   6300
cagctgttct ggctgtccag cgcggtcttg attttacaat tgacaaccct aacaacatat   6360
taccacatta cgcctttgac ttttcaaccc tcaatgcaga agaccagtct accattttgg   6420
agagtggttg tgctaaaggc aatctcaagg gcactaatgt tggtgttgtt ctttcagcta   6480
gccttgttac acgtcttagt cagcaggcta tacgtgtgat tgctaatgct gcttcacgta   6540
atggtgttac atgcgctgtt actccttcta cacttgttat gcgtgggaat attgcaacac   6600
agcccttgac tcgcatcaaa gctggtgcac ctcccatgcg tcaaaaaatt ttatgtgtta   6660
tcctggcact tgctattgtg tactttgctg ctatggcttt tggctttttg gcaagtcaaa   6720
```

-continued

```
ttacgcttaa tacagtgcct acgattaaat ctgatatccg cgcctctacc ttctacgttg   6780
ttagagatgg agtcttggat actgttcgtt caaatgacaa gtgctttgca aataagtttt   6840
tggcatttga tagcttcatt caagcacctt acactaattc acctgactgt ccagttgttg   6900
tgggagttgt tgatgtaacg acgcactcta ttcctggaat tccagcaggt gtcattcata   6960
gagacggtct catacttaac atttatgaac agtctcttta tgaaactcat cagcgtcagt   7020
ctatggttag ggatgcgttg tcactcaaga cagcaaatct ctttaaccta ggcaagcgtg   7080
ttgtagtagg atacactcaa catgaagttg ttgtgggtac ctcctatttt aattctcctg   7140
cactttttaa tgcaaagtgc accttcttac agtatcagga cactagacaa ctctattgct   7200
atgatactgt tcctactgaa cataagctct actctgatgt gcttccgcac gtcgagtata   7260
aggctattga cattaatggt gatcttgttc ctttcaagat accagagcag ataatgttct   7320
atccacatat tgtgcgctat actagcaatt cctattgccg tatggggcat tgttttaata   7380
ctaaccctgg tatttgcatt tcatttacgg acgaatttcc gtatagtgaa aatgtcaaac   7440
ctggtgtgta ctgtgctgat acctctttgc agttgttttc aaacctcgtt ttgggcactg   7500
tatctggtat tcacatcttt acatcaacag ctgcattgct tggatctact attgtgatca   7560
tactatgcgt tgttgctgtt cttgcagttc agcgattctt caaggagtac acaacttttg   7620
ttatgtacac ttgtggtctt gctcttgtca acattgtagg cattgcactt atgtacaagt   7680
gccttgtctt cgcgattttc tattatgcaa tctaccttta ctttgtcctt actttcccct   7740
cctttaagag gaatgtggca ttgttttact tcgctgtagt gatcgtgccg cacgtgagta   7800
acatgcaatt gcttgcgctc attgtgtgta gcattatcta ctttctctac acctatgttc   7860
atactgtagc taagacagct gggaaatttt cttccttctt agacgcagct aaagctactt   7920
ttgtcattga caatgaaaag tacgtgttgc ttaaagacct cgctggtgct gaatttgacc   7980
agtatctggc ctcttacaac aagtacaaat atttttctgg tactgcttct gataaggatt   8040
atgataaggt ctgtatggca tttcttgcca aggctttgtc atcttttcgt gaaggaggcg   8100
gttcacagtt gtacacacca cctaaatttg cagttgttca gagtcttaag accaagctgc   8160
aagcaggtat caaaatcctc ctgcaccctt caggtgtagt tgagcgatgt atggtctcag   8220
ttgtctacaa tggatctgca ttgaatggca tctggcttaa gaatgttgtc tactgcccac   8280
gccatgtaat tggaaaattc cgtggtgacc agtggactca catggtctca attgctgatt   8340
gccgcgactt tatagtcaag tgtccaatac agggtattca gctaaatgtc caatcagtta   8400
agatggtagg agctctcctc cagttaactg ttcataccaa caacacagcc actccagact   8460
ataagtttga aaggctacaa ccaggatcat cgatgacaat tgcttgtgct tatgatggca   8520
ttgtacggca tgtctatcac gtggtcctcc aacttaataa tcttatttat gcaagcttcc   8580
ttaacggagc ttgtggtagt gtgggttaca ctcttaaggg taaaacactc tacttacatt   8640
acatgcacca cattgagttt aacaacaaaa ctcatagtgg tacagatctt gaaggtaact   8700
tctatggccc ctatgtggat gaggaagtta ttcagcaaca aacagcattc cagtattaca   8760
ctgataatgt tgttgctcaa ttatatgcac acttactgac tgttgatgct agaccaaaat   8820
ggctggcaca atctcagata agtatcgagg atttcaactc atgggctgct aacaattcct   8880
ttgctaactt cccatgtgaa caaactaata tgtcctacat tatgggactc tcgcaaacag   8940
ctcgagtccc tgtagaacgt atcctcaata ccattataca gctaaccacc aatagagatg   9000
gtgcttgtat tatgggatct tatgatttcg agtgcgattg gacgccagag atggtataca   9060
atcaggctcc aatttcattg cagtcaggag tagttaagaa aacttgtacg tggttcttcc   9120
```

```
acttcttgtt tatggctatt accatgctac tcgctgccat gcatgttttc cctgtacact   9180
tgtatccaat agtactgcca tgcttcactg tcgtggcatt cctgttgact ttaaccatta   9240
aacacactgt tgtgtttacc actacatact tgcttccgtc acttttgatg atggttgtaa   9300
atgctaacac tttttggata ccgaacacat ttctgcgcac ctgctacgaa actatattcg   9360
gttccccaat tgctcagcga ctgtatggtt acactgttgc tctttatatg ctgatctatg   9420
ctggacttgc aatcaactat acgttgaaaa cactccggta tagagcaact tcattcttat   9480
ctttttgcat gcagtggttt caatatggtt atgttgcaca cattgcgtac aaactgctta   9540
ataaaccctg gacagaatca ctactcttca cagccttcac aatgctaacc agtcatccct   9600
tgttggctgc tcttagctgg tggctagctg gtcgcgtaac tctgcccatt atcatgcctg   9660
acttagctat tcgtgttttg gcgtataacg tcattggcta tgtcatatgt gttcgatttg   9720
gccttatgtg gcttgcaaat cggttcacaa ctgtacctat gggcacatac cagtatatgg   9780
tgtctgtaga gcaacttaag tacatgatgg cagttaagat gtccccaccg cgtaatgcgt   9840
ttgaggtgct tatagccaac attagacttc ttggtttggg tggaaaccgt aacattgctg   9900
tttctactgt ccaaaacaaa attcttgatg caaaagctac tgctgttgtt gttgctaacc   9960
ttcttgaaaa ggctggcgtc acaaacaagc acgctatttg caaaaagatt gtgaaactcc  10020
acaatgatac ccttaaagcc accacttatg aggaggttga ggtagcactt gtgaaacttc  10080
tttctcacat aattgagttc ttgccaactg atcaggtaga tgcttatcta gctgatgcgg  10140
ccaatgctca acatgttaat acctatttag acaacttgct tgagaacaaa gctgttgttc  10200
aggctgttgc cgatatcaac attaatctgg attcttatag aatttataag gaggcagatg  10260
ctatttataa acgatctgtt gagatgaacg aatctccgca ggagcaaaag aaaaagctta  10320
aagctgttaa cattgcaaag gcggaatggg agcgtgaggc tgcttctcag cgtaagcttg  10380
aaaagcttgc tgatgctgct atgaagtcta tgtatcttgc agaacgtgct gaggatcgtc  10440
gcattaagct aacctctgga cttactgcaa tgctttacca tatgcttaga cgtcttgact  10500
cagatagggt aaaagctctg tttgagtgcg ctaaggcaca aatcttgcca atacatgctg  10560
tagtcggaat ttctaatgac aaccttaaag ttatttttaa cgataaggac agctactctc  10620
attatgtaga gggcaacaca cttatacata agggagttcg ctacactatt gtgaagaaac  10680
tctccttaga taatgcacct attgaaggcg taccagaaga attccctgtg gtcgttgaga  10740
ctgttaggga aggtgtgccc cagttgcaaa ataatgagct atgtttgcgc aatgttttca  10800
ctgctcagaa cacagctcag gacttcaatg gcaatgaatc cactgtaaaa tctttttatg  10860
ttactagaac cggtaagaag attttggttg ccattacatc aactaaagac aatcttaaga  10920
ctgtgacctg ccttactgag accggtaaga cagtccttaa cttggacccc cctatgcgct  10980
tcacacatac cgtaggtgga aaacagtctg ttgtctatct ctattttatt cagaatatta  11040
gttcactcaa cagaggtatg gttattggcc acatctctga aactactatc cttcaggcaa  11100
gtggcactca aattgagtac cagcaaaatg cctctctttt gacctatttg gctttcgctg  11160
tagaccctaa gacagcctac cttaagcatc ttgctgatgg tgggtctcct atacagggtt  11220
gtattcagat gattgctact atgggtcctg gatttgcagt tactactaaa ccacaaccta  11280
atgagcatca gtattcttat ggtggtgctt caatttgtct ttattgccgt gctcatatac  11340
cacatcctgg tgttgatgga cggtgcccct acaaaggccg ctttgttcac atcgacaaag  11400
ataaggaacc tgtttccttc gctttgactc atgagccatg cagttcttgt caacggtggg  11460
```

-continued

```
ttaattatga ctgcacctgc ggatctagtc tgcagaattc ggcttattta aacgcgtaac  11520
gggttctagt gacgcccggc tagaacccct gcagcctgga actcaaccag atgctgtaaa  11580
aagggccttc catgtgcata atgataccac ctctggtata ttcttaagca caaaatctaa  11640
ctgcgctcgg tttaaaacca cacgcagtgc cctgccttta cctaataagg gagaggttga  11700
attgtacttt gttactaagc agtgtgcagc taaagtcttc gaaatcgagg aggaatgcta  11760
caacgctctt agtacagagc tttatactac tgatgataca tttggtgtcc ttgccaaaac  11820
tgagttcttt aagtttgaca agatacctaa tgtcaatcgc cagtatctga ctaaatatac  11880
actcctggac ttggcttatg ctctacgtca tttgtcaaca tctaaggatg ttattcaaga  11940
aatcttgatc accatgtgcg gaacccctga agattggttt ggggaaaatt ggtttgatcc  12000
aattgagaac ccatcctttt acaaggagtt ccataaactt ggggatattc ttaaccgttg  12060
tgttcttaat gccaataagt ttgctagtgc ctgtatagac gctggtcttg ttggcatatt  12120
aacacccgac aaccaagacc tcctgggtca gatctatgac tttggagatt ttattattac  12180
acaaccaggt aatggatgtg tggacttagc atcctattat tcttatttaa tgcccattat  12240
gtccatgact cacatgttaa agtgtgagtg tatggatagt gatggcaacc cacttgagta  12300
tgatggattt cagtatgact tcacggactt caagcttggc ttgttcgaga agtattttaa  12360
gtactgggac cgtccttacc atcctaacac tgttgaatgt ccagatgacc gttgcgtatt  12420
gcactgtgcg aacttcaatg tgttgtttgc tatgtgtata cctaatacgg catttggcaa  12480
tctttgttca agagctactg ttgatggcca ccttgtggtc cagacagtgg gtgtacactt  12540
gaaagaacty ggtatagtcc ttaaccagga cgttaccaca cacatggcaa atattaatct  12600
aaacactcta ttgcgattgg ttggtgatcc caccactatt gcaagtgtct cagacaagtg  12660
tgtagattta agaactcctt gtcagacctt ggctactatg tctagcggaa ttgctaaaca  12720
gtcagtcaag cccgggcatt ttaatcaaca cttctacaag catttgcttg atagtaacct  12780
attagaccaa cttggaatag acattcgcca cttctactat atgcaggatg gtgaagcggc  12840
tatcacagac tacagctact acaggtataa tacccccacg atggtagata tcaagatgtt  12900
cttattttgc cttgaggtgg cagataagta tcttgagccc tacgaaggtg gatgtattaa  12960
tgcacagtca gttgtggtct ctaatttgga caagtcagcg ggctacccct ttaacaagct  13020
aggtaaggct cgtaactatt acgacatgac tcatgccgag caaaatcaac tgtttgagta  13080
tacaaaacgc aatgttttgc ctacactcac tcagatgaac cttaagtatg caatttcagc  13140
caaggatcgt gctcgcactg tggcaggagt gtctataatt agcaccatga ctaacaggca  13200
gtaccatcaa aagatgctga aatctatttc acttgcacgc aatcagacca tcgtgattgg  13260
aacaaccaaa ttctatggtg gttgggacaa catgttacga cgactgatgt gtaatatcaa  13320
caatcccatt ttagtgggtt gggattaccc taagtgtgat cgttctatgc caaacatgct  13380
gcgcattgcc gcttcgtgct tgctagcacg aaaacacact tgctgtaacc aaagccagcg  13440
attctaccgt ttggctaatg aatgttgcca agtactatct gaagtggtag tctctggtaa  13500
caacctctat gtaaaaccag gtggcactag cagtggtgat gcaaccacag cttatgccaa  13560
ctcggtattt aacatcttac aggtggtttc tgctaatgta gccaccttct tatcaacttc  13620
caccacgaca catcttaata aggacattgc ggacttgcat cgtagtcttt atgaagatat  13680
ttatcgtggt gactctaatg atatcaccgt catcaataga ttctaccagc atctccaaag  13740
ttactttgga cttatgatat tgtctgatga tggtgtcgca tgcatagact cagccgttgc  13800
aaaggctgga gctgttgctg atcttgatgg tttccgagac attttgtttt accaaaacaa  13860
```

tgtttacatg gcagactcaa agtgttggac agaaactgac atgaatgttg gccctcatga 13920
attttgctca cagcatactg tgttagcaga gcatgatggt aaaccttact acttacctta 13980
cccagatgtc tctcgcattc tgggtgcatg catctttgtg gatgacgtta acaaggctga 14040
ccctgttcag aaccttgaac gttacatctc acttgcaatt gatgcatatc ccctcaccaa 14100
ggttgaccct attaagggta aagtctttta tttgttacta gactacatac gtgttcttgc 14160
tcaggagtta caggacggta tccttgatgc tttccaatca ctcactgaca tgtcgtatgt 14220
aaataacttt atgaatgagg ccttttatgc tcagatgtat gagcaaagtc ctacactaca 14280
ggccagcggt gtttgtgtgg tgtgtaattc acccactata ctgcgctgtg gtgattgcat 14340
tcgtcgacca ctactttgtt gcgtctgtgc ctaccagcat gttacgcaga ctacacataa 14400
acgtatcatt gctatcaaca actacatctg tagtgttgag aattgcaatg aggacaatgt 14460
tgaaaaactt ttcatttctg gcactgcgat ttattgtgag aatcacaaac ccacgctgtg 14520
catacccatt gtagctaatg gttctgtttt tggtatctat cgccacactg cccgtggtag 14580
tgatgacata gacctcttta acgagcttgc tacatctaac tatgacacta ttgaacctta 14640
tcagaaggcc aatcgtgcac ctttatcact tatgctcttc gctgctgaaa ccattaaggc 14700
actcgaggag tctatcaaga agtcatatgc taccgcaacc gtcaaggatg tgtatgacca 14760
acgcttcatt aaacttctat gggaacaggg taaaaagccg ccacccataa cgaagaacca 14820
cattttcact ggctaccatt ttaacaagaa tggaaaaacc caagttggtg attacattct 14880
tgctaaaaca gatggcagtg acacttatac ttacagagga acatctacct acaaactcca 14940
aacaggtgat gttctagtct taatggcaca tgttgttaca ccgctctcag cacccccctgt 15000
gttaacgcag acaacatatg tcagaaaatc acttttaccc gactctgttg gtgcgtctta 15060
ttatgtgcaa cattttaagt catataatga gatagctatg cagagggtta caacagtatt 15120
aggtccacca ggcacaggta agtcaacctt tgctattggt ttggctaagt actttcccag 15180
tgcacgtatt tgctacactg cgtcttcgca tgcagcaatc gatgcactct gtgaaaaagc 15240
tttcaagaca atacctgtag gccaatgcag tcgtatcgta cccacacgta caactgttga 15300
gtgctttcag gagtttgtcg taaataacac aactgcacag tatatcttct cgactatcaa 15360
tgccttacct gacattaagt gtgacattgt agttgtagat gaggtttcta tgttgaccaa 15420
ttatgagctt tcctctgtga atgctcgttt ggtttacaat cacattgtgt atgttggtga 15480
tccttatcag ttaccttcac ctagaactat gcttacgtct ggccagcttt cgccagctga 15540
ctataacgta gttactgata taatggtaca tgcaggagcg gatgttatgc tcgacatgtg 15600
ctacagatgc ccacgtgaaa tcgttgagac agtgtctaaa cttgtctacg ataacaaact 15660
aaaagcggcg aaaccgaact caagacagtg ttacaagacc attgtgaact ttggtcctgg 15720
agacgttgct catgagggac aatctgccta caacgaagca cagttgcgtt tcgcactcgc 15780
atttagacaa caaaagcggt gggataacgt gactttcata tctccatata atgctatgaa 15840
tgtgaaagca tccttagcag gtttctctac tcagaccgtt gactcttctc aaggttctga 15900
gtatgattat gttatctttt gcgtgaccac tgattcagca cacgcactta acatggctcg 15960
tttgaacgtt gcccttacac gcgcaaagat aggtatcctt gtggtgttta ggcaggcaaa 16020
cgaactttac aatagtttgc agtttgaatc tattgattca cagcttcagt cgagtgctga 16080
gaaaaacctc acaccactgt ttaagcgctg cggctatgag tataatggcg tccatccagc 16140
tcatgctttg acctggcatg attgtggtgc agagtaccgc tgtgaggagc cacttgctaa 16200
attagtagga gttgccgatg gcactcttat atcatacaaa accctagtat ccacacttgg 16260
gtttcttcca tcacttaaaa ttgatgcata tcataatatg ttcctaacac gtgacgcgtg 16320
tcgcacctat gttcagagtt ggatcggcat agatgttgaa gcagcacacg ccataaaacc 16380
taacaccggg actaacctgc cattgcaaat aggttttagt accggaaaga atttttcagt 16440
cactccagag ggaatttggg taaacgagca cggatcttgc actgagcccg tccctgccaa 16500
aatacctcct ggagaacaat ttcgtcacct taaaaaggac atgcgccagg cgcgtccttg 16560
gaaggttgtt cgacgtgaga ttgctactca cattgctgag gtagctcctc acactgatta 16620
tatatgcttt gtcacttggg ctcaccagct tgagctagcg acaatgcgct actttgtcaa 16680
actaggtatg gaagagaaat gcttttgtgg caggcgggct tgtttcacta atggaactga 16740
gttcgcttgc aaagcacacc attctctcac cattccacaa tgtgattatg tgtacaatcc 16800
attcctcatc gacgtggcta cgtggggatt ctcgggacgg ctttccacca accatgacgc 16860
tgtgtgcaca tatcatgcta atgcccatgt tgcatcagct gatgcaatca tgacggtatg 16920
tttagctatc catgaactgt tcagtactgt tgactggaac tttgaatttc cagtaactgc 16980
tgagcaatcg caacttaaca aggcctgtcg cttagtacag gcgaattact taaatatact 17040
actcactaca accaaagcca cggtggttca cgatattggt aacccaaaag gtatccctat 17100
cgtgcgcaaa cctggtgtta aatatcactt ctatgatcaa gcacccattg tcaaacacgt 17160
tcaaaaacta aagtacaagc cagagatgga ggcccgtttc accgatggtt tgactatgtt 17220
ttggaattgt aatgttgaca catacccctgc taacgccctt gtgtgccgct acgacactca 17280
tcggcagaag catttaattg gacctaatgg ttcagcacta tatgttaata agcatgcttt 17340
tctcacccct gagatgcata cttatgctac acataaactc aacttggctc cactcatcta 17400
ctactccacc acagattgta gtagtgaaca gcctattgtt gttacctaca gagattgtgt 17460
cacccggtgc aatactggaa aaactctctg tccaaatcat gctcttgaat accaagagtt 17520
tatcaatgca tacaatctca tggctcgcca tggatttaat gtttacatac cacgcaatgt 17580
caacgtttac aactgttggc ttactttcac taatctccaa aaccttgaaa acttagctta 17640
caactgttat tataagaact gcaatgctca cgttgatggg cagcttgatg tagttattaa 17700
taataacgct gtatatgcta aggtcgacaa taatcttgtc aaacttttcg acaaccgcac 17760
taacttacct gtctcagtgg cctttgaaca ttacactaac aggcataccc gttcactgcc 17820
aactacacag ctgttatctg gtttaggcgt aaccgccacc agaaatttca ctgtgtggtt 17880
cgacaatgat acaattttcc aatacactat taatgtatct acgtatactg acatcgaccc 17940
tagtacccat gttgtcctct gtgatgatag gtacggaaca gattggagtc agtttaacca 18000
acttcctaat gcagtattcc tcaccaaaac taaggtgaag aaaacagaac cgtttgtttg 18060
tacagcactg accctaaatg gcgtcgccat tgacggtgaa gagctataca tctatgtacg 18120
ctataacaat caactgacca catttgctac tacttgtaca cagggtagaa atgttgagca 18180
gtttatacct aaaacaccta tggaaagaga cttccttgag atgtctcaac agtccttcat 18240
ccagcaacat caattgcagg aactgggtgt tgaacacatt atctatggtg atgattccag 18300
tccagtcatt ggcggaactc acacacttat ctcactagtt aaaaacaagt ttgaacatca 18360
gcttgtcaac catgtttaca acccagtcca gaactgtgtt gttacctcac ctaacgcaag 18420
ctccaagaac gtttgcactg ttcttgatgt tcttcttgat gactacattg acatcataag 18480
acaagcacat gccagttaca caagtaaatc caaagtattc actgtgtcaa ttgacaacca 18540
acaaattaga ttcatgcttt ggcatgatga gcaagtcaag acttgctacc caatcttaca 18600

```
gtcacttacc aatggttacc agatgccatc tgtgtacaaa acattggtta ctgacttaca  18660

accagctgac atccctaatt atcattccta caccccccgg gtgcctggag tagttaagaa  18720

tgttatcaag taccgccaac ttttcaacta catagttaaa aaggataggt tggcagtacc  18780

acacaatatg accgtattac accttggagc tgcatctgca ctaggtacag caccaggttc  18840

ttcagtcata aaacaaatgt ttcctgaagg aactgttctt attgacctcg atataagaga  18900

gttcacttca gatgctaacc aaataatagt tacagactac agaacttaca taccaccaca  18960

ccacgtagac gtcatatttt ctgacctcta ctgttgtgat gacatacact tctttgacaa  19020

tctaataagg atagttaagg agaggctcgc cctcggtggt tctatctttg ttaagataac  19080

tgaacattca ttctcacccg aactctactc acttgcgggt tggttcgatg attatcaact  19140

attttgcaca gcagtcaatg cctcgtcttc agaagcattt ttatgctgtt ttaattattt  19200

ggggcttgct aaggaaaaca ttaatggttt taacttacat gcttcctata ttcaatggcg  19260

caatgaaata gcgttgacac caacctattc tcctttagcg gacaacccgg ctacggcctg  19320

taagctaaaa gcaacgccta ttatctcggc tcgtgagtta gagaagaagc ctattcttcg  19380

ctatctcgtt gcatcagggc gccttcttgt gaggccacca gaatgcagag agctctattg  19440

attatgacct tattttgtct cgttcgagca aagtttgctg atgatctact cgatttgctc  19500

accttcccgg gtgcacatcg cttcttacat aaacccacga ggaattccag cagtctctac  19560

tcgcgggcta ataataattt tgatgttggc gttcttcctg gctaccccac taagaacgtt  19620

aacctcttct caccacttac taactccact ttgcccatta atggccttca tcggagttac  19680

caaccactca tgctgaattg tcttactaaa ataactaacc acactctcag catgtatctc  19740

ctacctagtg agatacaaac ttatagctgc ggcggtgcca tggttaaata ccagacacat  19800

gatgcagttc gtatcatttt agacctcact gccactgacc acatctctgt tgaagtcgtt  19860

ggccaacatg gtgaaaatta tgtgtttgtt tgcagtgagc agtttaacta caccactgca  19920

ttacacaact ctaccttctt ctcacttaat tctgagcttt attgctttac taataacacc  19980

tacttaggta ttcttccacc tgatttaact gactttacgg tctaccgtac tggtcagttc  20040

tatgctaatg gttacctttt aggtacttta cctattacgg ttaactatgt taggttgtat  20100

cggggtcatt ttagtgccca ctttgccctt gcaaacctaa ccgatacact cataacactt  20160

accaatacta ctatatcgca aatcacttat tgtgataagt ctgtagttga ttcaatagca  20220

tgccagcgct cttctcacga agtggaggat gggttttact ccgaccctaa atctgccgtt  20280

agagctaggc aacgtactat tgttacacta cctaagctcc ctgagcttga agtagtgcag  20340

ttaaatattt ctgcacacat ggattttggc gaagccagac ttgacagcgt taccatcaat  20400

ggtaacacat cctattgtgt cactaagcct tacttcaggc ttgaaactaa ctttatgtgt  20460

acaggttgca ctatgaatct gcgcactgat acctgtagtt ttgacctgtc agcagtaaac  20520

aatggcatgt cattctctca attctgtcta agcactgaat ctggtgcttg tgagatgaaa  20580

attattgtta cctacgtatg gaattacttg ctaaggcagc gtttgtatgt tactgctgta  20640

gagggccaga ctcacactgg aaccacttca gtacatgcaa cagacacttc tagtgtaatc  20700

actgatgtct gcactgacta cactatctat ggagtctctg gtactggcat tattaagcca  20760

tcagatctct tattgcacaa tggcatagca ttcacctctc caacaggtga gctttatgca  20820

tttaaaaata taaccactgg caaaaccctt caggtcttac cgtgtgaaac cccttctcaa  20880

ctgattgtga taaacaacac cgttgtcggt gctatcacat ccagtaattc aactgaaaat  20940
```

-continued

```
aataggttta ctactactat tgtcacacct actttctttt attccacaaa tgccaccact  21000
ttcaactgca ctaagcctgt tttgtcctat ggacctatca gcgtgtgtag tgatggtgca  21060
attgtgggaa catccacatt acagaatact cgaccatcca tagtttcact atacgatggc  21120
gaagttgaaa taccatctgc attttctctt tccgttcaga cggagtactt gcaagttcaa  21180
gcagagcaag ttatagttga ttgtcctcag tatgtatgca atggcaacag ccgttgtcta  21240
caattactgg cacaatacac ctcagcttgc tctaacattg aagcagctct gcattcctct  21300
gcacagttgg atagcagaga gattataaat atgtttcaaa catcaacaca gtccttgcag  21360
ttagctaata ttaccaactt caagggtgac tacaatttta gcagcatact aaccaccaga  21420
attggtggca gatctgctat tgaagacctt ctttttaata aagttgttac tagtggcctt  21480
ggcactgttg atcaggacta caaatcctgc tctagagaca tggccatcgc tgacttagtt  21540
tgttcccagt attacaatgg catcatggtt ctacctggtg ttgttgatgc tgagaaaatg  21600
gcaatgtata ctggctctct tactggagct atggtatttg gaggactgac tgccgcagcg  21660
gcaataccat ttgccacggc agtacaagct cgcctcaatt atgtcgcact gcaaacaaat  21720
gtactacaag aaaaccagaa aattcttgca gaatcattta accaagcagt tggcaatata  21780
tcacttgcac tatcttctgt taatgatgcc atccagcaaa cttctgaggc tcttaacacc  21840
gtagctattg ctattaaaaa gattcaaaca gttgttaacc agcagggcga ggcattatca  21900
cacctgactg cacagctgtc aaacaatttt caagcaattt cgacttctat tcaagacatt  21960
tacaaccgtc ttgaggaagt agaggctaac cagcaagttg accgtctcat cacaggacgg  22020
ttggctgcac ttaatgcata tgttactcag ttactcaatc agatgtctca gattagacaa  22080
tctcgattgt tagctcagca aaagattaat gagtgtgtca aatcacagtc gtccagatac  22140
ggtttctgtg gaaatggcac acacatcttc tcacttacac agactgcacc aaatggcata  22200
tttttcatgc atgcagtgct agtacccaac aaattcacac gtgtcaacgc ttctgccggc  22260
atttgtgtgg ataatacgag aggctactca ttgcagcctc aacttatact ctaccagttt  22320
aataactcct ggagagttac acctagaaat atgtatgaac ccagactgcc ccggcaggct  22380
gatttcatac aattaactga ttgcagcgtt actttttaca acaccaccgc tgctaatctt  22440
cccaatatta tccctgacat tatagatgtc aatcaaacag tcagtgatat tattgacaat  22500
ttacctacag caacacctcc tcagtgggat gttggtatct ataacaacac tattctcaac  22560
ctcaccgttg agattaatga tctacaagag cggtctaaaa acctctcaca gattgcagat  22620
cgtttacaaa attatattga caatcttaac aatactctag ttgaccttga atggctcaac  22680
agagtggaaa cttaccttaa atggccgtgg tatatatggc ttgccattgc cctggctctt  22740
attgcatttg tgacaatcct cataacaatc tttctttgta ctggttgttg tggtggttgc  22800
tttggttgtt gtggcggttg ttttggcctt ttctctaaga agaaaaggta taccgacgac  22860
caaccaacac cgtcctttaa gtttaaggaa tggtagtcga cgactgggcc gttaccatcc  22920
ctggacaata tattattgct atactagttg tcatctgcat tggtgtggca ctacttttta  22980
ttaatacttg cttagcttgt gttaaattat tttacaagtg ctacctaggg gcagcatatc  23040
ttgttaggcc tattatagtg tactactcca agccgaaccc cgtacctgag gatgagtttg  23100
taaaagtaca ccaatttcct agaaacactc actatgtctg acgcagaaga gtggcaaatt  23160
attgttttca ttgcgatcat atgggcgctt ggcgtcatcc tccagggagg ctatgccacg  23220
cgtaatcgtg tgatctatgt tattaaactt attctgcttt ggctgctcca acccttcacc  23280
ctagtggtga ccatttggac cgcagtcgac agatcatcta agaaggacgc agttttcatt  23340
```

gtgtccataa tttttgccgt actgaccttc atatcctggg ccaagtactg gtatgactca 23400
attcgtttat taatgaaaac cagatctgca tgggcactct cacctgagag tagactcctt 23460
gcagggatta tggatccaat gggtacatgg aggtgcattc ccatcgacca catggctcca 23520
attctcacac cagtcgttaa gcatggcaag ctcaagctac atgggcaaga gctggccaat 23580
ggcatatcag tcagaaatcc gccacaggat atggtgatag tgtcaccaag tgacaccttt 23640
cactacactt ttaagaaacc tgtggaatca aacaacgatc cagaatttgc tgttctgata 23700
taccagggtg accgcgcttc aaacgctgga cttcacacca taaccacttc aaaggccggt 23760
gacgctcgcc tgtataagta tatgtaatgt gcaactgcca tctgcagctg cgagatttat 23820
atagattgtg caataagcgg cacatcagaa gagaggatgt tcctgagctt attgaccctc 23880
tcgttaaaac tcgctgtttt gcttacagtc tcgtggttct tgctaatgct aatccaattg 23940
catttagcat actacctcgg aaaattctta tcaatggtga gcctttactg cttgaatatg 24000
gtagcatata tggtaaagac tttatcattc gaccatcgct ccaagtcatt cttgaagatg 24060
aattaaatta aagttttgac accaatctat catggctgca ccagtagtcc ctactactga 24120
cgcgtcttgg tttcaggtgc tcaaagctca aaacaaaaag gctactcatc ctcagtttcg 24180
tggcaatgga gttccgctta actccgccat caaacccgtt gaaaaccatg gctactggct 24240
gcgttacacc agacaaaagc caggtggtac tcccattcct ccatcctatg ccttttatta 24300
tactggcaca ggtcccagag gaaatcttaa gtatggtgaa ctccctccta atgatacccc 24360
agcaaccact cgtgttactt gggttaaggg ttcgggagct gacacttcta ttaaacctca 24420
tgttgccaaa cgcaacccca acaatcctaa acatcagctg ctacctctcc gattcccaac 24480
cggagatggc ccagctcaag gtttcagagt tgaccccttc aacgctagag gaagacctca 24540
ggagcgtgga agtggcccaa gatctcaatc tgttaactcc agaggcacag gcaatcagcc 24600
caggaaacgc gaccaatctg caccagctgc ggtacgtcgt aagacccagc atcaagctcc 24660
caagcggact ttacccaagg gtaaaaccat ttctcaggta tttggcaacc ggtctcgtac 24720
tggtgccaat gtcggctctg cagacactga gaagacgggt atggctgatc ctcgcatcat 24780
ggctctagcc agacatgtgc ctggtgttca ggaaatgctt tttgctggcc accttgagag 24840
caactttcag gcgggggcaa taacccttac cttctcctac tcaatcacag tcaaggaggg 24900
ttctcctgac tatgagagac ttaaggatgc gctcaatacg gtcgttaacc agacctatga 24960
gccacctacc aaaccaacta aggacaagaa gcctgacaaa caagaccagt ctgctaaacc 25020
caaacagcag aagaaaccta aaaaggtaac tctgccagca gacaaacagg attgggagtg 25080
ggatgatgct tttgagataa agcaggaatc agcagcgtag acatcaatct atgtctgtta 25140
aacccaccca actccactca aatatctctt tggttccaga gagtcgtagt gtatagccag 25200
agagccagtc agagggcgct atcatgcaaa ctagggctgg ctactctagc acagaatcac 25260
atcccgataa tcaacagtgc tagaaggttg attataccat ttaatatgcc gaggccacgc 25320
ggagtacgat cgagggtaca gcataatctc aacttttgtt gagccacaat tttaatccta 25380
attggagaag gccaaaggac tgtactactt ttgtgggtgt agcagtcgcc cagtgggaaa 25440
gcgccaacta ggttacaatt gtggtgggga caaattaggg gaaattaaat tggcttat 25498

<210> SEQ ID NO 10
<211> LENGTH: 25498
<212> TYPE: RNA
<213> ORGANISM: Deltacoronavirus
<220> FEATURE:

<223> OTHER INFORMATION: Porcine Deltacorona Virus ssRNA +

<400> SEQUENCE: 10

```
cuuugagcac cugaaaccaa gacgcgucag uaguagggac uacuggugca gccaugauag     60
auuggugucg guagagaacu agcgaagcua gggagauaaa auuauagacu aaugcuauaa    120
uuuuuaucuu uagucuauaa uuuuaucucc cuagcuucgc uaguucucua ccgacaccaa    180
uccaggugcg ucugccacca aguuggcuac ccuuccuagg ggcgcuuucg cgcuugcuca    240
ccauuagauu accuggaaac cagccauuca gguuggaguu uccccaggcu cuuuugugug    300
ggcauuagcg gcuugugguu uuugcacaaa aucuaagcua cuuaccguuc cucugaccau    360
ccaccacuuc uauagacagc acugauuacc guaggguuua agucacaccg gucugcaccg    420
cccgucagcg gacacauuac ccagcauagc acuccuugca ccgcgccuag guaggauaaa    480
acccccuacc gggugacucu uaaggcguuu ccuccacggg auagccacua gucacuaggu    540
guaagugauc ugaucugggc guauuguguu gcgcaagugu gauacccaua ggagcgugga    600
auccuauucu gcggcucagu gccugauaua gcugugaaau ggccaagaac aaguccaagc    660
gcgacgcuau ugcguugccu gaaaauguac caccaccucu gcaacuuuuc auucauguug    720
cagcugcuga agagggucac ccuaagguua cuacuuaccu uggcaacuau aaccucuaug    780
ccaccaaggc uccgccuggc gugcagguuc uuagugcuaa aaccucucuu acugacuuug    840
agaaugucuu uggagcucaa cccaccuugc gaucaauucg uaaucugguu ugugaggcuc    900
gcucggcuga auggacaacu uccaagaaug cuuuugcacu caaagccacu caacuugacu    960
acucugaugc cguuuugagg gcaaugauuc guuucugccc uccaaaggug uccacacucg   1020
cugccuuugc ucuuuuuggc cgauugguua aaauugagga caaggaacuu gcugaguuag   1080
cucgugauac ugcccuugag uuggcguaca cggcuaaaau ugguacaucu cuugcugaca   1140
cgagaucugu cucacuuauu cauaaggacg cuuaucuaac ucucaguaau gagguuguug   1200
gcguaacuuu uacugccgca cuuauggcaa aggcuaccac uguuaaugga gcaaugcaau   1260
acucaaacuu uuaccucuac ccucgugcca cuauuaaggu aaccgauggu aaggcugaag   1320
caauugcaac uaagccucug ucugcugcca cuaaaggcaa gcaaaucaca gaggauguca   1380
accuucuccc ugacuaucag cagcugcuug uugaucaagu gacuggcacu gagguuaagg   1440
uuggagcucu aaccuauguu aagaccacug auucgccacc ccuuuacuuu cccaaaguca   1500
agggugguge uauugguauu gcacuuaagc agcagggcac uguggcuaag aagcucaaug   1560
uagucuucca ugcucaaccu gaugauguuc ugcuagccuu cauacaacuu cagcaauucu   1620
ugaaccguac uucggauuca aguguugaaa uuacugauug ccagaguuau gaaguaucuc   1680
caacugugac ggucaaaauu ggcccgucua aaccuggggga ugucaucgug gcuacugaug   1740
aggaauaccu uaaaugcuuu gaaaccccug agguagguag gcucuauaag guuuuccaaa   1800
cucaaucuug ggcuaucauu gagcgugccu ucuccaguuu gaagauccgc guguccaaag   1860
cuuuaucagc auuuauaagu uuucugcaaa accuugcaga uaacuuuacu gcaauaagug   1920
guguugucac ugcacucauu cgugaacucc aggaucuuac ccuggaugug gcgacacgua   1980
ucacuaacau acaauuuguu uaccgugccg guaagcuuau ugucgacacg acaaguguca   2040
uagcuaaacu uuuccagcca uuuugugauu uuauaucacc uuuccuucgg aaaguugcug   2100
guuuugcaau uuacacuguu gguaaucgca ugcuuauguu uaccagcacu ggcaccuuuc   2160
uucucacaaa ggcaacuacu aagauacuca auaaggcaaa guacaucuuu gauguggagc   2220
cugaguaccc aguagaugua acaacaucca aaguuguagu acaugaagca cuccagcaaa   2280
```

-continued

```
ccgacacuaa gccuacuaga gcucuggagg cuguugaugu cguuguuggu aauacuguac   2340
ugcaaauggc uacugauggc acugcguucu acccaucgga ugguacgcac gccucucuuc   2400
caggauucaa agcagguucg gaugagcuuu ucauaagcuu caacugcgac cucuuugaug   2460
augagacuaa ugcucaaauc aacgaaacac ucgcugcaua ugagcuuaac caacuagugg   2520
cuccagguga uucuacaccg cgucaaauug cgacguuggu ugucgauaca cuugcagaug   2580
cuauaacaga ccacuuuccg gagaaaacca uugaucuacc ugaagacuau caagucuuuu   2640
cugaccauga ugaccuccca cucgcacaau accacauccc ugaucaccug agccuguaua   2700
uucaggcuau ggaaggugaa gaugauagug gugaugaaau auguauugag gacgaugauu   2760
acgacugucc ucaagccgac gaagacacag aaggaguaau uccccaacag ugggaacuuc   2820
cugauguuga uaaauuuuua cucaagaucc aggaacggaa gaccagcagc gacgaaguac   2880
uuagcgucga cgucuauccu aaaccagagc cggucggcaa uguugggauu gacgacagcg   2940
cgucggaaaa gaagccaaau ggggacucag uaccggaucc ugagguccau ccaacacuag   3000
agagugugga uguugaacga ccaaccgaaa cagcaaacca ggcuguugaa gacaaaccuu   3060
cugauaccac cuuugugguu gaugaggaac aauuacaaga aucaacacca gaacaugaac   3120
uccgcuccua ugaaggggag uuugauucug augaugaaau uauuauuccu auaguaccag   3180
uaacaccugc ggauuuaaaa ccacagacua uuacuauaaa ggaguacuuu aagucugaaa   3240
aacuugagac uauuaacgaa ggauccacag agucaguuac acaaucugac gauucguuug   3300
acgagucauu uguugaugcu gagucugaug auccacaaga uccugcugua uaugaugaua   3360
caacaauuau aacggacagc acugauguag gcgaugagcc ugagacaacu cuagcuacca   3420
ucguuaacac accucugaca cucgauaaua acuugccacc ugaagccauu aaacaaccca   3480
gcccaacuaa gguugaguua guuguuggug aauuggcgag uauuaaauuu gacaauucug   3540
uucuagucaa cccugcuaau gcgcaauuaa caaauggcgg uggagcugcu cgugcaauug   3600
caaaauuagc ugguccaaaa uaucaagagu acuguaauag uguggcuccu aucucaggac   3660
cgcuuaccac ggacucuuuu gaugccaaga aauuuggugu agccugcauc uugcauguag   3720
ugccacccaa agguucugac ccuaauguac aagaacuccu guaucaagcu uacaagagua   3780
uccuuacuga accagcacac uauguuauac cuauacuagg ugcugguauc uuuggaugca   3840
acccagucca cucucuggau gcguucagga aagcaugucc aagugacaua ggucguguca   3900
cccuugucac uaugaacaaa aaccauuugc aggugugga ugcucucaau aggaccauug   3960
uacgcaccac uacugacuau gaucaaguua ccaccaaggc ccuuacaccc cagggagugu   4020
uagaagccaa ucucuuugau ggugaggacu uuguucaaga accaaaaccc ggucaaaucu   4080
accuugaggu uacugaagaa guucagaacc aagccaagga acuugaccuu aaccuucagc   4140
aauacugcgu cuaccugaag acuugccacc auaaaugggu ugugagucgu acgaacgggu   4200
ugaugcaucu aaaacaaaaa gauaacaauu guuuuguuag ugcaggugua aaccuguuuc   4260
aaaacacugc uuaucaacuu agaccugcua uugaugcucu cuauagggag uaucuuaaug   4320
guaauccaaa uagauuuguu gcuuggaucu acgcauccac uaaccgucgu guuggugaga   4380
uggguugucc acagcaaguu auuucuuugc ucguuaguaa cucugacgca gcauuuucag   4440
caacuacagc cuguuguaac accuacuuua accacacagg uguuauuuca guagcucgug   4500
aauaugaccc aauacaacca aaggucuacu gcaugaagug ugaugugugg acucccuuua   4560
caccccagag uggaaaaggu gcaguugcaa uugguauuuc ugcagaugaa ccuaccgguc   4620
```

-continued

```
cugccauuaa auuugccgca gcucacugcu gguacacuaa uggcaagaaa acaguuaaug   4680
gcuaugacac uaaagcuaau guuguagcua ccuaucauag guuugacgug ccuaagccuc   4740
aacuugucga ggacgugguu gcgcugccua cuaaaaauga cuuugaaguu cucaauguug   4800
aagaacugcc gcaggauagu gugcuccauu uggacccacc ucccuguacag gccuuacaac   4860
cuaaggcuaa ccaacacauu gagauucuag aaaacccaga uuaucuggac auuuuggauc   4920
uuuggauucg uaaacccaaa uucauccucg uaaagucgug gaguguuuug gguagagcac   4980
uauguaaggc agguaaaguu gucuuuguca gugcuucgcu uuugacccgu uucuacaauu   5040
accuuguaga gauuggugcu cuugacucaa caauaagguu gucagucgau cuuaccugua   5100
aauuuguuag aacgguucuc ccaucgucua acacuguaca caaaacuugu cuuggucugu   5160
auuauucagc ccagacacuu uuuguuucuu uagcaccauu ccuuauguua ccagcuguag   5220
uuagucugcu uaauucaggc uauacaauug gcacauauuu guaugcaaaa acuggcuggc   5280
cuuguaauua caaugccacg caacacuuug auuauaauuc uuacugugca ggugacuugg   5340
uuugucaagc cuguuuugac ggucaagacu cccuacauuu guauccgcau uuacguguua   5400
aucagcagcc ccuucagacc acugacuaca cuguuuaugc gcuuucacua auacuacuau   5460
uagcuaacau gacucuuguc augggcacgc uaaauaguuac uuucuuugug aacuucuaug   5520
gugugcaaau accauuuuau gguacacuuu ugauagauua ucaauccgca cuggugauua   5580
cuuucucagu guacuacuuu uauaagguaa ugaaguuuuu ccgccaucuc acacauggau   5640
guaaaauucc aacgugugug guaugugcca aacuucguac cccaccuacu auaacaguug   5700
agacugucgu ucagggcagg aaauacccau cuguuauuga aacaaauggc ggguuuacaa   5760
uuuguaaaga acacaacuuc uauugcaagg acugcucuuu acaaacaccc ggcacuuuca   5820
ucccgacaga agcuauugag ucgcucucac gagcuaccag gcuuaguguc aaaccaacag   5880
caccagcauu cuuacuugcu agagauguug agugccaaac ugauguuguc guugcucgcg   5940
caaugcauaa ccaaaaugcg caugugugca uuucaaaaua cucugauauc cguaccguug   6000
accaacuacu uaagccuacu ccacuguuuu cauacacucc cgauguuauc aucgcggcag   6060
acuuugacaa cagagguagu cuuaagacag cuaaagaauu agcuguggu uugucaaugg   6120
accuuaaacg uacuauaauu aucauugauc aggccuauuc uagaccuauu gauaauuauc   6180
aggaaguugc uucucguauu gagaaguauu acccaguugc aaagaucaca cccacaggug   6240
acaucuuuac agacauuaag caagcgacca auggccaagc uagugacucu gcuauuaaug   6300
cagcuguucu ggcuguccag cgcggucuug auuuuacaau ugacaacccu aacaacauau   6360
uaccacauua cgccuuugac uuuucaaccc ucaaugcaga agaccagucu accauuuugg   6420
agagugguug ugcuaaaggc aaucucaagg gcacuaaugu ugguguuguu cuuucagcua   6480
gccuuguuac acgucuuagu cagcaggcua uacgugugau ugcuaaugcu gcuucacgua   6540
augguguuac augcgcuguu acuccuucua cacuuguuau gcgugggaau auugcaacac   6600
agcccuugac ucgcaucaaa gcuggugcac cucccaugcg ucaaaaaauu uuaugugua   6660
uccuggcacu ugcuauugug uacuuugcug cuauggcuuu uggcuuuuug gcaagucaaa   6720
uuacgcuuaa uacagugccu acgauuaaau cugauauccg cgccucuacc uucuacguug   6780
uuagagaugg agucuuggau acuguucguu caaaugacaa gugcuuugca aauaaguuuu   6840
uggcauuuga uagcuucauu caagcaccuu acacuaauuc accugacugu ccaguuguug   6900
ugggaguugu ugauguaacg acgcacucua uuccuggaau uccagcaggu gucauucaua   6960
gagacggucu cauacuuaac auuuaugaac agucucuuua ugaaacucau cagcgucagu   7020
```

cuaugguuag ggaugcguug ucacucaaga cagcaaaucu cuuuaaccua ggcaagcgug 7080
uuguaguagg auacacucaa caugaaguug uuguggguac cuccuauuuu aauucuccug 7140
cacuuuuuaa ugcaaagugc accuucuuac aguaucagga cacuagacaa cucuauugcu 7200
augauacugu uccuacugaa cauaagcucu acucugaugu gcuuccgcac gucgaguaua 7260
aggcuauuga cauuaauggu gaucuuguuc cuuucaagau accagagcag auaauguucu 7320
auccacauau ugugcgcuau acuagcaauu ccuauugccg uauggggcau uguuuuaaua 7380
cuaacccugg uauuugcauu ucauuuacgg acgaauuucc guauagugaa aaugucaaac 7440
cuggugugua cugugcugau accucuuugc aguuguuuuc aaaccucguu uugggcacug 7500
uaucugguau ucacaucuuu acaucaacag cugcauugcu uggaucuacu auugugauca 7560
uacuaugcgu uguugcuguu cuugcaguuc agcgauucuu caaggaguac acaacuuuug 7620
uuauguacac uuguggucuu gcucuuguca acauuguagg cauugcacuu auguacaagu 7680
gccuugucuu cgcgauuuuc uauuaugcaa ucuaccuuua cuuuguccuu acuuuccccu 7740
ccuuuaagag gaauguggca uuguuuuacu ucgcuguagu gaucgugccg cacgugagua 7800
acaugcaauu gcuugcgcuc auugugugua gcauuaucua cuuucucuac accuauguuc 7860
auacuguagc uaagacagcu gggaaauuuu cuuccuucuu agacgcagcu aaagcuacuu 7920
uugucauuga caaugaaaag uacguguugc uuaaagaccu cgcugguguu gaauuugacc 7980
aguaucuggc cucuuacaac aaguacaaau auuuuucugg uacugcuucu gauaaggauu 8040
augauaaggu cuguauggca uuucuugcca aggcuuuguc aucuuuucgu gaaggaggcg 8100
guucacaguu guacacacca ccuaaauuug caguuguuca gagucuuaag accaagcugc 8160
aagcagguau caaaauccuc cugcacccuu cagguguagu ugagcgaugu auggucucag 8220
uugucuacaa uggaucugca uugaauggca ucuggcuuaa gaauguuguc uacugcccac 8280
gccauguaau uggaaaauuc cgguggugacc aguggacuca cauggucuca auugcugauu 8340
gccgcgacuu uauagucaag uguccaauac aggguauuca gcuaaauguc caaucaguua 8400
agaugguagg agcucuccuc caguuaacug uucauaccaa caacacagcc acuccagacu 8460
auaaguuuga aaggcuacaa ccaggaucau cgaugacaau ugcuugugcu uaugauggca 8520
uuguacggca ugucuaucac gugguccucc aacuuaauaa ucuuauuuau gcaagcuucc 8580
uuaacggagc uuguggguagu gugggguuaca cucuuaaggg uaaaacacuc uacuuacauu 8640
acaugcacca cauugaguuu aacaacaaaa cucauagugg uacagaucuu gaagguaacu 8700
ucuauggccc cuauguggau gaggaaguua uucagcaaca aacagcauuc caguauuaca 8760
cugauaaugu uguugcucaa uuauaugcac acuuacugac uguugaugcu agaccaaaau 8820
ggcuggcaca aucucagaua aguaucgagg auuucaacuc augggcugcu aacaauuccu 8880
uugcuaacuu cccaugugaa caaacuaaua uguccuacau uaugggacuc ucgcaaacag 8940
cucgaguccc uguagaacgu auccucaaua ccauuauaca gcuaaccacc aauagagaug 9000
gugcuuguau uaugggaucu uaugauuucg agugcgauug gacgccagag augguauaca 9060
aucaggcucc aauuucauug cagucaggag uaguuaagaa aacuuguacg ugguucuucc 9120
acuucuuguu uauggcuauu accaugcuac ucgcugccau gcauguuuuc ccuguacacu 9180
uguauccaau aguacugcca ugcuucacug ucguggcauu ccuguugacu uuaaccauua 9240
aacacacugu uguguuuacc acuacauacu ugcuuccguc acuuuugaug augguuguaa 9300
augcuaacac uuuuuggaua ccgaacacau uucugcgcac cugcuacgaa acuauauucg 9360
guuccccaau ugcucagcga cuguaugguu acacuguugc ucuuuauaug cugaucuaug 9420
cuggacuugc aaucaacuau acguugaaaa cacuccggua uagagcaacu ucauucuuau 9480
cuuuuugcau gcagugguuu caauaugguu auguugcaca cauugcguac aaacugcuua 9540
auaaacccug gacagaauca cuacucuuca cagccuucac aaugcuaacc agucaucccu 9600
uguuggcugc ucuuagcugg uggcuagcug gucgcguaac ucugcccauu aucaugccug 9660
acuuagcuau ucguguuuug gcguauaacg ucauuggcua ugucauaugu guucgauuug 9720
gccuuaugug gcuugcaaau cgguucacaa cuguaccuau gggcacauac caguauaugg 9780
ugucuguaga gcaacuuaag uacaugaugg caguuaagau guccccaccg cguaaugcgu 9840
uugaggugcu uauagccaac auuagacuuc uugguuuggg uggaaaccgu aacauugcug 9900
uuucuacugu ccaaaacaaa auucuugaug caaaagcuac ugcuguuguu guugcuaacc 9960
uucuugaaaa ggcuggcguc acaaacaagc acgcuauuug caaaaagauu gugaaacucc 10020
acaaugauac ccuuaaagcc accacuuaug aggagguuga gguagcacuu gugaaacuuc 10080
uuucucacau aauugaguuc uugccaacug aucagguaga ugcuuaucua gcugaugcgg 10140
ccaaugcuca acauguuaau accuauuuag acaacuugcu ugagaacaaa gcuguuguuc 10200
aggcuguugc cgauaucaac auuaaucugg auucuuauag aauuuauaag gaggcagaug 10260
cuauuuauaa acgaucuguu gagaugaacg aaucuccgca ggagcaaaag aaaaagcuua 10320
aagcuguuaa cauugcaaag gcggaauggg agcgugaggc ugcuucucag cguaagcuug 10380
aaaagcuugc ugaugcugcu augaagucua uguaucuugc agaacgugcu gaggaucguc 10440
gcauuaagcu aaccucugga cuuacugcaa ugcuuuacca uaugcuuaga cgucuugacu 10500
cagauagggu aaaagcucug uuugagugcg cuaaggcaca aaucuugcca auacaugcug 10560
uagucggaau uucuaaugac aaccuuaaag uuauuuuuaa cgauaaggac agcuacucuc 10620
auuauguaga gggcaacaca cuuauacaua agggaguucg cuacacuauu gugaagaaac 10680
ucuccuuaga uaaugcaccu auugaaggcg uaccagaaga auucccugug gucguugaga 10740
cuguuaggga aggugugccc caguugcaaa auaaugagcu auguuugcgc aauguuuuca 10800
cugcucagaa cacagcucag gacuucaaug gcaaugaauc cacuguaaaa ucuuuuuaug 10860
uuacuagaac cgguaagaag auuuugguug ccauuacauc aacuaaagac aaucuuaaga 10920
cugugaccug ccuuacugag accgguaaga caguccuuaa cuuggacccc ccuaugcgcu 10980
ucacacauac cguaggugga aaacagucug uugucuaucu cuauuuuauu cagaauauua 11040
guucacucaa cagagguaug guuauuggcc acaucucuga aacuacuauc cuucaggcaa 11100
guggcacuca aauugaguac cagcaaaaug ccucucuuuu gaccuauuug gcuuucgcug 11160
uagacccuaa gacagccuac cuuaagcauc uugcugaugg ugggucuccu auacaggguu 11220
guauucagau gauugcuacu augggguccug gauuugcagu uacuacuaaa ccacaaccua 11280
augagcauca guauucuuau gguggugcuu caauuugucu uuauugccgu gcucauauac 11340
cacauccugg uguugaugga cggugccccu acaaaggccg cuuuguucac aucgacaaag 11400
auaaggaacc uguuuccuuc gcuuugacuc augagccaug caguucuugu caacggugg 11460
uuaauuauga cugcaccugc ggaucuaguc ugcagaauuc ggcuuauuua aacgcguaac 11520
ggguucuagu gacgcccggc uagaaccccu gcagccugga acucaaccag augcuguaaa 11580
aagggccuuc caugugcaua augauaccac cucugguaua uucuuaagca caaaaucuaa 11640
cugcgcucgg uuuaaaacca cacgcagugc ccugccuuua ccuaauaagg gagagguuga 11700
auuguacuuu guuacuaagc agugugcagc uaaagucuuc gaaaucgagg aggaaugcua 11760

-continued caacgcucuu aguacagagc uuuauacuac ugaugauaca uuuggugucc uugccaaaac 11820
ugaguucuuu aaguuugaca agauaccuaa ugucaaucgc caguaucuga cuaaauauac 11880
acuccuggac uuggcuuaug cucuacguca uuugucaaca ucuaaggaug uuauucaaga 11940
aaucuugauc accaugugcg gaaccccuga agauugguuu ggggaaaauu gguuugaucc 12000
aauugagaac ccauccuuuu acaaggaguu ccauaaacuu ggggauauuc uuaaccguug 12060
uguucuuaau gccaauaagu uugcuagugc cuguauagac gcuggucuug uuggcauauu 12120
aacacccgac aaccaagacc uccuggguca gaucuaugac uuuggagauu uuauuauuac 12180
acaaccaggu aauggaugug uggacuuagc auccuauuau ucuuauuuaa ugcccauuau 12240
guccaugacu cacauguuaa agugugagug uauggauagu gauggcaacc cacuugagua 12300
ugauggauuu caguaugacu ucacggacuu caagcuuggc uuguucgaga aguauuuuaa 12360
guacugggac cguccuuacc auccuaacac uguugaaugu ccagaugacc guugcguauu 12420
gcacugugcg aacuucaaug uguuguuugc uauguguaua ccuaauacgg cauuuggcaa 12480
ucuuuguuca agagcuacug uugauggcca ccuugugguc cagacagugg guguacacuu 12540
gaaagaacuy gguauagucc uuaaccagga cguuaccaca cacauggcaa auauuaaucu 12600
aaacacucua uugcgauugg uuggugaucc caccacuauu gcaagugucu cagacaagug 12660
uguagauuua agaacuccuu gucagaccuu ggcuacuaug ucuagcggaa uugcuaaaca 12720
gucagucaag cccgggcauu uuaaucaaca cuucuacaag cauuugcuug auaguaaccu 12780
auuagaccaa cuuggaauag acauucgcca cuucuacuau augcaggaug gugaagcggc 12840
uaucacagac uacagcuacu acagguauaa uacccccacg augguagaua ucaagauguu 12900
cuuauuuugc cuugaggugg cagauaagua ucuugagccc uacgaaggug gauguauuaa 12960
ugcacaguca guuguggucu cuaauuugga caagucagcg ggcuaccccu uuaacaagcu 13020
agguaaggcu cguaacuauu acgacaugac ucaugccgag caaaaucaac uguuugagua 13080
uacaaaacgc aauguuuugc cuacacucac ucagaugaac cuuaaguaug caauuucagc 13140
caaggaucgu gcucgcacug uggcaggagu gucuauaauu agcaccauga cuaacaggca 13200
guaccaucaa aagaugcuga aaucuauuuc acuugcacgc aaucagacca ucgugauugg 13260
aacaaccaaa uucuauggug guugggacaa cauguuacga cgacugaugu guaauaucaa 13320
caaucccauu uuagugggu gggauuaccc uaagugugau cguucuaugc caaacaugcu 13380
gcgcauugcc gcuucgugcu ugcuagcacg aaaacacacu ugcuguaacc aaagccagcg 13440
auucuaccgu uuggcuaaug aauguugcca aguacuaucu gaaguggug ucucugguaa 13500
caaccucuau guaaaaccag guggcacuag caguggugau gcaaccacag cuuaugccaa 13560
cucgguauuu aacaucuuac aggugguuuc ugcuaaugua gccaccuucu uaucaacuuc 13620
caccacgaca caucuuaaua aggacauugc ggacuugcau cguagucuuu augaagauau 13680
uuaucguggu gacucuaaug auaucaccgu caucaauaga uucuaccagc aucuccaaag 13740
uuacuuugga cuuaugauau ugucugauga uggugucgca ugcauagacu cagccguugc 13800
aaaggcugga gcuguugcug aucuugaugg uuuccgagac auuuuguuuu accaaaacaa 13860
uguuuacaug gcagacucaa aguguuggac agaaacugac augaauguug gcccucauga 13920
auuuugcuca cagcauacug uguuagcaga gcaugauggu aaaccuuacu acuuaccuua 13980
cccagauguc ucucgcauuc ugggugcaug caucuuugug gaugacguua acaaggcuga 14040
cccuguucag aaccuugaac guuacaucuc acuugcaauu gaugcauauc cccucaccaa 14100

-continued

```
ggugacccu auuaagggua aagucuuuua uuuguuacua gacuacauac guguucuugc  14160
ucaggaguua caggacggua uccuugaugc uuuccaauca cucacugaca ugucguaugu  14220
aaauaacuuu augaaugagg ccuuuuaugc ucagauguau gagcaaaguc cuacacuaca  14280
ggccagcggu guuugugugg uguguaauuc acccacuaua cugcgcugug gugauugcau  14340
ucgucgacca cuacuuuguu gcgucugugc cuaccagcau guuacgcaga cuacacauaa  14400
acguaucauu gcuaucaaca acuacaucug uaguguugag aauugcaaug aggacaaugu  14460
ugaaaaacuu uucauuucug gcacugcgau uuauugugag aaucacaaac ccacgcugug  14520
cauacccauu guagcuaaug guucuguuuu ugguaucuau cgccacacug cccgugguag  14580
ugaugacaua gaccucuuua acgagcuugc uacaucuaac uaugacacua uugaaccuua  14640
ucagaaggcc aaucgugcac cuuuaucacu uaugcucuuc gcugcugaaa ccauuaaggc  14700
acucgaggag ucuaucaaga agucauaugc uaccgcaacc gucaaggaug uguaugacca  14760
acgcuucauu aaacuucuau gggaacaggg uaaaaagccg ccacccauaa cgaagaacca  14820
cauuuucacu ggcuaccauu uuaacaagaa uggaaaaacc caaguuggug auuacauucu  14880
ugcuaaaaca gauggcagug acacuuauac uuacagagga acaucuaccu acaaacucca  14940
aacaggugau guucuagucu uaauggcaca uguuguuaca ccgcucucag cacccccugu  15000
guuaacgcag acaacauaug ucagaaaauc acuuuuaccc gacucuguug gugcgucuua  15060
uuaugugcaa cauuuuaagu cauauaauga gauagcuaug cagaggguua caacaguauu  15120
agguccacca ggcacaggua agucaaccuu ugcuauuggu uuggcuaagu acuuucccag  15180
ugcacguauu ugcuacacug cgucuucgca ugcagcaauc gaugcacucu gugaaaaagc  15240
uuucaagaca auaccuguag gccaaugcag ucguaucgua cccacacgua caacuguuga  15300
gugcuuucag gaguuugucg uaaauaacac aacugcacag uauaucuucu cgacuaucaa  15360
ugccuuaccu gacauuaagu gugacauugu aguuguagau gagguuucua uguugaccaa  15420
uuaugagcuu uccucuguga augcucguuu gguuuacaau cacauugugu auguugguga  15480
ucccuuaucag uuaccuucac cuagaacuau gcuuacgucu ggccagcuuu cgccagcuga  15540
cuauaacgua guuacugaua uaaugguaca ugcaggagcg gauguuaugc ucgacaugug  15600
cuacagaugc ccacgugaaa ucguugagac agugucuaaa cuugucuacg auaacaaacu  15660
aaaagcggcg aaaccgaacu caagacagug uuacaagacc auugugaacu uugguccugg  15720
agacguugcu caugagggac aaucugccua caacgaagca caguugcguu ucgcacucgc  15780
auuuagacaa caaaagcggu gggauaacgu gacuuucaua ucuccauaua augcuaugaa  15840
ugugaaagca ucccuuagcag guuucucuac ucagaccguu gacucuucuc aagguucuga  15900
guaugauuau guuaucuuuu gcgugaccac ugauucagca cacgcacuua acauggcucg  15960
uuugaacguu gcccuuacac gcgcaaagau agguauccuu gugguguuua ggcaggcaaa  16020
cgaacuuuac aauaguuugc aguuugaauc uauugauuca cagcuucagu cgagugcuga  16080
gaaaaaccuc acaccacugu uuaagcgcug cggcuaugag uauaauggcg uccauccagc  16140
ucaugcuuug accuggcaug auuguggugc agaguaccgc ugugaggagc cacuugcuaa  16200
auuaguagga guugccgaug gcacucuuau aucauacaaa acccuaguau ccacacuugg  16260
guuucuucca ucacuuaaaa uugaugcaua ucauaaauaug uuccuaacac gugacgcgug  16320
ucgcaccuau guucagaguu ggaucggcau agauguugaa gcagcacacg ccauaaaacc  16380
uaacaccggg acuaaccugc cauugcaaau agguuuuagu accggaaaga auuuuucagu  16440
cacuccagag ggaauuuggg uaaacgagca cggaucuugc acugagcccg ucccugccaa  16500
```

-continued aauaccuccu ggagaacaau uucgucaccu uaaaaaggac augcgccagg cgcguccuug 16560
gaagguuguu cgacgugaga uugcuacuca cauugcugag guagcuccuc acacugauua 16620
uauaugcuuu gucacuuggg cucaccagcu ugagcuagcg acaaugcgcu acuuugucaa 16680
acuagguaug gaagagaaau gcuuuugugg caggcgggcu uguuucacua auggaacuga 16740
guucgcuugc aaagcacacc auucucucac cauuccacaa ugugauuaug uguacaaucc 16800
auuccucauc gacguggcua cgugggggauu cucgggacgg cuuuccacca accaugacgc 16860
ugugugcaca uaucaugcua augcccaugu ugcaucagcu gaugcaauca ugacgguaug 16920
uuuagcuauc caugaacugu ucaguacugu ugacuggaac uuugaauuuc caguaacugc 16980
ugagcaaucg caacuuaaca aggccugucg cuuaguacag gcgaauuacu uaaauauacu 17040
acucacuaca accaaagcca cggugguuca cgauauuggu aacccaaaag guaucccuau 17100
cgugcgcaaa ccugguguua aauaucacuu cuaugaucaa gcacccauug ucaaacacgu 17160
ucaaaaacua aaguacaagc cagagaugga ggcccguuuc accgaugguu ugacuauguu 17220
uuggaauugu aauguugaca cauacccugc uaacgcccuu gugugccgcu acgacacuca 17280
ucggcagaag cauuuaauug gaccuaaugg uucagcacua uauguuaaua agcaugcuuu 17340
ucucaccccu gagaugcaua cuuaugcuac acauaaacuc aacuuggcuc cacucaucua 17400
cuacuccacc acagauugua guagugaaca gccuauuguu guuaccuaca gagauugugu 17460
cacccggugc aauacuggaa aaacucucug uccaaaucau gcucuugaau accaagaguu 17520
uaucaaugca uacaaucuca uggcucgcca uggauuuaau guuuacauac cacgcaaugu 17580
caacguuuac aacuguuggc uuacuuucac uaaucuccaa aaccuugaaa acuuagcuua 17640
caacuguuau uauaagaacu gcaaugcuca cguugauggg cagcuugaug uaguuauuaa 17700
uaauaacgcu guauaugcua aggucgacaa uaaucuuguc aaacuuuucg acaaccgcac 17760
uaacuuaccu gucucagugg ccuuugaaca uuacacuaac aggcauaccc guucacugcc 17820
aacuacacag cuguuaucug guuuaggcgu aaccgccacc agaaauuuca cugugugguu 17880
cgacaaugau acaauuuucc aauacacuau uaauguaucu acguauacug acaucgaccc 17940
uaguacccau guuguccucu gugaugauag guacggaaca gauuggaguc aguuuaacca 18000
acuuccuaau gcaguauucc ucaccaaaac uaaggugaag aaaacagaac cguuuguuug 18060
uacagcacug acccuaaaug gcgucgccau ugacggugaa gagcuauaca ucuauguacg 18120
cuauaacaau caacugacca cauuugcuac uacuuguaca cagggguagaa auguugagca 18180 guuuauaccu aaaacaccua uggaaagaga cuuccuugag augucucaac aguccuucau 18240
ccagcaacau caauugcagg aacugggugu ugaacacauu aucuauggug augauuccag 18300
uccagucauu ggcggaacuc acacacuuau cucacuaguu aaaaacaagu uugaacauca 18360
gcuugucaac cauguuuaca acccagucca gaacuguguu guuaccucac cuaacgcaag 18420
cuccaagaac guuugcacug uucuugaugu ucuucuugau gacuacauug acaucauaag 18480
acaagcacau gccaguuaca caaguaaauc caaaguauuc acugugucaa uugacaacca 18540
acaaauuaga uucaugcuuu ggcaugauga gcaagucaag acuugcuacc caaucuuaca 18600
gucacuuacc aaugguuacc agaugccauc uguguacaaa acauugguua cugacuuaca 18660
accagcugac aucccuaauu aucauuccua caccccccgg gugccuggag uaguuaagaa 18720
uguuaucaag uaccgccaac uuuucaacua cauaguuaaa aaggauaggu uggcaguacc 18780
acacaauaug accguauuac accuuggagc ugcaucugca cuagguacag caccagguuc 18840
uucagucaua aaacaaaugu uuccugaagg aacuguucuu auugaccucg auauaagaga 18900
guucacuuca gaugcuaacc aaauaauagu uacagacuac agaacuuaca uaccaccaca 18960
ccacguagac gucauauuuu cugaccucua cuguugugau gacauacacu ucuuugacaa 19020
ucuaauaagg auaguuaagg agaggcucgc ccucggugggu ucuaucuuug uuaagauaac 19080
ugaacauuca uucucacccg aacucuacuc acuugcgggu ugguucgaug auuaucaacu 19140
auuuugcaca gcagucaaug ccucgucuuc agaagcauuu uuaugcuguu uuaauuauuu 19200
ggggcuugcu aaggaaaaca uuaaugguuu uaacuuacau gcuuccuaua uucaauggcg 19260
caaugaaaua gcguugacac caaccuauuc ucccuuuagcg gacaacccgg cuacggccug 19320
uaagcuaaaa gcaacgccua uuaucucggc ucgugaguua gagaagaagc cuauucuucg 19380
cuaucucguu gcaucagggc gccuucuugu gaggccacca gaaugcagag agcucuauug 19440
auuaugaccu uauuuugucu cguucgagca aaguuugcug augaucuacu cgauuugcuc 19500
accuucccgg gugcacaucg cuucuuacau aaacccacga ggaauuccag cagucucuac 19560
ucgcgggcua auaauaauuu ugauguuggc guucuuccug gcuaccccac uaagaacguu 19620
aaccucuucu caccacuuac uaacuccacu uugcccauua auggccuuca ucggaguuac 19680
caaccacuca ugcugaauug ucuuacuaaa auaacuaacc acacucucag cauguaucuc 19740
cuaccuagug agauacaaac uuauagcugc ggcggugcca ugguuaaaua ccagacacau 19800
gaugcaguuc guaucauuuu agaccucacu gccacugacc acaucucugu ugaagucguu 19860
ggccaacaug gugaaaauua uguguuuguu ugcagugagc aguuuaacua caccacugca 19920
uuacacaacu cuaccuucuu cucacuuaau ucugagcuuu auugcuuuac uaauaacacc 19980
uacuuaggua uucuuccacc ugauuuaacu gacuuuacgg ucuaccguac uggucaguuc 20040
uaugcuaaug guuaccuuuu agguacuuua ccuauuacgg uuaacuaugu uagguuguau 20100
cggggucauu uuagugccca cuuugcccuu gcaaaccuaa ccgauacacu cauaacacuu 20160
accaauacua cuauaucgca aaucacuuau ugugauaagu cuguaguuga uucaauagca 20220
ugccagcgcu cuucucacga aguggaggau ggguuuuacu ccgacccuaa aucugccguu 20280
agagcuaggc aacguacuau uguuacacua ccuaagcucc cugagcuuga aguagugcag 20340
uuaaauauuu cugcacacau ggauuuuggc gaagccagac uugacagcgu uaccaucaau 20400
gguaacacau ccuauugugu cacuaagccu uacuucaggc uugaaacuaa cuuuaugugu 20460
acagguugca cuaugaaucu gcgcacugau accuguaguu uugaccuguc agcaguaaac 20520
aauggcaugu cauucucuca auucugucua agcacugaau cuggugcuug ugagaugaaa 20580
auuauuguua ccuacguaug gaauuacuug cuaaggcagc guuuguaugu uacugcugua 20640
gagggccaga cucacacugg aaccacuuca guacaugcaa cagacacuuc uaguguaauc 20700
acugaugucu gcacugacua cacuaucuau ggagucucug guacuggcau uauuaagcca 20760
ucagaucucu uauugcacaa uggcauagca uucaccucuc caacagguga gcuuuaugca 20820
uuuaaaaaua uaaccacugg caaaacccuu caggucuuac cgugugaaac cccuucucaa 20880
cugauuguga uaaacaacac cguugucggu gcuaucacau ccaguaauuc aacugaaaau 20940
aauagguuua cuacuacuau ugucacaccu acuuucuuuu auuccacaaa ugccaccacu 21000
uucaacugca cuaagccugu uuuguccuau ggaccuauca gcguguguag ugauggugca 21060
auugugggaa cauccacauu acagaauacu cgaccaucca uaguuucacu auacgauggc 21120
gaaguugaaa uaccaucugc auuuucucuu uccguucaga cggaguacuu gcaaguucaa 21180
gcagagcaag uuauaguuga uuguccucag uauguaugca auggcaacag ccguugucua 21240
caauuacugg cacaauacac cucagcuugc ucuaacauug aagcagcucu gcauuccucu 21300
gcacaguugg auagcagaga gauuauaaau auguuucaaa caucaacaca guccuugcag 21360
uuagcuaaua uuaccaacuu caagggugac uacaauuuua gcagcauacu aaccaccaga 21420
auugguggca gaucugcuau ugaagaccuu cuuuuuaaua aaguuguuac uaguggccuu 21480
ggcacuguug aucaggacua caaauccugc ucuagagaca uggccaucgc ugacuuaguu 21540
uguucccagu auuacaaugg caucaugguu cuaccuggug uuguugaugc ugagaaaaug 21600
gcaauguaua cuggcucucu uacuggagcu augguauuug gaggacugac ugccgcagcg 21660
gcaauaccau uugccacggc aguacaagcu cgccucaauu augucgcacu gcaaacaaau 21720
guacuacaag aaaaccagaa aauucuugca gaaucauuua accaagcagu uggcaauaua 21780
ucacuugcac uaucuucugu uaaugaugcc auccagcaaa cuucugaggc ucuuaacacc 21840
guagcuauug cuauuaaaaa gauucaaaca guuguuaacc agcagggcga ggcauuauca 21900
caccugacug cacagcuguc aaacaauuuu caagcaauuu cgacuucuau ucaagacauu 21960
uacaaccguc uugaggaagu agaggcuaac cagcaaguug accgucucau cacaggacgg 22020
uuggcugcac uuaaugcaua uguuacucag uuacucaauc agaugucuca gauuagacaa 22080
ucucgauugu uagcucagca aaagauuaau gaguguguca aaucacaguc guccagauac 22140
gguuucugug gaaauggcac acacaucuuc ucacuuacac agacugcacc aaauggcaua 22200
uuuuucaugc augcagugcu aguacccaac aaauucacac gugucaacgc uucugccggc 22260
auuugugugg auaauacgag aggcuacuca uugcagccuc aacuuauacu cuaccaguuu 22320
aauaacuccu ggagaguuac accuagaaau auguaugaac ccagacugcc ccggcaggcu 22380
gauuucauac aauuaacuga uugcagcguu acuuuuuaca acaccaccgc ugcuaaucuu 22440
cccaauauua ucccugacau uauagauguc aaucaaacag ucagugauau uauugacaau 22500
uuaccuacag caacaccucc ucagugggau guugguaucu auaacaacac uauucucaac 22560
cucaccguug agauuaauga ucuacaagag cggucuaaaa accucucaca gauugcagau 22620
cguuuacaaa auuauauuga caaucuuaac aauacucuag uugaccuuga auggcucaac 22680
agaguggaaa cuuaccuuaa auggccgugg uauauauggc uugccauugc ccuggcucuu 22740
auugcauuug ugacaauccu cauaacaauc uuucuuugua cugguuguug uggugguugc 22800
uuugguuguu guggcgguug uuuuggccuu uucucuaaga agaaaaggua uaccgacgac 22860
caaccaacac cguccuuuaa guuuaaggaa ugguagucga cgacugggcc guuaccaucc 22920
cuggacaaua uauuauugcu auacuaguug ucaucugcau uggugugggca cuacuuuuua 22980
uuaauacuug cuuagcuugu guuaaauuau uuuacaagug cuaccuaggg gcagcauauc 23040
uuguuaggcc uauuauagug uacuacucca agccgaaccc cguaccugag gaugaguuug 23100
uaaaaguaca ccaauuuccu agaaacacuc acuaugucug acgcagaaga guggcaaauu 23160
auuguuuuca uugcgaucau augggcgcuu ggcgucaucc uccagggagg cuaugccacg 23220
cguaaucgug ugaucuaugu uauuaaacuu auucugcuuu ggcugcucca acccuucacc 23280
cuaguggug a ccauuuggac cgcagucgac agaucaucua agaaggacgc aguuuucauu 23340
guguccauaa uuuuugccgu acugaccuuc auauccuggg ccaaguacug guaugacuca 23400
auucguuuau uaaugaaaac cagaucugca ugggcacucu caccugagag uagacuccuu 23460
gcagggauua uggauccaau ggguacaugg aggugcauuc ccaucgacca cauggcucca 23520
auucucacac cagucguuaa gcauggcaag cucaagcuac augggcaaga gcuggccaau 23580

-continued ggcauaucag ucagaaaucc gccacaggau auggugauag ugucaccaag ugacaccuuu 23640
cacuacacuu uuaagaaacc uguggaauca aacaacgauc cagaauuugc uguucugaua 23700
uaccagggug accgcgcuuc aaacgcugga cuucacacca uaaccacuuc aaaggccggu 23760
gacgcucgcc uguauaagua uauguaaugu gcaacugcca ucugcagcug cgagauuuau 23820
auagauugug caauaagcgg cacaucagaa gagaggaugu uccugagcuu auugacccuc 23880
ucguuaaaac ucgcuguuuu gcuuacaguc ucgugguucu ugcuaaugcu aauccaauug 23940
cauuuagcau acuaccucgg aaaauucuua ucaaugguga gccuuuacug cuugaauaug 24000
guagcauaua ugguaaagac uuuaucauuc gaccaucgcu ccaagucauu cuugaagaug 24060
aauuaaauua aaguuuugac accaaucuau cauggcugca ccaguagucc cuacuacuga 24120
cgcgucuugg uuucaggugc ucaaagcuca aaacaaaaag gcuacucauc cucaguuucg 24180
uggcaaugga guuccgcuua acuccgccau caaacccguu gaaaaccaug gcuacuggcu 24240
gcguuacacc agacaaaagc cagguggua c ucccauuccu ccauccuaug ccuuuuauua 24300
uacuggcaca ggucccagag gaaaucuuaa guauggugaa cucccuccua augauacccc 24360
agcaaccacu cguguuacuu ggguuaaggg uucgggagcu gacacuucua uuaaaccuca 24420
uguugccaaa cgcaacccca acaauccuaa acaucagcug cuaccucucc gauucccaac 24480
cggagauggc ccagcucaag guuucagagu ugaccccuuc aacgcuagag gaagaccuca 24540
ggagcgugga aguggcccaa gaucucaauc uguuaacucc agaggcacag gcaaucagcc 24600
caggaaacgc gaccaaucug caccagcugc gguacgucgu aagacccagc aucaagcucc 24660
caagcggacu uuacccaagg guaaaaccau uucucaggua uuuggcaacc ggucucguac 24720
uggugccaau gucggcucug cagacacuga gaagacgggu auggcugauc cucgcaucau 24780
ggcucuagcc agacaugugc cugguguuca ggaaaugcuu uuugcuggcc accuugagag 24840
caacuuucag gcgggggcaa uaacccuuac cuucuccuac ucaaucacag ucaaggaggg 24900
uucuccugac uaugagagac uuaaggaugc gcucaauacg gucguuaacc agaccuauga 24960
gccaccuacc aaaccaacua aggacaagaa gccugacaaa caagaccagu cugcuaaacc 25020
caaacagcag aagaaaccua aaaagguaac ucugccagca gacaaacagg auugggagug 25080
ggaugaugcu uuugagauaa agcaggaauc agcagcguag acaucaaucu augucuguua 25140
aacccaccca acuccacuca aauaucucuu ugguuccaga gagucguagu guauagccag 25200
agagccaguc agagggcgcu aucaugcaaa cuagggcugg cuacucuagc acagaaucac 25260
aucccgauaa ucaacagugc uagaagguug auuauaccau uuaauaugcc gaggccacgc 25320
ggaguacgau cgaggguaca gcauaaucuc aacuuuuguu gagccacaau uuuaauccua 25380
auuggagaag gccaaaggac uguacuacuu uugugggugu agcagucgcc caguggqaaa 25440 gcgccaacua gguuacaauu guggugggga caaauuaggg gaaauuaaau uggcuuau 25498

<210> SEQ ID NO 11
<211> LENGTH: 3471
<212> TYPE: DNA
<213> ORGANISM: Artificial Sequence
<220> FEATURE:
<223> OTHER INFORMATION: Porcine Deltacorona Virus BIV-Isolate 5.0327
Spike Antigen cDNA

<400> SEQUENCE: 11
atgcagagag ctctattgat tatgacctta ttttgtctcg ttcgagcaaa gtttgctgat 60
gatctactcg atttgctcac cttcccgggt gcacatcgct tcttacataa acccacgagg 120

```
aattccagca gtctctactc gcgggctaat aataattttg atgttggcgt tcttcctggc    180
taccccacta agaacgttaa cctcttctca ccacttacta actccacttt gcccattaat    240
ggccttcatc ggagttacca accactcatg ctgaattgtc ttactaaaat aactaaccac    300
actctcagca tgtatctcct acctagtgag atacaaactt atagctgcgg cggtgccatg    360
gttaaatacc agacacatga tgcagttcgt atcattttag acctcactgc cactgaccac    420
atctctgttg aagtcgttgg ccaacatggt gaaaattatg tgtttgtttg cagtgagcag    480
tttaactaca ccactgcatt acacaactct accttcttct cacttaattc tgagctttat    540
tgctttacta ataacaccta cttaggtatt cttccacctg atttaactga ctttacggtc    600
taccgtactg gtcagttcta tgctaatggt taccttttag gtactttacc tattacggtt    660
aactatgtta ggttgtatcg gggtcatttt agtgcccact ttgcccttgc aaacctaacc    720
gatacactca taacacttac caatactact atatcgcaaa tcacttattg tgataagtct    780
gtagttgatt caatagcatg ccagcgctct tctcacgaag tggaggatgg gttttactcc    840
gaccctaaat ctgccgttag agctaggcaa cgtactattg ttacactacc taagctccct    900
gagcttgaag tagtgcagtt aaatatttct gcacacatgg attttggcga agccagactt    960
gacagcgtta ccatcaatgg taacacatcc tattgtgtca ctaagcctta cttcaggctt   1020
gaaactaact ttatgtgtac aggttgcact atgaatctgc gcactgatac ctgtagtttt   1080
gacctgtcag cagtaaacaa tggcatgtca ttctctcaat tctgtctaag cactgaatct   1140
ggtgcttgtg agatgaaaat tattgttacc tacgtatgga attacttgct aaggcagcgt   1200
ttgtatgtta ctgctgtaga gggccagact cacactggaa ccacttcagt acatgcaaca   1260
gacacttcta gtgtaatcac tgatgtctgc actgactaca ctatctatgg agtctctggt   1320
actggcatta ttaagccatc agatctctta ttgcacaatg gcatagcatt cacctctcca   1380
acaggtgagc tttatgcatt taaaaatata accactggca aaacccttca ggtcttaccg   1440
tgtgaaaccc cttctcaact gattgtgata aacaacaccg ttgtcggtgc tatcacatcc   1500
agtaattcaa ctgaaaataa taggtttact actactattg tcacacctac tttcttttat   1560
tccacaaatg ccaccacttt caactgcact aagcctgttt tgtcctatgg acctatcagc   1620
gtgtgtagtg atggtgcaat tgtgggaaca tccacattac agaatactcg accatccata   1680
gtttcactat acgatggcga agttgaaata ccatctgcat ttctctcttc cgttcagacg   1740
gagtacttgc aagttcaagc agagcaagtt atagttgatt gtcctcagta tgtatgcaat   1800
ggcaacagcc gttgtctaca attactggca caatacacct cagcttgctc taacattgaa   1860
gcagctctgc attcctctgc acagttggat agcagagaga ttataaatat gtttcaaaca   1920
tcaacacagt ccttgcagtt agctaatatt accaacttca agggtgacta caattttagc   1980
agcatactaa ccaccagaat tggtggcaga tctgctattg aagaccttct tttaataaa   2040
gttgttacta gtggccttgg cactgttgat caggactaca aatcctgctc tagagacatg   2100
gccatcgctg acttagtttg ttcccagtat tacaatggca tcatggttct acctggtgtt   2160
gttgatgctg agaaaatggc aatgtatact ggctctctta ctggagctat ggtatttgga   2220
ggactgactg ccgcagcggc aataccattt gccacggcag tacaagctcg cctcaattat   2280
gtcgcactgc aaacaaatgt actacaagaa aaccagaaaa ttcttgcaga atcatttaac   2340
caagcagttg gcaatatatc acttgcacta tcttctgtta atgatgccat ccagcaaact   2400
tctgaggctc ttaacaccgt agctattgct attaaaaaga ttcaaacagt tgttaaccag   2460
cagggcgagg cattatcaca cctgactgca cagctgtcaa acaattttca agcaatttcg   2520
```

```
acttctattc aagacattta caaccgtctt gaggaagtag aggctaacca gcaagttgac   2580

cgtctcatca caggacggtt ggctgcactt aatgcatatg ttactcagtt actcaatcag   2640

atgtctcaga ttagacaatc tcgattgtta gctcagcaaa agattaatga gtgtgtcaaa   2700

tcacagtcgt ccagatacgg tttctgtgga aatggcacac acatcttctc acttacacag   2760

actgcaccaa atggcatatt tttcatgcat gcagtgctag tacccaacaa attcacacgt   2820

gtcaacgctt ctgccggcat ttgtgtggat aatacgagag gctactcatt gcagcctcaa   2880

cttatactct accagtttaa taactcctgg agagttacac ctagaaatat gtatgaaccc   2940

agactgcccc ggcaggctga tttcatacaa ttaactgatt gcagcgttac tttttacaac   3000

accaccgctg ctaatcttcc caatattatc cctgacatta tagatgtcaa tcaaacagtc   3060

agtgatatta ttgacaattt acctacagca acacctcctc agtgggatgt tggtatctat   3120

aacaacacta ttctcaacct caccgttgag attaatgatc tacaagagcg gtctaaaaac   3180

ctctcacaga ttgcagatcg tttacaaaat tatattgaca atcttaacaa tactctagtt   3240

gaccttgaat ggctcaacag agtggaaact taccttaaat ggccgtggta tatatggctt   3300

gccattgccc tggctcttat tgcatttgtg acaatcctca taacaatctt tctttgtact   3360

ggttgttgtg gtggttgctt tggttgttgt ggcggttgtt ttggcctttt ctctaagaag   3420

aaaaggtata ccgacgacca accaacaccg tcctttaagt ttaaggaatg g             3471
```

```
<210> SEQ ID NO 12
<211> LENGTH: 1157
<212> TYPE: PRT
<213> ORGANISM: Porcine Deltacorona Virus

<400> SEQUENCE: 12

Met Gln Arg Ala Leu Leu Ile Met Thr Leu Phe Cys Leu Val Arg Ala
1               5                   10                  15

Lys Phe Ala Asp Asp Leu Leu Asp Leu Leu Thr Phe Pro Gly Ala His
            20                  25                  30

Arg Phe Leu His Lys Pro Thr Arg Asn Ser Ser Ser Leu Tyr Ser Arg
        35                  40                  45

Ala Asn Asn Asn Phe Asp Val Gly Val Leu Pro Gly Tyr Pro Thr Lys
    50                  55                  60

Asn Val Asn Leu Phe Ser Pro Leu Thr Asn Ser Thr Leu Pro Ile Asn
65                  70                  75                  80

Gly Leu His Arg Ser Tyr Gln Pro Leu Met Leu Asn Cys Leu Thr Lys
                85                  90                  95

Ile Thr Asn His Thr Leu Ser Met Tyr Leu Leu Pro Ser Glu Ile Gln
            100                 105                 110

Thr Tyr Ser Cys Gly Gly Ala Met Val Lys Tyr Gln Thr His Asp Ala
        115                 120                 125

Val Arg Ile Ile Leu Asp Leu Thr Ala Thr Asp His Ile Ser Val Glu
    130                 135                 140

Val Val Gly Gln His Gly Glu Asn Tyr Val Phe Val Cys Ser Glu Gln
145                 150                 155                 160

Phe Asn Tyr Thr Thr Ala Leu His Asn Ser Thr Phe Phe Ser Leu Asn
                165                 170                 175

Ser Glu Leu Tyr Cys Phe Thr Asn Asn Thr Tyr Leu Gly Ile Leu Pro
            180                 185                 190

Pro Asp Leu Thr Asp Phe Thr Val Tyr Arg Thr Gly Gln Phe Tyr Ala
        195                 200                 205
```

-continued

```
Asn Gly Tyr Leu Leu Gly Thr Leu Pro Ile Thr Val Asn Tyr Val Arg
    210                 215                 220

Leu Tyr Arg Gly His Phe Ser Ala His Phe Ala Leu Ala Asn Leu Thr
225                 230                 235                 240

Asp Thr Leu Ile Thr Leu Thr Asn Thr Thr Ile Ser Gln Ile Thr Tyr
                245                 250                 255

Cys Asp Lys Ser Val Val Asp Ser Ile Ala Cys Gln Arg Ser Ser His
            260                 265                 270

Glu Val Glu Asp Gly Phe Tyr Ser Asp Pro Lys Ser Ala Val Arg Ala
        275                 280                 285

Arg Gln Arg Thr Ile Val Thr Leu Pro Lys Leu Pro Glu Leu Glu Val
    290                 295                 300

Val Gln Leu Asn Ile Ser Ala His Met Asp Phe Gly Glu Ala Arg Leu
305                 310                 315                 320

Asp Ser Val Thr Ile Asn Gly Asn Thr Ser Tyr Cys Val Thr Lys Pro
                325                 330                 335

Tyr Phe Arg Leu Glu Thr Asn Phe Met Cys Thr Gly Cys Thr Met Asn
            340                 345                 350

Leu Arg Thr Asp Thr Cys Ser Phe Asp Leu Ser Ala Val Asn Asn Gly
        355                 360                 365

Met Ser Phe Ser Gln Phe Cys Leu Ser Thr Glu Ser Gly Ala Cys Glu
    370                 375                 380

Met Lys Ile Ile Val Thr Tyr Val Trp Asn Tyr Leu Leu Arg Gln Arg
385                 390                 395                 400

Leu Tyr Val Thr Ala Val Glu Gly Gln Thr His Thr Gly Thr Thr Ser
                405                 410                 415

Val His Ala Thr Asp Thr Ser Ser Val Ile Thr Asp Val Cys Thr Asp
            420                 425                 430

Tyr Thr Ile Tyr Gly Val Ser Gly Thr Gly Ile Ile Lys Pro Ser Asp
        435                 440                 445

Leu Leu Leu His Asn Gly Ile Ala Phe Thr Ser Pro Thr Gly Glu Leu
    450                 455                 460

Tyr Ala Phe Lys Asn Ile Thr Thr Gly Lys Thr Leu Gln Val Leu Pro
465                 470                 475                 480

Cys Glu Thr Pro Ser Gln Leu Ile Val Ile Asn Asn Thr Val Val Gly
                485                 490                 495

Ala Ile Thr Ser Ser Asn Ser Thr Glu Asn Asn Arg Phe Thr Thr Thr
            500                 505                 510

Ile Val Thr Pro Thr Phe Phe Tyr Ser Thr Asn Ala Thr Thr Phe Asn
        515                 520                 525

Cys Thr Lys Pro Val Leu Ser Tyr Gly Pro Ile Ser Val Cys Ser Asp
    530                 535                 540

Gly Ala Ile Val Gly Thr Ser Thr Leu Gln Asn Thr Arg Pro Ser Ile
545                 550                 555                 560

Val Ser Leu Tyr Asp Gly Glu Val Glu Ile Pro Ser Ala Phe Ser Leu
                565                 570                 575

Ser Val Gln Thr Glu Tyr Leu Gln Val Gln Ala Glu Gln Val Ile Val
            580                 585                 590

Asp Cys Pro Gln Tyr Val Cys Asn Gly Asn Ser Arg Cys Leu Gln Leu
        595                 600                 605

Leu Ala Gln Tyr Thr Ser Ala Cys Ser Asn Ile Glu Ala Ala Leu His
    610                 615                 620
```

-continued

```
Ser Ser Ala Gln Leu Asp Ser Arg Glu Ile Ile Asn Met Phe Gln Thr
625                 630                 635                 640

Ser Thr Gln Ser Leu Gln Leu Ala Asn Ile Thr Asn Phe Lys Gly Asp
                645                 650                 655

Tyr Asn Phe Ser Ser Ile Leu Thr Thr Arg Ile Gly Gly Arg Ser Ala
            660                 665                 670

Ile Glu Asp Leu Leu Phe Asn Lys Val Val Thr Ser Gly Leu Gly Thr
        675                 680                 685

Val Asp Gln Asp Tyr Lys Ser Cys Ser Arg Asp Met Ala Ile Ala Asp
    690                 695                 700

Leu Val Cys Ser Gln Tyr Tyr Asn Gly Ile Met Val Leu Pro Gly Val
705                 710                 715                 720

Val Asp Ala Glu Lys Met Ala Met Tyr Thr Gly Ser Leu Thr Gly Ala
                725                 730                 735

Met Val Phe Gly Gly Leu Thr Ala Ala Ala Ala Ile Pro Phe Ala Thr
            740                 745                 750

Ala Val Gln Ala Arg Leu Asn Tyr Val Ala Leu Gln Thr Asn Val Leu
        755                 760                 765

Gln Glu Asn Gln Lys Ile Leu Ala Glu Ser Phe Asn Gln Ala Val Gly
    770                 775                 780

Asn Ile Ser Leu Ala Leu Ser Ser Val Asn Asp Ala Ile Gln Gln Thr
785                 790                 795                 800

Ser Glu Ala Leu Asn Thr Val Ala Ile Ala Ile Lys Lys Ile Gln Thr
                805                 810                 815

Val Val Asn Gln Gln Gly Glu Ala Leu Ser His Leu Thr Ala Gln Leu
            820                 825                 830

Ser Asn Asn Phe Gln Ala Ile Ser Thr Ser Ile Gln Asp Ile Tyr Asn
        835                 840                 845

Arg Leu Glu Glu Val Glu Ala Asn Gln Gln Val Asp Arg Leu Ile Thr
    850                 855                 860

Gly Arg Leu Ala Ala Leu Asn Ala Tyr Val Thr Gln Leu Leu Asn Gln
865                 870                 875                 880

Met Ser Gln Ile Arg Gln Ser Arg Leu Leu Ala Gln Gln Lys Ile Asn
                885                 890                 895

Glu Cys Val Lys Ser Gln Ser Ser Arg Tyr Gly Phe Cys Gly Asn Gly
            900                 905                 910

Thr His Ile Phe Ser Leu Thr Gln Thr Ala Pro Asn Gly Ile Phe Phe
        915                 920                 925

Met His Ala Val Leu Val Pro Asn Lys Phe Thr Arg Val Asn Ala Ser
    930                 935                 940

Ala Gly Ile Cys Val Asp Asn Thr Arg Gly Tyr Ser Leu Gln Pro Gln
945                 950                 955                 960

Leu Ile Leu Tyr Gln Phe Asn Asn Ser Trp Arg Val Thr Pro Arg Asn
                965                 970                 975

Met Tyr Glu Pro Arg Leu Pro Arg Gln Ala Asp Phe Ile Gln Leu Thr
            980                 985                 990

Asp Cys Ser Val Thr Phe Tyr Asn  Thr Thr Ala Ala Asn  Leu Pro Asn
        995                 1000                1005

Ile Ile  Pro Asp Ile Ile Asp  Val Asn Gln Thr Val  Ser Asp Ile
    1010                 1015                 1020

Ile Asp  Asn Leu Pro Thr Ala  Thr Pro Pro Gln Trp  Asp Val Gly
    1025                 1030                 1035

Ile Tyr  Asn Asn Thr Ile Leu  Asn Leu Thr Val Glu  Ile Asn Asp
```

```
    1040                1045                1050

Leu Gln  Glu Arg Ser Lys Asn  Leu Ser Gln Ile Ala  Asp Arg Leu
    1055                1060                1065

Gln Asn  Tyr Ile Asp Asn Leu  Asn Asn Thr Leu Val  Asp Leu Glu
    1070                1075                1080

Trp Leu  Asn Arg Val Glu Thr  Tyr Leu Lys Trp Pro  Trp Tyr Ile
    1085                1090                1095

Trp Leu  Ala Ile Ala Leu Ala  Leu Ile Ala Phe Val  Thr Ile Leu
    1100                1105                1110

Ile Thr  Ile Phe Leu Cys Thr  Gly Cys Cys Gly Gly  Cys Phe Gly
    1115                1120                1125

Cys Cys  Gly Gly Cys Phe Gly  Leu Phe Ser Lys Lys  Lys Arg Tyr
    1130                1135                1140

Thr Asp  Asp Gln Pro Thr Pro  Ser Phe Lys Phe Lys  Glu Trp
    1145                1150                1155
```

<210> SEQ ID NO 13
<211> LENGTH: 33
<212> TYPE: DNA
<213> ORGANISM: Artificial Sequence
<220> FEATURE:
<223> OTHER INFORMATION: P2967167A PDCoV SPIKE FORWARD PRIMER

<400> SEQUENCE: 13
ggatccatgc agagagctct attgattatg acc 33

<210> SEQ ID NO 14
<211> LENGTH: 42
<212> TYPE: DNA
<213> ORGANISM: Artificial Sequence
<220> FEATURE:
<223> OTHER INFORMATION: P2967167B PDCoV SPIKE REVERSE PRIMER

<400> SEQUENCE: 14
ggtcgagccg cctctgccac caattctggt ggttagtaag ct 42

<210> SEQ ID NO 15
<211> LENGTH: 31
<212> TYPE: DNA
<213> ORGANISM: Artificial Sequence
<220> FEATURE:
<223> OTHER INFORMATION: P2967167C  FC FORWARD PRIMER

<400> SEQUENCE: 15
tggtggcaga ggcggctcga ccaagaccaa g 31

<210> SEQ ID NO 16
<211> LENGTH: 36
<212> TYPE: DNA
<213> ORGANISM: Artificial Sequence
<220> FEATURE:
<223> OTHER INFORMATION: P2968014E FC FORWARD PRIMER

<400> SEQUENCE: 16
gcggccgcct acttgcccgg cgtcttcgaa atggat 36

<210> SEQ ID NO 17
<211> LENGTH: 2718
<212> TYPE: DNA
<213> ORGANISM: Artificial Sequence
<220> FEATURE:
<223> OTHER INFORMATION: PDCoV S1-IgG2a Fc CDS cDNA Expression Casette

```
<400> SEQUENCE: 17

atgcagagag ctctattgat tatgacctta ctttgtctcg ttcgagcaaa gtttgctgat    60
gatctactcg atttgctcac cttcccgggt gcacatcgct tcttacataa acccacgagg   120
aattccagca gtctctactc gcgggctaat aataattttg atgttggcgt tcttcctggc   180
taccccacta agaacgttaa cctcttctca ccacttacta actccacttt gcccattaat   240
ggccttcatc ggagttacca accactcatg ctgaattgtc ttactaaaat aactaaccac   300
actctcagca tgtatctcct acctagtgag atacaaactt atagctgcgg cggtgccatg   360
gttaaatacc agacacatga tgcagttcgt atcattttag acctcactgc cactgaccac   420
atctctgttg aagtcgttgg ccaacatggt gaaaattatg tgtttgtttg cagtgagcag   480
tttaactaca ccactgcatt acacaactct accttcttct cacttaattc tgagctttat   540
tgctttacta ataacaccta cttaggtatt cttccacctg atttaactga ctttacggtc   600
taccgtactg gtcagttcta tgctaatggt taccttttag gtactttacc tattacggtt   660
aactatgtta ggttgtatcg gggtcatttg tctgccaata gtgcctactt tgcccttgca   720
aacctaaccg atacactcat aacacttacc aatactacta tatcgcaaat cacttattgt   780
gataagtcag tagttgattc aatagcatgc cagcgctctt ctcacgaagt ggaggatggg   840
ttttactccg accctaaatc tgccgttaga gctaggcaac gtactattgt tacactacct   900
aagctccctg agcttgaagt agtgcagtta aatatttctg cacacatgga ttttggcgaa   960
gccagacttg acagcgttac catcaatggt aacacatcct attgtgtcac taagccttac  1020
ttcaggcttg aaactaactt tatgtgtaca ggttgcacta tgaatctgcg cactgatacc  1080
tgtagttttg acctgtcagc agtaaacaat ggcatgtcat tctctcaatt ctgtctaagc  1140
actgaatctg gtgcttgtga gatgaaaatt attgttacct acgtatggaa ttacttgcta  1200
aggcagcgtt tgtatgttac tgctgtagag ggccagactc acactggaac cacttcagta  1260
catgcaacag acacttctag tgtaatcact gatgtctgca ctgactacac tatctatgga  1320
gtctcaggta ctggcattat taagccatca gatctcttat tgcacaatgg catagcattc  1380
acctctccaa caggtgagct ttatgcattt aaaaatataa ccactggcaa aacccttcag  1440
gtcttaccgt gtgaaacccc ttctcaactg attgtgataa acaacaccgt tgtcggtgct  1500
atcacatcca gtaattcaac tgaaaataat aggtttacta ctactattgt cacacctact  1560
ttcttttatt ccacaaatgc caccacttcc aactgcacta agcctgtttt gtcctatgga  1620
cctatcagcg tgtgtagtga tggtgcaatt gtgggaacat ccacattaca gaatactcga  1680
ccatccatag tttcactata cgatggcgaa gttgaaatac catctgcatt ttctctttcc  1740
gttcagacgg agtacttgca agttcaagca gagcaagtta tagttgattg tcctcagtat  1800
gtatgcaatg gcaacagccg ttgtctacaa ttactggcac aatacacctc agcttgctct  1860
aacattgaag cagctctgca ttcctctgca cagttggata gcagagagat tataaatatg  1920
tttcaaacat caacacagtc cttgcagtta gctaatatta ccaacttcaa gggtgactac  1980
aattttagca gcttactaac caccagaatt ggtggcagag gcggctcgac caagaccaag  2040
cccccctgtc ctatttgccc ggcatgcgag agtccgggtc cgtccgtctt tattttcccc  2100
ccaaagccaa aagatacgct gatgatcagc cgcaccccccc aggtcacatg cgtggttgta  2160
gatgtaagcc aagaaaatcc cgaagtgcag ttttcctggt atgtcgatgg cgtggaggtt  2220
cacacagcac agacgcggcc gaaggaagag cagtttaatt ccacgtaccg agtggtgagt  2280
gtgctgccta ttcagcatca ggattggttg aacggaaagg agttcaagtg caaggtgaac  2340
```

aacaaagacc tgcccgcacc aatcactcgc ataatcagca aggctaaggg acagacacgc 2400
gagccacagg tgtacaccct gccaccgcat gcagaagagc tgagccgatc caaggtatcc 2460
ataacctgcc tggtgatcgg attctacccc cccgatatcg acgtcgagtg gcagaggaat 2520
ggccagccgg agccagaggg caactaccgg accacgcctc cgcagcagga tgtcgatggt 2580
acatattttc tgtacagcaa atttagcgtg gacaaggcca gttggcaggg cggcggtatc 2640
ttccagtgtg ctgtcatgca cgaggcactc cacaatcatt acacccagaa atccatttcg 2700
aagacgccgg gcaagtag 2718

<210> SEQ ID NO 18
<211> LENGTH: 905
<212> TYPE: PRT
<213> ORGANISM: Artificial Sequence
<220> FEATURE:
<223> OTHER INFORMATION: PDCoV S1-IgG2a Fc Amino Acid Sequence

<400> SEQUENCE: 18

Met Gln Arg Ala Leu Leu Ile Met Thr Leu Leu Cys Leu Val Arg Ala
1 5 10 15

Lys Phe Ala Asp Asp Leu Leu Asp Leu Leu Thr Phe Pro Gly Ala His
20 25 30

Arg Phe Leu His Lys Pro Thr Arg Asn Ser Ser Ser Leu Tyr Ser Arg
35 40 45

Ala Asn Asn Asn Phe Asp Val Gly Val Leu Pro Gly Tyr Pro Thr Lys
50 55 60

Asn Val Asn Leu Phe Ser Pro Leu Thr Asn Ser Thr Leu Pro Ile Asn
65 70 75 80

Gly Leu His Arg Ser Tyr Gln Pro Leu Met Leu Asn Cys Leu Thr Lys
85 90 95

Ile Thr Asn His Thr Leu Ser Met Tyr Leu Leu Pro Ser Glu Ile Gln
100 105 110

Thr Tyr Ser Cys Gly Gly Ala Met Val Lys Tyr Gln Thr His Asp Ala
115 120 125

Val Arg Ile Ile Leu Asp Leu Thr Ala Thr Asp His Ile Ser Val Glu
130 135 140

Val Val Gly Gln His Gly Glu Asn Tyr Val Phe Val Cys Ser Glu Gln
145 150 155 160

Phe Asn Tyr Thr Thr Ala Leu His Asn Ser Thr Phe Phe Ser Leu Asn
165 170 175

Ser Glu Leu Tyr Cys Phe Thr Asn Asn Thr Tyr Leu Gly Ile Leu Pro
180 185 190

Pro Asp Leu Thr Asp Phe Thr Val Tyr Arg Thr Gly Gln Phe Tyr Ala
195 200 205

Asn Gly Tyr Leu Leu Gly Thr Leu Pro Ile Thr Val Asn Tyr Val Arg
210 215 220

Leu Tyr Arg Gly His Leu Ser Ala Asn Ser Ala Tyr Phe Ala Leu Ala
225 230 235 240

Asn Leu Thr Asp Thr Leu Ile Thr Leu Thr Asn Thr Thr Ile Ser Gln
245 250 255

Ile Thr Tyr Cys Asp Lys Ser Val Val Asp Ser Ile Ala Cys Gln Arg
260 265 270

Ser Ser His Glu Val Glu Asp Gly Phe Tyr Ser Asp Pro Lys Ser Ala
275 280 285

-continued

```
Val Arg Ala Arg Gln Arg Thr Ile Val Thr Leu Pro Lys Leu Pro Glu
    290                 295                 300

Leu Glu Val Val Gln Leu Asn Ile Ser Ala His Met Asp Phe Gly Glu
305                 310                 315                 320

Ala Arg Leu Asp Ser Val Thr Ile Asn Gly Asn Thr Ser Tyr Cys Val
                325                 330                 335

Thr Lys Pro Tyr Phe Arg Leu Glu Thr Asn Phe Met Cys Thr Gly Cys
            340                 345                 350

Thr Met Asn Leu Arg Thr Asp Thr Cys Ser Phe Asp Leu Ser Ala Val
        355                 360                 365

Asn Asn Gly Met Ser Phe Ser Gln Phe Cys Leu Ser Thr Glu Ser Gly
    370                 375                 380

Ala Cys Glu Met Lys Ile Ile Val Thr Tyr Val Trp Asn Tyr Leu Leu
385                 390                 395                 400

Arg Gln Arg Leu Tyr Val Thr Ala Val Glu Gly Gln Thr His Thr Gly
                405                 410                 415

Thr Thr Ser Val His Ala Thr Asp Thr Ser Ser Val Ile Thr Asp Val
            420                 425                 430

Cys Thr Asp Tyr Thr Ile Tyr Gly Val Ser Gly Thr Gly Ile Ile Lys
        435                 440                 445

Pro Ser Asp Leu Leu Leu His Asn Gly Ile Ala Phe Thr Ser Pro Thr
    450                 455                 460

Gly Glu Leu Tyr Ala Phe Lys Asn Ile Thr Thr Gly Lys Thr Leu Gln
465                 470                 475                 480

Val Leu Pro Cys Glu Thr Pro Ser Gln Leu Ile Val Ile Asn Asn Thr
                485                 490                 495

Val Val Gly Ala Ile Thr Ser Ser Asn Ser Thr Glu Asn Asn Arg Phe
            500                 505                 510

Thr Thr Thr Ile Val Thr Pro Thr Phe Phe Tyr Ser Thr Asn Ala Thr
        515                 520                 525

Thr Phe Asn Cys Thr Lys Pro Val Leu Ser Tyr Gly Pro Ile Ser Val
    530                 535                 540

Cys Ser Asp Gly Ala Ile Val Gly Thr Ser Thr Leu Gln Asn Thr Arg
545                 550                 555                 560

Pro Ser Ile Val Ser Leu Tyr Asp Gly Glu Val Glu Ile Pro Ser Ala
                565                 570                 575

Phe Ser Leu Ser Val Gln Thr Glu Tyr Leu Gln Val Gln Ala Glu Gln
            580                 585                 590

Val Ile Val Asp Cys Pro Gln Tyr Val Cys Asn Gly Asn Ser Arg Cys
        595                 600                 605

Leu Gln Leu Leu Ala Gln Tyr Thr Ser Ala Cys Ser Asn Ile Glu Ala
    610                 615                 620

Ala Leu His Ser Ser Ala Gln Leu Asp Ser Arg Glu Ile Ile Asn Met
625                 630                 635                 640

Phe Gln Thr Ser Thr Gln Ser Leu Gln Leu Ala Asn Ile Thr Asn Phe
                645                 650                 655

Lys Gly Asp Tyr Asn Phe Ser Ser Leu Leu Thr Thr Arg Ile Gly Gly
            660                 665                 670

Arg Gly Gly Ser Thr Lys Thr Lys Pro Pro Cys Pro Ile Cys Pro Ala
        675                 680                 685

Cys Glu Ser Pro Gly Pro Ser Val Phe Ile Phe Pro Pro Lys Pro Lys
    690                 695                 700

Asp Thr Leu Met Ile Ser Arg Thr Pro Gln Val Thr Cys Val Val Val
```

-continued 705 710 715 720

Asp Val Ser Gln Glu Asn Pro Glu Val Gln Phe Ser Trp Tyr Val Asp
725 730 735

Gly Val Glu Val His Thr Ala Gln Thr Arg Pro Lys Glu Glu Gln Phe
740 745 750

Asn Ser Thr Tyr Arg Val Val Ser Val Leu Pro Ile Gln His Gln Asp
755 760 765

Trp Leu Asn Gly Lys Glu Phe Lys Cys Lys Val Asn Asn Lys Asp Leu
770 775 780

Pro Ala Pro Ile Thr Arg Ile Ile Ser Lys Ala Lys Gly Gln Thr Arg
785 790 795 800

Glu Pro Gln Val Tyr Thr Leu Pro Pro His Ala Glu Glu Leu Ser Arg
805 810 815

Ser Lys Val Ser Ile Thr Cys Leu Val Ile Gly Phe Tyr Pro Pro Asp
820 825 830

Ile Asp Val Glu Trp Gln Arg Asn Gly Gln Pro Glu Pro Glu Gly Asn
835 840 845

Tyr Arg Thr Thr Pro Pro Gln Gln Asp Val Asp Gly Thr Tyr Phe Leu
850 855 860

Tyr Ser Lys Phe Ser Val Asp Lys Ala Ser Trp Gln Gly Gly Gly Ile
865 870 875 880

Phe Gln Cys Ala Val Met His Glu Ala Leu His Asn His Tyr Thr Gln
885 890 895

Lys Ser Ile Ser Lys Thr Pro Gly Lys
900 905

<210> SEQ ID NO 19
<211> LENGTH: 22
<212> TYPE: DNA
<213> ORGANISM: Artificial Sequence
<220> FEATURE:
<223> OTHER INFORMATION: P290194A F Primer PDCoVS BD

<400> SEQUENCE: 19
ggatccgcca ccatggtatc tg 22

<210> SEQ ID NO 20
<211> LENGTH: 21
<212> TYPE: DNA
<213> ORGANISM: Artificial Sequence
<220> FEATURE:
<223> OTHER INFORMATION: P290194B R Primer PDCoVS BD

<400> SEQUENCE: 20
gcttaaatac atatttagta c 21

<210> SEQ ID NO 21
<211> LENGTH: 100
<212> TYPE: DNA
<213> ORGANISM: Artificial Sequence
<220> FEATURE:
<223> OTHER INFORMATION: O2967002 A Primer Gp64 signal sequence

<400> SEQUENCE: 21
ggatccgcca ccatggtatc tgctattgtt ctttatgttt tgcttgctgc cgccgctcac 60
tcagctttcg cggatgatct actcgatttg ctcaccttcc 100

<210> SEQ ID NO 22
<211> LENGTH: 63

<212> TYPE: DNA
<213> ORGANISM: Artificial Sequence
<220> FEATURE:
<223> OTHER INFORMATION: O2967002B AcNPV gp64 C-terminal tail coding sequence

<400> SEQUENCE: 22
gcggccgctt agtactgacg attgcggttt ctaagaaaga ttgttatgag gattgtcaca 60
aat 63

<210> SEQ ID NO 23
<211> LENGTH: 28
<212> TYPE: DNA
<213> ORGANISM: Artificial Sequence
<220> FEATURE:
<223> OTHER INFORMATION: P2967002C F Primer PDCoVS BD

<400> SEQUENCE: 23
gatgatctac tcgatttgct caccttcc 28

<210> SEQ ID NO 24
<211> LENGTH: 26
<212> TYPE: DNA
<213> ORGANISM: Artificial Sequence
<220> FEATURE:
<223> OTHER INFORMATION: P2967002D R Primer PDCoVS BD

<400> SEQUENCE: 24
cgatggccat gtctctagag caggat 26

<210> SEQ ID NO 25
<211> LENGTH: 25
<212> TYPE: DNA
<213> ORGANISM: Artificial Sequence
<220> FEATURE:
<223> OTHER INFORMATION: P2967002E F Primer PDCoVS BD

<400> SEQUENCE: 25
tgtcctatgg acctatcagc gtgtg 25

<210> SEQ ID NO 26
<211> LENGTH: 31
<212> TYPE: DNA
<213> ORGANISM: Artificial Sequence
<220> FEATURE:
<223> OTHER INFORMATION: P2968002F R Primer PDCoVS BD

<400> SEQUENCE: 26
aagaaagatt gttatgagga ttgtcacaaa t 31

<210> SEQ ID NO 27
<211> LENGTH: 3390
<212> TYPE: DNA
<213> ORGANISM: Artificial Sequence
<220> FEATURE:
<223> OTHER INFORMATION: PDCoVS BD CDS Expression Cassette

<400> SEQUENCE: 27
atggtatctg ctattgttct ttatgttttg cttgctgccg ccgctcactc agctttcgcg 60
gatgatctac tcgatttgct caccttcccg ggtgcacatc gcttcttaca taaacccacg 120
aggaattcca gcagtctcta ctcgcgggct aataataatt ttgatgttgg cgttcttcct 180
ggctacccca ctaagaacgt taacctcttc tcaccactta ctaactccac tttgcccatt 240
aatggccttc atcggagtta ccaaccactc atgctgaatt gtcttactaa aataactaac 300
cacactctca gcatgtatct cctacctagt gagatacaaa cttatagctg cggcggtgcc 360
atggttaaat accagacaca tgatgcagtt cgtatcattt tagacctcac tgccactgac 420
cacatctctg ttgaagtcgt tggccaacat ggtgaaaatt atgtgtttgt ttgcagtgag 480
cagtttaact acaccactgc attacacaac tctaccttct tctcacttaa ttctgagctt 540
tattgcttta ctaataacac ctacttaggt attcttccac ctgatttaac tgactttacg 600
gtctaccgta ctggtcagtt ctatgctaat ggttaccttt taggtacttt acctattacg 660
gttaactatg ttaggttgta tcggggtcat ttgtctgcca atagtgccta ctttgccctt 720
gcaaacctaa ccgatacact cataacactt accaatacta ctatatcgca aatcacttat 780
tgtgataagt cagtagttga ttcaatagca tgccagcgct cttctcacga agtggaggat 840
gggttttact ccgaccctaa atctgccgtt agagctaggc aacgtactat tgttacacta 900
cctaagctcc ctgagcttga agtagtgcag ttaaatattt ctgcacacat ggattttggc 960
gaagccagac ttgacagcgt taccatcaat ggtaacacat cctattgtgt cactaagcct 1020
tacttcaggc ttgaaactaa ctttatgtgt acaggttgca ctatgaatct gcgcactgat 1080
acctgtagtt ttgacctgtc agcagtaaac aatggcatgt cattctctca attctgtcta 1140
agcactgaat ctggtgcttg tgagatgaaa attattgtta cctacgtatg gaattacttg 1200
ctaaggcagc gtttgtatgt tactgctgta gagggccaga ctcacactgg aaccacttca 1260
gtacatgcaa cagacacttc tagtgtaatc actgatgtct gcactgacta cactatctat 1320
ggagtctcag gtactggcat tattaagcca tcagatctct tattgcacaa tggcatagca 1380
ttcacctctc caacaggtga gctttatgca tttaaaaata taaccactgg caaaaccctt 1440
caggtcttac cgtgtgaaac cccttctcaa ctgattgtga taaacaacac cgttgtcggt 1500
gctatcacat ccagtaattc aactgaaaat aataggttta ctactactat tgtcacacct 1560
actttctttt attccacaaa tgccaccact ttcaactgca ctaagcctgt tttgtcctat 1620
ggacctatca gcgtgtgtag tgatggtgca attgtgggaa catccacatt acagaatact 1680
cgaccatcca tagtttcact atacgatggc gaagttgaaa taccatctgc attttctctt 1740
tccgttcaga cggagtactt gcaagttcaa gcagagcaag ttatagttga ttgtcctcag 1800
tatgtatgca atggcaacag ccgttgtcta caattactgg cacaatacac ctcagcttgc 1860
tctaacattg aagcagctct gcattcctct gcacagttgg atagcagaga gattataaat 1920
atgtttcaaa catcaacaca gtccttgcag ttagctaata ttaccaactt caagggtgac 1980
tacaatttta gcagcttact aaccaccaga attggtggca gatctgctat tgaagacctt 2040
ctttttaata aagttgttac tagtggcctt ggcactgttg atcaggacta caaatcctgc 2100
tctagagaca tggccatcgc tgacttagtt tgttcccagt attacaatgg catcatggtt 2160
ctacctggtg ttgttgatgc tgagaaaatg gcaatgtata ctggctctct tactggagct 2220
atggtatttg gaggactgac tgccgcagcg gcaataccat ttgccacggc agtacaagct 2280
cgcctcaatt atgtcgcact gcaaacaaat gtactacaag aaaaccagaa aattcttgca 2340
gaatcattta accaagcagt tggcaatata tcacttgcac tatcttctgt taatgatgcc 2400
atccagcaaa cttctgaggc tcttaacacc gtagctattg ctattaaaaa gattcaaaca 2460
gttgttaacc agcagggcga ggcattatca cacctgactg cacagctgtc aaacaatttt 2520
caagcaattt cgacttctat tcaagacatt tacaaccgtc ttgaggaagt agaggctaac 2580
cagcaagttg accgtctcat cacaggacgg ttggctgcac ttaatgcata tgttactcag 2640

-continued ttactcaatc agatgtctca gattagacaa tctcgattgt tagctcagca aaagattaat 2700
gagtgtgtca aatcacagtc gtccagatac ggtttctgtg gaaatggcac acacatcttc 2760
tcacttacac agactgcacc aaatggcata tttttcatgc atgcagtgct agtacccaac 2820
aaattcacac gtgtcaacgc ttctgccggc atttgtgtgg ataatacgag aggctactca 2880
ttgcagcctc aacttatact ctaccagttt aataactcct ggagagttac acctagaaat 2940
atgtatgaac ccagactgcc ccggcaggct gatttcatac aattaactga ttgcagcgtt 3000
actttttaca acaccaccgc tgctaatctt cccaatatta tccctgacat tatagatgtc 3060
aatcaaacag tcagtgatat tattgacaat ttacctacag caacacctcc tcagtgggat 3120
gttggtatct ataacaacac tattctcaac ctcaccgttg agattaatga tctacaagag 3180
cggtctaaaa acctctcaca gattgcagat cgtttacaaa attatattga caatcttaac 3240
aatactctag ttgaccttga atggctcaac agagtggaaa cttaccttaa atggccgtgg 3300
tatatatggc ttgccattgc cctggctctt attgcatttg tgacaatcct cataacaatc 3360
tttcttagaa accgcaatcg tcagtactaa 3390

<210> SEQ ID NO 28
<211> LENGTH: 1129
<212> TYPE: PRT
<213> ORGANISM: Artificial Sequence
<220> FEATURE:
<223> OTHER INFORMATION: PDCoVS BD Protein - expressed baculodisplay

<400> SEQUENCE: 28

Met Val Ser Ala Ile Val Leu Tyr Val Leu Leu Ala Ala Ala Ala His
1 5 10 15

Ser Ala Phe Ala Asp Asp Leu Leu Asp Leu Leu Thr Phe Pro Gly Ala
20 25 30

His Arg Phe Leu His Lys Pro Thr Arg Asn Ser Ser Ser Leu Tyr Ser
35 40 45

Arg Ala Asn Asn Asn Phe Asp Val Gly Val Leu Pro Gly Tyr Pro Thr
50 55 60

Lys Asn Val Asn Leu Phe Ser Pro Leu Thr Asn Ser Thr Leu Pro Ile
65 70 75 80

Asn Gly Leu His Arg Ser Tyr Gln Pro Leu Met Leu Asn Cys Leu Thr
85 90 95

Lys Ile Thr Asn His Thr Leu Ser Met Tyr Leu Leu Pro Ser Glu Ile
100 105 110

Gln Thr Tyr Ser Cys Gly Gly Ala Met Val Lys Tyr Gln Thr His Asp
115 120 125

Ala Val Arg Ile Ile Leu Asp Leu Thr Ala Thr Asp His Ile Ser Val
130 135 140

Glu Val Val Gly Gln His Gly Glu Asn Tyr Val Phe Val Cys Ser Glu
145 150 155 160

Gln Phe Asn Tyr Thr Thr Ala Leu His Asn Ser Thr Phe Phe Ser Leu
165 170 175

Asn Ser Glu Leu Tyr Cys Phe Thr Asn Asn Thr Tyr Leu Gly Ile Leu
180 185 190

Pro Pro Asp Leu Thr Asp Phe Thr Val Tyr Arg Thr Gly Gln Phe Tyr
195 200 205

Ala Asn Gly Tyr Leu Leu Gly Thr Leu Pro Ile Thr Val Asn Tyr Val
210 215 220

Arg Leu Tyr Arg Gly His Leu Ser Ala Asn Ser Ala Tyr Phe Ala Leu

```
225                 230                 235                 240

Ala Asn Leu Thr Asp Thr Leu Ile Thr Leu Thr Asn Thr Thr Ile Ser
                245                 250                 255

Gln Ile Thr Tyr Cys Asp Lys Ser Val Val Asp Ser Ile Ala Cys Gln
            260                 265                 270

Arg Ser Ser His Glu Val Glu Asp Gly Phe Tyr Ser Asp Pro Lys Ser
        275                 280                 285

Ala Val Arg Ala Arg Gln Arg Thr Ile Val Thr Leu Pro Lys Leu Pro
    290                 295                 300

Glu Leu Glu Val Val Gln Leu Asn Ile Ser Ala His Met Asp Phe Gly
305                 310                 315                 320

Glu Ala Arg Leu Asp Ser Val Thr Ile Asn Gly Asn Thr Ser Tyr Cys
                325                 330                 335

Val Thr Lys Pro Tyr Phe Arg Leu Glu Thr Asn Phe Met Cys Thr Gly
            340                 345                 350

Cys Thr Met Asn Leu Arg Thr Asp Thr Cys Ser Phe Asp Leu Ser Ala
        355                 360                 365

Val Asn Asn Gly Met Ser Phe Ser Gln Phe Cys Leu Ser Thr Glu Ser
    370                 375                 380

Gly Ala Cys Glu Met Lys Ile Ile Val Thr Tyr Val Trp Asn Tyr Leu
385                 390                 395                 400

Leu Arg Gln Arg Leu Tyr Val Thr Ala Val Glu Gly Gln Thr His Thr
                405                 410                 415

Gly Thr Thr Ser Val His Ala Thr Asp Thr Ser Ser Val Ile Thr Asp
            420                 425                 430

Val Cys Thr Asp Tyr Thr Ile Tyr Gly Val Ser Gly Thr Gly Ile Ile
        435                 440                 445

Lys Pro Ser Asp Leu Leu Leu His Asn Gly Ile Ala Phe Thr Ser Pro
    450                 455                 460

Thr Gly Glu Leu Tyr Ala Phe Lys Asn Ile Thr Thr Gly Lys Thr Leu
465                 470                 475                 480

Gln Val Leu Pro Cys Glu Thr Pro Ser Gln Leu Ile Val Ile Asn Asn
                485                 490                 495

Thr Val Val Gly Ala Ile Thr Ser Ser Asn Ser Thr Glu Asn Asn Arg
            500                 505                 510

Phe Thr Thr Thr Ile Val Thr Pro Thr Phe Phe Tyr Ser Thr Asn Ala
        515                 520                 525

Thr Thr Phe Asn Cys Thr Lys Pro Val Leu Ser Tyr Gly Pro Ile Ser
    530                 535                 540

Val Cys Ser Asp Gly Ala Ile Val Gly Thr Ser Thr Leu Gln Asn Thr
545                 550                 555                 560

Arg Pro Ser Ile Val Ser Leu Tyr Asp Gly Glu Val Glu Ile Pro Ser
                565                 570                 575

Ala Phe Ser Leu Ser Val Gln Thr Glu Tyr Leu Gln Val Gln Ala Glu
            580                 585                 590

Gln Val Ile Val Asp Cys Pro Gln Tyr Val Cys Asn Gly Asn Ser Arg
        595                 600                 605

Cys Leu Gln Leu Leu Ala Gln Tyr Thr Ser Ala Cys Ser Asn Ile Glu
    610                 615                 620

Ala Ala Leu His Ser Ser Ala Gln Leu Asp Ser Arg Glu Ile Ile Asn
625                 630                 635                 640

Met Phe Gln Thr Ser Thr Gln Ser Leu Gln Leu Ala Asn Ile Thr Asn
                645                 650                 655
```

```
Phe Lys Gly Asp Tyr Asn Phe Ser Ser Leu Leu Thr Thr Arg Ile Gly
            660                 665                 670

Gly Arg Ser Ala Ile Glu Asp Leu Leu Phe Asn Lys Val Val Thr Ser
        675                 680                 685

Gly Leu Gly Thr Val Asp Gln Asp Tyr Lys Ser Cys Ser Arg Asp Met
    690                 695                 700

Ala Ile Ala Asp Leu Val Cys Ser Gln Tyr Tyr Asn Gly Ile Met Val
705                 710                 715                 720

Leu Pro Gly Val Val Asp Ala Glu Lys Met Ala Met Tyr Thr Gly Ser
                725                 730                 735

Leu Thr Gly Ala Met Val Phe Gly Gly Leu Thr Ala Ala Ala Ala Ile
            740                 745                 750

Pro Phe Ala Thr Ala Val Gln Ala Arg Leu Asn Tyr Val Ala Leu Gln
        755                 760                 765

Thr Asn Val Leu Gln Glu Asn Gln Lys Ile Leu Ala Glu Ser Phe Asn
    770                 775                 780

Gln Ala Val Gly Asn Ile Ser Leu Ala Leu Ser Ser Val Asn Asp Ala
785                 790                 795                 800

Ile Gln Gln Thr Ser Glu Ala Leu Asn Thr Val Ala Ile Ala Ile Lys
                805                 810                 815

Lys Ile Gln Thr Val Val Asn Gln Gln Gly Glu Ala Leu Ser His Leu
            820                 825                 830

Thr Ala Gln Leu Ser Asn Asn Phe Gln Ala Ile Ser Thr Ser Ile Gln
        835                 840                 845

Asp Ile Tyr Asn Arg Leu Glu Glu Val Glu Ala Asn Gln Gln Val Asp
    850                 855                 860

Arg Leu Ile Thr Gly Arg Leu Ala Ala Leu Asn Ala Tyr Val Thr Gln
865                 870                 875                 880

Leu Leu Asn Gln Met Ser Gln Ile Arg Gln Ser Arg Leu Leu Ala Gln
                885                 890                 895

Gln Lys Ile Asn Glu Cys Val Lys Ser Gln Ser Ser Arg Tyr Gly Phe
            900                 905                 910

Cys Gly Asn Gly Thr His Ile Phe Ser Leu Thr Gln Thr Ala Pro Asn
        915                 920                 925

Gly Ile Phe Phe Met His Ala Val Leu Val Pro Asn Lys Phe Thr Arg
    930                 935                 940

Val Asn Ala Ser Ala Gly Ile Cys Val Asp Asn Thr Arg Gly Tyr Ser
945                 950                 955                 960

Leu Gln Pro Gln Leu Ile Leu Tyr Gln Phe Asn Asn Ser Trp Arg Val
                965                 970                 975

Thr Pro Arg Asn Met Tyr Glu Pro Arg Leu Pro Arg Gln Ala Asp Phe
            980                 985                 990

Ile Gln Leu Thr Asp Cys Ser Val  Thr Phe Tyr Asn Thr  Thr Ala Ala
        995                 1000                1005

Asn Leu  Pro Asn Ile Ile Pro  Asp Ile Ile Asp Val  Asn Gln Thr
    1010                1015                1020

Val Ser  Asp Ile Ile Asp Asn  Leu Pro Thr Ala Thr  Pro Pro Gln
    1025                1030                1035

Trp Asp  Val Gly Ile Tyr Asn  Asn Thr Ile Leu Asn  Leu Thr Val
    1040                1045                1050

Glu Ile  Asn Asp Leu Gln Glu  Arg Ser Lys Asn Leu  Ser Gln Ile
    1055                1060                1065
```

```
Ala Asp  Arg Leu Gln Asn Tyr  Ile Asp Asn Leu Asn  Asn Thr Leu
    1070                 1075                 1080

Val Asp  Leu Glu Trp Leu Asn  Arg Val Glu Thr Tyr  Leu Lys Trp
    1085                 1090                 1095

Pro Trp  Tyr Ile Trp Leu Ala  Ile Ala Leu Ala Leu  Ile Ala Phe
    1100                 1105                 1110

Val Thr  Ile Leu Ile Thr Ile  Phe Leu Arg Asn Arg  Asn Arg Gln
    1115                 1120                 1125

Tyr


<210> SEQ ID NO 29
<211> LENGTH: 27960
<212> TYPE: DNA
<213> ORGANISM: Artificial Sequence
<220> FEATURE:
<223> OTHER INFORMATION: Complete Genome Nucleic Acid (cDNA) Sequence
      equivalent of the (+) single-stranded RNA genome of PEDV Isolate
      1251-125-10 (125-10)

<400> SEQUENCE: 29

agactcttgt ctactcaatt caactaaacg aaattttgtc cttccggccg catgtccatg     60

ctgctggaag ctgacgtgga atttcattag gtttgcttaa gtagccatcg caagtgctgt    120

gctgtcctct agttcctggt tggcgttccg tcgccttcta catactagac aaacagcctt    180

cctccggttc cgtctggggg ttgtgtggat aactagttcc gtctagtttg aaaccagtaa    240

ctgtcggcta tggctagcaa ccatgttaca ttggcttttg ccaatgatgc agaaatttca    300

gcttttggct tttgcactgc tagtgaagcc gtctcatact attctgaggc cgccgctagt    360

ggatttatgc aatgccgttt cgtgtccttc gatctcgctg acactgttga gggattgctt    420

cccgaagact atgtcatggt ggtggtcggc actaccaagc ttagtgcgta tgtggacact    480

tttggtagcc gccccaaaaa catttgtggt tggctgttat tttctaactg taattacttc    540

ctcgaagagt tagagcttac ttttggtcgt cgtggtggta acatcgtgcc agttgaccaa    600

tacatgtgtg gcgctgacgg taaacctgtt cttcaggaat ccgaatggga gtatacagat    660

ttctttgctg actccgaaga cggtcaactc aacattgctg gtatcactta tgtgaaggcc    720

tggattgtag agcgatcgga tgtctcttat gcgagtcaga atttaacatc tattaagtct    780

attacttact gttcaaccta tgagcatact tttcctgatg gtactgccat gaaggttgca    840

cgtactccaa agattaagaa gactgttgtc ttgtctgagc cacttgctac tatctacagg    900

gaaattggtt ctccttttgt ggataatggg agcgatgctc gttctatcat taagagacca    960

gtgttcctcc acgcttttgt taagtgtaag tgtggtagtt atcattggac tgttggtgat   1020

tggacttcct atgtctccac ttgctgtggc tttaagtgta agccagtcct tgtggcttca   1080

tgctctgcta cgcctggttc tgttgtggtt acgcgcgctg gtgctggcac tggtgttaag   1140

tattacaaca acatgttcct gcgccatgtg gcagacattg atgggttggc attctggcga   1200

attctcaagg tgcagtccaa agacgacctc gcttgctctg gtaaattcct tgaacaccat   1260

gaggaaggtt tcacagatcc ttgctacttt ttgaatgact cgagcattgc tactaagctc   1320

aagtttgaca tccttagtgg caagttttct gatgaagtca aacaagctat ctttgctggt   1380

catgttgttg ttggcagcgc gctcgttgac attgttgacg atgcactggg acagccttgg   1440

tttatacgta agcttggtga ccttgcaagt gcagcttggg agcagcttaa ggctgtcgtt   1500

agaggcctta acctcctgtc tgatgaggtc gtgctctttg gcaaaagact tagctgtgcc   1560

actcttagta tcgttaacgg tgtttttgag ttcatcgccg aagtgcctga gaagttggct   1620
```

```
gcggctgtta cagtttttgt caacttcttg aatgagcttt ttgagtctgc ctgtgactgc   1680
ttaaaggtcg gaggtaaaac ctttaacaag gttggctctt atgttctttt tgacaacgca   1740
ttggttaagc ttgtcaaggc aaaagttcgc ggcccacgac aggcaggtgt ttgtgaagtt   1800
cgttacacaa gccttgttat tgggagtact accaaggtgg tttccaagcg cgttgaaaat   1860
gccaatgtga atctcgtcgt cgttgacgag gatgtgaccc tcaacaccac tggtcgtaca   1920
gttgttgttg acggacttgc attcttcgag agtgacgggt tttacagaca tcttgctgat   1980
gctgacgttg tcattgaaca tcctgtttat aagtctgctt gtgagctcaa gccagttttt   2040
gagtgtgacc caatacctga ttttcctatg cctgtggccg ctagtgttgc agagctttgt   2100
gtgcaaactg atctgttgct taaaaattac aacactcctt ataaaactta cagctgcgtt   2160
gtgagaggtg ataagtgttg tatcacttgc accttacatt tcacagcacc aagttatatg   2220
gaggctgctg ctaattttgt agacctctgt accaagaaca ttggtactgc tggttttcat   2280
gagttttaca ttacggccca tgaacaacag gatctgcaag ggttcgtaac cacttgttgc   2340
acgatgtcag gttttgagtg ttttatgcct ataatcccac agtgtccagc agtgcttgaa   2400
gagattgatg gtggtagcat ctggcggtct tttatcactg gtcttaatac aatgtgggat   2460
ttttgcaagc atcttaaagt cagctttgga ctagatggca ttgttgtcac tgtagcacgc   2520
aaatttaaac gacttggtgc tctcttggca gaaatgtata acacttacct ttcaactgtg   2580
gtggaaaact tggtactggc cggtgttagc ttcaagtatt atgccaccag tgtcccaaaa   2640
attgttttgg gctgttgttt tcacagtgtt aaaagtgttc ttgcaagtgc cttccagatt   2700
cctgtccagg caggcgttga gaagtttaaa gtcttcctta actgtgttca ccctgttgta   2760
ccacgtgtca ttgaaacttc ttttgtggaa ttagaagaga cgacatttaa accaccagca   2820
ctcaatggta gtattgctat tgttgatggc tttgctttct attatgatgg aacactatac   2880
tatcccaccg atggtaatag cgttgttcct atctgcttta agaagaaagg tggtggtgat   2940
gtcaaattct ctgatgaagt ctctgttaaa accattgacc cagtttataa ggtctccctt   3000
gaatttgagt tcgagtctga gactattatg gctgtgctta ataaggctgt tggtaattgt   3060
atcaaggtta caggtggttg ggacgatgtt gttgagtata tcaatgttgc cattgaggtt   3120
cttaaagatc acatcgatgt gcctaagtac tacatctatg atgaggaagg tggcaccgat   3180
cctaatctgc ccgtaatggt ttctcagtgg ccgttgaatg atgacacgat ctcacaggat   3240
ctgcttgatg ttgaagttgt tactgatgcg ccagttgatt tcgagggtga tgaagtagac   3300
tcctctgacc ctgataaggt ggcagacgtg gctaactctg agcctgagga tgacggtctt   3360
aatgtagctc ctgaaacaaa tgtagagtct gaagttgagg aagttgccgc aaccttgtcc   3420
tttattaaag atacaccttc cacagttact aaggatcctt ttgcttttga ctttgcaagc   3480
tatggaggac ttaaggtttt aagacaatct cataacaact gctgggttac ttctaccttg   3540
gtgcagctac aattgcttgg catcgttgat gaccctgcaa tggagctttt tagtgctggt   3600
agagttggtc caatggttcg caaatgctat gagtcacaaa aggctatctt gggatctttg   3660
ggtgatgtgt cggcttgcct agagtctctg actaaggacc tacacacact taagattacc   3720
tgttctgtag tctgtggttg tggtactggt gaacgtatct atgatggttg tgcttttcgt   3780
atgacgccaa ctttggaacc gttcccatat ggtgcttgtg ctcagtgtgc tcaagttttg   3840
atgcacactt ttaaaagtat tgttggcacc ggcatctttt gtcgagatac tactgctctc   3900
tccttggatt ctttggttgt aaaacctctt tgtgcggctg cttttatagg caaggatagt   3960
```

-continued

```
ggtcattatg tcactaactt ttatgatgct gctatggcta ttgatggtta tggtcgtcat   4020
cagataaagt atgacacact gaacactatt tgtgttaaag acgttaattg gacagcacct   4080
tttgtcccag acgttgagcc tgtattggag cctgttgtca aacctttcta ttcttataag   4140
aatgttgatt tttaccaagg agattttagt gaccttgtta aacttccatg tgattttgtt   4200
gttaatgctg caaatgagaa tttgtctcac ggtggcggca tagcaaaggc cattgatgtt   4260
tataccaagg gcatgttgca gaagtgctcg aatgattaca ttaaagcaca cggtcccatt   4320
aaagttggac gtggtgtcat gttggaggca ttaggtctta aggtctttaa tgttgttggt   4380
ccacgtaagg gtaagcatgc acctgagctt cttgttaagg cttataagtc cgtttttgct   4440
aattcaggtg ttgctcttac acctttgatt agtgttggaa tttttagtgt tcctttggaa   4500
gaatctttat ctgcttttct tgcatgtgtt ggtgatcgcc actgtaagtg cttttgttat   4560
agtgacaaag agcgcgaggc gatcattaat tacatggatg gcttggtaga tgctattttc   4620
aaagatgcac ttgttgatac tactcctgtc caggaagatg ttcaacaagt ttcacaaaaa   4680
ccagttttgc ctaattttga acctttcagg attgaaggtg ctcatgcttt ctatgagtgc   4740
aaccctgaag gtttgatgtc attaggtgct gacaagctgg tgttgtttac aaattccaat   4800
ttggattttt gtagcgttgg taagtgtctt aacaatgtga ctggcggtgc attgcttgaa   4860
gccataaatg tatttaaaaa gagtaacaaa acagtgcctg ctggcaactg tgttactttt   4920
gagtgtgcag atatgatttc tattactatg gtagtattgc catctgacgg tgatgctaat   4980
tatgacaaaa attatgcacg cgccgtcgtc aaggtatcta agcttaaagg caagttattg   5040
cttgctgttg gtgatgccat gttgtattcc aagttgtccc acctcagcgt gttaggtttc   5100
gtatccacac ctgatgatgt ggagcgtttc tacgcaaata agagtgtggt tattaaagtt   5160
actgaggata cacgtagtgt taagactgtt aaagtagaat ccactgttac ttatggacaa   5220
caaattggac cttgtcttgt taatgacacc gttgtcacag acaacaaacc tgttgttgct   5280
gatgttgtag ctaaggttgt accaagtgct aattgggatt cacattatgg ttttgataag   5340
gctggtgagt tccacatgct agaccatact gggtttgcct ttcctagtga agttgttaac   5400
ggtaggcgtg tgcttaaaac cacagataat aactgttggg ttaatgttac atgtttacaa   5460
ttacagtttg ctagatttag gttcaagtca gcaggtctac aggctatgtg ggagtcctat   5520
tgtactggtg atgttgctat gtttgtgcat tggttgtact ggcttactgg tgttgacaaa   5580
ggtcagccta gtgattcaga aaatgcactt aacatgttgt ctaagtacat tgttcctgct   5640
ggttctgtca ctattgaacg tgtcacgcat gacggttgtt gttgtagtaa gcgtgttgtc   5700
actgcaccag ttgtgaatgc tagcgtgttg aagcttggcg tcgaggatgg tctttgtcca   5760
catggtctta actacattga caaagttgtt gtagttaaag gtactacaat tgttgtcaat   5820
gttggaaaac ctgtagtggc accatcgcac ctctttctta agggtgtttc ctacacaaca   5880
ttcctagata atggtaacgg tgttgccggc cattatactg tttttgatca tgacactggt   5940
atggtgcatg atggagatgt ttttgtacca ggtgatctca atgtgtctcc tgttacaaat   6000
gttgtcgtct cagagcagac ggctgttgtg attaaagacc ctgtgaagaa agtagagtta   6060
gacgctacaa agctgttaga cactatgaat tatgcatcgg aaagattctt ttcctttggt   6120
gattttatgt cacgtaattt aattacagtg tttttgtaca tccttagtat tttgggtctc   6180
tgttttaggg cctttcgtaa gagggatgtt aaagttctag ctggtgtacc ccaacgtact   6240
ggtattatat tgcgtaaaag tgtgcgctat aatgcaaagg ctttgggtgt cttcttcaag   6300
ctaaaacttt attggttcaa agttcttggt aagtttagtt tgggtattta tgcattgtat   6360
```

gcattactat tcatgacaat acgctttaca cctataggtg gccctgtttg tgatgatgtt 6420
gttgctggtt atgctaattc tagttttgac aagaatgagt attgcaacag tgttatttgt 6480
aaggtctgtc tctatgggta ccaggaactt tcggacttct ctcacacaca ggtagtatgg 6540
caacacctta gagacccatt aattggtaat gtgatgcctt tcttttattt ggcatttctg 6600
gcaatttttg ggggtgttta tgtaaaggct attactctct attttatttt ccagtatctt 6660
aacatacttg gtgtgttttt gggcctacaa cagtccattt ggtttttgca gcttgtgcct 6720
tttgatgtct ttggtgacga gatcgtcgtc tttttcatcg ttacacgcgt attgatgttc 6780
cttaagcatg ttttccttgg ctgcgataag gcatcttgtg tggcttgctc taagagtgct 6840
cgccttaagc gcgttcctgt ccagactatt tttcagggta ctagcaaatc cttctacgta 6900
catgccaatg gtggttctaa gttctgtaag aagcacaatt tcttttgttt aaattgtgat 6960
tcttatggtc caggctgcac ttttattaat gacgtcattg caactgaagt tggtaatgtt 7020
gtcaaactta atgtgcaacc gacaggtcct gccactattc ttattgacaa ggttgaattc 7080
agtaatggtt tttactatct ttatagtggt gacacatttt ggaagtacaa ctttgacata 7140
acagataaca aatacacttg caaagagtca cttaaaaatt gtagcataat cacagacttt 7200
attgttttta acaataatgg ttccaatgta aatcaggtta agaatgcatg tgtgtatttt 7260
tcacagatgc tttgtaaacc tgttaagtta gtggactcag cgttgttggc cagtttgtct 7320
gttgattttg gtgcaagctt acatagtgct tttgttagtg tgttgtcgaa tagttttggc 7380
aaagacctgt caagttgtaa tgacatgcag gattgcaaga gcacattggg ttttgatgat 7440
gtaccattgg ataccttaa tgctgctgtt gctgaggctc atcgttacga tgtcctcttg 7500
actgacatgt cgttcaacaa ttttaccacc agttatgcaa aaccagagga aaaacttccc 7560
gtccatgaca ttgccacgtg tatgcgtgta ggtgccaaga ttgttaatca taacgttctt 7620
gtcaaggata gtatacctgt ggtgtggctt gtacgtgatt tcattgccct ttctgaagaa 7680
actaggaagt acattattcg tacgactaaa gttaagggta taaccttcat gttgaccttt 7740
aatgattgtc gtatgcatac taccatacct actgtttgca ttgcaaataa gaagggtgca 7800
ggtcttccta gtttttcaaa ggttaagaaa ttcttctggt tttgtgtct gttcatagtt 7860
gctgttttct ttgcactaag ctttttgat tttagtactc aggttagcag tgatagtgat 7920
tatgacttca agtatattga gagtggccag ttgaagactt ttgacaatcc acttagttgt 7980
gtgcataatg tctttagtaa cttcgaccag tggcatgatg ccaagtttgg tttcacccc 8040
gtcaacaatc ctagttgtcc tatagtcgtt ggtgtatcag acgaagcgcg cactgttcca 8100
ggtatcccag caggtgttta tttagctggt aaaacacttg tttttgctat taacaccatt 8160
tttggtacat ctggtttgtg ctttgatgct agtggcgttg ctgataaggg cgcttgcatt 8220
tttaattcgg cttgcaccac attatctggt ttgggtggaa ctgctgtcta ctgttataag 8280
aatggtctag ttgaaggtgc taaactttat agtgagttgg cacctcatag ctactataaa 8340
atggtagatg gtaatgctgt gtctttacct gaaattatct cacgcggctt tggcatccgt 8400
actatccgta caaaggctat gacctactgt cgcgttggcc agtgtgtgca atctgcagaa 8460
ggtgtttgtt ttggcgccga tagattcttt gtctataatg cagaatctgg ttctgacttt 8520
gtttgtggca cagggctctt tacattgttg atgaacgtta ttagtgtttt ttccaagaca 8580
gtaccagtaa ctgtgttgtc tggtcaaata ctttttaatt gcattattgc ttttgctgct 8640
gttgcggtgt gtttcttatt tacaaagttt aagcgcatgt tcggtgatat gtctgttggc 8700

-continued gttttcactg tcggtgcttg tactttgttg aacaatgttt cctacattgt aacacagaac 8760
acacttggca tgttgggcta tgcaactttg tactttttgt gcactaaagg tgttagatat 8820
atgtggattt ggcatttggg atttttgatc tcatatatac ttattgcacc atggtgggtt 8880
ttgatggttt atgccttttc agccattttt gagtttatgc ctaacctttt taagcttaag 8940
gtttcaacac aactttttga gggtgacaag ttcgtaggct cttttgaaaa tgctgcagca 9000
ggtacatttg tgcttgatat gcatgcctat gagagacttg ccaactctat ctcaactgaa 9060
aaactgcgtc agtatgctag tacttacaat aagtacaagt attattcagg cagtgcttca 9120
gaggctgatt acaggcttgc ttgttttgcc catttggcca aggctatgat ggattatgct 9180
tctaatcaca acgacacgtt atacacacca cccactgtga gttacaattc aactctacag 9240
gctggcttgc gtaagatggc acaaccatct ggtgttgttg agaagtgcat agttcgtgtt 9300
tgctatggta atatggctct taatggccta tggcttggtg atactgttat ctgcccacgc 9360
catgttatag cgtctagtac tactagcact atagattatg actatgccct ttctgtttta 9420
cgcctccaca acttctccat ttcatctggt aatgttttcc taggtgttgt gggtgtaacc 9480
atgcgaggtg ctttgttgca gataaaggtt aatcaaaaca atgtccacac gcctaagtac 9540
acctatcgca cagttagacc gggtgaatct tttaatatct tggcgtgcta tgatggttct 9600
gcagctggtg tttacggcgt taacatgcgc tctaattaca ctattagagg ctcgttcatt 9660
aatggcgctt gtggttcacc tggttataac attaacaatg gtaccgttga gttttgctat 9720
ttacaccagc ttgaacttgg ttcaggctgt catgttggta gcgacttaga tggtgttatg 9780
tatggtggtt atgaggacca acctactttg caagttgaag gcgctagtag tctgtttaca 9840
gagaatgtgt tggcatttct ttatgcagca ctcattaatg gttctacctg gtggcttagt 9900
tcttctagga ttgctgtaga caggtttaat gagtgggctg ttcataatgg tatgacaaca 9960
gtagttaata ctgattgctt ttctattctt gctgctaaga ctggtgttga tgtacaacgt 10020
ttgttggcct caatccagtc tctgcataag aattttggtg gaaagcaaat tcttggctat 10080
acctcgttga cagatgagtt tactacaggt gaagttatac gtcaaatgta tggcgttaat 10140
cttcagagtg gttatgtttc acgcgcctgt agaaatgtct tgctggttgg ttcttttctg 10200
actttctttt ggtcagaatt agtttcctac actaagttct tttgggtaaa tcctggttat 10260
gtcacaccta tgtttgcgtg tttgtcattg ctgtcctcac ttttgatgtt cacactcaag 10320
cataagacat tgtttttcca ggtctttcta atacctgctc tgattgttac atcttgcatt 10380
aatttggcat ttgatgttga agtctacaac tatttggcag agcattttga ttaccatgtt 10440
tctctcatgg gttttaatgc acaaggtctt gttaacatct ttgtctgctt tgttgttacc 10500
attttacacg gcacatacac atggcgcttt tttaacacac ctgtgagttc tgtcacttat 10560
gtggtagctt tgctgactgc ggcatataac tatttttacg ctagtgacat tcttagttgt 10620
gctatgacac tatttgctag tgtgactggc aactggttcg ttggtgctgt ttgttataaa 10680
gctgctgttt atatggcctt gagatttcct actttgtgg ctatttttgg tgatattaag 10740
agtgttatgt tctgttacct tgtgttgggt tattttacct gttgcttcta cggtattctc 10800
tactggttca acaggttttt taaggttagt gtaggtgtct atgactatac tgttagtgct 10860
gctgagttta agtatatggt tgctaacggc ctacgtgcac caactggaac acttgattca 10920
ctacttctgt ctgccaaatt gattggtatt ggtggtgagc ggaatattaa gatttcttcc 10980
gttcagtcta aactgactga tattaagtgt agtaacgttg tgcttttagg ctgtctctct 11040
agcatgaatg tctcagcaaa ttcaacagaa tgggcctatt gtgttgactt gcataacaag 11100
atcaacttgt gtaatgaccc agaaaaagcg caggaaatgc tacttgcttt gttggcattt 11160
ttccttagta agaatagtgc ttttggttta gatgacttat tggaatccta ttttaatgac 11220
aatagtatgt tgcagagtgt tgcatctact tatgtcggtt tgccttctta tgtcatttat 11280
gaaaatgcac gccaacagta tgaagatgct gttaataatg gttctccacc tcagttggtt 11340
aagcaattgc gccatgccat gaatgtagca aagagcgaat ttgaccgtga ggcttctact 11400
cagcgtaagc ttgatagaat ggcggaacag gctgcagcac agatgtacaa agaggcacga 11460
gcagttaata ggaagtccaa agttgtaagt gctatgcatt cactgctttt tggtatgttg 11520
agacgtttgg acatgtcttc tgtagacacc attctcaact tggcaaagga tggggttgta 11580
cctctgtctg tcataccggc agtcagtgct actaagctta acattgttac ttctgatatc 11640
gattcttata atcgtatcca gcgtgaggga tgtgtccact acgctggtac catttggaat 11700
ataattgata tcaaggacaa tgatggcaag gtggtacacg ttaaggaggt aaccgcacag 11760
aatgctgagt ccctgtcatg gcccctggtc cttgggtgtg agcgtattgt caagctccag 11820
aataatgaaa ttattcctgg taagctgaag cagcgctcca ttaaggcaga aggagatggc 11880
atagttggag aaggtaaggc actttacaat aatgagggtg gacgtacttt tatgtatgct 11940
ttcatctcgg acaaaccgga cctgcgtgta gtcaagtggg agttcgatgg tggttgtaac 12000
actattgagc tagaaccacc acgtaagttc ttggtggatt ctcctaatgg tgcacagatc 12060
aagtatctct actttgttcg taaccttaac acgttacgta ggggtgctgt tctcggctac 12120
ataggtgcca ctgtacgctt gcaggctggt aaacaaacag aacaggctat taactcttca 12180
ttgttgacac tttgcgcttt cgctgtggat cctgctaaga cctacatcga tgctgtcaaa 12240
agtggtcaca aaccagtagg taactgtgtt aagatgttgg ccaatggttc tggtaatgga 12300
caagctgtta ctaatggtgt ggaggctagt actaaccagg attcatacgg tggtgcgtcc 12360
gtgtgtctat attgtagagc acatgttgag catccatcta tggatggttt ttgcagactg 12420
aaaggcaagt acgtacaggt tccactaggt acagtggatc ctatacgttt tgtacttgag 12480
aatgacgttt gcaaggtttg tggttgttgg ctggctaatg gctgcacttg tgacagatcc 12540
attatgcaaa gcactgatat ggcttattta aacgagtacg gggctctagt gcagctcgac 12600
tagagccctg taacggtact gatacacaac atgtgtatcg tgcttttgac atctacaaca 12660
aggatgttgc ttgtctaggt aaattcctca aggtgaactg tgttcgcctg aagaatttgg 12720
ataagcatga tgcattctat gttgtcaaaa gatgtaccaa gtctgcgatg gaacacgagc 12780
aatccatcta tagcagactt gaaaagtgtg gagccgtagc cgaacacgat ttcttcactt 12840
ggaaggatgg tcgtgccatc tatggtaacg tttgtagaaa ggatcttacc gagtatacta 12900
tgatggattt gtgttacgct ttacgtaact ttgatgaaaa caattgcgat gttcttaaga 12960
gcattttaat taaggtaggc gcttgtgagg agtcctactt caataataaa gtctggtttg 13020
accctgttga aaatgaagac attcatcgtg tctatgcatt gttaggtacc attgtttcac 13080
gtgctatgct taaatgcgtt aagttctgtg atgcaatggt tgaacaaggt atagttggtg 13140
ttgtcacatt agataatcag gatcttaatg gtgatttta tgattttggt gattttactt 13200
gtagcatcaa gggaatgggt atacccattt gcacatcata ttactcttat atgatgcctg 13260
ttatgggtat gactaattgc cttgctagtg agtgttttgt taagagtgat atatttggtg 13320
aggatttcaa gtcatatgac ctgctggaat atgatttcac ggagcataag acagcactct 13380
tcaacaagta tttcaagtat tggggactgc aataccaccc taactgtgtg gactgcagtg 13440

-continued

```
atgagcagtg catagttcac tgtgccaact tcaatacgtt gttttccact actataccta  13500
ttacggcatt tggacctttg tgtcgcaagt gttggattga tggtgttcca ctggtaacta  13560
cagctggtta tcattttaaa cagttaggta tagtttggaa caatgacctc aacttacact  13620
ctagcaggct ctctattaac gaattactcc agttttgtag tgatcctgca ttgcttatag  13680
catcatcacc agcccttgtt gatcagcgta ctgtttgctt ttcagttgca gcgctaggta  13740
caggtatgac taaccagact gttaaacctg gccatttcaa taaggagttt tatgacttct  13800
tacttgagca aggtttcttt tctgagggct ctgagcttac tttaaagcac ttcttctttg  13860
cacagaaggg tgatgcagct gttaaggatt ttgactacta taggtataat agacctactg  13920
ttctggacat ttgccaagct cgcgtcgtgt atcaaatagt gcaacgctat tttgatattt  13980
acgaaggtgg ttgtatcact gctaaagagg tggttgttac aaaccttaac aagagcgcag  14040
gttatccttt gaacaagttt ggtaaagctg gtctttacta tgagtcttta tcctatgagg  14100
aacaggatga actttatgct tatactaagc gtaacatcct gcccactatg acacagctca  14160
accttaaata tgctataagt ggcaaagaac gtgcacgcac agtgggtggt gtttcgcttt  14220
tgtcaaccat gactactcgg cagtatcatc agaaacacct taagtccata gttaatacta  14280
ggggcgcttc ggttgttatt ggtactacta agttttatgg tggttgggac aatatgctta  14340
agaaccttat tgatggtgtt gaaaatccgt gtcttatggg ttgggactac ccaaagtgcg  14400
acagagcact gcccaatatg atacgtatga tttcagccat gattttaggc tctaagcaca  14460
ccacatgctg cagttccact gaccgctttt tcaggttgtg caatgaattg gctcaagtcc  14520
ttactgaggt tgtttattct aatggaggtt tttatttgaa gccaggtggt actacctctg  14580
gtgatgcaac caccgcatat gcaaactcag tttttaatat cttccaagca gtaagtgcca  14640
atgttaacaa acttcttagt gttgacagca atgtctgtca taatttagaa gttaagcaat  14700
tgcagcgtaa gctttatgag tgctgttata gatcaactac cgtcgatgac cagttcgtcg  14760
ttgagtatta tggttacttg cgtaaacatt tttcaatgat gattctttct gatgatggcg  14820
ttgtttgtta taacaatgac tatgcatcac ttggttatgt cgctgatctt aacgcattca  14880
aggctgtttt gtattaccag aacaatgtct tcatgagcgc ctctaaatgt tggatcgagc  14940
ctgacattaa taaaggtcct catgaatttt gctcgcagca tactatgcag attgtcgata  15000
aagatggtac ttattacctt ccttaccctg atccttcaag aattctctct gcaggtgtgt  15060
ttgttgatga cgttgttaaa actgatgcag ttgtattgct tgaacgttat gtgtcattgg  15120
ctatagatgc ctacccgtta tctaagcatg aaaaccctga atataagaag gtgttttatg  15180
tgcttttgga ttgggttaag catctgtaca aaactcttaa tgctggtgtg ttagagtctt  15240
tttctgtcac acttttggaa gattctactg ctaaattctg ggatgagagc ttttatgcca  15300
acatgtatga gaaatctgca gttttacaat ctgcagggct ttgtgttgtt tgtggctctc  15360
aaactgtttt acgttgtggt gattgtctac ggcgtcctat gctttgtact aagtgtgctt  15420
atgatcatgt cattggaaca actcacaagt tcattttggc catcactcca tatgtgtgtt  15480
gtgcttcaga ttgtggtgtc aatgatgtaa ctaagctcta cttaggtggt cttagttatt  15540
ggtgtcatga ccacaagcca cgtcttgcat tcccgttgtg ctctgctggt aatgtttttg  15600
gcttgtacaa aaattctgct accggctcac ccgatgttga agactttaat cgcattgcta  15660
catccgattg gactgatgtt tctgactaca ggttggcaaa tgatgtcaag gactcattgc  15720
gtctgtttgc agcggaaact atcaaggcca aggaggagag cgttaagtca tcctatgctt  15780
gtgcaacact acatgaggtt gtaggaccta aagagttgtt gctcaaatgg gaagtcggca  15840
```

gacccaaacc accccttaat agaaattcgg ttttcacttg ttatcatata acgaagaaca 15900
ccaaatttca aatcggtgag tttgtgtttg agaaggcaga atatgataat gatgctgtaa 15960
catataaaac taccgccaca acaaaacttg ttcctggcat ggtttttgtg cttacctcac 16020
ataatgttca gccattgcgc gcaccgacca ttgctaatca agaacgttat tccactatac 16080
ataagttgca tcctgctttt aacatacctg aagcttattc tagcttagtg ccctattacc 16140
aattgattgg taagcagaag attacaacta ttcagggacc tcccggtagt ggtaaatctc 16200
actgtgttat agggctaggt ttgtactatc caggtgcacg tatagtgttt acagcttgtt 16260
ctcatgcagc ggtcgattca ctttgtgtga aagcttccac tgcttatagc aatgacaaat 16320
gttcacgcat cataccacag cgcgctcgtg ttgagtgtta tgatggtttc aagtctaata 16380
atactagtgc tcagtacctt ttctctactg tcaatgcttt gccagagtgc aatgcggaca 16440
ttgttgtggt ggatgaggtc tctatgtgca ctaattatga cttgtctgtc ataaatcagc 16500
gcatcagcta taggcatgta gtctatgttg gtgaccctca acagctgcct gcaccacgtg 16560
ttatgatttc acgtggtact ttggaaccaa aggactacaa cgttgtcact caacgcatgt 16620
gtgcccttaa gcctgatgtt ttcttgcaca agtgttatcg ctgtcctgct gagatagtgc 16680
gtactgtgtc tgagatggtc tatgaaaacc aattcattcc tgtgcaccca gatagcaagc 16740
agtgttttaa aatcttttgc aagggtaatg ttcaggttga taatggttca agcattaatc 16800
gcaggcaatt ggatgttgtg cgtatgtttt tggctaaaaa tcctaggtgg tcaaaggctg 16860
tttttatttc tccttataac agccagaatt atgttgccag ccgcatgcta ggtctacaaa 16920
ttcagacagt tgactcatcc cagggtagtg agtatgacta tgtcatttac acacaaactt 16980
cagatactgc ccatgcctgt aatgttaaca ggtttaatgt tgccatcaca agggccaaga 17040
aaggcatatt atgtataatg tgcgataggt cccttttttga tgtgcttaaa ttctttgagc 17100
ttaaattgtc tgatttgcag gctaatgagg gttgtggtct ttttaaagac tgtagcagag 17160
gtgatgatct gttgccacca tctcacgcta acaccttcat gtctttagcg gacaatttta 17220
agactgatca agatcttgct gttcaaatag gtgttaatgg acccattaaa tatgagcatg 17280
ttatctcgtt tatgggtttc cgttttgata tcaacatacc caaccatcat actctctttt 17340
gcacacgcga ctttgccatg cgcaatgtta gaggttggtt aggctttgac gttgaaggag 17400
cacatgttgt tggctctaac gtcggtacaa atgtcccatt gcaattaggg ttttctaacg 17460
gtgttgattt tgttgtcaga cctgaaggtt gcgttgtaac agagtctggt gactacatta 17520
aacccgtcag agctcgtgct ccaccagggg aacaattcgc acaccttttg cctttactta 17580
aacgcggcca accatgggat gttgtccgca aacgtatagt gcagatgtgt agtgactacc 17640
tggccaacct atcagacata ctaatttttg tgttgtgggc tggtggtttg gagttgacaa 17700
ctatgcgtta ttttgtcaag attggaccaa gtaagagttg tgattgtggt aaggttgcta 17760
cttgttacaa tagtgcgctg catacgtact gttgtttcaa acatgccctt ggttgtgatt 17820
atctgtataa cccatactgt attgatatac agcagtgggg atacaaggga tcacttagcc 17880
ttaaccacca tgagcattgt aatgtacata gaaacgagca tgtggcttct ggtgatgcca 17940
taatgactcg ctgtctggcc atacatgatt gctttgtcaa gaacgttgac tggtccatca 18000
catacccatt tattggtaat gaggctgtta ttaataagag cggccgaatt gtgcaatcac 18060
acactatgcg gtcagttctt aagttataca atccgaaagc catatatgat attggcaatc 18120
ctaagggcat tagatgtgcc gtaacggatg ctaagtggtt ttgctttgac aagaatccta 18180

-continued

```
ctaattctaa tgtcaagaca ttggagtatg actatataac acatggccaa tttgatgggt  18240
tgtgcttgtt ttggaattgc aatgtagaca tgtatccaga attttctgtg gtctgtcgtt  18300
ttgatactcg ctgtaggtca ccactcaact tggagggttg taatggtggt tcactgtatg  18360
ttaataatca tgcattccat acaccggctt ttgacaagcg tgcttttgct aagttgaagc  18420
caatgccatt tttcttttat gatgatactg agtgtgacaa gttacaggac tccataaact  18480
atgttcctct tagggctagt aactgcatta ctaaatgtaa tgttggtggt gctgtctgta  18540
gtaagcattg tgctatgtat catagctatg ttaatgctta caacactttt acgtcggcgg  18600
gctttactat ttgggtgcct acttcgtttg acacctataa tctgtggcag acatttagta  18660
acaatttgca aggtcttgag aacattgctt tcaatgtcgt aaagaaagga tcttttgttg  18720
gtgccgaagg tgaacttcct gtagctgtgg ttaatgacaa agtgctcgtt agagatggta  18780
ctgttgatac tcttgttttt acaaacaaga catcactacc cactaacgta gcttttgagt  18840
tgtatgccaa gcgtaaggta ggactcaccc cacccattac gatcctacgt aacttgggtg  18900
tagtttgtac atctaagtgt gtcatttggg actatgaagc cgaacgtcca cttactactt  18960
ttacaaagga tgtttgtaaa tataccgact ttgagggtga cgtctgtaca ctctttgata  19020
acagcattgt tggttcatta gagcgattct ccatgaccca aaatgctgtg cttatgtcac  19080
ttacagctgt taaaaagctt actggcataa agttaactta tggttatctt aatggtgtcc  19140
cagttaacac acatgaagat aaacctttta cttggtatat ttacactagg aagaacggca  19200
agttcgagga ccatcctgat ggctatttta cccaaggtag aacaaccgct gattttagcc  19260
ctcgtagcga catggaaaag gacttcctaa gtatggatat gggtctgttt attaacaagt  19320
acggacttga agattacggc tttgagcacg ttgtgtatgg tgatgtttca aaaaccaccc  19380
ttggtggttt gcatctacta atttcgcagg tgcgtctggc ctgtatgggt gtgctcaaaa  19440
tagacgagtt tgtgtctagt aatgatagca cgttaaagtc ttgtactgtt acatatgctg  19500
ataaccctag tagtaagatg gtttgtacgt atatggatct cctgcttgac gattttgtca  19560
gcattcttaa atctttggat ttgggcgttg tatctaaagt tcatgaagtt atggtcgatt  19620
gtaaaatgtg gaggtggatg ttgtggtgta aggatcataa actccagaca ttttatccgc  19680
aacttcaggc cagtgaatgg aagtgtggtt attccatgcc ttctatttac aagatacaac  19740
gtatgtgttt agaaccttgc aatctctaca actatggtgc tggtattaag ttacctgatg  19800
gcattatgtt taacgtagtt aaatacacac agctttgtca atatctcaat agcaccacaa  19860
tgtgtgtacc ccatcacatg cgtgtgctac atcttggtgc tggctccgac aagggtgttg  19920
cacctggcac ggctgtctta cgacgttggt tgccactgga tgccattata gttgacaatg  19980
atagtgtgga ttacgttagc gatgctgatt atagtgttac aggagattgc tctaccttat  20040
acctgtcaga taagtttgat ttagttatat ctgatatgta tgatggtaag attaaaagtt  20100
gtgatgggga gaacgtgtct aaagaaggct tctttcccta tattaatggt gtcatcaccg  20160
aaaagttggc acttggtggt actgtagcta ttaaggtgac ggagtttagt tggaataaga  20220
agttgtatga actcattcag aggtttgagt attggacaat gttctgtacc agtgttaaca  20280
cgtcatcgtc agaggcattc ttaattggtg ttcactattt aggtgatttt gcaagtggcg  20340
ctgtgattga cggcaacact atgcatgcca attatatctt ctggcgtaat tccacaatta  20400
tgactatgtc ttacaatagt gtacttgatt taagcaagtt caattgtaag cataaggcta  20460
cagttgtcat taatttaaaa gattcatcca ttagtgatgt tgtgttaggt ttgttgaaga  20520
atggtaagtt gctagtgcgt aataatgacg ccatttgtgg tttttctaat catttggtca  20580
```

acgtaaacaa atgaagtctt taacctactt ctggttgttc ttaccagtac tttcaacact 20640
tagcctacca caagatgtca ccaggtgctc agctaacact aattttaggc ggttcttttc 20700
aaaatttaat gttcaggcgc ctgcagttgt tgtactgggc ggttatctac ctattggtga 20760
aaaccagggt gtcaattcaa cttggtactg tgctggccaa catccaactg ctagtggcgt 20820
tcatggtatc tttgttagcc atattagagg tggtcatggc tttgagattg gcatttcgca 20880
agagcctttt gaccctagtg gttaccagct ttatttacat aaggctacta acggtaacac 20940
taatgctact gcgcgactgc gcatttgcca gtttcctagc attaataatg atgttacaat 21000
aggtcgtaat tgcctattta acaaagccat cccagctcat atgagtgaac atagtgttgt 21060
cggcataaca tgggataatg atcgtgtcac tgtcttttct gacaagatct attattttta 21120
ttttaaaaat gattggtccc gtgttgcgac aaagtgttac aacagtggag gttgtgctat 21180
gcaatatgtt tacgaaccca cctattacat gcttaatgtt actagtgctg gtgaggatgg 21240
tatttcttat caaccctgta cagctaattg cattggttat gctgccaatg tatttgctac 21300
tgagcccaat ggccacatac cagaaggttt tagttttaat aattggtttc ttttgtccaa 21360
tgattccact ttggtgcatg gtaaggtggt ttccaaccaa ccattgttgg tcaattgtct 21420
tttggccatt cctaagattt atggactagg ccaatttttc tcctttaatc aaacgatcga 21480
tggtgtttgt aatggagctg ctgtgcagcg tgcaccagag gctctgaggt ttaatattaa 21540
tgacacctct gtcattcttg ctgaaggctc aattgtactt catactgctt taggaacaaa 21600
tttttctttt gtttgcagta attcctcaaa tcctcactta gccaccttcg ccatacctct 21660
gggtgctacc caagtacctt attattgttt tcttaaagtg gatacttaca actccactgt 21720
ttataaattt ttggctgttt tacctcctac cgtcagggaa attgtcatca ccaagtatgg 21780
tgatgtttat gtcaatgggt ttggatactt gcatctcggt ttgttggatg ctgtcacaat 21840
taatttcact ggtcatggca ctgacgatga tgtttctggt ttttggacca tagcatcgac 21900
taattttgtt gatgcactca tcgaagttca aggaaccgcc attcagcgta ttctttattg 21960
tgatgatcct gttagccaac tcaagtgttc tcaggttgct tttgaccttg acgatggttt 22020
ttaccctatt tcttctagaa accttctgag tcatgaacag ccaatttctt ttgttactct 22080
gccatcattt aatgatcatt cttttgttaa cattactgta tctgcttcct ttggtggtca 22140
tagtggtgcc aaccttattg catctgacac tactatcaat gggtttagtt ctttctgtgt 22200
tgacactaga caatttacca tttcactgtt ttataacgtt acaaacagtt atggttatgt 22260
gtctaaatca caggacagta attgcccttt caccttgcaa tctgttaatg attacctgtc 22320
ttttagcaaa ttttgtgttt ccaccagcct tttggctagt gcctgtacca tagatctttt 22380
tggttaccct gagtttggta gtggtgttaa gtttacgtcc ctttattttc aattcacaaa 22440
gggtgagttg attactggca cgactaaacc acttgaaggt gtcacggacg tttcttttat 22500
gactctggat gtgtgtacca agtatactat ctatggcttt aaaggtgagg gtatcattac 22560
ccttacaaat tctagctttt tggcaggtgt ttattacaca tctgattctg gacagttgtt 22620
agcctttaag aatgtcacta gtggtgctgt ttattctgtt acgccatgtt ctttttcaga 22680
gcaggctgca tatgttgatg atgatatagt gggtgttatt tctagtttgt ctagctccac 22740
ttttaacagt actagggagt tgcctggttt cttctaccat tctaatgatg gctctaattg 22800
tacagagcct gtgttggtgt atagtaacat aggtgtttgt aaatctggca gtattggcta 22860
cgtcccatct cagtctggcc aagtcaagat tgcacccacg gttactggga atattagtat 22920
tcccaccaac tttagtatga gtattaggac agaatattta cagctttaca acacgcctgt 22980
tagtgttgat tgtgccacat atgtttgtaa tggtaactct cgttgtaaac aattactcac 23040
ccagtacact gcagcatgta agaccataga gtcagcatta caactcagcg ctaggcttga 23100
gtctgttgaa gttaactcta tgcttactat ttctgaagag gctctacagt tagctaccat 23160
tagttcgttt aatggtgatg gatataattt tactaatgtg ctgggtgttt ctgtgtatga 23220
tcctgcaagt ggcagggtgg tacaaaaaag gtcttttatt gaagacctgc tttttaataa 23280
agtggttact aatggccttg gtactgttga tgaagactat aagcgctgtt ctaatggtcg 23340
ctctgtggca gatctagtct gtgcacagta ttactctggt gtcatggtac tacctggtgt 23400
tgttgacgct gagaagcttc acatgtatag tgcgtctctc atcggtggta tggtgctagg 23460
aggttttact tctgcagcgg cattgccttt tagctatgct gttcaagcta gactcaatta 23520
tcttgctcta cagacggatg ttctacagcg gaaccagcaa ttgcttgctg agtcttttaa 23580
ctctgctatt ggtaatataa cttcagcctt tgagagtgtt aaagaggcta ttagtcaaac 23640
ttccaagggt ttgaacactg tggctcatgc gcttactaag gttcaagagg ttgttaactc 23700
gcagggtgca gctttgactc aacttaccgt acagctgcaa cacaacttcc aagccatttc 23760
tagttctatt gatgacattt actctcgact ggacattctt tcagccgatg ttcaggttga 23820
ccgtctcatc accggcagat tatcagcact taatgctttt gttgctcaaa ccctcactaa 23880
gtatactgag gttcaggcta gcaggaagtt agcacagcaa aaggttaatg agtgcgttaa 23940
atcgcaatct cagcgttatg gtttttgtgg tggtgatggc gagcacattt tctctctggt 24000
acaggcagca cctcagggcc tgctgttttt acatacagta cttgtaccga gtgattttgt 24060
agatgttatt gccatcgctg gcttatgcgt taacgatgaa attgccttga ctctacgtga 24120
gcctggctta gtcttgttta cgcatgaact tcaaaatcat actgcgacgg aatattttgt 24180
ttcatcgcga cgtatgtttg aacctagaaa acctaccgtt agtgattttg ttcaaattga 24240
gagttgtgtg gtcacctatg tcaatttgac tagagaccaa ctaccagatg taatcccaga 24300
ttacatcgat gttaacaaaa cacttgatga gattttagct tctctgccca atagaactgg 24360
tccaagtctt cctttagatg tttttaatgc cacttatctt aatctcactg gtgaaattgc 24420
agatttagag cagcgttcag agtctctccg taatactaca gaggagctcc aaagtcttat 24480
atataatatc aacaacacac tagttgacct tgagtggctc aaccgagttg agacatatat 24540
caagtggccg tggtgggttt ggttgattat tttcattgtt ctcatctttg ttgtgtcatt 24600
actagtgttc tgctgcattt ccacgggttg ttgtggatgc tgcggctgct gctgtgcttg 24660
tttctcaggt tgttgtaggg gtcctagact tcaaccttac gaagtttttg aaaaggtcca 24720
cgtgcagtga tgtttcttgg actttttcaa tacacgattg acacagttgt caaagatgtc 24780
tcaaagtctg ctaacttgtc tttggatgct gtccaagagt tggagctcaa tgtagttcca 24840
attagacaag cttcaaatgt gacgggtttt cttttcacca gtgtttttat ctacttcttt 24900
gcactgttta aagcgtcttc tttgaggcgc aattatatta tgttggcagc gcgttttgct 24960
gtcattgttc tttattgccc acttttatat tattgtggtg catttttaga tgcaactatt 25020
atttgttgca cacttattgg caggctttgt ttagtctgct tttactcctg gcgctataaa 25080
aatgcgctct ttattatttt taatactacg acactttctt tcctcaatgg taaagcagct 25140
tattatgacg gcaaatccat tgtgatttta gaaggtggtg accattacat cacttttggc 25200
aactcttttg ttgcttttgt tagtagcatc gacttgtatc tagctatacg tgggcggcaa 25260
gaagctgacc tacagctgtt gcgaactgtt gagcttcttg atggcaagaa gctttatgtc 25320

```
ttttcgcaac atcaaattgt tggcattact aatgctgcat ttgactcaat tcaactagac  25380
gagtatgcta caattagtga atgataatgg tctagtagtt aatgttatac tttggctttt  25440
cgtactcttt ttcctgctta ttataagcat tactttcgtc caattggtta atctgtgctt  25500
cacttgtcac cggttgtgta atagcgcagt ttacacacct atagggcgtt tgtatagagt  25560
ttataagtct tacatgcaaa tagacccccct ccctagtact gttattgacg tataaacgaa  25620
atatgtctaa cggttctatt cccgttgatg aggtgattca acaccttaga aactggaatt  25680
tcacatggaa tatcatactg acgatactac ttgtagtgct tcagtatggc cattacaagt  25740
actctgcgtt cttgtatggt gtcaagatgg ctattctatg gatactttgg cctcttgtgt  25800
tagcactgtc actttttgat gcatgggcta gctttcaggt caattgggtc tttttgcttt  25860
tcagcatcct tatggcttgc atcactctta tgctgtggat aatgtacttt gtcaatagca  25920
ttcggttgtg gcgcaggaca cattcttggt ggtctttcaa tcctgaaaca gacgcgcttc  25980
tcactacttc tgtgatgggc cgacaggtct gcattccagt gcttggagca ccaactggtg  26040
taacgctaac actccttagt ggtacattgc ttgtagaggg ctataaggtt gctactggcg  26100
tacaggtaag tcaattacct aatttcgtca cagtcgccaa ggccactaca acaattgtct  26160
acggacgtgt tggtcgttca gtcaatgctt catctggcac tggttgggct ttctatgtcc  26220
ggtccaaaca cggcgactac tcagctgtga gtaatccgag ttcggttctc acagatagtg  26280
agaaagtgct tcatttagtc taaacagaaa ctttatggct tctgtcagtt ttcaggatcg  26340
tggccgcaaa cgggtgccat tatccctcta tgcccctctt agggttacta atgacaaacc  26400
cctttctaag gtacttgcaa ataatgctgt acccactaat aaaggaaata aggaccagca  26460
aattggatac tggaatgagc aaattcgctg gcgcatgcgc cgtggtgagc gaattgaaca  26520
accttccaat tggcatttct actacctcgg aacaggacct cacgccgacc tccgctacag  26580
gactcgtact gagggtgttt tctgggttgc taaagaaggc gcaaagactg aacccactaa  26640
cctgggtgtc agaaaggcgt ctgaaaagcc aattattcca aatttctctc aacagcttcc  26700
cagcgtagtt gagattgttg aacctaacac acctcctact tcacgtgcaa attcacgtag  26760
caggagtcgt ggtaatggca acaacaggtc cagatctcca agtaacaaca gaggcaataa  26820
ccagtcccgc ggtaattcac agaatcgtgg aaataaccag ggtcgtggag cttctcagaa  26880
cagaggaggc aataataata acaataacaa gtctcgtaac cagtccaaga acagaaacca  26940
gtcaaatgac cgtggtggtg taacatcacg cgatgatctg gtggctgctg tcaaggatgc  27000
ccttaaatct ttgggtattg gcgaaaaccc tgacaagctt aagcaacagc agaagcccaa  27060
acaggaaagg tctgacagca gcggcaaaaa tacacctaag aagaacaaat ccagagccac  27120
ttcgaaagaa cgtgacctca aagacatccc agagtggagg agaattccca agggcgaaaa  27180
tagcgtagca gcttgcttcg gacccagggg aggcttcaaa aattttggag atgcggaatt  27240
tgtcgaaaaa ggtgttgatg cctcaggcta tgctcagatc gccagtttag caccaaatgt  27300
tgcagcattg ctctttggtg gtaatgtggc tgttcgtgag ctagcggact cttacgagat  27360
tacatataat tataaaatga ctgtgccaaa gtctgatcca aatgtagagc ttcttgtttc  27420
acaggtggat gcatttaaaa ctgggaatgc aaaaccccag agaaagaagg aaaagaagaa  27480
caagcgtgaa accacgcagc agctgaatga agaggccatc tacgatgatg tgggtgtgcc  27540
atctgatgtg actcatgcca atttggaatg ggacacagct gttgatggtg gtgacacggc  27600
cgttgaaatt atcaacgaga tcttcgacac aggaaattaa acaatgtttg actggcttat  27660
```

```
cctggctatg tcccagggta gtgccattac actgttatta ctgagtgttt ttctagcgac  27720

ttggctgctg ggctatggct ttgccctcta actagcggtc ttggtcttgc acacaacggt  27780

aagccagtgg taatgtcagt gcaagaagga tattaccata gcactgtcat gaggggaacg  27840

cagtaccttt tcatctaaac ctttgcacga gtaatcaaag atccgcttga cgagcctata  27900

tggaagagcg tgccaggtat ttgactcaag gactgttagt aactgaagac ctgacggtgt  27960


<210> SEQ ID NO 30
<211> LENGTH: 4140
<212> TYPE: DNA
<213> ORGANISM: Artificial Sequence
<220> FEATURE:
<223> OTHER INFORMATION: PEDV Isolate 1251-125-10 (125-10) Spike-protein
      cDNA Sequence

<400> SEQUENCE: 30

atgaagtctt taacctactt ctggttgttc ttaccagtac tttcaacact tagcctacca     60

caagatgtca ccaggtgctc agctaacact aattttaggc ggttcttttc aaaatttaat    120

gttcaggcgc ctgcagttgt tgtactgggc ggttatctac ctattggtga aaaccagggt    180

gtcaattcaa cttggtactg tgctggccaa catccaactg ctagtggcgt tcatggtatc    240

tttgttagcc atattagagg tggtcatggc tttgagattg gcatttcgca agagcctttt    300

gaccctagtg gttaccagct ttatttacat aaggctacta acggtaacac taatgctact    360

gcgcgactgc gcatttgcca gtttcctagc attaataatg atgttacaat aggtcgtaat    420

tgcctattta acaaagccat cccagctcat atgagtgaac atagtgttgt cggcataaca    480

tgggataatg atcgtgtcac tgtcttttct gacaagatct attattttta ttttaaaaat    540

gattggtccc gtgttgcgac aaagtgttac aacagtggag gttgtgctat gcaatatgtt    600

tacgaaccca cctattacat gcttaatgtt actagtgctg gtgaggatgg tatttcttat    660

caaccctgta cagctaattg cattggttat gctgccaatg tatttgctac tgagcccaat    720

ggccacatac cagaaggttt tagttttaat aattggtttc ttttgtccaa tgattccact    780

ttggtgcatg gtaaggtggt ttccaaccaa ccattgttgg tcaattgtct tttggccatt    840

cctaagattt atggactagg ccaatttttc tcctttaatc aaacgatcga tggtgtttgt    900

aatggagctg ctgtgcagcg tgcaccagag gctctgaggt ttaatattaa tgacacctct    960

gtcattcttg ctgaaggctc aattgtactt catactgctt taggaacaaa tttttctttt   1020

gtttgcagta attcctcaaa tcctcactta gccaccttcg ccatacctct gggtgctacc   1080

caagtacctt attattgttt tcttaaagtg gatacttaca actccactgt ttataaattt   1140

ttggctgttt tacctcctac cgtcagggaa attgtcatca ccaagtatgg tgatgtttat   1200

gtcaatgggt ttggatactt gcatctcggt ttgttggatg ctgtcacaat taatttcact   1260

ggtcatggca ctgacgatga tgtttctggt ttttggacca tagcatcgac taattttgtt   1320

gatgcactca tcgaagttca aggaaccgcc attcagcgta ttctttattg tgatgatcct   1380

gttagccaac tcaagtgttc tcaggttgct tttgaccttg acgatggttt ttaccctatt   1440

tcttctagaa accttctgag tcatgaacag ccaatttctt ttgttactct gccatcattt   1500

aatgatcatt cttttgttaa cattactgta tctgcttcct ttggtggtca tagtggtgcc   1560

aaccttattg catctgacac tactatcaat gggtttagtt ctttctgtgt tgacactaga   1620

caatttacca tttcactgtt ttataacgtt acaaacagtt atggttatgt gtctaaatca   1680

caggacagta attgcccttt caccttgcaa tctgttaatg attacctgtc ttttagcaaa   1740
```

-continued

```
ttttgtgttt ccaccagcct tttggctagt gcctgtacca tagatctttt tggttaccct   1800
gagtttggta gtggtgttaa gtttacgtcc ctttattttc aattcacaaa gggtgagttg   1860
attactggca cgactaaacc acttgaaggt gtcacggacg tttcttttat gactctggat   1920
gtgtgtacca agtatactat ctatggcttt aaaggtgagg gtatcattac ccttacaaat   1980
tctagctttt tggcaggtgt ttattacaca tctgattctg gacagttgtt agcctttaag   2040
aatgtcacta gtggtgctgt ttattctgtt acgccatgtt ctttttcaga gcaggctgca   2100
tatgttgatg atgatatagt gggtgttatt tctagtttgt ctagctccac ttttaacagt   2160
actagggagt tgcctggttt cttctaccat tctaatgatg gctctaattg tacagagcct   2220
gtgttggtgt atagtaacat aggtgtttgt aaatctggca gtattggcta cgtcccatct   2280
cagtctggcc aagtcaagat tgcacccacg gttactggga atattagtat tcccaccaac   2340
tttagtatga gtattaggac agaatattta cagctttaca acacgcctgt tagtgttgat   2400
tgtgccacat atgtttgtaa tggtaactct cgttgtaaac aattactcac ccagtacact   2460
gcagcatgta agaccataga gtcagcatta caactcagcg ctaggcttga gtctgttgaa   2520
gttaactcta tgcttactat ttctgaagag gctctacagt tagctaccat tagttcgttt   2580
aatggtgatg gatataattt tactaatgtg ctgggtgttt ctgtgtatga tcctgcaagt   2640
ggcagggtgg tacaaaaaag gtcttttatt gaagacctgc tttttaataa agtggttact   2700
aatggccttg gtactgttga tgaagactat aagcgctgtt ctaatggtcg ctctgtggca   2760
gatctagtct gtgcacagta ttactctggt gtcatggtac tacctggtgt tgttgacgct   2820
gagaagcttc acatgtatag tgcgtctctc atcggtggta tggtgctagg aggttttact   2880
tctgcagcgg cattgccttt tagctatgct gttcaagcta gactcaatta tcttgctcta   2940
cagacggatg ttctacagcg gaaccagcaa ttgcttgctg agtcttttaa ctctgctatt   3000
ggtaatataa cttcagcctt tgagagtgtt aaagaggcta ttagtcaaac ttccaagggt   3060
ttgaacactg tggctcatgc gcttactaag gttcaagagg ttgttaactc gcagggtgca   3120
gctttgactc aacttaccgt acagctgcaa cacaacttcc aagccatttc tagttctatt   3180
gatgacattt actctcgact ggacattctt tcagccgatg ttcaggttga ccgtctcatc   3240
accggcagat tatcagcact taatgctttt gttgctcaaa ccctcactaa gtatactgag   3300
gttcaggcta gcaggaagtt agcacagcaa aaggttaatg agtgcgttaa atcgcaatct   3360
cagcgttatg gtttttgtgg tggtgatggc gagcacattt tctctctggt acaggcagca   3420
cctcagggcc tgctgttttt acatacagta cttgtaccga gtgattttgt agatgttatt   3480
gccatcgctg gcttatgcgt taacgatgaa attgccttga ctctacgtga gcctggctta   3540
gtcttgttta cgcatgaact tcaaaatcat actgcgacgg aatattttgt ttcatcgcga   3600
cgtatgtttg aacctagaaa acctaccgtt agtgattttg ttcaaattga gagttgtgtg   3660
gtcacctatg tcaatttgac tagagaccaa ctaccagatg taatcccaga ttacatcgat   3720
gttaacaaaa cacttgatga gattttagct tctctgccca atagaactgg tccaagtctt   3780
cctttagatg tttttaatgc cacttatctt aatctcactg gtgaaattgc agatttagag   3840
cagcgttcag agtctctccg taatactaca gaggagctcc aaagtcttat atataatatc   3900
aacaacacac tagttgacct tgagtggctc aaccgagttg agacatatat caagtggccg   3960
tggtgggttt ggttgattat tttcattgtt ctcatctttg ttgtgtcatt actagtgttc   4020
tgctgcattt ccacgggttg ttgtggatgc tgcggctgct gctgtgcttg tttctcaggt   4080
tgttgtaggg gtcctagact tcaaccttac gaagtttttg aaaaggtcca cgtgcagtga   4140
```

<210> SEQ ID NO 31
<211> LENGTH: 1379
<212> TYPE: PRT
<213> ORGANISM: porcine epidemic diarrhea virus

<400> SEQUENCE: 31

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Asn Asn Asp Val Thr Ile Gly Arg Asn Cys Leu Phe Asn
    130                 135                 140

Lys Ala Ile Pro Ala His Met Ser Glu His Ser Val Val Gly Ile Thr
145                 150                 155                 160

Trp Asp Asn Asp Arg Val Thr Val Phe Ser Asp Lys Ile Tyr Tyr Phe
                165                 170                 175

Tyr Phe Lys Asn Asp Trp Ser Arg Val Ala Thr Lys Cys Tyr Asn Ser
            180                 185                 190

Gly Gly Cys Ala Met Gln Tyr Val Tyr Glu Pro Thr Tyr Tyr Met Leu
        195                 200                 205

Asn Val Thr Ser Ala Gly Glu Asp Gly Ile Ser Tyr Gln Pro Cys Thr
    210                 215                 220

Ala Asn Cys Ile Gly Tyr Ala Ala Asn Val Phe Ala Thr Glu Pro Asn
225                 230                 235                 240

Gly His Ile Pro Glu Gly Phe Ser Phe Asn Asn Trp Phe Leu Leu Ser
                245                 250                 255

Asn Asp Ser Thr Leu Val His Gly Lys Val Val Ser Asn Gln Pro Leu
            260                 265                 270

Leu Val Asn Cys Leu Leu Ala Ile Pro Lys Ile Tyr Gly Leu Gly Gln
        275                 280                 285

Phe Phe Ser Phe Asn Gln Thr Ile Asp Gly Val Cys Asn Gly Ala Ala
    290                 295                 300

Val Gln Arg Ala Pro Glu Ala Leu Arg Phe Asn Ile Asn Asp Thr Ser
305                 310                 315                 320

Val Ile Leu Ala Glu Gly Ser Ile Val Leu His Thr Ala Leu Gly Thr
                325                 330                 335

Asn Phe Ser Phe Val Cys Ser Asn Ser Ser Asn Pro His Leu Ala Thr
            340                 345                 350

Phe Ala Ile Pro Leu Gly Ala Thr Gln Val Pro Tyr Tyr Cys Phe Leu
        355                 360                 365

Lys Val Asp Thr Tyr Asn Ser Thr Val Tyr Lys Phe Leu Ala Val Leu
```

```
    370                 375                 380

Pro Pro Thr Val Arg Glu Ile Val Ile Thr Lys Tyr Gly Asp Val Tyr
385                 390                 395                 400

Val Asn Gly Phe Gly Tyr Leu His Leu Gly Leu Leu Asp Ala Val Thr
                405                 410                 415

Ile Asn Phe Thr Gly His Gly Thr Asp Asp Asp Val Ser Gly Phe Trp
            420                 425                 430

Thr Ile Ala Ser Thr Asn Phe Val Asp Ala Leu Ile Glu Val Gln Gly
        435                 440                 445

Thr Ala Ile Gln Arg Ile Leu Tyr Cys Asp Asp Pro Val Ser Gln Leu
    450                 455                 460

Lys Cys Ser Gln Val Ala Phe Asp Leu Asp Asp Gly Phe Tyr Pro Ile
465                 470                 475                 480

Ser Ser Arg Asn Leu Leu Ser His Glu Gln Pro Ile Ser Phe Val Thr
                485                 490                 495

Leu Pro Ser Phe Asn Asp His Ser Phe Val Asn Ile Thr Val Ser Ala
            500                 505                 510

Ser Phe Gly Gly His Ser Gly Ala Asn Leu Ile Ala Ser Asp Thr Thr
        515                 520                 525

Ile Asn Gly Phe Ser Ser Phe Cys Val Asp Thr Arg Gln Phe Thr Ile
    530                 535                 540

Ser Leu Phe Tyr Asn Val Thr Asn Ser Tyr Gly Tyr Val Ser Lys Ser
545                 550                 555                 560

Gln Asp Ser Asn Cys Pro Phe Thr Leu Gln Ser Val Asn Asp Tyr Leu
                565                 570                 575

Ser Phe Ser Lys Phe Cys Val Ser Thr Ser Leu Leu Ala Ser Ala Cys
            580                 585                 590

Thr Ile Asp Leu Phe Gly Tyr Pro Glu Phe Gly Ser Gly Val Lys Phe
        595                 600                 605

Thr Ser Leu Tyr Phe Gln Phe Thr Lys Gly Glu Leu Ile Thr Gly Thr
    610                 615                 620

Thr Lys Pro Leu Glu Gly Val Thr Asp Val Ser Phe Met Thr Leu Asp
625                 630                 635                 640

Val Cys Thr Lys Tyr Thr Ile Tyr Gly Phe Lys Gly Glu Gly Ile Ile
                645                 650                 655

Thr Leu Thr Asn Ser Ser Phe Leu Ala Gly Val Tyr Tyr Thr Ser Asp
            660                 665                 670

Ser Gly Gln Leu Leu Ala Phe Lys Asn Val Thr Ser Gly Ala Val Tyr
        675                 680                 685

Ser Val Thr Pro Cys Ser Phe Ser Glu Gln Ala Ala Tyr Val Asp Asp
    690                 695                 700

Asp Ile Val Gly Val Ile Ser Ser Leu Ser Ser Ser Thr Phe Asn Ser
705                 710                 715                 720

Thr Arg Glu Leu Pro Gly Phe Phe Tyr His Ser Asn Asp Gly Ser Asn
                725                 730                 735

Cys Thr Glu Pro Val Leu Val Tyr Ser Asn Ile Gly Val Cys Lys Ser
            740                 745                 750

Gly Ser Ile Gly Tyr Val Pro Ser Gln Ser Gly Gln Val Lys Ile Ala
        755                 760                 765

Pro Thr Val Thr Gly Asn Ile Ser Ile Pro Thr Asn Phe Ser Met Ser
    770                 775                 780

Ile Arg Thr Glu Tyr Leu Gln Leu Tyr Asn Thr Pro Val Ser Val Asp
785                 790                 795                 800
```

-continued

```
Cys Ala Thr Tyr Val Cys Asn Gly Asn Ser Arg Cys Lys Gln Leu Leu
                805                 810                 815

Thr Gln Tyr Thr Ala Ala Cys Lys Thr Ile Glu Ser Ala Leu Gln Leu
            820                 825                 830

Ser Ala Arg Leu Glu Ser Val Glu Val Asn Ser Met Leu Thr Ile Ser
        835                 840                 845

Glu Glu Ala Leu Gln Leu Ala Thr Ile Ser Ser Phe Asn Gly Asp Gly
    850                 855                 860

Tyr Asn Phe Thr Asn Val Leu Gly Val Ser Val Tyr Asp Pro Ala Ser
865                 870                 875                 880

Gly Arg Val Val Gln Lys Arg Ser Phe Ile Glu Asp Leu Leu Phe Asn
                885                 890                 895

Lys Val Val Thr Asn Gly Leu Gly Thr Val Asp Glu Asp Tyr Lys Arg
            900                 905                 910

Cys Ser Asn Gly Arg Ser Val Ala Asp Leu Val Cys Ala Gln Tyr Tyr
        915                 920                 925

Ser Gly Val Met Val Leu Pro Gly Val Val Asp Ala Glu Lys Leu His
    930                 935                 940

Met Tyr Ser Ala Ser Leu Ile Gly Gly Met Val Leu Gly Gly Phe Thr
945                 950                 955                 960

Ser Ala Ala Ala Leu Pro Phe Ser Tyr Ala Val Gln Ala Arg Leu Asn
                965                 970                 975

Tyr Leu Ala Leu Gln Thr Asp Val Leu Gln Arg Asn Gln Gln Leu Leu
            980                 985                 990

Ala Glu Ser Phe Asn Ser Ala Ile  Gly Asn Ile Thr Ser  Ala Phe Glu
        995                 1000                 1005

Ser Val  Lys Glu Ala Ile Ser  Gln Thr Ser Lys Gly  Leu Asn Thr
    1010                 1015                 1020

Val Ala  His Ala Leu Thr Lys  Val Gln Glu Val Val  Asn Ser Gln
    1025                 1030                 1035

Gly Ala  Ala Leu Thr Gln Leu  Thr Val Gln Leu Gln  His Asn Phe
    1040                 1045                 1050

Gln Ala  Ile Ser Ser Ser Ile  Asp Asp Ile Tyr Ser  Arg Leu Asp
    1055                 1060                 1065

Ile Leu  Ser Ala Asp Val Gln  Val Asp Arg Leu Ile  Thr Gly Arg
    1070                 1075                 1080

Leu Ser  Ala Leu Asn Ala Phe  Val Ala Gln Thr Leu  Thr Lys Tyr
    1085                 1090                 1095

Thr Glu  Val Gln Ala Ser Arg  Lys Leu Ala Gln Gln  Lys Val Asn
    1100                 1105                 1110

Glu Cys  Val Lys Ser Gln Ser  Gln Arg Tyr Gly Phe  Cys Gly Gly
    1115                 1120                 1125

Asp Gly  Glu His Ile Phe Ser  Leu Val Gln Ala Ala  Pro Gln Gly
    1130                 1135                 1140

Leu Leu  Phe Leu His Thr Val  Leu Val Pro Ser Asp  Phe Val Asp
    1145                 1150                 1155

Val Ile  Ala Ile Ala Gly Leu  Cys Val Asn Asp Glu  Ile Ala Leu
    1160                 1165                 1170

Thr Leu  Arg Glu Pro Gly Leu  Val Leu Phe Thr His  Glu Leu Gln
    1175                 1180                 1185

Asn His  Thr Ala Thr Glu Tyr  Phe Val Ser Ser Arg  Arg Met Phe
    1190                 1195                 1200
```

```
Glu Pro  Arg Lys Pro Thr Val  Ser Asp Phe Val Gln  Ile Glu Ser
    1205                 1210                 1215

Cys Val  Val Thr Tyr Val Asn  Leu Thr Arg Asp Gln  Leu Pro Asp
    1220                 1225                 1230

Val Ile  Pro Asp Tyr Ile Asp  Val Asn Lys Thr Leu  Asp Glu Ile
    1235                 1240                 1245

Leu Ala  Ser Leu Pro Asn Arg  Thr Gly Pro Ser Leu  Pro Leu Asp
    1250                 1255                 1260

Val Phe  Asn Ala Thr Tyr Leu  Asn Leu Thr Gly Glu  Ile Ala Asp
    1265                 1270                 1275

Leu Glu  Gln Arg Ser Glu Ser  Leu Arg Asn Thr Thr  Glu Glu Leu
    1280                 1285                 1290

Gln Ser  Leu Ile Tyr Asn Ile  Asn Asn Thr Leu Val  Asp Leu Glu
    1295                 1300                 1305

Trp Leu  Asn Arg Val Glu Thr  Tyr Ile Lys Trp Pro  Trp Trp Val
    1310                 1315                 1320

Trp Leu  Ile Ile Phe Ile Val  Leu Ile Phe Val Val  Ser Leu Leu
    1325                 1330                 1335

Val Phe  Cys Cys Ile Ser Thr  Gly Cys Cys Gly Cys  Cys Gly Cys
    1340                 1345                 1350

Cys Cys  Ala Cys Phe Ser Gly  Cys Cys Arg Gly Pro  Arg Leu Gln
    1355                 1360                 1365

Pro Tyr  Glu Val Phe Glu Lys  Val His Val Gln
    1370                 1375
```

<210> SEQ ID NO 32
<211> LENGTH: 27960
<212> TYPE: RNA
<213> ORGANISM: porcine epidemic diarrhea virus

<400> SEQUENCE: 32

```
agacucuugu cuacucaauu caacuaaacg aaauuuuguc cuuccggccg cauguccaug     60

cugcuggaag cugacgugga auuucauuag guuugcuuaa guagccaucg caagugcugu    120

gcuguccucu aguuccuggu uggcguuccg ucgccuucua cauacuagac aaacagccuu    180

ccuccgguuc cgucuggggg uuguguggau aacuaguucc gucuaguuug aaaccaguaa    240

cugucggcua uggcuagcaa ccauguuaca uuggcuuuug ccaaugaugc agaaauuuca    300

gcuuuuggcu uuugcacugc uagugaagcc gucucauacu auucugaggc cgccgcuagu    360

ggauuuaugc aaugccguuu cguguccuuc gaucucgcug acacuguuga gggauugcuu    420

cccgaagacu augucauggu gguggucggc acuaccaagc uuagugcgua uguggacacu    480

uuugguagcc gccccaaaaa cauuuguggu uggcuguuau uuucuaacug uaauuacuuc    540

cucgaagagu uagagcuuac uuuuggucgu cgugguggua acaucgugcc aguugaccaa    600

uacaugugug gcgcugacgg uaaaccuguu cuucaggaau ccgaauggga guauacagau    660

uucuuugcug acuccgaaga cggucaacuc aacauugcug guaucacuua ugugaaggcc    720

uggauuguag agcgaucgga ugucucuuau gcgagucaga auuuaacauc uauuaagucu    780

auuacuuacu guucaaccua ugagcauacu uuuccugaug guacugccau gaagguugca    840

cguacuccaa agauuaagaa gacuguuguc uugucugagc cacuugcuac uaucuacagg    900

gaaauugguu cuccuuuugu ggauaauggg agcgaugcuc guucuaucau uaagagacca    960

guguuccucc acgcuuuugu uaaguguaag ugugguaguu aucauuggac uguuggugau   1020

uggacuuccu augucuccac uugcuguggc uuuaagugua agccaguccu uguggcuuca   1080
```

ugcucugcua cgccugguuc uguugugguu acgcgcgcug gugcuggcac ugguguuaag 1140
uauuacaaca acauguuccu gcgccaugug gcagacauug augguuggc auucuggcga 1200
auucucaagg ugcaguccaa agacgaccuc gcuugcucug guaaauuccu ugaacaccau 1260
gaggaagguu ucacagaucc uugcuacuuu uugaaugacu cgagcauugc uacuaagcuc 1320
aaguuugaca uccuuagugg caaguuuucu gaugaaguca aacaagcuau cuuugcuggu 1380
cauguuguug uuggcagcgc gcucguugac auuguugacg augcacuggg acagccuugg 1440
uuuauacgua agcuugguga ccuugcaagu gcagcuuggg agcagcuuaa ggcugucguu 1500
agaggccuua accuccuguc ugaugagguc gugcucuuug gcaaaagacu uagcugugcc 1560
acucuuagua ucguuaacgg uguuuuugag uucaucgccg aagugccuga gaaguuggcu 1620
gcggcuguua caguuuuugu caacuucuug aaugagcuuu uugagucugc cugugacugc 1680
uuaaaggucg gagguaaaac cuuuaacaag guuggcucuu auguucuuuu ugacaacgca 1740
uugguuaagc uugucaaggc aaaaguucgc ggcccacgac aggcaggugu uugugaaguu 1800
cguuacacaa gccuuguuau ugggaguacu accaaggugg uuuccaagcg cguugaaaau 1860
gccaauguga aucucgucgu cguugacgag gaugugaccc ucaacaccac uggucguaca 1920
guuguuguug acggacuugc auucuucgag agugacgggu uuuacagaca ucuugcugau 1980
gcugacguug ucauugaaca uccuguuuau aagucugcuu gugagcucaa gccaguuuuu 2040
gagugugacc caauaccuga uuuuccuaug ccuguggccg cuaguguugc agagcuuugu 2100
gugcaaacug aucuguugcu uaaaaauuac aacacuccuu auaaaaacuua cagcugcguu 2160
gugagaggug auaaguguug uaucacuugc accuuacauu ucacagcacc aaguuauaug 2220
gaggcugcug cuaauuuugu agaccucugu accaagaaca uugguacugc ugguuuucau 2280
gaguuuuaca uuacggccca ugaacaacag gaucugcaag gguucguaac cacuuguugc 2340
acgaugucag guuuugagug uuuuaugccu auaaucccac aguguccagc agugcuugaa 2400
gagauugaug gugguagcau cuggcggucu uuuaucacug gucuuaauac aaugugggau 2460
uuuugcaagc aucuuaaagu cagcuuugga cuagauggca uuguugucac uguagcacgc 2520
aaauuuaaac gacuuggugc ucucuuggca gaaauguaua acacuuaccu uucaacugug 2580
guggaaaacu ugguacuggc cgguguuagc uucaaguauu augccaccag ugucccaaaa 2640
auuguuuugg gcuguuguuu ucacaguguu aaaaguguuc uugcaagugc cuuccagauu 2700
ccuguccagg caggcguuga gaaguuuaaa gucuuccuua acuguguuca cccuguugua 2760
ccacguguca uugaaacuuc uuuuguggaa uuagaagaga cgacauuuaa accaccagca 2820
cucaauggua guauugcuau uguugauggc uuugcuuucu auuaugaugg aacacuauac 2880
uaucccaccg augguaauag cguuguuccu aucugcuuua agaagaaagg ugguggugau 2940
gucaaauucu cugaugaagu cucuguuaaa accauugacc caguuuauaa ggucucccuu 3000
gaauuugagu ucgagucuga gacuauuaug gcugugcuua auaaggcugu ugguaauugu 3060
aucaagguua cagguggguug ggacgauguu guugaguaua ucaauguugc cauugagguu 3120
cuuaaagauc acaucgaugu gccuaaguac uacaucuaug augaggaagg uggcaccgau 3180
ccuaaucugc ccguaauggu uucucagugg ccguugaaug augacacgau cucacaggau 3240
cugcuugaug uugaaguugu uacugaugcg ccaguugauu ucgaggguga ugaaguagac 3300
uccucugacc cugauaaggu ggcagacgug gcuaacucug agccugagga ugacggucuu 3360
aauguagcuc cugaaacaaa uguagagucu gaaguugagg aaguugccgc aaccuugucc 3420

```
uuuauuaaag auacaccuuc cacaguuacu aaggauccuu uugcuuuuga cuuugcaagc   3480
uauggaggac uuaagguuuu aagacaaucu cauaacaacu gcuggguuac uucuaccuug   3540
gugcagcuac aauugcuugg caucguugau gacccugcaa uggagcuuuu uagugcuggu   3600
agaguugguc caaugguucg caaaugcuau gagucacaaa aggcuaucuu gggaucuuug   3660
ggugaugugu cggcuugccu agagucucug acuaaggacc uacacacacu uaagauuacc   3720
uguucuguag ucugugguug ugguacuggu gaacguaucu augaugguug ugcuuuucgu   3780
augacgccaa cuuuggaacc guucccauau ggugcuugug cucagugugc ucaaguuuug   3840
augcacacuu uuaaaaguau uguuggcacc ggcaucuuuu gucgagauac uacugcucuc   3900
uccuuggauu cuuugguugu aaaaccucuu ugugcggcug cuuuuauagg caaggauagu   3960
ggucauuaug ucacuaacuu uuaugaugcu gcuauggcua uugaugguua uggucgucau   4020
cagauaaagu augacacacu gaacacuauu uguguuaaag acguuaauug gacagcaccu   4080
uuugucccag acguugagcc uguauuggag ccuguuguca aaccuuucua uucuuauaag   4140
aauguugauu uuuaccaagg agauuuuagu gaccuuguua aacuuccaug ugauuuuguu   4200
guuaaugcug caaaugagaa uuugucucac gguggcggca uagcaaaggc cauugauguu   4260
uauaccaagg gcauguugca gaagugcucg aaugauuaca uuaaagcaca cggucccauu   4320
aaaguuggac guggugucau guuggaggca uuaggucuua aggucuuuaa uguuguuggu   4380
ccacguaagg guaagcaugc accugagcuu cuuguuaagg cuuauaaguc cguuuuugcu   4440
aauucaggug uugcucuuac accuuugauu aguguuggaa uuuuuagugu uccuuuggaa   4500
gaaucuuuau cugcuuuucu ugcauguguu ggugaucgcc acuguaagug cuuuuguuau   4560
agugacaaag agcgcgaggc gaucauuaau uacauggaug gcuugguaga ugcuauuuuc   4620
aaagaugcac uuguugauac uacuccuguc caggaagaug uucaacaagu uucacaaaaa   4680
ccaguuuugc cuaauuuuga accuuucagg auugaaggug cucaugcuuu cuaugagugc   4740
aacccugaag guuugauguc auuaggugcu gacaagcugg uguuguuuac aaauuccaau   4800
uuggauuuuu guagcguugg uaagugucuu aacaauguga cuggcggugc auugcuugaa   4860
gccauaaaug uauuuaaaaa gaguaacaaa acagugccug cuggcaacug uguuacuuuu   4920
gagugugcag auaugauuuc uauuacuaug guaguauugc caucugacgg ugaugcuaau   4980
uaugacaaaa auuaugcacg cgccgucguc aagguaucua agcuuaaagg caaguuauug   5040
cuugcuguug gugaugccau guuguauucc aaguuguccc accucagcgu guuagguuuc   5100
guauccacac cugaugaugu ggagcguuuc uacgcaaaua agagugugg uauuaaaguu   5160
acugaggaua cacguagugu uaagacuguu aaaguagaau ccacuguuac uuauggacaa   5220
caaauuggac cuugucuugu uaaugacacc guugucacag acaacaaacc uguuguugcu   5280
gauguuguag cuaagguugu accaagugcu aauugggauu cacauuaugg uuuugauaag   5340
gcuggugagu uccacaugcu agaccauacu ggguuugccu uuccuaguga aguuguuaac   5400
gguaggcgug ugcuuaaaac cacagauaau aacuguuggg uuaauguuac auguuuacaa   5460
uuacaguuug cuagauuuag guucaaguca gcaggucuac aggcuaugug ggaguccuau   5520
uguacuggug auguugcuau guuugugcau ugguuguacu ggcuuacugg uguugacaaa   5580
ggucagccua gugauucaga aaaugcacuu aacauguugu cuaaguacau uguuccugcu   5640
gguucuguca cuauugaacg ugucacgcau gacgguuguu guuguaguaa gcguguuguc   5700
acugcaccag uugugaaugc uagcguguug aagcuuggcg ucgaggaugg ucuuugucca   5760
cauggucuua acuacauuga caaaguuguu guaguuaaag guacuacaau uguugucaau   5820
```

-continued

```
guuggaaaac cuguaguggc accaucgcac cucuuucuua agggguguuuc cuacacaaca   5880
uuccuagaua augguaacgg uguugccggc cauuauacug uuuuugauca ugacacuggu   5940
auggugcaug auggagaugu uuuuguacca ggugaucuca augugucucc uguuacaaau   6000
guugucgucu cagagcagac ggcuguugug auuaaagacc cugugaagaa aguagaguua   6060
gacgcuacaa agcuguuaga cacuaugaau uaugcaucgg aaagauucuu uuccuuuggu   6120
gauuuuaugu cacguaauuu aauuacagug uuuuuguaca uccuuaguau uuugggucuc   6180
uguuuuaggg ccuuucguaa gagggauguu aaaguucuag cugguguacc ccaacguacu   6240
gguauuauau ugcguaaaag ugugcgcuau aaugcaaagg cuuugggugu cuucuucaag   6300
cuaaaacuuu auugguucaa aguucuuggu aaguuuaguu uggguauuua ugcauuguau   6360
gcauuacuau ucaugacaau acgcuuuaca ccuauaggug gcccuguuug ugaugauguu   6420
guugcugguu augcuaauuc uaguuuugac aagaaugagu auugcaacag uguuauuugu   6480
aaggucuguc ucuaugggua ccaggaacuu ucggacuucu cucacacaca gguaguaugg   6540
caacaccuua gagacccauu aauugguaau gugaugccuu ucuuuuauuu ggcauuucug   6600
gcaauuuuug ggggguguuua uguaaaggcu auuacucucu auuuuauuuu ccaguaucuu   6660
aacauacuug guguguuuuu gggccuacaa caguccauuu gguuuuugca gcuugugccu   6720
uuugaugucu uuggugacga gaucgucguc uuuuucaucg uuacacgcgu auugauguuc   6780
cuuaagcaug uuuuccuugg cugcgauaag gcaucuugug uggcuugcuc uaagagugcu   6840
cgccuuaagc gcguuccugu ccagacuauu uuucagggua cuagcaaauc cuucuacgua   6900
caugccaaug gugguucuaa guucuguaag aagcacaauu ucuuuuguuu aaauugugau   6960
ucuuaugguc caggcugcac uuuuauuaau gacgucauug caacugaagu ugguaauguu   7020
gucaaacuua augugcaacc gacagguccu gccacuauuc uuauugacaa gguugaauuc   7080
aguaaugguu uuuacuaucu uuauaguggu gacacauuuu ggaaguacaa cuuugacaua   7140
acagauaaca aauacacuug caaagaguca cuuaaaaauu guagcauaau cacagacuuu   7200
auuguuuuua acaauaaugg uuccaaugua aaucagguua agaaugcaug uguguauuuu   7260
ucacagaugc uuuguaaacc uguuaaguua guggacucag cguuguuggc caguuugucu   7320
guugauuuug gugcaagcuu acauagugcu uuuguuagug uguugucgaa uaguuuuggc   7380
aaagaccugu caaguuguaa ugacaugcag gauugcaaga gcacauuggg uuuugaugau   7440
guaccauugg auaccuuuaa ugcugcuguu gcugaggcuc aucguuacga uguccucuug   7500
acugacaugu cguucaacaa uuuuaccacc aguuaugcaa aaccagagga aaaacuuccc   7560
guccaugaca uugccacgug uaugcgugua ggugccaaga uuguuaauca uaacguucuu   7620
gucaaggaua guauaccugu ggugugguu guacgugauu ucauugcccu uucugaagaa   7680
acuaggaagu acauuauucg uacgacuaaa guuaagggua uaaccuucau guugaccuuu   7740
aaugauuguc guaugcauac uaccauaccu acuguuugca uugcaaauaa gaagggugca   7800
ggucuuccua guuuuucaaa gguuaagaaa uucuucuggu uuuuguguucu guucauaguu   7860
gcuguuuucu uugcacuaag cuuuuuugau uuuaguacuc agguuagcag ugauagugau   7920
uaugacuuca aguauauuga gaguggccag uugaagacuu uugacaaucc acuuaguugu   7980
gugcauaaug ucuuuaguaa cuucgaccag uggcaugaug ccaaguuugg uuucaccccc   8040
gucaacaauc cuaguugucc uauagucguu gguguaucag acgaagcgcg cacuguucca   8100
gguaucccag cagguguuua uuuagcuggu aaaacacuug uuuuugcuau uaacaccauu   8160
```

-continued

```
uuugguacau cugguuugug cuuugaugcu aguggcguug cugauaaggg cgcuugcauu   8220
uuuaauucgg cuugcaccac auuaucuggu uuggguggaa cugcugucua cuguuauaag   8280
aauggucuag uugaaggugc uaaacuuuau agugaguugg caccucauag cuacuauaaa   8340
augguagaug guaaugcugu gucuuuaccu gaaauuaucu cacgcggcuu uggcauccgu   8400
acuauccgua caaaggcuau gaccuacugu cgcguuggcc agugugugca aucugcagaa   8460
gguguuuguu uuggcgccga uagauucuuu gucuauaaug cagaaucugg uucugacuuu   8520
guuuguggca cagggcucuu uacauuguug augaacguua uuaguguuuu uuccaagaca   8580
guaccaguaa cuguguuguc uggucaaaua cuuuuuaauu gcauuauugc uuuugcugcu   8640
guugcggugu guuucuuauu uacaaaguuu aagcgcaugu ucggugauau gucuguuggc   8700
guuuucacug ucggugcuug uacuuuguug aacaauguuu ccuacauugu aacacagaac   8760
acacuuggca uguugggcua ugcaacuuug uacuuuuugu gcacuaaagg uguuagauau   8820
auguggauuu ggcauuuggg auuuuugauc ucauauauac uuauugcacc auggugggui   8880
uugaugguuu augccuuuuc agccauuuuu gaguuuaugc cuaaccuuuu uaagcuuaag   8940
guuucaacac aacuuuuuga gggugacaag uucguaggcu cuuuugaaaa ugcugcagca   9000
gguacauuug ugcuugauau gcaugccuau gagagacuug ccaacucuau cucaacugaa   9060
aaacugcguc aguaugcuag uacuuacaau aaguacaagu auuauucagg cagugcuuca   9120
gaggcugauu acaggcuugc uuguuuugcc cauuuggcca aggcuaugau ggauuaugcu   9180
ucuaaucaca acgacacguu auacacacca cccacuguga guuacaauuc aacucuacag   9240
gcuggcuugc guaagauggc acaaccaucu gguguuguug agaagugcau aguucguguu   9300
ugcuauggua auauggcucu uaauggccua uggcuuggug auacuguuau cugcccacgc   9360
cauguuauag cgucuaguac uacuagcacu auagauuaug acuaugcccu uucuguuuua   9420
cgccuccaca acuucuccau uucaucuggu aauguuuucc uagguguugu ggguguaacc   9480
augcgaggug cuuuguugca gauaaagguu aaucaaaaca auguccacac gccuaaguac   9540
accuaucgca caguuagacc gggugaaucu uuuaauaucu uggcgugcua ugaugguucu   9600
gcagcuggug uuuacggcgu uaacaugcgc ucuaauuaca cuauuagagg cucguucauu   9660
aauggcgcuu gugguucacc ugguuauaac auuaacaaug guaccguuga guuuugcuau   9720
uuacaccagc uugaacuugg uucaggcugu cauguuggua gcgacuuaga ugguguuaug   9780
uaugguggui augaggacca accuacuuug caaguugaag gcgcuaguag ucuguuuaca   9840
gagaaugugu uggcauuucu uuaugcagca cucauuaaug guucuaccug guggcuuagu   9900
ucuucuagga uugcuguaga cagguuuaau gagugggcug uucauaaugg uaugacaaca   9960
guaguuaaua cugauugcuu uucuauucuu gcugcuaaga cuggguguuga uguacaacgu  10020
uuguuggccu caauccaguc ucugcauaag aauuuuggug gaaagcaaau ucuuggcuau  10080
accucguuga cagaugaguu uacuacaggu gaaguuauac gucaaaugua uggcguuaau  10140
cuucagagug guuauguuuc acgcgccugu agaaaugucu ugcugguugg uucuuuucug  10200
acuuucuuuu ggucagaauu aguuuccuac acuaaguucu uuuggguaaa uccugguuau  10260
gucacaccua uguuugcgug uuugucauug cuguccucac uuuugauguu cacacucaag  10320
cauaagacau uguuuuucca ggucuuucua auaccugcuc ugauuguuac aucuugcauu  10380
aauuuggcau uugauguuga agucuacaac uauuuggcag agcauuuuga uuaccauguu  10440
ucucucaugg guuuuaaugc acaaggucuu guuaacaucu uugucugcuu uguuguuacc  10500
auuuuacacg gcacauacac auggcgcuuu uuuaacacac cugugaguuc ugucacuuau  10560
```

-continued gugguagcuu ugcugacugc ggcauauaac uauuuuuacg cuagugacau ucuuaguugu 10620
gcuaugacac uauuugcuag ugugacuggc aacugguucg uuggugcugu uuguuauaaa 10680
gcugcuguuu auauggccuu gagauuuccu acuuuugugg cuauuuuugg ugauauuaag 10740
aguguuaugu ucuguuaccu uguguugggu uauuuuaccu guugcuucua cgguauucuc 10800
uacugguuca acagguuuuu uaagguuagu guaggugucu augacuauac uguuagugcu 10860
gcugaguuua aguauauggu ugcuaacggc cuacgugcac caacuggaac acuugauuca 10920
cuacuucugu cugccaaauu gauugguauu gguggugagc ggaauauuaa gauuucuucc 10980
guucagucua aacugacuga uauuaagugu aguaacguug ugcuuuuagg cugucucucu 11040
agcaugaaug ucucagcaaa uucaacagaa ugggccuauu guguugacuu gcauaacaag 11100
aucaacuugu guaaugaccc agaaaaagcg caggaaaugc uacuugcuuu guuggcauuu 11160
uuccuuagua agaauagugc uuuugguuua gaugacuuau uggaauccua uuuuaaugac 11220
aauaguaugu ugcagagugu ugcaucuacu uaugucgguu ugccuucuua ugucauuuau 11280
gaaaaugcac gccaacagua ugaagaugcu guuaauaaug guucuccacc ucaguugguu 11340
aagcaauugc gccaugccau gaauguagca aagagcgaau uugaccguga ggcuucuacu 11400
cagcguaagc uugauagaau ggcggaacag gcugcagcac agauguacaa agaggcacga 11460
gcaguuaaua ggaaguccaa aguuguaagu gcuaugcauu cacugcuuuu ugguauguug 11520
agacguuugg acaugucuuc uguagacacc auucucaacu uggcaaagga uggggguugua 11580 ccucugucug ucauaccggc agucagugcu acuaagcuua acauuguuac uucugauauc 11640
gauucuuaua aucguaucca gcgugaggga uguguccacu acgcugguac cauuuggaau 11700 auaaauugaua ucaaggacaa ugauggcaag gugguacacg uuaaggaggu aaccgcacag 11760
aaugcugagu cccugucaug gccccugguc cuugggugug agcguauugu caagcuccag 11820 aauaaaugaaa uuauuccugg uaagcugaag cagcgcucca uuaaggcaga aggagauggc 11880
auaguuggag aagguaaggc acuuuacaau aaugagggug gacguacuuu uauguaugcu 11940
uucaucucgg acaaaccgga ccugcgugua gucaagugggg aguucgaugg ugguuguaac 12000
acuauugagc uagaaccacc acguaaguuc uugguggauu cuccuaaugg ugcacagauc 12060
aaguaucucu acuuuguucg uaaccuuaac acguuacgua ggggugcugu ucucggcuac 12120
auaggugcca cuguacgcuu gcaggcuggu aaacaaacag aacaggcuau uaacucuuca 12180
uuguugacac uuugcgcuuu cgcuguggau ccugcuaaga ccuacaucga ugcugucaaa 12240 agugguca ca aaccaguagg uaacugugui aagauguugg ccaaugguuc ugguaaugga 12300
caagcuguua cuaauggugu ggaggcuagu acuaaccagg auucauacgg uggugcgucc 12360
gugugucuau auuguagagc acauguugag cauccaucua uggaugguuu uugcagacug 12420
aaaggcaagu acguacaggu uccacuaggu acaguggauc cuauacguuu uguacuugag 12480
aaugacguuu gcaagguuug ugguuguugg cuggcuaaug gcugcacuug ugacagaucc 12540
auuaugcaaa gcacugauau ggcuuauuua aacgaguacg gggcucuagu gcagcucgac 12600
uagagcccug uaacgguacu gauacacaac auguguaucg ugcuuuugac aucuacaaca 12660
aggauguugc uugucuaggu aaauuccuca aggugaacug uguucgccug aagaauuugg 12720
auaagcauga ugcauucuau guugucaaaa gauguaccaa gucugcgaug gaacacgagc 12780
aauccaucua uagcagacuu gaaaagugug gagccguagc cgaacacgau uucuucacuu 12840
ggaaggaugg ucgugccauc uaugguaacg uuuguagaaa ggaucuuacc gaguauacua 12900
ugauggauuu guguuacgcu uuacguaacu uugaugaaaa caauugcgau guucuuaaga 12960
gcauuuuaau uaagguaggc gcuugugagg aguccuacuu caauaauaaa gucugguuug 13020
acccuguuga aaaugaagac auucaucgug ucuaugcauu guuagguacc auuguuucac 13080
gugcuaugcu uaaaugcguu aaguucugug augcaauggu ugaacaaggu auaguuggug 13140
uugucacauu agauaaucag gaucuuaaug gugauuuuua ugauuuuggu gauuuuacuu 13200
guagcaucaa gggaaugggu auacccauuu gcacaucaua uuacucuuau augaugccug 13260 uuaugggguau gacuaauugc cuugcuagug aguguuuugu uaagagugau auauuuggug 13320
aggauuucaa gucauaugac cugcuggaau augauuucac ggagcauaag acagcacucu 13380
ucaacaagua uuucaaguau uggggacugc aauaccaccc uaacugugug gacugcagug 13440
augagcagug cauaguucac ugugccaacu ucaauacguu guuuuccacu acuauaccua 13500
uuacggcauu uggaccuuug ugucgcaagu guuggauuga ugguguucca cugguaacua 13560
cagcugguua ucauuuuaaa caguuaggua uaguuuggaa caaugaccuc aacuuacacu 13620
cuagcaggcu cucuauuaac gaauuacucc aguuuuguag ugauccugca uugcuuauag 13680
caucaucacc agcccuuguu gaucagcgua cuguuugcuu uucaguugca gcgcuaggua 13740
cagguaugac uaaccagacu guuaaaccug gccauuucaa uaaggaguuu uaugacuucu 13800
uacuugagca agguuucuuu ucugagggcu cugagcuuac uuuaaagcac uucuucuuug 13860
cacagaaggg ugaugcagcu guuaaggauu uugacuacua uagguauaau agaccuacug 13920
uucuggacau uugccaagcu cgcgucgugu aucaaauagu gcaacgcuau uuugauauuu 13980
acgaaggugg uuguaucacu gcuaaagagg ugguuguuac aaaccuuaac aagagcgcag 14040
guuauccuuu gaacaaguuu gguaaagcug gucuuuacua ugagucuuua uccuaugagg 14100
aacaggauga acuuuaugcu uauacuaagc guaacauccu gcccacuaug acacagcuca 14160
accuuaaaua ugcuauaagu ggcaaagaac gugcacgcac agugggguggu guuucgcuuu 14220 ugucaaccau gacuacucgg caguaucauc agaaacaccu uaaguccaua guuaauacua 14280
ggggcgcuuc gguuguuauu gguacuacua aguuuuaugg ugguugggac aauaugcuua 14340
agaaccuuau ugaugguguu gaaaauccgu gucuuauggg uugggacuac ccaaagugcg 14400
acagagcacu gcccaauaug auacguauga uuucagccau gauuuuaggc ucuaagcaca 14460
ccacaugcug caguuccacu gaccgcuuuu ucagguugug caaugaauug gcucaagucc 14520
uuacugaggu uguuuauucu aauggagguu uuuauuugaa gccaggugu acuaccucug 14580 gugaugcaac caccgcauau gcaaacucag uuuuuaauau cuuccaagca guaagugcca 14640
auguuaacaa acuucuuagu guugacagca augucuguca uaauuuagaa guuaagcaau 14700
ugcagcguaa gcuuuaugag ugcuguuaua gaucaacuac cgucgaugac caguucgucg 14760
uugaguauua ugguuacuug cguaaacauu uuucaaugau gauucuuucu gaugauggcg 14820
uuguuuguua uaacaaugac uaugcaucac uugguuaugu cgcugaucuu aacgcauuca 14880
aggcuguuuu guauuaccag aacaaugucu ucaugagcgc cucuaaaugu uggaucgagc 14940
cugacauuaa uaaagguccu caugaauuuu gcucgcagca uacuaugcag auugucgaua 15000
aagaugguac uuauuaccuu ccuuacccug auccuucaag aauucucucu gcaggugugu 15060
uuguugauga cguuguuaaa acugaugcag uuguauugcu ugaacguuau gugucauugg 15120
cuauagaugc cuacccguua ucuaagcaug aaaacccuga auauaagaag guguuuuaug 15180
ugcuuuugga uuggguuaag caucuguaca aaacucuuaa ugcuggugug uuagagucuu 15240
uuucugucac acuuuuggaa gauucuacug cuaaauucug ggaugagagc uuuuaugcca 15300

```
acauguauga gaaaucugca guuuuacaau cugcagggcu uuguguuguu uguggcucuc  15360
aaacuguuuu acguuguggu gauugucuac ggcguccuau gcuuuguacu aagugugcuu  15420
augaucaugu cauuggaaca acucacaagu ucauuuuggc caucacucca uaugugugu u  15480
gugcuucaga uuguggugu c aaugauguaa cuaagcucua cuuaggugg u cuuaguuauu  15540
ggugucauga ccacaagcca cgucuugcau ucccguugug cucugcuggu aauguuuuug  15600
gcuuguacaa aaauucugcu accggcucac ccgauguuga agacuuuaau cgcauugcua  15660
cauccgauug gacugauguu ucugacuaca gguuggcaaa ugaugucaag gacucauugc  15720
gucuguuugc agcggaaacu aucaaggcca aggaggagag cguuaaguca ucccuaugcuu  15780
gugcaacacu acaugagguu guaggaccua aagaguuguu gcucaaaugg gaagucggca  15840
gacccaaacc accccuuaau agaaauucgg uuuucacuug uuaucauaua acgaagaaca  15900
ccaaauuuca aaucggugag uuuguguuug agaaggcaga auaugauaau gaugcuguaa  15960
cauauaaaac uaccgccaca acaaaacuug uuccuggcau gguuuuugug cuuaccucac  16020
auaauguuca gccauugcgc gcaccgacca uugcuaauca agaacguuau uccacuauac  16080
auaaguugca uccugcuuuu aacauaccug aagcuuauuc uagcuuagug cccuauuacc  16140
aauugauugg uaagcagaag auuacaacua uucagggacc ucccgguagu gguaaaucuc  16200
acuguguuau agggcuaggu uuguacuauc caggugcacg uauaguguuu acagcuuguu  16260
cucaugcagc ggucgauuca cuuuguguga aagcuuccac ugcuuauagc aaugacaaau  16320
guucacgcau cauaccacag cgcgcucgug uugaguguua ugaugguuuc aagucuaaua  16380
auacuagugc ucaguaccuu uucucuacug ucaaugcuuu gccagagugc aaugcggaca  16440
uuguuguggu ggaugagguc ucuaugugca cuaauuauga cuugucuguc auaaaucagc  16500
gcaucagcua uaggcaugua gucuauguug gugacccuca acagcugccu gcaccacgug  16560
uuaugauuuc acgugguacu uuggaaccaa aggacuacaa cguugucacu caacgcaugu  16620
gugcccuuaa gccugauguu uucuugcaca aguguuaucg cuguccugcu gagauagugc  16680
guacuguguc ugagauggu c uaugaaaacc aauucauucc ugugcaccca gauagcaagc  16740
aguguuuuaa aaucuuuugc aaggguaaug uucagguuga uaaugguuca agcauuaaauc  16800
gcaggcaauu ggauguugug cguauguuuu uggcuaaaaa ucccuaggugg ucaaaggcug  16860
uuuuuauuuc ucccuuauaac agccagaauu auguugccag ccgcaugcua ggucuacaaa  16920
uucagacagu ugacucaucc cagggguagug aguaugacua ugucauuuac acacaaacuu  16980
cagauacugc ccaugccugu aauguuaaca gguuuaaugu ugccaucaca agggccaaga  17040
aaggcauauu auguauaaug ugcgauaggu cccuuuuuga ugugcuuaaa uucuuugagc  17100
uuaaauuguc ugauuugcag gcuaaugagg guuguggucu uuuuaaagac uguagcagag  17160
gugaugaucu guugccacca ucucacgcua acaccuucau gucuuuagcg gacaauuuua  17220
agacugauca agaucuugcu guucaaauag guguuaaugg acccauuaaa uaugagcaug  17280
uuaucucguu uaugggguuuc cguuuugaua ucaacauacc caaccaucau acucucuuuu  17340
gcacacgcga cuuugccaug cgcaauguua gagguuggu u aggcuuugac guugaaggag  17400
cacauguugu uggcucuaac gucgguacaa augucccauu gcaauuaggg uuuucuaacg  17460
guguugauuu uguugucaga ccugaagguu gcguuguaac agagucuggu gacuacauua  17520
aacccgucag agcucgugcu ccaccagggg aacaauucgc acaccuuuug ccuuuacuua  17580
aacgcggcca accaugggau guuguccgca aacguauagu gcagaugugu agugacuacc  17640
```

uggccaaccu aucagacaua cuaauuuuug uguugugggc uggugguuug gaguugacaa 17700
cuaugcguua uuuugucaag auuggaccaa guaagaguug ugauuguggu aagguugcua 17760
cuuguuacaa uagugcgcug cauacguacu guuguuucaa acaugcccuu gguugugauu 17820
aucuguauaa cccauacugu auugauauac agcaguggggg auacaaggga ucacuuagcc 17880
uuaaccacca ugagcauugu aauguacaua gaaacgagca uguggcuucu ggugaugcca 17940
uaaugacucg cugucuggcc auacaugauu gcuuugucaa gaacguugac ugguccauca 18000
cauacccauu uauugguaau gaggcuguua uuaauaagag cggccgaauu gugcaaucac 18060
acacuaugcg gucaguucuu aaguuauaca auccgaaagc cauauaugau auuggcaauc 18120
cuaagggcau uagaugugcc guaacggaug cuaagugguu uugcuuugac aagaauccua 18180
cuaauucuaa ugucaagaca uuggaguaug acuauauaac acauggccaa uuugaugggu 18240
ugugcuuguu uuggaauugc aauguagaca uguauccaga auuuucugug gucugucguu 18300
uugauacucg cuguagguca ccacucaacu uggaggguug uaaugguggu ucacuguaug 18360
uuaauaauca ugcauuccau acaccggcuu uugacaagcg ugcuuuugcu aaguugaagc 18420
caaugccauu uuucuuuuau gaugauacug agugugacaa guuacaggac uccauaaacu 18480
auguuccucu uagggcuagu aacugcauua cuaaauguaa uguuggugguu gcugucugua 18540
guaagcauug ugcuauguau cauagcuaug uuaaugcuua caacacuuuu acgucggcgg 18600
gcuuuacuau uugggugccu acuucguuug acaccuauaa ucuguggcag acauuuagua 18660
acaauuugca aggucuugag aacauugcuu ucaaugucgu aaagaaagga ucuuuuguug 18720
gugccgaagg ugaacuuccu guagcugugg uuaaugacaa agugcucguu agagauggua 18780
cuguugauac ucuuguuuuu acaaacaaga caucacuacc cacuaacgua gcuuuugagu 18840
uguaugccaa gcguaaggua ggacucaccc cacccauuac gauccuacgu aacuugggug 18900
uaguuuguac aucuaagugu gucauuuggg acuaugaagc cgaacgucca cuuacuacuu 18960
uuacaaagga uguuuguaaa uauaccgacu uugagggugga cgucuguaca cucuuugaua 19020
acagcauugu ugguucauua gagcgauucu ccaugaccca aaaugcugug cuuaugucac 19080
uuacagcugu uaaaaagcuu acuggcauaa aguuaacuua ugguuaucuu aaugguguccc 19140
caguuaacac acaugaagau aaaccuuuua cuugguauau uuacacuagg aagaacggca 19200
aguucgagga ccauccugau ggcuauuuua cccaagguag aacaaccgcu gauuuuagcc 19260
cucguagcga cauggaaaag gacuuccuaa guauggauau gggucuguuu auuaacaagu 19320
acggacuuga agauuacggc uuugagcacg uuguguaugg ugauguuuca aaaaccaccc 19380
uuggugguuu gcaucuacua auuucgcagg ugcgucuggc cuguaugggu gugcucaaaa 19440
uagacgaguu ugugucuagu aaugauagca cguuaaaguc uuguacuguu acauaugcug 19500
auaacccuag uaguaagaug guuuguacgu auauggaucu ccugcuugac gauuuuguca 19560
gcauucuuaa aucuuuggau uugggcguug uaucuaaagu ucaugaaguu auggucgauu 19620
guaaaaugug gagguggaug uuguggugua aggaucauaa acuccagaca uuuuauccgc 19680
aacuucaggc cagugaaugg aaguguggguu auuccaugcc uucuauuuac aagauacaac 19740
guauguguuu agaaccuugc aaucucuaca acuauggugc ugguauuaag uuaccugaug 19800
gcauuauguu uaacguaguu aaauacacac agcuuuguca auaucucaau agcaccacaa 19860
uguguguacc ccaucacaug cgugugcuac aucuuggugc uggcuccgac aagggguguug 19920
caccuggcac ggcugucuua cgacguuggu ugccacugga ugccauuaua guugacaaug 19980
auagugugga uuacguuagc gaugcugauu auaguguuac aggagauugc ucuaccuuau 20040
accugucaga uaaguuugau uuaguuauau cugauaugua ugaugguaag auuaaaaguu 20100
gugaugggga gaacgugucu aaagaaggcu ucuuucccua uauuaauggu gucaucaccg 20160
aaaaguuggc acuuggugu acuguagcua uuaaggugac ggaguuuagu uggaauaaga 20220
aguuguauga acucauucag agguuugagu auuggacaau guucuguacc aguguuaaca 20280
cgucaucguc agaggcauuc uuaauuggug uucacuauuu aggugauuuu gcaaguggcg 20340
cugugauuga cggcaacacu augcaugcca auuauaucuu cuggcguaau uccacaauua 20400
ugacuauguc uuacaauagu guacuugauu uaagcaaguu caauuguaag cauaaggcua 20460
caguugucau uaauuuaaaa gauucaucca uuagugaugu uguguuaggu uuguugaaga 20520
augguaaguu gcuagugcgu aauaaugacg ccauuugugg uuuuucuaau cauuugguca 20580
acguaaacaa augaagucuu uaaccuacuu cugguuguuc uuaccaguac uuucaacacu 20640
uagccuacca caagauguca ccaggugcuc agcuaacacu aauuuuaggc gguucuuuuc 20700
aaaauuuaau guucaggcgc cugcaguugu uguacugggc gguuaucuac cuauugguga 20760
aaaccagggu gucaauucaa cuugguacug ugcuggccaa cauccaacug cuaguggcgu 20820
ucaugguauc uuuguuagcc auauuagagg uggucauggc uuugagauug gcauuucgca 20880
agagccuuuu gacccuagug guuaccagcu uuauuuacau aaggcuacua acgguaacac 20940
uaaugcuacu gcgcgacugc gcauuugcca guuuccuagc auuaauaaug auguuacaau 21000
aggucguaau ugccuauuua acaaagccau cccagcucau augagugaac auaguguugu 21060
cggcauaaca ugggauaaug aucgugucac ugucuuuucu gacaagaucu auuauuuuua 21120
uuuuaaaaau gauugguccc guguugcgac aaaguguuac aacaguggag guugugcuau 21180
gcaauauguu uacgaaccca ccuauuacau gcuuaauguu acuagugcug gugaggaugg 21240
uauuucuuau caacccugua cagcuaauug cauugguuau gcugccaaug uauuugcuac 21300
ugagcccaau ggccacauac cagaagguuu uaguuuuaau aauugguuuc uuuuguccaa 21360
ugauuccacu uuggugcaug guaagguggu uuccaaccaa ccauuguugg ucaauugucu 21420
uuuggccauu ccuaagauuu auggacuagg ccaauuuuuc uccuuuaauc aaacgaucga 21480
ugguguuugu aauggagcug cugugcagcg ugcaccagag gcucugaggu uuaauauuaa 21540
ugacaccucu gucauucuug cugaaggcuc aauuguacuu cauacugcuu uaggaacaaa 21600
uuuuucuuuu guuugcagua auuccucaaa uccucacuua gccaccuucg ccauaccucu 21660
gggugcuacc caaguaccuu auuauuguuu ucuuaaagug gauacuuaca acuccacugu 21720
uuauaaauuu uuggcuguuu uaccuccuac cgucagggaa auugucauca ccaaguaugg 21780
ugauguuuau gucaaugggu uuggauacuu gcaucucggu uuguuggaug cugucacaau 21840
uaauuucacu ggucauggca cugacgauga uguuucuggu uuuuggacca uagcaucgac 21900
uaauuuuguu gaugcacuca ucgaaguuca aggaaccgcc auucagcgua uucuuuauug 21960
ugaugauccu guuagccaac ucaaguguuc ucagguugcu uuugaccuug acgaugguuu 22020
uuacccuauu ucuucuagaa accuucugag ucaugaacag ccaauuucuu uuguuacucu 22080
gccaucauuu aaugaucauu cuuuuguuaa cauuacugua ucugcuuccu uugguggguca 22140 uaguggugcc aaccuuauug caucugacac uacuaucaau ggguuuaguu cuuucugugu 22200
ugacacuaga caauuuacca uuucacuguu uuauaacguu acaaacaguu augguuaugu 22260
gucuaaauca caggacagua auugcccuuu caccuugcaa ucuguuaaug auuaccuguc 22320
uuuuagcaaa uuuuguguuu ccaccagccu uuuggcuagu gccuguacca uagaucuuuu 22380

-continued ugguuacccu gaguuuggua gugguguuaa guuuacgucc cuuuauuuuc aauucacaaa 22440
gggugaguug auuacuggca cgacuaaacc acuugaaggu gucacggacg uuucuuuuau 22500
gacucuggau guguguacca aguauacuau cuauggcuuu aaaggugagg guaucauuac 22560
ccuuacaaau ucuagcuuuu uggcaggugu uuauuacaca ucugauucug gacaguuguu 22620
agccuuuaag aaugucacua guggugcugu uuauucuguu acgccauguu cuuuuucaga 22680
gcaggcugca uauguugaug augauauagu ggguguuauu ucuaguuugu cuagcuccac 22740
uuuuaacagu acuagggagu ugccugguuu cuucuaccau ucuaaugaug gcucuaauug 22800
uacagagccu guguuggugu auaguaacau agguguuugu aaaucuggca guauuggcua 22860
cgucccaucu cagucuggcc aagucaagau ugcacccacg guuacuggga auauuaguau 22920
ucccaccaac uuuaguauga guauuaggac agaauauuua cagcuuuaca acacgccugu 22980
uaguguugau ugugccacau auguuuguaa ugguaacucu cguuguaaac aauuacucac 23040
ccaguacacu gcagcaugua agaccauaga gucagcauua caacucagcg cuaggcuuga 23100
gucuguugaa guuaacucua ugcuuacuau uucugaagag gcucuacagu uagcuaccau 23160
uaguucguuu aauggugaug gauauaauuu uacuaaugug cuggguguuu cuguguauga 23220
uccugcaagu ggcagggugg uacaaaaaag gucuuuuauu gaagaccugc uuuuuaauaa 23280
agugguuacu aauggccuug guacuguuga ugaagacuau aagcgcuguu cuaauggucg 23340
cucuguggca gaucuagucu gugcacagua uuacucuggu gucaugguac uaccuggugu 23400
uguugacgcu gagaagcuuc acauguauag ugcgucucuc aucgguggua uggugcuagg 23460
agguuuuacu ucugcagcgg cauugccuuu uagcuaugcu guucaagcua gacucaauua 23520
ucuugcucua cagacggaug uucuacagcg gaaccagcaa uugcuugcug agucuuuuaa 23580
cucugcuauu gguaauauaa cuucagccuu ugagaguguu aaagaggcua uuagucaaac 23640
uuccaagggu uugaacacug uggcucaugc gcuuacuaag guucaagagg uuguuaacuc 23700
gcagggugca gcuuugacuc aacuuaccgu acagcugcaa cacaacuucc aagccauuuc 23760
uaguucuauu gaugacauuu acucucgacu ggacauucuu ucagccgaug uucagguuga 23820
ccgucucauc accggcagau uaucagcacu uaaugcuuuu guugcucaaa cccucacuaa 23880
guauacugag guucaggcua gcaggaaguu agcacagcaa aagguuaaug agugcguuaa 23940
aucgcaaucu cagcguuaug guuuuugugg uggugauggc gagcacauuu ucucucuggu 24000
acaggcagca ccucagggcc ugcuguuuuu acauacagua cuuguaccga gugauuuugu 24060
agauguuauu gccaucgcug gcuuaugcgu uaacgaugaa auugccuuga cucuacguga 24120
gccuggcuua gucuuguuua cgcaugaacu ucaaaaucau acugcgacgg aauauuuugu 24180
uucaucgcga cguauguuug aaccuagaaa accuaccguu agugauuuug uucaaauuga 24240
gaguugugug gucaccuaug ucaauuugac uagagaccaa cuaccagaug uaaucccaga 24300
uuacaucgau guuaacaaaa cacuugauga gauuuuagcu ucucugccca auagaacugg 24360
uccaagucuu ccuuuagaug uuuuuaaugc cacuuaucuu aaucucacug gugaaauugc 24420
agauuuagag cagcguucag agucucuccg uaauacuaca gaggagcucc aaagucuuau 24480
auauaauauc aacaacacac uaguugaccu ugaguggcuc aaccgaguug agacauauau 24540
caaguggccg ugguggguuu gguugauuau uuucauuguu cucaucuuug uugugucauu 24600
acuaguguuc ugcugcauuu ccacggguug uuguggaugc ugcggcugcu gcugugcuug 24660
uuucucaggu uguuguaggg guccuagacu ucaaccuuac gaaguuuuug aaaaggucca 24720
cgugcaguga uguuucuugg acuuuuucaa uacacgauug acacaguugu caaagauguc 24780
ucaaagucug cuaacuuguc uuuggaugcu guccaagagu uggagcucaa uguaguucca 24840
auuagacaag cuucaaaugu gacggguuuu cuuuucacca guguuuuuau cuacuucuuu 24900
gcacuguuua aagcgucuuc uuugaggcgc aauuauauua uguuggcagc gcguuuugcu 24960
gucauuguuc uuuauugccc acuuuuauau uauuguggug cauuuuuaga ugcaacuauu 25020
auuuguugca cacuuauugg caggcuuugu uuagucugcu uuuacuccug gcgcuauaaa 25080
aaugcgcucu uuauuauuuu uaauacuacg acacuuucuu uccucaaugg uaaagcagcu 25140
uauuaugacg gcaaauccau ugugauuuua gaagguggug accauuacau cacuuuuggc 25200
aacucuuuug uugcuuuugu uaguagcauc gacuuguauc uagcuauacg ugggcggcaa 25260
gaagcugacc uacagcuguu gcgaacuguu gagcuucuug auggcaagaa gcuuuauguc 25320
uuuucgcaac aucaaauugu uggcauuacu aaugcugcau uugacucaau ucaacuagac 25380
gaguaugcua caauuaguga augauaaugg ucuaguaguu aauguuauac uuuggcuuuu 25440
cguacucuuu uuccugcuua uuauaagcau uacuuucguc caauugguua aucugugcuu 25500
cacuugucac cgguugugua auagcgcagu uuacacaccu auagggcguu uguauagagu 25560
uuauaagucu uacaugcaaa uagaccccu cccuaguacu guuauugacg uauaaacgaa 25620
auaugucuaa cgguucuauu cccguugaug aggugauuca acaccuuaga aacuggaauu 25680
ucacauggaa uaucauacug acgauacuac uuguagugcu ucaguauggc cauuacaagu 25740
acucugcguu cuuguauggu gucaagaugg cuauucuaug gauacuuugg ccucuugugu 25800
uagcacuguc acuuuuugau gcaugggcua gcuuucaggu caauugggucuuuuuugcuu 25860
ucagcauccu uauggcuugc aucacucuua ugcuguggau aauguacuuu gucaauagca 25920
uucgguugug gcgcaggaca cauucuuggu ggucuuucaa uccugaaaca gacgcgcuuc 25980
ucacuacuuc ugugaugggc cgacaggucu gcauuccagu gcuuggagca ccaacuggug 26040
uaacgcuaac acuccuuagu gguacauugc uuguagaggg cuauaagguu gcuacuggcg 26100
uacagguaag ucaauuaccu aauuucguca cagucgccaa ggccacuaca acaauugucu 26160
acggacgugu uggucguuca gucaaugcuu caucuggcac ugguugggcu uucuaugucc 26220
gguccaaaca cggcgacuac ucagcuguga guaauccgag uucgguucuc acagauagug 26280
agaaagugcu ucauuuaguc uaaacagaaa cuuuauggcu ucugucaguu uucaggaucg 26340
uggccgcaaa cgggugccau uaucccucua ugccccucuu aggguuacua augacaaacc 26400
ccuuucuaag guacuugcaa auaaugcugu acccacuaau aaaggaaaua aggaccagca 26460
aauuggauac uggaaugagc aaauucgcug gcgcaugcgc cgguggugagc gaauugaaca 26520
accuuccaau uggcauuucu acuaccucgg aacaggaccu cacgccgacc uccgcuacag 26580
gacucguacu gaggguguuu ucuggguugc uaaagaaggc gcaaagacug aacccacuaa 26640
ccuggguguc agaaaggcgu cugaaaagcc aauuauucca aauuucucuc aacagcuucc 26700
cagcguaguu gagauuguug aaccuaacac accuccuacu ucacgugcaa auucacguag 26760
caggagucgu gguaauggca acaacagguc cagaucucca aguaacaaca gaggcaauaa 26820
ccagucccgc gguaauucac agaaucgugg aaauaaccag ggucguggag cuucucagaa 26880
cagaggaggc aauaauaaua acaauaacaa gucucguaac caguccaaga acagaaacca 26940
gucaaaugac cgugguggug uaacaucacg cgaugaucug guggcugcug ucaaggaugc 27000
ccuuaaaucu uuggguauug gcgaaaaccc ugacaagcuu aagcaacagc agaagcccaa 27060
acaggaaagg ucugacagca gcggcaaaaa uacaccuaag aagaacaaau ccagagccac 27120
uucgaaagaa cgugaccuca aagacauccc agaguggagg agaauuccca agggcgaaaa 27180
uagcguagca gcuugcuucg gacccagggg aggcuucaaa aauuuuggag augcggaauu 27240
ugucgaaaaa gguguugaug ccucaggcua ugcucagauc gccaguuuag caccaaaugu 27300
ugcagcauug cucuuuggug guaaugugge uguucgugag cuagcggacu cuuacgagau 27360
uacauauaau uauaaaauga cugugccaaa gucugaucca aauguagagc uucuuguuuc 27420
acagguggau gcauuuaaaa cugggaaugc aaaaccccag agaaagaagg aaaagaagaa 27480
caagcgugaa accacgcagc agcugaauga agaggccauc uacgaugaug ugggugugcc 27540
aucugaugug acucaugcca auuuggaaug ggacacagcu guugauggug gugacacggc 27600
cguugaaauu aucaacgaga ucuucgacac aggaaauuaa acaauguuug acuggcuuau 27660
ccuggcuaug ucccagggua gugccauuac acuguuauua cugaguguuu uucuagcgac 27720
uuggcugcug ggcuauggcu uugcccucua acuagcgguc uuggucuugc acacaacggu 27780
aagccagugg uaaugucagu gcaagaagga uauuaccaua gcacugucau gaggggaacg 27840
caguaccuuu ucaucuaaac cuuugcacga guaaucaaag auccgcuuga cgagccuaua 27900
uggaagagcg ugccagguau uugacucaag gacuguuagu aacugaagac cugacggugu 27960

<210> SEQ ID NO 33
<211> LENGTH: 27976
<212> TYPE: DNA
<213> ORGANISM: Artificial Sequence
<220> FEATURE:
<223> OTHER INFORMATION: PEDV 1251-125-10 (125-10) passage30 Genomic cDNA

<400> SEQUENCE: 33
aattcaacta aacgaaattt tgtccttccg gccgcatgtc catgctgctg gaagctgacg 60
tggaatttca ttaggtttgc ttaagtagcc atcgcaagtg ctgtgctgtc ctctagttcc 120
tggttggcgt tccgtcgcct tctacatact agacaaacag ccttcctccg gttccgtctg 180
ggggttgtgt ggataactag ttccgtctag tttgaaacca gtaactgtcg gctatggcta 240
gcaaccatgt tacattggct tttgccaatg atgcagaaat ttcagctttt ggcttttgca 300
ctgctagtga agccgtctca tactattctg aggccgccgc tagtggattt atgcaatgcc 360
gtttcgtgtc cttcgatctc gctgacactg ttgagggatt gcttccccgaa gactatgtca 420 tggtggtggt cggcactacc aagcttagtg cgtatgtgga cacttttggt agccgcccca 480
aaaacatttg tggttggctg ttattttcta actgtaatta cttcctcgaa gagttagagc 540
ttacttttgg tcgtcgtggt ggtaacatcg tgccagttga ccaatacatg tgtggcgctg 600
acggtaaacc tgttcttcag gaatccgaat gggagtatac agatttcttt gctgactccg 660
aagacggtca actcaacatt gctggtatca cttatgtgaa ggcctggatt gtagagcgat 720
cggatgtctc ttatgcgagt cagaatttaa catctattaa gtctattact tactgttcaa 780
cctatgagca tacttttcct gatggtactg ccatgaaggt tgcacgtact ccaaagatta 840
agaagactgt tgtcttgtct gagccacttg ctactatcta cagggaaatt ggttctcctt 900
ttgtggataa tgggagcgat gctcgttcta tcattaagag accagtgttc ctccacgctt 960
ttgttaagtg taagtgtggt agttatcatt ggactgttgg tgattggact tcctatgtct 1020
ccacttgctg tggctttaag tgtaagccag tccttgtggc ttcatgctct gctacgcctg 1080
gttctgttgt ggttacgcgc gctggtgctg gcactggtgt taagtattac aacaacatgt 1140
tcctgcgcca tgtggcagac attgatgggt tggcattctg gcgaattctc aaggtgcagt 1200

```
ccaaagacga cctcgcttgc tctggtaaat tccttgaaca ccatgaggaa ggtttcacag   1260
atccttgcta ctttttgaat gactcgagca ttgctactaa gctcaagttt gacatcctta   1320
gtggcaagtt ttctgatgaa gtcaaacaag ctatctttgc tggtcatgtt gttgttggca   1380
gcgcgmtcgt tgacattgtt gacgatgcac tgggacagcc ttggtttata cgtaagcttg   1440
gtgaccttgc aagtgcagct tgggagcagc ttaaggctgt cgttagaggc cttaacctcc   1500
tgtctgatga ggtcgtgctc tttggcaaaa gacttagctg tgccactctt agtatcgtta   1560
acggtgtttt tgagttcatc gccgaagtgc ctgagaagtt ggctgcggct gttacagttt   1620
ttgtcaactt cttgaatgag ctttttgagt ctgcctgtga ctgcttaaag gtcggaggta   1680
aaacctttaa caaggttggc tcttatgttc tttttgacaa cgcattggtt aagcttgtca   1740
aggcaaaagt tcgcggccca cgacaggcag gtgtttgtga agttcgttac acaagccttg   1800
ttattgggag tactaccaag gtggtttcca agcgcgttga aaatgccaat gtgaatctcg   1860
tcgtcgttga cgaggatgtg accctcaaca ccactggtcg tacagttgtt gttgacggac   1920
ttgcattctt cgagagtgac gggttttaca gacatcttgc tgatgctgac gttgtcattg   1980
aacatcctgt ttataagtct gcttgtgagc tcaagccagt tttgagtgt gacccaatac    2040
ctgattttcc tatgcctgtg gccgctagtg ttgcagagct ttgtgtgcaa actgatctgt   2100
tgcttaaaaa ttacaacact ccttataaaa cttacagctg cgttgtgaga ggtgataagt   2160
gttgtatcac ttgcacctta catttcacag caccaagtta tatggaggct gctgctaatt   2220
ttgtagacct ctgtaccaag aacattggta ctgctggttt tcatgagttt tacattacgg   2280
cccatgaaca acaggatctg caagggttcg taaccacttg ttgcacgatg tcaggttttg   2340
agtgttttat gcctataatc ccacagtgtc cagcagtgct tgaagagatt gatggtggta   2400
gcatctggcg gtcttttatc actggtctta atacaatgtg ggatttttgc aagcatctta   2460
aagtcagctt tggactagat ggcattgttg tcactgtagc acgcaaattt aaacgacttg   2520
gtgctctctt ggcagaaatg tataacactt acctttcaac tgtggtggaa aacttggtac   2580
tggccggtgt tagcttcaag tattatgcca ccagtgtccc aaaaattgtt ttgggctgtt   2640
gttttcacag tgttaaaagt gttcttgcaa gtgccttcca gattcctgtc caggcaggcg   2700
ttgagaagtt taaagtcttc cttaactgtg ttcaccctgt tgtaccacgt gtcattgaaa   2760
cttcttttgt ggaattagaa gagacgacat ttaaaccacc agcactcaat ggtagtattg   2820
ctattgttga tggctttgct ttctattatg atggaacact atactatccc accgatggta   2880
atagcgttgt tcctatctgc tttaagaaga aaggtggtgg tgatgtcaaa ttctctgatg   2940
aagtctctgt taaaaccatt gacccagttt ataaggtctc ccttgaattt gagttcgagt   3000
ctgagactat tatggctgtg cttaataagg ctgttggtaa ttgtatcaag gttacaggtg   3060
gttgggacga tgttgttgag tatatcaatg ttgccattga ggttcttaaa gatcacatcg   3120
atgtgcctaa gtactacatc tatgatgagg aaggtggcac cgatcctaat ctgcccgtaa   3180
tggtttctca gtggccgttg aatgatgaca cgatctcaca ggatctgctt gatgttgaag   3240
ttgttactga tgcgccagtt gatttcgagg gtgatgaagt agactcctct gaccctgwta   3300
aggtggcaga cgtggctaac tctgagcctg aggatgacgg tcttaatgta gctcctgaaa   3360
caaatgtaga gtctgaagtt gaggaagttg ccgcaacctt gtcctttaaa gatacacctt   3420
ccacagttac taaggatcct tttgcttttg actttgcaag ctatggagga cttaaggttt   3480
taagacaatc tcataacaac tgctgggtta cttctacctt ggtgcagcta caattgcttg   3540
gcatcgttga tgaccctgca atggagcttt ttagtgctgg tagagttggt ccaatggttc   3600
```

-continued

```
gcaaatgcta tgagtcacaa aaggctatct tgggatcttt gggtgatgtg tcggcttgcc   3660
tagagtctct gactaaggac ctacacacac ttaagattac ctgttctgta gtctgtggtt   3720
gtggtactgg tgaacgtatc tatgatggtt gtgcttttcg tatgacgcca actttggaac   3780
cgttcccata tggtgcttgt gctcagtgtg ctcaagtttt gatgcacact tttaaaagta   3840
ttgttggcac cggcatcttt tgtcgagata ctactgctct ctccttggat tctttggttg   3900
taaaacctct ttgtgcggct gcttttatag gcaaggatag tggtcattat gtcactaact   3960
tttatgatgc tgctatggct attgatggtt atggtcgtca tcagataaag tatgacacac   4020
tgaacactat ttgtgttaaa gacgttaatt ggacagcacc ttttgtccca gacgttgagc   4080
ctgtattgga gcctgttgtc aaacctttct attcttataa gaatgttgat ttttaccaag   4140
gagattttag tgaccttgtt aaacttccat gtgattttgt tgttaatgct gcaaatgaga   4200
atttgtctca cggtggcggc atagcaaagg ccattgatgt ttataccaag ggcatgttgc   4260
agaagtgctc gaatgattac attaaagcac acggtcccat taaagttgga cgtggtgtca   4320
tgttggaggc attaggtctt aaggtcttta atgttgttgg tccacgtaag ggtaagcatg   4380
cacctgagct tcttgttaag gcttataagt ccgtttttgc taattcaggt gttgctctta   4440
cacctttgat tagtgttgga atttttagtg ttcctttgga agaatcttta tctgcttttc   4500
ttgcatgtgt tggtgatcgc cactgtaagt gcttttgtta tagtgacaaa gagcgcgagg   4560
cgatcattaa ttacatggat ggcttggtag atgctatttt caaagatgca cttgttgata   4620
ctactcctgt ccaggaagat gttcaacaag tttcacaaaa accagttttg cctaattttg   4680
aacctttcag gattgaaggt gctcatgctt tctatgagtg caaccctgaa ggtttgatgt   4740
cattaggtgc tgacaagctg gtgttgttta caaattccaa tttggatttt tgtagcgttg   4800
gtaagtgtct taacaatgtg actggcggtg cattgcttga agccataaat gtatttaaaa   4860
agagtaacaa aacagtgcct gctggcaact gtgttacttt tgagtgtgca gatatgattt   4920
ctattactat ggtagtattg ccatctgacg gtgatgctaa ttatgacaaa aattatgcac   4980
gcgccgtcgt caaggtatct aagcttaaag gcaagttatt gcttgctgtt ggtgatgcca   5040
tgttgtattc caagttgtcc cacctcagcg tgttaggttt cgtatccaca cctgatgatg   5100
tggagcgttt ctacgcaaat aagagtgtgg ttattaaagt tactgaggat acacgtagtg   5160
ttaagactgt taaagtagaa tccactgtta cttatggaca acaaattgga ccttgtcttg   5220
ttaatgacac cgttgtcaca gacaacaaac ctgttgttgc tgatgttgta gctaaggttg   5280
taccaagtgc taattgggat tcacattatg gttttgataa ggctggtgag ttccacatgc   5340
tagaccatac tgggtttgcc tttcctagtg aagttgttaa cggtaggcgt gtgcttaaaa   5400
ccacagataa taactgttgg gttaatgtta catgtttaca attacagttt gctagattta   5460
ggttcaagtc agcaggtcta caggctatgt gggagtccta ttgtactggt gatgttgcta   5520
tgtttgtgca ttggttgtac tggcttactg gtgttgacaa aggtcagcct agtgattcag   5580
aaaatgcact taacatgttg tctaagtaca ttgttcctgc tggttctgtc actattgaac   5640
gtgtcacgca tgacggttgt tgttgtagta agcgtgttgt cactgcacca gttgtgaatg   5700
ctagcgtgtt gaagcttggc gtcgaggatg gtctttgtcc acatggtctt aactacattg   5760
acaaagttgt tgtagttaaa ggtactacaa ttgttgtcaa tgttggaaaa cctgtagtgg   5820
caccatcgca cctctttctt aagggtgttt cctacacaac attcctagat aatggtaacg   5880
gtgttgccgg ccattatact gtttttgatc atgacactgg tatggtgcat gatggagatg   5940
```

-continued

```
tttttgtacc aggtgatctc aatgtgtctc ctgttacaaa tgttgtcgtc tcagagcaga   6000
cggctgttgt gattaaagac cctgtgaaga aagtagagtt agacgctaca aagctgttag   6060
acactatgaa ttatgcatcg gaaagattct tttcctttgg tgattttatg tcacgtaatt   6120
taattacagt gtttttgtac atccttagta ttttgggtct ctgttttagg gcctttcgta   6180
agagggatgt taaagttcta gctggtgtac cccaacgtac tggtattata ttgcgtaaaa   6240
gtgtgcgcta taatgcaaag gctttgggtg tcttcttcaa gctaaaactt tattggttca   6300
aagttcttgg taagtttagt ttgggtattt atgcattgta tgcattacta ttcatgacaa   6360
tacgctttac acctataggt ggccctgttt gtgatgatgt tgttgctggt tatgctaatt   6420
ctagttttga caagaatgag tattgcaaca gtgttatttg taaggtctgt ctctatgggt   6480
accaggaact ttcggacttc tctcacacac aggtagtatg gcaacacctt agagacccat   6540
taattggtaa tgtgatgcct ttcttttatt tggcatttct ggcaattttt gggggtgttt   6600
atgtaaaggc tattactctc tattttattt tccagtatct taacatactt ggtgtgtttt   6660
tgggcctaca acagtccatt tggtttttgc agcttgtgcc ttttgatgtc tttggtgacg   6720
agatcgtcgt ctttttcatc gttacacgcg tattgatgtt ccttaagcat gttttccttg   6780
gctgcgataa ggcatcttgt gtggcttgct ctaagagtgc tcgccttaag cgcgttcctg   6840
tccagactat tttcagggt actagcaaat ccttctacgt acatgccaat ggtggttcta   6900
agttctgtaa gaagcacaat ttcttttgtt taaattgtga ttcttatggt ccaggctgca   6960
cttttattaa tgacgtcatt gcaactgaag ttggtaatgt tgtcaaactt aatgtgcaac   7020
cgacaggtcc tgccactatt cttattgaca aggttgaatt cagtaatggt ttttactatc   7080
tttatagtgg tgacacattt tggaagtaca actttgacat aacagataac aaatacactt   7140
gcaaagagtc acttaaaaat tgtagcataa tcacagactt tattgttttt aacaataatg   7200
gttccaatgt aaatcaggtt aagaatgcat gtgtgtattt ttcacagatg ctttgtaaac   7260
ctgttaagtt agtggactca gcgttgttgg ccagtttgtc tgttgatttt ggtgcaagct   7320
tacatagtgc ttttgttagt gtgttgtcga atagttttgg caaagacctg tcaagttgta   7380
atgacatgca ggattgcaag agcacattgg gttttgatga tgtaccattg gataccttta   7440
atgctgctgt tgctgaggct catcgttacg atgtcctctt gactgacatg tcgttcaaca   7500
attttaccac cagttatgca aaaccagagg aaaaacttcc cgtccatgac attgccacgt   7560
gtatgcgtgt aggtgccaag attgttaatc ataacgttct tgtcaaggat agtatacctg   7620
tggtgtggct tgtacgtgat ttcattgccc tttctgaaga aactaggaag tacattattc   7680
gtacgactaa agttaagggt ataaccttca tgttgacctt taatgattgt cgtatgcata   7740
ctaccatacc tactgtttgc attgcaaata agaagggtgc aggtcttcct agtttttcaa   7800
aggttaagaa attcttctgg tttttgtgtc tgttcatagt tgctgttttc tttgcactaa   7860
gctttttga ttttagtact caggttagca gtgatagtga ttatgacttc aagtatattg   7920
agagtggcca gttgaagact tttgacaatc cacttagttg tgtgcataat gtctttagta   7980
acttcgacca gtggcatgat gccaagtttg gtttcacccc cgtcaacaat cctagttgtc   8040
ctatagtcgt tggtgtatca gacgaagcgc gcactgttcc aggtatccca gcaggtgttt   8100
atttagctgg taaaacactt gtttttgcta ttaacaccat ttttggtaca tctggtttgt   8160
gctttgatgc tagtggcgtt gctgataagg gcgcttgcat ttttaattcg gcttgcacca   8220
cattatctgg tttgggtgga actgctgtct actgttataa gaatggtcta gttgaaggtg   8280
ctaaacttta tagtgagttg gcacctcata gctactataa aatggtagat ggtaatgctg   8340
```

tgtctttacc tgaaattatc tcacgcggct ttggcatccg tactatccgt acaaaggcta 8400
tgacctactg tcgcgttggc cagtgtgtgc aatctgcaga aggtgtttgt tttggcgccg 8460
atagattctt tgtctataat gcagaatctg gttctgactt tgtttgtggc acagggctct 8520
ttacattgtt gatgaacgtt attagtgttt tttccaagac agtaccagta actgtgttgt 8580
ctggtcaaat actttttaat tgcattattg cttttgctgc tgttgcggtg tgtttcttat 8640
ttacaaagtt taagcgcatg ttcggtgata tgtctgttgg cgttttcact gtcggtgctt 8700
gtactttgtt gaacaatgtt tcctacattg taacacagaa cacacttggc atgttgggct 8760
atgcaacttt gtactttttg tgcactaaag gtgttagata tatgtggatt tggcatttgg 8820
gatttttgat ctcatatata cttattgcac catggtgggt tttgatggtt tatgcctttt 8880
cagccatttt tgagtttatg cctaaccttt ttaagcttaa ggtttcaaca caactttttg 8940
agggtgacaa gttcgtaggc tcttttgaaa atgctgcagc aggtacattt gtgcttgata 9000
tgcatgccta tgagagactt gccaactcta tctcaactga aaaactgcgt cagtatgcta 9060
gtacttacaa taagtacaag tattattcag gcagtgcttc agaggctgat tacaggcttg 9120
cttgttttgc ccatttggcc aaggctatga tggattatgc ttctaatcac aacgacacgt 9180
tatacacacc acccactgtg agttacaatt caactctaca ggctggcttg cgtaagatgg 9240
cacaaccatc tggtgttgtt gagaagtgca tagttcgtgt ttgctatggt aatatggctc 9300
ttaatggcct atggcttggt gatactgtta tctgcccacg ccatgttata gcgtctagta 9360
ctactagcac tatagattat gactatgccc tttctgtttt acgcctcyac aacttctcca 9420
tttcatctgg taatgttttc ctaggtgttg tgggtgtaac catgcgaggt gctttgttgc 9480
agataaaggt taatcaaaac aatgtccaca cgcctaagta cacctatcgc acagttagac 9540
cgggtgaatc ttttaatatc ttggcgtgct atgatggttc tgcagctggt gtttacggcg 9600
ttaacatgcg ctctaattac actattagag gctcgttcat taatggcgct tgtggttcac 9660
ctggttataa cattaacaat ggtaccgttg agttttgcta tttacaccag cttgaacttg 9720
gttcaggctg tcatgttggt agcgacttag atggtgttat gtatggtggt tatgaggacc 9780
aacctacttt gcaagttgaa ggcgctagta gtctgtttac agagaatgtg ttggcatttc 9840
tttatgcagc actcattaat ggttctacct ggtggcttag ttcttctagg attgctgtag 9900
acaggtttaa tgagtgggct gttcataatg gtatgacaac agtagttaat actgattgct 9960
tttctattct tgctgctaag actggtgttg atgtacaacg tttgttggcc tcaatccagt 10020
ctctgcataa gaattttggt ggaaagcaaa ttcttggcta tacctcgttg acagatgagt 10080
ttactacagg tgaagttata cgtcaaatgt atggcgttwa tcttcagagt ggttatgttt 10140
cacgcgcctg tagaaatgtc ttgctggttg gttcttttct gactttcttt tggtcagaat 10200
tagtttccta cactaagttc ttttgggtaa atcctggtta tgtcacacct atgtttgcgt 10260
gtttgtcatt gctgtcctca cttttgatgt tcacactcaa gcataagaca ttgtttttcc 10320
aggtctttct aatacctgct ctgattgtta catcttgcat taatttggca tttgatgttg 10380
aagtctacaa ctatttggca gagcattttg attaccatgt ttctctcatg ggttttaatg 10440
cacaaggtct tgttaacatc tttgtctgct ttgttgttac cattttacac ggcacataca 10500
catggcgctt ttttaacaca cctgtgagtt ctgtcactta tgtggtagct ttgctgactg 10560
cggcatataa ctatttttac gctagtgaca ttcttagttg tgctatgaca ctatttgcta 10620
gtgtgactgg caactggttc gttggtgctg tttgttataa agctgctgtt tatatggcct 10680

-continued tgagatttcc tacttttgtg gctatttttg gtgatattaa gagtgttatg ttctgttacc 10740
ttgtgttggg ttattttacc tgttgcttct acggtattct ctactggttc aacaggtttt 10800
ttaaggttag tgtaggtgtc tatgactata ctgttagtgc tgctgagttt aagtatatgg 10860
ttgctaacgg cctacgtgca ccaactggaa cacttgattc actacttctg tctgccaaat 10920
tgattggtat tggtggtgag cggaatatta agatttcttc cgttcagtct aaactgactg 10980
atattaagtg tagtaacgtt gtgcttttag gctgtctctc tagcatgaat gtctcagcaa 11040
attcaacaga atgggcctat tgtgttgact tgcataacaa gatcaacttg tgtaatgacc 11100
cagaaaaagc gcaggaaatg ctacttgctt tgttggcatt tttccttagt aagaatagtg 11160
cttttggttt agatgactta ttggaatcct attttaatga caatagtatg ttgcagagtg 11220
ttgcatctac ttatgtcggt ttgccttctt atgtcattta tgaaaatgca cgccaacagt 11280
atgaagatgc tgttaataat ggttctccac ctcagttggt taagcaattg cgccatgcca 11340
tgaatgtagc aaagagcgaa tttgaccgtg aggcttctac tcagcgtaag cttgatagaa 11400
tggcggaaca ggctgcagca cagatgtaca aagaggcacg agcagttaat aggaagtcca 11460
aagttgtaag tgctatgcat tcactgcttt ttggtatgtt gagacgtttg gacatgtctt 11520
ctgtagacac cattctcaac ttggcaaagg atggggttgt acctctgtct gtcataccgg 11580
cagtcagtgc tactaagctt aacattgtta cttctgatat cgattcttat aatcgtatcc 11640
agcgtgaggg atgtgtccac tacgctggta ccatttggaa tataattgat atcaaggaca 11700
atgatggcaa ggtggtacac gttaaggagg taaccgcaca gaatgctgag tccctgtcat 11760
ggcccctggt ccttgggtgt gagcgtattg tcaagctcca gaataatgaa attattcctg 11820
gtaagctgaa gcagcgctcc attaaggcag aaggagatgg catagttgga gaaggtaagg 11880
cactttacaa taatgagggt ggacgtactt ttatgtatgc tttcatctcg gacaaaccgg 11940
acctgcgtgt agtcaagtgg gagttcgatg gtggttgtaa cactattgag ctagaaccac 12000
cacgtaagtt cttggtggat tctcctaatg gtgcacagat caagtatctc tactttgttc 12060
gtaaccttaa cacgttacgt aggggtgctg ttctcggcta cataggtgcc actgtacgct 12120
tgcaggctgg taaacaaaca gaacaggcta ttaactcttc attgttgaca ctttgcgctt 12180
tcgctgtgga tcctgctaag acctacatcg atgctgtcaa aagtggtcac aaaccagtag 12240
gtaactgtgt taagatgttg gccaatggtt ctggtaatgg acaagctgtt actaatggtg 12300
tggaggctag tactaaccag gattcatacg gtggtgcgtc cgtgtgtcta tattgtagag 12360
cacatgttga gcatccatct atggatggtt tttgcagact gaaaggcaag tacgtacagg 12420
ttccactagg tacagtggat cctatacgtt ttgtacttga gaatgacgtt tgcaaggttt 12480
gtggttgttg gctggctaat ggctgcactt gtgacagatc cattatgcaa agcactgata 12540
tggcttattt aaacgagtac ggggctctag tgcagctcga ctagagccct gtaacggtac 12600
tgatacacaa catgtgtatc gtgcttttga catctacaac aaggatgttg cttgtctagg 12660
taaattcctc aaggtgaact gtgttcgcct gaagaatttg gataagcatg atgcattcta 12720
tgttgtcaaa agatgtacca agtctgcgat ggaacacgag caatccatct atagcagact 12780
tgaaaagtgt ggagccgtag ccgaacacga tttcttcact tggaaggatg gtcgtgccat 12840
ctatggtaac gtttgtagaa aggatcttac cgagtatact atgatggatt tgtgttacgc 12900
tttacgtaac tttgatgaaa acaattgcga tgttcttaag agcattttaa ttaaggtagg 12960
cgcttgtgag gagtcctact tcaataataa agtctggttt gaccctgttg aaaatgaaga 13020
cattcatcgt gtctatgcat tgttaggtac cattgtttca cgtgctatgc ttaaatgcgt 13080
taagttctgt gatgcaatgg ttgaacaagg tatagttggt gttgtcacat tagataatca 13140
ggatcttaat ggtgattttt atgattttgg tgattttact tgtagcatca agggaatggg 13200
tatacccatt tgcacatcat attactctta tatgatgcct gttatgggta tgactaattg 13260
ccttgctagt gagtgttttg ttaagagtga tatatttggt gaggatttca agtcatatga 13320
cctgctggaa tatgatttca cggagcataa gacagcactc ttcaacaagt atttcaagta 13380
ttggggactg caataccacc ctaactgtgt ggactgcagt gatgagcagt gcatagttca 13440
ctgtgccaac ttcaatacgt tgttttccac tactatacct attacggcat ttggaccttt 13500
gtgtcgcaag tgttggattg atggtgttcc actggtaact acagctggtt atcattttaa 13560
acagttaggt atagtttgga acaatgacct caacttacac tctagcaggc tctctattaa 13620
cgaattactc cagttttgta gtgatcctgc attgcttata gcatcatcac cagcccttgt 13680
tgatcagcgt actgtttgct tttcagttgc agcgctaggt acaggtatga ctaaccagac 13740
tgttaaacct ggccatttca ataaggagtt ttatgacttc ttacttgagc aaggtttctt 13800
ttctgagggc tctgagctta ctttaaagca cttcttcttt gcacagaagg gtgatgcagc 13860
tgttaaggat tttgactact ataggtataa tagacctact gttctggaca tttgccaagc 13920
tcgcgtcgtg tatcaaatag tgcaacgcta ttttgatatt tacgaaggtg gttgtatcac 13980
tgctaaagag gtggttgtta caaaccttaa caagagcgca ggttatcctt tgaacaagtt 14040
tggtaaagct ggtctttact atgagtcttt atcctatgag gaacaggatg aactttatgc 14100
ttatactaag cgtaacatcc tgcccactat gacacagctc aaccttaaat atgctataag 14160
tggcaaagaa cgtgcacgca cagtgggtgg tgtttcgctt ttgtcaacca tgactactcg 14220
gcagtatcat cagaaacacc ttaagtccat agttaatact aggggcgctt cggttgttat 14280
tggtactact aagttttatg gtggttggga caatatgctt aagaacctta ttgatggtgt 14340
tgaaaatccg tgtcttatgg gttgggacta cccaaagtgc gacagagcac tgcccaatrt 14400
gatacgtatg atttcagcca tgattttagg ctctaagcac accacatgct gcagttccac 14460
tgaccgcttt ttcaggttgt gcaatgaatt ggctcaagtc cttactgagg ttgtttattc 14520
taatggaggt tttatttga agccaggtgg tactacctct ggtgatgcaa ccaccgcata 14580
tgcaaactca gtttttaata tcttccaagc agtaagtgcc aatgttaaca aacttcttag 14640
tgttgacagc aatgtctgtc ataatttaga agttaagcaa ttgcagcgta agctttatga 14700
gtgctgttat agatcaacta ccgtcgatga ccagttcgtc gttgagtatt atggttactt 14760
gcgtaaacat ttttcaatga tgattctttc tgatgatggc gttgtttgtt ataacaatga 14820
ctatgcatca cttggttatg tcgctgatct taacgcattc aaggctgttt tgtattacca 14880
gaacaatgtc ttcatgagcg cctctaaatg ttggatcgag cctgacatta ataaaggtcc 14940
tcatgaattt tgctcgcagc atactatgca gattgtcgat aaagatggta cttattacct 15000
tccttaccct gatccttcaa gaattctctc tgcaggtgtg tttgttgatg acgttgttaa 15060
aactgatgca gttgtattgc ttgaacgtta tgtgtcattg gctatagatg cctacccgtt 15120
atctaagcat gaaaaccctg aatataagaa ggtgttttat gtgcttttgg attgggttaa 15180
gcatctgtac aaaactctta atgctggtgt gttagagtct tttctgtca cacttttgga 15240 agattctact gctaaattct gggatgagag cttttatgcc aacatgtatg agaaatctgc 15300
agttttacaa tctgcagggc tttgtgttgt ttgtggctct caaactgttt tacgttgtgg 15360
tgattgtcta cggcgtccta tgctttgtac taagtgtgct tatgatcatg tcattggaac 15420
aactcacaag ttcattttgg ccatcactcc atatgtgtgt tgtgcttcag attgtggtgt 15480
caatgatgta actaagctct acttaggtgg tcttagttat tggtgtcatg accacaagcc 15540
acgtcttgca ttcccgttgt gctctgctgg taatgttttt ggcttgtaca aaaattctgc 15600
taccggctca cccgatgttg aagactttaa tcgcattgct acatccgatt ggactgatgt 15660
ttctgactac aggttggcaa atgatgtcaa ggactcattg cgtctgtttg cagcggaaac 15720
tatcaaggcc aaggaggaga gcgttaagtc atcctatgct tgtgcaacac tacatgaggt 15780
tgtaggacct aaagagttgt tgctcaaatg ggaagtcggc agacccaaac caccccttaa 15840
tagaaattcg gttttcactt gttatcatat aacgaagaac accaaatttc aaatcggtga 15900
gtttgtgttt gagaaggcag aatatgataa tgatgctgta acatataaaa ctaccgccac 15960
aacaaaactt gttcctggca tggtttttgt gcttacctca cataatgttc agccattgcg 16020
cgcaccgacc attgctaatc aagaacgtta ttccactata cataagttgc atcctgcttt 16080
taacatacct gaagcttatt ctagcttagt gccctattac caattgattg gtaagcagaa 16140
gattacaact attcagggac ctcccggtag tggtaaatct cactgtgtta tagggctagg 16200
tttgtactat ccaggtgcac gtatagtgtt tacagcttgt tctcatgcag cggtcgattc 16260
actttgtgtg aaagcttcca ctgcttatag caatgacaaa tgttcacgca tcataccaca 16320
gcgcgctcgt gttgagtgtt atgatggttt caagtctaat aatactagtg ctcagtacct 16380
tttctctact gtcaatgctt tgccagagtg caatgcggac attgttgtgg tggatgaggt 16440
ctctatgtgc actaattatg acttgtctgt cataaatcag cgcatcagct ataggcatgt 16500
agtctatgtt ggtgaccctc aacagctgcc tgcaccacgt gttatgattt cacgtggtac 16560
tttggaacca aaggactaca acgttgtcac tcaacgcatg tgtgccctta agcctgatgt 16620
tttcttgcac aagtgttatc gctgtcctgc tgagatagtg cgtactgtgt ctgagatggt 16680
ctatgaaaac caattcattc ctgtgcaccc agatagcaag cagtgtttta aaatcttttg 16740
caagggtaat gttcaggttg ataatggttc aagcattaat cgcaggcaat tggatgttgt 16800
gcgtatgttt ttggctaaaa atcctaggtg gtcaaaggct gtttttattt ctccttataa 16860
cagccagaat tatgttgcca gccgcatgct aggtctacaa attcagacag ttgactcatc 16920
ccagggtagt gagtatgact atgtcattta cacacaaact tcagatactg cccatgcctg 16980
taatgttaac aggtttaatg ttgccatcac aagggccaag aaaggcatat tatgtataat 17040
gtgcgatagg tccctttttg atgtgcttaa attctttgag cttaaattgt ctgatttgca 17100
ggctaatgag ggttgtggtc tttttaaaga ctgtagcaga ggtgatgatc tgttgccacc 17160
atctcacgct aacaccttca tgtctttagc ggacaatttt aagactgatc aagatcttgc 17220
tgttcaaata ggtgttaatg gacccattaa atatgagcat gttatctcgt ttatgggttt 17280
ccgttttgat atcaacatac ccaaccatca tactctcttt tgcacacgcg actttgccat 17340
gcgcaatgtt agaggttggt taggctttga cgttgaagga gcacatgttg ttggctctaa 17400
cgtcggtaca aatgtcccat tgcaattagg gttttctaac ggtgttgatt ttgttgtcag 17460
acctgaaggt tgcgttgtaa cagagtctgg tgactacatt aaacccgtca gagctcgtgc 17520
tccaccaggg gaacaattcg cacacctttt gcctttactt aaacgcggcc aaccatggga 17580
tgttgtccgc aaacgtatag tgcagatgtg tagtgactac ctggccaacc tatcagacat 17640
actaattttt gtgttgtggg ctggtggttt ggagttgaca actatgcgtt attttgtcaa 17700
gattggacca agtaagagtt gtgattgtgg taaggttgct acttgttaca atagtgcgct 17760
gcatacgtac tgttgtttca aacatgccct tggttgtgat tatctgtata acccatactg 17820

```
tattgatata cagcagtggg gatacaaggg atcacttagc cttaaccacc atgagcattg  17880
taatgtacat agaaacgagc atgtggcttc tggtgatgcc ataatgactc gctgtctggc  17940
catacatgat tgctttgtca agaacgttga ctggtccatc acatacccat ttattggtaa  18000
tgaggctgtt attaataaga gcggccgaat tgtgcaatca cacactatgc ggtcagttct  18060
taagttatac aatccgaaag ccatatatga tattggcaat cctaagggca ttagatgtgc  18120
cgtaacggat gctaagtggt tttgctttga caagaatcct aytaattcta atgtcaagac  18180
attggagtat gactatataa cacatggcca atttgatggg ttgtgcttgt tttggaattg  18240
caatgtagac atgtatccag aattttctgt ggtctgtcgt tttgatactc gctgtaggtc  18300
accactcaac ttggagggtt gtaatggtgg ttcactgtat gttaataatc atgcattcca  18360
tacaccggct tttgacaagc gtgcttttgc taagttgaag ccaatgccat ttttctttta  18420
tgatgatact gagtgtgaca agttacagga ctccataaac tatgttcctc ttagggctag  18480
taactgcatt actaaatgta atgttggtgg tgctgtctgt agtaagcatt gtgctatgta  18540
tcatagctat gttaatgctt acaacacttt tacgtcggcg ggctttacta tttgggtgcc  18600
tacttcgttt gacacctata atctgtggca gacatttagt aacaatttgc aaggtcttga  18660
gaacattgct ttcaatgtcg taaagaaagg atcttttgtt ggtgccgaag gtgaacttcc  18720
tgtagctgtg gttaatgaca aagtgctcgt tagagatggt actgttgata ctcttgtttt  18780
tacaaacaag acatcactac ccactaacgt agcttttgag ttgtatgcca agcgtaaggt  18840
aggactcacc ccacccatta cgatcctacg taacttgggt gtagtttgta catctaagtg  18900
tgtcatttgg gactatgaag ccgaacgtcc acttactact tttacaaagg atgtttgtaa  18960
atataccgac tttgagggtg acgtctgtac actctttgat aacagcattg ttggttcatt  19020
agagcgattc tccatgaccc aaaatgctgt gcttatgtca cttacagctg ttaaaaagct  19080
taytggcata aagttaactt atggttatct taatggtgtc ccagttaaca cacatgaaga  19140
taaacctttt acttggtata tttacactag gaagaacggc aagttcgagg accatcctga  19200
tggctatttt acccaaggta gaacaaccgc tgattttagc cctcgtagcg acatggaaaa  19260
ggacttccta agtatggata tgggtctgtt tattaacaag tacggacttg aagattacgg  19320
ctttgagcac gttgtgtatg gtgatgtttc aaaaaaccacc cttggtggtt tgcatctact  19380
aatttcgcag gtgcgtctgg cctgtatggg tgtgctcaaa atagacgagt ttgtgtctag  19440
taatgatagc acgttaaagt cttgtactgt tacatatgct gataacccta gtagtaagat  19500
ggtttgtacg tatatggatc tcctgcttga cgattttgtc agcattctta aatctttgga  19560
tttgggcgtt gtatctaaag ttcatgaagt tatggtcgat tgtaaaatgt ggaggtggat  19620
gttgtggtgt aaggatcata aactccagac attttatccg caacttcagg ccagtgaatg  19680
gaagtgtggt tattccatgc cttctattta caagatacaa cgtatgtgtt tagaaccttg  19740
caatctctac aactatggtg ctggtattaa gttacctgat ggcattatgt ttaacgtagt  19800
taaatacaca cagctttgtc aatatctcaa tagcaccaca atgtgtgtac cccatcacat  19860
gcgtgtgcta catcttggtg ctggctccga caagggtgtt gcacctggca cggctgtctt  19920
acgacgttgg ttgccactgg atgccattat agttgacaat gatagtgtgg attacgttag  19980
cgatgctgat tatagtgtta caggagattg ctctacctta tacctgtcag ataagtttga  20040
tttagttata tctgatatgt atgatggtaa gattaaaagt tgtgatgggg agaacgtgtc  20100
taaagaaggc ttctttccct atattaatgg tgtcatcacc gaaaagttgg cacttggtgg  20160
```

tactgtagct attaaggtga cggagtttag ttggaataag aagttgtatg aactcattca 20220
gaggtttgag tattggacaa tgttctgtac cagtgttaac acgtcatcgt cagaggcatt 20280
cttaattggt gttcactatt taggtgattt tgcaagtggc gctgtgattg acggcaacac 20340
tatgcatgcc aattatatct tctggcgtaa ttccacaatt atgactatgt cttacaatag 20400
tgtacttgat ttaagcaagt tcaattgtaa gcataaggct acagttgtca ttaatttaaa 20460
agattcatcc attagtgatg ttgtgttagg tttgttgaag aatggtaagt tgctagtgcg 20520
taataatgac gccatttgtg gtttttctaa tcatttggtc aacgtaaaca aatgaagtct 20580
ttaacctact tctggttgtt cttaccagta ctttcaacac ttagcctacc acaagatgtc 20640
accaggtgct cagctaacac taattttagg cggttctttt caaaatttaa tgttcaggcg 20700
cctgcagttg ttgtactggg cggttatcta cctattggtg aaaaccaggg tgtcaattca 20760
acttggtact gtgctggcca acatccaact gctagtggcg ttcatggtat ctttgttagc 20820
catattagag gtggtcatgg ctttgagatt ggcatttcgc aagagccttt tgaccctagt 20880
ggttaccagc tttatttaca taaggctact aacggtaaca ctaatgctac tgcgcgactg 20940
cgcatttgcc agtttcctag cattaaaaca ttgggcccca ctgctaataa tgatgttaca 21000
ataggtcgta attgcctatt taacaaagcc atcccagctc atatgagtga acatagtgtt 21060
gtcggcataa catgggataa tgatcgtgtc actgtctttt ctgacaagat ctattatttt 21120
tattttaaaa atgattggtc ccgtgttgcg acaaagtgtt acaacagtgg aggttgtgct 21180
atgcaatatg tttacgaacc cacctattac atgcttaatg ttactagtgc tggtgaggat 21240
ggtatttctt atcaaccctg tacagctaat tgcattggtt atgctgccaa tgtatttgct 21300
actgagccca atggccacat accagaaggt tttagtttta ataattggtt tcttttgtcc 21360
aatgattcca ctttggtgca tggtaaggtg gtttccaacc aaccattgtt ggtcaattgt 21420
cttttggcca ttcctaagat ttatggacta ggccaatttt tctcctttaa tcaaacgatc 21480
gatggtgttt gtaatggagc tgctgtgcag cgtgcaccag aggctctgag gtttaatatt 21540
aatgacacct ctgtcattct tgctgaaggc tcaattgtac ttcatactgc tttaggaaca 21600
aatttttctt ttgtttgcag taattcccca aatcctcact tagccacctt cgccatacct 21660
ctgggtgcta cccaagtacc ttattattgt tttcttaaag tggatactta caactccact 21720
gtttataaat ttttggctgt tttacctcct accgtcaggg aaattgtcat caccaagtat 21780
ggtgatgttt atgtcaatgg gtttggatac ttgcatctcg gtttgttgga tgctgtcaca 21840
attaatttca ctggtcatgg cactgacgat gatgtttctg gtttttggac catagcatcg 21900
actaattttg ttgatgcact catcgaagtt caaggaaccg ccattcagcg tattctttat 21960
tgtgatgatc ctgttagcca actcaagtgt tctcaggttg cttttgacct tgacgatggt 22020
ttttacccta tttcttctag aaaccttctg agtcatgaac agccaatttc ttttgttact 22080
ctgccatcat ttaatgatca ttcttttgtt aacattactg tatctgcttc ctttggtggt 22140
catagtggtg ccaaccttat tgcatctgac actactatca atgggtttag ttctttctgt 22200
gttgacacta gacaatttac catttcactg ttttataacg ttacaaacag ttatggttat 22260
gtgtctaaat cacaggacag taattgccct ttcaccttgc aatctgttaa tgattacctg 22320
tcttttagca aatttttgtgt ttccaccagc cttttggcta gtgcctgtac catagatctt 22380
tttggttacc ctgagtttgg tagtggtgtt aagtttacgt ccctttactt tcaattcaca 22440
aagggtgagt tgattactgg cacgactaaa ccacttgaag gtgtcacgga cgtttctttt 22500
atgactctgg atgtgtgtac caagtatact atctatggct ttaaaggtga gggtatcatt 22560

-continued

```
acccttacaa attctagctt tttggcaggt gtttattaca catctgtttc tggacagttg  22620
ttagccttta agaatgtcac tagtggtgct gtttattctg ttacgccatg ttctttttca  22680
gagcaggctg catatgttga tgatgatata gtgggtgtta tttctagttt gtctagctcc  22740
acttttaaca gtactaggga gttgcctggt ttcttctacc attctaatga tggctctaat  22800
tgtacagagc ctgtgttggt gtatagtaac ataggtgttt gtaaatctgg cagtattggc  22860
tacgtcccat ctcagtctgg ccaagtcaag attgcaccca cggttactgg gaatattagt  22920
attcccacca actttagtat gagtattagg acagaatatt tacagcttta caacacgcct  22980
gttagtgttg attgtgccac atatgtttgt aatggtaact ctcgttgtaa acaattactc  23040
acccagtaca ctgcagcatg taagaccata gagtcagcat tacractcag cgctaggctt  23100
gagtctgttg aagttaactc tatgcttact atttctgaag aggctctaca gttagctacc  23160
attagttcgt ttaatggtga tggatataat tttactaatg tgctgggtgt ttctgtgtat  23220
gatcctgcaa ggggcagggt ggtacaaaaa aggtctttta ttgaagacct gctttttaat  23280
aaagtggtta ctaatggcct tggtactgtt gatgaagact ataagcgctg ttctaatggt  23340
cgctctgtgg cagatctagt ctgtgcacag tattactctg gtgtcatggt actacctggt  23400
gttgttgacg ctgagaagct tcacatgtat agtgcgtctc tcatcggtgg tatggtgcta  23460
ggaggtttta cttctgcagc ggcattgcct tttagctatg ctgttcaagc tagactcaat  23520
tatcttgctc tacagacgga tgttctacag cggaaccagc aattgcttgc tgagtctttt  23580
aactctgcta ttggtaatat aacttcagcc tttgagagtg ttaaagaggc tattagtcaa  23640
acttccaagg gtttgaacac tgtggctcat gcgcttacta aggttcaaga ggttgttaac  23700
tcgcagggtg cagctttgac tcaacttacc gtacagctgc aacacaactt ccaagccatt  23760
tctagttcta ttgatgacat ttactctcga ctggacattc tttcagccga tgttcaggtt  23820
gaccgtctca tcaccggcag attatcagca cttaatgctt ttgttgctca aaccctcact  23880
aagtatactg aggttcaggc tagcaggaag ttagcacagc aaaaggttaa tgagtgcgtt  23940
aaatcgcaat cccagcgtta tggtttttgt ggtggtgatg gcgagcacat tttctctctg  24000
gtacaggcag cacctcaggg cctgctgttt ttacatacag tacttgtacc gagtgatttt  24060
gtagatgtta ttgccatcgc tggcttatgc gttaacgatg aaattgcctt gactctacgt  24120
gagcctggct tagtcttgtt tacgcatgaa cttcaaaatc atactgcgac ggaatatttt  24180
gtttcatcgc gacgtatgtt tgaacctaga aaacctaccg ttagtgattt tgttcaaatt  24240
gagagttgtg tggtcaccta tgtcaatttg actagagacc aactaccaga tgtaatccca  24300
gattacatcg atgttaacaa aacacttgat gagattttag cttctctgcc caatagaact  24360
ggtccaagtc ttcctttaga tgtttttaat gccacttatc ttaatctcac tggtgaaatt  24420
gcagatttag agcagcgttc agagtctctc cgtaatacta cagaggagct ccaaagtctt  24480
atatataata tcaacaacac actagttgac cttgagtggc tcaaccgagt tgagacatat  24540
atcaagtggc cgtggtgggt ttggttgatt attttcattg ttctcatctt tgttgtgtca  24600
ttactagtgt tctgctgcat ttccacgggt tgttgtggat gctgcggctg ctgctgtgct  24660
tgtttctcag gttgttgtag ggtcctagaa cttcaacctt acgaagtttt tgaaaaggtc  24720
cacgtgcagt gatgtttctt ggactttttc aatacacgat tgacacagtt gtcaaagatg  24780
tctcaaagtc tgctaacttg tctttggatg ctgtccaaga gttggagctc aatgtagttc  24840
caattagaca agcttcaaat gtgacgggtt ttcttttcac cagtgttttt atctacttct  24900
```

ttgcactgtt taaagcgtct tctttgaggc gcaattatat tatgttggca gcgcgttttg 24960
ctgtcattgt tctttattgc ccacttttat attattgtgg tgcattttta gatgcaacta 25020
ttatttgttg cacacttatt caaagtcggt ggcaggcttt gtttagtctg cttttactcc 25080
tggcgctata aaaatgcgct ctttattatt tttaatacta cgacactttc tttcctcaat 25140
ggtaaagcag ctttgacggc aaatccattg tgattttaga aggtggtgac cattacatca 25200
cttttggcaa ctcttttgtt gcttttgtta gtagcatcga cttgtatcta gctatacgtg 25260
ggcggcaaga agctgaccta cagctgttgc gaactgttga gcttcttgat ggcaagaagc 25320
tttatgtctt ttcgcaacat caaattgttg gcattactaa tgctgcattt gactcaattc 25380
aactagacga gtatgctaca attagtgaat gataatggtc tagtagttaa tgttatactt 25440
tggcttttcg tactcttttt cctgcttatt ataagcatta ctttcgtcca attggttaat 25500
ctgtgcttca cttgtcaccg gttgtgtaat agcgcagttt acacacctat agggcgtttg 25560
tatagagttt ataagtctta catgcaaata gaccccctcc ctagtactgt tattgacgta 25620
taaacgaaat atgtctaacg gttctattcc cgttgatgag gtgattcaac accttagaaa 25680
ctggaatttc acatggaata tcatactgac gatactactt gtagtgcttc agtatggcca 25740
ttacaagtac tctgcgttct tgtatggtgt caagatggct attctatgga tactttggcc 25800
tcttgtgtta gcactgtcac tttttgatgc atgggctagc tttcaggtca attgggtctt 25860
ttttgctttc agcatcctta tggcttgcat cactcttatg ctgtggataa tgtactttgt 25920
caatagcatt cggttgtggc gcaggacaca ttcttggtgg tctttcaatc ctgaaacaga 25980
cgcgcttctc actacttctg tgatgggccg acaggtctgc attccagtgc ttggagcacc 26040
aactggtgta acgctaacac tccttagtgg tacattgctt gtagagggct ataaggttgc 26100
tactggcgta caggtaagtc aattacctaa tttcgtcaca gtcgccaagg ccactacaac 26160
aattgtctac ggacgtgttg gtcgttcagt caatgcttca tctggcactg gttgggcttt 26220
ctatgtccgg tccaaacacg gcgactactc agctgtgagt aatccgagtt cggttctcac 26280
agatagtgag aaagtgcttc atttagtcta aacagaaact ttatggcttc tgtcagtttt 26340
caggatcgtg gccgcaaacg ggtgccatta tccctctatg cccctcttag ggttactaat 26400
gacaaacccc tttctaaggt acttgcaaat aatgctgtac ccactaataa aggaaataag 26460
gaccagcaaa ttggatactg gaatgagcaa attcgctggc gcatgcgccg tggtgagcga 26520
attgaacaac cttccaattg gcatttctac tacctcggaa caggacctca cgccgacctc 26580
cgctatagga ctcgtactga gggtgttttc tgggttgcta aagaaggcgc aaagactgaa 26640
cccactaacc tgggtgtcag aaaggcgtct gaaaagccaa ttattccaaa tttctctcaa 26700
cagcttccca gcgtagttga gattgttgaa cctaacacac ctcctacttc acgtgcaaat 26760
tcacgtagca ggagtcgtgg taatggcaac aacaggtcca gatctccaag taacaacaga 26820
ggcaataacc agtcccgcgg taattcacag aatcgtggaa ataaccaggg tcgtggagct 26880
tctcagaaca gaggaggcaa taataataac aataacaagt ctcgtaacca gtccaagaac 26940
agaaaccagt caaatgaccg tggtggtgta acatcacgcg atgatctggt ggctgctgtc 27000
aaggatgccc ttaaatcttt gggtattggc gaaaaccctg acaagcttaa gcaacagcag 27060
aagcccaaac aggaaaggtc tgacagcagc ggcaaaaata cacctaagaa gaacaaatcc 27120
agagccactt cgaaagaacg tgacctcaaa gacatcccag agtggaggag aattcccaag 27180
ggcgaaaata gcgtagcagc ttgcttcgga cccaggggag gcttcaaaaa ttttggagat 27240
gcggaatttg tcgaaaaagg tgttgatgcc tcaggctatg ctcagatcgc cagtttagca 27300
ccaaatgttg cagcattgct ctttggtggt aatgtggctg ttcgtgagct agcggactct 27360
tacgagatta catataatta taaaatgact gtgccaaagt ctgatccaaa tgtagagctt 27420
cttgtttcac aggtggatgc atttaaaact gggaatgcaa aaccccagag aaagaaggaa 27480
aagaagaaca agcgtgaaac cacgcagcag ctgaatgaag aggccatcta cgatgatgtg 27540
ggtgtgccat ctgatgtgac tcatgccaat ttggaatggg acacagctgt tgatggtggt 27600
gacacggccg ttgaaattat caacgagatc ttcgacacag gaaattaaac aatgtttgac 27660
tggcttatcc tggctatgtc ccagggtagt gccattacac tgttattact gagtgttttt 27720
ctagcgactt ggctgctggg ctatggcttt gccctctaac tagcggtctt ggtcttgcac 27780
acaacggtaa gccagtggta atgtcagtgc aagaaggata ttaccatagc actgtcatga 27840
ggggaacgca gtaccttttc atctaaacct ttgcacgagt aatcaaagat ccgcttgacg 27900
agcctatatg gaagagcgtg ccaggtattt gactcaagga ctgttagtaa ctgaagacct 27960
gacggtgttg atatgg 27976

<210> SEQ ID NO 34
<211> LENGTH: 4161
<212> TYPE: DNA
<213> ORGANISM: Artificial Sequence
<220> FEATURE:
<223> OTHER INFORMATION: PEDV 1251-125-10 (125-10) passage30 spike protein CDS sequence

<400> SEQUENCE: 34
atgaagtctt taacctactt ctggttgttc ttaccagtac tttcaacact tagcctacca 60
caagatgtca ccaggtgctc agctaacact aattttaggc ggttcttttc aaaatttaat 120
gttcaggcgc ctgcagttgt tgtactgggc ggttatctac ctattggtga aaaccagggt 180
gtcaattcaa cttggtactg tgctggccaa catccaactg ctagtggcgt tcatggtatc 240
tttgttagcc atattagagg tggtcatggc tttgagattg gcatttcgca agagcctttt 300
gaccctagtg gttaccagct ttatttacat aaggctacta acggtaacac taatgctact 360
gcgcgactgc gcatttgcca gtttcctagc attaaaacat tgggccccac tgctaataat 420
gatgttacaa taggtcgtaa ttgcctattt aacaaagcca tcccagctca tatgagtgaa 480
catagtgttg tcggcataac atgggataat gatcgtgtca ctgtcttttc tgacaagatc 540
tattattttt attttaaaaa tgattggtcc cgtgttgcga caaagtgtta caacagtgga 600
ggttgtgcta tgcaatatgt ttacgaaccc acctattaca tgcttaatgt tactagtgct 660
ggtgaggatg gtatttctta tcaaccctgt acagctaatt gcattggtta tgctgccaat 720
gtatttgcta ctgagcccaa tggccacata ccagaaggtt ttagttttaa taattggttt 780
cttttgtcca atgattccac tttggtgcat ggtaaggtgg tttccaacca accattgttg 840
gtcaattgtc ttttggccat tcctaagatt tatggactag gccaattttt ctcctttaat 900
caaacgatcg atggtgtttg taatggagct gctgtgcagc gtgcaccaga ggctctgagg 960
tttaatatta atgacacctc tgtcattctt gctgaaggct caattgtact tcatactgct 1020
ttaggaacaa atttttcttt tgtttgcagt aattccccaa atcctcactt agccaccttc 1080
gccatacctc tgggtgctac ccaagtacct tattattgtt ttcttaaagt ggatacttac 1140
aactccactg tttataaatt tttggctgtt ttacctccta ccgtcaggga aattgtcatc 1200
accaagtatg gtgatgttta tgtcaatggg tttggatact tgcatctcgg tttgttggat 1260
gctgtcacaa ttaatttcac tggtcatggc actgacgatg atgtttctgg tttttggacc 1320
atagcatcga ctaattttgt tgatgcactc atcgaagttc aaggaaccgc cattcagcgt 1380
attctttatt gtgatgatcc tgttagccaa ctcaagtgtt ctcaggttgc ttttgacctt 1440
gacgatggtt tttaccctat ttcttctaga aaccttctga gtcatgaaca gccaatttct 1500
tttgttactc tgccatcatt taatgatcat tcttttgtta acattactgt atctgcttcc 1560
tttggtggtc atagtggtgc caaccttatt gcatctgaca ctactatcaa tgggtttagt 1620
tctttctgtg ttgacactag acaatttacc atttcactgt tttataacgt tacaaacagt 1680
tatggttatg tgtctaaatc acaggacagt aattgccctt tcaccttgca atctgttaat 1740
gattacctgt cttttagcaa attttgtgtt tccaccagcc ttttggctag tgcctgtacc 1800
atagatcttt ttggttaccc tgagtttggt agtggtgtta agtttacgtc cctttacttt 1860
caattcacaa agggtgagtt gattactggc acgactaaac cacttgaagg tgtcacggac 1920
gtttctttta tgactctgga tgtgtgtacc aagtatacta tctatggctt taaaggtgag 1980
ggtatcatta cccttacaaa ttctagcttt ttggcaggtg tttattacac atctgtttct 2040
ggacagttgt tagcctttaa gaatgtcact agtggtgctg tttattctgt tacgccatgt 2100
tctttttcag agcaggctgc atatgttgat gatgatatag tgggtgttat ttctagtttg 2160
tctagctcca cttttaacag tactagggag ttgcctggtt tcttctacca ttctaatgat 2220
ggctctaatt gtacagagcc tgtgttggtg tatagtaaca taggtgtttg taaatctggc 2280
agtattggct acgtcccatc tcagtctggc caagtcaaga ttgcacccac ggttactggg 2340
aatattagta ttcccaccaa ctttagtatg agtattagga cagaatattt acagctttac 2400
aacacgcctg ttagtgttga ttgtgccaca tatgtttgta atggtaactc tcgttgtaaa 2460
caattactca cccagtacac tgcagcatgt aagaccatag agtcagcatt acractcagc 2520
gctaggcttg agtctgttga agttaactct atgcttacta tttctgaaga ggctctacag 2580
ttagctacca ttagttcgtt taatggtgat ggatataatt ttactaatgt gctgggtgtt 2640
tctgtgtatg atcctgcaag gggcagggtg gtacaaaaaa ggtcttttat tgaagacctg 2700
ctttttaata aagtggttac taatggcctt ggtactgttg atgaagacta taagcgctgt 2760
tctaatggtc gctctgtggc agatctagtc tgtgcacagt attactctgg tgtcatggta 2820
ctacctggtg ttgttgacgc tgagaagctt cacatgtata gtgcgtctct catcggtggt 2880
atggtgctag gaggttttac ttctgcagcg gcattgcctt ttagctatgc tgttcaagct 2940
agactcaatt atcttgctct acagacggat gttctacagc ggaaccagca attgcttgct 3000
gagtctttta actctgctat tggtaatata acttcagcct ttgagagtgt taaagaggct 3060
attagtcaaa cttccaaggg tttgaacact gtggctcatg cgcttactaa ggttcaagag 3120
gttgttaact cgcagggtgc agctttgact caacttaccg tacagctgca acacaacttc 3180
caagccattt ctagttctat tgatgacatt tactctcgac tggacattct ttcagccgat 3240
gttcaggttg accgtctcat caccggcaga ttatcagcac ttaatgcttt tgttgctcaa 3300
accctcacta agtatactga ggttcaggct agcaggaagt tagcacagca aaaggttaat 3360
gagtgcgtta aatcgcaatc ccagcgttat ggtttttgtg gtggtgatgg cgagcacatt 3420
ttctctctgg tacaggcagc acctcagggc ctgctgtttt tacatacagt acttgtaccg 3480
agtgattttg tagatgttat tgccatcgct ggcttatgcg ttaacgatga aattgccttg 3540
actctacgtg agcctggctt agtcttgttt acgcatgaac ttcaaaatca tactgcgacg 3600
gaatattttg tttcatcgcg acgtatgttt gaacctagaa aacctaccgt tagtgatttt 3660

```
gttcaaattg agagttgtgt ggtcacctat gtcaatttga ctagagacca actaccagat   3720

gtaatcccag attacatcga tgttaacaaa acacttgatg agattttagc ttctctgccc   3780

aatagaactg gtccaagtct tcctttagat gtttttaatg ccacttatct taatctcact   3840

ggtgaaattg cagatttaga gcagcgttca gagtctctcc gtaatactac agaggagctc   3900

caaagtctta tatataatat caacaacaca ctagttgacc ttgagtggct caaccgagtt   3960

gagacatata tcaagtggcc gtggtgggtt tggttgatta ttttcattgt tctcatcttt   4020

gttgtgtcat tactagtgtt ctgctgcatt tccacgggtt gttgtggatg ctgcggctgc   4080

tgctgtgctt gtttctcagg ttgttgtagg ggtcctagac ttcaacctta cgaagttttt   4140

gaaaaggtcc acgtgcagtg a                                             4161
```

<210> SEQ ID NO 35
<211> LENGTH: 1386
<212> TYPE: PRT
<213> ORGANISM: porcine epidemic diarrhea virus
<220> FEATURE:
<221> NAME/KEY: misc_feature
<222> LOCATION: (838)..(838)
<223> OTHER INFORMATION: Xaa can be any naturally occurring amino acid

<400> SEQUENCE: 35

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Ile
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
```

-continued

```
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Pro Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Thr Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Val Ser Gly Gln Leu Leu Ala Phe Lys Asn
        675                 680                 685
```

```
Val Thr Ser Gly Ala Val Tyr Ser Val Thr Pro Cys Ser Phe Ser Glu
    690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Xaa Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Arg Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
        995                 1000                1005

Asn Ile  Thr Ser Ala Phe Glu  Ser Val Lys Glu Ala  Ile Ser Gln
    1010                 1015                 1020

Thr Ser  Lys Gly Leu Asn Thr  Val Ala His Ala Leu  Thr Lys Val
    1025                 1030                 1035

Gln Glu  Val Val Asn Ser Gln  Gly Ala Ala Leu Thr  Gln Leu Thr
    1040                 1045                 1050

Val Gln  Leu Gln His Asn Phe  Gln Ala Ile Ser Ser  Ser Ile Asp
    1055                 1060                 1065

Asp Ile  Tyr Ser Arg Leu Asp  Ile Leu Ser Ala Asp  Val Gln Val
    1070                 1075                 1080

Asp Arg  Leu Ile Thr Gly Arg  Leu Ser Ala Leu Asn  Ala Phe Val
    1085                 1090                 1095
```

```
Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125

Arg Tyr Gly Phe Cys Gly Gly Asp Gly Glu His Ile Phe Ser Leu
    1130                1135                1140

Val Gln Ala Ala Pro Gln Gly Leu Leu Phe Leu His Thr Val Leu
    1145                1150                1155

Val Pro Ser Asp Phe Val Asp Val Ile Ala Ile Ala Gly Leu Cys
    1160                1165                1170

Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln
    1385
```

<210> SEQ ID NO 36
<211> LENGTH: 27976
<212> TYPE: RNA
<213> ORGANISM: Artificial Sequence
<220> FEATURE:
<223> OTHER INFORMATION: PEDV 1251-125-10 (125-10) passage30 spike protein genomic RNA

<400> SEQUENCE: 36

```
aauucaacua aacgaaauuu uguccuuccg gccgcauguc caugcugcug gaagcugacg      60

uggaauuuca uuagguuugc uuaaguagcc aucgcaagug cugugcuguc cucuaguucc     120

ugguuggcgu uccgucgccu ucuacauacu agacaaacag ccuuccuccg guuccgucug     180

gggguugugu ggauaacuag uuccgucuag uuugaaacca guaacugucg gcuauggcua     240
```

-continued

```
gcaaccaugu uacauuggcu uuugccaaug augcagaaau uucagcuuuu ggcuuuugca    300
cugcuaguga agccgucuca uacuauucug aggccgccgc uaguggauuu augcaaugcc    360
guuucguguc cuucgaucuc gcugacacug uugagggauu gcuucccgaa gacuauguca    420
ugguggugga cggcacuacc aagcuuagug cguaugugga cacuuuuggu agccgcccca    480
aaaacauuug ugguuggcug uuauuuucua acuguaauua cuuccucgaa gaguuagagc    540
uuacuuuugg ucgucguggu gguaacaucg ugccaguuga ccaauacaug uguggcgcug    600
acgguaaacc uguucuucag gaauccgaau gggaguauac agauuucuuu gcugacuccg    660
aagacgguca acucaacauu gcugguauca cuuaugugaa ggccuggauu guagagcgau    720
cggaugucuc uuaugcgagu cagaauuuaa caucuauuaa gucuauuacu uacuguucaa    780
ccuaugagca uacuuuuccu gaugguacug ccaugaaggu ugcacguacu ccaaagauua    840
agaagacugu ugucuugucu gagccacuug cuacuaucua cagggaaauu gguucuccuu    900
uuguggauaa ugggagcgau gcucguucua ucauuaagag accaguguuc cuccacgcuu    960
uuguuaagug uaaguguggu aguuaucauu ggacuguugg ugauuggacu uccuaugucu   1020
ccacuugcug uggcuuuaag uguaagccag uccuuguggc uucaugcucu gcuacgccug   1080
guucuguugu gguuacgcgc gcugguguug gcacuggugu uaaguauuac aacaacaugu   1140
uccugcgcca uguggcagac auugaugggu uggcauucug gcgaauucuc aaggugcagu   1200
ccaaagacga ccucgcuugc ucugguaaau uccuugaaca ccaugaggaa gguuucacag   1260
auccuugcua cuuuuugaau gacucgagca uugcuacuaa gcucaaguuu gacauccuua   1320
guggcaaguu uucugaugaa gucaaacaag cuaucuuugc uggucauguu guuguuggca   1380
gcgcgmucgu ugacauuguu gacgaugcac ugggacagcc uugguuuaua cguaagcuug   1440
gugaccuugc aagugcagcu ugggagcagc uuaaggcugu cguuagaggc cuuaaccucc   1500
ugucugauga ggucgugcuc uuuggcaaaa gacuuagcug ugccacucuu aguaucguua   1560
acgguguuuu ugaguucauc gccgaagugc cugagaaguu ggcugcggcu guuacaguuu   1620
uugucaacuu cuugaaugag cuuuuugagu cugccugdga cugcuuaaag gucggaggua   1680
aaaccuuuaa caagguuggc ucuuauguuc uuuuugacaa cgcauugguu aagcuuguca   1740
aggcaaaagu ucgcggccca cgacaggcag guguuuguga aguucguuac acaagccuug   1800
uuauugggag uacuaccaag gugguuucca agcgcguuga aaaugccaau gugaaucucg   1860
ucgucguuga cgaggaugug acccucaaca ccacuggucg uacaguuguu guugacggac   1920
uugcauucuu cgagagugac ggguuuuaca gacaucuugc ugaugcugac guugucauug   1980
aacauccugu uuauaagucu gcuugugagc ucaagccagu uuuugagugu gacccaauac   2040
cugauuuucc uaugccugug gccgcuagug uugcagagcu uugugugcaa acugaucugu   2100
ugcuuaaaaa uuacaacacu ccuuauaaaa cuuacagcug cguuguguga gugugauaagu   2160
guuguaucac uugcaccuua cauuucacag caccaaguua uauggaggcu gcugcuaauu   2220
uuguagaccu cuguaccaag aacauuggua cugcugguuu ucaugaguuu uacauuacgg   2280
cccaugaaca acaggaucug caaggguucg uaaccacuug uugcacgaug ucagguuuug   2340
aguguuuuau gccuauaauc ccacaguguc cagcagugcu ugaagagauu gauggugua   2400
gcaucuggcg gucuuuuauc acuggucuua auacaaugug ggauuuuugc aagcaucuua   2460
aagucagcuu uggacuagau ggcauuguug ucacuguagc acgcaaauuu aaacgacuug   2520
gugcucucuu ggcagaaaug uauaacacuu accuuucaac ugugguggaa aacuugguac   2580
uggccggugu uagcuucaag uauuaugcca ccagugucc aaaaaauugu uugggcuguu   2640
```

guuuucacag uguuaaaagu guucuugcaa gugccuucca gauuccuguc caggcaggcg 2700
uugagaaguu uaaagucuuc cuuaacugug uucacccugu uguaccacgu gucauugaaa 2760
cuucuuuugu ggaauuagaa gagacgacau uuaaaccacc agcacucaau gguaguauug 2820
cuauuguuga uggcuuugcu uucuauuaug auggaacacu auacuauccc accgauggua 2880
auagcguugu uccuaucugc uuuaagaaga aaggugugg ugaugucaaa uucucugaug 2940
aagucucugu uaaaaccauu gacccaguuu auaaggucuc ccuugaauuu gaguucgagu 3000
cugagacuau uauggcugug cuuaauaagg cuguugguaa uuguaucaag guuacaggug 3060
guugggacga uguuguugag uauaucaaug uugccauuga gguucuuaaa gaucacaucg 3120
augugccuaa guacuacauc uaugaugagg aaggugcac cgauccuaau cugcccguaa 3180
ugguuucuca guggccguug aaugaugaca cgaucucaca ggaucugcuu gauguugaag 3240
uuguuacuga ugcgccaguu gauuucgagg gugaugaagu agacuccucu gacccugwua 3300
agguggcaga cguggcuaac ucugagccug aggaugacgg ucuuaaugua gcuccugaaa 3360
caaauguaga gucugaaguu gaggaaguug ccgcaaccuu guccuuuaaa gauacaccuu 3420
ccacaguuac uaaggauccu uuugcuuuug acuuugcaag cuauggagga cuuaagguuu 3480
uaagacaauc ucauaacaac ugcugguua cuucuaccuu ggugcagcua caauugcuug 3540
gcaucguuga ugacccugca auggagcuuu uuagugcugg uagaguuggu ccaaugguuc 3600
gcaaaugcua ugagucacaa aaggcuaucu ugggaucuuu gggugaugug ucggcuugcc 3660
uagagucucu gacuaaggac cuacacacac uuaagauuac cuguucugua gucugugguu 3720
gugguacugg ugaacguauc uaugauggu gugcuuuucg uaugacgcca acuuuggaac 3780
cguucccaua uggugcuugu gcucagugug cucaaguuuu gaugcacacu uuuaaaagua 3840
uuguuggcac cggcaucuuu ugucgagaua cuacugcucu cuccuuggau ucuuugguug 3900
uaaaaccucu uugugcggcu gcuuuuauag gcaaggauag uggucauuau gucacuaacu 3960
uuuaugaugc ugcuauggcu auugaugguu augucguca ucagauaaag uaugacacac 4020
ugaacacuau uuguguuaaa gacguuaauu ggacagcacc uuuuguccca gacguugagc 4080
cuguauugga gccuguuguc aaaccuuucu auucuuauaa gaauguugau uuuuaccaag 4140
gagauuuuag ugaccuuguu aaacuuccau gugauuuugu uguuaaugcu gcaaaugaga 4200
auuugucuca cgguggcggc auagcaaagg ccauugaugu uuauaccaag ggcauguugc 4260
agaagugcuc gaaugauuac auuaaagcac acggucccau uaaaguugga cgugguguca 4320
uguuggaggc auuaggucuu aaggucuuua auguguuugg uccacguaag gguaagcaug 4380
caccugagcu ucuuguuaag gcuuauaagu ccguuuuugc uaauucaggu guugcucuua 4440
caccuuugau uaguguugga auuuuuagug uuccuuugga agaaucuuua ucugcuuuuc 4500
uugcaugugu uggugaucgc cacuguaagu gcuuuuguua uagugacaaa gagcgcgagg 4560
cgaucauuaa uuacauggau ggcuugguag augcuauuuu caaagaugca cuuguugaua 4620
cuacuccugu ccaggaagau guucaacaag uuucacaaaa accaguuuug ccuaauuuug 4680
aaccuuucag gauugaaggu gcucaugcuu ucuaugagug caacccugaa gguuugaugu 4740
cauuaggugc ugacaagcug guguuguuua caaauuccaa uuuggauuuu uguagcguug 4800
guaagugucu uaacaaugug acuggcggug cauugcuuga agccauaaau guauuuaaaa 4860
agaguaacaa aacagugccu gcuggcaacu guguuacuuu ugagugugca gauaugauuu 4920
cuauuacuau gguaguauug ccaucugacg gugaugcuaa uuaugacaaa aauuaugcac 4980
gcgccgucgu caagguaucu aagcuuaaag gcaaguuauu gcuugcuguu ggugaugcca 5040
uguuguauuc caaguugucc caccucagcg uguuagguuu cguauccaca ccugaugaug 5100
uggagcguuu cuacgcaaau aagagugugg uuauuaaagu uacugaggau acacguagug 5160
uuaagacugu uaaaguagaa uccacuguua cuuauggaca acaaauugga ccuugucuug 5220
uuaaugacac cguugucaca gacaacaaac cuguuguugc ugauguugua gcuaagguug 5280
uaccaagugc uaauugggau ucacauuaug guuuugauaa ggcuggugag uuccacaugc 5340
uagaccauac ugggguuugcc uuuccuagug aaguuguuaa cgguaggcgu gugcuuaaaa 5400
ccacagauaa uaacuguugg guuaauguua cauguuuaca auuacaguuu gcuagauuua 5460
gguucaaguc agcaggucua caggcuaugu gggaguccua uuguacuggu gauguugcua 5520
uguuugugca uugguuguac uggcuuacug guguugacaa aggucagccu agugauucag 5580
aaaaugcacu uaacauguug ucuaaguaca uuguuccugc ugguucuguc acuauugaac 5640
gugucacgca ugacgguugu uguuguagua agcguguugu cacugcacca guugugaaug 5700
cuagcguguu gaagcuuggc gucgaggaug gucuuugucc acauggucuu aacuacauug 5760
acaaaguugu uguaguuaaa gguacuacaa uuguugucaa uguuggaaaa ccuguagugg 5820
caccaucgca ccucuuucuu aagggugwuu ccuacacaac auuccuagau aaugguaacg 5880
guguugccgg ccauuauacu guuuuugauc augacacugg uauggugcau gauggagaug 5940
uuuuuguacc aggugaucuc aaugugucuc cuguuacaaa uguugucguc ucagagcaga 6000
cggcuguugu gauuaaagac ccugugaaga aaguagaguu agacgcuaca aagcuguuag 6060
acacuaugaa uuaugcaucg gaaagauucu uuuccuuugg ugauuuuaug ucacguaauu 6120
uaauuacagu guuuuuguac auccuuagua uuuugggucu cuguuuuagg gccuuucgua 6180
agagggaugu uaaaguucua gcugguguac cccaacguac ugguauuaua uugcguaaaa 6240
gugugcgcua uaaugcaaag gcuuugggug ucuucuucaa gcuaaaacuu uauugguuca 6300
aaguucuugg uaaguuuagu uuggguauuu augcauugua ugcauuacua uucaugacaa 6360
uacgcuuuac accuauaggu ggcccuguuu gugaugaugu uguugcuggu uaugcuaauu 6420
cuaguuuuga caagaaugag uauugcaaca guguuauuug uaaggucugu cucuaugggu 6480
accaggaacu uucggacuuc ucucacacac agguaguaug gcaacaccuu agagacccau 6540
uaauugguaa ugugaugccu uucuuuuauu uggcauuucu ggcaauuuuu gggggguguu 6600
auguaaaggc uauuacucuc uauuuuauuu uccaguaucu uaacauacuu ggugugucuuu 6660 ugggccuaca acaguccauu ugguuuuugc agcuugugcc uuuugauguc uuuggugacg 6720
agaucgucgu cuuuuucauc guuacacgcg uauugauguu ccuuaagcau guuuuccuug 6780
gcugcgauaa ggcaucuugu guggcuugcu cuaagagugc ucgccuuaag cgcguuccug 6840
uccagacuau uuuucagggu acuagcaaau ccuucuacgu acaugccaau ggugguucua 6900
aguucuguaa gaagcacaau uucuuuuguu uaaauuguga uucuuauggu ccaggcugca 6960
cuuuuauuaa ugacgucauu gcaacugaag uugguaaugu ugucaaacuu aaugugcaac 7020
cgacaggucc ugccacuauu cuuauugaca agguugaauu caguaauggu uuuuacuauc 7080
uuuauagugg ugacacauuu uggaaguaca acuuugacau aacagauaac aaauacacuu 7140
gcaaagaguc acuuaaaaau uguagcauaa ucacagacuu uauuguuuuu aacaauaaug 7200
guuccaaugu aaaucagguu aagaaugcau guguguauuu uucacagaug cuuuguaaac 7260
cuguuaaguu aguggacuca gcguuguugg ccaguuuguc uguugauuuu ggugcaagcu 7320
uacauagugc uuuuguuagu guguugucga auaguuuugg caaagaccug ucaaguugua 7380

-continued

```
augacaugca ggauugcaag agcacauugg guuuugauga uguaccauug gauaccuuua   7440
augcugcugu ugcugaggcu caucguuacg auguccucuu gacugacaug ucguucaaca   7500
auuuuaccac caguuaugca aaaccagagg aaaaacuucc cguccaugac auugccacgu   7560
guaugcgugu aggugccaag auuguuaauc auaacguucu ugucaaggau aguauaccug   7620
uggugugguc uguacgugau uucauugccc uuucugaaga aacuaggaag uacauuauuc   7680
guacgacuaa aguuaagggu auaaccuuca uguugaccuu uaaugauugu cguaugcaua   7740
cuaccauacc uacuguuugc auugcaaaua agaagggugc aggucuuccu aguuuuucaa   7800
agguuaagaa auucuucugg uuuuugugc uguucauagu ugcuguuuuc uuugcacuaa   7860
gcuuuuuuga uuuuaguacu cagguuagca gugauaguga uuaugacuuc aaguauauug   7920
agaguggcca guugaagacu uuugacaauc cacuuaguug ugugcauaau gucuuuagua   7980
acuucgacca guggcaugau gccaaguuug guuucacccc cgucaacaau ccuaguuguc   8040
cuauagucgu uggugauca gacgaagcgc gcacuguucc agguauccca gcagguguuu   8100
auuuagcugg uaaaacacuu guuuuugcua uuaacaccau uuuugguaca ucugguuugu   8160
gcuuugaugc uaguggcguu gcugauaagg gcgcuugcau uuuuaauucg gcuugcacca   8220
cauuaucugg uuugggugga acugcugucu acuguuauaa gaauggucua guugaaggug   8280
cuaaacuuua uagugaguug gcaccucaua gcuacuauaa aaugguagau gguaaugcug   8340
ugucuuuacc ugaaauuauc ucacgcggcu uuggcauccg uacuauccgu acaaaggcua   8400
ugaccuacug ucgcguuggc cagugugugc aaucugcaga agguguuugu uuuggcgccg   8460
auagauucuu ugucuauaau gcagaaucug guucugacuu uguuuguggc acagggcucu   8520
uuacauuguu gaugaacguu auuaguguuu uuuccaagac aguaccagua acuguguugu   8580
cuggucaaau acuuuuuaau ugcauuauug cuuuugcugc uguugcggug uguuucuuau   8640
uuacaaaguu uaagcgcaug uucggugaua ugucuguugg cguuuucacu gucggugcuu   8700
guacuuuguu gaacaauguu uccuacauug uaacacagaa cacacuuggc auguugggcu   8760
augcaacuuu guacuuuuug ugcacuaaag guguuagaua uauguggauu uggcauuugg   8820
gauuuuugau cucauauaua cuuauugcac cauggugggu uuugaugguu uaugccuuuu   8880
cagccauuuu ugaguuuaug ccuaaccuuu uuaagcuuaa gguuucaaca caacuuuuug   8940
agggugacaa guucguaggc ucuuuugaaa augcugcagc agguacauuu gugcuugaua   9000
ugcaugccua ugagagacuu gccaacucua ucucaacuga aaaacugcgu caguaugcua   9060
guacuuacaa uaaguacaag uauuauucag gcagugcuuc agaggcugau uacaggcuug   9120
cuuguuuugc ccauuuggcc aaggcuauga uggauuaugc uucuaaucac aacgacacgu   9180
uauacacacc acccacugug aguuacaauu caacucuaca ggcuggcuug cguaagaugg   9240
cacaaccauc ugguguuguu gagaagugca uaguucgugu uugcuauggu aauauggcuc   9300
uuaauggccu auggcuuggu gauacuguua ucugcccacg ccauguuaua gcgucuagua   9360
cuacuagcac uauagauuau gacuaugccc uuucuguuuu acgccucyac aacuucucca   9420
uuucaucugg uaauguuuuc cuaggugug ugggguguaac caugcgaggu gcuuuguugc   9480
agauaaaggu uaaucaaaac aauguccaca cgccuaagua caccuaucgc acaguuagac   9540
cgggugaauc uuuuaauauc uuggcgugcu augaugguuc ugcagcuggu guuuacggcg   9600
uuaacaugcg cucuaauuac acuauuagag gcucguucau uaauggcgcu ugugguucac   9660
cugguuauaa cauuaacaau gguaccguug aguuugcua uuuacaccag cuugaacuug   9720
```

```
guucaggcug ucauguuggu agcgacuuag augguguuau guaugguggu uaugaggacc   9780
aaccuacuuu gcaaguugaa ggcgcuagua gucuguuuac agagaaugug uuggcauuuc   9840
uuuaugcagc acucauuaau gguucuaccu gguggcuuag uucuucuagg auugcuguag   9900
acagguuuaa ugagugggcu guucauaaug guaugacaac aguaguuaau acugauugcu   9960
uuucuauucu ugcugcuaag acugguguug auguacaacg uuuguuggcc ucaauccagu  10020
cucugcauaa gaauuuuggu ggaaagcaaa uucuuggcua uaccucguug acagaugagu  10080
uuacuacagg ugaaguuaua cgucaaaugu auggcguuwa ucuucagagu gguuauguuu  10140
cacgcgccug uagaaauguc uugcugguug guucuuuucu gacuuucuuu uggucagaau  10200
uaguuuccua cacuaaguuc uuuuggguaa auccugguua ugucacaccu auguuugcgu  10260
guuugucauu gcuguccuca cuuuugaugu ucacacucaa gcauaagaca uuguuuuucc  10320
aggucuuucu aauaccugcu cugauuguua caucuugcau uaauuuggca uuugauguug  10380
aagucuacaa cuauuuggca gagcauuuug auuaccaugu uucucucaug gguuuuaaug  10440
cacaaggucu uguuaacauc uuugucugcu uuguuguuac cauuuuacac ggcacauaca  10500
cauggcgcuu uuuuaacaca ccugugaguu cugucacuua ugugguagcu uugcugacug  10560
cggcauauaa cuauuuuuac gcuagugaca uucuuaguug ugcuaugaca cuauuugcua  10620
gugugacugg caacugguuc guuggugcug uuuguuauaa agcugcuguu uauauggccu  10680
ugagauuucc uacuuuugug gcuauuuuug gugauauuaa gaguguuaug uucuguuacc  10740
uuguguuggg uuauuuuacc uguugcuucu acgguauucu cuacugguuc aacagguuuu  10800
uuaagguuag uguaggugu c uaugacuaua cuguuagugc ugcugaguuu aaguauaugg  10860
uugcuaacgg ccuacgugca ccaacuggaa cacuugauuc acuacuucug ucugccaaau  10920
ugauugguau ugguggugag cggaauauua agauuucuuc cguucagucu aaacugacug  10980
auauuaagug uaguaacguu gugcuuuuag gcugucucuc uagcaugaau gucucagcaa  11040
auucaacaga augggccuau uguguugacu ugcauaacaa gaucaacuug uguaaugacc  11100
cagaaaaagc gcaggaaaug cuacuugcuu uguuggcauu uuuccuuagu aagaauagug  11160
cuuuugguuu agaugacuua uuggaauccu auuuuaauga caauaguaug uugcagagug  11220
uugcaucuac uuaugucggu uugccuucuu augucauuua ugaaaaugca cgccaacagu  11280
augaagaugc uguuaauaau gguucuccac cucaguuggu uaagcaauug cgccaugcca  11340
ugaauguagc aaagagcgaa uuugaccgug aggcuucuac ucagcguaag cuugauagaa  11400
uggcggaaca ggcugcagca cagauguaca aagaggcacg agcaguuaau aggaagucca  11460
aaguuguaag ugcuaugcau ucacugcuuu uugguauguu gagacguuug gacaugucuu  11520
cuguagacac cauucucaac uuggcaaagg auggggguugu accucugucu gucauaccgg  11580
cagucagugc uacuaagcuu aacauuguua cuucugauau cgauucuuau aaucguaucc  11640
agcgugaggg augugucac uacgcuggua ccauuuggaa uauaauugau aucaaggaca  11700
augauggcaa ggugguacac guuaaggagg uaaccgcaca gaaugcugag ucccugucau  11760
ggccccuggu ccuugggugu gagcguauug ucaagcucca gaauaaugaa auuauuccug  11820
guaagcugaa gcagcgcucc auuaaggcag aaggagaugg cauaguugga gaagguaagg  11880
cacuuuacaa uaaugagggu ggacguacuu uuauguaugc uuucaucucg gacaaaccgg  11940
accugcgugu agucaagugg gaguucgaug gugguuguaa cacuauugag cuagaaccac  12000
cacguaaguu cuuggugau ucuccuaaug gugcacagau caaguaucuc uacuuuguuc  12060
guaaccuuaa cacguuacgu aggggugcug uucucggcua cauaggugcc acuguacgcu  12120
```

-continued ugcaggcugg uaaacaaaca gaacaggcua uuaacucuuc auuguugaca cuuugcgcuu 12180
ucgcugugga uccugcuaag accuacaucg augcugucaa aaguggucac aaaccaguag 12240
guaacugugu uaagauguug gccaaugguu cugguaaugg acaagcuguu acuaauggug 12300
uggaggcuag uacuaaccag gauucauacg gugguggcguc cgugugucua uauuguagag 12360
cacauguuga gcauccaucu auggaugguu uuugcagacu gaaaggcaag uacguacagg 12420
uuccacuagg uacaguggau ccuauacguu uuguacuuga gaaugacguu ugcaagguuu 12480
gugguuguug gcuggcuaau ggcugcacuu gugacagauc cauuaugcaa agcacugaua 12540
uggcuuauuu aaacgaguac ggggcucuag ugcagcucga cuagagcccu guaacgguac 12600
ugauacacaa cauguguauc gugcuuuuga caucuacaac aaggauguug cuugucuagg 12660
uaaauuccuc aaggugaacu guguucgccu gaagaauuug gauaagcaug augcauucua 12720
uguugucaaa agauguacca agucugcgau ggaacacgag caauccaucu auagcagacu 12780
ugaaaagugu ggagccguag ccgaacacga uuucuucacu uggaaggaug gucgugccau 12840
cuaugguaac guuuguagaa aggaucuuac cgaguauacu augauggauu uguguuacgc 12900
uuuacguaac uuugaugaaa acaauugcga uguucuuaag agcauuuuaa uuaagguagg 12960
cgcuugugag gaguccuacu ucaauaauaa agucugguuu gacccuguug aaaaugaaga 13020
cauucaucgu gucuaugcau uguuagguac cauuguuuca cgugcuaugc uuaaaugcgu 13080
uaaguucugu gaugcaaugg uugaacaagg uauaguuggu guugucacau uagauaauca 13140
ggaucuuaau ggugauuuuu augauuuugg ugauuuuacu uguagcauca agggaauggg 13200
uauacccauu ugcacaucau auuacucuua uaugaugccu guuaugggua ugacuaauug 13260
ccuugcuagu gaguguuuug uuaagaguga uauauuuggu gaggauuuca agucauauga 13320
ccugcuggaa uaugauuuca cggagcauaa gacagcacuc uucaacaagu auuucaagua 13380
uuggggacug caauaccacc cuaacugugu ggacugcagu gaugagcagu gcauaguuca 13440
cugugccaac uucaauacgu uguuuuccac uacuauaccu auuacggcau uuggaccuuu 13500
gugucgcaag uguuggauug augguguucc acugguaacu acagcugguu aucauuuuaa 13560
acaguuaggu auaguuugga acaaugaccu caacuuacac ucuagcaggc ucucuauuaa 13620
cgaauuacuc caguuuugua gugauccugc auugcuuaua gcaucaucac cagcccuugu 13680
ugaucagcgu acuguuugcu uuucaguugc agcgcuaggu acagguauga cuaaccagac 13740
uguuaaaccu ggccauuuca auaaggaguu uuaugacuuc uuacuugagc aagguuucuu 13800
uucugagggc ucugagcuua cuuuaaagca cuucuucuuu gcacagaagg gugaugcagc 13860
uguuaaggau uuugacuacu auagguauaa uagaccuacu guucuggaca uuugccaagc 13920
ucgcgucgug uaucaaauag ugcaacgcua uuuugauauu uacgaaggug guuguaucac 13980
ugcuaaagag gugguuguua caaaccuuaa caagagcgca gguuauccuu ugaacaaguu 14040
ugguaaagcu ggucuuuacu augagucuuu auccuaugag gaacaggaug aacuuuaugc 14100
uuauacuaag cguaacaucc ugcccacuau gacacagcuc aaccuuaaau augcuauaag 14160
uggcaaagaa cgugcacgca caguggguggg uguuucgcuu uugucaacca ugacuacucg 14220
gcaguaucau cagaaacacc uuaaguccau aguuaauacu aggggcgcuu cgguuguuau 14280
ugguacuacu aaguuuuaug gugguuggga caauaugcuu aagaaccuua uugauggugu 14340
ugaaaauccg ugucuuaugg guugggacua cccaaagugc gacagagcac ugcccaauru 14400
gauacguaug auuucagcca ugauuuuagg cucuaagcac accacaugcu gcaguuccac 14460

-continued

```
ugaccgcuuu uucagguugu gcaaugaauu ggcucaaguc cuuacugagg uuguuuauuc  14520
uaauggaggu uuuuauuuga agccaggugg uacuaccucu ggugaugcaa ccaccgcaua  14580
ugcaaacuca guuuuuaaua ucuuccaagc aguaagugcc aauguuaaca aacuucuuag  14640
uguugacagc aaugucuguc auaauuuaga aguuaagcaa uugcagcgua agcuuuauga  14700
gugcuguuau agaucaacua ccgucgauga ccaguucguc guugaguauu augguuacuu  14760
gcguaaacau uuuucaauga ugauucuuuc ugaugauggc guuguuuguu auaacaauga  14820
cuaugcauca cuugguuaug ucgcugaucu uaacgcauuc aaggcuguuu uguauuacca  14880
gaacaauguc uucaugagcg ccucuaaaug uuggaucgag ccugacauua auaaaggucc  14940
ucaugaauuu ugcucgcagc auacuaugca gauugucgau aaagauggua cuuauuaccu  15000
uccuuacccu gauccuucaa gaauucucuc ugcaggugug uuuguugaug acguuguuaa  15060
aacugaugca guuguauugc uugaacguua ugugucauug gcuauagaug ccuacccguu  15120
aucuaagcau gaaaacccug aauauaagaa gguguuuuau gugcuuuugg auuggguuaa  15180
gcaucuguac aaaacucuua augcuggugu guuagagucu uuuucuguca cacuuuugga  15240
agauucuacu gcuaaauucu gggaugagag cuuuuaugcc aacauguaug agaaaucugc  15300
aguuuuacaa ucugcagggc uuuguguugu uuguggcucu caaacuguuu uacguugugg  15360
ugauugucua cggcguccua ugcuuuguac uaagugugcu uaugaucaug ucauuggaac  15420
aacucacaag uucauuuugg ccaucacucc auaugugugu ugugcuucag auuguggugu  15480
caaugaugua acuaagcucu acuuaggugg ucuuaguuau uggugucaug accacaagcc  15540
acgucuugca uucccguugu gcucugcugg uaauguuuuu ggcuuguaca aaaauucugc  15600
uaccggcuca cccgauguug aagacuuuaa ucgcauugcu acauccgauu ggacugaugu  15660
uucugacuac agguuggcaa augaugucaa ggacucauug cgucuguuug cagcggaaac  15720
uaucaaggcc aaggaggaga gcguuaaguc auccuaugcu ugugcaacac uacaugaggu  15780
uguaggaccu aaagaguugu ugcucaaaug ggaagucggc agacccaaac caccccuuaa  15840
uagaaauucg guuuucacuu guuaucauau aacgaagaac accaaauuuc aaaucgguga  15900
guuuguguuu gagaaggcag aauaugauaa ugaugcugua acauauaaaa cuaccgccac  15960
aacaaaacuu guuccuggca ugguuuuugu gcuuaccuca cauaauguuc agccauugcg  16020
cgcaccgacc auugcuaauc aagaacguua uuccacuaua cauaaguugc auccugcuuu  16080
uaacauaccu gaagcuuauu cuagcuuagu gcccuauuac caauugauug guaagcagaa  16140
gauuacaacu auucagggac cucccgguag ugguaaaucu cacuguguua uagggcuagg  16200
uuuguacuau ccaggugcac guauaguguu uacagcuugu ucucaugcag cggucgauuc  16260
acuuugugug aaagcuucca cugcuuauag caaugacaaa uguucacgca ucauaccaca  16320
gcgcgcucgu guugaguguu augaugguuu caagucuaau aauacuagug cucaguaccu  16380
uuucucuacu gucaaugcuu ugccagagug caaugcggac auuguugugg uggaugaggu  16440
cucuaugugc acuaauuaug acuugucugu cauaaaucag cgcaucagcu auaggcaugu  16500
agucuauguu ggugacccuc aacagcugcc ugcaccacgu guuaugauuu cacgugguac  16560
uuuggaacca aaggacuaca acguugucac ucaacgcaug ugugcccuua agccugaugu  16620
uuucuugcac aaguguuauc gcuguccugc ugagauagug cguacugugu cugagauggu  16680
cuaugaaaac caauucauuc cugugcaccc agauagcaag caguguuuua aaaucuuuug  16740
caaggguaau guucagguug auaaugguuc aagcauuaau cgcaggcaau uggauguugu  16800
gcguauguuu uuggcuaaaa auccuaggug gucaaaggcu guuuuuauuu cuccuuauaa  16860
```

-continued

```
cagccagaau uauguugcca gccgcaugcu aggucuacaa auucagacag uugacucauc  16920
ccaggguagu gaguaugacu augucauuua cacacaaacu ucagauacug cccaugccug  16980
uaauguuaac agguuuaaug uugccaucac aagggccaag aaaggcauau uauguauaau  17040
gugcgauagg ucccuuuuug augugcuuaa auucuuugag cuuaaauugu cugauuugca  17100
ggcuaaugag gguuguggu uuuuuaaaga cuguagcaga ggugaugauc uguugccacc  17160
aucucacgcu aacaccuuca ugucuuuagc ggacaauuuu aagacugauc aagaucuugc  17220
uguucaaaua gguguuaaug gacccauuaa auaugagcau guuaucucgu uuauggguuu  17280
ccguuuugau aucaacauac ccaaccauca uacucucuuu ugcacacgcg acuuugccau  17340
gcgcaauguu agagguuggu uaggcuuuga cguugaagga gcacauguug uuggcucuaa  17400
cgucgguaca aaugucccau ugcaauuagg guuuucuaac gguguugauu uuguugucag  17460
accugaaggu ugcguuguaa cagagucugg ugacuacauu aaacccguca gagcucgugc  17520
uccaccaggg gaacaauucg cacaccuuuu gccuuuacuu aaacgcggcc aaccauggga  17580
uguuguccgc aaacguauag ugcagaugug uagugacuac cuggccaacc uaucagacau  17640
acuaauuuuu guguugugg cugguggguuu ggaguugaca acuaugcguu auuuugucaa  17700
gauuggacca aguaagaguu gugauugugg uaagguugcu acuuguuaca auagugcgcu  17760
gcauacguac uguuguuuca aacaugcccu ugguugugau uaucuguaua acccauacug  17820
uauugauaua cagcaguggg gauacaaggg aucacuuagc cuuaaccacc augagcauug  17880
uaauguacau agaaacgagc auguggcuuc uggugaugcc auaaugacuc gcugucuggc  17940
cauacaugau ugcuuuguca agaacguuga cugguccauc acauacccau uuauugguaa  18000
ugaggcuguu auuaauaaga gcggccgaau ugugcaauca cacacuaugc ggucaguucu  18060
uaaguuauac aauccgaaag ccauauauga uauuggcaau ccuaagggca uuagaugugc  18120
cguaacggau gcuaaguggu uuugcuuuga caagaauccu ayuaauucua augucaagac  18180
auuggaguau gacuauauaa cacauggcca auuugauggg uugugcuugu uuuggaauug  18240
caauguagac auguauccag aauuuucugu ggucugucgu uuugauacuc gcuguagguc  18300
accacucaac uuggaggguu guaaugugg uucacuguau guuaauaauc augcauucca  18360
uacaccggcu uuugacaagc gugcuuuugc uaaguugaag ccaaugccau uuuucuuuua  18420
ugaugauacu gagugugaca aguuacagga cuccauaaac uauguuccuc uuagggcuag  18480
uaacugcauu acuaaaugua auguuggugg ugcugucugu aguaagcauu gugcuaugua  18540
ucauagcuau guuaaugcuu acaacacuuu uacgucggcg ggcuuuacua uuugggugcc  18600
uacuucguuu gacaccuaua aucuguggca gacauuuagu aacaauuugc aaggucuuga  18660
gaacauugcu uucaaugucg uaaagaaagg aucuuuuguu ggugccgaag gugaacuucc  18720
uguagcugug guuaaugaca aagugcucgu uagagauggu acuguugaua cucuuguuuu  18780
uacaaacaag acaucacuac ccacuaacgu agcuuuugag uuguaugcca agcguaaggu  18840
aggacucacc ccacccauua cgauccuacg uaacuugggu guaguuugua caucuaagug  18900
ugucauuugg gacuaugaag ccgaacgucc acuuacuacu uuuacaaagg auguuuguaa  18960
auauaccgac uuugagggug acgucuguac acucuuugau aacagcauug uugguucauu  19020
agagcgauuc uccaugaccc aaaaugcugu gcuuauguca cuuacagcug uuaaaaagcu  19080
uayuggcaua aaguuaacuu augguuaucu uaauggguguc ccaguuaaca cacaugaaga  19140
uaaaccuuuu acuugguaua uuuacacuag gaagaacggc aaguucgagg accauccuga  19200
```

uggcuauuuu acccaaggua gaacaaccgc ugauuuuagc ccucguagcg acauggaaaa 19260
ggacuuccua aguauggaua ugggucuguu uauuaacaag uacggacuug aagauuacgg 19320
cuuugagcac guuguguaug gugauguuuc aaaaaccacc cuuggugguu ugcaucuacu 19380
aauuucgcag gugcgucugg ccuguauggg ugugcucaaa auagacgagu uugugucuag 19440
uaaugauagc acguuaaagu cuuguacugu uacauaugcu gauaacccua guaguaagau 19500
gguuuguacg uauauggauc uccugcuuga cgauuuuguc agcauucuua aaucuuugga 19560
uuugggcguu guaucuaaag uucaugaagu uauggucgau uguaaaaugu ggaggugggau 19620 guugugguggu aaggaucaua aacuccagac auuuuauccg caacuucagg ccagugaaug 19680 gaagugugggu uauuccaugc cuucuauuua caagauacaa cguaugugguu uagaaccuug 19740 caaucucuac aacuauggug cugguauuaa guuaccugau ggcauuaugu uuaacguagu 19800
uaaauacaca cagcuuuguc aauaucucaa uagcaccaca augugugguac cccaucacau 19860 gcgugugcua caucuuggug cuggcuccga caagggguguu gcaccuggca cggcugucuu 19920
acgacguugg uugccacugg augccauuau aguugacaau gauagugugg auuacguuag 19980
cgaugcugau uauaguguua caggagauug cucuaccuua uaccugucag auaaguuuga 20040
uuuaguuaua ucugauaugu augaugguaa gauuaaaagu ugugaugggg agaacguguc 20100
uaaagaaggc uucuuucccu auauuaaugg ugucaucacc gaaaaguugg cacuuggugg 20160
uacuguagcu auuaagguga cggaguuuag uuggaauaag aaguuguaug aacucauuca 20220
gagguuugag uauuggacaa uguucuguac caguguuaac acgucaucgu cagaggcauu 20280
cuuaauuggu guucacuauu uaggugauuu ugcaaguggc gcugugauug acggcaacac 20340
uaugcaugcc aauuauaucu ucuggcguaa uuccacaauu augacuaugu cuuacaauag 20400
uguacuugau uuaagcaagu ucaauuguaa gcauaaggcu acaguuguca uuaauuuaaa 20460
agauucaucc auuagugaug uugugguuagg uuuguugaag aaugguaagu ugcuagugcg 20520
uaauaaugac gccauuugug guuuuucuaa ucauuugguc aacguaaaca aaugaagucu 20580
uuaaccuacu ucugguuguu cuuaccagua cuuucaacac uuagccuacc acaagauguc 20640
accaggugcu cagcuaacac uaauuuuagg cgguucuuuu caaaauuuaa uguucaggcg 20700
ccugcaguug uuguacuggg cgguuaucua ccuauuggug aaaaccaggg ugucaauuca 20760
acuugguacu gugcuggcca acauccaacu gcuaguggcg uucaugguau cuuuguuagc 20820
cauauuagag guggucaugg cuuugagauu ggcauuucgc aagagccuuu ugacccuagu 20880
gguuaccagc uuuauuuaca uaaggcuacu aacgguaaca cuaaugcuac ugcgcgacug 20940
cgcauuugcc aguuuccuag cauuaaaaca uugggcccca cugcuaauaa ugauguuaca 21000
auaggucgua auugccuauu uaacaaagcc aucccagcuc auaugaguga acauaguguu 21060
gucggcauaa caugggauaa ugaucguguc acugucuuuu cugacaagau cuauuauuuu 21120
uauuuuaaaa augauugguc ccguguuggcg acaaagugguu acaacagugg agguugugcu 21180
augcaauaug uuuacgaacc caccuauuac augcuuaaug uuacuagugc ugguguaggau 21240 gguauuucuu aucaacccug uacagcuaau ugcauugguu augcugccaa uguauuugcu 21300
acugagccca auggccacau accagaaggu uuuaguuuua auaauugguu ucuuuugucc 21360
aaugauucca cuuuggugca ugguaaggug guuuccaacc aaccauuguu ggucaauugu 21420
cuuuuggcca uuccuaagau uuauggacua ggccaauuuu ucuccuuuaa ucaaacgauc 21480
gaugguguuu guaauggagc ugcugugcag cgugcaccag aggcucugag guuuaauauu 21540
aaugacaccu cugucauucu ugcugaaggc ucaauuguac uucauacugc uuuaggaaca 21600
aauuuuucuu uuguuugcag uaauucccca aauccucacu uagccaccuu cgccauaccu 21660
cugggugcua cccaaguacc uuauuauugu uuucuuaaag uggauacuua caacuccacu 21720
guuuauaaau uuuuggcugu uuuaccuccu accgucaggg aaauugucau caccaaguau 21780
ggugauguuu augucaaugg guuuggauac uugcaucucg guuuguugga ugcugucaca 21840
auuaauuuca cuggucaugg cacugacgau gauguuucug guuuuuggac cauagcaucg 21900
acuaauuuug uugaugcacu caucgaaguu caaggaaccg ccauucagcg uauucuuuau 21960
ugugaugauc cuguuagcca acucaagugu ucucagguug cuuuugaccu ugacgauggu 22020
uuuuacccua uuucuucuag aaaccuucug agucaugaac agccaauuuc uuuuguuacu 22080
cugccaucau uuaaugauca uucuuuuguu aacauuacug uaucugcuuc cuuuggugguu 22140
cauaguggug ccaaccuuau ugcaucugac acuacuauca auggguuuag uucuuucugu 22200
guugacacua gacaauuuac cauuucacug uuuuauaacg uuacaaacag uuaugguuau 22260
gugucuaaau cacaggacag uaauugcccu uucaccuugc aaucuguuaa ugauuaccug 22320
ucuuuuagca aauuuugugu uuccaccagc cuuuuggcua gugccuguac cauagaucuu 22380
uuugguuacc cugaguuugg uaguggugguu aaguuuacgu cccuuuacuu ucaauucaca 22440
aagggugagu ugauuacugg cacgacuaaa ccacuugaag gugucacgga cguuucuuuu 22500
augacucugg auguguguac caaguauacu aucuauggcu uuaaagguga ggguaucauu 22560
acccuuacaa auucuagcuu uuuggcaggu guuuauuaca caucuguuuc uggacaguug 22620
uuagccuuua agaaugucac uaguggugcu guuuauucug uuacgccaug uucuuuuuca 22680
gagcaggcug cauauguuga ugaugauaua gugggguuaa uuucuaguuu gucuagcucc 22740
acuuuuaaca guacuaggga guugccuggu uucuucuacc auucuaauga uggcucuaau 22800
uguacagagc cuguguuggu guauaguaac auagguguuu guaaaucugg caguauuggc 22860
uacgucccau cucagucugg ccaagucaag auugcaccca cgguuacugg gaauauuagu 22920
auucccacca acuuuaguau gaguauuagg acagaauauu uacagcuuua caacacgccu 22980
guuaguguug auugugccac auauguuugu aaugguaacu cucguuguaa acaauuacuc 23040
acccaguaca cugcagcaug uaagaccaua gagucagcau uacracucag cgcuaggcuu 23100
gagucuguug aaguuaacuc uaugcuuacu auuucugaag aggcucuaca guuagcuacc 23160
auuaguucgu uuaaugguga uggauauaau uuuacuaaug ugcugggugu uucuguguau 23220
gauccugcaa ggggcagggu gguacaaaaa aggucuuuua uugaagaccu gcuuuuuaau 23280
aaagugguua cuaauggccu ugguacuguu gaugaagacu auaagcgcug uucuaauggu 23340
cgcucugugg cagaucuagu cugugcacag uauuacucug gugucauggu acuaccuggu 23400
guuguugacg cugagaagcu ucacauguau agugcgucuc ucaucggugg uaugggugcua 23460
ggagguuuua cuucugcagc ggcauugccu uuuagcuaug cuguucaagc uagacucaau 23520
uaucuugcuc uacagacgga uguucuacag cggaaccagc aauugcuugc ugagucuuuu 23580
aacucugcua uugguaauau aacuucagcc uuugagagug uuaaagaggc uauuagucaa 23640
acuuccaagg guuugaacac uguggcucau gcgcuuacua agguucaaga gguuguuaac 23700
ucgcagggug cagcuuugac ucaacuuacc guacagcugc aacacaacuu ccaagccauu 23760
ucuaguucua uugaugacau uuacucucga cuggacauuc uuucagccga uguucagguu 23820
gaccgucuca ucaccggcag auuaucagca cuuaaugcuu uuguugcuca aacccucacu 23880
aaguauacug agguucaggc uagcaggaag uuagcacagc aaaagguuaa ugagugcguu 23940

-continued aaaucgcaau cccagcguua ugguuuuugu gguggugaug gcgagcacau uuucucucug 24000
guacaggcag caccucaggg ccugcuguuu uuacauacag uacuuguacc gagugauuuu 24060
guagauguua uugccaucgc uggcuuaugc guuaacgaug aaauugccuu gacucuacgu 24120
gagccuggcu uagucuuguu uacgcaugaa cuucaaaauc auacugcgac ggaauauuuu 24180
guuucaucgc gacguauguu ugaaccuaga aaaccuaccg uuagugauuu uguucaaauu 24240
gagaguugug uggucaccua ugucaauuug acuagagacc aacuaccaga uguaauccca 24300
gauuacaucg auguuaacaa aacacuugau gagauuuuag cuucucugcc caauagaacu 24360
gguccaaguc uuccuuuaga uguuuuuaau gccacuuauc uuaaucucac uggugaaauu 24420
gcagauuuag agcagcguuc agagucucuc cguaauacua cagaggagcu ccaaagucuu 24480
auauauaaua ucaacaacac acuaguugac cuugaguggc ucaaccgagu ugagacauau 24540
aucaaguggc cguggugggu uugguugauu auuuucauug uucucaucuu uguuguguca 24600
uuacuagugu ucugcugcau uuccacgggu uguuguggau gcugcggcug cugcugugcu 24660
uguuucucag guuguuguag ggguccuaga cuucaaccuu acgaaguuuu ugaaaagguc 24720
cacgugcagu gauguuucuu ggacuuuuuc aauacacgau ugacacaguu gucaaagaug 24780
ucucaaaguc ugcuaacuug ucuuuggaug cuguccaaga guuggagcuc aauguaguuc 24840
caauuagaca agcuucaaau gugacggguu uucuuuucac caguguuuuu aucuacuucu 24900
uugcacuguu uaaagcgucu ucuuugaggc gcaauuauau uauguuggca gcgcguuuug 24960
cugucauugu ucuuuauugc ccacuuuuau auuauugugg ugcauuuuua gaugcaacua 25020
uuauuuguug cacacuuauu caaagucggu ggcaggcuuu guuuagucug cuuuuacucc 25080
uggcgcuaua aaaaugcgcu cuuuauuauu uuuaauacua cgacacuuuc uuuccucaau 25140
gguaaagcag cuuugacggc aaauccauug ugauuuuaga agguggugac cauuacauca 25200
cuuuuggcaa cucuuuuguu gcuuuuguua guagcaucga cuuguaucua gcuauacgug 25260
ggcggcaaga agcugaccua cagcuguugc gaacuguuga gcuucuugau ggcaagaagc 25320
uuuaugucuu uucgcaacau caaauuguug gcauuacuaa ugcugcauuu gacucaauuc 25380
aacuagacga guaugcuaca auuagugaau gauaaugguc uaguaguuaa uguuauacuu 25440
uggcuuuucg uacucuuuuu ccugcuuauu auaagcauua cuuucgucca auugguuaau 25500
cugugcuuca cuugucaccg guuguguaau agcgcaguuu acacaccuau agggcguuug 25560
uauagaguuu auaagucuua caugcaaaua gaccccccucc cuaguacugu uauugacgua 25620
uaaacgaaau augucuaacg guucuauucc cguugaugag gugauucaac accuuagaaa 25680
cuggaauuuc acauggaaua ucauacugac gauacuacuu guagugcuuc aguauggcca 25740
uuacaaguac ucugcguucu uguauggugu caagauggcu auucuaugga uacuuuggcc 25800
ucuuguguua gcacugucac uuuuugaugc augggcuagc uuucagguca auugggucuu 25860
uuuugcuuuc agcauccuua uggcuugcau cacucuuaug cuguggauaa uguacuuugu 25920
caauagcauu cgguuguggc gcaggacaca uucuuggugg ucuuucaauc cugaaacaga 25980
cgcgcuucuc acuacuucug ugaugggccg acaggucugc auuccagugc uuggagcacc 26040
aacuggugua acgcuaacac uccuuagugg uacauugcuu guagagggcu auaagguugc 26100
uacuggcgua cagguaaguc aauuaccuaa uuucgucaca gucgccaagg ccacuacaac 26160
aauugucuac ggacguguug gucguucagu caaugcuuca ucuggcacug guugggcuuu 26220
cuauguccgg uccaaacacg gcgacuacuc agcugugagu aauccgaguu cgguucucac 26280
agauagugag aaagugcuuc auuuagucua aacagaaacu uuauggcuuc ugucaguuuu 26340

```
caggaucgug gccgcaaacg ggugccauua ucccucuaug ccccucuuag gguuacuaau  26400
gacaaacccc uuucuaaggu acuugcaaau aaugcuguac ccacuaauaa aggaaauaag  26460
gaccagcaaa uuggauacug gaaugagcaa auucgcuggc gcaugcgccg uggugagcga  26520
auugaacaac cuuccaauug gcauuucuac uaccucggaa caggaccuca cgccgaccuc  26580
cgcuauagga cucguacuga ggguguuuuc ugggguugcua aagaaggcgc aaagacugaa  26640
cccacuaacc ugggugucag aaaggcgucu gaaaagccaa uuauuccaaa uuucucucaa  26700
cagcuuccca gcguaguuga gauuguugaa ccuaacacac cuccuacuuc acgugcaaau  26760
ucacguagca ggagucgugg uaauggcaac aacaggucca gaucuccaag uaacaacaga  26820
ggcaauaacc agucccgcgg uaauucacag aaucguggaa auaaccaggg ucguggagcu  26880
ucucagaaca gaggaggcaa uaauaauaac aauaacaagu cucguaacca guccaagaac  26940
agaaaccagu caaaugaccg ugguggugua acaucacgcg augaucuggu ggcugcuguc  27000
aaggaugccc uuaaaucuuu ggguauuggc gaaaacccug acaagcuuaa gcaacagcag  27060
aagcccaaac aggaaagguc ugacagcagc ggcaaaaaua caccuaagaa gaacaaaucc  27120
agagccacuu cgaaagaacg ugaccucaaa gacaucccag aguggaggag aauucccaag  27180
ggcgaaaaua gcguagcagc uugcuucgga cccaggggag gcuucaaaaa uuuuggagau  27240
gcggaauuug ucgaaaaagg uguugaugcc ucaggcuaug cucagaucgc caguuuagca  27300
ccaaauguug cagcauugcu cuuugguggu aauguggcug uucgugagcu agcggacucu  27360
uacgagauua cauauaauua uaaaaugacu gugccaaagu cugauccaaa uguagagcuu  27420
cuuguuucac agguggaugc auuuaaaacu gggaaugcaa aaccccagag aaagaaggaa  27480
aagaagaaca agcgugaaac cacgcagcag cugaaugaag aggccaucua cgaugaugug  27540
ggugugccau cugaugugac ucaugccaau uuggaauggg acacagcugu ugauggugggu  27600
gacacggccg uugaaauuau caacgagauc uucgacacag gaaauuaaac aauguuugac  27660
uggcuuaucc uggcuauguc ccaggguagu gccauuacac uguuauuacu gaguguuuuu  27720
cuagcgacuu ggcugcuggg cuauggcuuu gcccucuaac uagcggucuu ggucuugcac  27780
acaacgguaa gccaguggua augucagugc aagaaggaua uuaccauagc acugucauga  27840
ggggaacgca guaccuuuuc aucuaaaccu uugcacgagu aaucaaagau ccgcuugacg  27900
agccuauaug gaagagcgug ccagguauuu gacucaagga cuguuaguaa cugaagaccu  27960
gacgguguug auaugg                                                  27976
```

<210> SEQ ID NO 37
<211> LENGTH: 24
<212> TYPE: DNA
<213> ORGANISM: Artificial Sequence
<220> FEATURE:
<223> OTHER INFORMATION: P1360110A PEDV 2a BD- FORWARD PRIMER N-terminal fragment

<400> SEQUENCE: 37

```
gatgtcacca ggtgctcagc taac                                             24
```

<210> SEQ ID NO 38
<211> LENGTH: 32
<212> TYPE: DNA
<213> ORGANISM: Artificial Sequence
<220> FEATURE:
<223> OTHER INFORMATION: PEDV-S2-R PEDV 2a BD- REVERSE PRIMER N-terminal fragment

<400> SEQUENCE: 38
ctatacatgt gaagcttctc agcgtcaaca ac 32

<210> SEQ ID NO 39
<211> LENGTH: 26
<212> TYPE: DNA
<213> ORGANISM: Artificial Sequence
<220> FEATURE:
<223> OTHER INFORMATION: PEDV-S1-F PEDV 2a BD- FORWARD PRIMER C-terminal fragment

<400> SEQUENCE: 39
catctgattc tggacagttg ttagcc 26

<210> SEQ ID NO 40
<211> LENGTH: 33
<212> TYPE: DNA
<213> ORGANISM: Artificial Sequence
<220> FEATURE:
<223> OTHER INFORMATION: P1360110B.PEDV 2a BD- Reverse PRIMER C-terminal fragment

<400> SEQUENCE: 40
gaacactagt aatgacacaa caaagatgag aac 33

<210> SEQ ID NO 41
<211> LENGTH: 107
<212> TYPE: DNA
<213> ORGANISM: Artificial Sequence
<220> FEATURE:
<223> OTHER INFORMATION: O1360110C gp64 signal sequence (AcNPV) cDNA

<400> SEQUENCE: 41
gatccgccac catggtatct gctattgttc tttatgtttt gcttgctgcc gccgctcact 60
cagctttcgc ggatgtcacc aggtgctcag ctaacactaa ttttagg 107

<210> SEQ ID NO 42
<211> LENGTH: 68
<212> TYPE: DNA
<213> ORGANISM: Artificial Sequence
<220> FEATURE:
<223> OTHER INFORMATION: O1360110D gp64 C-terminal tail coding sequence (AcNPV) cDNA

<400> SEQUENCE: 42
gcttaaatac atatttagta ctgacgattg cggtttctga acactagtaa tgacacaaca 60
aagatgag 68

<210> SEQ ID NO 43
<211> LENGTH: 21
<212> TYPE: DNA
<213> ORGANISM: Artificial Sequence
<220> FEATURE:
<223> OTHER INFORMATION: P290194B Gp64 Forward Primer

<400> SEQUENCE: 43
gcttaaatac atatttagta c 21

<210> SEQ ID NO 44
<211> LENGTH: 26
<212> TYPE: DNA
<213> ORGANISM: Artificial Sequence
<220> FEATURE:
<223> OTHER INFORMATION: PEDV-S1-F Gp64 Reverse Primer

<400> SEQUENCE: 44
catctgattc tggacagttg ttagcc 26

<210> SEQ ID NO 45
<211> LENGTH: 22
<212> TYPE: DNA
<213> ORGANISM: Artificial Sequence
<220> FEATURE:
<223> OTHER INFORMATION: P290194A (OE Primer)

<400> SEQUENCE: 45
ggatccgcca ccatggtatc tg 22

<210> SEQ ID NO 46
<211> LENGTH: 4062
<212> TYPE: DNA
<213> ORGANISM: Artificial Sequence
<220> FEATURE:
<223> OTHER INFORMATION: PEDVS 2a BD Coding Sequence Expression Casette

<400> SEQUENCE: 46
atggtatctg ctattgttct ttatgttttg cttgctgccg ccgctcactc agctttcgcg 60
gatgtcacca ggtgctcagc taacactaat tttaggcggt tcttttcaaa atttaatgtt 120
caggcgcctg cagttgttgt actgggcggt tatctaccta ttggtgaaaa ccagggtgtc 180
aattcaactt ggtactgtgc tggccaacat ccaactgcta gtggcgttca tggtatcttt 240
gttagccata ttagaggtgg tcatggcttt gagattggca tttcgcaaga gccttttgac 300
cctagtggtt accagcttta tttacataag gctactaacg gtaacactaa tgctactgcg 360
cgactgcgca tttgccagtt tcctagcatt aaaacattgg gccccactgc taataatgat 420
gttacaacag gtcgtaattg cctatttaac aaagccatcc cagctcatat gagtgaacat 480
agtgttgtcg gcataacatg ggataatgat cgtgtcactg tcttttctga caagatctat 540
tatttttatt ttaaaaatga ttggtcccgt gttgcgacaa agtgttacaa cagtggaggt 600
tgtgctatgc aatatgttta cgaacccacc tattacatgc ttaatgttac tagtgctggt 660
gaggatggta tttcttatca accctgtaca gctaattgca ttggttatgc tgccaatgta 720
tttgctactg agcccaatgg ccacatacca gaaggtttta gttttaataa ttggtttctt 780
ttgtccaatg attccacttt ggtgcatggt aaggtggttt ccaaccaacc attgttggtc 840
aattgtcttt tggccattcc taagatttat ggactaggcc aatttttctc ctttaatcaa 900
acgatcgatg gtgtttgtaa tggagctgct gtgcagcgtg caccagaggc tctgaggttt 960
aatattaatg acacctctgt cattcttgct gaaggctcaa ttgtacttca tactgcttta 1020
ggaacaaatt tttcttttgt ttgcagtaat tcctcaaatc ctcacttagc caccttcgcc 1080 ataccttttgg gtgctaccca agtaccctat tattgttttc ttaaagtgga tacttacaac 1140
tccactgttt ataaattctt ggctgtttta cctccaaccg tcagggaaat tgtcatcacc 1200
aagtatggtg atgtttatgt caatgggttt ggatacttgc atctcggttt gttggatgct 1260
gtcacaatta atttcactgg tcatggcact gacgatgatg tttctggttt ttggaccata 1320
gcatcgacta attttgttga tgcactcatc gaagttcaag gaaccgccat tcagcgtatt 1380
ctttattgtg atgatcctgt tagccaactc aagtgttctc aggttgcttt tgaccttgac 1440
gatggttttt accctatttc ttctagaaac cttctgagtc atgaacagcc aatttctttt 1500
gttactctgc catcatttaa tgatcattct tttgttaaca ttactgtatc tgcttccttt 1560
ggtggtcata gtggtgccaa ccttattgca tctgacacta ctatcaatgg gtttagttct 1620

-continued

```
ttctgtgttg acactagaca atttaccatt tcactgtttt ataacgttac aaacagttat   1680
ggttatgtgt ctaaatcaca ggacagtaat tgccctttca ccttgcaatc tgttaatgat   1740
tacctgtctt ttagcaaatt ttgtgtttcc accagccttt tggctagtgc ctgtaccata   1800
gatcttttttg gttaccctga gtttggtagt ggtgttaagt ttacgtccct ttactttcaa   1860
ttcacaaagg gtgagttgat tactggcacg cctaaaccac ttgaaggtgt cacggacgtt   1920
tcttttatga ctctggatgt gtgtaccaag tatactatct atggctttaa aggtgagggt   1980
atcattaccc ttacaaattc tagctttttg gcaggtgttt attacacatc tgattctgga   2040
cagttgttag cctttaagaa tgtcactagt ggtgctgttt attctgttac gccatgttct   2100
ttttcagagc aggctgcata tgttgatgat gatatagtgg gtgttatttc tagtttgtct   2160
agctccactt ttaacagtac tagggagttg cctggtttct tctaccattc taatgatggc   2220
tctaattgta cagagcctgt gttggtgtat agtaacatag gtgtttgtaa atctggcagt   2280
attggctacg tcccatctca gtctggccaa gtcaagattg cacccacggt tactgggaat   2340
attagtattc ccaccaactt tagtatgagt attaggacag aatatttaca gctttacaac   2400
acgcctgtta gtgttgattg tgccacatat gtttgtaatg gtaactctcg ttgtaaacaa   2460
ttactcaccc agtacactgc agcatgtaag accatagagt cagcattaca actcagcgct   2520
aggcttgagt ctgttgaagt taactctatg cttactattt ctgaagaggc tctacagtta   2580
gctaccatta gttcgtttaa tggtgatgga tataatttta ctaatgtgct gggtgtttct   2640
gtgtatgatc ctgcaagtgg cagggtggta caaaaaaggt cttttattga agacctgctt   2700
tttaataaag tggttactaa tggccttggt actgttgatg aagactataa gcgctgttct   2760
aatggtcgct ctgtggcaga tctagtctgt gcacagtatt actctggtgt catggtacta   2820
cctggtgttg ttgacgctga gaagcttcac atgtatagtg cgtctctcat cggtggtatg   2880
gtgctaggag gttttacttc tgcagcggca ttgcctttta gctatgctgt tcaagctaga   2940
ctcaattatc ttgctctaca gacggatgtt ctacagcgga accagcaatt gcttgctgag   3000
tcttttaact ctgctattgg taatataact tcagcctttg agagtgttaa agaggctatt   3060
agtcaaactt ccaagggttt gaacactgtg gctcatgcgc ttactaaggt tcaagaggtt   3120
gttaactcgc agggtgcagc tttgactcaa cttaccgtac agctgcaaca caacttccaa   3180
gccatttcta gttctattga tgacatttac tctcgactgg acattctttc agccgatgtt   3240
caggttgacc gtctcatcac cggcagatta tcagcactta atgcttttgt tgctcaaacc   3300
ctcactaagt atactgaggt tcaggctagc aggaagttag cacagcaaaa ggttaatgag   3360
tgcgttaaat cgcaatctca gcgttatggt ttttgtggtg gtgatggcga gcacattttc   3420
tctctggtac aggcagcacc tcagggcctg ctgtttttac atacagtact tgtaccgagt   3480
gattttgtag atgttattgc catcgctggc ttatgcgtta acgatgaaat tgccttgact   3540
ctacgtgagc ctggcttagt cttgtttacg catgaacttc aaaatcatac tgcgacggaa   3600
tattttgttt catcgcgacg tatgtttgaa cctagaaaac ctaccgttag tgattttgtt   3660
caaattgaga gttgtgtggt cacctatgtc aatttgacta gagaccaact accagatgta   3720
atcccagatt acatcgatgt taacaaaaca cttgatgaga ttttagcttc tctgcccaat   3780
agaactggtc caagtcttcc tttagatgtt tttaatgcca cttatcttaa tctcactggt   3840
gaaattgcag atttagagca gcgttcagag tctctccgta atactacaga ggagctccaa   3900
agtcttatat ataatatcaa caacacacta gttgaccttg agtggctcaa ccgagttgag   3960
```

```
acatatatca agtggccgtg gtgggtttgg ttgattattt tcattgttct catctttgtt   4020

gtgtcattac tagtgttcag aaaccgcaat cgtcagtact aa                      4062


<210> SEQ ID NO 47
<211> LENGTH: 1353
<212> TYPE: PRT
<213> ORGANISM: Artificial Sequence
<220> FEATURE:
<223> OTHER INFORMATION: PEDVS 2a BD Amino Acid from Expression Casette

<400> SEQUENCE: 47

Met Val Ser Ala Ile Val Leu Tyr Val Leu Leu Ala Ala Ala Ala His
1               5                   10                  15

Ser Ala Phe Ala Asp Val Thr Arg Cys Ser Ala Asn Thr Asn Phe Arg
            20                  25                  30

Arg Phe Phe Ser Lys Phe Asn Val Gln Ala Pro Ala Val Val Val Leu
        35                  40                  45

Gly Gly Tyr Leu Pro Ile Gly Glu Asn Gln Gly Val Asn Ser Thr Trp
    50                  55                  60

Tyr Cys Ala Gly Gln His Pro Thr Ala Ser Gly Val His Gly Ile Phe
65                  70                  75                  80

Val Ser His Ile Arg Gly Gly His Gly Phe Glu Ile Gly Ile Ser Gln
                85                  90                  95

Glu Pro Phe Asp Pro Ser Gly Tyr Gln Leu Tyr Leu His Lys Ala Thr
            100                 105                 110

Asn Gly Asn Thr Asn Ala Thr Ala Arg Leu Arg Ile Cys Gln Phe Pro
        115                 120                 125

Ser Ile Lys Thr Leu Gly Pro Thr Ala Asn Asn Asp Val Thr Thr Gly
    130                 135                 140

Arg Asn Cys Leu Phe Asn Lys Ala Ile Pro Ala His Met Ser Glu His
145                 150                 155                 160

Ser Val Val Gly Ile Thr Trp Asp Asn Asp Arg Val Thr Val Phe Ser
                165                 170                 175

Asp Lys Ile Tyr Tyr Phe Tyr Phe Lys Asn Asp Trp Ser Arg Val Ala
            180                 185                 190

Thr Lys Cys Tyr Asn Ser Gly Gly Cys Ala Met Gln Tyr Val Tyr Glu
        195                 200                 205

Pro Thr Tyr Tyr Met Leu Asn Val Thr Ser Ala Gly Glu Asp Gly Ile
    210                 215                 220

Ser Tyr Gln Pro Cys Thr Ala Asn Cys Ile Gly Tyr Ala Ala Asn Val
225                 230                 235                 240

Phe Ala Thr Glu Pro Asn Gly His Ile Pro Glu Gly Phe Ser Phe Asn
                245                 250                 255

Asn Trp Phe Leu Leu Ser Asn Asp Ser Thr Leu Val His Gly Lys Val
            260                 265                 270

Val Ser Asn Gln Pro Leu Leu Val Asn Cys Leu Leu Ala Ile Pro Lys
        275                 280                 285

Ile Tyr Gly Leu Gly Gln Phe Phe Ser Phe Asn Gln Thr Ile Asp Gly
    290                 295                 300

Val Cys Asn Gly Ala Ala Val Gln Arg Ala Pro Glu Ala Leu Arg Phe
305                 310                 315                 320

Asn Ile Asn Asp Thr Ser Val Ile Leu Ala Glu Gly Ser Ile Val Leu
                325                 330                 335

His Thr Ala Leu Gly Thr Asn Phe Ser Phe Val Cys Ser Asn Ser Ser
            340                 345                 350
```

```
Asn Pro His Leu Ala Thr Phe Ala Ile Pro Leu Gly Ala Thr Gln Val
        355                 360                 365

Pro Tyr Tyr Cys Phe Leu Lys Val Asp Thr Tyr Asn Ser Thr Val Tyr
    370                 375                 380

Lys Phe Leu Ala Val Leu Pro Pro Thr Val Arg Glu Ile Val Ile Thr
385                 390                 395                 400

Lys Tyr Gly Asp Val Tyr Val Asn Gly Phe Gly Tyr Leu His Leu Gly
                405                 410                 415

Leu Leu Asp Ala Val Thr Ile Asn Phe Thr Gly His Gly Thr Asp Asp
            420                 425                 430

Asp Val Ser Gly Phe Trp Thr Ile Ala Ser Thr Asn Phe Val Asp Ala
        435                 440                 445

Leu Ile Glu Val Gln Gly Thr Ala Ile Gln Arg Ile Leu Tyr Cys Asp
    450                 455                 460

Asp Pro Val Ser Gln Leu Lys Cys Ser Gln Val Ala Phe Asp Leu Asp
465                 470                 475                 480

Asp Gly Phe Tyr Pro Ile Ser Ser Arg Asn Leu Leu Ser His Glu Gln
                485                 490                 495

Pro Ile Ser Phe Val Thr Leu Pro Ser Phe Asn Asp His Ser Phe Val
            500                 505                 510

Asn Ile Thr Val Ser Ala Ser Phe Gly Gly His Ser Gly Ala Asn Leu
        515                 520                 525

Ile Ala Ser Asp Thr Thr Ile Asn Gly Phe Ser Ser Phe Cys Val Asp
    530                 535                 540

Thr Arg Gln Phe Thr Ile Ser Leu Phe Tyr Asn Val Thr Asn Ser Tyr
545                 550                 555                 560

Gly Tyr Val Ser Lys Ser Gln Asp Ser Asn Cys Pro Phe Thr Leu Gln
                565                 570                 575

Ser Val Asn Asp Tyr Leu Ser Phe Ser Lys Phe Cys Val Ser Thr Ser
            580                 585                 590

Leu Leu Ala Ser Ala Cys Thr Ile Asp Leu Phe Gly Tyr Pro Glu Phe
        595                 600                 605

Gly Ser Gly Val Lys Phe Thr Ser Leu Tyr Phe Gln Phe Thr Lys Gly
    610                 615                 620

Glu Leu Ile Thr Gly Thr Pro Lys Pro Leu Glu Gly Val Thr Asp Val
625                 630                 635                 640

Ser Phe Met Thr Leu Asp Val Cys Thr Lys Tyr Thr Ile Tyr Gly Phe
                645                 650                 655

Lys Gly Glu Gly Ile Ile Thr Leu Thr Asn Ser Ser Phe Leu Ala Gly
            660                 665                 670

Val Tyr Tyr Thr Ser Asp Ser Gly Gln Leu Leu Ala Phe Lys Asn Val
        675                 680                 685

Thr Ser Gly Ala Val Tyr Ser Val Thr Pro Cys Ser Phe Ser Glu Gln
    690                 695                 700

Ala Ala Tyr Val Asp Asp Asp Ile Val Gly Val Ile Ser Ser Leu Ser
705                 710                 715                 720

Ser Ser Thr Phe Asn Ser Thr Arg Glu Leu Pro Gly Phe Phe Tyr His
                725                 730                 735

Ser Asn Asp Gly Ser Asn Cys Thr Glu Pro Val Leu Val Tyr Ser Asn
            740                 745                 750

Ile Gly Val Cys Lys Ser Gly Ser Ile Gly Tyr Val Pro Ser Gln Ser
        755                 760                 765
```

-continued

```
Gly Gln Val Lys Ile Ala Pro Thr Val Thr Gly Asn Ile Ser Ile Pro
    770                 775                 780

Thr Asn Phe Ser Met Ser Ile Arg Thr Glu Tyr Leu Gln Leu Tyr Asn
785                 790                 795                 800

Thr Pro Val Ser Val Asp Cys Ala Thr Tyr Val Cys Asn Gly Asn Ser
                805                 810                 815

Arg Cys Lys Gln Leu Leu Thr Gln Tyr Thr Ala Ala Cys Lys Thr Ile
            820                 825                 830

Glu Ser Ala Leu Gln Leu Ser Ala Arg Leu Glu Ser Val Glu Val Asn
        835                 840                 845

Ser Met Leu Thr Ile Ser Glu Glu Ala Leu Gln Leu Ala Thr Ile Ser
    850                 855                 860

Ser Phe Asn Gly Asp Gly Tyr Asn Phe Thr Asn Val Leu Gly Val Ser
865                 870                 875                 880

Val Tyr Asp Pro Ala Ser Gly Arg Val Val Gln Lys Arg Ser Phe Ile
                885                 890                 895

Glu Asp Leu Leu Phe Asn Lys Val Val Thr Asn Gly Leu Gly Thr Val
            900                 905                 910

Asp Glu Asp Tyr Lys Arg Cys Ser Asn Gly Arg Ser Val Ala Asp Leu
        915                 920                 925

Val Cys Ala Gln Tyr Tyr Ser Gly Val Met Val Leu Pro Gly Val Val
    930                 935                 940

Asp Ala Glu Lys Leu His Met Tyr Ser Ala Ser Leu Ile Gly Gly Met
945                 950                 955                 960

Val Leu Gly Gly Phe Thr Ser Ala Ala Ala Leu Pro Phe Ser Tyr Ala
                965                 970                 975

Val Gln Ala Arg Leu Asn Tyr Leu Ala Leu Gln Thr Asp Val Leu Gln
            980                 985                 990

Arg Asn Gln Gln Leu Leu Ala Glu  Ser Phe Asn Ser Ala  Ile Gly Asn
        995                 1000                1005

Ile Thr  Ser Ala Phe Glu Ser  Val Lys Glu Ala Ile  Ser Gln Thr
    1010                1015                1020

Ser Lys  Gly Leu Asn Thr Val  Ala His Ala Leu Thr  Lys Val Gln
    1025                1030                1035

Glu Val  Val Asn Ser Gln Gly  Ala Ala Leu Thr Gln  Leu Thr Val
    1040                1045                1050

Gln Leu  Gln His Asn Phe Gln  Ala Ile Ser Ser Ser  Ile Asp Asp
    1055                1060                1065

Ile Tyr  Ser Arg Leu Asp Ile  Leu Ser Ala Asp Val  Gln Val Asp
    1070                1075                1080

Arg Leu  Ile Thr Gly Arg Leu  Ser Ala Leu Asn Ala  Phe Val Ala
    1085                1090                1095

Gln Thr  Leu Thr Lys Tyr Thr  Glu Val Gln Ala Ser  Arg Lys Leu
    1100                1105                1110

Ala Gln  Gln Lys Val Asn Glu  Cys Val Lys Ser Gln  Ser Gln Arg
    1115                1120                1125

Tyr Gly  Phe Cys Gly Gly Asp  Gly Glu His Ile Phe  Ser Leu Val
    1130                1135                1140

Gln Ala  Ala Pro Gln Gly Leu  Leu Phe Leu His Thr  Val Leu Val
    1145                1150                1155

Pro Ser  Asp Phe Val Asp Val  Ile Ala Ile Ala Gly  Leu Cys Val
    1160                1165                1170

Asn Asp  Glu Ile Ala Leu Thr  Leu Arg Glu Pro Gly  Leu Val Leu
```

-continued

```
    1175                1180                1185

Phe Thr  His Glu Leu Gln Asn  His Thr Ala Thr Glu  Tyr Phe Val
    1190                1195                1200

Ser Ser  Arg Arg Met Phe Glu  Pro Arg Lys Pro Thr  Val Ser Asp
    1205                1210                1215

Phe Val  Gln Ile Glu Ser Cys  Val Val Thr Tyr Val  Asn Leu Thr
    1220                1225                1230

Arg Asp  Gln Leu Pro Asp Val  Ile Pro Asp Tyr Ile  Asp Val Asn
    1235                1240                1245

Lys Thr  Leu Asp Glu Ile Leu  Ala Ser Leu Pro Asn  Arg Thr Gly
    1250                1255                1260

Pro Ser  Leu Pro Leu Asp Val  Phe Asn Ala Thr Tyr  Leu Asn Leu
    1265                1270                1275

Thr Gly  Glu Ile Ala Asp Leu  Glu Gln Arg Ser Glu  Ser Leu Arg
    1280                1285                1290

Asn Thr  Thr Glu Glu Leu Gln  Ser Leu Ile Tyr Asn  Ile Asn Asn
    1295                1300                1305

Thr Leu  Val Asp Leu Glu Trp  Leu Asn Arg Val Glu  Thr Tyr Ile
    1310                1315                1320

Lys Trp  Pro Trp Trp Val Trp  Leu Ile Ile Phe Ile  Val Leu Ile
    1325                1330                1335

Phe Val  Val Ser Leu Leu Val  Phe Arg Asn Arg Asn  Arg Gln Tyr
    1340                1345                1350
```

<210> SEQ ID NO 48
<211> LENGTH: 22
<212> TYPE: DNA
<213> ORGANISM: Artificial Sequence
<220> FEATURE:
<223> OTHER INFORMATION: P290194A PEDV 2b BD- FORWARD PRIMER N-terminal fragment

<400> SEQUENCE: 48
ggatccgcca ccatggtatc tg 22

<210> SEQ ID NO 49
<211> LENGTH: 25
<212> TYPE: DNA
<213> ORGANISM: Artificial Sequence
<220> FEATURE:
<223> OTHER INFORMATION: P3183131B PEDV 2b BD- Reverse PRIMER N-terminal fragment

<400> SEQUENCE: 49
gtcgatgcta tggtccaaaa accag 25

<210> SEQ ID NO 50
<211> LENGTH: 22
<212> TYPE: DNA
<213> ORGANISM: Artificial Sequence
<220> FEATURE:
<223> OTHER INFORMATION: P3183131A PEDV 2b BD- FORWARD PRIMER C-terminal fragment

<400> SEQUENCE: 50
ggatccgcca ccatggtatc tg 22

<210> SEQ ID NO 51
<211> LENGTH: 21
<212> TYPE: DNA
<213> ORGANISM: Artificial Sequence -continued
<220> FEATURE:
<223> OTHER INFORMATION: P290194B PEDV 2b BD- REVERSE PRIMER C-terminal fragment

<400> SEQUENCE: 51
gcttaaatac atatttagta c 21

<210> SEQ ID NO 52
<211> LENGTH: 4053
<212> TYPE: DNA
<213> ORGANISM: Artificial Sequence
<220> FEATURE:
<223> OTHER INFORMATION: PEDVS 2b BD CDS cDNA

<400> SEQUENCE: 52
atggtatctg ctattgttct ttatgttttg cttgctgccg ccgctcactc agctttcgcg 60
gatgtcacta ggtgccagtc cactattaac ttcaggcggt tcttttcaaa atttaatgtg 120
caggcacctg ctgtcgttgt gttgggtggt tatctaccta gtatgaactc ctctagctgg 180
tactgtggca caggtcttga aactgctagt ggcgtgcatg gtatttttcct cagttacatc 240 gattctggtc agggctttga gattggcatt tcacaggagc cgtttgatcc tagtggttac 300
cagctttatt tacataaggc cactaatggt aaccataatg ctattgcacg actgcgcatt 360
tgccagtttc caaataataa tacattgggc cctactgtta atgatgttac aacaggtcgt 420
aactgcctat tcaacaaagc cattccagct tatatgcagg atggaaaaaa catcgttgtc 480
ggcataacat gggacaatga tcgtgtcact gtttttgctg acaagatcta tcatttttat 540
ctcaaaaatg attggtcccg tgttgcgaca agatgttaca ataaaagaag ttgtgctatg 600
caatatgttt atacacctac ctactacatg cttaatgtta ctagtgcagg tgaggatggc 660
atttattatg aaccatgtac agctaattgc agtggttacg ctgccaatgt gtttgccact 720
gattctaatg gccacatacc agaaggtttt agttttaata attggtttct tttgtccaat 780
gattccactt tgttgcatgg taaggtggtt tccaaccaac ctttgttggt caattgtctt 840
ttggccattc ctaagattta tggactaggc caatttttct cattcaatca aacgatggat 900
ggcgtttgta atggagctgc tgcgcagcgt gcaccagagg ctctgaggtt taatattaat 960
gacacctctg tcattcttgc tgaaggctca attgtacttc acactgcttt aggaacaaat 1020
ctttcttttg tttgcagtaa ttcttcagat cctcatttag ctaccttcac catacctctg 1080
ggtgctaccc aagtacccta ttattgtttt cttaaagtgg atacttacaa ctccactgtt 1140
tataaatttt tggctgtttt acctcctacc gtcagggaaa ttgtcatcac caagtatggt 1200
gatgtttatg tcaatgggtt tggatacttg catctcggtt tgttggatgc tgtcacaatt 1260
aatttcactg gtcatggcac tgacgatgat gtttctggtt tttggaccat agcatcgact 1320
aattttgttg atgcactcat cgaagttcaa ggaaccgcca ttcagcgtat tctttattgt 1380
gatgatcctg ttagccaact caagtgttct caggttgctt ttgaccttga cgatggtttt 1440
taccctattt cttctagaaa ccttctgagt catgaacagc caatttcttt tgttactctg 1500
ccatcattta atgatcattc ttttgttaac attactgtat ctgcttcctt tggtggtcat 1560
agtggtgcca accttattgc atctgacact actatcaatg ggtttagttc tttctgtgtt 1620
gacactagac aatttaccat ttcactgttt tataacgtta caaacagtta tggttatgtg 1680
tctaaatcac aggacagtaa ttgccctttc accttgcaat ctgttaatga ttacctgtct 1740
tttagcaaat tttgtgtttc caccagcctt ttggctagtg cctgtaccat agatcttttt 1800
ggttaccctg agtttggtag tggtgttaag tttacgtccc tttactttca attcacaaag 1860
ggtgagttga ttactggcac gcctaaacca cttgaaggtg tcacggacgt ttcttttatg 1920
actctggatg tgtgtaccaa gtatactatc tatggcttta aaggtgaggg tatcattacc 1980
cttacaaatt ctagcttttt ggcaggtgtt tattacacat ctgattctgg acagttgtta 2040
gcctttaaga atgtcactag tggtgctgtt tattctgtta cgccatgttc tttttcagag 2100
caggctgcat atgttgatga tgatatagtg ggtgttattt ctagtttgtc tagctccact 2160
tttaacagta ctagggagtt gcctggtttc ttctaccatt ctaatgatgg ctctaattgt 2220
acagagcctg tgttggtgta tagtaacata ggtgtttgta aatctggcag tattggctac 2280
gtcccatctc agtctggcca agtcaagatt gcacccacgg ttactgggaa tattagtatt 2340
cccaccaact ttagtatgag tattaggaca gaatatttac agctttacaa cacgcctgtt 2400
agtgttgatt gtgccacata tgtttgtaat ggtaactctc gttgtaaaca attactcacc 2460
cagtacactg cagcatgtaa gaccatagag tcagcattac aactcagcgc taggcttgag 2520
tctgttgaag ttaactctat gcttactatt tctgaagagg ctctacagtt agctaccatt 2580
agttcgttta atggtgatgg atataatttt actaatgtgc tgggtgtttc tgtgtatgat 2640
cctgcaagtg gcagggtggt acaaaaaagg tcttttattg aagacctgct tttaataaa 2700
gtggttacta atggccttgg tactgttgat gaagactata agcgctgttc taatggtcgc 2760
tctgtggcag atctagtctg tgcacagtat tactctggtg tcatggtact acctggtgtt 2820
gttgacgctg agaagcttca catgtatagt gcgtctctca tcggtggtat ggtgctagga 2880
ggttttactt ctgcagcggc attgcctttt agctatgctg ttcaagctag actcaattat 2940
cttgctctac agacggatgt tctacagcgg aaccagcaat tgcttgctga gtcttttaac 3000
tctgctattg gtaatataac ttcagccttt gagagtgtta aagaggctat tagtcaaact 3060
tccaagggtt tgaacactgt ggctcatgcg cttactaagg ttcaagaggt tgttaactcg 3120
cagggtgcag ctttgactca acttaccgta cagctgcaac acaacttcca agccatttct 3180
agttctattg atgacattta ctctcgactg gacattcttt cagccgatgt tcaggttgac 3240
cgtctcatca ccggcagatt atcagcactt aatgcttttg ttgctcaaac cctcactaag 3300
tatactgagg ttcaggctag caggaagtta gcacagcaaa aggttaatga gtgcgttaaa 3360
tcgcaatctc agcgttatgg tttttgtggt ggtgatggcg agcacatttt ctctctggta 3420
caggcagcac ctcagggcct gctgttttta catacagtac ttgtaccgag tgattttgta 3480
gatgttattg ccatcgctgg cttatgcgtt aacgatgaaa ttgccttgac tctacgtgag 3540
cctggcttag tcttgtttac gcatgaactt caaaatcata ctgcgacgga atattttgtt 3600
tcatcgcgac gtatgtttga acctagaaaa cctaccgtta gtgattttgt tcaaattgag 3660
agttgtgtgg tcacctatgt caatttgact agagaccaac taccagatgt aatcccagat 3720
tacatcgatg ttaacaaaac acttgatgag attttagctt ctctgcccaa tagaactggt 3780
ccaagtcttc ctttagatgt ttttaatgcc acttatctta atctcactgg tgaaattgca 3840
gatttagagc agcgttcaga gtctctccgt aatactacag aggagctcca aagtcttata 3900
tataatatca acaacacact agttgacctt gagtggctca accgagttga gacatatatc 3960
aagtggccgt ggtgggtttg gttgattatt ttcattgttc tcatctttgt tgtgtcatta 4020
ctagtgttca gaaaccgcaa tcgtcagtac taa 4053

<210> SEQ ID NO 53
<211> LENGTH: 1350
<212> TYPE: PRT

```
<213> ORGANISM: Artificial Sequence
<220> FEATURE:
<223> OTHER INFORMATION: PEDVS 2b BD Expression Casetter Amino Acid
      Sequence

<400> SEQUENCE: 53

Met Val Ser Ala Ile Val Leu Tyr Val Leu Leu Ala Ala Ala Ala His
1               5                   10                  15

Ser Ala Phe Ala Asp Val Thr Arg Cys Gln Ser Thr Ile Asn Phe Arg
            20                  25                  30

Arg Phe Phe Ser Lys Phe Asn Val Gln Ala Pro Ala Val Val Val Leu
        35                  40                  45

Gly Gly Tyr Leu Pro Ser Met Asn Ser Ser Ser Trp Tyr Cys Gly Thr
    50                  55                  60

Gly Leu Glu Thr Ala Ser Gly Val His Gly Ile Phe Leu Ser Tyr Ile
65                  70                  75                  80

Asp Ser Gly Gln Gly Phe Glu Ile Gly Ile Ser Gln Glu Pro Phe Asp
                85                  90                  95

Pro Ser Gly Tyr Gln Leu Tyr Leu His Lys Ala Thr Asn Gly Asn His
            100                 105                 110

Asn Ala Ile Ala Arg Leu Arg Ile Cys Gln Phe Pro Asn Asn Asn Thr
        115                 120                 125

Leu Gly Pro Thr Val Asn Asp Val Thr Thr Gly Arg Asn Cys Leu Phe
    130                 135                 140

Asn Lys Ala Ile Pro Ala Tyr Met Gln Asp Gly Lys Asn Ile Val Val
145                 150                 155                 160

Gly Ile Thr Trp Asp Asn Asp Arg Val Thr Val Phe Ala Asp Lys Ile
                165                 170                 175

Tyr His Phe Tyr Leu Lys Asn Asp Trp Ser Arg Val Ala Thr Arg Cys
            180                 185                 190

Tyr Asn Lys Arg Ser Cys Ala Met Gln Tyr Val Tyr Thr Pro Thr Tyr
        195                 200                 205

Tyr Met Leu Asn Val Thr Ser Ala Gly Glu Asp Gly Ile Tyr Tyr Glu
    210                 215                 220

Pro Cys Thr Ala Asn Cys Ser Gly Tyr Ala Ala Asn Val Phe Ala Thr
225                 230                 235                 240

Asp Ser Asn Gly His Ile Pro Glu Gly Phe Ser Phe Asn Asn Trp Phe
                245                 250                 255

Leu Leu Ser Asn Asp Ser Thr Leu Leu His Gly Lys Val Val Ser Asn
            260                 265                 270

Gln Pro Leu Leu Val Asn Cys Leu Leu Ala Ile Pro Lys Ile Tyr Gly
        275                 280                 285

Leu Gly Gln Phe Phe Ser Phe Asn Gln Thr Met Asp Gly Val Cys Asn
    290                 295                 300

Gly Ala Ala Ala Gln Arg Ala Pro Glu Ala Leu Arg Phe Asn Ile Asn
305                 310                 315                 320

Asp Thr Ser Val Ile Leu Ala Glu Gly Ser Ile Val Leu His Thr Ala
                325                 330                 335

Leu Gly Thr Asn Leu Ser Phe Val Cys Ser Asn Ser Ser Asp Pro His
            340                 345                 350

Leu Ala Thr Phe Thr Ile Pro Leu Gly Ala Thr Gln Val Pro Tyr Tyr
        355                 360                 365

Cys Phe Leu Lys Val Asp Thr Tyr Asn Ser Thr Val Tyr Lys Phe Leu
    370                 375                 380
```

-continued

```
Ala Val Leu Pro Pro Thr Val Arg Glu Ile Val Ile Thr Lys Tyr Gly
385                 390                 395                 400

Asp Val Tyr Val Asn Gly Phe Gly Tyr Leu His Leu Gly Leu Leu Asp
                405                 410                 415

Ala Val Thr Ile Asn Phe Thr Gly His Gly Thr Asp Asp Asp Val Ser
            420                 425                 430

Gly Phe Trp Thr Ile Ala Ser Thr Asn Phe Val Asp Ala Leu Ile Glu
        435                 440                 445

Val Gln Gly Thr Ala Ile Gln Arg Ile Leu Tyr Cys Asp Asp Pro Val
    450                 455                 460

Ser Gln Leu Lys Cys Ser Gln Val Ala Phe Asp Leu Asp Asp Gly Phe
465                 470                 475                 480

Tyr Pro Ile Ser Ser Arg Asn Leu Leu Ser His Glu Gln Pro Ile Ser
                485                 490                 495

Phe Val Thr Leu Pro Ser Phe Asn Asp His Ser Phe Val Asn Ile Thr
            500                 505                 510

Val Ser Ala Ser Phe Gly Gly His Ser Gly Ala Asn Leu Ile Ala Ser
        515                 520                 525

Asp Thr Thr Ile Asn Gly Phe Ser Ser Phe Cys Val Asp Thr Arg Gln
    530                 535                 540

Phe Thr Ile Ser Leu Phe Tyr Asn Val Thr Asn Ser Tyr Gly Tyr Val
545                 550                 555                 560

Ser Lys Ser Gln Asp Ser Asn Cys Pro Phe Thr Leu Gln Ser Val Asn
                565                 570                 575

Asp Tyr Leu Ser Phe Ser Lys Phe Cys Val Ser Thr Ser Leu Leu Ala
            580                 585                 590

Ser Ala Cys Thr Ile Asp Leu Phe Gly Tyr Pro Glu Phe Gly Ser Gly
        595                 600                 605

Val Lys Phe Thr Ser Leu Tyr Phe Gln Phe Thr Lys Gly Glu Leu Ile
    610                 615                 620

Thr Gly Thr Pro Lys Pro Leu Glu Gly Val Thr Asp Val Ser Phe Met
625                 630                 635                 640

Thr Leu Asp Val Cys Thr Lys Tyr Thr Ile Tyr Gly Phe Lys Gly Glu
                645                 650                 655

Gly Ile Ile Thr Leu Thr Asn Ser Ser Phe Leu Ala Gly Val Tyr Tyr
            660                 665                 670

Thr Ser Asp Ser Gly Gln Leu Leu Ala Phe Lys Asn Val Thr Ser Gly
        675                 680                 685

Ala Val Tyr Ser Val Thr Pro Cys Ser Phe Ser Glu Gln Ala Ala Tyr
    690                 695                 700

Val Asp Asp Asp Ile Val Gly Val Ile Ser Ser Leu Ser Ser Ser Thr
705                 710                 715                 720

Phe Asn Ser Thr Arg Glu Leu Pro Gly Phe Phe Tyr His Ser Asn Asp
                725                 730                 735

Gly Ser Asn Cys Thr Glu Pro Val Leu Val Tyr Ser Asn Ile Gly Val
            740                 745                 750

Cys Lys Ser Gly Ser Ile Gly Tyr Val Pro Ser Gln Ser Gly Gln Val
        755                 760                 765

Lys Ile Ala Pro Thr Val Thr Gly Asn Ile Ser Ile Pro Thr Asn Phe
    770                 775                 780

Ser Met Ser Ile Arg Thr Glu Tyr Leu Gln Leu Tyr Asn Thr Pro Val
785                 790                 795                 800

Ser Val Asp Cys Ala Thr Tyr Val Cys Asn Gly Asn Ser Arg Cys Lys
```

-continued

```
                805                 810                 815

Gln Leu Leu Thr Gln Tyr Thr Ala Ala Cys Lys Thr Ile Glu Ser Ala
            820                 825                 830

Leu Gln Leu Ser Ala Arg Leu Glu Ser Val Glu Val Asn Ser Met Leu
        835                 840                 845

Thr Ile Ser Glu Glu Ala Leu Gln Leu Ala Thr Ile Ser Ser Phe Asn
    850                 855                 860

Gly Asp Gly Tyr Asn Phe Thr Asn Val Leu Gly Val Ser Val Tyr Asp
865                 870                 875                 880

Pro Ala Ser Gly Arg Val Val Gln Lys Arg Ser Phe Ile Glu Asp Leu
                885                 890                 895

Leu Phe Asn Lys Val Val Thr Asn Gly Leu Gly Thr Val Asp Glu Asp
            900                 905                 910

Tyr Lys Arg Cys Ser Asn Gly Arg Ser Val Ala Asp Leu Val Cys Ala
        915                 920                 925

Gln Tyr Tyr Ser Gly Val Met Val Leu Pro Gly Val Val Asp Ala Glu
    930                 935                 940

Lys Leu His Met Tyr Ser Ala Ser Leu Ile Gly Gly Met Val Leu Gly
945                 950                 955                 960

Gly Phe Thr Ser Ala Ala Ala Leu Pro Phe Ser Tyr Ala Val Gln Ala
                965                 970                 975

Arg Leu Asn Tyr Leu Ala Leu Gln Thr Asp Val Leu Gln Arg Asn Gln
            980                 985                 990

Gln Leu Leu Ala Glu Ser Phe Asn  Ser Ala Ile Gly Asn  Ile Thr Ser
        995                 1000                 1005

Ala Phe  Glu Ser Val Lys Glu  Ala Ile Ser Gln Thr  Ser Lys Gly
    1010                 1015                 1020

Leu Asn  Thr Val Ala His Ala  Leu Thr Lys Val Gln  Glu Val Val
    1025                 1030                 1035

Asn Ser  Gln Gly Ala Ala Leu  Thr Gln Leu Thr Val  Gln Leu Gln
    1040                 1045                 1050

His Asn  Phe Gln Ala Ile Ser  Ser Ser Ile Asp Asp  Ile Tyr Ser
    1055                 1060                 1065

Arg Leu  Asp Ile Leu Ser Ala  Asp Val Gln Val Asp  Arg Leu Ile
    1070                 1075                 1080

Thr Gly  Arg Leu Ser Ala Leu  Asn Ala Phe Val Ala  Gln Thr Leu
    1085                 1090                 1095

Thr Lys  Tyr Thr Glu Val Gln  Ala Ser Arg Lys Leu  Ala Gln Gln
    1100                 1105                 1110

Lys Val  Asn Glu Cys Val Lys  Ser Gln Ser Gln Arg  Tyr Gly Phe
    1115                 1120                 1125

Cys Gly  Gly Asp Gly Glu His  Ile Phe Ser Leu Val  Gln Ala Ala
    1130                 1135                 1140

Pro Gln  Gly Leu Leu Phe Leu  His Thr Val Leu Val  Pro Ser Asp
    1145                 1150                 1155

Phe Val  Asp Val Ile Ala Ile  Ala Gly Leu Cys Val  Asn Asp Glu
    1160                 1165                 1170

Ile Ala  Leu Thr Leu Arg Glu  Pro Gly Leu Val Leu  Phe Thr His
    1175                 1180                 1185

Glu Leu  Gln Asn His Thr Ala  Thr Glu Tyr Phe Val  Ser Ser Arg
    1190                 1195                 1200

Arg Met  Phe Glu Pro Arg Lys  Pro Thr Val Ser Asp  Phe Val Gln
    1205                 1210                 1215
```

-continued

```
Ile Glu  Ser Cys Val Val Thr  Tyr Val Asn Leu Thr  Arg Asp Gln
    1220                 1225                 1230

Leu Pro  Asp Val Ile Pro Asp  Tyr Ile Asp Val Asn  Lys Thr Leu
    1235                 1240                 1245

Asp Glu  Ile Leu Ala Ser Leu  Pro Asn Arg Thr Gly  Pro Ser Leu
    1250                 1255                 1260

Pro Leu  Asp Val Phe Asn Ala  Thr Tyr Leu Asn Leu  Thr Gly Glu
    1265                 1270                 1275

Ile Ala  Asp Leu Glu Gln Arg  Ser Glu Ser Leu Arg  Asn Thr Thr
    1280                 1285                 1290

Glu Glu  Leu Gln Ser Leu Ile  Tyr Asn Ile Asn Asn  Thr Leu Val
    1295                 1300                 1305

Asp Leu  Glu Trp Leu Asn Arg  Val Glu Thr Tyr Ile  Lys Trp Pro
    1310                 1315                 1320

Trp Trp  Val Trp Leu Ile Ile  Phe Ile Val Leu Ile  Phe Val Val
    1325                 1330                 1335

Ser Leu  Leu Val Phe Arg Asn  Arg Asn Arg Gln Tyr
    1340                 1345                 1350
```

PORCINE CORONAVIRUS VACCINES

CROSS-REFERENCE TO RELATED APPLICATIONS

This application is a national stage application of International Application No. PCT/US2018/015507, filed Jan. 26, 2018, which claims the benefit of U.S. Provisional Application No. 62/452,026, filed Jan. 30, 2017, the entire contents of which are hereby incorporated by reference herein.

SEQUENCE LISTING

This application contains a sequence listing in accordance with 37 C.F.R. 1.821-1.825. The content of the ASCII text file of the sequence listing named 10-0176-WO-1-SEQ which is 480 kb in size was created on Jan. 23, 2017 and electronically submitted via EFS-Web herewith the application is incorporated herein by reference in its entirety.

BACKGROUND OF THE INVENTION

Field of the Invention

The present invention relates to immunogenic compositions that protect swine from disease caused by porcine epidemic diarrhea virus (PEDV) vaccine specific and porcine deltacoronavirus (PDCoV), and combination vaccines providing both PEDV and PDCoV antigens. Due to the high mortality (up to 100%) in less than 10 day old piglets, the prevalent enteric diseases, often present together, are of major economic concern to the U.S. swine industry.

Description of the Related Art

The porcine epidemic diarrhea virus is an enveloped, positive-sense single-stranded RNA virus that causes acute diarrhea, vomiting, and dehydration in pigs. It was first identified in Europe but has become increasingly problematic in many Asian countries, including Korea, China, Japan, the Philippines, and Thailand. In April of 2013, PEDV emerged in U.S. swine in the Midwest, swiftly spreading across the country. By October 2013, PEDV was detected in swine herds in 18 States. The economic impact of PEDV infection has already been substantial. North American isolates of PEDV have been identified (Huang, et al. 2013; Stevenson et al. 2013), however no fully licensed vaccine is commercially available in the United States. Accordingly, there is a continuing need to develop vaccines capable of protecting pigs against disease associated with PEDV. It would be advantageous to develop a vaccine that is effective against emerging North American PEDV strains which could be administered via a mucosal route (oral or intranasal) as well as via parenteral methods (e.g., intramuscularly, subcutaneously or intravenously).

PEDV is a member of the subfamily Coronavirinae of genus Alphacoronavirus (Bridgen et al. 1993) and was first identified in England in 1971 and later in other countries, such as Belgium, China, Hungary, Italy, Japan, Korea, and Thailand (Oldham J. 1972; Pensaert and De Bouck P. 1978; Chen et al. 2008; Nagy et al. 1996; Martelli et al. 2008; Takahashi et al. 1983; Chae et al. 2000; and Puranaveja et al. 2009). Other members of this family include Porcine Respiratory Coronavirus (PRCV), Hemagglutinating Encephalomyelitis Coronavirus (PHE), and Transmissible Gastroenteritis Virus (TGEV). Although PEDV and TGEV viruses are related and the clinical signs are very similar, there is no immune cross-protection.

PEDV is an enveloped virus possessing approximately a 28 kb, positive-sense, single stranded RNA genome, with a 5' cap and a 3' polyadenylated tail. (Pensaert and De Bouck P. 1978). The genome comprises a 5' untranslated region (UTR), a 3' UTR, and at least seven open reading frames (ORFs) that encode four structural proteins (spike (S), envelope (E), membrane (M), and nucleocapsid (N)) and three non-structural proteins (replicases 1a and 1b and ORF3); these are arranged on the genome in the order 5'-replicase (1a/1b)-S-ORF3-E-M-N-3' (Oldham J. 1972; and Bridgen et al. 1993). The first three emergent North American PEDV genomic sequences characterized, Minnesota MN (GenBank: KF468752.1), Iowa IA1 (GenBank: KF468753.1), and Iowa IA2 (GenBank: KF468754.1), have the same size of 28,038 nucleotides (nt), excluding the polyadenosine tail and share the genome organization with the prototype PEDV CV777 strain (GenBank: AF353511.1). These three North American PEDV sequences shared 99.8 to 99.9% nucleotide identities. In particular, strains MN and IA2 had only 11 nucleotide differences across the entire genome.

The PEDV S protein is a type I glycoprotein composed of 1,383 amino acids (aa). The S protein can be divided into S1 (1-789 aa) and S2 (790-1,383 aa) domains based on its homology with S protein of other coronaviruses (Chang et al; 2002; Cruz et al, 1994; Godet, et al 1994; Jackwood et al. 2001; Sturman and Holmes; 1984; and Sun et al. 2008). The S protein in coronaviruses is a surface antigen, where it plays a role in regulating interactions with host cell receptor glycoproteins to mediate viral entry, and stimulating induction of neutralizing antibodies in the natural host. Thus the S glycoprotein is a primary target for the development of effective vaccines against PEDV.

The PEDV M protein is the most abundant envelope component playing an important role in the viral assembly process and also induces antibodies that neutralize the virus. Likewise the PEDV N protein, which binds to virion RNA providing a structural basis for the nucleocapsid, may also be important for induction of cell-mediated immunity (Saif, L. 1993).

The only accessory gene in PEDV is ORF3. While accessory genes are generally maintained in field strains, alteration of ORF3 is thought to influence virulence; cell culture adaptation has been used to alter the ORF3 gene in order to reduce virulence (Song et al. 2003). In fact, through investigation of the ORF3 gene, researchers have charted the emergence of new genogroups of PEDV in immunized swine herds in China since 2006. Phylogenic studies of these strains and the geographical reemergence of PEDV in China have demonstrated that those field strains causing devastating enteric disease differ genetically in ORF3 from the European strains and vaccine strains (Park et al. 2011).

It is well know that different strains of PEDV do exist with varying levels of virulence. During the 1980s and 1990s, PEDV was prevalent throughout Europe, in countries such as Belgium, England, Germany, France, the Netherlands, and Switzerland. The frequency of reported cases in Europe subsequently tapered off and/or the disease caused by PEDV was not of sufficient economic importance to start commercial development of a vaccine (Song and Park 2012). While outbreaks of PEDV have been documented in China since the 1980s, variant strains of PEDV emerging since 2010 associated with large-scale outbreaks of diarrhea have been more acute and severe. Thus the trial of vaccine development was mainly accomplished in Asian countries (Song and Park 2012). Variants emerging since 2010 have been reported as having 80-90% morbidity and 50-90% mortality in suckling piglets (Bi et al. 2012; Pan et al. 2012; and Li et al. 1012). Recent evidence suggests that the emerging virulent forms of PEDV in China may be a result of evolution of the live vaccine strains (Chen et al. 2010).

As an enteric disease affecting the pig's intestine, PEDV spreads via fecal-oral exposure. Contaminated trucks and equipment are frequent sources of infection to naïve animals. The clinical signs of PEDV infection are similar to transmissible gastroenteritis virus (TGEV) infection (Pijpers et al. 1993). In pigs three weeks of age and younger, clinical signs (including acute watery, diarrhea, vomiting, and dehydration) can be seen as soon as 24 hours after PEDV infection leading to 100% mortality. PEDV-infected feeder and grower pigs, as well as sows and boars, can develop diarrhea and vomiting. The animals can also show signs of anorexia and can be lethargic. The full impact on older pigs is yet to be determined, but reduced feed efficiency, additional days to market, and the susceptibility of infected animals to secondary infections is likely. For sows, reduced body condition may negatively impact reproductive performance. Reports have indicated that there are signs that PEDV could become endemic in North American herds, resulting in persistent diarrhea and other challenges.

The gross and histological changes in the gut of animals infected with PEDV are similar in the United States as those observed in China; essentially the virus destroys the villi of a pig's intestine so that there is a failure to absorb nutrients. Huang et al. 2012 reported that animals succumbing to the disease in the Minnesota and Iowa outbreaks had gross pathological lesions confined to the small intestine and that the small intestine was characterized by thin translucent walls distended with yellow fluid. Histological evaluations revealed regions of small intestines with villus blunting and fusion and minimal lymphoblastic infiltration of the villi of the lamia propria.

Huang et al. 2013 characterized three different strains of PEDV from outgoing outbreaks in the United States—one from Minnesota and two from Iowa, designated MN (GenBank accession No: KF468752) and IA1 (GenBank accession No: KF468753) and IA2 (GenBank accession No: KF48754), respectively. Huang's phylogenic survey grouped PEDV strains as falling into two distinct genogroups, designated genogroup 1 (G1) and genogroup 2 (G2). The significant changes in the N-terminal domain (NTD) of the spike gene differentiated genogroup 1 and 2. Huang et al. 2013 suggests that the second deletion region (DR2) in the N-terminal domain (NTD) appears to have a higher degree of antigenic change than DR1, suggesting that the emerging North American strains may be less "antigenically" related to the G1a vaccine strains.

Genogroup 1 includes at least three clusters 1a, 1b, and R. Subgroup 1a includes the early European, Chinese, and Korean isolates, e.g., prototype CV777 strain (Belgium, 1978, GenBank: AF353511.1) and strains LZC (Gansu, China, 2006; GenBank: EF185992) and SM98 (Korea, 1998; GenBank: GU937797.1). Subgroup 1b contains five strains—one from South Korea (the DR13 attenuated vaccine strain, GenBank: JQ023162.1) and the others from China linked by the common "genetic signature" 8-aa deletion in nsp3 and the large ORF3 deletion at the C terminus. Group "R" is associated with recombinants of the other genogroups. However, the newly emergent PEDV strains, including those arising in China since 2010 and in North America since 2013, belong to genogroup G2a. The Chinese strain AH2012 (GenBank accession no: KC210145) and the North American strains share several unique nucleotides changes and are clustered together in genogroup 2a. Nucleotide identity to AH2012 for strains MN and IA2 was 99.6% and for strain IA1 was 99.5%. Researchers have speculated that an AH2012-like virus was possibly transmitted to the eastern China regions and then transported to the United States and is most likely the closest ancestor to the North American strains. Members of the genogroup 2a share only approximately 96.9% similarity to the prototype PEDV strain CV777 of genogroup 1a (Bridgen, et al. 1993; Huang et al. 2013; GenBank: AF353511.1). As such, the attenuated PEDV vaccines based on the historical CV777-derived G1a strains or DR13-derived G1b strains may be antigenically less related to the newly emergent Chinese and North American G2a PEDV strains and therefore may be poor vaccine candidates.

A closely related North American isolate US/Colorado/2013 (GenBank Accession No: KF272920.1) has also been reported by Marthaler et al, 2013. Like the North American isolates above, the complete PEDV genome of CO/13 has a nucleotide identity of 96.5 to 99.5% with other complete PEDV genomes available in GenBank, with the highest nucleotide identity (99.5%) with Chinese strain AH2012 (GenBank Accession No. KC210145). It is a member of the 2a genogroup. Comparison of the complete genome of CO/13 to that of PEDV reference strain CV777, demonstrates that CO/13 contains a 1-nt insertion (at position 48) and deletions of 5 nucleotides in the 5' UTR (at positions 73 and 83 to 86). This North American virus exhibits increased divergence within S1 at genomic positions 20,696 and 21,125 sharing only 82% nucleotide identity with several insertions/deletions.

Several PEDV vaccines, which differ in their genomic sequence, mode of delivery, and efficacy, have been developed. A cell culture adaptation of the European CV777 strain has been used in Asian countries where the PEDV outbreaks have been severe. These have been in use since the 1990s.

In the early 1980s Japanese researchers isolated a causative PED virus strain 83P-5 from the diarrhea of an infected pig. Kusanagi et al. 1989 isolated and adapted the strain in Vero cells. An attenuated virus vaccine of cell culture adapted PEDV (P-5V) (83P-5) has been used in Japan in sows since 1997. The $100^{th}$-passaged 83P-5 strain was licensed for use as an attenuated PEDV vaccine in Japan by Nisseiken Co., Ltd. (Sato et al. 2011). It has been reported that adaptation and attenuation of the 83P-5 strain showed mutations in the extra-cellular portion of the S protein with sequence similarity to that of the attenuated DR13 strain (Sato et al. 2011; See Strain 83P-5 Spike gene sequence at $100^{th}$ passage, GenBank: AB548621.1). Although this later Japanese vaccine is considered efficacious, not all sows were able to pass immunity to their piglets (Usami et al. 1998). The Japanese strains and the European strains are members of genogroup G1a or G1b. As discussed above these attenuated vaccine strains are less related to the divergent North American strains than the newly emergent Chinese strains of genogroup 2a.

Oral vaccination with an attenuated Korean PEDV strain, DR13 (passage level 100) (GenBank. JQ023162.1), a member of genogroup G1b, has been shown to be efficacious as a vaccine. The viral strain was licensed and used as an oral vaccine in South Korea since 2004, and registered and commercialized in the Philippines in 2011 (Song and Park 2012). However, it has been reported that attenuated DR13 does not significantly alter the duration of virus shedding in challenged piglets—an indication that immune protection is incomplete. Moreover, oral immunization with highly attenuated PEDV only conferred protection at very high doses of vaccine (Song and Park 2012).

Other known vaccines include SUISHOT® PT-100 (ChoongAng Vaccine Laboratories, South Korea) a combination killed PEDV and TGEV vaccine, and SUISHOT® PED a killed PEDV vaccine. The strain and subtypes offered through ChoonAng Vaccine Laboratories are unknown. Also Komipharm International Co., another South Korean company, offers a series of killed, live, and combination vaccines marketed under the tradename PRO-VAC® which include the PEDV strain SM98P of genogroup G1a. Qilu Animal Health Products Factory of China, also markets a combination killed vaccine in China containing PEDV and TGEV whose strain and subtypes are unknown.

The newly emerging porcine deltacorona virus (PDCoV), also known as swine deltacorona virus SDCoV or SDCV and used interchangeably herein, is similar to porcine epidemic diarrhea virus (PEDV), and often implicated with the morbidity in neonatal animals and contributing to the global spread and impact of the disease on the swine industry. PDCoV struck the US within a short time after PEDV with similar morbidity patterns. In the US, unlike PEDV, deltacoronavirus does not seem to cause mortality in piglets but causes acute morbidity including severe diarrhea, vomiting and weight loss in piglets. Although milder than PEDV infection, PDCoV infection can result in 30-40% death rates in neonates. More severe disease may be seen in in coinfections with PEDV, rotaviruses and TGEV (Marthaler et al., 2014a; and Wang et al. 2014). Additionally, in May of 2015 a third new agent, porcine orthoreovirus (PORV) was detected in the US, potentially contributing to disease severity when present in co-infection. While more knowledge of the pathogenesis and clinical implication of PDCoV and other co-infective agents is needed, this recent co-emergence of PEDV and PDCoV has potentially enhanced the severity and impact of disease on herds.

Porcine deltacoronavirus (PDCoV) is a member of the Coronaviridae family, genus deltacoronavirus. The virus was first identified in Hong Kong SAR among porcine rectal swab samples collected in 2009 (Woo, P. C., et al., Discovery of seven novel Mammalian and avian coronaviruses in the genus deltacoronavirus supports bat coronaviruses as the gene source of alphacoronavirus and betacoronavirus and avian coronaviruses as the gene source of gammacoronavirus and deltacoronavirus. J Virol, 2012. 86(7): p. 3995-4008) but was not known to be associated with any disease. SDCV, referred to herein as PDCoV, was first detected in US swine herds in February 2014 in Ohio and Indiana and has quickly spread to other states (Hu, H., et al., Isolation and Characterization of Porcine Deltacoronavirus from Pigs with Diarrhea in the United States. J Clin Microbiol, 2015. 53(5): p. 1537-1548; Chen, Q., et al., Pathogenicity and pathogenesis of a United States porcine deltacoronavirus cell culture isolate in 5-day-old neonatal piglets. Virology, 2015. 482: p. 51-59; Li, G., et al., Full-Length Genome Sequence of Porcine Deltacoronavirus Strain USA/IA/2014/8734. Genome Announc, 2014. 2(2); Marthaler, D., et al., Rapid detection, complete genome sequencing, and phylogenetic analysis of porcine deltacoronavirus. Emerg Infect Dis, 2014a. 20(8): p. 1347-50; Marthaler, D., et al., Complete Genome Sequence of Strain SDCV/USA/Illinois121/2014, a Porcine Deltacoronavirus from the United States. Genome Announc, 2014b. 2(2); Wang, L., B. Byrum, and Y. Zhang, Detection and genetic characterization of deltacoronavirus in pigs, Ohio, USA, 2014. Emerg Infect Dis, 2014. 20(7): p. 1227-30; Jung, K., et al., Pathogenicity of 2 porcine deltacoronavirus strains in gnotobiotic pigs. Emerg Infect Dis, 2015. 21(4): p. 650-4). PDCoV was also detected in Korea in April 2014 (Lee, S. and C. Lee, Complete Genome Characterization of Korean Porcine Deltacoronavirus Strain KOR/KNU14-04/2014. Genome Announc, 2014. 2(6)), in mainland China (Dong, N., et al., Porcine Deltacoronavirus in Mainland China. Emerg Infect Dis, 2015. 21(12): p. 2254-5; and Song, D., et al., Newly Emerged Porcine Deltacoronavirus Associated With Diarrhoea in Swine in China: Identification, Prevalence and Full-Length Genome Sequence Analysis. Transbound Emerg Dis, 2015. 62(6): p. 575-80), and in Japan (ISERPD 2015).

Following identification, three research groups have confirmed that infection with cell culture derived material and/or tissue homogenate from clinical cases results in acute gastroenteric clinical signs in gnotobiotic and/or conventional piglets (Chen et al., 2015; Ma, Y., et al., *Origin, evolution, and virulence of porcine deltacoronaviruses in the United States*. MBio, 2015. 6(2); and Vitosh-Sillman, S., et al. *Histopathological and immunohistochemical characterization of pigs experimentally infected with porcine deltacoronavirus*. in *American Association of Swine Veterinarians*. 2015. Orlando, FL). PDCoV has been shown to cause acute diarrhea in sows and piglets in farrowing rooms 8-9 days post onset of clinical signs (Li et al. 2014), along with vomiting and dehydration (Ma, et al. 2015). The virus has similar clinical signs and symptoms as porcine enteric coronavirus (PEDV), transmissible gastroenteritis coronavirus (TGEV) and porcine orthoreoviruses (PORV).

A recent disclosure by Marx et al. (WO201600757A2) describes immunogenic compositions that allegedly protect swine from disease caused by porcine epidemic diarrhea virus (PEDV) and PDCoV. However, it is clear that the PEDV vaccine of Marx et al., based on the North American Colorado strain virus, is only partially protective (e.g., when comparing the modest reductions in the clinical symptoms of mortality, weight loss, or diarrhea) when challenged with an attenuated European INDEL-strain Calaf14 (causing only 23.8% mortality in control animals). Moreover, while Marx et al. also describe a deltacorona virus vaccine, protection or reduction of clinical symptoms of disease was not demonstrated with either a monovalent PDCoV vaccine or a bivalent PEDV and PDCoV vaccine Therefore, what is needed is a PEDV and PDCoV vaccine capable of reducing the clinical signs of disease caused by PEDV and PDCoV and inducing protective immunity in immunized animals, including the reduction of viral shedding in immunized animals.

SUMMARY OF THE INVENTION

The present invention provides immunogenic compositions, vaccines, and related methods that overcome deficiencies in the art. The present invention relates to immunogenic compositions which include inactivated/killed and/or recombinant forms of enveloped (+) single-stranded RNA viruses of the Coronaviridae family: porcine epidemic diarrhea virus, or PEDV and/or porcine deltacoronavirus, or PDCoV. In particular, the application provides immunogenic compositions reducing the clinical symptoms in pigs with diseases associated with PEDV and PDCoV infection. The present PDCoV isolates (NSVL) (SEQ ID NO:1 and 2) and isolates PDCoV 2.0307 and PDCoV 5.0327 (SEQ ID NOs:5, 6, 9, and 10, respectively) have genetic profiles similar to those of other North American and Asian strains. The present PEDV isolate BI1251-125-10 (herein referred to as "125-10") (SEQ ID NO:29, 32) is a virulent North American RNA virus strain with a genetic profile similar to those of other North American PEDVs reported of genogroup 2a. The PEDV derivative isolate "125-10 p30" (SEQ ID NO:34, 36). is a passage attenuate virus, also with a genetic profile consistent with the North American genogroup 2a.

Immunogenic compositions and vaccines of the invention comprise inactivated/killed PDCoV (e.g., chemically inactivated NSVL isolate (SEQ ID NO:1 and 2) and/or isolates PDCoV 2.0307 and PDCoV 5.0.327 (SEQ ID NO:5 and 6 and SEQ ID NO:9 and 10, respectively), and/or inactivated/killed PEDV (e.g., chemically inactivated PEDV isolate "125-10" or "125-10 p30" (SEQ ID NO:29 or 32 and SEQ ID NO:33 or 36, respectively)) and typically also includes an adjuvant. The vaccine may also include other components, such as preservative(s), antimicrobial agents, stabilizer(s), for example a stabilizer that can increase the shelf-life of the vaccine, emulsions, and antigens against other porcine pathogens.

Immunogenic compositions and vaccines of the invention comprise a Spike antigen, expressed in one non-limiting example in insect cells via a recombinant baculovirus expressing a PDCoV and/or PEDV Spike protein e.g., a PDCoV Spike protein (e.g., comprising nucleic acid sequences SEQ ID NO:3, 7, 11, 17 or 27 encoding the amino acid sequences SEQ ID NO:4, 8, 12, 18, or 28), and/or a PEDV Spike nucleic acid sequence (comprising SEQ ID NO:30, 34, 46, or 52) encoding amino acid sequence SEQ ID NO:31, 35, 47, or 53), and typically also includes an adjuvant. The vaccine may also include other components, such as preservative(s), stabilizer(s) and antigens against other porcine pathogens.

A preferred PDCoV and/or PEDV spike nucleic acid sequence suitable for use in the invention is a polynucleotide encoding a Spike polypeptide, said polynucleotide having at least at least will have at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.41%, 97.42%, 97.43%, 97.44%, 97.45%, 97.46%, 97.47%, 97.48%, 97.49%, 97.5%, 97.51%, 97.52%, 97.53%, 97.54%, 97.55%, 97.56%, 97.57%, 97.58%, 97.59%, 97.6%, 97.61%, 97.62%, 97.63%, 97.64%, 97.65%, 97.66%, 97.67%, 97.68%, 97.69% 97.7%, 97.71%, 97.72%, 97.73%, 97.74%, 97.75%, 97.76%, 97.77%, 97.78%, 97.79%, 97.8%, 97.81%, 97.82%, 97.83%, 97.84%, 97.85%, 97.86%, 97.87%, 97.88%, 97.89%, 97.9%, 97.91%, 97.92%, 97.93%, 97.94%, 97.95%, 97.96%, 97.97%, 97.98%, 97.99%, 98%, 98.01%, 98.02%, 98.03%, 98.04%, 98.05%, 98.06%, 98.07%, 98.08%, 98.09%, 98.1%, 98.11%, 98.12%, 98.13%, 98.14%, 98.15%, 98.16%, 98.17%, 98.18%, 98.19%, 98.2%, 98.21%, 98.22%, 98.23%, 98.24%, 98.25%, 98.26%, 98.27%, 98.28%, 98.29%, 98.3%, 98.31%, 98.32%, 98.33%, 98.34%, 98.35%, 98.36%, 98.37%, 98.38%, 98.39%, 98.4%, 98.41%, 98.42%, 98.43%, 98.44%, 98.45%, 98.46%, 98.47%, 98.48%, 98.49%, 98.5%, 98.51%, 98.52%, 98.53%, 98.54%, 98.55%, 98.56%, 98.57%, 98.58%, 98.59%, 98.6%, 98.61%, 98.62%, 98.63%, 98.64%, 98.65%, 98.66%, 98.67%, 98.68%, 98.69%, 98.7%, 98.71%, 98.72%, 98.73%, 98.74%, 98.75%, 98.76%, 98.77%, 98.78%, 98.79%, 98.8%, 98.81%, 98.82%, 98.83%, 98.84%, 98.85%, 98.86%, 98.87%, 98.88%, 98.89%, 98.9%, 98.91%, 98.92%, 98.93%, 98.94%, 98.95%, 98.96%, 98.97%, 98.98%, 98.99%, 99%, 99.01%, 99.02%, 99.03%, 99.04%, 99.05%, 99.06%, 99.07%, 99.08%, 99.09%, 99.1%, 99.11%, 99.12%, 99.13%, 99.14%, 99.15%, 99.16%, 99.17%, 99.18%, 99.19%, 99.2%, 99.21%, 99.22%, 99.23%, 99.24%, 99.25%, 99.26%, 99.27%, 99.28%, 99.29%, 99.3%, 99.31%, 99.32%, 99.33%, 99.34%, 99.35%, 99.36%, 99.37%, 99.38%, 99.39%, 99.4%, 99.41%, 99.42%, 99.43%, 99.44%, 99.45%, 99.46%, 99.47%, 99.48%, 99.49%, 99.5%, 99.51%, 99.52%, 99.53%, 99.54%, 99.55%, 99.56%, 99.57%, 99.58%, 99.59%, 99.6%, 99.61%, 99.62%, 99.63%, 99.64%, 99.65%, 99.66%, 99.67%, 99.68%, 99.69%, 99.7% 99.71%, 99.72%, 99.73%, 99.74%, 99.75%, 99.76%, 99.77%, 99.78%, 99.79%, 99.8%, 99.81%, 99.82%, 99.83% 99.84%, 99.85%, 99.86%, 99.87%, 99.88%, 99.89%, 99.9%, 99.91%, 99.92%, 99.93%, 99.94%, 99.95%, 99.96%, 99.97%, 99.98% and 99.99% sequence identity to PDCoV Spike polypeptides SEQ ID NO:3, 7, 11, 17, or 27, or functional fragments thereof, and/or PEDV Spike SEQ ID NO:30, 34, 46, or 52, or functional fragments thereof. As used herein, it is in particular understood that the term "sequence identity to SEQ ID NO:X" or "identical SEQ ID NO:X", respectively, is equivalent to the term "sequence identity with the sequence of SEQ ID NO:X over the length of SEQ ID NO: X" or "identical to the sequence of SEQ ID NO:X over the length of SEQ ID NO: X", respectively.

A preferred spike polypeptide suitable for use in the invention is the polypeptide having the sequence set out in PDCoV Spike SEQ ID NOs:4, 8, 12, 18, or 28 and/or PEDV Spike SEQ ID NOs:31, 35, 47, or 53 having at least 80% homology with SEQ ID NOs:4, 8, 12, 18, 28, 31, 35, 47,and/or 53, for example at least 85% homology with SEQ ID NOs: 4, 8, 12, 18, 28, 31, 35, 47,and/or 53, such as a least 85% homology with SEQ ID NOs: 4, 8, 12, 18, 28, 31, 35, 47,and/or 53, such as at least 90% homology with SEQ ID NOs:4, 8, 12, 18, 28, 31, 35, 47,and/or 53, for example at least 95%, at least 98% or at least 99% homology with SEQ ID NOs: 4, 8, 12, 18, 28, 31, 35, 47, and/or 53.

The terms "vaccine" and "immunogenic composition" are defined herein in a broad sense to refer to any type of biological agent in an administrable form capable of stimulating an immune response in an animal inoculated with the vaccine. Vaccines in general may be based on either the virus itself (e.g., killed/inactivated or attenuated) or an immunogenic (antigenic) component of the virus. In one embodiment of the invention, the vaccine (immunogenic composition) preferably includes the viral agent in a killed/inactivated form or an antigenic portion of the virus presented as a sub-unit vaccine. Herein, the term "reduction of clinical symptoms" when used in reference to an immunogenic composition refers to the lessening or amelioration (either partial or complete) of any of the symptoms associated with the disease or condition in question. Thus, reduction of clinical symptoms of pigs infected with PDCoV and/or PEDV by the present immunogenic compositions generally results in a diminishing of virus shedding and/or one or more of the clinical symptoms associated with infection with PDCoV and/or PEDV (e.g., acute watery diarrhea, acute vomiting, dehydration, anorexia, lethargy, depression, and high mortality in pigs less than 10 days old). Likewise, the reduction of clinical symptoms of pigs infected with PDCoV and/or PEDV by the present immunogenic compositions generally results in a diminishing of virus shedding and/or one or more of the clinical symptoms associated with infection with PDCoV and/or PEDV (e.g., acute watery diarrhea, acute vomiting, dehydration, anorexia, lethargy, depression, and high mortality in pigs less than 10 days old)

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a PDCoV infection and/or PEDV infection, either singularly or in combination with each other or other co-infections, in a subject comprising the step of administering to the subject an immunogenic composition comprising an inactivated/killed PDCoV and/or PEDV, attenuated PDCoV and/or PEDV, and/or recombinant Spike antigens derived from PDCoV and/or PEDV. Preferably, the immune response is provoked against more than one serotype, or strain of PDCoV or PEDV. Compositions of the invention may be used to prevent a PDCoV infection, a PEDV infection, and/or a PEDV/PDCoV co-infection. Preferably, such immune response reduces the incidence of or severity of one or more clinical signs associated with or caused by the infection with one or more PDCoV genotypes and/or PEDV genotypes/genogroups.

Herein, suitable subjects and subjects in need to which compositions of the invention may be administered include animals in need of prophylactic treatment for a viral associated infection, disease, or condition. Animals in which the immune response is stimulated by use of compositions or methods of the invention include livestock, such as swine, bovines, poultry (e.g., chickens, ducks, geese, or turkeys) goats, and sheep, and domestic animals, such as mice, rabbits, dogs, cats, and horses. Preferred animals include porcine, murids, equids, lagomorphs, and bovids. Most preferably, an immune response is stimulated in pigs.

The invention also provides a method of reducing the incidence of or severity of one or more clinical signs associated with or caused by PDCoV infection, and/or PEDV infection comprising the step of administering an immunogenic composition of the invention that comprises inactivated/killed PDCoV vaccine, inactivated/killed PEDV vaccine, and/or in combination with a recombinant Spike antigen derived from PDCoV and/or PEDV as provided herewith and preferably a carrier molecule, such that the incidence of or the severity of a clinical sign of the PDCoV and/or PEDV infection is reduced by at least 10%, preferably at least 20%, even more preferred at least 30%, even more preferred at least 50%, even more preferred at least 70%, most preferred 100% relative to a subject that has not received the immunogenic composition as provided herewith. Such clinical signs include watery diarrhea, vomiting, and dehydration. Any of these clinical signs may result from an infection with PEDV having the genogroup of 2a or any other PEDV genogroup including G1a, G1b, or G2b. Likewise any of these clinical signs may result from an infection and/or a co-infection with PDCoV of varying genotypes.

In one embodiment, the present immunogenic compositions include a chemically inactivated form of PEDV. Vaccines which include chemically inactivated PDCoV (SEQ ID NOs:1 or 2, 5 or 6, 9 or 10) virus are particularly desirable. Additionally, the present immunogenic compositions may include a chemically inactivated form of PEDV. Vaccines which include chemically inactivated PEDV (SEQ ID NO:29 or 32 or SEQ ID NO:33 or 36) virus are particularly desirable. A variety of chemical inactivating agents known to those skilled in the art may be employed to inactivate the virus. Ethylenimine and related derivatives, such as binary ethylenimine ("BEI") and acetylethylenimine, are examples of suitable chemical inactivating agents for use in inactivating the SDCo and/or PED virus. Other chemical inactivating agents, e.g., beta-propiolactone or aldehydes (such as formaldehyde and glutaraldehyde), can also be used to inactivate the virus.

The present immunogenic compositions and/or vaccines generally include an adjuvant which desirably may have bioadhesive properties, particularly where the virus is designed to be capable of intranasal administration. Examples of suitable adjuvants include cross-linked olefinically unsaturated carboxylic acid polymers, such as cross-linked acrylic acid polymers. As used herein the term "cross-linked acrylic acid polymer" refers to polymer and copolymers formed from a monomer mixture which includes acrylic acid as the predominant monomer in the mixture. Examples of suitable cross-linked acrylic acid polymers include those commercially available under the tradenames CARBOPOL® 934P and CARBOPOL® 971 (available from B.F. Goodrich Co., Cleveland, Ohio). One particularly suitable adjuvant for use in the present vaccines is a cross-linked acrylic acid polymer having a Brookfield viscosity of no more than about 20,000 cPs (as measured at 20 rpm as a 1.0 wt. % aqueous solution at pH 7.5). Where a bioadhesive adjuvant is desired, it may be advantageous to utilize an adjuvant which has a bioadhesive property of at least about 50 dynes/cm2 as measured between two pieces of freshly excised rabbit stomach tissue (as determined by the procedure described in U.S. Pat. No. 4,615,697).

The present invention also relates to a method of immunizing a subject, comprising administering to a subject any of the immunogenic compositions as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PDCoV infection in a herd, alone or in combination with PEDV infection, or in the reduction in the severity of clinical signs caused by or associated with the particular PDCoV and/or PEDV infection.

Further, the immunization of a subject in need with the immunogenic compositions as provided herewith, results in preventing infection of a subject by PDCoV and/or PEDV infection. Even more preferably, immunization results in an effective, long-lasting, immunological-response against PDCoV and/or PEDV infection. It will be understood that the said period of time will last more than 2 months, preferably more than 3 months, more preferably more than 4 months, more preferably more than 5 months, more preferably more than 6 months. It is to be understood that immunization may not be effective in all subjects immunized.

Preferably, a herd of subjects is envisaged in this context which normally, i.e. without immunization, would develop clinical signs normally caused by or associated with a PDCoV infection and/or PEDV infection. Whether the subjects of a herd are effectively immunized can be determined without further ado by the person skilled in the art. Preferably, the immunization shall be effective if clinical signs in at least 20%, at least 30%, at least 40%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PDCoV and/or PEDV.

Methods for preventing clinical signs caused by PDCoV and/or PEDV in a subject in need, or methods of protecting pigs against diseases associated with PDCoV and/or PEDV include administering an immunogenic composition and/or vaccine containing inactivated/killed PDCoV, and/or inactivated/killed PEDV, and/or Spike antigens derived from PDCoV and/or PEDV to the pigs. The vaccine can be administered using a variety of methods including intranasal, oral and/or parenteral (e.g., intramuscular) administration. In one embodiment of the method, for example, the inactivated PDCoV and/or the inactivated PEDV containing immunogenic composition is administered intramuscularly one or more times (e.g., at intervals of 2-4 weeks). In another embodiment of the method, for example, the inactivated PDCoV and/or inactivated PEDV containing vaccine is administered orally one or more times (e.g., at intervals of 2-4 weeks). In an alternative embodiment oral administration can be followed by and/or precede administration of the vaccine at least once, intramuscularly (e.g., 2-4 weeks after and/or before the parenteral administration of vaccine). Ideally, all pigs in a given herd are vaccinated at the prescribed intervals in order to protect against the spread of symptoms of the disease.

A method of producing an inactivated/killed PDCoV vaccine, an inactivated/killed PEDV vaccine, or a combination PDCoV/PEDV immunogenic composition is also provided. For the production of the PDCoV, the method typically includes inoculating swine testes cells with PDCo virus, e.g., with PDCo virus SEQ ID NO:1 or 2, 5 or 6, and 9 or 10. The inoculated swine testes cells are incubated, generally at least until CPE is, and then the PED virus is harvested from the incubated cells. The harvested virus-containing fluids can be treated with a chemical inactivating agent, such as binary ethylenimine, to form inactivated/killed PDCo virus. Typically, the inactivated virus is further processed, e.g., by concentration and blending with other components, to produce a commercial formulation. For example, the fluids containing the inactivated virus may be concentrated and blended with an adjuvant and/or antigen(s) to one or more other porcine pathogens. For the production of the PEDV, the method typically includes inoculating simian cells with PED virus, e.g., with PED virus SEQ ID NO:29 or SEQ ID NO:33. The inoculated simian cells are incubated, generally at least until CPE is observed, and then the PED virus is harvested from the incubated cells. The harvested virus-containing fluids can be treated with a chemical inactivating agent, such as binary ethylenimine, to form inactivated/killed PED virus. Typically, the inactivated virus is further processed, e.g., by concentration and blending with other components, to produce a commercial formulation. For example, the fluids containing the inactivated virus may be concentrated and blended with an adjuvant and/or antigen(s) to one or more other porcine pathogens.

A method of producing recombinantly expressed Spike antigen vaccines generated in insect cells via a recombinant baculovirus expressing PDCoV and/or PEDV Spike proteins is also provided. The method in one exemplary embodiment includes cloning the PDCoV Spike coding sequences (e.g., SEQ ID NOs:3, 7, 11, 17, or 27) and or/or PEDV Spike coding sequences (SEQ ID NO:30, 34, 46, or 52), including for example the PDCoV Spike-Fc antigen construct (SEQ ID NO:17), and/or the PDCoV Spike Baculodisplay construct (SEQ ID NO:27), and/or the PEDV 2a Spike construct (SEQ ID NO:46), and/or the PEDV 2b SPIKE construct (SEQ ID NO:52), into a baculovirus vector, and co-transfecting Sf9 insect cells.

The present application is also directed to a kit which includes in combination, (1) a dispenser capable of administering a vaccine to a pig; and (2) a chemically inactivated PDCoV, and/or a chemically inactivated PEDV, and/or recombinant Spike antigens derived from PDCoV and/or PEDV containing vaccine capable of protecting against diseases associated with PDCoV and/or PEDV. The kit may include a dispenser which is capable of dispensing its contents as droplets, e.g., as aerosol, atomized spray and/or liquid droplets, and a form of the vaccine which is capable of protecting against diseases associated with PDCoV and/or PEDV, for example when administered intranasally and/or intramuscularly.

Throughout this application, the text refers to various embodiments of the present compositions and/or related methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
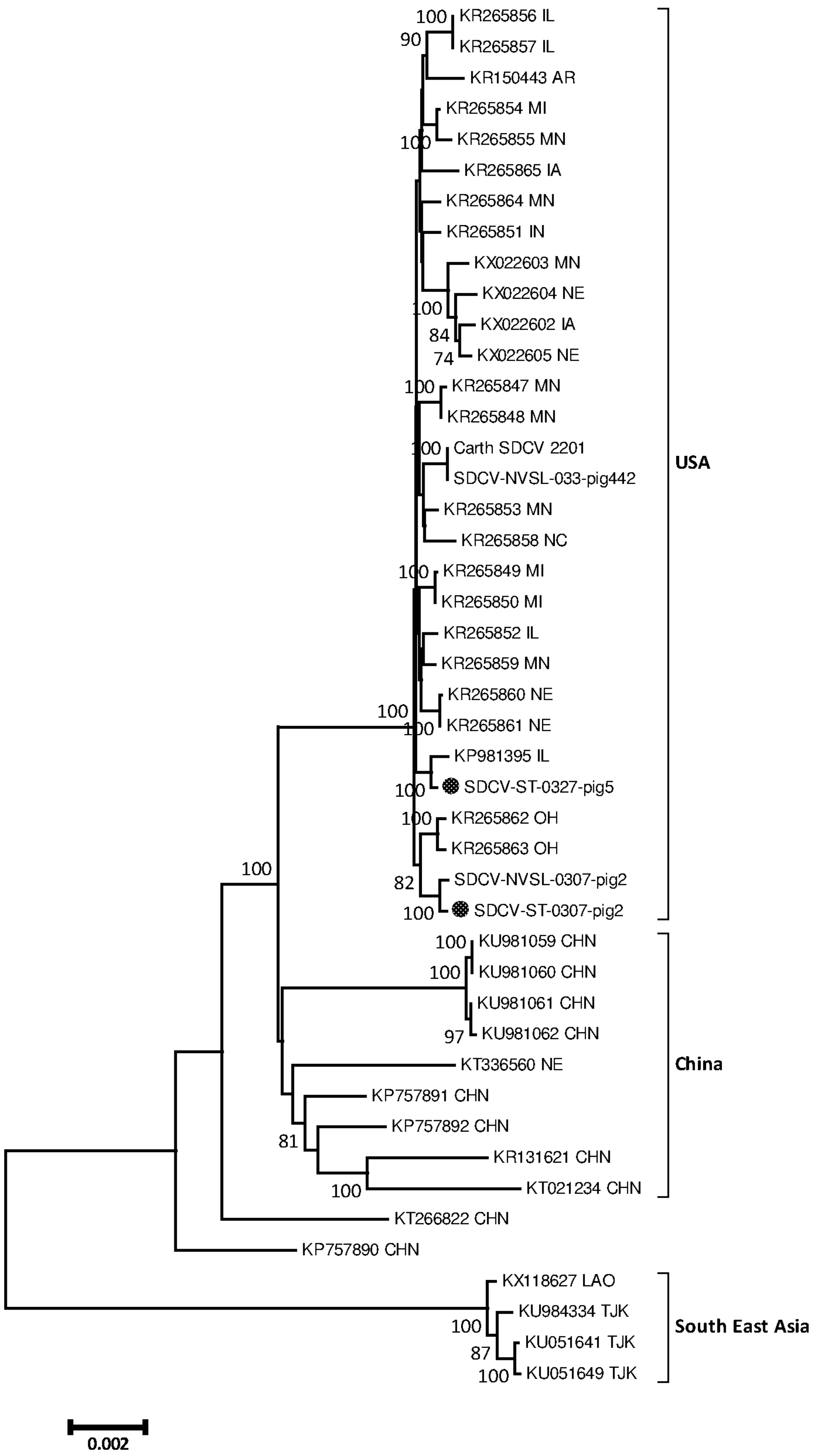
FIG. 1 Complete genome nucleotide neighbor-joining tree for PDCoV isolates/strains. Scale indicates p-distance. GenBank accession numbers listed along with two letter state or three letter country code (CHN—China, TJK—Thailand, LAO—Laos).

The invention provides immunogenic compositions including inactivated/killed, forms of PDCoV and/or PEDV and/or recombinantly expressed PDCoV and/or PEDV-Spike antigens. The immunogenic compositions are designed for protecting swine against diseases associated with PDCoV and/or PEDV. The immunogenic compositions typically include a chemically inactivated form of PDCoV and/or PEDV and those which include chemically inactivated/killed PDCoV and/or PEDV virus are particularly desirable. In another embodiment the immunogenic compositions include recombinant expressed PDCoV and/or PEDV Spike antigens generated, for example, in insect cells via a recombinant baculovirus expressing a PDCoV and/or PEDV Spike proteins.

Generally, the present invention provides an immunogenic composition comprising one or more antigens of porcine deltacoronavirus (PDCoV) and an adjuvant, wherein in the porcine deltacoronavirus (PDCoV) is any PDCoV: a.) that is encoded by SEQ ID NO:1, 5 or 9 and/or comprises the sequence of SEQ ID NO:1, 5 or 9 and/or comprises the RNA equivalent of SEQ ID NO:1, 5 or 9; b.) which sequence is at least 99% identical with SEQ ID NO:1, 5, or 9 and/or is at least 99% identical with the RNA equivalent of SEQ ID. NO:1; 5, or 9 c.) which spike protein is encoded by nucleic acid sequences of SEQ ID NO:3, 7, or 11; d.) which spike protein is encoded by a nucleic acid sequence that is at least 90% identical with the SEQ ID NO:3, 7, or 11; e.) that is encoded by SEQ ID NO:2, 6, or 10; or f) which sequence is at least 99% identical SEQ ID NO:2, 6, or 10.

In a specific aspect the immunogenic composition according the sentence above, wherein the adjuvant is an oil-in-water emulsion.

In a further specific aspect of the invention, the immunogenic composition is as described in any of the above sentences, wherein the immunogenic composition is a recombinant antigen or an inactivated whole porcine deltacoronavirus PDCoV antigen.

In a further specific aspect of the invention, the immunogenic composition is as described in any of the above sentences, wherein the antigen is an inactivated whole PDCoV antigen.

In a further specific aspect of the invention, the immunogenic composition is as described in any of the above sentences, wherein the PDCoV antigen is chemically inactivated.

In a further specific aspect of the invention, the immunogenic composition is as described in any of the above sentences, wherein the PDCoV antigen is chemically inactivated by treatment with a chemical inactivating agent which includes a compound selected from the group consisting of ethylenimine, binary ethylenimine, acetylethylenimine and mixtures thereof.

In a further specific aspect of the invention, the immunogenic composition is as described in any of the above sentences, wherein the PDCoV is chemically inactivated by treatment with binary ethylenimine.

In a further specific aspect of the invention, the immunogenic composition is as described in any of the above sentences, wherein the adjuvant is an EMULSIGEN® oil-in-water emulsion-based adjuvant.

In a further specific aspect of the invention, the immunogenic composition is as described in any of the above sentences, wherein an inactivated porcine deltacoronavirus (PDCoV) comprises SEQ ID NO:1, 5, or 9 and/or comprises the RNA equivalent of SEQ ID NO:1, 5, or 9.

In a further specific aspect of the invention, the immunogenic composition is as described in any of the above sentences, wherein the PDCoV antigen is a recombinant antigen.

In a further specific aspect of the invention, the immunogenic composition is as described in any of the above sentences, wherein the recombinant antigen comprises one or more immunogenic components selected from the group consisting of: a.) an isolated nucleic acid encoding an antigen of porcine deltacoronavirus (PDCoV) spike protein, wherein the recombinant Spike polypeptide has at least 90% homology with SEQ ID NO:4, 8, 12, 18, or 28; b.) a recombinant vector comprising the isolated nucleic acid of a); c.) the recombinant PDCoV Spike protein encoded by the nucleic acid of a); and d.) any combination thereof.

In a further specific aspect of the invention, the immunogenic composition is as described in any of the above sentences, wherein such immunogenic composition comprises a pharmaceutical acceptable carrier and/or an excipient.

In a further specific aspect of the invention, the immunogenic composition is as described in any of the above sentences, wherein the oil-in-water emulsion is an EMULSIGEN® oil-in-water emulsion-based adjuvant.

In a further specific aspect of the invention, the immunogenic composition is as described in any of the above sentences, wherein the immunogenic composition further comprises one or more additional antigens.

In a further specific aspect of the invention, the immunogenic composition is as described in any of the above sentences, wherein an additional antigen is an antigen of porcine epidemic diarrhea virus (PEDV), wherein the porcine epidemic diarrhea virus (PEDV) is any PEDV: a.) that is encoded by SEQ ID NO:29 or 33, and/or comprises the sequence of SEQ ID NO:29 or 33 and/or comprises the RNA equivalent of SEQ ID NO:29 or 33; b.) which sequence is at least 99% identical with SEQ ID NO:29 or 33 and/or is at least 99% identical with the RNA equivalent of SEQ ID. NO:29 or 33; c.) which spike protein is encoded by the nucleic acid sequence of SEQ ID NO:30, 34, 46, or 52; d.) which spike protein is encoded by a nucleic acid sequence that is at least 90% identical with SEQ ID NO:30, 34, 46, or 52; e.) that is encoded by SEQ ID NO:32 or 36; or f) that is encoded by a sequence that is at least 99% identical to SEQ ID NO:32 or 36.

In a further specific aspect of the invention, the immunogenic composition is as described in any of the above sentences, wherein the additional PEDV antigen is a recombinant antigen or an inactivated whole porcine epidemic diarrhea virus (PEDV).

In a further specific aspect of the invention, the immunogenic composition is as described in any of the above sentences, wherein the antigen is an inactivated whole porcine epidemic diarrhea virus (PEDV).

In a further specific aspect of the invention, the immunogenic composition is as described in any of the above sentences, wherein the antigen is a recombinant PEDV antigen.

In a further specific aspect of the invention, the immunogenic composition is as described in any of the above sentences, wherein the recombinant antigen comprises one or more immunogenic components selected from the group consisting of: a.) an isolated nucleic acid encoding an antigen of porcine epidemic diarrhea virus (PEDV) spike protein, wherein the antigen has at least 90% homology with SEQ ID NO:31, 35, 47, or 53; b.) a recombinant vector comprising the isolated nucleic acid of a); c.) the recombinant PEDV Spike protein encoded by the nucleic acid of a); and d.) any combination thereof.

In a further specific aspect of the invention, the immunogenic composition is as described in any of the above sentences, wherein the recombinant antigen comprises one or more immunogenic components selected from the group consisting of: a structural protein M, E, or N of a porcine epidemic diarrhea virus (PEDV).

In a further specific aspect of the invention, the immunogenic composition is as described in any of the above sentences, wherein an immunogenic component is the isolated nucleic acid.

In a further specific aspect of the invention, the immunogenic composition is as described in any of the above sentences, wherein an immunogenic component is the recombinant vector.

In a further specific aspect of the invention, the immunogenic composition is as described in any of the above sentences, wherein an immunogenic component is the recombinant porcine epidemic diarrhea virus (PEDV) Spike protein.

In a further specific aspect of the invention, the immunogenic composition is as described in any of the above sentences, wherein an immunogenic component is a combination.

The present invention further concerns a method for reducing the clinical symptoms of disease associated with porcine deltacoronavirus (PDCoV), comprising administering to a pig the immunogenic composition the immunogenic composition as described in any of the above sentences.

In a further specific aspect of the invention, the method is as described in any of the above sentences, comprising administering to a pig the immunogenic composition comprising an inactivated whole PDCoV antigen.

In a further specific aspect of the invention, the method is as described in any of the above sentences, comprising administering to a pig the immunogenic composition comprising the PDCoV antigen as a recombinant antigen.

In a further specific aspect of the invention, the method is as described in any of the above sentences, wherein such administered immunogenic composition comprises one or more immunogenic components selected from the group consisting of: a.) that is encoded by SEQ ID NO:1, and/or comprises the sequence of SEQ ID NOs:1, 5, or 9 and/or comprises the RNA equivalent of SEQ ID NO:1, 5, or 9; b.) which sequence is at least 99% identical with the SEQ ID NO:1, 5, or 9, and/or is at least 99% identical with the RNA equivalent of SEQ ID. NO:1, 5 or 9; c.) which Spike protein is encoded by nucleic acid sequences of SEQ ID NO:3, 7, 11, 17, 27; d.) which Spike protein is encoded by a nucleic acid sequence that is at least 90% identical with the SEQ ID NO:3, 7, 11, 17 or 27; e.) that is encoded by SEQ ID NO:2, 6, or 10; and f.) which sequence is at least 99% identical SEQ ID NO:2, 6, or 10.

In a further specific aspect of the invention, the method is as described in any of the above sentences, wherein such administered immunogenic composition comprises one or more immunogenic components selected from the group consisting of: a.) that is encoded by or comprises the sequence of SEQ ID NO:1, 5, or 9; b.) which sequence is at least 99% identical with the SEQ ID NO:1, 5, or 9; d.) which spike protein is encoded by nucleic acid sequences of SEQ ID NO:3, 7, 11, 17, or 27; and e.) which spike protein is encoded by a nucleic acid sequence that is at least 90% identical with the SEQ ID NO:3, 7, 11, 17, or 27.

In a further specific aspect of the invention, the method is as described in any of the above sentences, wherein such administered immunogenic composition comprises a recombinant antigen comprising one or more immunogenic components selected from the group consisting of: a.) an isolated nucleic acid encoding an antigen of porcine epidemic diarrhea virus porcine deltacoronavirus (PDCoV) spike protein, wherein the recombinant Spike polypeptide has at least 90% homology with SEQ ID NO:4, 8, 12, 18, or 28; b.) a recombinant vector comprising the isolated nucleic acid of a); c.) the recombinant porcine deltacoronavirus (PDCoV) Spike protein encoded by the nucleic acid of a); and d.) any combination thereof.

The present invention further concerns a method for reducing the clinical symptoms of disease associated with porcine deltacoronavirus (PDCoV) and porcine epidemic diarrhea virus (PEDV) comprising administering to a pig the immunogenic composition of any of the immunogenic compositions as described in any of the above sentences, preferably wherein the immunogenic composition comprising one or more antigens of PDCoV and one or more additional antigens, wherein the additional antigen is an antigen of porcine epidemic diarrhea virus (PEDV).

In a further specific aspect of the invention, the method is as described in the above sentence, comprising administering to such pig the immunogenic composition wherein the additional PEDV antigen is a recombinant antigen or an inactivated whole porcine epidemic diarrhea virus (PEDV).

In a further specific aspect of the invention, the method is as described in the above sentence, comprises administering to such pig the immunogenic composition as described in any of the above sentences.

The present invention further concerns a kit for inducing an immunogenic response in a pig against diseases associated with porcine deltacoronavirus (PDCoV) comprising: a.) a dispenser capable of administering an immunogenic composition to a pig; and b.) the immunogenic composition as described in any of the above sentences The present invention further concerns a kit for inducing an immunogenic response in a pig against diseases associated with porcine deltacoronavirus (PDCoV) comprising: a.) a dispenser capable of administering an immunogenic to a pig; and b.) the immunogenic composition as described in any of the above sentences, more specifically wherein the antigen is an inactivated whole PDCoV antigen, even more specifically wherein the PDCoV antigen is chemically inactivated; more specifically wherein the PDCoV antigen is chemically inactivated by treatment with a chemical inactivating agent which includes a compound selected from the group consisting of ethylenimine, binary ethylenimine, acetylethylenimine and mixtures thereof, preferably wherein the PDCoV is chemically inactivated by treatment with binary ethylenimine. more specifically wherein the adjuvant is an EMIULSIGEN® oil-in-water emulsion-based adjuvant; and even more preferably wherein the inactivated porcine deltacoronavirus (PDCoV) comprises SEQ ID NO:1, 5, or 9, and/or comprises the RNA equivalent of SEQ ID NO:1, 5, or 9.

The present invention further concerns a kit for inducing an immunogenic response in a pig against diseases associated with porcine deltacoronavirus (PDCoV) comprising: a.) a dispenser capable of administering an immunogenic composition to a pig; and b.) the immunogenic composition as described in any of the above sentences, more specifically wherein the PDCoV antigen is a recombinant antigen, even more specifically wherein the recombinant antigen comprises one or more immunogenic components selected from the group consisting of: a.) an isolated nucleic acid encoding an antigen of porcine deltacoronavirus (PDCoV) spike protein, wherein the recombinant Spike polypeptide has at least 90% homology with SEQ ID NO:4, 8, 12, 18, or 28; b.) a recombinant vector comprising the isolated nucleic acid of a); c.) the recombinant PDCoV Spike protein encoded by the nucleic acid of a); and d.) any combination thereof., even more specifically wherein such immunogenic composition comprises a pharmaceutical acceptable carrier and/or an excipient; and even more specifically wherein the oil-in-water emulsion is an EMULSIGEN® oil-in-water emulsion-based adjuvant.

The present invention further concerns a kit for inducing an immunogenic response in a pig against diseases associated with porcine deltacoronavirus (PDCoV) and porcine epidemic diarrhea virus (PEDV) comprising a.) a dispenser capable of administering an immunogenic composition to a pig; and b.) the immunogenic composition as described in any of the sentences above, specifically wherein the additional antigen is the porcine epidemic diarrhea virus (PEDV) and is any PEDV antigen as described in any of the sentences above.

The present invention further concerns a kit for inducing an immunogenic response in a pig against diseases associated with porcine deltacoronavirus (PDCoV) and porcine epidemic diarrhea virus (PEDV) comprising: a.) a dispenser capable of administering an immunogenic composition to a pig; and b.) and the immunogenic composition as described in any of the sentences above, specifically wherein the additional antigen is the porcine epidemic diarrhea virus (PEDV) is any recombinant PEDV antigen or an any inactivated whole porcine epidemic diarrhea virus (PEDV) as described in any of the sentences above.

The present invention further concerns a kit for inducing an immunogenic response in a pig against diseases associated with porcine deltacoronavirus (PDCoV) and porcine epidemic diarrhea virus (PEDV) comprising: a.) a dispenser capable of administering an immunogenic composition to a pig; and b.) the immunogenic composition as described in any of the sentences above, specifically wherein the additional antigen is any recombinant PEDV antigen as described in any of the sentences above.

The present invention further concerns a method of producing a porcine deltacoronavirus (PDCoV) immunogenic composition as described in any of the sentences above, further comprising: a.) inoculating swine testes cells with the porcine deltacoronavirus (PDCoV); b.) incubating the inoculated swine testes cells; c.) harvesting porcine deltacoronavirus (PDCoV) from the incubated cells; and d.) treating the harvested cells with a chemical inactivating agent, preferably with a compound selected from the group consisting of ethylenimine, binary ethylenimine, acetylethylenimine or a mixture thereof to form inactivated porcine deltacoronavirus (PDCoV) antigen.

In a further specific aspect of the invention, the method is as described in the above sentence, wherein the porcine deltacoronavirus (PDCoV) comprises the additional features: a.) a sequence that is encoded by or comprises the sequence of SEQ ID NO:1, 5, or 9, b.) a sequence that is at least 99% identical with the SEQ ID NO:1, 5, or 9, c.) a spike protein that is encoded by nucleic acid sequences of SEQ ID NO:3, 7, 11, 17, or 27; d.) a spike protein that is encoded by a nucleic acid sequence that is at least 90% identical with the SEQ ID NO:3, 7, 11, 17, or 27.

In a further specific aspect of the invention, the method is as described in either of the above sentences, wherein the porcine deltacoronavirus (PDCoV) comprises the additional features SEQ ID NO:1, 5, or 9 and/or the RNA equivalent of SEQ ID NO:1, 5, or 9.

In a further specific aspect of the invention, the method is as described in any of the above sentences, wherein the swine testes cells are AI-ST cells.

In a further specific aspect of the invention, the method is as described in any of the above sentences, wherein the chemical inactivating agent includes binary ethylenimine.

In a further specific aspect of the invention, the method is as described in any of the above sentences, further comprising the additional feature of adding an oil-in-water emulsion-based adjuvant EMULSIGEN® to the porcine deltacoronavirus (PDCoV) antigen.

The present invention further concerns a method of producing an immunogenic composition comprising the recombinant porcine deltacoronavirus (PDCoV) antigen as described in any of the preceding sentences comprising: a.) expressing an antigen of porcine deltacoronavirus (PDCoV) in a host cell, b.) harvesting the antigen of porcine deltacoronavirus (PDCoV) cells; and c.) adding an oil-in-water emulsion-based adjuvant to the porcine deltacoronavirus (PDCoV) antigen of step b).

In a further specific aspect of the invention, the method is as described in the above sentence, wherein the porcine deltacoronavirus (PDCoV) antigen comprises: a.) an isolated nucleic acid encoding an antigen of porcine deltacoronavirus (PDCoV) spike protein, wherein the recombinant Spike polypeptide has at least 90% homology with SEQ ID NO: 3, 7, 11, 17, or 27; b.) a recombinant vector comprising the isolated nucleic acid of a); c.) the recombinant porcine deltacoronavirus (PDCoV) Spike protein encoded by the nucleic acid of a); and d.) any combination thereof.

In a further specific aspect of the invention, the method is as described in any of the above sentences, wherein the antigen of porcine deltacoronavirus (PDCoV) is expressed by a recombinant baculovirus vector.

In a further specific aspect of the invention, the method is as described in any of the above sentences, wherein the antigen of porcine deltacoronavirus (PDCoV) is expressed in insect cells.

In a further specific aspect of the invention, the method is as described in any of the above sentences, wherein as an additional feature the oil-in-water based adjuvant is an EMULSIGEN® oil-in-water emulsion-based adjuvant.

The present invention further concerns the immunogenic composition comprising PDCoV as described in any of the above sentences, for the use for the reduction of symptoms of disease associated with porcine deltacoronavirus (PDCoV).

The present invention further concerns the immunogenic composition comprising PDCoV and at least one additional antigen, wherein at least one additional antigen is an antigen of porcine epidemic diarrhea virus (PEDV) for the use for the reduction symptoms of disease associated with porcine deltacoronavirus (PDCoV) and/or porcine epidemic virus (PEDV).

In a further specific aspect of the invention, the immunogenic composition is as described in any of the above sentences, further comprising one or more antigens of PEDV genotype 2a, specifically the PEDV is of North American origin.

In a further specific aspect of the invention, the immunogenic composition is as described in any of the above sentences further comprising one or more antigens of PDCoV wherein the PDCoV is of North American origin.

In more general terms, a variety of chemical inactivating agents known to those skilled in the art may be employed to inactivate the virus. Ethylenimine and related derivatives, such as binary ethylenimine (BEI) and acetylethylenimine, are examples of suitable chemical inactivating agents for use in inactivating the PED virus. Other chemical inactivating agents, e.g., beta-propiolactone, aldehydes (such as formaldehyde) and/or detergents (e.g., Tween® detergent, Triton® X, or alkyl trimethylammonium salts) can also be used to inactivate the virus. The inactivation can be performed using standard methods known to those of skill in the art. Samples can be taken at periodic time intervals and assayed for residual live virus. Monitoring of cytopathic effect on an appropriate cell line and/or fluorescent staining with an appropriate specific monoclonal or polyclonal antibody can be used to detect the presence of residual live virus.

Inactivation with BEI can be accomplished by combining a stock BEI solution (e.g., a solution formed by adding 0.1-0.2 M 2-bromo-ethylamine hydrobromide to 0.1-0.2 N aqueous NaOH) with viral fluids to a final concentration of about 1-5 mM BEI. Inactivation is commonly performed by holding the BEI-virus mixture at 35-40° C. (e.g., 37° C.) with constant mixing for 24-72 hours. Virus inactivation can be halted by the addition of sodium thiosulfate solution to a final concentration in excess of the BEI concentration (e.g., addition of sodium thiosulfate at 17% of the volume of BEI to neutralize excess BEI) followed by mixing.

The present immunogenic compositions usually include an adjuvant and, if desired, one or more emulsifiers such as Tween® detergent incorporated with the inactivated/killed PEDV. Suitable adjuvants include, for example, vitamin E acetate solubilisate, aluminum hydroxide, aluminum phosphate or aluminum oxide, (mineral) oil emulsions, non-ionic detergents, squalene and saponins. Other adjuvants which may be used include an oil based adjuvants such as Freund's complete adjuvant (FCA), and Freund's incomplete adjuvant (FIA). It has been found that cross-linked olefinically unsaturated carboxylic acid polymers, such as CARBOPOL® 971 polymer, are particularly suitable adjuvants for use in the present inactivated PEDV immunogenic compositions.

Examples for suitable oil-in water emulsions are EMULSIGEN® based adjuvants, such as EMULSIGEN® (an oil-in-water emulsion), EMULSIGEN-D® (an oil-in-water) with dimethyldioctadecylammonium bromide (DDA)), EMULSIGEN-P® (an oil-in-water) with a proprietary immunostimulant), EMULSIGEN-75@ (a double adjuvant comprised of an oil-in-water) with a cross-linked polymer), and EMULSIGEN®-BCL (an oil-in-water emulsion that is free of animal origin components). (MVP Technologies, Inc. Omaha, Nebr., USA). Pharmaceutical/vaccine compositions that comprise inactivated PEDV or recombinant PEDV proteins, have been effectively adjuvanted with oil-in water emulsions, preferably with such EMULSIGEN®-based adjuvants, more preferably with EMULSIGEN® (an oil-in-water emulsion that is free of animal origin components) and EMULSIGEN®-BCL (an oil-in-water emulsion that is free of animal origin components).

It is generally advantageous to formulate the present compositions in dosage unit form for ease of administration and uniformity of dosage. Dosage unit form as used herein refers to physically discrete units suited as unitary dosages for the mammalian subjects to the treated; each unit containing a predetermined quantity of the active material calculated to produce the desired therapeutic effect in association with the required pharmaceutical carrier. The specification for the dosage unit forms of inactivated/killed PDCoV and/or PEDV, and/or recombinantly expressed PDCoV and/or PEDV antigens are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form.

The principal active ingredient is typically compounded for convenient and effective administration in effective amounts with a suitable pharmaceutically acceptable carrier in dosage unit form as disclosed herein. A unit dosage form can, for example, contain the PDCoV and/or PEDV antigen in amounts ranging from 1 to about 5 relative potency units ("RPUs"). This amount of the antigen is generally present in from about 1 to about 25/ml of carrier. In the case of compositions containing supplementary active ingredients, the dosages are determined by reference to the usual dose and manner of administration of the supplementary active ingredients.

The present vaccines typically include inactivated PDCoV and/or PEDV formulated with a pharmaceutically acceptable carrier. The pharmaceutical forms suitable for injectable use commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabenes, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

Sterile injectable solutions may be prepared by incorporating the inactivated virus in the desired amount in an appropriate solvent with various other ingredients as enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from a previously sterile-filtered solution thereof.

It may also be advantageous to add a stabilizer to the present compositions to improve the stability of inactivated virus. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

The compositions and methods of the present invention may be illustrated by the following examples, which are presented to illustrate the present invention and to assist in teaching one of ordinary skill how to make and use the same. These examples are not intended in any way to narrow or otherwise limit the scope of the present invention.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is to be understood that this invention is not limited to particular DNA, RNA, polypeptide sequences, or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens; reference to "an excipient" includes mixtures of two or more excipients, and the like.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of PEDV. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably PDCoV and/or PEDV, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge with the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" refers to a composition of matter that comprises at least one porcine deltacorona virus and/or porcine epidemic diarrhea virus and/or immunogenic portions thereof that elicit an immunological response in the host of a cellular or antibody-mediated immune response to the composition. In a preferred embodiment of the present invention, an immunogenic composition induces an immune response and, more preferably, confers protective immunity against one or more of the clinical signs of PDCoV and/or PEDV infection.

The immunogenic composition as used herein also refers to a composition that comprises any of the PDCoV and/or PEDV Spike polypeptides described herein. According to a further embodiment, such immunogenic composition further comprises at least a portion of a viral vector expressing said PDCoV and/or PEDV Spike protein, preferably of a recombinant baculovirus. Moreover, the immunogenic composition can comprise i) any of the PDCoV or PEDV proteins described above, preferably in concentrations described above, ii) at least a portion of the viral vector expressing said PDCoV and/or PEDV Spike protein, preferably of a recombinant baculovirus, and iii) a portion of the cell culture supernatant.

Thus according to one aspect, the present invention relates to a method for reducing the percentage of PDCoV and/or PEDV infections in a herd of pigs comprising the step administering to said pig(s) an effective amount of PDCoV and/or PEDV Spike antigen or an immunogenic composition comprising PDCoV and/or PEDV antigen, wherein the PDCoV and/or PEDV antigen is recombinant PDCoV and/or PEDV Spike antigen, preferably a baculovirus expressed PDCoV and/or PEDV Spike protein. Preferably those recombinant or baculovirus expressed PDCoV and/or PEDV Spike having the sequence as described herein.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity. "Immunogenic" means evoking an immune or antigenic response. Thus an immunogenic composition would be any composition that induces an immune response.

"Therapeutically effective amount" refers to an amount of an antigen or vaccine that would induce an immune response in a subject receiving the antigen or vaccine which is adequate in preventing or reducing the clinical signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

As used herein, "a pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion.

The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al. The Theory and Practical Application of Adjuvants (Ed. Stewart-Tull, D. E. S.), JohnWiley and Sons, NY, pp 51-94 (1995) and Todd et al. Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

Examples for suitable oil-in water emulsions are EMULSIGEN® based adjuvants, such as EMULSIGEN® (an oil-in-water emulsion o/w), EMULSIGEN-D® (an oil-in-water (o/w) with dimethyldioctadecylammonium bromide (DDA)), EMULSIGEN-P® (an oil-in-water (o/w) with a proprietary immunostimulant), EMULSIGEN-75@ (a double adjuvant comprised of an oil-in-water (o/w) with a cross-linked polymer), and EMULSIGEN®-BCL (an oil-in-water emulsion that is free of animal origin components).

(MVP Laboratories, Inc. Omaha, Nebr., USA). Pharmaceutical/vaccine compositions that comprise inactivated PDCoV, inactivated PEDV, and/or recombinant PDCoV and/or PEDV proteins, have been effectively adjuvanted with oil-in water emulsions, preferably with such EMULSIGEN®-based adjuvants, more preferably with EMULSIGEN® (an oil-in-water emulsion o/w) and/or EMULSIGEN®-BCL (an oil-in-water emulsion that is free of animal origin components).

Examples of suitable adsorbent aluminum hydroxide gels for use in veterinary vaccines include REHYDRAGEL®, REHYDRAGEL-CG®; REHYDRAGEL-LV; REHYDRAGEL-HPA; REHYDRAPHOS (General Chemical, Berkeley Heights, New Jersey, USA).

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (also known as polyacrylic acid); (BF Goodrich, Ohio, USA) are particularly appropriate. They are cross-linked with an allyl sucrose or with allyl pentaerythritol. Among then, there may be mentioned CARBOPOL® 974P (also known as polyacrylic acid), CARBOPOL® 934P (also known as polyacrylic acid) and CARBOPOL® 971P (also known as polyacrylic acid). Most preferred is the use of CARBOPOL® 971P (also known as polyacrylic acid). Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, or muramyl dipeptide among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a viral-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in the animal against PDCoV and/or PEDV.

"Mortality", in the context of the present invention, refers to death caused by PDCoV infection, PEDV infection, and/or co-infection with PDCoV and PEDV, and includes the situation where the infection is so severe that an animal is euthanized to prevent suffering and provide a humane ending to its life.

Herein, "effective dose" means, but is not limited to, an amount of antigen that elicits, or is able to elicit, an immune response that yields a reduction of clinical symptoms in an animal to which the antigen is administered.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference.

Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al. Nucleic Acids Research, 12(1):387 (1984)), BLASTP, BLASTN and FASTA (Altschul, S. F. et al. J. Molec. Biol., 215:403-410 (1990). The BLAST programs are publicly available from NCBI and other sources (BLAST Manual, Altschul, S. et al. NCVI NLM NIH Bethesda, MD 20894, Altschul, S. F. et al. J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence homology.

A "conservative substitution" refers to the substitution of an amino acid residue or with another amino acid residue having similar characteristics or properties including size, hydrophobicity, etc., such that the overall functionality does not change significantly.

"Sequence homology", as used herein, refers to a method of determining the relatedness of two sequences discounting conservative substitutions. To determine sequence homology, two or more sequences are optimally aligned, and gaps are introduced if necessary. In other words, to obtain a polypeptide having 95% sequence homology with a reference sequence, 85%, preferably 90%, even more preferably 95% of the amino acid residues in the reference sequence must match or comprise a conservative substitution with another amino acid, or a number of amino acids up to 15%, preferably up to 10%, even more preferably up to 5% of the total amino acid residues, not including conservative substitutions, in the reference sequence may be inserted into the reference sequence. Preferably the homolog sequence comprises at least a stretch of 50, even more preferred of 100, even more preferred of 250, even more preferred of 500 amino acids.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. When sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol.

Biol. (48): 444-453 (1970)) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov/.

The claimed PEDV of the invention shall also encompass variants of the PEDV isolate 1251-125-10 ("125-10") and variants of sub-fragments thereof. Such variants have essentially the same immunological properties as characteristic of the Oklahoma strain (SEQ ID NO 29 and 34). The term "having essentially the same immunological properties" encompass (but is not restricted to) that said variants are essentially effective in treating or preventing the clinical signs caused by PEDV as described below or in improving the efficacy parameters as described below.

The claimed PDCoV of the invention shall also encompass variants of the PDCoV isolates NSVL, PDCoV 2.0307, and PDCoV 5.0327 and variants of sub-fragments thereof. Such variants have essentially the same immunological properties as characteristic of the NSVL strain (SEQ ID NO: 1 and 2), and isolates PDCoV 2.0307 (SEQ ID NO:5 and 6) and PDCoV 5.0327 (SEQ ID NO:9 and 10). The term "having essentially the same immunological properties" encompass (but is not restricted to) that said variants are essentially effective in treating or preventing the clinical signs caused by PDCoV as described herein or in improving the efficacy parameters as described herein. Besides the various PDCoV strains that may be used in a vaccine, recombinant SPIKE protein antigens, including subfragments thereof, may also be used in a vaccine. Likewise, exemplary spike protein sequences include, but are not limited to, those with essentially the same immunological properties of the PDCoV isolates or 'variants' listed below.

The term "variant" with respect to PDCoV sequences (SEQ ID NO:1, 2, 3, 4, 5, 6, 7, 8, 9, 10, 11, 12, 17, 18, 27 and 28) or PEDV sequences SEQ ID NO:29, 30, 31, 32, 33, 34, 35, 36, 46, 47, 52, and 53) (e.g., a polypeptide or nucleic acid sequence) is intended to mean substantially similar sequences. For nucleotide sequences comprising an open reading frame, variants include those sequences that, because of the degeneracy of the genetic code, encode the identical amino acid sequence of the native protein. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein for the purposes of codon optimization. Generally, nucleotide sequence variants of the invention will have at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.41%, 97.42%, 97.43%, 97.44%, 97.45%, 97.46%, 97.47%, 97.48%, 97.49%, 97.5%, 97.51%, 97.52%, 97.53%, 97.54%, 97.55%, 97.56%, 97.57%, 97.58%, 97.59%, 97.6%, 97.61%, 97.62%, 97.63%, 97.64%, 97.65%, 97.66%, 97.67%, 97.68%, 97.69% 97.7%, 97.71%, 97.72%, 97.73%, 97.74%, 97.75%, 97.76%, 97.77%, 97.78%, 97.79%, 97.8%, 97.81%, 97.82%, 97.83%, 97.84%, 97.85%, 97.86%, 97.87%, 97.88%, 97.89%, 97.9%, 97.91%, 97.92%, 97.93%, 97.94%, 97.95%, 97.96%, 97.97%, 97.98%, 97.99%, 98%, 98.01%, 98.02%, 98.03%, 98.04%, 98.05%, 98.06%, 98.07%, 98.08%, 98.09%, 98.1%, 98.11%, 98.12%, 98.13%, 98.14%, 98.15%, 98.16%, 98.17%, 98.18%, 98.19%, 98.2%, 98.21%, 98.22%, 98.23%, 98.24%, 98.25%, 98.26%, 98.27%, 98.28%, 98.29%, 98.3%, 98.31%, 98.32%, 98.33%, 98.34%, 98.35%, 98.36%, 98.37%, 98.38%, 98.39%, 98.4%, 98.41%, 98.42%, 98.43%, 98.44%, 98.45%, 98.46%, 98.47%, 98.48%, 98.49%, 98.5%, 98.51%, 98.52%, 98.53%, 98.54%, 98.55%, 98.56%, 98.57%, 98.58%, 98.59%, 98.6%, 98.61%, 98.62%, 98.63%, 98.64%, 98.65%, 98.66%, 98.67%, 98.68%, 98.69%, 98.7%, 98.71%, 98.72%, 98.73%, 98.74%, 98.75%, 98.76%, 98.77%, 98.78%, 98.79%, 98.8%, 98.81%, 98.82%, 98.83%, 98.84%, 98.85%, 98.86%, 98.87%, 98.88%, 98.89%, 98.9%, 98.91%, 98.92%, 98.93%, 98.94%, 98.95%, 98.96%, 98.97%, 98.98%, 98.99%, 99%, 99.01%, 99.02%, 99.03%, 99.04%, 99.05%, 99.06%, 99.07%, 99.08%, 99.09%, 99.1%, 99.11%, 99.12%, 99.13%, 99.14%, 99.15%, 99.16%, 99.17%, 99.18%, 99.19%, 99.2%, 99.21%, 99.22%, 99.23%, 99.24%, 99.25%, 99.26%, 99.27%, 99.28%, 99.29%, 99.3%, 99.31%, 99.32%, 99.33%, 99.34%, 99.35%, 99.36%, 99.37%, 99.38%, 99.39%, 99.4%, 99.41%, 99.42%, 99.43%, 99.44%, 99.45%, 99.46%, 99.47%, 99.48%, 99.49%, 99.5%, 99.51%, 99.52%, 99.53%, 99.54%, 99.55%, 99.56%, 99.57%, 99.58%, 99.59%, 99.6%, 99.61%, 99.62%, 99.63%, 99.64%, 99.65%, 99.66%, 99.67%, 99.68%, 99.69%, 99.7%, 99.71%, 99.72%, 99.73%, 99.74%, 99.75%, 99.76%, 99.77%, 99.78%, 99.79%, 99.8%, 99.81%, 99.82%, 99.83% 99.84%, 99.85%, 99.86%, 99.87%, 99.88%, 99.89%, 99.9%, 99.91%, 99.92%, 99.93%, 99.94%, 99.95%, 99.96%, 99.97%, 99.98% and 99.99% sequence identity compared to a reference sequence using one of the alignment programs described using standard parameters.

The term "variant" with respect to PDCoV sequences (SEQ ID NO:1, 2, 3, 4, 5, 6, 7, 8, 9, 10, 11, 12, 17, 18, 27 and 28) (e.g., a polypeptide or nucleic acid sequence) is intended to mean substantially similar sequences. Thus immunogenic compositions of the invention can effectively incorporate all recognized strains or isolates of PDCoV, including preferably, but not necessarily limited to, all strains that have at least about 90% overall nucleotide identity to isolate NSVL-SCDV (Porcine deltacoronavirus strain USA/IL/2014/026PDV_P11) deposited as GenBank accession No. KP981395.1; isolate CHN-AH-2004, deposited as GenBank accession No. KP757890; isolate CHN-HB-2014, deposited as GenBank accession No. KP757891;

isolate CHN-JS-2014, deposited as GenBank accession No. KP757892; isolate PDCoV/CHJXNI2/2015, deposited as GenBank accession No. KR131621; strain USA/Arkansas61/2015, deposited as GenBank accession No. KR150443; strain USA/Minnesota442/2014, deposited as GenBank accession No. KR265847; strain USA/Minnesota214/2014, deposited as GenBank accession No. KR265848; strain USA/Michigan447/2014, deposited as GenBank accession No. KR265849; strain USA/Michigan448/2014, deposited as GenBank accession No. KR265850; strain USA/Indiana453/2014, deposited as GenBank accession No. KR265851; strain USA/Illinois449/2014, deposited as GenBank accession No. KR265852; strain USA/Minnesota/2013 deposited as GenBank accession No. KR265853; strain USA/Minnesota454/2014 deposited as GenBank accession No. KR265854; strain USA/Minnesota455/2014 deposited as GenBank accession No. KR265855; strain USA/Illinois272/2014 deposited as GenBank accession No. KR265856; strain USA/Illinois273/2014 deposited as GenBank accession No. KR265857; strain USA/NorthCarolina452/2014 deposited as GenBank accession No. KR265858; strain USA/Minnesota159/2014 deposited as GenBank accession No. KR265859; strain USA/Nebraska209/2014 deposited as GenBank accession No. KR265860; strain USA/Nebraska210/2014 deposited as GenBank accession No. KR265861; strain USA/Ohio444/2014 deposited as GenBank accession No. KR265862; strain USA/Ohio445/2014 deposited as GenBank accession No. KR265863; strain USA/Minnesota292/2014 deposited as GenBank accession No. KR265864; strain USA/Iowa459/2014 deposited as GenBank accession No. KR265865; strain CH/SXD1/2015 deposited as GenBank accession No. KT021234; strain CH/Sichuan/S27/2012 deposited as GenBank accession No. KT266822; isolate CHN-HN-2014 deposited as GenBank accession No. KT336560; strain PDCoV/Swine/Thailand/S5011/2015 deposited as GenBank accession No. KU051641; strain PDCoV/Swine/Thailand/S5015L/2015 deposited as GenBank accession No. KU051649; strain NH deposited as GenBank accession No. KU981059; strain NH isolate passage 0 deposited as GenBank accession No. KU981060; NH isolate passage 5 deposited as GenBank accession No. KU981061; strain NH isolate passage 10 deposited as GenBank accession No. KU981062; isolate TT_1115 deposited as GenBank accession No. KU984334; strain PDCoV/USA/Iowa136/2015 deposited as GenBank accession No. KX022602; strain PDCoV/USA/Minnesota140/2015 deposited as GenBank accession No. KX022603; strain PDCoV/USA/Nebraska137/2015 deposited as GenBank accession No. KX022604; strain PDCoV/USA/Nebraska145/2015 deposited as GenBank accession No. KX022605; and isolate P1_16_BTL_0115/PDCoV/2016/Lao deposited as GenBank accession No. KX118627.

The term "genogroup" as it is known in the art refers to related viruses within a genus; which may be further subdivided into genetic clusters. Identified genogroups of PEDV include group G1, comprising subgroups G1a, G1b, R (attenuated/adapted); and G2, comprising subgroups G2a, and G2b. Members of the G2a genogroup include the Chinese strain AH2012 (GenBank accession no: KC210145) and the North American strains, sharing several unique nucleotides changes. Strains MN and IA2 had 99.6% and strain IA1 had 99.5% nucleotide identity with AH2012, respectively. Researchers have speculated that an AH2012-like virus was possibly transmitted to the eastern China regions and then transported to the United States and is the most likely closest ancestor to the North American strains. Members of the genogroup 2a share only approximately 96.9% similarity to the prototype PEDV strain CV777 of genogroup 1a (Bridgen, et al. 1993; Huang et al. 2013; GenBank: AF353511.1). As such, the attenuated PEDV vaccines based on the historical CV777-derived G1a strains or DR13-derived G1b strains may be antigenically less related to the newly emergent Chinese and North American G2a PEDV strains.

A closely related North American PEDV isolate US/Colorado/2013 (GenBank Accession No: KF272920.1) has also been reported by Marthaler et al. 2013. Like the North American isolates above the complete PEDV genome of CO/13 has a nucleotide identity of 96.5 to 99.5% with other complete PEDV genomes available in GenBank, with the highest nucleotide identity (99.5%) with Chinese strain AH2012 (GenBank Accession No. KC210145). Chinese strain AH2012 is a member of the 2a genogroup. Comparison of the complete genome of North American isolate CO/13 to that of PEDV reference strain CV777, shows that CO/13 contains a 1-nucleotide insertion (at position 48) and deletions of 5 nucleotides in the 5' UTR (at positions 73 and 83 to 86), while the spike gene contains insertions of 16 nucleotides (positions 20804, 20810 to 20820, 20843, and 21053 to 21055) and deletions of 7 nucleotides (positions 20853 and 21118 to 21124).

Other variants of PEDV have emerged, referred to as 'INDEL' strains which are often naturally attenuated compared to older prototype strains. These too may be used as vaccines wherein the virus is live attenuated, or inactivated. In such case only minimal further passaging may be needed to provide a safe vaccine attenuate. Exemplary vaccine viruses of the invention therefor also include those that have at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.41%, 97.42%, 97.43%, 97.44%, 97.45%, 97.46%, 97.47%, 97.48%, 97.49%, 97.5%, 97.51%, 97.52%, 97.53%, 97.54%, 97.55%, 97.56%, 97.57%, 97.58%, 97.59%, 97.6%, 97.61%, 97.62%, 97.63%, 97.64%, 97.65%, 97.66%, 97.67%, 97.68%, 97.69% 97.7%, 97.71%, 97.72%, 97.73%, 97.74%, 97.75%, 97.76%, 97.77%, 97.78%, 97.79%, 97.8%, 97.81%, 97.82%, 97.83%, 97.84%, 97.85%, 97.86%, 97.87%, 97.88%, 97.89%, 97.9%, 97.91%, 97.92%, 97.93%, 97.94%, 97.95%, 97.96%, 97.97%, 97.98%, 97.99%, 98%, 98.01%, 98.02%, 98.03%, 98.04%, 98.05%, 98.06%, 98.07%, 98.08%, 98.09%, 98.1%, 98.11%, 98.12%, 98.13%, 98.14%, 98.15%, 98.16%, 98.17%, 98.18%, 98.19%, 98.2%, 98.21%, 98.22%, 98.23%, 98.24%, 98.25%, 98.26%, 98.27%, 98.28%, 98.29%, 98.3%, 98.31%, 98.32%, 98.33%, 98.34%, 98.35%, 98.36%, 98.37%, 98.38%, 98.39%, 98.4%, 98.41%, 98.42%, 98.43%, 98.44%, 98.45%, 98.46%, 98.47%, 98.48%, 98.49%, 98.5%, 98.51%, 98.52%, 98.53%, 98.54%, 98.55%, 98.56%, 98.57%, 98.58%, 98.59%, 98.6%, 98.61%, 98.62%, 98.63%, 98.64%, 98.65%, 98.66%, 98.67%, 98.68%, 98.69%, 98.7%, 98.71%, 98.72%, 98.73%, 98.74%, 98.75%, 98.76%, 98.77%, 98.78%, 98.79%, 98.8%, 98.81%, 98.82%, 98.83%, 98.84%, 98.85%, 98.86%, 98.87%, 98.88%, 98.89%, 98.9%, 98.91%, 98.92%, 98.93%, 98.94%, 98.95%, 98.96%, 98.97%, 98.98%, 98.99%, 99%, 99.01%, 99.02%, 99.03%, 99.04%, 99.05%, 99.06%, 99.07%, 99.08%, 99.09%, 99.1%, 99.11%, 99.12%, 99.13%, 99.14%, 99.15%, 99.16%, 99.17%, 99.18%, 99.19%, 99.2%, 99.21%, 99.22%, 99.23%, 99.24%, 99.25%, 99.26%, 99.27%, 99.28%, 99.29%, 99.3%, 99.31%, 99.32%, 99.33%, 99.34%, 99.35%, 99.36%, 99.37%, 99.38%, 99.39%, 99.4%, 99.41%, 99.42%, 99.43%, 99.44%, 99.45%, 99.46%, 99.47%, 99.48%, 99.49%, 99.5%, 99.51%, 99.52%, 99.53%, 99.54%, 99.55%, 99.56%, 99.57%, 99.58%, 99.59%, 99.6%, 99.61%, 99.62%, 99.63%, 99.64%, 99.65%, 99.66%, 99.67%, 99.68%, 99.69%, 99.7%, 99.71%, 99.72%, 99.73%, 99.74%, 99.75%, 99.76%, 99.77%, 99.78%, 99.79%, 99.8%, 99.81%, 99.82%, 99.83% 99.84%, 99.85%, 99.86%, 99.87%, 99.88%, 99.89%, 99.9%, 99.91%, 99.92%, 99.93%, 99.94%, 99.95%, 99.96%, 99.97%, 99.98% and 99.99% sequence identity or higher sequence identify with such strains, whether measured amino acid or encoding nucleotide sequence, for the spike protein or based on the full viral sequence.

The term "PEDV of North American origin" means a PEDV isolate comprising SEQ ID NO:29 and/or 33 and/or SEQ ID NO:32 and/or 36, and/or any PEDV isolates having at least 99% sequence identity to SEQ ID NO:29 and/or 33, and/or is at least 99% identical with the RNA equivalent of SEQ ID. NO:29 and/or 33, and/or a PEDV isolate in which a Spike protein is encoded by SEQ ID NO:30, 34, 46, or 52, and/or any PEDV isolate in which a Spike protein has at least 98% sequence identity to SEQ ID:30, 34, 46, or 52, and/or any PEDV isolate in which the expressed Spike protein has at least 90% homology with SEQ ID NO:31, 35, 47, 53.

The term "clade" as it is known in the art refers to a group consisting of an ancestor and all its descendants, a single "branch" in a phylogenetic tree. The ancestor may be, as an example an individual, a population or a species. A genogroup can include multiple clades, for example AH2012 is in a different clade than the North American isolates.

According to a further embodiment, the present invention also relates to a vector that comprises any of such nucleic acid molecules as described herein. In other words, the present invention relates to a vector, that includes the coding sequence of any such Spike, M, E, N PEDV protein, or part thereof. Preferably, said vector is an expression vector, which allows the expression of any such Spike, M, E, and/or N PEDV protein or part of the protein. Vectors according to the invention are those which are suitable for the transfection or infection of bacterial, yeast or animal cells, in vitro or in vivo.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382,425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051(recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred viral vectors include baculovirus such as BaculoGold (BD Biosciences Pharmingen, San Diego, Calif), in particular provided that the production cells are insect cells. Although the baculovirus expression system is preferred, it is understood by those of skill in the art that other expression systems will work for purposes of the present invention, namely the expression of HG into the supernatant of a cell culture. Such other expression systems may require the use of a signal sequence in order to cause H5 expression into the media.

Effective Dose:

The compounds described herein can be administered to a subject at therapeutically effective doses to prevent PDCoV and/or PEDV-associated diseases. The dosage will depend upon the host receiving the vaccine as well as factors such as the size, weight, and age of the host.

The precise amount of immunogenic composition of the invention to be employed in a formulation will depend on the route of administration and the nature of the subject (e.g., age, size, stage/level of disease), and should be decided according to the judgment of the practitioner and each subject's circumstances according to standard clinical techniques. An effective immunizing amount is that amount sufficient to treat or prevent a PDCoV and/or PEDV infectious disease in a subject.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response. Test subjects may include animals such as pigs, mice, hamsters, dogs, cats, rabbits, cows, horses, sheep, poultry (e.g. chickens, ducks, geese, and turkeys), and humans.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, virus neutralization, etc.; or, by protection of immunized hosts from infection by the pathogen and/or attenuation of symptoms due to infection by the pathogen in immunized hosts as determined by any method known in the art, for assaying the levels of an infectious disease agent, e.g., the viral levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal with PDCoV and/or PEDV using the methods and compositions of the present invention, any binding assay known in the art can be used to assess the binding between the resulting antibody and the particular molecule. These assays may also be performed to select antibodies that exhibit a higher affinity or specificity for the particular antigen.

Administration to a Subject:

Preferred routes of administration include but are not limited to intranasal, oral, intradermal, and intramuscular. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Isolation and Production of PEDV Strain

To produce the porcine epidemic diarrhea virus vaccine, killed virus, a master seed culture of a PEDV (isolate) was first produced. From this master seed, a culture of PEDV was grown and then inactivated. The inactivated virus culture was then mixed with an adjuvant in order to produce the porcine epidemic diarrhea virus vaccine. The following method was used to produce the porcine epidemic diarrhea virus vaccine.

Animals or tissues from animals exhibiting extreme diarrhea were acquired in 2013. Homogenates from mucosal scrapings were generated from these animals filtered through a 0.2 micron syringe filter and the filtrate was used to inoculate African Green Monkey kidney cells (VERO). Virus was grown in the presence of PEDV maintenance media containing modified MEM, porcine trypsin, tryptose phosphate broth, yeast extract and HEPES buffer. Virus growth was evaluated and visualized by checking for characteristic syncytia formation and fusion of cell monolayer. CPE positive material was subjected to sequencing using Illumina-based MISEQ® sequencer technology.

In order to produce the PEDV master seed virus culture ("PEDV MSV"), porcine epidemic diarrhea virus strain (isolate) (PEDV isolate) was isolated in BI VERO cells and passed a total nineteen times in BI VERO cells and then virus was grown in 2013 EU VERO cells till passage 30. The $30^{th}$ passage of the virus was diluted and put down as the master seed virus designated PEDV KV-1251-125-10-OK.

From the master seed virus, a culture of PEDV (KV-1251-125-10-OK, to be referred to herein as "125-10") was produced by infecting 2013 EU VERO cells with PEDV KV-1251-125-10-OK MSV in PEDV maintenance media containing modified Minimal Essential Media, porcine trypsin (10 μg/ml), tryptose phosphate broth (0.3%), yeast extract (0.02%) and 1M HEPES buffer (2.5%) The 2013 EU VERO cells were typically infected with the PEDV (125-10) MSV at a minimum dose of $10^4$ $TCID_{50}/850$ $cm^2$ roller bottle. Such cultures can be grown in sterile disposable roller bottles or on microcarrier beads. The culture was incubated at 36° C.±2° C. for 24 to 48 hours until cytopathic effect ("CPE") was observed. Typically, characteristic syncytia can be seen within 12 hours of infection, syncytia expand and cell monolayer fuses from 24-48 hours followed by sloughing of cells. During incubation, the culture was monitored for PEDV induced CPE to ensure a pure PEDV strain. If atypical CPE was observed or any macroscopic or microscopic evidence of contamination existed, the culture was discarded. Pure virus culture was aseptically harvested into sterile polypropylene carboys. Virus was freeze thawed to release cell associated virions and was clarified by centrifugation or by filtration through filters of 0.45 microns followed by 0.2 microns. Bulk virus harvest fluids were tested to ensure the absence of *mycoplasma* prior to inactivation. Harvested fluids which were not immediately inactivated were stored at −70° C. or below.

The volume of harvested fluids is determined and the temperature of the fluids is brought to 36±2° C. A 0.4 M solution of 2-bromoethyleneamine (BEA) is mixed with a stock solution of 0.3 N NaOH to generate a binary ethyleneimine (BEI) stock solution which is then added to the harvest fluids to give a final concentration of BEI of 5 mM. The fluids are stirred continuously for a minimum of 24 hours. A 1.0 M sodium thiosulfate solution to give a final minimum concentration of 5 mM is added to neutralize any residual BEI. The inactivated fluids can be stored at −70±3° C. for long term storage or at 4±3° C. for short term.

After treatment with BEI, the culture was tested for its ability to induce CPE typical of PEDV to ensure inactivation of the virus. This task was accomplished by passing the BEI treated viral fluids over Vero cells and checking the Vero cells for any viral infection. The BEI treated culture fluids were typically stored at −70° C. or below until the inactivation assay had been completed.

The inactivated virus was formulated as an adjuvanted vaccine by thoroughly blending the inactivated PEDV culture with adjuvant EMULSIGEN®-BCL at a 20% inclusion rate to form a bulk serial. The bulk serial was maintained at 2-8° C. until being transferred into vials containing either one or ten doses (@2.0 ml per dose).

Example 2: Isolation and Production of Porcine Deltacoronavirus Strain

The Porcine Deltacoronavirus (PDCoV) was purchased from the National Veterinary Service laboratory (NVSL), Ames, IA. This virus was isolated at NVSL from a swine intestinal sample from Illinois in 2014. The virus was isolated on Swine testes (ST) cells in serum free media in the presence of 5 µg/mL TPCK trypsin. The original virus went through two rounds of plaque purification at NVSL and the tenth passage of the virus was utilized as the starting material.

The pass 10 virus was inoculated and adapted to swine testes (ST) cells at BI with PDCoV maintenance media that contained Modified Minimal Essential Media with HEPES, tryptose phosphate broth, yeast extract and porcine trypsin. The cells were incubated at 24-48 hours at 37° C. with 5% CO2 and observed for evidence of PDCoV-induced cytopathic effect. When the CPE was complete and cells had sloughed off, the flasks were freeze-thawed once and the lysate was harvested. The harvested material was then inoculated onto a fresh monolayer for continued passage. Passage continued in this manner through pass 12. Virus harvested from pass 12 was inoculated and adapted to an alternate, derivative swine testes (ST) cell lineage designated “AI-ST 2015” cells. Four more passages of the virus were carried out in AI-ST 2015 cells in the same manner as passes 11 and 12 to get P16 virus. P16 virus was inoculated into roller bottles yield the final “P17” master seed virus isolate which was harvested, filtered through 0.2 µm filter, pooled to obtain a bulk virus stock and stored below −60° C. The average titer of the master seed virus “P17” was determined to be 4.91 log 10 FAID50 per mL.

Example 3: Genome Sequence Analysis of PEDV Isolate and PDCoV Isolate

Sample Preparation and Analysis:

Prior to extraction virus tissue culture supernatants were pre-treated with a cocktail of DNase and RNase to remove residual host cell genomic nucleic acids. Viral genomic RNA was then extracted from the nuclease-treated samples using the RNEASY® viral RNA extraction kit (Qiagen, Cat #52906). Post extraction, samples were again treated with DNase to further enrich for viral genomic RNA. Subsequently, viral genomic RNA was converted to double stranded cDNA (ds cDNA) through randomly primed reverse transcription and Klenow fragment treatment. The ds cDNA products were then used to generate a library for Illumina MISEQ® sequencer-based sequencing using the NEXTERA® XT library preparation kit (Cat #FC-131-1024). Each sample was barcoded with unique tags on both the 5'- and 3'-ends to minimize the chances of bioinformatic mis-binning. This library was run on the MISEQ® sequencer using the 500-cycle kit (Cat #MS-102-2003) and data was analyzed using a combination of NextGene (version 2.3.4) and Sequencher software (version 5.1). High quality sequences were selected as those containing a median Q-score of greater than 25 and trimmed with a cut-off of no more than three uncalled bases at 3'-end or 3-consecutive bases with Q-score measuring less than 16. The sequences were then assembled de novo using criteria of 85% or greater match over a 35 bp stretch to generate a putative full genome for each isolate. The putative complete genome sequence for each was then verified by template-based alignment to verify single nucleotide polymorphisms (SNP) or variable small insertions/deletions.

For PEDV isolate 1251-125-10, a total of 570,253 sequences were generated with an average length of 136 bp after trimming of low quality data. Of those sequences; 484,247 (84.9%) assembled into a single contig 27,995 bp long which through BLASTn analysis revealed strong identity to the single-stranded RNA alphacoronavirus PEDV. A total of 11 positions exhibited polymorphism at either a single nucleotide or a small insertion/deletion, these positions are listed in TABLE 1.

TABLE 1

Polymorphic Residues in Isolate 1251-125-10 “125-10”

| Position | Residue Frequencies | Gene |
|---|---|---|
| 3,315 | T (51%)<br>A (49%) | ORF1A/B |
| 3,423-3,426 | DEL (50%)<br>TTA (50%) | ORF1A/B |
| 9,425 | C (64%)<br>T (36%) | ORF1A/B |
| 10,136 | T (52%)<br>A (48%) | ORF1A/B |
| 14,416 | A (69%)<br>G (31%) | ORF1A/B |
| 18,179 | C (73%)<br>T (27%) | ORF1A/B |
| 19,100 | C (73%)<br>T (27%) | ORF1A/B |
| 23,101 | G (63%)<br>A (37%) | Spike |
| 25,057 | T (59%)<br>10bp INS (41%) | Spike |
| 25,165-25,169 | TTATG (74%)<br>DEL (26%) | ORF3 |
| 27,510 | C (73%)<br>T (27%) | ORF3 |

The putative complete/near-complete PEDV genome of 1251-125-10 (SEQ ID NO:29) was aligned to the closest Chinese AH2012 (GenBank Accession No: KC210145) and North American Colorado 2013 isolate of PEDV (GenBank Accession No: AGO58924). The identities to both isolates exceed 99.2% indicating very close relation to both strains, both in genogroup 2a.

Next, the immunogenic spike protein sequence was examined for protein identity/similarity to the larger GenBank repository of PEDV spike proteins. Again, the closest GenBank isolate submitted was derived from the North American Colorado 2013 strain deposited by the University of Minnesota Veterinary diagnostic laboratory (GenBank Accession No. AGO58924) exhibiting over 99.5% identity (1380/1386 identical amino acids) (SEQ ID NO:X). Of the 6 amino acid changes, 1 was due to the polymorphism at position 23,101 which would encode either CGA (Arg) in the majority or CAA (Gln) in minority at position 838. The North American Colorado 2013 strain contains a Gln at this position.

For PDCoV, 12 individually isolated samples were sequenced. Materials were extracted following viral particle protected nucleic acid digestion (RNase+DNase) in order to enrich for viral RNA. Post-extraction, nucleic acids treated with DNase to enrich for RNA. Double-stranded cDNA was generated through reverse transcription and klenow treatment using priming with random hexamers. These products were then used for library generation.

Samples were processed for MISEQ® sequencer based sequencing through library generation using the NEXTERA® XT library preparation kit (Illumina, Cat #FC-131-1024). Each sample was barcoded with unique tags on both the 5'- and 3'-ends to minimize the chances of bioinformatic mis-binning. The library was run on the MISEQ™ sequencer using the 500-cycle kit (Illumina, Cat #MS-102-2003) and data was analyzed using a combination of NEXTGENE® sequencing software (SoftGenetics, LLC, version 2.3.4.2) and SEQUENCER® software (Gene Codes Corp., version 5.1). High quality sequences were selected as those containing a median Q-score of greater than 25 and trimmed with a cut-off of no more than 3 uncalled bases at 3'-end or 3-consecutive bases with Q-score measuring less than 16. These sequences were both assembled de novo and aligned to reference files using criteria of 85% or greater match over a 35 bp stretch. Reference sequences for alignment were from de novo sequence assemblies or MISEQ® sequencer derived references for Carthage and NVSL PDCoV strains (NSVL, porcine deltacoronavirus strain USA/IL/2014/026PDV_P11, Genbank Accession No. KP981395.1).

Figure 2:
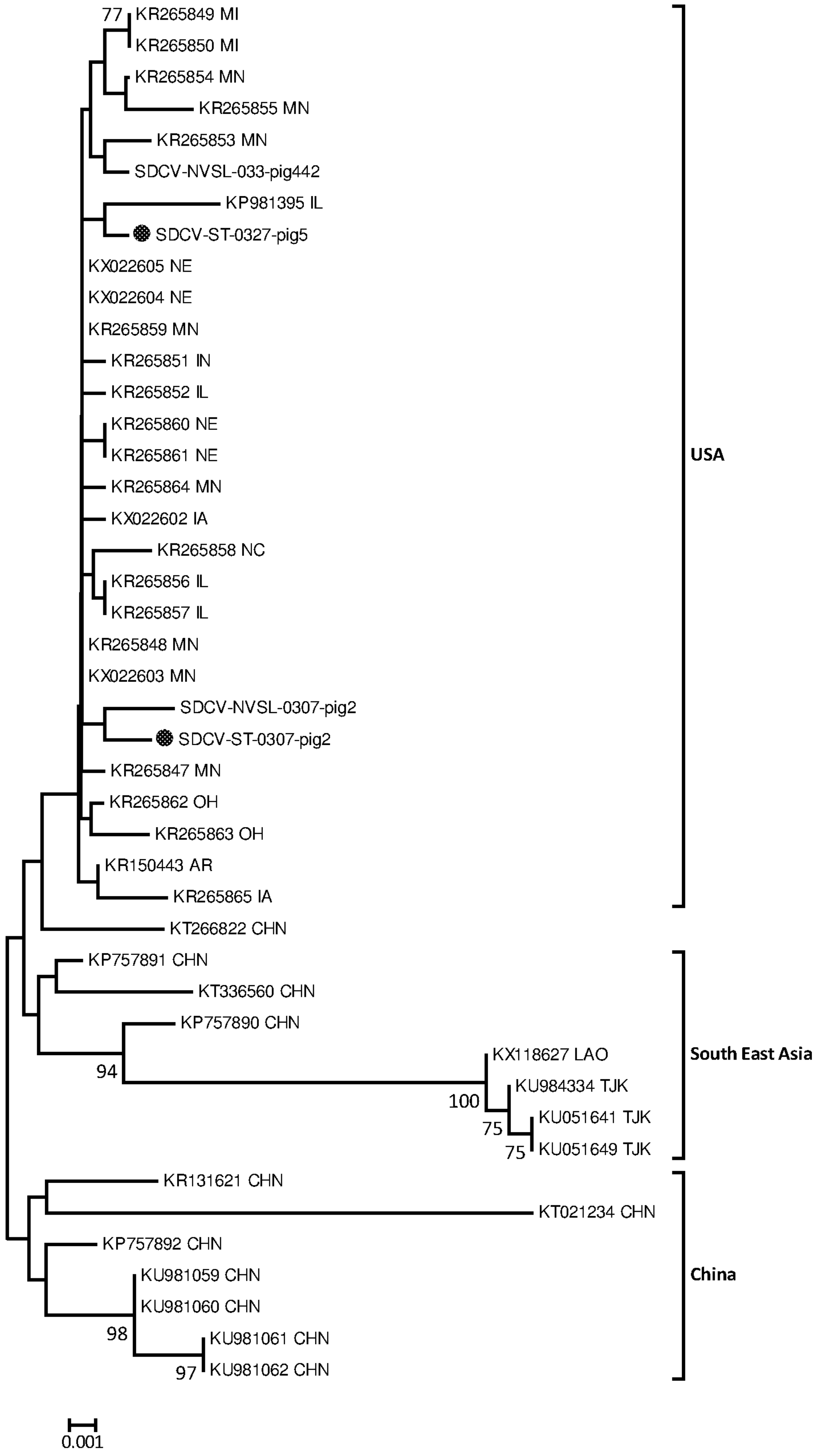
FIG. 2 Spike amino acid neighbor-joining tree for PDCoV isolates/strains. Scale indicates p-distance. GenBank accession numbers listed along with two letter state or three letter country code (CHN—China, TJK—Thailand, LAO—Laos).

Overall, the genetic similarity between each of the BI virus isolates and other strains ("Carthage" original isolate and NVSL strain) was high (>99.8% identity) and differences between variants of NVSL and BI-ST cell grown viruses exhibiting even fewer changes (>99.95% identity) (TABLE 2) See also FIGS. 1 and 2 schematically showing a complete genome nucleotide neighbor-joining tree for PDCoV isolates/strains, and a Spike amino acid neighbor-joining tree for PDCoV isolates/strains, respectively. Scale indicates p-distance.

The similarities between variants of NVSL and BI-ST cell grown viruses are most likely due to the shared origin of the some of the samples. One notable sequence difference is the presence of an in-frame 9 bp deletion in spike (amino acid positions 229-231) within the cultured PDCoV_2201-1 isolates; but not observed in either the original homogenate or materials from pigs. This position appears to be a "hot spot" for IN/DEL variability as the BI PDCoV-5.0327 isolate, which has no known connection to the "Carthage" isolate, also exhibits the identical deletion in the "BI-ST" cell line, but not the NVSL-ST cell line. These changes may be indicative of tissue culture adaptation of the virus.

TABLE 2: genetic similarity between each of the BI virus isolates.

TABLE 2 genetic similarity between each of the BI virus isolates.

| | Full Genome Nucleotide Distance | | | SPIKE Protein Amino Acid Distance | | |
|---|---|---|---|---|---|---|
| | PDCoVST0 2.0307 | PDCoVST0 5.0327 | BIVI_NVSL isolate | PDCoVST0 2.0307 | PDCoVST0 5.0327 | BIVI_NVSL isolate |
| KP757890_CHN | 98.97% | 99.05% | **98.89%** | 98.97% | 99.05% | 98.62% |
| KP757891_CHN | 99.22% | 99.40% | 99.25% | 99.22% | 99.40% | 98.88% |
| KP757892_CHN | 99.14% | 99.22% | 99.19% | 99.14% | 99.22% | 98.79% |
| KP981395_IL | 99.22% | 99.48% | 99.94% | 99.22% | 99.48% | 99.91% |
| KR131621_CHN | 98.79% | 98.88% | **98.91%** | 98.79% | 98.88% | 98.45% |
| KR150443_AR | 99.66% | 99.74% | 99.76% | 99.66% | 99.74% | 99.31% |
| KR265847_MN | 99.57% | 99.66% | 99.82% | 99.57% | 99.66% | 99.22% |
| KR265848_MN | 99.66% | 99.74% | 99.83% | 99.66% | 99.74% | 99.31% |
| KR265849_MI | 99.57% | 99.66% | 99.85% | 99.57% | 99.66% | 99.22% |
| KR265850_MI | 99.57% | 99.66% | 99.85% | 99.57% | 99.66% | 99.22% |
| KR265851_IN | 99.66% | 99.74% | 99.84% | 99.66% | 99.74% | 99.31% |
| KR265852_IL | 99.66% | 99.74% | 99.84% | 99.66% | 99.74% | 99.31% |
| KR265853_MN | 99.48% | 99.57% | 99.84% | 99.48% | 99.57% | 99.14% |
| KR265854_MI | 99.57% | 99.66% | 99.83% | 99.57% | 99.66% | 99.22% |
| KR265855_MN | 99.31% | 99.40% | 99.79% | 99.31% | 99.40% | 98.97% |
| KR265856_IL | 99.66% | 99.74% | 99.80% | 99.66% | 99.74% | 99.31% |
| KR265857_IL | 99.66% | 99.74% | 99.80% | 99.66% | 99.74% | 99.31% |
| KR265858_NC | 99.48% | 99.57% | 99.79% | 99.48% | 99.57% | 99.14% |
| KR265859_MN | 99.74% | 99.83% | 99.85% | 99.74% | 99.83% | 99.40% |
| KR265860_NE | 99.66% | 99.74% | 99.84% | 99.66% | 99.74% | 99.31% |
| KR265861_NE | 99.66% | 99.74% | 99.84% | 99.66% | 99.74% | 99.31% |
| KR265862_OH | 99.66% | 99.74% | 99.80% | 99.66% | 99.74% | 99.31% |
| KR265863_OH | 99.40% | 99.48% | 99.80% | 99.40% | 99.48% | 99.05% |
| KR265864_MN | 99.66% | 99.74% | 99.83% | 99.66% | 99.74% | 99.31% |
| KR265865_IA | 99.40% | 99.48% | 99.78% | 99.40% | 99.48% | 99.05% |
| KT021234_CHN | **97.50%** | **97.59%** | **98.82%** | **97.50%** | **97.59%** | **97.16%** |

TABLE 2-continued genetic similarity between each of the BI virus isolates.

| | Full Genome Nucleotide Distance | | | SPIKE Protein Amino Acid Distance | | |
|---|---|---|---|---|---|---|
| | PDCoVST0 2.0307 | PDCoVST0 5.0327 | BIVI_NVSL isolate | PDCoVST0 2.0307 | PDCoVST0 5.0327 | BIVI_NVSL isolate |
| KT266822_CHN | 99.14% | 99.22% | **98.90%** | 99.14% | 99.22% | 98.79% |
| KT336560_NE | 98.88% | 98.97% | 99.00% | 98.88% | 98.97% | 98.53% |
| KU051641_TJK | **97.59%** | **97.59%** | **97.37%** | **97.59%** | **97.59%** | **97.16%** |
| KU051649_TJK | **97.50%** | **97.50%** | **97.36%** | **97.50%** | **97.50%** | **97.07%** |
| KU981059_CHN | 98.97% | 99.05% | 98.96% | 98.97% | 99.05% | 98.62% |
| KU981060_CHN | 98.97% | 99.05% | 98.96% | 98.97% | 99.05% | 98.62% |
| KU981061_CHN | 98.71% | 98.79% | **98.96%** | 98.71% | 98,79% | 98.36% |
| KU981062_CHN | 98.71% | 98.79% | **98.95%** | 98.71% | 98.79% | 98.36% |
| KU984334_TJK | **97.67%** | **97.67%** | **97.39%** | **97.67%** | **97.67%** | **97.24%** |
| KX022602_IA | 99.57% | 99.74% | 99.75% | 99.57% | 99.74% | 99.22% |
| KX022603_MN | 99.66% | 99.83% | 99.76% | 99.66% | 99.83% | 99.31% |
| KX022604_NE | 99.66% | 99.83% | 99.74% | 99.66% | 99.83% | 99.31% |
| KX022605_NE | 99.66% | 99.83% | 99.76% | 99.66% | 99.83% | 99.31% |
| KX118627_LAO | 97.76% | 97.76% | **97.43%** | 97.76% | 97.76% | 97.33% |
| PDCoV-NVSL-0307-pig2 | 99.57% | 99.48% | 99.83% | 99.57% | 99.48% | 99.05% |
| PDCOV-NVSL-033-pig442 | 99.57% | 99.66% | 99.83% | 99.57% | 99.66% | 99.22% |
| PDCOV-ST-0307-pig2 | | 99.57% | 99.84% | | 99.57% | 99.14% |
| PDCOV-ST-0327-pig5 | | | 99.94% | | | 99.40% |

bottom 10% lowest values in identity (most divergent).
Top 10% highest in identity (least divergent).

Example 4: Inactivation of Whole PEDV and PDCoV Isolates

Each lot of PEDV virus or pool is tested for inactivation by passage in VERO cells. Seventy five $cm^2$ of 24 hour cell culture are inoculated with 2.0 mL of inactivated PEDV fluids and maintained at 36±3° C. for 48 hours. One flask of VERO cells remains uninoculated. For positive virus controls one culture of VERO cells is inoculated with a positive control PEDV. At the end of the incubation period, the cell monolayers are examined for CPE typical of PEDV. The material is frozen and thawed three times and then 2 ml of each material is inoculated onto one day old VERO cells. The culture should be maintained at 37±2° C. for 48 hours. Following the second passage, a third passage is performed. After incubation and passage, the absence of virus-infected cells in the BEI treated viral fluids as determined by lack of immunofluorescence staining constitutes a satisfactory inactivation test. The control cells inoculated with the positive control virus shall show CPE typical of PEDV and the uninoculated flask shall show no evidence of PEDV CPE.

PDCoV viral harvest is inactivated with 5 mM BEI for 24 hours at 37° C. Following inactivation, the harvest is neutralized with sodium thiosulfate. Inactivation was confirmed by TCID50 evaluation of the inactivated harvest. No live virus was detected in the inactivated material. Inactivated, neutralized viral harvest is concentrated using a 10 kd hollow fiber PES cartridge (GC Healthcare cat #UFP-10-C-3MA). Concentrated antigen is aseptically diluted with modified minimal essential media (final concentration=10×). A portion of the diluted antigen is combined with EMULSIGEN D® (MVP Laboratories, item #10005408) to achieve a 12.5% formulation.

Figure 3A:
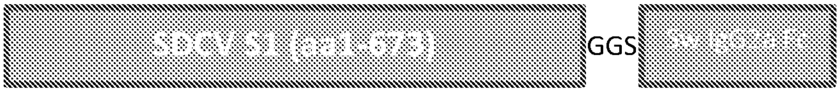
FIG. 3A Schematic diagram of PDCoV S1-IgG2a Fc Baculovirus—Protein Map of PDCoV S1-IgG2a Fc.
Figure 3B:
FIG. 3B Schematic diagram of PDCoVS BD Baculodisplay Baculovirus—Protein Map of PDCoVS BD.

Example 5: Construction of a Recombinant Baculoviruses Coding for and Expressing PDCoV Spike Antigens Preparation of PDCoV S1-IgG2a Fc Baculovirus The S1 region of porcine deltacoronavirus (PDCoV) spike (aa 1-673) was amplified by PCR from plasmid DNA using primers P2967167A (SEQ ID NO:13) and P2967167B (SEQ ID NO:14). The Fc region of swine IgG2a including a short GGS linker and the hinge region was amplified from plasmid DNA using primers P2967167C (SEQ ID NO:15) and P2968014E (SEQ ID NO:16). The two fragments were fused by overlap-extension PCR using primers P2967167A (SEQ ID NO:13) and P2968014E (SEQ ID NO:16) to generate the PDCoV S1-IgG2a Fc coding sequence (SEQ ID NO:17) containing a Kozak consensus sequence immediately 5' of the start codon. See the schematic diagram in FIG. 3.A. The final coding sequence was flanked by BamHI and NotI restriction sites to facilitate cloning into baculovirus transfer plasmid pVL1393. Once completed, plasmid pVL1393-PDCoV S1-IgG2a Fc was used with linearized BaculoGold baculovirus DNA to transfect Sf9 insect cells to produce recombinant baculovirus.

Preparation of PDCoVS BD Baculodisplay Baculovirus

The PDCoV Spike gene from porcine deltacoronavirus (PDCoV) was cloned in two overlapping fragments (N-term and C-term) from plasmid DNA. The N-terminal fragment was amplified using primers P2967002C (SEQ ID NO:23) and P2967002D (SEQ ID NO:24) while the C-term fragment was amplified using primers P2967002E (SEQ ID NO:25) and P2967002F (SEQ ID NO:26). The N-terminal and C-terminal fragments were amplified so as to remove the native signal sequence and C-terminal tail. The N-term fragment was fused with the *Autographa californica* nucleopolyhedrovirus (AcNPV) gp64 signal sequence (02967002A) (SEQ ID NO:21) by overlap-extension PCR (OE-PCR) using primers P290194A (SEQ ID NO:19) and P2967002D (SEQ ID NO:20). The C-term fragment was fused with the AcNPV gp64 C-terminal tail coding sequence (02967002B) (SEQ ID NO:22) by OE-PCR using primers P290194B (SEQ ID NO:20) and P2967002E (SEQ ID NO:25). The two resulting fragments were fused by OE-PCR using primers P290194A (SEQ ID NO:19) and P290194B (SEQ ID NO:20) to generate the PDCoV spike BaculoDisplay (PDCoVS BD) coding sequence (SEQ ID NO:27) containing a Kozak consensus sequence immediately 5' of the start codon. See the schematic diagram in FIG. 3B. The final coding sequence was flanked by BamHI and NotI restriction sites to facilitate cloning into baculovirus transfer plasmid pVL1393. Once completed, plasmid pVL1393-PDCoVS BD was used with linearized BaculoGold baculovirus DNA to transfect Sf9 insect cells to produce recombinant baculovirus.

Example 6: Preparation of Pharmaceutical Compositions (Vaccines) Comprising PEDV Spike Antigens For the inactivated PEDV material, PEDV viral harvest was inactivated for a minimum of 24 hours using 5 mM BEI, clarified and 0.45 μm filtered.

After neutralization various adjuvants were added and the following vaccine/pharmaceutical compositions were generated.

Example 7: Preparation of Pharmaceutical Compositions (Vaccines) Comprising PDCoV Spike Antigens Batches of PDCoV antigen (BacluloS-BD-PDCoV and BaculoS-FC-PDCoV) were grown in 3 L spinners. For infection, SF+ cells were inoculated with the virus at an approximate MOI of between 1.0-2.1. Flasks were incubated at 27° C. with agitation set at 100 rpm. Harvest was initiated at five days post-infection. At the time of harvest cell viability was between 24% and 26% and viable cells/mL was between $0.31\times10^6$ and $0.36\times10^6$. Harvest fluids were clarified by centrifugation at 10,000×g for 10 minutes and 0.2 m filtered. Clarified harvest fluids are combined with EMULSIGEN® D to achieve a 12.5% formulation.

Example 8: Inoculation of Pigs with Inactivated PDCoV and Baculovirus Spike Vaccine and Assessment of the Serological Response The study objective was to evaluate the serological response of PDCoV vaccine prototypes in conventional piglets. Several prototype vaccines in which the spike protein of PDCoV is expressed in various backbones have been generated. In addition, a whole cell inactivated viral preparation has been generated.

See TABLE 3 below for an explanation of the experimental groups. Groups 1-4 were randomized and held in the same room. Additionally, strict control animal (Group 5) weaned at approximately four weeks of age were included in the current study. On D0, pigs were randomized into four groups and administered a 2 mL dose of each of the prototype PDCoV vaccines or a placebo. On D21, pigs received a second, or booster administration of each of the prototype vaccines. Serum and oral fluids were collected from the pigs prior to administration of the treatment at each vaccination and on D35. Samples were assayed for evidence of seroconversion. General health observations were recorded by room daily. Injection sites were observed for reactions for a minimum of three days following administration of the vaccine.

TABLE 3

Experimental Groups

| Group | N (Pigs) | Vaccine |
|---|---|---|
| 1 | 10 | BaculoS-BD-PDCoV |
| 2 | 11 | Whole-cell PDCoV |
| 3 | 11 | Placebo |
| 4 | 10 | BaculoS-FC-PDCoV |

Serological Response Following Vaccination as Detected by IFA

Indirect Immunofluorescent Assay (IFA)

Two-fold serial dilutions from 1:40 to 1:320 were made of each sample in 1× phosphate buffered saline (PBS; Gibco c #10010-023). 100 μl of each diluted sample was added to PDCoV infected plates and incubated for one hour at 37° C. Following incubation, serum was removed and monolayers were washed two times with 1×PBS. Cells were then stained using l/well of a 1:100 dilution of FITC-conjugated-goat-anti-swine-IgG antibody. Titers were reported as the greatest serum dilution showing PDCoV staining in comparison to non-infected control wells.

Figure 4:
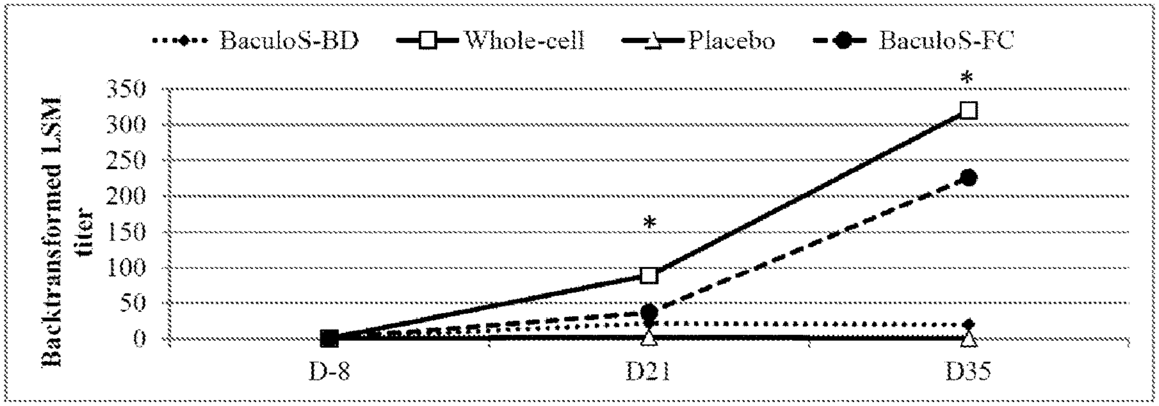
FIG. 4 Serology Study with PDCoV Prototypes (Groups 1, 2, and 4, BaculoS-BD-PDCoV, Whole-cell PDCoV, and BaculoS-FC-PDCoV, respectively) compared to the placebo (Group 3).

The serological response at D-8, D21 and D35 are presented by group in TABLE 4 below. Least square means and frequency of detection by day and group is presented in TABLE 5. No animals had a detectable serological response prior to vaccination. (See also FIG. 4).

Following a signal vaccination, 20-73% of animals had a response with animals vaccinated with BaculoS-BD prototype. By D35, all animals vaccinated with either the Whole-cell or BaculoS-FC prototypes had a detectable response. Only 50% of animals vaccinated with the BaculoS-BD prototype had a detectable response by D35.

No significant differences were observed at D-8 between the serological responses in pigs vaccinated with a prototype or a placebo. By D21 and 35, the serological response was higher in animals receiving a prototype vaccine ($p<0.002$ for all groups at all days). Numerically, the BaculoS-FC and Whole-cell prototype vaccines appeared to stimulate higher IgG responses by D35 in comparison to the BaculoSBD construct.

TABLE 4

Serological Data by Day and Group as measured by IFA

| Group | N (Pigs) | Vaccine | D-8 LSM | D-8 % | D21 LSM | D21 % | D35 LSM | D35 % |
|---|---|---|---|---|---|---|---|---|
| 1 | 10 | BaculoS-BD-PDCoV | 1 | 0 | 22* | 20 | 20* | 50 |
| 2 | 11 | Whole-cell PDCoV | 1 | 0 | 89* | 73 | 320* | 100 |
| 3 | 11 | Placebo | 1 | 0 | 1 | 0 | 2 | 0 |
| 4 | 10 | BaculoS-FC-PDCoV | 1 | 0 | 36* | 40 | 226* | 100 |

*Indicates that the value is significantly different from the Placebo group (Dunnett's method)

Serological Response Following Vaccination as Detected by S1-IgG2a-Fc Based ELISA PDCoV IgG ELISA Purified PDCoV-S1-IgG2aFc antigen (BIVI L #3091-141; 0.2 mg/mL) was diluted 1:6666.67 incarbonate buffer (BIVI L #3144-180). ELISA plates (high binding 96 well plates; Greiner cat #655061) were coated with 100 μl/well of diluted antigen and incubated overnight at 4° C. Plates were washed five times with 300 μl/well of TBST (0.05% Tween 20) using an automated plate washer. Following the wash step, 150 μl of blocking solution (Casein blocker, Thermo catalog #37532) was added per well and the plates were incubated at 15-30° C. for one hour. Initial serum dilutions were prepared in casein blocker at a dilution of 1:200 (negative control and test samples). Following incubation, the casein blocker was removed from the plate and serial two-fold dilutions (made in casein blocker) of the test samples were made from 1:200 through 12800. Serial two-fold dilutions of the negative control were made from 1:200 through 1:204800. Dilutions were prepared on the plate with an end volume of 100 μl/well. Plates were incubated at 37° C. for one hour with shaking (100 rpm). Following incubation, plates were washed as described previously. A 1:2000 dilution (in casein blocker) of a HRP conjugated goat-anti-swine-IgG (H+L) (Jackson ImmunoResearch catalog #114-035-003) was prepared and 1001d was added to each well. The plates were incubated at 37° C. for one hour with shaking at 100 rpm then washed as previously described. For detection, 100 μl/well of prepared TMB substrate (KPL cat #50-76-00) was added per well. The plates were incubated at 15-30° C. for 10 minutes. The reaction was stopped with 100 μl/well of 1N HCl and immediately read at 450 nm with an automated plate reader.

Results were generated through the following calculations. First, the mean and standard deviation optical density (OD) readings from the final five negative serum dilution wells were calculated. A cut-off was then established as the mean plus three standard deviations. Each sample optical density reading (at their initial dilution) was divided by the background cut-off for that plate. Data was reported as the signal:background ratio.

Figure 5:
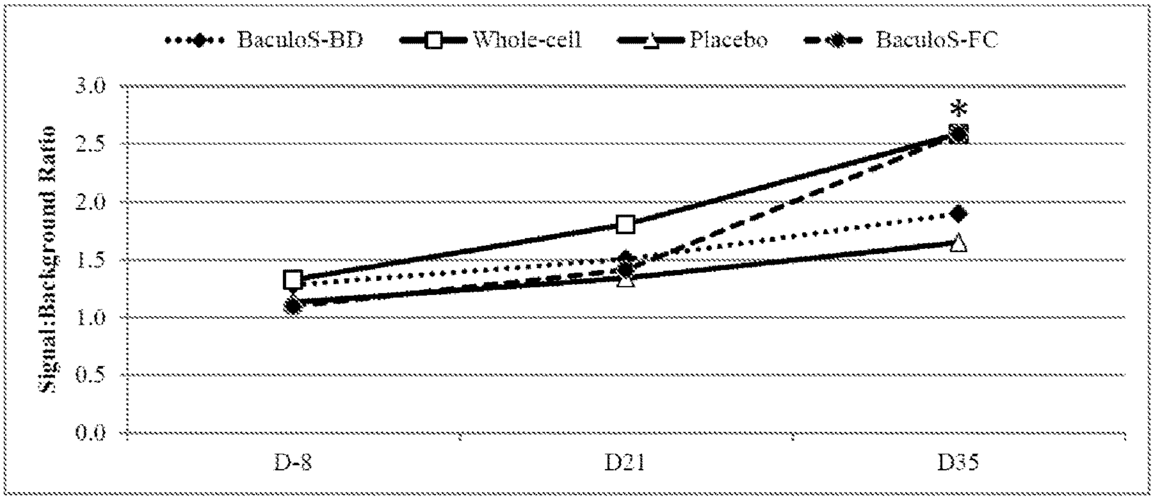
FIG. 5 Serological response following vaccination with PDCoV Prototypes as detected by S1-IgG2a-Fc based ELISA: (Groups 1, 2, and 4, BaculoS-BD-PDCoV, Whole-cell PDCoV, and BaculoS-FC-PDCoV, respectively) compared to the placebo (Group 3).

The serological response at D-8, D21 and D35 are presented by group. Least square means and frequency of detection by day and group is presented in TABLE 5 (See also FIG. 5). No animals had a detectable serological response prior to vaccination.

Following a second vaccination, 40-45% of animals had a response regardless of group. By D35, all animals vaccinated with either the Whole-cell or BaculoS-FC prototypes had a detectable response. No significant differences were observed at D8 or D21 between the serological responses in pigs vaccinated with a prototype or a placebo. By D35, the serological response was higher in animals receiving a prototype vaccine (p=0.0039, <0.0001 or <0.0001 for Groups 1, 2 and 4 respectively).Similar to the IFA results, the BaculoS-FC and Whole-cell prototype vaccines stimulated higher IgG responses by D35 in comparison to the BaculoS-BD construct.

TABLE 5

Serological Data by Day and Group as measured by IgG ELISA

| | N | | D-8 | | D21 | | D35 | |
|---|---|---|---|---|---|---|---|---|
| Group | (Pigs) | Vaccine | LSM | % | LSM | % | LSM | % |
| 1 | 10 | BaculoS-BD-PDCoV | 1.2840 | 0 | 1.5068 | 40 | 1.8965* | 70 |
| 2 | 11 | Whole-cell PDCoV | 1.3275 | 0 | 1.8040 | 45 | 2.5857* | 100 |
| 3 | 11 | Placebo | 1.1350 | 0 | 1.3409 | 9 | 1.6487 | 9 |
| 4 | 10 | BaculoS-FC-PDCoV | 1.0997 | 0 | 1.4120 | 40 | 2.5857* | 100 |

*Indicates that the value is significantly different from the Placebo group (Dunnett's method)

Example 9: Efficacy of PEDV Baculovirus Vaccines

The following study evaluated the serological response to vaccination with two 2-mL does of a killed Porcine Epidemic Diarrhea Virus (PEDV) Vaccine, or a baculovirus construct vaccine, as measured after administration of either vaccine to pigs at three weeks of age. The primary outcome was serology tested by fluorescent focus neutralization (FFN) for serum samples collected following vaccination in the treated pigs.

The study groups included: T01=PBS (n=10); T02=6.93 log $TCID_{50}$/ml BEI PEDV+20% EMULSIGEN®-BCL (n=20); T03=Baculovirus with PEDV Spike Ag (n=9); 6× Concentrated Baculovirus with PEDV Spike Ag (n=10); Trypsin Baculovirus with PEDV Spike Ag (n=10); and Killed Positive Control vaccine conditionally licensed (POS CON) (n=10). On D0, pigs were administered the 2-mL treatment intramuscularly in the right neck. A second treatment was administered on D14 in the left neck for T01-T05 and on D21 for T06.

Preparation of PEDV2a-BD

Figure 6A:
FIG. 6A Schematic diagram of PEDV 2a BD Baculodisplay Baculovirus Protein map.

In this study, the spike gene from porcine epidemic diarrhea virus (PEDV) 2a was cloned in two overlapping fragments (N-term and C-term) from plasmid DNA. The N-terminal fragment was amplified using primers P1360110A (SEQ ID NO:37 and PEDV-S2-R (SEQ ID NO:38) while the C-term fragment was amplified using primers PEDV-S1-F (SEQ ID NO:39) and P13601 10B (SEQ ID NO:40). The N-terminal and C-terminal fragments were amplified so as to remove the native signal sequence and C-terminal tail. The N-term fragment was fused with the *Autographa californica* nucleopolyhedrovirus (AcNPV) gp64 signal sequence (O1360110C) (SEQ ID NO:41) by overlap-extension PCR (OE-PCR) using primers P290194A (SEQ ID NO:45) and PEDV-S2-R (SEQ ID NO:38). The C-term fragment was fused with the AcNPV gp64 C-terminal tail coding sequence (O1360110D) (SEQ ID NO:42) by OE-PCR using primers P290194B (SEQ ID NO:43) and PEDV-S1-F (SEQ ID NO:44). The two resulting fragments were fused by OE-PCR using primers P290194A (SEQ ID NO:45) and P290194B (SEQ ID NO:43) to generate the PEDV spike BaculoDisplay (PEDVS BD) (SEQ ID NO:46) coding sequence containing a Kozak consensus sequence immediately 5' of the start codon. The final coding sequence was flanked by BamHI and NotI restriction sites to facilitate cloning into baculovirus transfer plasmid pVL1393. Once completed, plasmid pVL1393-PEDVS BD was used with linearized BaculoGold baculovirus DNA to transfect Sf9 insect cells to produce recombinant baculovirus. See FIG. 6A. Schematic diagram of PEDV 2a BD Baculodisplay Baculovirus.

TABLE 6

PEDV Prototype Formulations and Controls

| | Treatment | Description |
|---|---|---|
| T01 | Negative Control (NC) | Saline (PBS 1×) |
| T02 | Experimental Vaccine (EV) | Porcine epidemic diarrhea virus at 6.93 $log_{10}$) $TCID_{50}$/mL PEDV inactivated with BEI, adjuvanted with 20% EMULSIGENO ® BCL. |
| T03 | EV | Recombinant baculovirus PEDV2a-BD (PEDV Spike glycoprotein displayed in the viral envelope.)* |
| T04 | EV | Recombinant baculovirus PEDV2a-BD (PEDV Spike glycoprotein displayed in the viral envelope.)* The clarified inactivated material was concentrated ~6X prior to formulation. |
| T05 | EV | Recombinant baculovirus PEDV2a-BD (PEDV Spikeglycoprotein displayed |

TABLE 6-continued

| PEDV Prototype Formulations and Controls | | |
|---|---|---|
| | Treatment | Description |
| | | in the viral envelope.)* Recombinant PEDV Spike-Display Baculovirus was produced in insect cells with 10 μg/mL trypsin added during infection. |
| T06 | Positive Control (PC) | iPED+ (Harris vaccine – Conditionally Licensed) |

BEI = binary ethyleneimine

*The PEDV Spike signal sequence and C-terminal tail were replaced with the baculovirus gp64 equivalent. Recombinant PEDv Spike-Display Baculovirus was produced in insect cells. Infected cultures were harvested and clarified by centrifugation and 0.2-μm filtration. Clarified harvest material was inactivated with 5 mM BEI for 72 hours at 37° C. then clarified by centrifugation and 0.2-μm filtration.

Serology:

Seroconversion post-vaccination (D28 & D35) occurred in 20% of pigs vaccinated with PEDv vaccine adjuvanted with 20% EMULSIGEN® BCL (T02; TABLE 7) and 60% of pigs vaccinated with trypsin-grown PEDV SPIKE-baculovirus (T05; TABLE 7). The geometric mean titer for seropositive pigs ≥1:20 for all treatment groups are presented below in TABLE 7. The frequency distribution of titers by treatment group of all pigs is presented in TABLE 8.

TABLE 7

| Proportion of seropositive pigs and geometric mean titer by group for pigs responding serologically | | |
|---|---|---|
| Group | Pigs with ≥1:20 Response | Geometric Mean Titer |
| T01 | 0/10 (0%) | Not applicable |
| T02 | 4/20 (20%) | 1:30.7 |
| T03 | 0/9 (0%) | Not applicable |
| T04 | 0/10 (0%) | Not applicable |
| T05 | 6/10 (60%) | 1:35.5 |
| T06 | 7/10 (70%) | 1:41.9 |

TABLE 8

| Frequency distribution of titers by group | | | | | | | | | |
|---|---|---|---|---|---|---|---|---|---|
| | | PEDv Neutralizing Antibodies* | | | | | | | |
| Group | n | <1:20 | 1:20 | 1:28 | 1:40 | 1:57 | 1:80 | 1:113 | 1:160 |
| T01 | 10 | 10 (100%) | 0 (0.0%) | 0 (0.0%) | 0 (0.0%) | 0 (0.0%) | 0 (0.0%) | 0 (0.0%) | 0 (0.0%) |
| T02 | 20 | 16 (80%) | 1 (5%) | 2 (10%) | 0 (0.0%) | 1 (5%) | 0 (0.0%) | 0 (0.0%) | 0 (0.0%) |
| T03 | 9 | 9 (100%) | 0 (0.0%) | 0 (0.0%) | 0 (0.0%) | 0 (0.0%) | 0 (0.0%) | 0 (0.0%) | 0 (0.0%) |
| T04 | 10 | 10 (100%) | 0 (0.0%) | 0 (0.0%) | 0 (0.0%) | 0 (0.0%) | 0 (0.0%) | 0 (0.0%) | 0 (0.0%) |
| T05 | 10 | 4 (40%) | 2 (20%) | 2 (20%) | 1 (10%) | 0 (0.0%) | 0 (0.0%) | 0 (0.0%) | 1 (10%) |
| T06 | 10 | 3 (30%) | 2 (20%) | 2 (20%) | 0 (0.0%) | 0 (0.0%) | 2 (20%) | 1 (10%) | 0 (0.0%) |

Conclusion:

Seroconversion occurred in 20% of T02 pigs after two administrations of the experimental vaccine formulated with 6.93 $\log_{10}$ $TCID_{50}$/mL PEDV inactivated with BEI and adjuvanted with 20% EMULSIGEN® BCL. Seroconversion occurred in 60% of T05 pigs after two administrations of the experimental recombinant trypsin grown-baculovirus vaccine formulated with PEDV Spike glycoprotein.

Example 10: Efficacy of PEDV 2a BD Baculovirus Vaccines

The primary objective of this study was to evaluate the efficacy of prototype PEDV baculovirus vaccines in a conventional sow model. Thirty-six sows were randomized into five groups. Sows were intramuscularly vaccinated at five and two weeks pre-farrow with an experimental PEDV vaccine, a placebo, a commercially available positive control or were left non-vaccinated (strict control). A brief description of the groups and vaccines used are listed in TABLE 9 below. Throughout gestation, farrowing and the challenge period, serum and fecal samples were collected from sows and pigs to monitor the presence of anti-PEDV-antibodies and PEDV RNA. Clinical signs were recorded once daily.

The primary outcome parameter of the study was pig mortality. Based on 69% pig mortality, the presence of clinical signs and identification of PEDV RNA in fecal material from pigs in the placebo group, the challenge model used for this study was considered valid. The use of two doses of the BaculoS-NT construct in sows was able to significantly reduce pig morality. In comparison, a PEDV vaccine currently on the market was also able to reduce pig morality; however, the reduction was not significant. As the BaculoS-NT prototype was not grown in the presence of trypsin and was adjuvanted with 12.5% EMULSIGEN® D, it is expected that this prototype would be the preferred format for production and have a 21 day withdrawal period.

A secondary outcome parameter of the study was the vaccine prototypes ability to prevent clinical signs in pigs. As greater than 93% of all pigs had pure liquid diarrhea for a minimum of two consecutive days, none of the vaccine prototypes or the commercially available product were able to prevent the onset of severe clinical signs. Similarly, none of the vaccines were able to reduce the duration of clinical signs in pigs.

TABLE 9

| Study Design: | | | | |
|---|---|---|---|---|
| Group | N (sows) | N (pigs) | Vaccine | Pigs Challenged (Y/N) |
| 1 | 8 | 82 | PEDV2a-BD Baculo S-T (12.5% EMULSIGEN ®D) | Y |
| 2 | 8 | 87 | PEDV2a-BD Baculo S-NT (12.% EMULSIGEN ®D) | Y |
| 5 | 8 | 81 | Placebo (1× PBS) | Y |
| 4 | 8 | 70 | Positive Control | Y |
| 5 | 4 | 46 | Strict Control | N |

Sows were intramuscularly vaccinated at five and two weeks pre-farrow with an experimental PEDV vaccine, a placebo, a commercially available positive control or were left non-vaccinated (strict control). During gestation, blood and a fecal sample were collected prior to each vaccination and assayed for evidence of seroconversion and shedding, respectively. Clinical observations were recorded on each sow daily.

Figure 7:
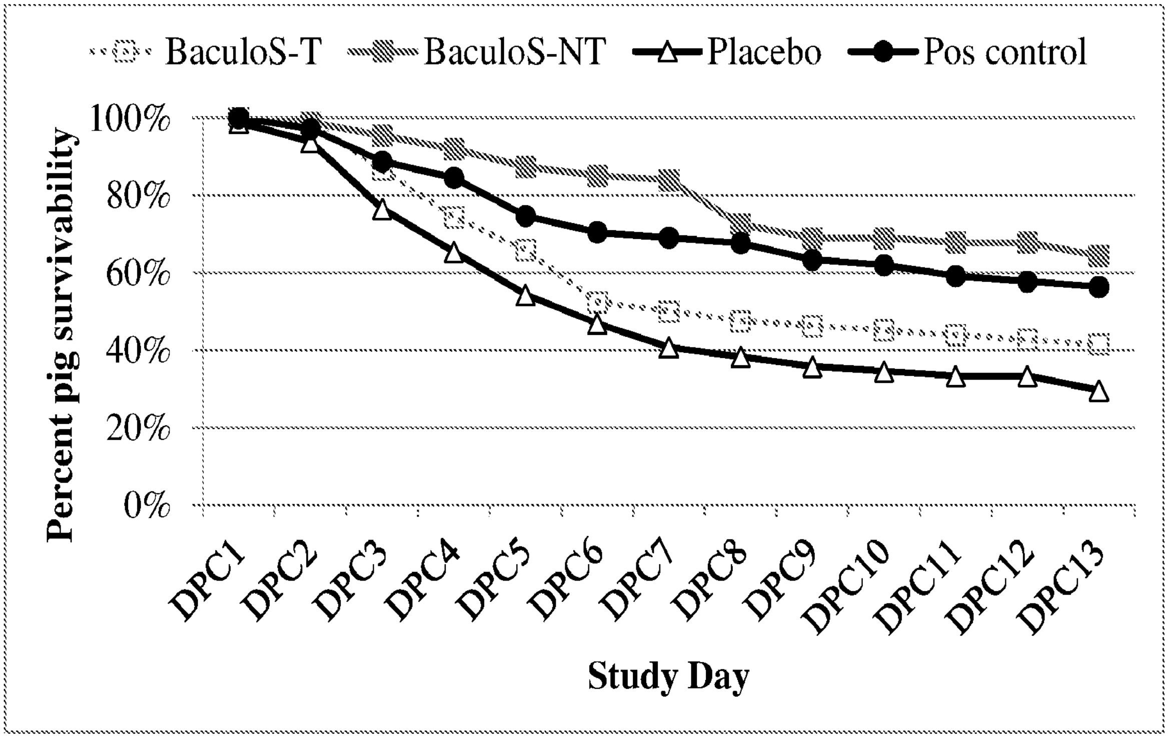
FIG. 7 Survivability by group and day after PEDV BD challenge.

Pig Mortality:

Pig mortality following challenge with a virulent PEDV isolate was the primary outcome parameter used to assess vaccine efficacy. A summary of mortality by group during the challenge period is presented in TABLE 10 below. Survivability by group and day is presented in FIG. 7. 'Percentage of surviving pigs by group and day'). On D0, the 2 mL dose of vaccine was administered to healthy sows into the musculature of the right neck using an appropriately-sized, sterile needle and syringe. On D21, the process was identical with the exception that the injection was given on the left side of the neck.

Challenge material was virulent PEDV stock material (PEDV 1251-140-4; p5; L #2842-174; titer=2.02×$10_5$ $TCID_{50}$/mL) which was diluted to a titer of 1.0×$10_3$ in PEDV viral growth media (modified minimal essential media with HEPES, tryptose phosphate broth, and yeast extract). Similar to previous studies, the majority of mortalities were seen within eight days of exposure to challenge material.

Overall, all groups had similar trends with clinical signs present in the majority of pigs within 48 hours of infection. Clinical signs were present in greater than 50% of the pigs in all groups through DPC6. From DPC7 through DPC11 clinical signs resolved. By DPC13, no clinical signs were observed in any of the pigs.

Analysis:

Biostatistics. All data were imported into SAS® version 9.4 for analysis. Data listings and summary statistics by treatment group, including frequency distributions, were generated. Analyses were conducted incorporating litter and housing effect as appropriate. Post-challenge mortality of pigs by group and litter was listed and descriptive statistics mean, median, minimum and maximum were used for summary by group. Mortality by group and litter was analyzed using a generalized linear model with Pearson's chi-square as over dispersion. Then, model-based Prevented Fraction and 95% Confidence Interval for each treatment group in comparison with the placebo group were estimated. A generalized linear model with Pearson's chi-square as over dispersion was fit to the mortality data one more time added with age, treated score and parity as fixed effects to look into if these factors have any effect on mortality. Study randomization data was listed. Fecal score for pigs was listed and summarized by group and day using frequency distribution. The summarization was done for prior to and during challenge separately. Score of clinical signs for sows (fecal, vomit, injection site lesion, Agalactia and treated) was listed and summarized separately for prior to and post farrow by group and day using frequency distribution. Pig weight data was listed and summarized using descriptive statistics median, minimum and maximum by litter, group and day. Average Daily Weight Gain (ADWG) was analyzed by a mixed model with group and weight at farrowing as fixed effects; litter and room for housing as random effects. Least square means and contrast of them between groups were estimated; the corresponding standard errors and 95% confidence intervals were estimated. Necropsy data for pigs, including pathology data for organ and content for cecum, colon, small intestine, and lung lesions, and stomach record, was listed and summarized using counts for each variable by group separated by mortality. Whether there existed any lesion was also summarized using counts and percentage by group. Lab data, including PED virus serum antibody titer (FFN) for sows, serum IgA whole cell ELISA for pigs and sows separately, IgA and IgG baculos ELISA for sows, IgA and IgG IDEXX ELISA and PCR for sows and pigs, were first listed. Next, descriptive statistics mean, minimum, maximum and standard deviation by group and day were calculated using either geometric means (FFN) (although for FFN, standard deviation was not provided) or means (ELISA, PCR). Next, least square means, standard errors and 95% confidence intervals by group and day were estimated using a mixed model with litter and room for housing as random effects. Contrast of least square means between pairs of groups and the corresponding 95% confidence intervals were estimated.

TABLE 10

Pig Mortality by Group

| Group | Description | % Pig Mortality Mean | Median | Minimum | Maximum | PF |
|---|---|---|---|---|---|---|
| 1 | BaculoS-T | 59.03 | 59.60 | 8.33 | 100.00 | 0.17 (−0.244, 0.444) |
| 2 | BaculoS-NT | 36.31 | 44.16 | 0.00 | 58.33 | 0.48 (0.103, 0.695) |
| 3 | Placebo | 68.95 | 69.32 | 45.45 | 91.67 | Not applicable |
| 4 | Positive control | 42.83 | 32.47 | 9.09 | 100.00 | 0.39 (−0.037, 0.642) |

The primary outcome parameter of the study was pig mortality. Based on this parameter, use of two doses of the BaculoS-NT construct in sows was able to significantly reduce pig morality (PF=0.48). In comparison, a PEDV vaccine currently on the market was also able to reduce pig morality; however, the reduction was not significant (Group 4). As the BaculoS-NT prototype was not grown in the presence of trypsin and was adjuvanted with 12.5% EMULSIGEN® D, it is expected that this prototype would be the preferred format for production and have a 21 day withdrawal period.

Secondary outcomes parameters of the study were the vaccine prototypes ability to prevent clinical signs in pigs and sows. As greater than 93% of all pigs had pure liquid diarrhea for a minimum of two consecutive days, none of the vaccine prototypes or the commercially available product were able to prevent the onset of severe clinical signs. Similarly, none of the vaccines were able to reduce the duration of clinical signs in pigs. Following resolution of clinical signs, PEDV RNA was identified in 12-33% of animals at DPC14. This suggests that vaccination did not protect against colonization. In 1-3 sows per group, severe diarrhea was observed for at least two consecutive days. This indicates that the vaccines were not able to fully protect sows against exposure to high amounts of virus shed by challenged pigs. In addition, the majority of sows (14/16) had detectable amounts of virus present in mesenteric lymph nodes indicating vaccination did not prevent colonization.

The majority of vaccinated sows had a detectable IgG (and FFN) response following two doses of vaccine; titers were higher in comparison to placebo-vaccinated controls (data not shown). As IgG ELISA and FFN results are very similar, it is likely that the FFN assay is mainly detecting IgG. While IgG can neutralize virus, it is unlikely to be the sole determinate of PEDV vaccine efficacy as clear differences between groups were not apparent.

Figure 8:
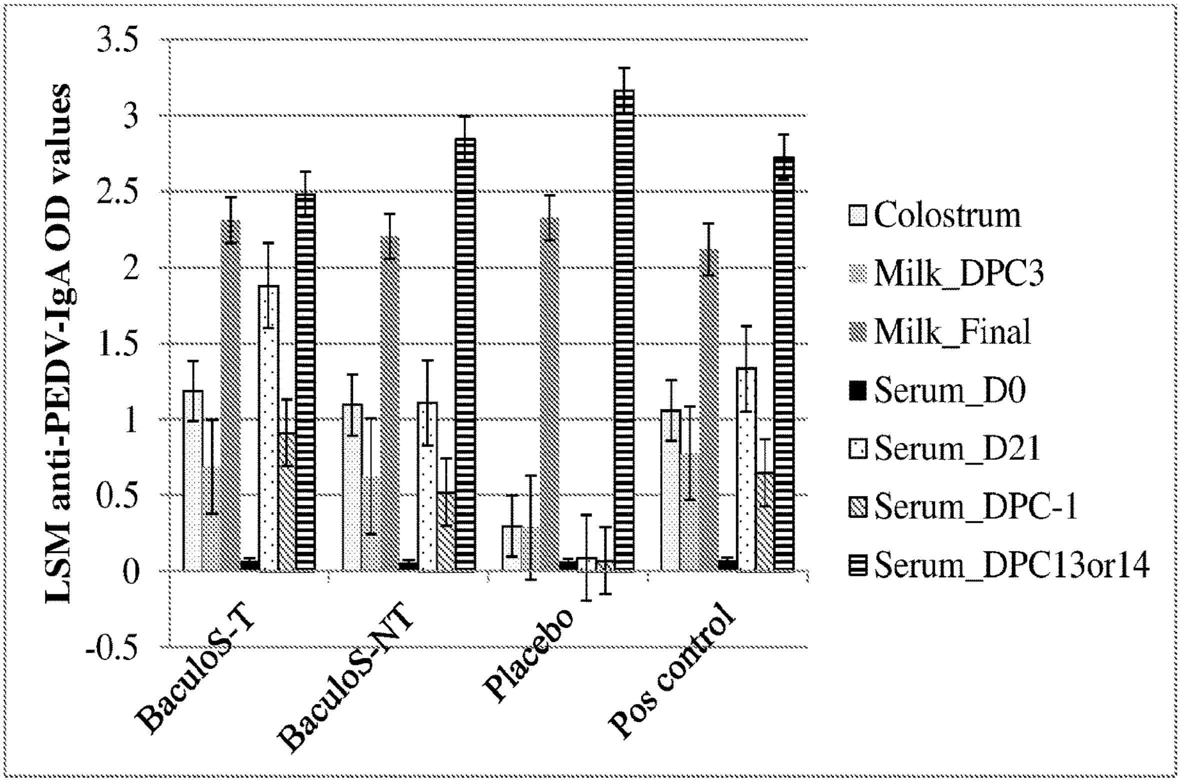
FIG. 8 IgA levels in vaccinated animals.

Based on IgA levels as measured IgA ELISA (IDEXX), naïve and vaccinated sows had similar serum and milk IgA titers by DPC13/14. However, increased IgA titers in serum, colostrum and milk collected at DPC3 were noted in vaccinated animals. As surviving pigs from vaccinated sows also had the highest IgA titers, this data supports previously published literature emphasizing the importance of IgA in enteric infections. (See FIG. 8).

Example 11: Preparation of PEDV2b Baculovirus Vaccines

Figure 6B:
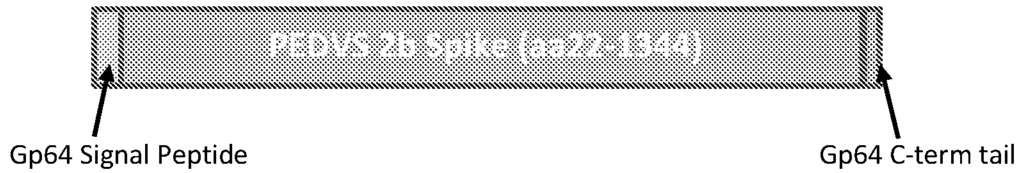
FIG. 6B Schematic diagram of PEDV 2b BD Baculodisplay Baculovirus—Protein map.

The spike gene from porcine epidemic diarrhea virus (PEDV) 2b was prepared in two overlapping fragments (N-term and C-term). The N-terminal fragment was amplified from synthetic DNA containing a fusion of the *Autographa californica* nucleopolyhedrovirus (AcNPV) gp64 signal sequence with amino acids 22-400 of PEDV 2b spike using primers P290194A (SEQ ID NO:48) and P3183131B (SEQ ID NO:49). The C-term fragment was amplified from pVL1393-PEDVS BD plasmid DNA which already contained the AcNPV gp64 C-terminal tail coding sequence using primers P3183131A (SEQ ID NO:50) and P290194B (SEQ ID NO:51). The two resulting fragments were fused by OE-PCR using primers P290194A (SEQ ID NO:48) and P290194B (SEQ ID NO:51) to generate the PEDV 2b spike BaculoDisplay (PEDVS 2b BD) coding sequence (SEQ ID NO:52) containing a Kozak's consensus sequence immediately 5' of the start codon. The final coding sequence was flanked by BamHI and NotI restriction sites to facilitate cloning into baculovirus transfer plasmid pVL1393. Once completed, plasmid pVL1393-PEDVS 2b BD was used with linearized BaculoGold baculovirus DNA to transfect Sf9 insect cells to produce recombinant baculovirus. See FIG. 6B. Schematic diagram of PEDV 2b BD Baculodisplay Baculovirus—Protein map.

Example 12: PEDV and PDCoV Efficacy Studies

The below study was designed to assess the efficacy of a killed PEDV vaccine and/or killed PDCoV vaccine or other prototype vaccines in pigs. The primary outcome parameter is piglet mortality following challenge with a porcine epidemic diarrhea virus (PEDV) and/or PDCoV. The secondary outcome parameter was dam serology. Other parameters measured included: clinical signs (including ISL) in sows following vaccination; viral shedding in sows following vaccination (via qRT-PCR); clinical signs in piglets; and PEDV and/or PDCoV serology in piglets PEDV Study:

At four and two weeks pre-farrow (D0 and D14), each gestating dam was administered 2 mL of one of the following treatments by three routes (intramuscular, intranasal and oral): T01 (negative control, NC) phosphate buffered saline; T02 (BEI-VH) adjuvanted with 20% EMULSIGEN® BCL; T03 (strict control, SC) served as non-vaccinated/non-challenged control. Eight animals were used per group, excluding T06 which had four animals. On D35 or D36, pigs were challenged orally with 1 mL of 2.0 log 10 TCID50/mL PEDV viral harvest. Clinical signs (vomiting and diarrhea) in dams and pigs were observed daily during the challenge phase. Serum was collected from dams at four- and two-weeks pre-farrow (D0 and D14), the day prior to piglet challenge (D34 or D35) and the day of off-test (D57).

On D0 and D14, the PEDV prototype immunogenic compositions were administered to the sows. At each vaccination, the sows received a total of 6 mL of material where 2 mL were administered by intramuscular, intranasal and oral route. For the intramuscular administration route, a 2 mL injection was given into the musculature of the neck below the ear. The side of the neck for administration was alternated for the initial and booster vaccination. For the oral administration route, 2 ml were delivered over the caudal oropharynx using an 8 Fr polypropylene catheter (2.7 mm diameter by 254 mm length) attached to a syringe. For the intranasal route, 1 ml was injected into each nare using a 4.5 inch catheter attached to a syringe.

TABLE 11

PEDV Experimental Immunogenic Compositions and Control Product

| Treatment | Group | Serial # | Description |
|---|---|---|---|
| T01 | NC | 2842-182-D | 1X Phosphate Buffered Saline; Gibco catalog no. 10010-023; Lot no. 1510272 |
| T02 | BEI-VH | 2842-182-E | KV-1251-125-10-OK, 0.2 μm filtered, passage MSV + 5, 6.04 log $TCID_{50}$/mL. Viral harvest was inactivated with 5mM BEI for 72 hr. at 37° C. For formulation, EMULSIGEN ® BCL (MVP lot no. 17006, manufacture date Feb. 11, 2011) was added at a 20% inclusion rate. |

TABLE 12

PEDV Challenge Material

| | |
|---|---|
| PEDV Challenge Strain: | Isolate id. 1251-140-4; passage 5 |
| Challenge preparation: | Propagated in Vero cells |
| Dose of Challenge material: | 1 mL at 2.0 $log_{10}$ $TCID_{50}$/mL |
| Testing of Challenge Material: | Challenge virus was titrated prior to administration on 2013 EU Vero cells (5.03 TCID50/ml) and diluted to 2 log $TCID_{50}$/mL. |
| Method of Administration: | Oral administration (by syringe) with pigs manually restrained. |

Vaccine Efficacy:

Pig mortality: Pig mortality following challenge with a virulent PEDV isolate was the primary outcome parameter used to assess vaccine efficacy. A summary of mortality by group during the challenge period is listed below. With 55% mortality and all litters affected in T01 (NC), the challenge was considered sufficiently virulent. In comparison to T01 (NC), T02 (BEI-VH) demonstrated a numerical reduction in pig mortality with a PF (95% CI) of 0.20 (−0.550, 0.586). The reduction was not statistically significant as the 95% CI (−0.550, 0.586) included zero. (See TABLE 13).

Extra-binomial variation was evident in this study, resulting in a wide confidence interval for T02 (BEI-VH) PF when utilizing the underlying binomial distribution. Mortality varied greatly among litters within a group, including ranging from 0% to 100% for T02 (BEI-VH).

An intestinal sample or intestinal content was taken at the time necropsy and tested by qRT-PCR to detect PEDV antigen. Of samples tested from animals during the time of peak mortality, PEDV was detected in 55.5% of samples.

TABLE 13

| Group | Proportion Mortality Estimate | Standard Error | Prevented Fraction* | 95% Confidence interval | Median Mortality | Minimum %/ Maximum % |
|---|---|---|---|---|---|---|
| NC | 0.55 | 0.11 | — | — | 52.78 | 12.50/ 100.00 |
| BEI-VH | 0.44 | 0.10 | 0.20 | (−0.550, 0.586) | 34.29 | 0.00/ 100.00 |

*Based on T01 (NC) proportion affected

**NC = Not Calculated. Confidence Interval possible for T02 (BEI-VH) based on study design Sow Serology:

Fluorescent Focus Neutralizing (FFN) assay: The FFN assay was used to assess the dam virus neutralizing response following vaccination and challenge. Geometric mean titers listed by group are presented below for days on which blood was collected from sows.

Following two doses of vaccine, 2/8 (25%) of sows in T02 (BEI-VH) had detectable levels of neutralizing antibody. Detectable levels of neutralizing antibody were not observed in any of the other groups.

Following lateral exposure to PEDV, all sows in exposed treatment groups had detectable levels of neutralizing antibody. Animals in T03 (SC) group remained seronegative throughout the trial. The geometric mean titer on D57 (approximately 21 days post-exposure) indicated that vaccination resulted in numerically higher titers in comparison to T01 (NC). Sows in T02 (BEI-VH) group had a GMT of 613, which is an approximately three-fold higher titer in comparison to the GMT of 200 for sows in T01 (NC) (p=0.005). As multiple samples in T02 (BEI-VH) group had detectable neutralizing antibodies at the highest dilution tested (1:640), these results likely represent a conservative estimate of the differences between groups.

TABLE 14

| Sow Serology | | | | | |
|---|---|---|---|---|---|
| | | Geometric Mean Titer* Study Day** | | | |
| Treatment | Group | D0 | D14 | D34 or D57 | D35 |
| T01 | NC | <20 | <20 | <20 | 200 |
| T02 | BEI-VH | <20 | <20 | 15 | 613 |
| T03 | SC | <20 | <20 | <20 | <20 |

Where all values were <20, geometric mean titer is presented as <20. Otherwise, values of <20 were set to 10 for GMT calculation

**D57 GMT for T01 (NC) and T02 (BEI-VH) are back-transformed Least-Squares Means S1-Based ELISA Data:

An S1-based ELISA was used to assess the dam's response to the PEDV-spike protein following vaccination and challenge. Assay results for colostrum, milk and serum are listed by group for days on which samples were collected.

At the time of pig challenge, sows in T02 (BEI-VH) had significantly higher geometric mean titer in serum as compared to sows in T01 (NC) (p=0.0005). Following exposure to PEDV, a larger significant difference was noted between the two groups (p<0.0001).

Significant differences in geometric mean titers of anti-PEDV IgA in colostrum and in milk were not observed between T02 (BEI-VH) and T04 (NC).

TABLE 15

| | | Geometric Mean Titer* Study Day | | | |
|---|---|---|---|---|---|
| Treatment | Group | D27 through D32: Colostrum | D34 or D35: Serum | D57: Serum | D57: Milk |
| T01 | NC | 0.186 | 0.098 | 0.504 | 0.220 |
| T02 | BEI-VH | 0.139 | 0.256 | 1.499 | 0.244 |
| T03 | SC | 0.134 | 0.125 | 0.164 | 0.088 |

*GMT for T01 (NC) and T02 (BEI-VH) are back-transformed Least-Squares Means

Pig Serology:

Serum was collected at the time of necropsy from pigs to evaluate the presence of neutralizing antibodies. TABLE 16 below presents the geometric mean FFN titers of positive pigs by group. TABLE 16 also includes the frequency of detection expressed as the number of pigs with a GMT greater than or equal to 20 over the number of animals tested. Testing was performed on all available samples. Samples from numerous pigs were unable to be obtained due to the time difference between death and necropsy.

Descriptive statistics for FFN titers by mortality status (Died: Yes/No) and group (Overall) are listed below. Overall, a similar proportion of pigs in the vaccinated groups seroconverted (or had maternal antibodies) regardless of time of necropsy. However, in T01 (NC), a higher percentage of pigs that died prior to off test had titers (88%) in comparison to pigs that lived for the duration of the study (43%).

When looking at the overall pig titers by group, the proportion mortality estimate was inversely related to the overall group FFN percentage for T02 (BEI-VH).

TABLE 16

| Group | Pigs (Died = yes) | Pigs (Died = no) | Overall | Proportion Mortality Estimate |
|---|---|---|---|---|
| NC | 55 (28/32; 88%) | 33 (9/21; 43%) | 63 (37/53; 59%) | 0.55 |
| BEI-VH | 44 (23/42; 55%) | 50 (9/16; 56%) | 64 (32/58; 55%) | 0.44 |

* GMT (no. animals titer ≥20/total pigs tested; percentage); note that serum was not obtained from all pigs.

Clinical Observations Following Challenge:

Pig fecal scores: Descriptive statistics for the duration of abnormal fecal observations in pigs, by group and mortality status (Died: Yes/No), are listed below. Overall, the median duration of abnormal fecal scores in pigs with the same mortality status was similar among groups. In animals that died or were euthanized, there was a numerically shorter median duration of abnormal fecal scores. This trend was most evident in T01 (NC) pigs and is likely secondary to the fact that the majority of these animals died within the first week following challenge.

TABLE 17

| Duration (days) abnormal fecal score | | | | | | |
|---|---|---|---|---|---|---|
| Died | Group | # pigs | Median | Minimum | Maximum | Std Dev |
| No | NC | 32 | 5.5 | 3.5 | 7.0 | 0.8 |
| | BEI-VH | 42 | 6.0 | 4.5 | 8.5 | 0.8 |
| Yes | NC | 39 | 2.3 | 0.5 | 6.0 | 1.3 |
| | BEI-VH | 33 | 4.3 | 2.0 | 6.0 | 1.4 |

The severity of fecal scores in pigs is summarized in the frequency TABLE 18 below. In all treatment groups a high portion of pigs (>91%) presented with a fecal score of 2 during at least one observation following challenge.

TABLE 18

| Maximum Fecal Score | | | | |
|---|---|---|---|---|
| Group | 0 | 1 | 2 | Total |
| NC | 1 | 5 | 65 | 71 |
| | 1.41 | 7.04 | 91.55 | |
| BEI-VH | 1 | 0 | 74 | 75 |
| | 1.33 | 0.00 | 98.67 | |
| Total | 2 | 5 | 139 | 146 |

Conclusions:

A 20% reduction in pig mortality was observed in T02 (BEI-VH) as compared to T01 (NC) group. Three routes of administration were attempted in this study. Although 3 routes were used, there is no expectation that routes other than IM contributed to the efficacy of T02 (BEI-VH) based on the adjuvant and vaccine formulation. Overall the inactivated PEDV adjuvanted with 20% EMULSIGEN®-BCL vaccine with a minimum pre-inactivation titer of 6.04 log $TCID_{50}$/ml appears to induce better immune responses in the piglets and sows. The preferred vaccination schedule is IM route of administration for piglets 3 weeks of age or older, three 2 ml doses at 2-week intervals. Clinical signs in sows following vaccination were not observed in T02 (BEI-VH) and were limited in the other treatment groups. The use of vaccination did not appear to affect the percentage of pigs born live (data not shown).

Dam serology was evaluated as a secondary parameter by two separate assays (focus fluorescent neutralization, S1-based ELISA). Both assays indicated a significant increase in titer in T02 (BEI-VH) following vaccination and exposure as compared to T01 (NC). Due to known limitations of the FFN assay, samples were also tested by an S1-based ELISA. This ELISA was chosen as the S1 domain of the spike protein is expected to contain neutralizing epitopes.

Following lateral exposure to PEDV, all animals in exposed treatment groups had detectable levels of neutralizing antibody. Sows in T02 (BEI-VH) had approximately three-fold higher titers in comparison to the T01 (NC) animals. This is evidence that use of the vaccine stimulated an initial primary response and resulted in a greater secondary response following exposure to the challenge virus. As multiple samples in T02 (BEI-VH) group had detectable neutralizing antibodies at the highest dilution tested (1:640), these results likely represent a conservative estimate of the differences between groups.

TABLE 19

| Pig mortality and sow serological data are summarized below. | | | | | |
|---|---|---|---|---|---|
| Treatment | Group | FFN (Sow serum, D21) | IgG ELISA (Sow serum, D21) | Pig Mortality (%) | Prevented Fraction (pig mortality) |
| T01 | NC | 200 | 0.504 | 55% | — |
| T02 | BEI-VH | 613 | 1.499 | 44% | 0.20 |
| T03 | SC | <20 | 0.164 | NA | NA |

PDCoV Study

The objective of this study was to determine the efficacy of prototype PDCoV vaccines in the host animal. Based on below preliminary study to develop challenge material and a disease model of PDCoV, unvaccinated piglets exhibited weight loss and diarrhea within a week of challenge and recovered. No mortality was observed.

TABLE 20

| Porcine Deltacoronavirus (PDCoV) Challenge Material: | | | | | |
|---|---|---|---|---|---|
| Group | No of Sows | No of Piglets | Challenge virus/treatment | Titer | Dose |
| 1 | 1 | 6 | NVSL-PDCoV P12 | 6.1 $log_{10}$ $TCID_{50}$/piglet | 1 mL/oral |
| 2 | 1 | 5 | Placebo (PDCoV maintenance media) | N/A | 1 mL/oral |
| 3 | 1 | 12 | BI PDCoV 5.0327 | 4.6 $log_{10}$ $TCID_{50}$/piglet | 1 mL/oral |
| 4 | 1 | 12 | BI PDCoV 2.0307 | 3.9 $log_{10}$ $TCID_{50}$/piglet | 1 mL/oral |

To establish a challenge strain for porcine deltacoronavirus (PDCoV), two internal challenge isolates (Groups 3 and 4) were grown on BI-ST cells and compared to the NVSL PDCoV isolate (Illinois 2014). Isolates in groups 3 and 4 were selected based on the mutations they possessed and their genetic distance from the NVSL (Illinois 2014) isolate. The group 3 virus (BI PDCoV-5.0327) had a 3 amino acid deletion in the spike glycoprotein and two changes in the ORF1AB gene in comparison to the NSVL PDCoV isolate. The group 4 virus (BI PDCoV 2.0307) had 4 amino acid differences in the spike glycoprotein and 3 differences in the ORF1AB gene in comparison to the NVSL PDCoV.

Challenged piglets were scored for diarrhea where 0=normal, 1=abnormal (not pure liquid) or 2=severe diarrhea (pure liquid feces) post challenge. No diarrhea was observed in the negative control group. Additionally, the group challenged with NVSL PDCoV did not show any clinical signs, weight loss, vomiting or diarrhea post challenge. Piglets in groups 3 and 4 exhibited severe clinical signs with a 100% of them experiencing severe diarrhea (score of 2) accompanied by vomiting and weight loss. In addition, the sows in groups 3 and 4 suffered from diarrhea (D6-D8 post challenge) and were treated. Previous published studies described prolonged infection (and shedding of virus) among piglets infected with PDCoV. Their observations are in agreement with our results.

Animals in the NVSL PDCoV and negative control groups gained weight post challenge. In comparison, animals challenged with the two challenge isolates BI PDCoV-5.0327 (Group 3) and BI PDCoV 2.0307 (Group 4) exhibited less robust weight gain during the same period as compared to the control group.

Efficacy Study:

TABLE 21

PDCoV Study design (vaccine groups, dose and routes)

| Group | N sows | Vaccine primary | Vaccine Route | Dose (5 and 2 weeks pre-farrow) |
|---|---|---|---|---|
| 1 | 4 | BEI inactivated PDCoV | IM | 2 mL |
| 2 | 4 | BEI inactivated Baculo-spike-FcR | IM | 2 mL |
| 3 | 4 | NVSL-PDCoV (Live attenuated) | Oral | 2 mL |
| 4 | 4 | Placebo (Virus maint. media) | IM | 2 mL |

For the efficacy study, four groups of sows are vaccinated with each vaccine formulation as detailed in TABLE 21 by the appropriate route at 5 and 2 weeks pre-farrow. Serum is collected from the sows prior to administration of the treatment at each vaccination for seroconversion assays. Fecal samples are collected from sows at each vaccination and assayed for evidence of vaccine shedding.

Piglets from the immunized sows are enrolled into the trial at the time of farrowing. Piglets are inoculated at approximately five to seven days of age, with 1.0 mL of challenge material using the oral route.

Both piglets and sows are monitored for clinical signs once daily from days post challenge (DPC) 0 through DPC14. Post challenge fecal and serum samples are taken from all piglets and sows. Fecal samples are tested for the presence of PDCoV RNA and serum is tested for the presence of anti-PDCoV antibodies. Colostrum is collected at or near the time of farrowing from all sows. Milk is collected from all sows at DPC3 and at one point between DPC10 through DPC14. Colostrum and milk are tested for the presence of anti-PDCoV antibodies. Piglets' weight is monitored on DPC 0, 7 and 21 with terminal serum collection on DPC21.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The following references, to the extent that they provide exemplary procedural or other details supplementary to those set forth herein, are specifically incorporated herein by reference.

REFERENCES

1. Bridgen A, Duarte M, Tobler K, Laude H, Ackermann M. 1993. Sequence determination of the nucleocapsid protein gene of the porcine epidemic diarrhoea virus confirms that this virus is a coronavirus related to human coronavirus 229E and porcine transmissible gastroenteritis virus. J. Gen. Virol. 74 (Pt 9):1795-1804.
2. Duarte M, Gelfi J, Lambert P, Rasschaert D, Laude H. 1993. Genome organization of porcine epidemic diarrhoea virus. Adv. Exp. Med. Biol. 342:55-60
3. Tobler K, Bridgen A, Ackermann M. 1993. Sequence analysis of the nucleocapsid protein gene of porcine epidemic diarrhoea virus. Adv. Exp. Med. Biol. 342:49-54.
4. Oldham J. 1972. Letter to the editor. Pig Farming 1972 (October suppl):72-73.
5. Pensaert M B, de Bouck P. 1978. A new coronavirus-like particle associated with diarrhea in swine. Arch. Virol. 58:243-247.
6. Chen J F, Sun D B, Wang C B, Shi H Y, Cui X C, Liu S W, Qiu H J, Feng L. 2008. Molecular characterization and phylogenetic analysis of membrane protein genes of porcine epidemic diarrhea virus isolates in China. Virus Genes 36:355-364.
7. Nagy B, Nagy G, Meder M, Mocsiri E. 1996. Enterotoxigenic *Escherichia coli*, rotavirus, porcine epidemic diarrhoea virus, adenovirus and calici-like virus in porcine postweaning diarrhoea in Hungary Acta Vet. Hung. 44:9-19.
8. Martelli P, Lavazza A, Nigrelli A D, Merialdi G, Alborali L G, Pensaert M B. 2008. Epidemic of diarrhoea caused by porcine epidemic diarrhoea virus in Italy. Vet. Rec. 162:307-310.
9. Takahashi K, Okada K, Ohshima K. 1983. An outbreak of swine diarrhea of a new-type associated with coronavirus-like particles in Japan. Nippon Juigaku Zasshi 45:829-832.
10. Chae C, Kim O, Choi C, Min K, Cho W S, Kim J, Tai J H. 2000. Prevalence of porcine epidemic diarrhoea virus and transmissible gastroenteritis virus infection in Korean pigs. Vet. Rec. 147:606-608
11. Puranaveja S, Poolperm P, Lertwatcharasarakul P, Kesdaengsakonwut S, Boonsoongnern A, Urairong K, Kitikoon P, Choojai P, Kedkovid R, Teankum K, Thanawongnuwech R. 2009. Chinese-like strain of porcine epidemic diarrhea virus, Thailand. Emerg. Infect. Dis. 15:1112-1115.
12. Stevenson G W, Hoang H, Schwartz K J, Burrough E R, Sun D, Madson D, Cooper V L, Pillatzki A, Gauger P, Schmitt B J, Koster L G, Killian M L, Yoon K J. 2013. Emergence of porcine epidemic diarrhea virus in the United States: clinical signs, lesions, and viral genomic sequences. J. Vet. Diagn. Invest. 25:649-654.
13. Kim S H, Kim I J, Pyo H M, Tark D S, Song J Y, Hyun B H. 2007. Multiplex real-time RT-PCR for the simultaneous detection and quantification of transmissible gastroenteritis virus and porcine epidemic diarrhea virus. J. Virol. Methods 146:172-177.
14. Hofmann M, Wyler R. 1988. Propagation of the virus of porcine epidemic diarrhea in cell culture. J. Clin. Microbiol. 26:2235-2239.
15. Marthaler D, Jiang Y, Otterson T, Goyal S, Rossow K, Collins J. 2013. Complete genome sequence of porcine epidemic diarrhea virus strain USA/Colorado/2013 from the United States. Genome Announc. 1(4):e00555-13.10.1128/genomeA.00555-13
16. Song D, Park B. 2012. Porcine epidemic diarrhoea virus: a comprehensive review of molecular epidemiology, diagnosis, and vaccines. Virus Genes 44:167-175.
17. Huang Y W, Dickerman A W, Pineyro P, Li L, Fang L, Kiehne R, Opriessnig T, Meng X J. 2013. Origin, evolution, and genotyping of emergent porcine epidemic diarrhea virus strains in the United States. mBio 4(5):e00737-13.

18. Bi J, Zeng S, Xiao S, Chen H, Fang L. 2012. Complete genome sequence of porcine epidemic diarrhea virus strain AJ1102 isolated from a suckling piglet with acute diarrhea in China. J. Virol. 86:10910-10911.

19. Chen J, Wang C, Shi H, Qiu H J, Liu S, Shi D, Zhang X, Feng L. 2011. Complete genome sequence of a Chinese virulent porcine epidemic diarrhea virus strain. J. Virol. 85:11538-11539.

20. Chen J, Liu X, Shi D, Shi H, Zhang X, Feng L. 2012. Complete genome sequence of a porcine epidemic diarrhea virus variant. J. Virol. 86:3408.10.1128/JVI.07150-11

21. Fan H, Zhang J, Ye Y, Tong T, Xie K, Liao M. 2012. Complete genome sequence of a novel porcine epidemic diarrhea virus in south China. J. Virol. 86:10248-10249.

22. Gao Y, Kou Q, Ge X, Zhou L, Guo X, Yang H. 2013. Phylogenetic analysis of porcine epidemic diarrhea virus field strains prevailing recently in China. Arch. Virol. 158:711-715.

23. Li B, Liu H, He K, Guo R, Ni Y, Du L, Wen L, Zhang X, Yu Z, Zhou J, Mao A, Lv L, Hu Y, Yu Y, Zhu H, Wang X. 2013. Complete genome sequence of a recombinant porcine epidemic diarrhea virus strain from eastern China. Genome Announc. 1(2):e00105-13.10.1128/genomeA.00105-13

24. Luo Y, Zhang J, Deng X, Ye Y, Liao M, Fan H. 2012. Complete genome sequence of a highly prevalent isolate of porcine epidemic diarrhea virus in south China. J. Virol. 86:9551-9551.

25. Wang X M, Niu B B, Yan H, Gao D S, Huo J Y, Chen L, Chang H T, Wang C Q, Zhao J. 2013. Complete genome sequence of a variant porcine epidemic diarrhea virus strain isolated in central China. Genome Announc. 1(1):e00243-12.10.1128/genomeA.00243-12

26. Wei Z Y, Lu W H, Li Z L, Mo J Y, Zeng X D, Zeng Z L, Sun B L, Chen F, Xie Q M, Bee Y Z, Ma J-Y. 2012. Complete genome sequence of novel porcine epidemic diarrhea virus strain GD-1 in China. J. Virol. 86:13824-13825.

27. Zhao M, Sun Z, Zhang Y, Wang G, Wang H, Yang F, Tian F, Jiang S. 2012. Complete genome sequence of a Vero cell-adapted isolate of porcine epidemic diarrhea virus in eastern China. J. Virol. 86:13858-13859.

28. S. H. Chang, J. L. Bae, T. J. Kang, J. Kim, G. H. Chung, C. W. Lim, H. Laude, M. S. Yang, Y. S. Jang. 2002. Identification of the epitope region capable of inducing neutralizing antibodies against the porcine epidemic diarrhea virus. Mol. Cells 14, 295-299.

29. D. J. Cruz, C. J. Kim, H. J. Shin. 2008. The GPRLQPY motif (SEQ ID NO: 20) located at the carboxy-terminal of the spike protein induces antibodies that neutralize Porcine epidemic diarrhea virus. Virus Res. 132, 192-196.

30. M. Godet, J. Grosclaude, B. Delmas, H. Laude. 1994. Major receptor-binding and neutralization determinants are located within the same domain of the transmissible gastroenteritis virus (coronavirus) spike protein. J. Virol. 68, 8008-8016.

31. M. W. Jackwood, D. A. Hilt, S. A. Callison, C. W. Lee, H. Plaza, E. Wade. 2001. Spike glycoprotein cleavage recognition site analysis of infectious bronchitis virus. Avian Dis. 45, 366-372.

32. L. S. Sturman, K. V. Holmes. 1984 Proteolytic cleavage of peplomeric glycoprotein E2 of MHV yields two 90K subunits and activates cell fusion. Adv. Exp. Med. Biol. 173, 25-35.

33. D. Sun, L. Feng, H. Shi, J. Chen, X. Cui, H. Chen, S. Liu, Y. Tong, Y. Wang, G. Tong. 2008. Identification of two novel B cell epitopes on porcine epidemic diarrhea virus spike protein. Vet. Microbiol. 131, 73-81.

34. S. J. Park, H. J. Moon, J. S. Yang, C. S. Lee, D. S. Song, B. K. Kang, B. K. Park. 2007. Sequence analysis of the partial spike glycoprotein gene of porcine epidemic diarrhea viruses isolated in Korea. Virus Genes 35, 321-332.

35. L. J. Saif. 1993. Coronavirus immunogens. Vet. Microbiol. 285-297.

36. S. J. Park, H. K. Kim, D. S. Song, H. J. Moon, B. K. Park. 2011 Molecular characterization and phylogenetic analysis of porcine epidemic diarrhea virus (PEDV) field isolates in Korea. Arch. Virol. 156, 577-585.

37. D. S. Song, J. S. Yang, J. S. Oh, J. H. Han, B. K. Park. Differentiation of a Vero cell adapted porcine epidemic diarrhea virus from Korean field strains by restriction fragment length polymorphism analysis of ORF 3. 2003. Vaccine 21, 1833-1842.

38. D. S. Song, J. S., B. K. Park. 2012 Porcine epidemic diarrhoea virus: a comprehensive review of molecular epidemiology, diagnosis, and vaccines. Virus Genes 44, 167-175.

39. J. F. Chen, D. B. Sun, C. B. Wang, H. Y. Shi, X. C. Cui, S. W. Liu, H. J. Qiu, L. Feng. 2008. Molecular characterization and phylogenetic analysis of membrane protein genes of porcine epidemic diarrhea virus isolates in China. Virus Genes 36, 355-364.

40. L. Yuan, S. Y. Kang, L. A. Ward, T. L. To, L. J. Saif. 1998 Antibody-secreting cell responses and protective immunity assessed in gnotobiotic pigs inoculated orally or intramuscularly with inactivated human rotavirus. J. Virol. 72, 330-338.

41. C. H. Kweon, B. J. Kwon, J. G. Lee, G. O. Kwon, Y. B. Kang. 1999. Derivation of attenuated porcine epidemic diarrhea virus (PEDV) as vaccine candidate. Vaccine 17, 2546-2553.

42. Y. Usami, O. Yamaguchi, K. Kumanomido, Y. Matsumura. 1998. Antibody response of pregnant sows to porcine epidemic diarrhea virus live vaccine and maternally-derived antibodies of the piglets. J. Jpn. Vet. Med. Assoc. 51, 652-655.

43. L. A. Ward, L. Yuan, B. I. Rosen, T. L. To, L. J. Saif 1996. Development of mucosal and systemic lymphoproliferative responses and protective immunity to human group A rotaviruses in a gnotobiotic pig model. Clin. Diagn. Lab. Immunol. 3, 342-350.

44. A. Pijpers, A. P. van Nieuwstadt, C. Terpstra, J. H. Verheijden. 1993. Porcine epidemic diarrhoea virus as a cause of persistent diarrhoea in a herd of breeding and finishing pigs. Vet. Rec. 132, 129-131.

45. T. Sato, Takeyama, N., Katsumata, A., Tuchiya, K., Kodama, T., Kusanagi, K. 2011. Mutations in the spike gene of porcine epidemic diarrhea virus associated with growth adaptation in vitro and attenuation of virulence in vivo. Virus Genes, 43, 1, 72.

46. Park, S. J., Kim, H. K., Song, D. S., An, D. J. and Park, B. K. 2012. Complete genome sequences of a Korean virulent porcine epidemic diarrhea virus and its attenuated counterpart J. Virol. 86 (10), 5964.

47. Kusanagi K, Kuwahara H, Katoh T, Nunoya T, Ishikawa Y, Samejima T, Tajima M. 1992. Isolation and serial propagation of porcine epidemic diarrhea virus in cell cultures and partial characterization of the isolate. J Vet Med Sci. 1992 April; 54(2):313-8.

48. Hofmann M, Wyler R. 1988. Propagation of the virus of porcine epidemic diarrhea in cell culture. J Clin Microbiol. November; 26(11):2235-9.49. de Arriba M L, Carvajal A, Pozo J, Rubio P. 2002. Mucosal and Systemic Isotype-specific Antibody Responses and Protection in Conventional Pigs Exposed to Virulent or Attenuated Porcine Epidemic Diarrhoea Virus. Vet Immunol Immunopathol. 85(1-2): p. 85-97.
50. Woo, P. C., et al., Discovery of seven novel Mammalian and avian coronaviruses in the genus deltacoronavirus supports bat coronaviruses as the gene source of alphacoronavirus and betacoronavirus and avian coronaviruses as the gene source of gammacoronavirus and deltacoronavirus. J Virol, 2012. 86(7): p. 3995-4008.
51. Hu, H., et al., Isolation and Characterization of Porcine Deltacoronavirus from Pigs with Diarrhea in the United States. J Clin Microbiol, 2015 53(5): p. 1537-1548.
52. Chen, Q., et al., Pathogenicity and pathogenesis of a United States porcine deltacoronavirus cell culture isolate in 5-day-old neonatal piglets. Virology, 2015. 482: p. 51-59.
53. Li, G., et al., Full-Length Genome Sequence of Porcine Deltacoronavirus Strain USA/IA/2014/8734. Genome Announc, 2014. 2(2).
54. Marthaler, D., et al., Rapid detection, complete genome sequencing, and phylogenetic analysis of porcine deltacoronavirus. Emerg Infect Dis, 2014a. 20(8): p. 1347-50.
55. Marthaler, D., et al., Complete Genome Sequence of Strain SDCV/USA/Illinois121/2014, a Porcine Deltacoronavirus from the United States. Genome Announc, 2014b. 2(2).
56. Wang, L., B. Byrum, and Y. Zhang, Detection and genetic characterization of deltacoronavirus in pigs, Ohio, USA, 2014. Emerg Infect Dis, 2014. 20(7): p. 1227-30.
57. Jung, K., et al., Pathogenicity of 2 porcine deltacoronavirus strains in gnotobiotic pigs. Emerg Infect Dis, 2015. 21(4): p. 650-4.
58. Lee, S. and C. Lee, Complete Genome Characterization of Korean Porcine Deltacoronavirus Strain KOR/KNU14-04/2014. Genome Announc, 2014. 2(6).
59. Dong, N., et al., Porcine Deltacoronavirus in Mainland China. Emerg Infect Dis, 2015. 21(12): p. 2254-5.
60. Song, D., et al., Newly Emerged Porcine Deltacoronavirus Associated With Diarrhoea in Swine in China: Identification, Prevalence and Full-Length Genome Sequence Analysis. Transbound Emerg Dis, 2015. 62(6): p. 575-80.
61. Ma, Y., et al., Origin, evolution, and virulence of porcine deltacoronaviruses in the United States. MBio, 2015. 6(2): p. e00064.
62. Vitosh-Sillman, S., et al. Histopathological and immunohistochemical characterization of pigs experimentally infected with porcine deltacoronavirus. in American Association of Swine Veterinarians. 2015. Orlando, FL.
63. Ma, Y., et al., Origin, evolution, and virulence of porcine deltacoronaviruses in the United States. MBio, 2015. 6(2).
64. ISERPD 2015. The 7$^{th}$ Annual International Symposium on Emerging and Re-emerging Pig Diseases. Kyoto, Japan Jun. 21-24, 2015. (See emerging2015.com/; emerging2015.com/pdf/ISERPD2015_Oral_Presentations_v8.pdf, and emerging2015.com/pdf/ISERPD2015_Poster_Presentations_v5.pdf, accessed Nov. 4, 2016).

What is claimed is:

1. An immunogenic composition comprising an antigen of a porcine epidemic diarrhea virus (PEDV) and an adjuvant, wherein the PEDV antigen comprises: a spike protein encoded by a nucleic acid sequence having at least 97.91% sequence identity to SEQ ID NO: 46, or having at least 98% sequence identity to SEQ ID NO: 52 or a spike protein encoded by the nucleic acid sequence of SEQ ID NO:30.

2. The immunogenic composition of claim 1, wherein the antigen is a recombinant antigen.

3. The immunogenic composition of claim 2, wherein the recombinant antigen comprises: (i) a PEDV spike protein having an amino acid sequence with at least 90% sequence identity to SEQ ID NO: 47 or having at least 98% sequence identity to SEQ ID NO: 53; (ii) a PEDV spike protein having an amino acid sequence of SEQ ID NO: 31 or 35; (iii) a polynucleotide encoding the PEDV spike protein having the amino acid sequence with at least 90% sequence identity to SEQ ID NO: 47 or 53; and/or (iv) a polynucleotide encoding the PEDV spike protein having the amino acid sequence of SEQ ID NO:31 or 35.

4. The immunogenic composition of claim 2, wherein the recombinant antigen comprises a M, E, S, or N protein of PEDV.

5. The immunogenic composition of claim 2, wherein the recombinant antigen is a recombinant vector, a recombinant PEDV spike protein, or a combination thereof.

6. The immunogenic composition of claim 1, wherein the adjuvant is an oil-in-water emulsion.

7. The immunogenic composition of claim 1, further comprising a pharmaceutically acceptable carrier and/or an excipient.

8. The immunogenic composition of claim 1, further comprising an antigen of a porcine deltacoronavirus (PDCoV).

9. The immunogenic composition of claim 8, wherein the PDCoV comprises: (i) a polynucleotide having at least 99% sequence identity to SEQ ID NO: 2, 6, or 10; (ii) a polynucleotide having at least 99% sequence identity to a RNA complement of SEQ ID NO: 1, 5, or 9; (iii) a polynucleotide having the RNA complement of SEQ ID NO: 3; (iv) a spike protein encoded by a nucleic acid sequence having at least 90% sequence identity to SEQ ID NO: 7, 11 or 17; and/or (v) a polynucleotide encoding the PEDV spike protein having the amino acid sequence of SEQ ID NO:27.

10. The immunogenic composition of claim 9, wherein the antigen of the PDCoV is an inactivated whole PDCoV.

11. The immunogenic composition of claim 9, wherein the antigen of the PDCoV is a recombinant antigen comprising: (i) a PDCoV spike protein having at least 99% sequence identity to SEQ ID NO: 8, 12 or 18; (ii) a PDCoV spike protein having the amino acid sequence of SEQ ID NO: 4 or 28; (iii) a polynucleotide encoding the PDCoV spike protein having at least 99% sequence identity to SEQ ID NO: 8, 12 or 18; and/or a polynucleotide encoding the PDCoV spike protein having the amino acid sequence of SEQ ID NO: 4 or 28.

* * * * *